(12) United States Patent
Goldsmith

(10) Patent No.: US 11,759,186 B2
(45) Date of Patent: Sep. 19, 2023

(54) DUCTUS SIDE-ENTRY AND PROSTHETIC DISORDER RESPONSE SYSTEMS

(71) Applicant: David S. Goldsmith, Atlanta, GA (US)

(72) Inventor: David S. Goldsmith, Atlanta, GA (US)

(73) Assignee: David S. Goldsmith, Atlanta, GA (US)

( * ) Notice: Subject to any disclaimer, the term of this patent is extended or adjusted under 35 U.S.C. 154(b) by 1282 days.

(21) Appl. No.: 15/998,002

(22) Filed: Jun. 8, 2018

(65) Prior Publication Data
US 2019/0374213 A1    Dec. 12, 2019

(51) Int. Cl.
*A61B 10/02* (2006.01)
*A61M 5/14* (2006.01)
(Continued)

(52) U.S. Cl.
CPC ............... *A61B 10/02* (2013.01); *A61B 1/32* (2013.01); *A61F 2/04* (2013.01); *A61M 1/3618* (2014.02); *A61M 1/3666* (2013.01); *A61M 3/0279* (2013.01); *A61M 5/14* (2013.01); *A61M 5/14228* (2013.01); *A61M 5/14276* (2013.01); *A61M 5/16813* (2013.01); *A61M 5/1723* (2013.01); *A61M 27/008* (2013.01); *A61M 39/24* (2013.01); *A61M 60/126* (2021.01); *A61N 5/1002* (2013.01); *A61B 17/3205* (2013.01); *A61B 2017/00566* (2013.01);
(Continued)

(58) Field of Classification Search
CPC . A61B 17/0218; A61B 17/11; A61B 17/1114; A61B 2017/00876; A61B 2017/1107; A61B 17/3205; A61B 17/320758; A61B 2017/1225; A61B 17/1227; A61B 2017/1139; A61B 2017/1121; A61M 5/14228; A61M 60/126; A61M 60/13; A61M 60/157–161; A61N 5/1002; A61F 2/064
See application file for complete search history.

(56) References Cited

U.S. PATENT DOCUMENTS 5,286,254 A * 2/1994 Shapland ............ A61M 25/104
                                                604/103.01
5,443,447 A * 8/1995 Kassis ................... A61M 29/00
                                                604/24
(Continued)

*Primary Examiner* — Brandy S Lee
*Assistant Examiner* — John J Crawford
(74) *Attorney, Agent, or Firm* — Meunier Carlin & Curfman LLC

(57) ABSTRACT

Described are means for the direct and continuous connection of a catheter to the lumen of any tubular anatomical structure, or ductus, without medically significant leakage. A port implanted at the body surface with piping to a periductal collar allows drug or radionuclide delivery that bypasses the upstream lumen. The port allows injection, infusion, aspiration, or attachment of an automatic ambulatory pump. A superparamagnetic nanoparticle carrier-bound drug, for example, can be introduced into the lumen to pass downstream until the particles, with or without the drug still bound, are drawn into the lumen wall by a magnetized jacket surrounding the ductus. Such constitutes a method of drug targeting whereby a segment of a vessel or the territory supplied by a branch of that segment can be circumscribed for exposure to the drug. A jacket with side-entry connector positioned in surrounding relation to a lesion requiring treatment can itself be magnetized.

13 Claims, 24 Drawing Sheets

(51) Int. Cl.

| | |
|---|---|
| *A61N 5/10* | (2006.01) |
| *A61M 5/142* | (2006.01) |
| *A61M 5/172* | (2006.01) |
| *A61M 39/24* | (2006.01) |
| *A61M 1/36* | (2006.01) |
| *A61F 2/04* | (2013.01) |
| *A61M 5/168* | (2006.01) |
| *A61M 60/126* | (2021.01) |
| *A61B 17/02* | (2006.01) |
| *A61B 17/00* | (2006.01) |
| *A61B 17/3205* | (2006.01) |
| *A61M 3/02* | (2006.01) |
| *A61M 27/00* | (2006.01) |
| *A61B 1/32* | (2006.01) |

(52) U.S. Cl.
CPC ............... *A61B 2017/00876* (2013.01); *A61B 2017/0212* (2013.01); *A61F 2002/044* (2013.01); *A61F 2220/0083* (2013.01); *A61M 5/14244* (2013.01); *A61M 2005/14208* (2013.01); *A61M 2205/0288* (2013.01); *A61M 2210/1025* (2013.01); *A61M 2210/1078* (2013.01); *A61M 2210/1085* (2013.01); *A61M 2240/00* (2013.01); *A61N 2005/1094* (2013.01)

(56) References Cited

U.S. PATENT DOCUMENTS

| | | | | |
|---|---|---|---|---|
| 5,458,615 A * | 10/1995 | Klemm | ............... | A61F 2/958 606/198 |
| 5,509,888 A * | 4/1996 | Miller | ............... | A61F 2/0036 600/29 |
| 5,534,007 A * | 7/1996 | St. Germain | ............ | A61F 2/95 606/191 |
| 5,772,669 A * | 6/1998 | Vrba | ............... | A61F 2/95 606/195 |
| 5,792,144 A * | 8/1998 | Fischell | ............... | A61F 2/958 606/108 |
| 5,795,331 A * | 8/1998 | Cragg | ............ | A61B 17/12022 604/103.01 |
| 5,797,952 A * | 8/1998 | Klein | ............... | A61F 2/88 606/198 |
| 5,891,154 A * | 4/1999 | Loeffler | ............... | A61F 2/958 623/1.11 |
| 5,910,145 A * | 6/1999 | Fischell | ............... | A61F 2/958 606/108 |
| 5,947,977 A * | 9/1999 | Slepian | ............... | A61L 24/0042 606/108 |
| 5,951,585 A * | 9/1999 | Cathcart | ............... | A61F 2/01 606/198 |
| 5,964,223 A * | 10/1999 | Baran | ............ | A61M 16/0463 128/207.14 |
| 5,980,533 A * | 11/1999 | Holman | ............... | A61F 2/95 606/191 |
| 6,190,353 B1 * | 2/2001 | Makower | ............ | A61B 1/3137 604/95.01 |
| 6,200,325 B1 * | 3/2001 | Durcan | ............... | A61F 2/958 604/101.05 |
| 6,342,066 B1 * | 1/2002 | Toro | ............... | A61F 2/95 606/108 |
| 6,379,365 B1 * | 4/2002 | Diaz | ............... | A61F 2/958 606/108 |
| 6,380,457 B1 * | 4/2002 | Yurek | ............... | A61F 2/95 623/1.11 |
| 6,423,032 B2 * | 7/2002 | Parodi | ............ | A61B 17/12172 604/103.07 |
| 6,613,075 B1 * | 9/2003 | Healy | ............... | A61F 2/95 606/108 |
| 6,695,812 B2 * | 2/2004 | Estrada | ............ | A61M 25/09 604/103.09 |
| 6,743,243 B1 * | 6/2004 | Roy | ............ | A61B 17/11 606/153 |
| 6,755,855 B2 * | 6/2004 | Yurek | ............... | A61F 2/95 623/1.11 |
| 6,932,091 B2 * | 8/2005 | Frazier | ............... | A61F 2/86 128/898 |
| 7,641,668 B2 * | 1/2010 | Perry | ............ | A61M 5/14566 606/192 |
| 8,224,449 B2 * | 7/2012 | Carbunaru | ............ | A61N 1/372 607/36 |
| 8,518,062 B2 * | 8/2013 | Cole | ............ | A61B 17/11 606/153 |
| 9,192,706 B2 * | 11/2015 | Bulent | ............ | A61M 60/122 |
| 2001/0044631 A1 * | 11/2001 | Akin | ............ | A61F 2/064 606/153 |
| 2002/0032429 A1 * | 3/2002 | Hjertman | ............ | A61M 5/14566 604/500 |
| 2002/0072758 A1 * | 6/2002 | Reo | ............ | H01F 41/026 606/153 |
| 2003/0176786 A1 * | 9/2003 | Maschke | ............ | A61B 34/73 600/435 |
| 2004/0084049 A1 * | 5/2004 | Baran | ............ | A61M 16/0484 128/207.14 |
| 2005/0059931 A1 * | 3/2005 | Garrison | ............ | A61M 25/1011 604/101.04 |
| 2005/0288551 A1 * | 12/2005 | Callister | ............ | A61B 17/12177 600/115 |
| 2006/0276552 A1 * | 12/2006 | Barbut | ............ | A61M 11/06 514/743 |
| 2006/0282106 A1 * | 12/2006 | Cole | ............ | A61B 17/0643 606/153 |
| 2007/0038259 A1 * | 2/2007 | Kieval | ............ | A61N 1/36114 607/44 |
| 2008/0161865 A1 * | 7/2008 | Hagen | ............ | A61N 1/0556 607/2 |
| 2010/0076247 A1 * | 3/2010 | Zilbershlag | ............ | A61M 60/422 600/17 |
| 2010/0121438 A1 * | 5/2010 | Jarvik | ............ | A61M 60/871 623/3.13 |
| 2011/0213309 A1 * | 9/2011 | Young | ............ | A61M 1/3661 604/175 |
| 2011/0264116 A1 * | 10/2011 | Kocur | ............ | A61B 17/12 606/139 |
| 2015/0190561 A1 * | 7/2015 | Bulent | ............ | A61M 60/419 600/17 |
| 2016/0000985 A1 * | 1/2016 | Consigny | ............ | A61M 1/3655 604/6.09 |
| 2016/0199065 A1 * | 7/2016 | Consigny | ............ | A61B 17/12009 606/153 |

* cited by examiner

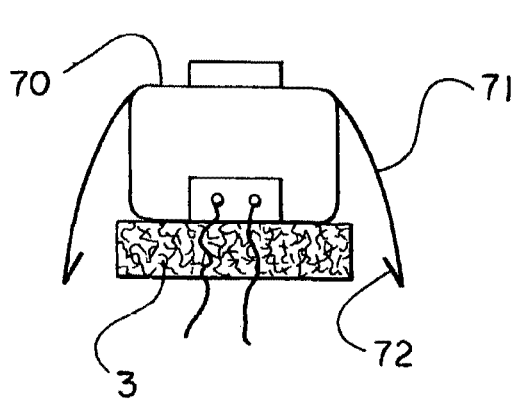
Fig.8
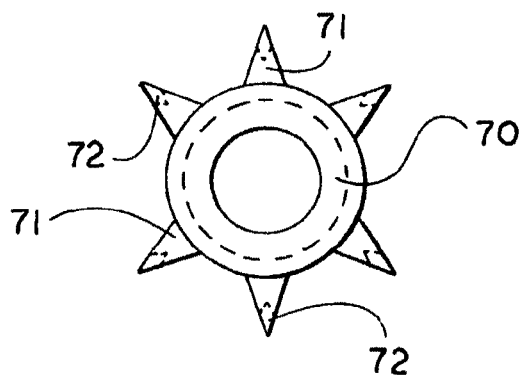
Fig.9
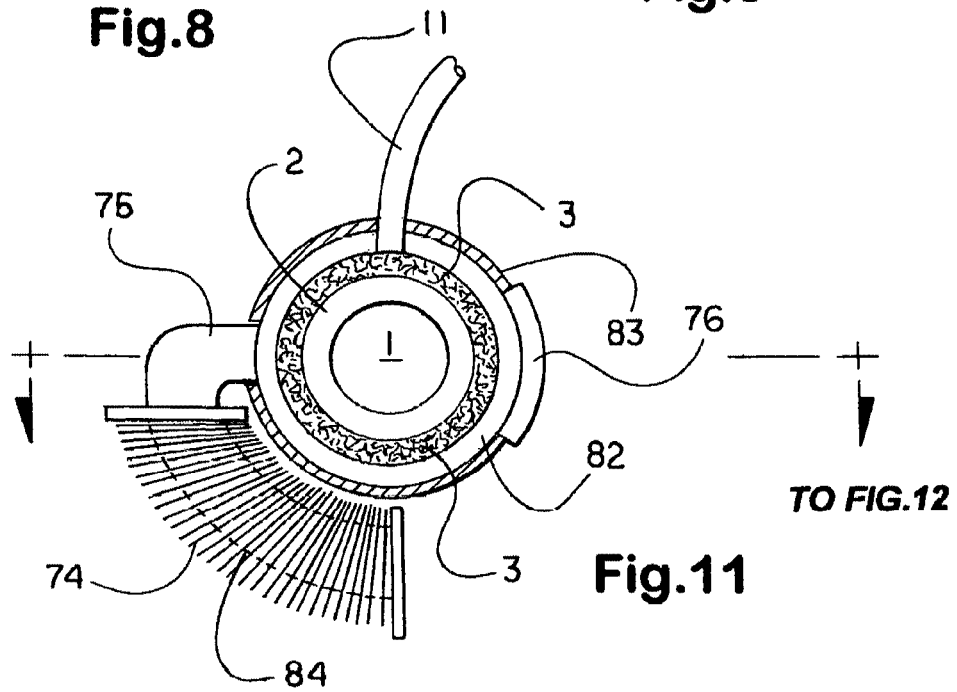
Fig.11
TO FIG.12
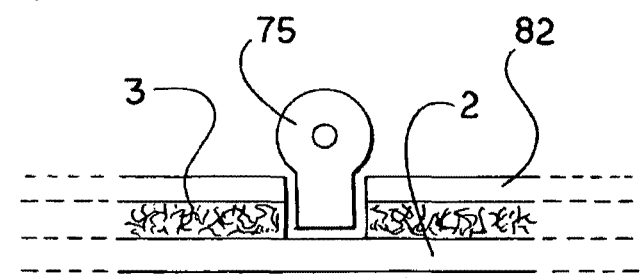
Fig. 12
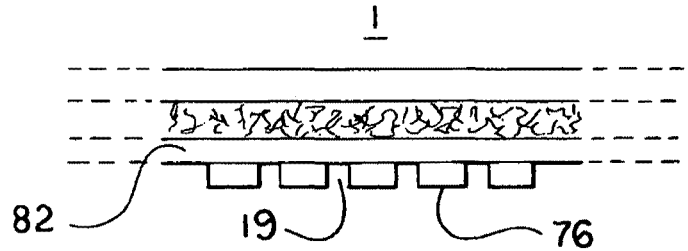

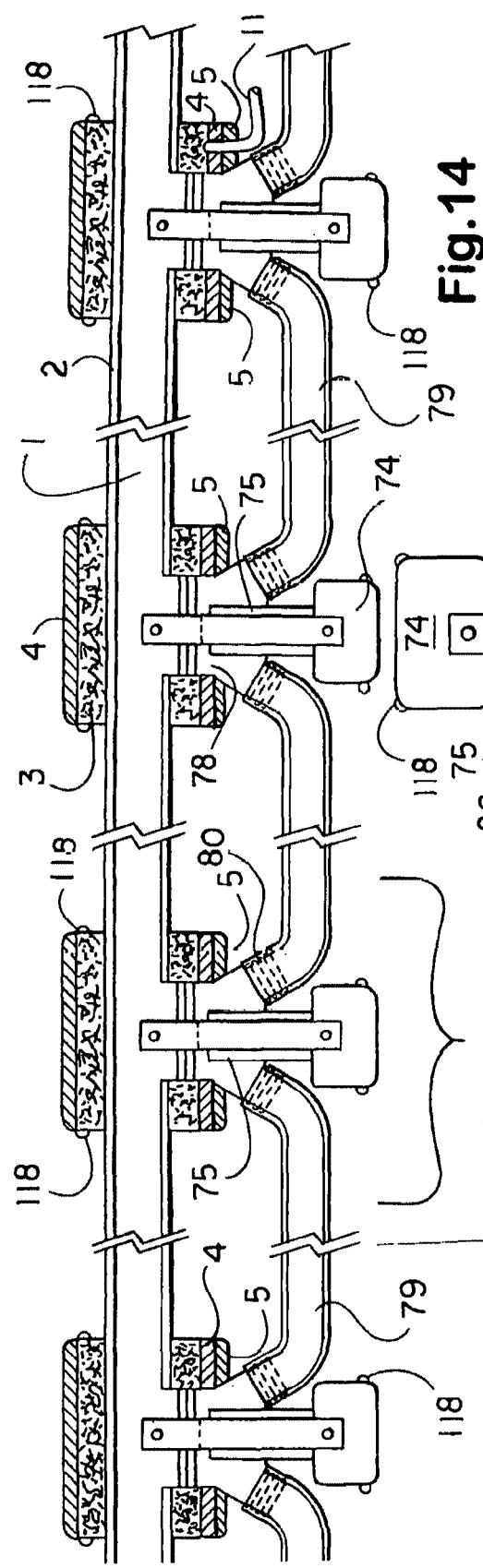
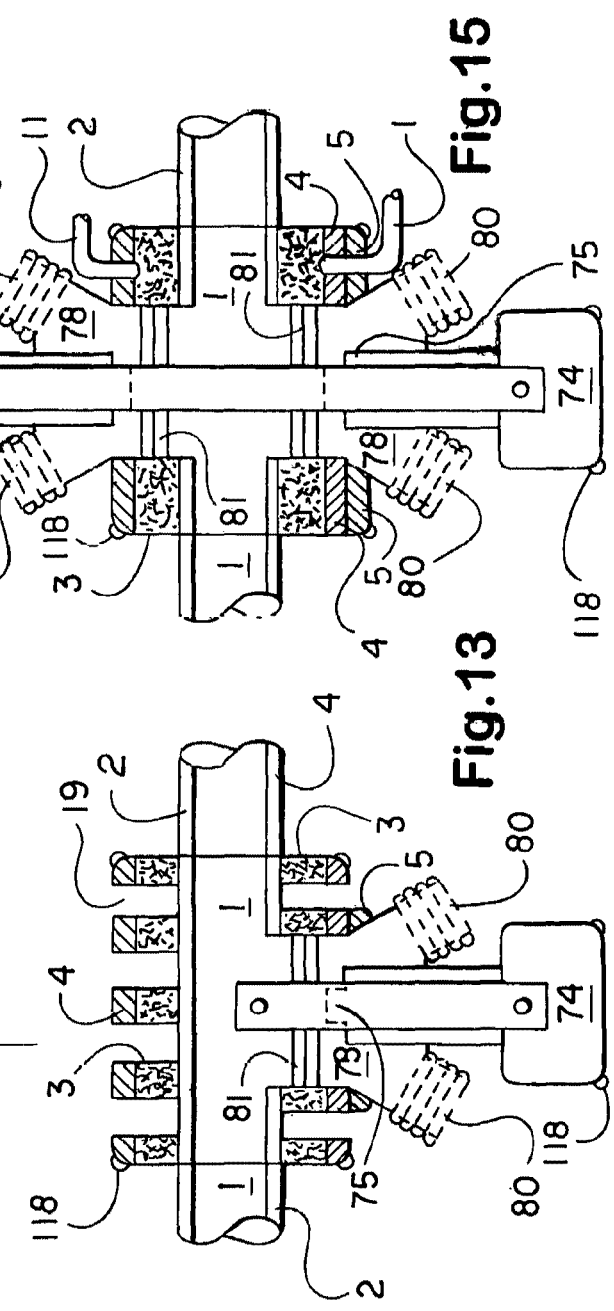

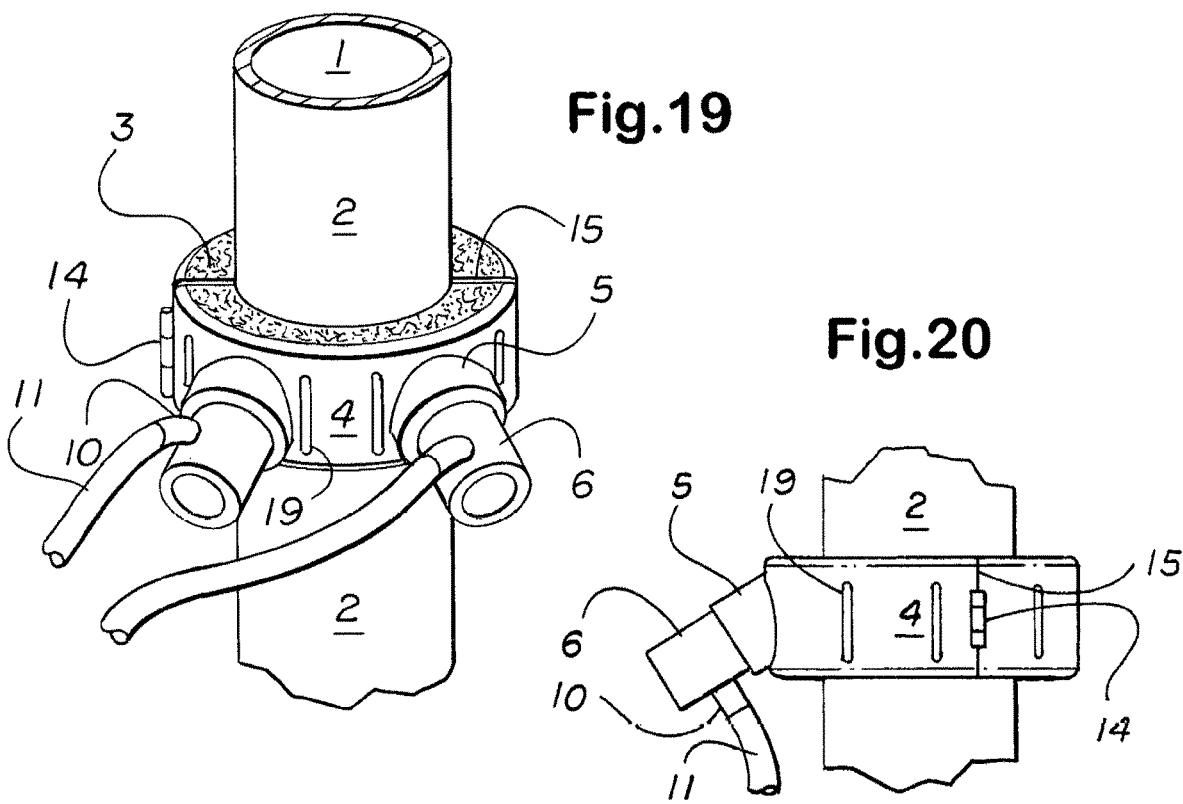
Fig.19
Fig.20
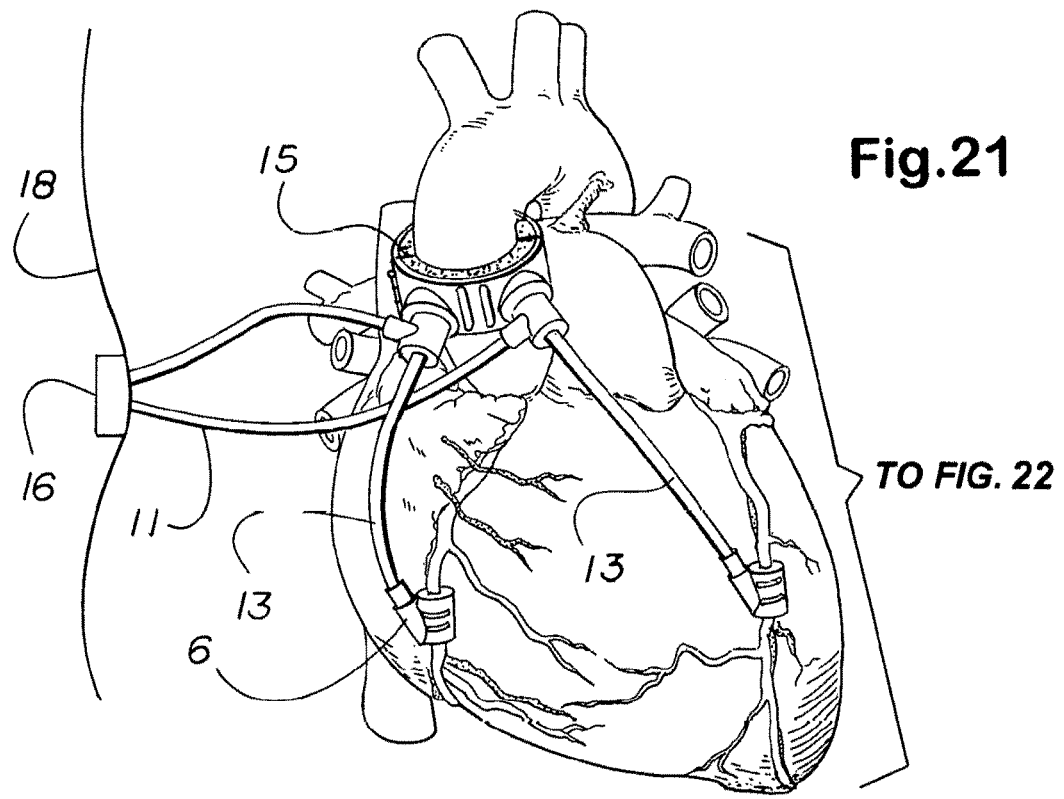
Fig.21
TO FIG. 22

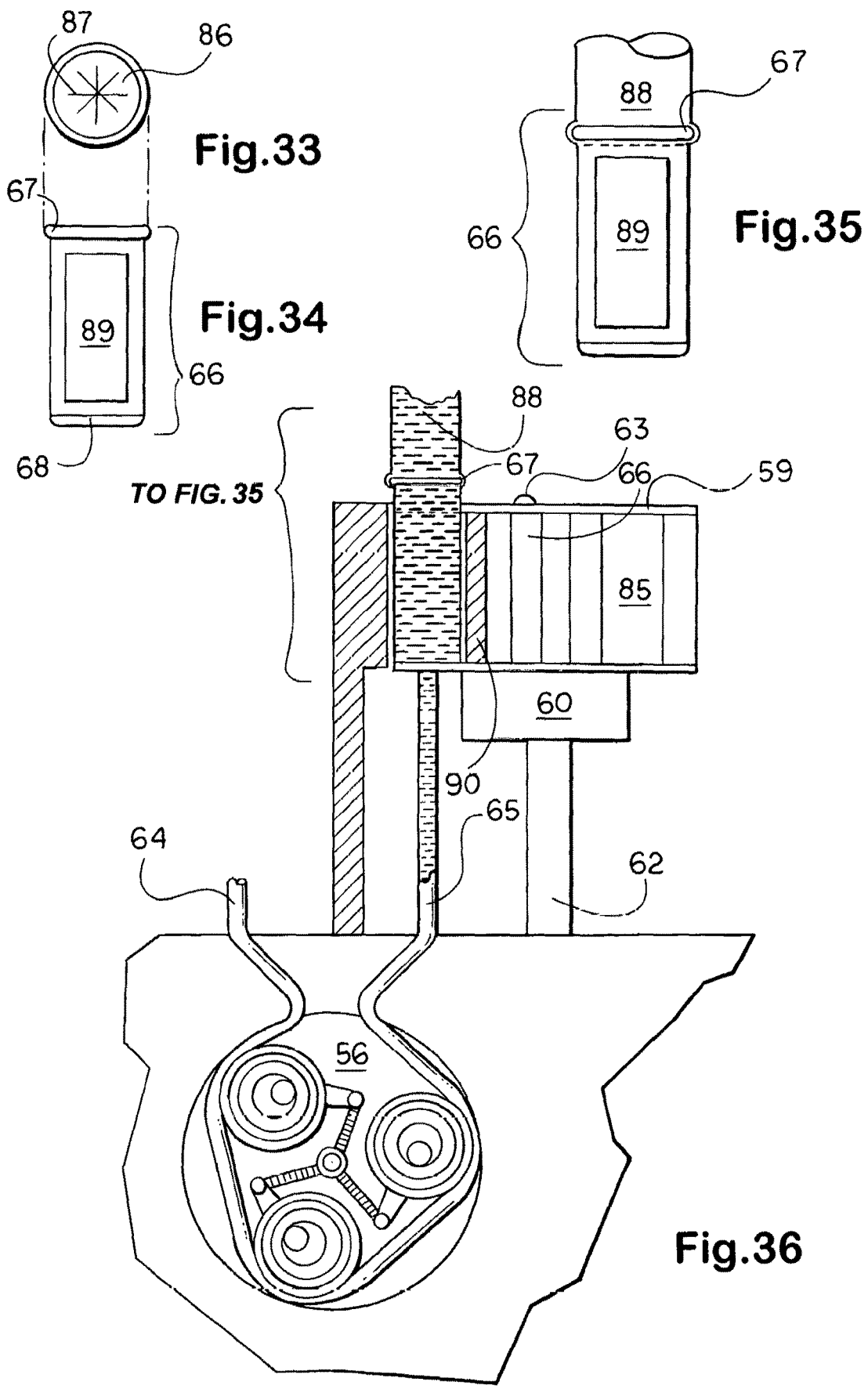

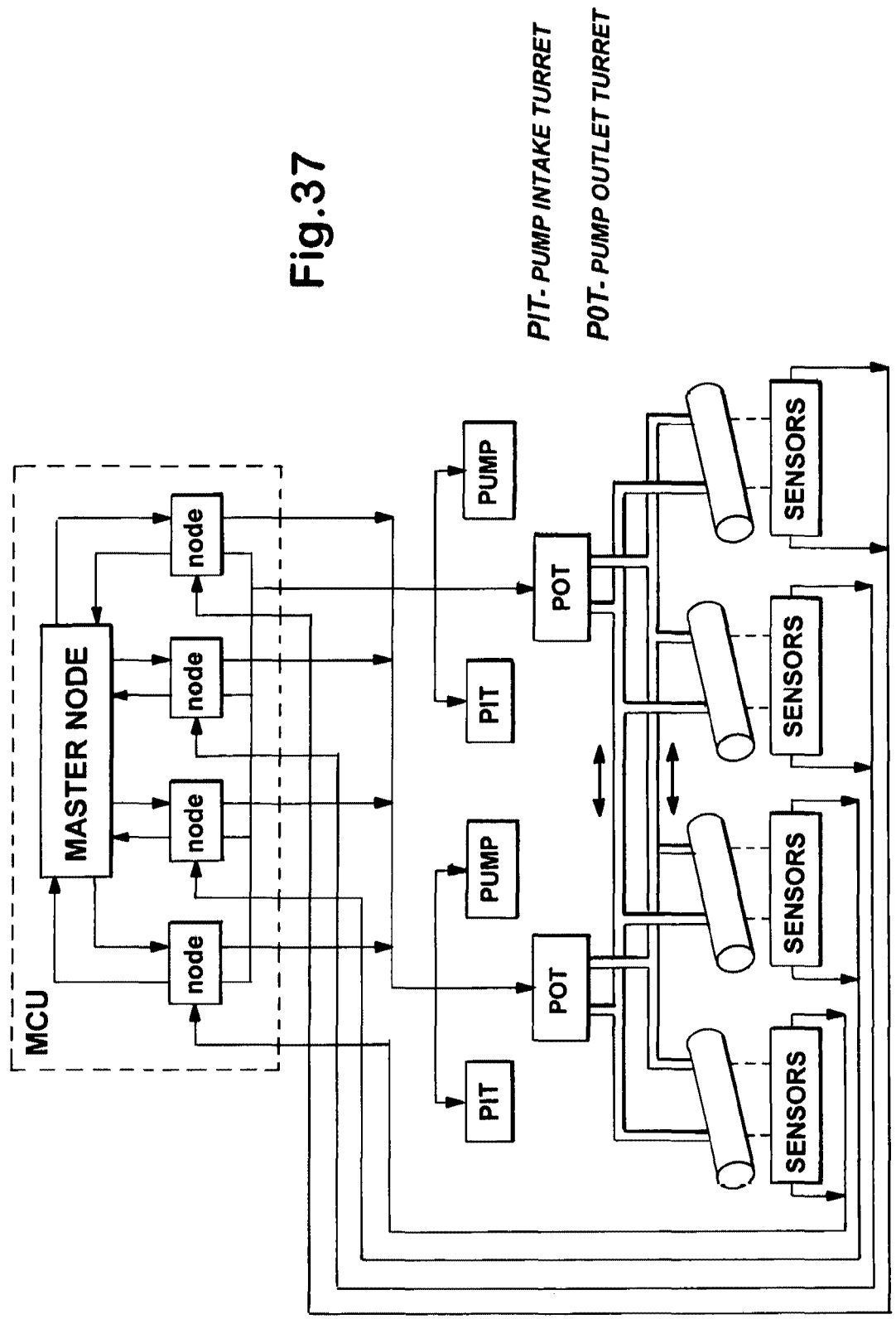

US 11,759,186 B2

DUCTUS SIDE-ENTRY AND PROSTHETIC DISORDER RESPONSE SYSTEMS

CROSS REFERENCE TO RELATED APPLICATIONS

This continuation-in-part application follows and claims the benefit of provisional application 61/959,560, filed on 27 Aug. 13 under 35 U.S.C. 119(e) and parent application, Ser. No. 14/121,365, filed on 25 Aug. 2014 under 35 U.S.C. 119(e), published as 2016/0051806, herewith superseded and abandoned. This application shows how ductus side-entry jackets can be used independently, in coordination, or unitized with periductally positioned magnetic collars, as described in copending continuation-in-part application parent Ser. No. 13/694,835, published as US 20140163664, entitled Integrated System for the Infixion and Retrieval of Implants with or without Drug Targeting, since retitled Integrated System for the Infixion and Retrieval of Implants, filed on 9 Jan. 13 and in Nonjacketing Side-entry Connectors and Prosthetic Disorder Response Systems, as described in copending application Ser. No. 14/998,495, published as 20170197028.

FEDERALLY SPONSORED RESEARCH OR DEVELOPMENT

None.

PARTIES TO A JOINT RESEARCH AGREEMENT

None.

SEQUENCE LISTING

Not applicable.

SUMMARY TABLE OF CONTENTS

1. Background of the Invention
a. General—
b. Apheresis and hemodialysis, stationary with or without an attendant, or carryable, or implanted magnetic
c. Intravascular valves and servovalves
d. Body surface ports, cutaneous, subcutaneous, and both
2. Summary of the Invention
3. Objects of the Invention
4. Description of the Drawings
5. Description of the Preferred Embodiments of the Invention

BACKGROUND OF THE INVENTION a. General

The methods and apparatus to be described are intended for use by general, vascular, cardiovascular, thoracic, gastroenterological, endourological, urological, neurological, endocrine, pediatric, and veterinary surgeons, interventional cardiologists, interventional radiologists, and nephrologists to allow the directly targeted delivery of drugs, other therapeutic substances, and/or thermal, high intensity focused ultrasound, electrosurgery, radiosurgery, laser, or electrostimulation therapy, and/or to provide drainage, or obtain diagnostic testing samples from or in relation to tubular anatomical structures, to include blood vessels, the urogenital and digestive tracts, and endocrine ducts, all tubular anatomical structures, referred to as ductus (pronounced "ductoos," not 'ducti,' when plural).

This nonprovisional application addresses the addition to periductal, or perivascular, jackets as described in copending continuation-in-part application Ser. No. 13/694,835, of a lumen side-entry hollow access stem to allow connection to such a periductal jacket of fluid delivery and electrical lines. Most of the procedures described herein can be performed laparoscopically or robotically as results in relatively few adhesions and scar tissue. In relatively simple use, such jackets fundamentally improve permanent or long-term ambulatory connection to the ductus of central venous catheters, total parenteral nutrition lines, and indwelling catheters, and afford superior vascular access for hemodialysis and apheresis.

In the past, indwelling catheters for use in ambulatory patients who, unlike the intracorporeal means described herein must still report for the use of extracorporeal equipment, have been considered acceptable for no longer than 8 months, and that with an unacceptable incidence of infecton (see, for example, Parekh, V. B., Niyyar, V. D., and Vachharajani, T. J. 2016. "Lower Extremity Permanent Dialysis Vascular Access," *Clinical Journal of the American Society of Nephrology* 11(9):1693-1702; Rehman, R., Schmidt, R. J., and Moss, A. H. 2009. "Ethical and Legal Obligation to Avoid Long-term Tunneled Catheter Access," *Clinical Journal of the American Society of Nephrology* 4(2):456-460; Budruddin, M., Mohsin, N., Amitabh, J., Ehab, M., Pramod, K., and 3 others 2009. "Femoral Vein Tunneled Catheters as a Last Resort to Vascular Access: Report of Five Cases and Review of Literature," *Renal Failure* 31(4):320-322; Al-Hwiesh, A. K. and Abdul-Rahaman, I. S. 2007. "Tunneled Femoral Vein Catheterization for Long Term Hemodialysis: A Single Center Experience,"*Saudi Journal of Kidney Diseases and Transplantation* 18(1):37-42; Weitzel, W. F., Boyer, C. J. Jr., el-Khatib, M. T., and Swartz, R. D. 1993. "Successful Use of Indwelling Cuffed Femoral Vein Catheters in Ambulatory Hemodialysis Patients," *American Journal of Kidney Diseases* 22(3):426-429).

In more advanced applications, such side-entry jackets and connectors allow the reliable automatic targeted release of drugs over an indeterminate period. If necessary, shielded components allow the use of radioisotopes. Also rendered directly targetable to one or a number of treatment sites are other forms of therapy such as thermal, and if pertinent, the diversion of bloodflow into bypasses and shunts for example, under the control of a sensor-driven microprocessor in accordance with a prescription-program. Such a system is not intended for short-term use. As will be described, implanted chained magnetized jackets can apply magnetic separation methods to accomplish apheresis and dialysis where the extractants are drawn into a flush-line for delivery into the urinary bladder for expulsion in the urine.

Magnetic separation plasmapheresis, cytapheresis, and hemodialysis are not for blood bank use but rather the direct intracorporeal treatment of the patient, the extractant, that is, the substance, substances, or cells removed directly from the blood discarded. Such means depend upon the ability to bond the target cells, analyte, or analytes to be extracted to magnetically susceptible micro- or nanoparticulate carriers, introduced into the bloodstream as a ferrofluid through a small body surface port placed subcutaneously, or subdermally, in the pectoral region. The port can be a portacath or mediport, but the distal end is a ductus side-entry jacket, not an indwelling catheter, which is unsuitable for permanent use. When the patient has multiple medical problems, other drug delivery lines and accessory channels go from a body surface port of the type to be described to the side-entry jackets and connectors respective of each axis of morbidity—generally, an organ, organ system, neurohormonal axis, or anatomical region.

Water passes through the semipermeable membranes separating the venous blood and dialysate in each magnet housing without a magnetic factor. The accessory channel or channels, or sidelines, to each jacket can be used to ameliorate any adverse reaction to placement of the jacket to include stenosis and inflammation, for example. Medication can often be delivered through the mainline, reserving one or more sidelines for another use. An accessory channel or sideline with passageway that is curved rather than through a narrow and sharp turn leading into the jacket can be used to pass a fine fiberscope or other cabled device into the jacket and substrate native lumen.

Where the removal of excess water is required, the membrane is not simple but compound, comprising many tiny semipermeable fibers as in an extracorporeal dialyzer for use in a clinic where an average treatment lasts hours several times a week, the experience odious as to promote the searching for alternative treatment that would replace the process (see, for example, Bahall, M. 2017. "Use of Complementary and Alternative Medicine by Patients with End-stage Renal Disease on Haemodialysis in Trinidad: A Descriptive Study," *BioMed Central Complementary and Alternative Medicine* 17(1):250; Thorsteinsdottir, B., Swetz, K. M., Feely, M. A., Mueller, P. S., and Williams, A. W. 2012. "Are There Alternatives to Hemodialysis for the Elderly Patient with End-stage Renal Failure?," *Mayo Clin Proceedings* 87(6):514-516). In this circumstance, a means for reducing if not eliminating a large investment of time in a repellent and inconvenient activity in the form of an intracorporeal means of hemodialysis would much improve the quality of life for these patients.

Both leukemics and patients with kidney failure remain ambulatory for a relatively long time during which an intracorporeal means of hemodialysis or cytaperesis would significantly reduce the number and duration of visits to the clinic, improving their quality of life (see, for example, Lowe, J. R., Yu, Y., Wolf, S., Samsa, G., and LeBlanc, T. W. 2018. "A Cohort Study of Patient-reported Outcomes and Healthcare Utilization in Acute Myeloid Leukemia Patients Receiving Active Cancer Therapy in the Last Six Months of Life," *Journal of Palliative Medicine* 21(5):592-597; Hochman, M. J., Yu, Y., Wolf, S. P., Samsa, G. P., Kamal, A. H., and LeBlanc, T. W. 2018. "Comparing the Palliative Care Needs of Patients with Hematologic and Solid Malignancies," *Journal of Pain and Symptom Management* 55(1):82-88.e1; Makroo, R. N., Kakkar, B., Chowdhry, M., Agrawal, S., Seth, S., and Thakur, U. K. 2017. "Therapeutic Leukapheresis in a Tertiary Care Hospital: A Case Series," *Asian Journal of Transfusion Science* 11(1):65-68; Forth, L. G1., Darmon, M., Ostermann, M., Oudemans-van Straaten, H. M., Pettilä, V., and 3 others 2017. "Renal Recovery after Acute Kidney Injury," *Intensive Care Medicine* 43(6): 855-866; Hickson, L. J., Chaudhary, S., Williams, A. W., Dillon, J. J., Norby, S. M., and 5 others 2015. "Predictors of Outpatient Kidney Function Recovery among Patients who Initiate Hemodialysis in the Hospital," *American Journal of Kidney Diseases* 65(4):592-602; Doyle, J. F. and Forth, L. G. 2015. "Long-term Follow-up of Acute Kidney Injury," *Critical Care Clinics* 31(4):763-772; Rimes-Stigare, C., Frumento, P., Bottai, M., Mårtensson, J., Martling, C. R., and 3 others 2015. "Evolution of Chronic Renal Impairment and Long-term Mortality after de Novo Acute Kidney Injury in the Critically Ill; a Swedish Multi-centre Cohort Study," *Critical Care* (London, England) 19:221; Smith, B. D., Beach, C. L., Mahmoud, D., Weber, L., and Henk, H. J. 2014. "Survival and Hospitalization among Patients with Acute Myeloid Leukemia Treated with Azacitidine or Decitabine in a Large Managed Care Population: A Real-world, Retrospective, Claims-based, Comparative Analysis," *Experimental Hematology and Oncology* 3(1):10; Zimmermann, C., Yuen, D., Mischitelle, A., Minden, M. D., Brandwein, J. M., and 5 others 2013. "Symptom Burden and Supportive Care in Patients with Acute Leukemia," *Leukemia Research* 37(7):731-736; Purnell, T. S., Auguste, P., Crews D. C., Lamprea-Montealegre, J., Olufade, T., and 8 others 2013. "Comparison of Life Participation Activities among Adults Treated by Hemodialysis, Peritoneal Dialysis, and Kidney Transplantation: A Systematic Review," *American Journal of Kidney Diseases* 62(5):953-973; Mohan, S., Huff, E., Wish, J., Lilly, M., Chen, S. C., and McClellan, W. M. 2013. "Recovery of Renal Function among ESRD [end-stage renal disease] Patients in the US Medicare Program," *Public Library of Science One* 8(12):e83447; Murugan, R. and Kellum, J. A. 2011. "Acute Kidney Injury: What's the Prognosis?," *National Reviews. Nephrology* 7(4):209-217).

The procedure in conventional dialysis is suspected to be a significant factor in the triggering of an arrhythmia resulting in sudden cardiac death (see, for example, Roy-Chaudhury, P., Tumlin, J. A., Koplan, B. A., Costea, A. I., Kher, V., and 3 others 2018. "Primary Outcomes of the Monitoring in Dialysis Study Indicate that Clinically Significant Arrhythmias are Common in Hemodialysis Patients and Related to Dialytic Cycle," *Kidney International* 93(4): 941-951; Makar, M. S. and Pun, P. H. 2017. "Sudden Cardiac Death among Hemodialysis Patients," *American Journal of Kidney Disease* 69(5):684-695; Roberts, P. R., Zachariah, D., Morgan, J. M., Yue, A. M., Greenwood, E. F., and 5 others 2017. "Monitoring of Arrhythmia and Sudden Death in a Hemodialysis Population: The CRASH-ILR [Cardio Renal Arrhythmia Study in Hemodialysis-Implantable Loop Recorder] Study," *Public Library of Science One* 12(12):e0188713; El Hage, N., Jaar, B. G., Cheng, A., Knight, C., Blasco-Colmenares, E., and 3 others 2017. "Frequency of Arrhythmia Symptoms and Acceptability of Implantable Cardiac Monitors in Hemodialysis Patients," *BioMed Central Nephrology* 18(1):309; Charytan, D. M., Foley, R., McCullough, P. A., Rogers, J. D., Zimetbaum, P., Herzog, C. A., and Tumlin, J. A. 2016. "Arrhythmia and Sudden Death in Hemodialysis Patients: Protocol and Baseline Characteristics of the Monitoring in Dialysis Study," *Clinical Journal of the American Society of Nephrology* 11(4):721-734).

Intracorporeal magnetic separation dialysis is nonepisodic, that is, performed on a continual basis, not in a clinic as a distinct procedure, so that intradialytic and interdialytic intervals are scarcely if at all noticed. Moreover, magnetically reinforced extraction allows a much lower volume ratio of dialysate to serum, attenuating rapid electrolyte shifts due to the gradient between serum and dialysate levels to which sudden death is attributed (see, for example, Karaboyas, A., Zee, J., Brunelli, S. M., Usvyat, L. A., Weiner, D. E., and 8 others 2017. "Dialysate Potassium, Serum Potassium, Mortality, and Arrhythmia Events in Hemodialysis: Results from the Dialysis Outcomes and Practice Patterns Study (DOPPS)," *American Journal of Kidney Diseases* 69(2):266-277; Pun, P. H. and Middleton, J. P. 2017. "Dialysate Potassium, Dialysate Magnesium, and Hemodialysis Risk," *Journal of the American Society of Nephrology* 28(12):3441-3451; Brunelli, S. M., Spiegel, D. M., Du Mond, C., Oestreicher, N., Winkelmayer, W. C., and Kovesdy, C. P. 2017. "Serum-to-dialysate Potassium Gradient and Its Association with Short-term Outcomes in Hemodialysis Patients," *Nephrology, Dialysis, Transplantion* August 19; Brunelli, S. M., Du Mond, C., Oestreicher, N., Rakov, V., and Spiegel, D. M. 2017. "Serum Potassium and Short-term Clinical Outcomes among Hemodialysis Patients: Impact of the Long Interdialytic Interval," *American Journal of Kidney Diseases* 70(1):21-29; Yusuf, A. A., Hu, Y., Singh, B., Menoyo, J. A., and Wetmore, J. B. 2016. "Serum Potassium Levels and Mortality in Hemodialysis Patients: A Retrospective Cohort Study," *American Journal of Nephrology* 44(3):179-186; Thornley-Brown, D. and Saha, M. 2015. "Dialysate Content and Risk of Sudden Cardiac Death," *Current Opinion in Nephrology and Hypertension* 24(6):557-562).

All drugs pose adverse side effects which can be nearly or completely eliminated when the drug or drugs are directly targeted to the organ or tissue requiring treatment without coming into contact with unintended tissue and without requiring the misdirection of the greater part of the dose which goes to the unintended tissue. Administration by self-injection through a clearly identified opening in a subdermal port directly targets otherwise potentially harmful if not dangerous drugs such as anticoagulants with negligible if any risk. In some instances, patients prevented from using effective oral medication due to adverse side effects can use intracorporeal hemodialysis as a less repellent alternative, and far less than conventional dialysis for hours several days a week in a clinic.

The space constraints simply given by nature severely limit the surface area of the permeable interface that can be used within the body—where the implanted system would be overwhelmed, the difference is entrusted to a conventional dialyzer; however, for certain uses, the implant system will prove adequate, and even when inadequate, the system is still of value by virtue of its continuity of operation, reducing the frequency and/or the duration of each treatment in the clinic. Replacing some of the time undergoing conventional apheresis or dialysis also avoids the complications associated with such treatment for that time.

The intracorporeal system is placed endoscopically and not involving any use of replacement fluid, requires only small openings into the substrate vein, depicted here as the inferior vena cava. Magnetic separation plasmapheresis does not involve the use of replacement fluid and therefore avoids the risks of provoking anaphylactoid or urticarial reactions. Albumin as a replacement fluid can cause depletion coagulopathy and immunoglobulin depletion which become progressively worse with each treatment (Kaplan, A. 2012. "Complications of Apheresis," *Seminars in Dialysis* 25(2): 152-158).

Not extracorporeal, magnetic separation apheresis and dialysis avoid the complications associated with large volume exchange: "As with all extracorporeal treatments requiring large bore vascular access, catheter-related trauma, clotting, infection, and bleeding may also occur." (Kaplan, A. 2012, Op cit.) (see also, for example, Vadakedath, S. and Kandi, V. 2017. "Dialysis: A Review of the Mechanisms Underlying Complications in the Management of Chronic Renal Failure," *Cureus* 9(8):e1603; Sirico, M. L., De Blasio, A., De Simone, E., Di Micco, L., Nardone, L., and Di Iorio, B. 2017. "Sudden Cardiac Death in Patient with CKD [chronic kidney disease]," (in Italian with English abstract at Pubmed), *Giornale Italiano di Nefrologia* 34(Suppl 69):49-58; Mavrakanas, T. A. and Charytan, D. M. 2016. "Cardiovascular Complications in Chronic Dialysis Patients," *Current Opinion in Nephrology and Hypertension* 25(6):536-544; Cavanaugh, P. K., Chen, A. F., Rasouli, M. R., Post, Z. D., Orozco, F. R., and Ong, A. C. 2016. "Complications and Mortality in Chronic Renal Failure Patients Undergoing Total Joint Arthroplasty: A Comparison between Dialysis and Renal Transplant Patients," *Journal of Arthroplasty* 31(2):465-472; Kara, A., Turgut, S., Cağli, A., Sahin, F., Oran, E., and Tunç, B. 2013. "Complications of Therapeutic Apheresis in Children," *Transfusion and Apheresis Science* 48(3):375-376; Philip, J., Sarkar, R. S., and Pathak, A. 2013. "Adverse Events Associated with Apheresis Procedures: Incidence and Relative Frequency," *Asian Journal of Transfusion Science* 7(1):37-41; Mokrzycki, M. H. and Balogun, R. A. 2011. "Therapeutic Apheresis: A Review of Complications and Recommendations for Prevention and Management," *Journal of Clinical Apheresis* 26(5):243-248; Michon, B., Moghrabi, A., Winikoff, R., Barrette, S., Bernstein, M. L., and 7 others 2007. "Complications of Apheresis in Children," *Transfusion* 47(10):1837-1842; Himmelfarb, J. 2005. "Hemodialysis Complications," *American Journal of Kidney Diseases* 45(6):1122-1131).

Neither does intracorporeal magnetic separation involve a donor, much less place the donor at risk (see, for example, Heuft, H. G., Fischer, E., Weingand; T., Burkhardt, T., Leitner, G., and 6 others 2017. "Donor Safety in Haemapheresis: Development of an Internet-based Registry for Comprehensive Assessment of Adverse Events from Healthy Donors," *Transfusion Medicine and Hemotherapy* 44(3):188-200; Keshelashvili, K., O'meara, A., Stern, M., Jirout, Z., Pehlic, V., and 4 others 2016. "Adverse Events and Retention of Donors of Double Red Cell Units by Apheresis," *Blood Transfusion* 14(5):391-399; Seheult, J. N., Lund, M. E., Yazer, M. H., and Titlestad, K. 2016. "Factors Associated with Vasovagal Reactions in Apheresis Plasma and Whole Blood Donors: A Statistical-epidemiological Study in a European Donor Cohort," *Blood Research* 51(4):293-296; Yuan, S., Ziman, A., Smeltzer, B., Lu, Q., and Goldfinger, D. 2010. "Moderate and Severe Adverse Events Associated with Apheresis Donations: Incidences and Risk Factors," *Transfusion* 50(2):478-486; Crocco, I., Franchini, M., Garozzo, G., Gandini, A. R., Gandini, G., Bonomo, P., and Aprili, G. 2009. "Adverse Reactions in Blood and Apheresis Donors: Experience from Two Italian Transfusion Centres," *Blood Transfusion* 7(1):35-38; Winters, J. L. 2006. "Complications of Donor Apheresis," *Journal of Clinical Aphereis* 21(2):132-141).

That the circuit shown in FIG. 39A can be made to function continuously allows interstitial water to enter the bloodstream for removal. Depiction of the extraction chain-magnet as comprising four magnets is exemplary—the number depends upon the permeable surface area required and is limited by the size of the patient. With respect to the magnetic separation apheresis or dialysis circuit depicted in FIG. 39A, the ferrofluid and other agents would pass from the port directly into the inferior vena cava through the mainline or an accessory channel, or sideline, at a level above that of the circuit.

Direct pipe-targeting to a ductus, here a vein, is shown in FIG. 16 where mainline 13 and its accessory channel, that is, its supporting or adjuvant agent delivery line, or sideline 11 are connected by means of a ductus side-entry jacket to left anterior descending artery 2. Chemical bonding can be to the analyte or through an intermediary substance having an inherent chemical affinity for the analyte. Substances introduced into the inferior vena cava are removed from it before the blood continues to the heart. In FIG. 39A, the dialysate filled flush-line is pressurized by the peristaltic, or roller, pump and the venous blood by the elastic and compressive properties of the venous circulation (such as the 'calf pump') and the heart.

The patient has then, one small—usually about 12.7 millimeters, or a half inch in diameter—fully subcutaneous pectoral port for the occasional administration by injection of drugs and other therapeutic and drug circuit maintenance agents, or if frequent, then with at least one opening to the outside, and another above-skin, or cutaneous port, with openings, this port placed to a side of the mons pubis to give access to the magnetic separation circuit shown in FIG. 39A. To conserve energy by initiating and sustaining extraction only when the analyte has entered the blood stream or has reached a certain level, also essential is a chemical sensor to detect the analyte, the signal strength from it indicating the concentration.

The need to remove and replace the dialysate is signaled by a turbidimetry sensor. As seen in FIG. 39B, an electromagnet positioned beneath the urinary bladder is used to draw the extracted analyte or analytes into the urinary bladder. Because the dialysate is continuously cleaned while the circuit of FIG. 39A is in operation, the dialysate should not require to be changed for several days if not longer. The chemical or diagnostic sensor signals the implant microprocessor to actuate the dialysate pump seen toward the top of FIG. 39A, and the turbidimetry sensor turns on a tiny lamp on the body surface port used to replace the dialysate.

In a prosthetic disorder response system placed to optimize the overall health of a patient with multiple comorbidities, the urinary tract—or in the absence of a urinary tract, equivalent removal of toxins from the blood of nocuous substances—is represented as one of the channels of control in a hierarchical control system. To optimize magnetic separation, or extraction, the electromagnets are made as light in weight as enclosure within a thin but tough nonallergenic plastic case and windings of silver wire, which provide greater field strength for the weight, will allow. If necessary, the micro- or nanoparticle carrier particles bonded to the target analyte or analytes are formulated to incorporate silicon-iron crystal, materially increasing their magnetic susceptibility.

If necessary, the weight or tendency to rotate of magnets or chain magnets as shown in FIGS. 13 thru 15 and 39A is alleviated by passing suture through small loops, eyelets, or tiny embedded suture anchor eyelets, referred to as suture loops, part number 118 in the drawing figures, placed about the magnet enclosure (shell, casing). If needed, which seldom pertains to individual jackets unless incorporating a neodymium magnet or a heavier electromagnet, but pertains rather to chains of jackets incorporating an electromagnet as shown in FIGS. 10, 13 thru 15, and 39A, suture loops are provided Suture loops also assist in assisting to support a neoureteral confluence chamber, which when filled can weigh down on supportive tissue, as shown in FIGS. 40 and 43.

To minimize protrusion into neighboring tissue, numerous parts of side-entry ductus jackets such as the suture loops and the diversion chute with obturator in intravascular valves are made of a strong but soft and rubbery material not degradable or absorbable when implanted, such as PEBAX® (Arkema, Colombes, France) or VESTAMID E (Evonik Industries, Essen, Germany), polyether block amide, or if the patient is not allergic to it, hypoallergenic guayule or Vytex® (Vystar Corporation, Atlanta, Ga.) natural rubber latex (see, for example, Pinchuk, L., Riss, I., Batlle, J. F., Kato, Y. P., Martin, J. B., and 6 others 2017. "The Development of a Micro-shunt Made from Poly(sty-rene-block-isobutylene-block-styrene) to Treat Glaucoma," *Journal of Biomedical Materials Research. Part B, Applied Biomaterials* 105(1):211-221; Pinchuk, L., Riss, I., Batlle, J. F., Kato, Y. P., Martin, J. B., and 6 others 2016. "The Use of Poly(styrene-block-isobutylene-block-styrene) as a Microshunt to Treat Glaucoma," *Regenerative Biomaterials* 3(2): 137-142; Serrani, M., Brubert, J., Stasiak, J., De Gaetano, F., Zaffora, A., Costantino, M. L., Moggridge, G. D. 2016. "A Computational Tool for the Microstructure Optimization of a Polymeric Heart Valve Prosthesis," *Journal of Biomechical Engineering* 138(6):061001; Rudolph, A., Teske, M., Illner, S., Kiefel, V., Sternberg, K., and 3 others 2015. "Surface Modification of Biodegradable Polymers towards Better Biocompatibility and Lower Thrombogenicity," *Public Library of Science One* 10(12):e0142075; Murray, K. A., Kennedy, J. E., McEvoy, B., Vrain, O., Ryan, D., Cowman, R., and Higginbotham, C. L. 2014. "Effects of Temperature, Packaging and Electron Beam Irradiation Processing Conditions on the Property Behaviour of Poly (Ether-block-amide) Blends," *Materials Science and Engineering. Part C, Matererials for Biological Applications* 39:380-394; Bianco, A., Calderon, M., and Cacciotti, I. 2013. "Electrospun PHBV/PEO [poly (3-hydroxybutyrate-co-3-hydroxyvalerate) and Polyethylene Oxide] Co-solution Blends: Microstructure, Thermal and Mechanical Properties," *Materials Science and Engineering. Part C, Materials for Biological Applications* 33(3):1067-1077; Murray, K. A., Kennedy, J. E., McEvoy, B., Vrain, O., Ryan, D., Cowman, R., and Higginbotham, C. L. 2013. "Effects of Gamma Ray and Electron Beam Irradiation on the Mechanical, Thermal, Structural and Physicochemical Properties of Poly (Ether-block-amide) Thermoplastic Elastomers," *Journal of the Mechanical Behavior of Biomedical Materials* 17:252-268; Duraiswamy, N., Choksi, T. D., Pinchuk, L., and Schoepho-erster, R. T. 2009. "A Phospholipid-modified Polystyrene-polyisobutylene-polystyrene (SIBS) Triblock Polymer for Enhanced Hemocompatibility and Potential Use in Artificial Heart Valves," *Journal of Biomaterials Applications* 23(4): 367-379; Pinchuk, L., Wilson, G. J., Barry, J. J., Schoephoerster, R. T., Parel, J. M., and Kennedy, J. P. 2008. "Medical Applications of Poly(styrene-block-isobutylene-block-styrene) ("SIBS")," *Biomaterials* 29(4):448-460).

Where a component would weigh down on subjacent tissue; suture loops are provided at points about the component to tack the component at several points to neighboring and superjacent tissue to support and balance and thereby alleviate the downward force or a tendency to rotate. The same material can be used to make the diversion chute and obturator in intravascular valves and servovalves as addressed below in the sections entitled Intravascular Valves and Servovalves and Description of the Preferred Embodiments of the Invention. The operator should always consider recumbency as well as erectness is selecting the points at which the weight should be supported.

In all instances where aeration would protect enclosed adventitia or fibrosa and release any buildup in temperature that would cause discomfort, small perforations part number 19 in FIGS. 4, 6, 13, 17 thru 20, 22, 29, 31, and 32, and 83 in FIG. 10 are placed in the shell, or casing, and down through any intervening material to expose the surface of the substrate ductus. The suture is passed through suture loops or eyelets 118 connected to surrounding tissue as a number of points to distribute and balance the weight. Suture loops or eyelets 118 differ from screwed suture anchors in being molded or strongly bonded to the substrate component rather than provided with a screw for insertion in bone.

The points about neighboring tissue to which the suture is attached if irritated will subside as the attachment points become fibrosed. Additionally, where the motor action of the substrate part is disturbed immediately following placement—for example, accordion tube 95 and electromagnet 93 in FIG. 39B—this should subside as the substrate structure, here the urinary bladder, adapts to the presence of the connector. Disruption in motor function is mollified by the interposition of viscoelastic polyurethane foam between the substrate tissue or organ and connector which is highly compliant and accommodative to the subjacent movement.

For long-term but not lifelong use, those system components which need not be implanted—the microprocessor, power source, drug reservoirs and switching means—are relegated to a waist-worn body pack, only the biosensors, fluid lines, and jackets implanted, with wireless 'Bluetooth' sensor, subordinate microcontroller, and control microprocessor intercommunications used when necessary to avoid the risk of tissue strangulation or the formation of accretions or adhesions on electrical wires given much slack, which is critical in a neonate or infant, for example. For lifelong use, the system is implanted to the extent possible, with the addition of a body area network and biotelemetry advantageous on a case by case basis.

Valveless ductus side-entry jackets make possible the replacement of indwelling catheters for long-term if not lifelong vascular access in central, hemodialysis, and apheresis lines, with connectors which are positionally stable, highly resistant to infection, and leak-free as to allow active ambulatory use, as well as capable of considerable accommodation for growth. This ambulatory capability makes possible the miniaturization of blood processing machines so that these can be carried in a small body pack. Magnetic dialysis and apheresis, whereby the extract or extracts are drawn from the bloodstream into a dialysate or water flush-line which empties into the bladder, or if the patient has no bladder, then into an implanted collection chamber, allows extract expulsion in the urine, no extracorporeal body pack or collection bag then required.

For implantable embodiments, the body pack peristaltic pumping means and turret drug changing mechanisms shown in FIGS. 29 and 31 thru 36 are much reduced in size. As indicated, in instances of multiple comorbidities where the patient is expected to survive but not long enough to justify full implantation, those components which need not be implanted are relegated to an extracorporeal body pack. The addition of one or more sideline service, or accessory, channels to such jackets allows the permanent implantation of catheteric lines to directly pipe and so target drugs and line maintenance agents from a port, usually positioned subcutaneously in the pectoral region, through the line and jacket to the lesions or nidi treated, making possible the use of catheters as artificial vessels or urinary outlet tracts, for example.

While large diameter woven polyethylene terephthalate or polyester (Dacron®, Invista Division, Koch Industries, Wichita, Kan.) and polytetrafluoroethylene tubing have long been used for femorofemoral and similar bypass grafts, the formation and occlusion by clot, for example, is a prime reason that smaller gauge synthetic tubing could not be used to replace diseased or occluded vessels. The initiation in clot alleviating endothelialization of acellular tissue engineered vessels takes at least a month (see, for example, Koobatian, M. T., Row, S., Smith, R. J. Jr., Koenigsknecht, C., Andreadis, S. T., and Swartz, D. D. 2016. "Successful Endothelialization and Remodeling of a Cell-free Dmall-diameter Arterial Graft in a Large Animal Model," *Biomaterials* 76:344-358).

During this time, the administration of an anticoagulant such as systemic, or nontargeted, heparin to a patient urgently in need of vessel replacement is likely to experience any of a number of serious side effects, to include osteoporosis, tachycardia, tachypnea, dysphasia, tussis, impaired equilibrium, impaired vision, confusion, wheezing, chest pain, and severe cephalalgia, or headache (see, for example, Mourão, P. A. 2015. "Perspective on the Use of Sulfated Polysaccharides from Marine Organisms as a Source of New Antithrombotic Drugs," *Marine Drugs* 13(5):2770-2784; Alban, S. 2012. "Adverse Effects of Heparin," *Handbook of Experimental Pharmacology* (207):211-263; Nelson-Piercy, C. 1997. "Hazards of Heparin: Allergy, Heparin-induced Thrombocytopenia, and Osteoporosis," *Bailliere's Clinical Obstetrics and Gynaecology* 11(3):489-509).

Similarly dispersed throughout the circulatory system, warfarin risks adverse side effects, to include osteoporosis, problem bleeding, adverse drug-drug and drug-food interactions, warfarin necrosis, cholesterol embolism with consequent gangrene and/or renal failure (see, for example, Patel, S. and Patel, N. 2018. "Warfarin," *StatPearls* at https://www.ncbi.nlm.nih.gov/books/NBK470313/; Joppa, S. A., Salciccioli, J., Adamski, J., Patel, S., Wysokinski, W., and 4 others 2018. "A Practical Review of the Emerging Direct Anticoagulants, Laboratory Monitoring, and Reversal Agents," *Journal of Clinial Medicine* 7(2); Igarashi, Y., Akimoto, T., Kobayashi, T., Iwazu, Y., Miki, T., and 7 others 2017. "Performing Anticoagulation: A Puzzling Case of Cholesterol Embolization Syndrome," *Clinical Medicine Insights. Case Reports* 10:1179547616684649; Nutescu, E., Chuatrisorn, I., and Hellenbart, E. 2011. "Drug and Dietary Interactions of Warfarin and Novel Oral Anticoagulants: An Update," *Journal of Thrombosis and Thrombolysis* 31(3):326-343; Piazza, G., Nguyen, T. N., Cios, D., Labreche, M., Hohlfelder, B., and 3 others 2011. "Anticoagulation-associated Adverse Drug Events," *American Journal of Medicine* 124(12):1136-1142).

While reversal agents are under development, newer factor Xa inhibitor oral anticoagulants and platelet blockers are by definition of systemic dispersion, and are likewise not free of adverse side effects (see, for example, Joppa, S. A., Salciccioli, J., 2018, Op cit.; Christopoulou, E. C., Filippatos, T. D., and Elisaf, M. S. 2017. "Non-hemorrhage-related Adverse Effects of Rivaroxaban," *Archives of Medical Sciences. Atherosclerotic Diseases* 2:e108-e112; Cunha, J. P. 2018. "Eliquis Side Effects Center," at https://www.rxlist.com/eliquis-side-effects-drug-center.htm; Mont, L., Marin, F., Dalmau, F. G., Martinez, M. S., and Cullere, J. G. 2015. "Clinical Development of Rivaroxaban: Emerging New Clinical Evidences?," "Clinical Development of Rivaroxaban: Emerging New Clinical Evidences?," *Future Cardiology* 11(5): 565-583; Snellgrove, O. 2017. "Case Report: Apixaban-induced Thrombocytopenia," *Clinical Case Reports* 5(3):268-269; Motta, R. H. L., Bergamaschi, C. C., de Andrade, N. K., Guimaraes, C. C., Ramacciato, J. C., Araújo, J. O., and Lopes, L. C. 2017. "Bleeding Risk in Patients Using Oral Anticoagulants Submitted to Surgical Procedures in Dentistry: A Systematic Review Protocol," *British Medical Journal Open* 7(12):e019161; Seecheran, R., Seecheran, V., Persad, S., Lalla, S., and Seecheran, N. A. 2017. "Ticagrelor-induced Angioedema: A Rare and Unexpected Phenomenon," *Case Reports in Cardiology* 2017:7612713; Harter, K., Levine, M., and Henderson, S. O. 2015. "Anticoagulation Drug Therapy: A Review," *Western*

*Journal of Emergency Medicine* 16(1):11-17; Hofmeier, K. S. 2015. "Hypersensitivity Reactions to Modern Antiplatelet and Anticoagulant Drugs," *Allergo Journal International* 24(2):58-66).

That the passageway from port to nidus is also treated with antimicrobials, anti-inflammatories, and anticoagulants exclusively of any other tissue, materially reduces if not eliminates concerns for thrombus, biofilm, or agent crystallization or congealing which had always prohibited the use of small caliber tubing for such purposes as moving blood or urine. Ductus side-entry jackets and nonjacketing side-entry connectors readily incorporate biosensors and therapeutic devices styloid in form as well as accommodate small cabled devices. The incorporation of a valve into such a jacket—which positions it within the lumen where it can completely close off, partially adjust, or divert the flow therethrough—makes possible, for example, the diversion of urine by ureteral takeoff leading to a small outlet port positioned subcutaneously, or subdermally, as shown in FIG. 39B, to a side of the mons pubis where the patient can see and manipulate its use with ease.

Such means can be permanent as an unadjustable prosthesis delivering the urine into a collection bag, or for a patient with intractable nocturia, or nocturnal enuresis, or one having to appear before an audience for an uninterrupted period of hours, can made manually controllable, that is, can be switched between normal voiding during the daytime and nonmicturative (nonarousing) voiding during sleep. More significantly, urinary elimination by the means described is less susceptible to infection or irritation of the skin about the outlet, and requires less attention. In replacing urinary diversion by means of an ileal conduit, the system eliminates the possibility of metaplastic degeneration leading to cancer, peristomal irritation, excessive maintenance, and the need for numerous drugs having adverse side effects.

A safe alternative to the use of drugs which act upon the kidneys, or upon neurotransmitters, or involve a surgical procedure that imposes the need for considerable maintenance and risk of complications is of distinct benefit. Drugs used to control urinary frequency have serious side effects, to include:

Desmopressin—anorexia, dizziness, falling, weakness, fatigue, light-headedness, and decreased concentration, especially with hyponatremia (Hossain, T., Ghazipura, M., Reddy, V., Rivera, P. J., and Mukherjee, V. 2018. "Desmopressin-induced Severe Hyponatremia with Central Pontine Myelinolysis: A Case Report," *Drug Safety-Case Reports* 5(1):19; Nardone, R., Brigo, F., and Trinka, E. 2016. "Acute Symptomatic Seizures. Caused by Electrolyte Disturbances," *Journal of Clinical Neurology* (Seoul, Korea) 12(1):21-33; Lucchini, B., Simonetti, G. D., Ceschi, A., Lava, S. A., Faré, P. B., and Bianchetti, M. G. 2013. "Severe Signs of Hyponatremia Secondary to Desmopressin Treatment for Enuresis: A Systematic Review," *Journal of Pediatric Urology* 9(6 Part B):1049-1053; Vande Walle, J., Stockner, M., Raes, A., and Nørgaard, J. P. 2007. "Desmopressin 30 Years in Clinical Use: A Safety Review," *Current Drug Safety* 2(3):232-238)).

In general, desmopressin can induce nausea, vomiting, muscle weakness/spasms/cramps, weight gain, unusual tiredness, dizziness, severe drowsiness, mental/mood changes (confusion, hallucinations, irritability), loss of consciousness, seizures, or slow/shallow breathing. Headache (cephalalgia), nausea, upset stomach or stomach pain, diarrhea, or flushing of the face, loss of appetite, allergic reactions, to include hives; difficulty breathing; swelling of the face, lips, tongue, or throat; feeling restless or irritable, confusion, hallucinations, muscle pain or weakness, a sense of impending loss of consciousness; swelling, weight gain, and; dangerously high blood pressure, to include tinnitus, arrhythmia (irregular heartbeat), anxiety, confusion, chest pain, dyspnea (shortness of breath), severe cephalalgia (headache), blurred vision, and even seizures.

Antimuscarinic anticholinergics, to include oxybutynin, tolterodine, and solifenacin—cognitive impairment and dementia (see, for example, Richardson, K., Fox, C., Maidment, I., Steel, N., Loke, Y. K., and 11 others 2018. "Anticholinergic Drugs and Risk of Dementia: Case-control Study," *British Medical Journal* (Clinical Research) 361: k1315; Cross, A. J., George, J., Woodward, M. C., Ames, D., Brodaty, H., and 3 others 2017. "Potentially Inappropriate Medication, Anticholinergic Burden, and Mortality in People Attending Memory Clinics," *Journal of Alzheimer's Disease* 60(2):349-358; Campbell, N. L., Perkins, A. J., Bradt, P., Perk, S., Wielage, R. C., Boustani, M. A., and Ng, D. B. 2016. "Association of Anticholinergic Burden with Cognitive Impairment and Health Care Utilization among a Diverse Ambulatory Older Adult Population," *Pharmacotherapy* 36(11):1123-1131; Gray, S. L., Anderson, M. L., Dublin, S., Hanlon, J. T., Hubbard, R., and 4 others 2015. "Cumulative Use of Strong Anticholinergics and Incident Dementia: A Prospective Cohort Study," *Journal of American Medical Association Internal Medicine* 175(3):401-407).

A partial list of antimuscarinic side effects includes anxiety, disordered thought, delirium, hallucinations, arrhythmias typically tachycardia, ataxia (incoordination), gastrointestinal hypomotility felt as stomach ache, constipation, cephalalgia (headache), mydriasis (dilated pupils) with consequent photophobia (sensitivity to light), cycloplegia (blurred vision), diplopia (double vision), slight fever, drowsiness, dizziness, hypohidrosis, xerostomia (dry mouth), keratoconjunctivitis sicca (dry eye), myoclonus (involuntary jerking), urinary retention, and urinary incontinence.

As will be described, also enabled by intravascular valves are vascular procedures, such as extracardiac transposition of the great vessels, and sudden switch solid organ transplantation, to include that of the heart itself, with zero ischemic time. In an extracranial carotid endarterectomy, rather than to insert a catheter into the common carotid, thence craniad into the internal carotid, thus diverting blood from the external carotid and obscuring access to athermoma or plaque underlying the catheter (see, for example, Chung, J. and Dodson, T. F. 2011. "Surgical Treatment of Carotid and Peripheral Vascular Disease," in Fuster, V., Walsh, R. A., Harrington, R. A. (eds.), *Hurst's The Heart,* 13th edition, New York, N.Y.: McGraw-Hill; pages 2347-2354, FIG. 110-1), the use of ductus side-entry jackets at the three spanning end-points—external, internal, and common carotids—allows continuous perfusion, eliminating ischemia, and therewith, the risk of midprocedural stroke.

Thus, connected by tubing to serve for bypass, plain ductus side-entry jackets and more particularly those containing an adjustable diversion chute making these intravascular valves, can be used midprocedurally to eliminate ischemic time. Using the means to be described, bypass to repair a carotid aneurysm, such as one resulting from Ehlers-Danlos syndrome along the internal carotid is the same as that used to repair a carotid endarterectomy. For a carotid endarterectomy, for example, an anticoagulant can be targeted directly through and to the ductus side-entry jacket accessory channel to and into the common, internal, or external artery without creating the risk of problem bleeding elsewhere in the body.

Here the procedure is accomplished using ordinary three-point distributed ductus side-entry jackets, one each on the common, internal, and external carotids, connected by catheters of a caliber as duplicate the flow rate through the native vessels. Flow from and return to the native vessels is so quick as to preclude ischemia. Significantly, when necessary, such as when the native vessels are diseased or missing, such shunts and bypasses can be left in place with the lines connecting these left in place indefinitely as a prosthesis.

Manually adjusted embodiments of the ureteral takeoff diversion system shown in FIGS. 40 thru 43 nonadjustable/prosthesis and adjustable are substantially the same, except that the prosthetic embodiment is adjusted once upon placement by the operator, and no access to the valve is provided. By contrast, an adjustable embodiment provides control knobs connected to miniature push/pull, or Bowden; cables for the wearer to divert urine to an extracorporeal collection bag on a discretionary, basis. Alternatively, the native vessels can be anastomosed with the bypass or shunt tubing and jackets used to target an anticoagulant, anti-inflammatory, or antimicrobial, for example directly to the site.

By a prosthetic disorder response system is meant an apparatus that uses the feedback from one or a combination of chemical, thermal, electrical, and mechanical implanted physiological diagnostic sensors (biosensors, microsensors, detectors), for example, to trigger adaptive drug dose computation, metering, and delivery through system conduits and unique junctions to ductus in response to a control program that is a prescription. The drugs are supplied from an extracorporeally worn pack and dispensed through catheteric lines connected directly to the lumina of the target ductus. Since the process of placing the junctions—the side-entry jackets—calls for a mainline and a supporting or subsidiary sideline, the sideline is left in place to serve as a second lumen, eliminating the need for a mainline with double lumen, for example.

Meaning of an Automatic Adaptive/Predictive Ambulatory Prosthetic Disorder Response System System desiderata and capabilities are addressed in with respect to various contexts and therefore addressed at numerous points such as in the section below entitled Local and Systemic Implications of Automatic Sensor-driven Targeted Drug Delivery. With a portable (wearable, ambulatory) prosthetic disorder response system, the clinician specifies the target ductus, the drugs to be delivered to each, the dose regimen, and any additional factors pertinent thereto. According to the present concept, a pharmacist-programmer enters this into a program whereby each drug is provided in response to the conditions sensed. To deliver drugs automatically and adjust the dosing, the prescription, or adaptive drug delivery program, responds to diagnostic sensor feedback under the control of a medically adapted hierarchical (nodal, nested-levels) 'intelligent' hard real-time 'pathfinding' control system.

Depending upon the intricacy and frequency of differential control required of either pump in the pump and jacket set, each node controls either one of the pumps or the modular plug-in pump-pair as a subsystem in the pump-pack, usually cinched about the waist. While sensors, fluid lines, and connectors must be implanted, the control circuitry, power source, and pumps need not. Generally, the latter are implanted only when the condition or conditions treated are expected to persist to the end of life. In the case of progressive disease, the sensor-driven automatic drug delivery system spontaneously adjusts the intervals and dose of drugs in accordance with the prescription-program.

Representation in the drawing figures of system componentry as housed in an extracorporeal pump-pack pertain no less to system implantation where these parts are much miniaturized to allow full, or closed-skin, implantation. To the extent practical, where comorbid conditions must be treated, each such component disease is assigned to a respective node and modular plug-in pump-pair and jacket set, and the master microprocessor programmed to coordinate the delivery of drugs among the nodes.

The addition of a module is coordinated with the module or modules already inserted; however, because when targeted to specific tissue, most if not all drugs are kept separate, the regimen overall as administered by the master controller over the nodes usually need not effect significant adjustments among these to accommodate the addition or removal of a pump-pack. Such a prescription-program can be executed by a multicore microcontroller of which each core or cog is programmed as a time division multiplexed node in the control hierarchy. Where magnetically susceptible carriers with or without a carried extractate (extractat) will be so small in volume as not to require removal, high energy product permanent magnets, ordinarily made of neodymium iron boron, are preferred.

Where this debris or detritus will be slight, a permanent magnet jacket that detains the debris has a side grating that allows the debris to be extracted with the aid of a powerful extracorporeal electromagnet. Generally, the debris if at all toxic will be equally so in the tissue surrounding the ductus; however, when extracted, it can be dispersed so as to reduce the immediate burden or concentration to a tolerable level. If the extractate debris is more toxic or radioactive, then electromagnetic extraction-jackets such as shown in FIGS. 13 thru 15 and described below remove the extractate entirely from the body. The consecutive jackets along the ductus in FIG. 15, ordinarily a vessel, are connected by a flush-line from a supply to a separate waste reservoir in the pump-pack, washing the pole of each electromagnet 75 where the debris accumulates along the way.

While various combined function or hybrid jackets are mentioned herein, clean separation and distinction among parts and functions, whereby each is clearly assigned to a specific modular subsystem for a component of the disease overall, is always to be preferred as minimizing the opportunities for human error. The drug-carrier to drug bond can be broken upon delivery of a bond-breaking substance, whereupon the carrier alone is drawn and the drug freed to continue through the circulation. One pump in the pump-pair may be assigned to provide the drug and the other the reversal agent, for example. Having been infused through a simple junction jacket upstream, for example, and substantially restricted from access to tissue of the ductus and tissue supplied by its branches outside the target segment, the diseased segment can be treated with drugs in combinations with component concentrations suitable for the diseased tissue alone.

Such differential treatment along a ductus is not to be construed as absolute: many conditions are systemic with only the most vulnerable and severely affected segments developing frank lesions. If left unenergized, an electromagnetic embodiment of the side-entry jacket shown in FIG. 5, for example, can still function as a simple junction jacket of the kind shown in FIG. 2, because unlike the jacket shown in FIG. 5, the electromagnetic impasse jacket will allow a magnetic carrier-bound drug sent from the pump to pass without detaining it. Any jacket which is piped, that is, includes a side-entry connector, can function as a simple junction jacket to pass magnetically nonsusceptible fluids in either direction.

Electromagnetic impasse jackets with or without side-entry or piping can thus differentially draw particular superparamagnetic iron oxide nanoparticles, or SPIONS, from the bloodstream, for example, according to which jackets are energized in coordination with the initiation of delivery of the drug at the pump. Electromagnetic impasse jackets therefore open the way for the development of ferrofluids containing superparamagnetic magnetite or maghemite iron oxide drug-carrier nanoparticle-bound drugs (references cited below), to take advantage of a capability to differentially distribute the drugs to only certain of the jackets along one and the same artery, for example. Nonmagnetized drugs included in the ferrofluid freely pass magnetized jackets.

The ability to energize and continuously adjust the field strength of the electromagnet in extraction jackets allows SPION drug-carriers that if not extracted would induce toxicological or adverse consequences to be eliminated before toxic sequelae can take hold (see, for example, Wahajuddin and Arora, S. 2012. "Superparamagnetic Iron Oxide Nanoparticles: Magnetic Nanoplatforms as Drug-carriers," *International Journal of Nanomedicine* 7:3445-3471; Hong, S. C., Lee, J. H., Lee, J., Kim, H. Y., Park, J. Y., Cho, J., Lee, J., and Han, D. W. 2011 "Subtle Cytotoxicity and Genotoxicity Differences in Superparamagnetic Iron Oxide Nanoparticles Coated with Various Functional Groups," *International Journal of Nanomedicine* 6:3219-3231; Naqvi, S., Samim, M., Abdin, M., Ahmed, F. J., Maitra, A., Prashant, C., and Dinda, A. K. 2010. "Concentration-dependent Toxicity of Iron Oxide Nanoparticles Mediated by Increased Oxidative Stress," *International Journal of Nanomedicine* 5:983-989).

Ductus side-entry jackets which incorporate an intravascular valve allow adjustment in the rate of blood flow, not necessary in a conventional endarterectomy but useful elsewhere in the vascular tree where it may be beneficial to intermittently or continuously reduce the velocity to enhance pickup of superparamagnetic iron oxide nanoparticles by magnetized jackets. The use of diversion jackets to redirect a portion of the flow through an artery to one much larger represents a means for adjusting the local blood pressure. Such a valve can, for example, replace bands on the pulmonary artery or variceal veins in portal hypertension where the ability to adjust the valve from outside the body can be used reduce complications without the need to reenter or even insert an endoscope. In an ambulatory adaptive prosthetic disorder response system, when the valve is driven by a microminiature linear motor, the implant master controller microprocessor can actively modulate the rate of flow through the ductus in coordination with the release of medication.

As indicated, when the condition of the bifurcation is poor or has been iatrogenically injured during the procedure, the jacket and connecting lines can be left in place indefinitely as a prosthesis. The use of catheter caliber fluid lines is made possible by service or accessory channel or channels, which allow the direct delivery into the line, jacket, and substrate ductus of anticoagulants, antimicrobials, and other agents to assure that the lines and ductus will remain clear. Accessory channels are an essential part of almost every jacket, and every jacket meant to remain in place postprocedurally. In an ambulatory adaptive prosthetic disorder response system, the periodic release of such agents is entered into the prescription-program to proceed automatically.

Such means make possible the use of catheters as artificial vessels in patients who, whether due to vascular degeneration or disease, have no harvestable vessels, or who could suffer significant degenerative alteration in the region which the graft had supplied or drained. FIGS. 21 and 22 show the use of catheters in lieu of harvestable vessels in a coronary artery bypass with direct drug targetability. Catheters to serve as prosthetic vessels served by service or accessory channels offer utility which is critical in that these enable the use of small caliber synthetic tubing, and provide directly pipe-targeted access to the treatment site—indefinitely if left in place as a synthetic bypass, for example—for drug delivery with little if any affect on other tissue as would cause adverse side effects, or result in contact with other drugs or food, causing adverse drug-drug or drug-food interactions.

When appropriate, as in an infant, senile or unruly patient, or where dosing involves multiple drugs to be released in a particular sequence, or when it is beneficial that drug delivery commence immediately as symptoms are detected by biosensors even before an experiential correlate obtains, an automatic ambulatory adaptive disorder response system is used to effect drug delivery. The system is thus able to suppress symptoms while inchoate, and by correlating the effect of releasing drugs responsive thereto, accumulates symptom-drug relational data which allows it to predict what combination of drugs and doses will best restore the patient to health. When comorbidities are present, the overall object is to restore the patient to the optimal state of health across the set of morbidities which the pre- or postsurgical anatomy will allow.

Thus, for any given pre- or postsurgical physiological status, such a fully implanted system has the overall object of restoring to optimal health a patient with one or several serious disorders intractable to conventional drug administration, or one demanding complicated dosing not likely to find compliance, or one exhibiting significant adverse reactions or drug-drug interactions when the otherwise optimal drugs for the disorder or disorders are introduced into the circulation rather than targeted. Other disorder response actions which can be implemented automatically using such a system when suitably equipped include blood component separation of disease causing cells or viruses when these can be bound to and thus tagged for removal by a magnetically susceptible carrier.

When such action demands a frequent intermittent if not continuous on-time duty cycle, batteries currently available must be frequently or continuously recharged. To sustain treatment while allowing freedom of movement within a circumscribed area necessitates either hardwire connection to an electrical outlet or the further development of transdermal energy transfer or transdermal resonance energy transfer recharging with increased transmission distance, analogous to an area covered by a wireless local area network as with a 'WiFi' system. Related transdermal energy transfer and implanted drug delivery means are addressed below and in copending application Ser. No. 14/998,495, entitled Nonjacketing Side-entry Jackets and Prosthetic Disorder Response Systems, filed on 12 Jan. 16 and published as 20170197028.

Described will be means for creating secure junctions between catheters and native ductus to deliver drugs and/or serve in lieu of native ductus or artificial ductus produced through tissue engineering or tissue expansion and tubularization. Ductus included are those vascular, gastrointestinal, urogenital, and when accessible without extensive dissection, endocrine. While the entry point is secure, the distal end of the catheter is not, so that existing fully implanted indwelling catheters to include those entered through a portacath, or mediport, cannot be depended upon for indefinite length of service with complete freedom of movement without the risks of perforation, dislodgement, and leakage. Ductus side-entry connectors remedy this limitation.

Secure and leak-free junctions are essential to provide a system able to sense the need for and automatically dispense a substance which due to a genetic defect is not produced, or which due to disease or a genetic defect, is not produced in sufficient volume. Unless secure and leak-free, a drug can be diverted from the intended injection or infusion point, so that the controlling microprocessor registers a release of medication which is erroneous. Instead, the drug resides in unintended tissue where it can provoke an adverse tissue response, the condition to have been treated left unaffected. This is seen in automatic insulin pumps, for example, where, as will be documented, the infusion set cannula or needle can become detached or displaced so that the machine reading looks good but the condition is unaffected.

The jacket prevents leaks or the intrusion of microbiota by closing off any path that a leak or pathogens might take before the wall of the ductus, whether vascular, is breached upon the introduction of an opening (ostium, aperture, fenestration) in its side, thus allowing the creation of a continuous passageway between a catheteric and native lumen. In simplest form as junction-type side-entry jackets, these can be used to establish fluid conducting junctions between a catheter or tissue engineered ductus with a native ductus as a safe, secure, and more versatile alternative to long-term indwelling catheters such as a Hickman catheter. However, unlike an indwelling catheter, the junction, indeed multiple such junctions, will hold without risk of disconnection or injury to the patient, who is able to move freely.

Also essential to provide such a system is the ability to implant small caliber tubing such as artificial vessels or catheters for use on a long-term if not lifelong basis and not have these become occluded with thrombus, biofilm, or the congealing, accretion, and adhesion to the wall surrounding the delivery tube of the agent passed. Currently, only the largest vessels, such as those used to create aortoiliofemoral, to include aortofemoral and femorofemoral bypasses in peripheral artery disease, can be replaced with polytetrafluoroethylene terephthalate (dacron) tubing.

This because smaller caliber tubing such as catheters become occluded without the need to frequently if not continuously introduce heparin, for example, into the circulation, raising the risk of thrombus-induced ischemic complications, to include heparin-induced thrombocytopenia, skin necrosis, deep venous thrombosis risking pulmonary embolism, skin necrosis, myocardial infarction, peripheral arterial occlusion further risking amputation, transient ischemic attacks, and stroke. To avoid such eventualities, heparin is not allowed in the circulation for more than a relatively brief interval.

In contrast to this limitation, the service, or accessory channel to the ductus jackets and connectors to be described allow the targeting of heparin or any other drug in fluid form, to be delivered into the implanted delivery catheter and jacket or connector, allowing the administration of heparin, for example, in minute volume compared to that which would otherwise be circulated, for however long the condition requires. Accessory channels can also be used by the controlling microprocessor to intermittently or continuously meter an adjuvant drug into that primary. Where the implanted lines are used to convey blood, the fact that anticoagulants, antimicrobials, and anti-inflammatory drugs can be directly targeted into the blood-conveying catheter in small volume is precisely the circumstance that makes the use of catheter-caliber tubing thus possible.

Should the blood become infected, a biofilm gradually accumulates along the internal walls of a catheter, eventually clogging it. Also, if used to target a drug or other agent to a certain level along a vessel, that substance, intact or having undgone conversion, may congeal and adhere, obstructing the lumen. The accessory or service channel provided with every side-entry jacket, shown as part number 11 in the drawing figures, and part number 13 in the drawing figures in copending application Ser. No. 14/998,495, entitled Nonjacketing Side-entry Jackets and Prosthetic Disorder Response Systems, published as 20170197028 allow the direct delivery into the catheter and jacket or nonjacketing connector of an anticoagulant, antimicrobial, and/or a diluent as necessary.

A system able to sense the need for and automatically dispense a substance effectively may be said to constitute a supplementary immune system, and demands junctions which will serve dependably for years. As will be addressed, depending upon the rate and dose of the missing agent or agents, such an adaptive prosthetic disorder system is partially or fully implanted. On a broader scale, such junctions allow replacing long-term indwelling catheters so that patients are allowed complete freedom of movement without risk of perforation, dislodgement, or leaks Existing means for forming junctions between a catheter and a native ductus afford no such reliability as allows the patient to safely engage in athletics or visit or reside at a location remote from an emergency medical service, for example.

Parent application Ser. No. 14/121,365 published as 20160051806 was directed to the creation of small caliber conduits to such jackets, copending application Ser. No. 14/998,495 published as 20170197028 describes stable and leak-free connectors for structures other than ductal, and copending continuation-in-part application, parent Ser. No. 13/694,835, published as US 20140163664 describes magnetized jackets to be placed in encircling relation to ductus for extraluminal stenting and/or for drawing magnetically susceptible or magnetically susceptible-carried medication directly to the sites of the jackets, positioned at treatment sites such as frank lesions or nidi. In this context, the jackets serve to directly join synthetic to native ductus and the reverse.

For medical use, such jackets and nonjacketing connectors must remain leak-free, nonmigrating or nondislodgeable, nondeformable, nonfracturing, and not injurious to the substrate or neighboring tissue indefinitely. Moreover, for pediatric use, these must adapt to growth over a period of years. Copending application Ser. No. 14/121,365 also addressed means for securely fastening catheteric lines, injection needles, and electrodes, for example, to native ductus through a small entry wound for the long-term treatment of chronic conditions, and delineated the assignment of channels or axes of control in a hierarchical control system to different organs or organ systems in the treatment of comorbid disease, for example.

A side-entry connector must provide a junction which is durable, positionally durable, and leak-free. Nonjacketing side-entry connectors extend this capability to nonductal anatomical structures such as the heart, stomach and colon, which abruptly motile and large in diameter, are not jacketed or collared. The same applies to nonductal tissue such as the serous lining of a body cavity, prompting revision of the title assigned to copending application Ser. No. 14/998,495 from 'nonductus' to 'nonjacketing.'

More specifically, ductus side-entry jackets and nonjacketing connectors allow a secure junction to be established between a catheter and a bodily conduit, or ductus or other structure over an indefinite period for the treatment of chronic disease or where the agent delivered is best directly targeted, whether because of side effects or drug-drug interactions, for example. Generally, a disorder response system to control the direct pipe-targeting of drugs to lesions or nidi is fully implanted when the morbidity or morbidities are chronic and unresponsive to or provoke adverse side effects with oral or parenteral medication. When the need therefor is not chronic but long-term, the control, power, and pumping components are relegated to an external (extracorporeal) body pack, as will be addressed.

Advocacy of Conclusive Measures

A central conviction behind the means to be described is that half-way measures, especially when applied to chronic disease, and more especially when the chronic disease is progressive, should always be avoided, and that when possible, true cures are structural, surgical, not medical, which is palliative in treating symptoms. For example, a properly performed herniorrhaphy is effectively a cure. By contrast, prescribing metformin to treat type 2 diabetes or an antihistamine to suppress an allergic immune response is a control measure, not a cure. An artificial pancreas once achieved will represent a cure, and will necessitate a surgical procedure to be put in place.

Basic medical surgery consists of relatively minor surgery to implant direct drug targeting means from a small port at the body surface to the site of the disorder, thus minimizing if not eliminating exposure to potentially harmful drugs of nontargeted tissue and adverse side effects. The implications of this for chemotherapy and enabling the use of drugs to which the patient is hypersensitive or who requires conflicting drugs is significant. This includes placement of the surface port, fluid lines, ductus connection jacket or jackets with accessory line or lines to connect the port to the treatment site or sites, and where necessary, electrical control lines or the establishment of Bluetooth connections.

In more advanced use—appropriate for the treatment of more complex comorbid disease where a certain apportionment of drugs among the treatment sites achieves the best overall consequence—the dispensing of drugs is automated, necessitating the implantation of additional components. Each component morbidity is assigned a channel or arm of control in a hierarchical control system which takes biosensor inputs at the lowest level. The inputs are passed for coordination to a control node, an intermediate chip-microcontroller, thence to a next higher node which coordinates treatment with its counterpart or counterparts in the other control channel or channels, the number thereof and need for coordination among these dependent upon the number of distinguishable morbidities.

These nodes then pass their outputs to a master node microprocessor. By analogy with the nervous system, such can be characterized as the system sensory function. Overall coordination of drug delivery (or other therapy, such as the application of heat), analogous to motor function, is then governed by the master node, a microprocessor which coordinates the inputs from the nodes next lower in rank and passes control signals down the channel in a motor sense, causing implanted drug reservoir outlet valves or pumps to release the drugs as directed.

When the condition of the patient allows, fitting of the system is preceded by an initial test period similar to that used in placing an elecrostimulatory neuromodulator except that the question is not whether to implant the device but rather what combination drugs would best be used. The implanted system is used to test different drugs, the best overall result with minimal drug interaction thereby made discernible. This determined, a pharmacist-programmer prepares a prescription-program for execution by the master node. Immediately lesion- or nidus-targeted and kept from the general circulation, medication delivered thus is substantially more effective in smaller doses and spares nontargeted tissue.

An automatic disorder response system requires the emplacement of drug delivery means which function automatically, in some instances, before the presentation of an experiential correlate, that is, before the patient becomes aware of the problem, such placement accomplished through endoscopic means under local anesthesia or regional nerve blockade. By comparison with the means for insulin delivery using an implanted system of the kind to be described, existing means for the treatment of diabetes, for example, are crude: rather than deeply, from the pancreas through the mesenteric vessels into the hepatic portal vein as physiological, insulin pumps release insulin superficially, into subcutaneous fat, through a thin cannula susceptible to dislodgement, leakage, and deformation.

Moreover, while recent pumps coordinate bolus size with the need therefor through continuous blood glucose monitoring, most pumps involve manual control by the patient, which if incorrect, will result in hypo- or hyperglycemia and diabetic ketoacidosis (see, for example, Oskarsson, P., Antuna, R., Geelhoed-Duijvestijn, P., Kröger, J., Weitgasser, R., and Bolinder, J. 2018. "Impact of Flash Glucose Monitoring on Hypoglycaemia in Adults with Type 1 Diabetes Managed with Multiple Daily Injection Therapy: A Prespecified Subgroup Analysis of the IMPACT [Novel Glucose-Sensing Technology and Hypoglycemia in Type 1 Diabetes: A Multicentre, Non-masked, Randomised Controlled Trial] Randomised Controlled Trial," *Diabetologia* 61(3):539-550; Haak, T., Hanaire, H., Ajjan, R., Hermanns, N., Riveline, J. P., and Rayman, G. 2017. "Use of Flash Glucose-sensing Technology for 12 Months as a Replacement for Blood Glucose Monitoring in Insulin-treated Type 2 Diabetes," *Diabetes Therapy* 8(3):573-586; Haak, T., Hanaire, H., Ajjan, R., Hermann, N., Riveline, J. P., and Rayman, G. 2017. "Flash Glucose-sensing Technology as a Replacement for Blood Glucose Monitoring for the Management of Insulin-treated Type 2 Diabetes: A Multicenter, Open-label Randomized Controlled Trial," *Diabetes Therapy* 8(1):55-73; Bolinder, J., Antuna, R., Geelhoed-Duijvestijn, P., Kröger, J., and Weitgasser, R. 2016. "Novel Glucose-sensing Technology and Hypoglycaemia in Type 1 Diabetes: A Multicentre, Non-masked, Randomised Controlled Trial," *Lancet* 388(10057):2254-2263; Heinemann, L. and Kamann, S. 2016. "Adhesives Used for Diabetes Medical Devices: A Neglected Risk with Serious Consequences?," *Journal of Diabetes Science and Technology* 10(6):1211-1215; Heinemann, L., Fleming, G. A., Petrie, J. R., Holl, R. W., Bergenstal, R. M., and Peters, A. L. 2015. "Insulin Pump Risks and Benefits: A Clinical Appraisal of Pump Safety Standards, Adverse Event Reporting, and Research Needs: A Joint Statement of the European Association for the Study of Diabetes and the American Diabetes Association Diabetes Technology Working Group," *Diabetes Care* 38(4):716-722 and *Diabetologia* 2015 58(5):862-870; Saboo, B. D. and Talaviya, P. A. 2012. Continuous Subcutaneous Insulin Infusion: Practical Issues," *Indian Journal of Endocrinology and Metabolism* 16(Supplement 2):S259-S262).

Subcutaneous infusion also causes time-dependent irritation from the infusion set (see, for example, Hauzenberger, J. R., Miinzker, J., Kotzbeck, P., Asslaber, M., Bubalo, V., Joseph, J. I., and Pieber, T. R. 2018. "Systematic in Vivo Evaluation of the Time-dependent Inflammatory Response to Steel and Teflon Insulin Infusion Catheters," *Scientific Reports* 8(1):1132; Hauzenberger, J. R., Hipszer, B. R.1, Loeum, C., McCue, P. A., DeStefano, M., and 6 others 2017. "Detailed Analysis of Insulin Absorption Variability and the Tissue Response to Continuous Subcutaneous Insulin Infusion Catheter Implantation in Swine," *Diabetes Technology and Therapy* 19(11):641-650; Heinemann, L. and Krinelke, L. 2012. "Insulin Infusion Set: The Achilles Heel of Continuous Subcutaneous Insulin Infusion," *Journal of Diabetes Science and Technology* 6(4):954-964), necessitating frequent removal and replacement (see, for example, Weber, C., Kammerer, D., Streit, B.1, and Licht, A. H. 2014. "Phenolic Excipients of Insulin Formulations Induce Cell Death, Pro-inflammatory Signaling and MCP-1 [monocyte chemotactic protein-1] Release," *Toxicology Reports* 2:194-202).

Setting aside irritation due to constituents in certain insulins (see, for example, Weber, C., Kammerer, D., Streit, B., and Licht, A. H. 2014. "Phenolic Excipients of Insulin Formulations Induce Cell Death, Pro-inflammatory Signaling and MCP-1 [monocyte chemoattractant protein 1] Release," *Toxicology Reports* 2:194-202), long-term use of a conventional insulin pump insulin infusion set results in scarring or lipohypertrophy at the cannula insertion point, often causes pain, pruritus necessitating resituation of the cannula, and seldom, can cause infection.

Steel needles in certain sets have been known to disconnect, and any needle or cannula can migrate so that infusion is not into the subcutaneous fat, diverting much of each dose. Yet another problem with insulin pumps is hyperglycemia due to interruptions in performance (Gibney, M., Xue, Z., Swinney, M., Bialonczyk, D., and Hirsch, L. 2016. 'Reduced Silent Occlusions with a Novel Catheter Infusion Set (BD FlowSmart): Results from Two Open-Label Comparative Studies," *Diabetes Technology and Therapeutics* 18(3):136-143).

Eventually, suitable sites for puncture that allow freedom of movement and the unobstructed delivery of insulin run out (see, for example, Hauzenberger, J. R., Münzker, J., Kotzbeck, P., Asslaber, M., Bubalo, V., Joseph, J. I., and Pieber, T. R. 2018. "Systematic in Vivo Evaluation of the Time-dependent Inflammatory Response to Steel and Teflon Insulin Infusion Catheters," *Scientific Reports* 8(1):1132; Hauzenberger, J. R., Hipszer, B. R., Loeum, C., McCue, P. A., DeStefano, M., and 6 others 2017. "Detailed Analysis of Insulin Absorption Variability and the Tissue Response to Continuous Subcutaneous Insulin Infusion Catheter Implantation in Swine," *Diabetes Technology and Therapeutics* 19(11):641-650; Klonoff, D. C., Freckmann, G., and Heinemann, L. 2017. "Insulin Pump Occlusions: For Patients Who Have Been Around the (Infusion) Block," *Journal of Diabetes Science and Technology* 11(3):451-454; Pozzilli, P., Battelino, T., Danne, T., Hovorka, R., Jarosz-Chobot, P., and Renard, E. 2016. "Continuous Subcutaneous Insulin Infusion in Diabetes: Patient Populations, Safety, Efficacy, and Pharmacoeconomics," *Diabetes Metabolism Research and Reviews* 32(1):21-39; Karlin, A. W., Ly, T. T., Pyle, L., Forlenza, G. P., Messer, L., and 7 others 2016. "Duration of Infusion Set Survival in Lipohypertrophy Versus Nonlipohypertrophied Tissue in Patients with Type 1 Diabetes," *Diabetes Technology and Therapeutics* 18(7):429-435; Cescon, M., DeSalvo, D. J., Ly, T. T., Maahs, D. M., Messer, L. H., and 3 others 2016. "Early Detection of Infusion Set Failure During Insulin Pump Therapy in Type 1 Diabetes," *Journal of Diabetes Science and Technology* 10(6):1268-1276; Bossi, A. C. 2016. "Skin Oil Staining to Avoid Infusion Set Cannula Crimping: A Personal Observation," *Journal of Diabetes Science and Technology* 10(5):1201-1202; George, M. M., Ruiz-Elizalde, A. R., and Beck, J. K. 2015. "A Continuous Subcutaneous Insulin Infusion Needle Break," *Clinical Diabetes* 33(4):195-197; Pfützner, A., Sachsenheimer, D., Grenningloh, M., Heschel, M., Walther-Johannsen, L., Gharabli, R., and Klonoff, D. 2015. "Using Insulin Infusion Sets in CSII [continuous subcutaneous insulin infusion] for Longer than the Recommended Usage Time Leads to a High Risk for Adverse Events: Results From a Prospective Randomized Crossover Study," *Journal of Diabetes Science and Technology* 9(6):1292-1298; Heinemann, L., Walsh, J., and Roberts, R. 2014. "We Need More Research and Better Designs for Insulin Infusion Sets," *Journal of Diabetes Science and Technology* 8(2):199-202; Pickup, J. C., Yemane, N., Brackenridge, A., and Pender, S. 2014. "Nonmetabolic Complications of Continuous Subcutaneous Insulin Infusion: A Patient Survey," *Diabetes Technology and Therapeutics* 16(3):145-149; Heinemann, L. and Krinelke, L. 2012. "Insulin Infusion Set: The Achilles Heel of Continuous Subcutaneous Insulin Infusion," *Journal of Diabetes Science and Technology* 6(4):954-964; Højbjerre, L., Skov-Jensen, C., Kaastrup, P., Pedersen, P. E., and Stallknecht, B. 2009. "Effect of Steel and Teflon Infusion Catheters on Subcutaneous Adipose Tissue Blood Flow and Infusion Counter Pressure in Humans," *Diabetes Technology and Therapeutics* 11(5):301-306; Clausen, T. S., Kaastrup, P., and Stallknecht, B. 2009. "Effect of Insulin Catheter Wear-time on Subcutaneous Adipose Tissue Blood Flow and Insulin Absorption in Humans," *Diabetes Technology and Therapeutics* 11(9):575-580; Pietri, A. and Raskin, P. 1981. "Cutaneous Complications of Chronic Continuous Subcutaneous Insulin Infusion Therapy," *Diabetes Care* 4(6):624-626).

Another problem with conventional insulin pumps is the accumulation of insulin along the internal walls of the infusion set cannula and/or thickening of the insulin, resulting in clogging, that is, the obstruction of flow of insulin into the subcutaneous fat (see, for example, Zapadka, K. L., Becher, F. J., Gomes Dos Santos, A. L., and Jackson, S. E. 2017. "Factors Affecting the Physical Stability (Aggregation) of Peptide Therapeutics," *Interface Focus* 7(6):20170030; Iannuzzi, C., Borriello, M., Portaccio, M., Trace, G., and Sirangelo, I. 2017. "Insights into Insulin Fibril Assembly at Physiological and Acidic pH and Related Amyloid Intrinsic Fluorescence," *International Journal of Molecular Sciences* 18(12). pii: E2551; Pitocco, D., Rizzi, A., Scavone, G., Tanese, L., Zaccardi, F., Manto, A., and Ghirlanda, G. 2013. "Fields of Application of Continuous Subcutaneous Insulin Infusion in the Treatment of Diabetes and Implications in the Use of Rapid-acting Insulin Analogues," *Minerva Endocrinologica* 38(3):321-328; Kerr, D., Wizemann, E., Senstius, J., Zacho, M., and Ampudia-Blasco, F. J. 2013. "Stability and Performance of Rapid-acting Insulin Analogs Used for Continuous Subcutaneous Insulin Infusion: A Systematic Review," *Journal of Diabetes Science and Technology* 7(6):1595-1606; Saboo, B. D. and Talaviya, P. A. 2012, Op cit.).

The means described allow the delivery of insulin so that it will not deteriorate; signifcantly, whereas the degradation and thickening, or fibrillogenesis, of insulin is implicated in the formation of Aβ oligomers which initiate the process that leads to the formation of amyloid plaques associated with dementia in type 2 diabetics, (see, for example, Surmacz-Chwedoruk, W., Malka, I., Bozycki, Ł., Nieznańska, H., and Dzwolak, W. 2014. "On the Heat Stability of Amyloid-based Biological Activity: Insights from Thermal Degradation of Insulin Fibrils," *Public Library of Science One* 9(1):e86320; Biessels, G. J. and Kappelle, L. J. 2005. "Increased Risk of Alzheimer's Disease in Type II Diabetes: Insulin Resistance of the Brain or Insulin-induced Amyloid Pathology?," *Biochemical Society Transactions* 33(Part 5):1041-1044), intact insulin appears to retard the onset of dementia (see, for example, Morris, J. K. and Burns, J. M. 2012. "Insulin: An Emerging Treatment for Alzheimer's Disease Dementia?," *Current Neurology and Neuroscience Reports* 12(5):520-527), possibly by alleviating oxidative stress on erythrocytes (see, for example, Carelli-Alinovi, C. and Misiti, F. 2017. "Erythrocytes as Potential Link between Diabetes and Alzheimer's Disease," *Fronters in Aging Neuroscience* 9:276).

Using the means described herein, an accessory or service channel allows the concurrent drip of heparin into the delivery line, which current evidence indicates neutralizes the potential harm of allowing the fibrillar heparin to remain intact (see, for example, Vilasi, S., Sarcina, R., Maritato, R., De Simone, A., Trace, G., and Sirangelo, I. 2011. "Heparin Induces Harmless Fibril Formation in Amyloidogenic W7FW14F Apomyoglobin and Amyloid Aggregation in Wild-type Protein in Vitro," *Public Library of Science One* 6(7):e22076).

The availability of a service channel, supplied and controlled in the same manner as the primary drug delivery catheter, or mainline, also allows the concurrent controlled delivery of other agents currently under study. For example, tetracyline has been found to prevent and to reverse the aggregation of fibrillogenesis; however, the use thereof must be closely monitored and kept to the minimum (see, for example, Malmo, C., Vilasi, S., Iannuzzi, C., Tacchi, S., Cametti, C., Trace, G., and Sirangelo, I. 2006. "Tetracycline Inhibits W7FW14F Apomyoglobin Fibril Extension and Keeps the Amyloid Protein in a Pre-fibrillar, Highly Cytotoxic State," *Federation of American Societies for Experimental Biology Journal* 20(2):346-347). Trehalose yields a similar outcome (see, for example, Vilasi, S., Iannuzzi, C., Portaccio, M., Irace, G., and Sirangelo, I. 2008. "Effect of Trehalose on W7FW14F Apomyoglobin and Insulin Fibrillization: New Insight into Inhibition Activity," *Biochemistry* 47(6):1789-1796).

A problem with insulin itself is temperature sensitivity (see, for example, Ogle, G. D., Abdullah, M., Mason, D., Januszewski, A. S., and Besancon, S. 2016. "Insulin Storage in Hot Climates without Refrigeration: Temperature Reduction Efficacy of Clay Pots and Other Techniques," *Diabetic Medicine* 33(11):1544-1553; Vimalavathini, R. and Gitanjali, B. 2009. "Effect of Temperature on the Potency and Pharmacological Action of Insulin," *Indian Jornal of Medical Research* 130(2):166-169). Hence, ordinary insulins cannot be stored at body temperature, nominally 37 degrees Celsius or 98.6 degrees Fahrenheit.

However, a collateral development makes possible heat-resistant insulin which can be stored at body temperature. The primary object in this development was to obtain an insulin which unlike previously existing insulins, would resist chemical degradation in areas of extreme temperatures without refrigeration, primarily, as indicated above, in the tropics (Farley, A. 2018. "After 35 Years of Dead Ends, Ohio Researcher Develops Heat-resistant Insulin," Insulin Nation January 2018 at http://insulinnation.com/treatment/after-35-years-of-dead-ends-ohio-researcher-develops-heat-resistant-insulin/) (see also, for example, Berenson, D. F., Weiss, A. R., Wan, Z. L., and Weiss, M. A. 2011. "Insulin Analogs for the Treatment of Diabetes Mellitus: Therapeutic Applications of Protein Engineering," *Annals of the New York Academy of Sciences* 1243:E40-E54; Hua, Q. X., Nakagawa, S. H., Jia, W., Huang, K., Phillips, N. B., Hu, S. Q., and Weiss, M. A. 2008. "Design of an Active Ultrastable Single-chain Insulin Analog: Synthesis, Structure, and Therapeutic Implications," *Journal of Biological Chemistry* 283(21): 14703-14716; Brange, J. and Langkjoer, L. 1993. "Insulin Structure and Stability," *Pharmaceutical Biotechnology* 5:315-350; Brange, J., Langkjaer, L., Havelund, S., and Vølund, A. 1992. "Chemical Stability of Insulin. 1. Hydrolytic Degradation During Storage of Pharmaceutical Preparations," *Pharmaceutical Research* 9(6):715-726; Brange, J., Havelund, S., and Hougaard, P. 1992. "Chemical Stability of Insulin. 2. Formation of Higher Molecular Weight Transformation Products During Storage of Pharmaceutical Preparations," *Pharmaceutical Research* 9(6):727-734; Brange, J., Hallund, O., and Sørensen, E. 1992. "Chemical Stability of Insulin. 5. Isolation, Characterization and Identification of Insulin Transformation Products," *Acta Pharmaceutica Nordica* 4(4):223-232; Pingel, M. and Volund, A. 1972. "Stability of Insulin Preparations," *Diabetes* 21(7): 805-813).

The same property means that as specified herein, this insulin can be stored at body temperature in a relatively small subcutaneously implanted flat bladder reservoir, usually positioned in the pectoral region, for dispensing under the control of an implanted microprocessor according to a prescription-program prepared for the patient (see, for example, Glidden, M. D., Aldabbagh, K., Phillips, N. B., Carr, K., Chen, Y. S., and 11 others 2018. "An Ultra-stable Single-chain Insulin Analog Resists Thermal Inactivation and Exhibits Biological Signaling Duration Equivalent to the Native Protein," *Journal of Biological Chemistry* 293 (1):47-68; Farley, A. 2018, Op cit.; Hua, Q. X., Nakagawa, S. H., Jia, W., Huang, K., Phillips, N. B., Hu, S. Q., and Weiss, M. A. 2008, Op cit.).

Automatic Control of Drug Delivery

For long-term but not lifelong use, system implantation is limited to only those components which must be internal—sensors, fluid and electrical lines, and connectors. A simple junction ductus side-entry jacket of this kind, or simple junction jacket, as shown in FIG. 2 is connected to an automated drug delivering and extractate collecting power, control, and pump body-pack, or simply body-pack, with a microprocessor that receives inputs from sensor implants and is programmed to function continuously under predictive control. Such a jacket or array thereof can serve as drug delivery points for the release of drugs and/or the extraction of a diagnostic test sample of lumen contents. For serious chronic conditions, the object is to eliminate the external pack with full implantation.

The automatic adaptive response hierarchical control system consists of local microcontrollers—usually positioned within the ductus side-entry and impasse jackets and non-jacketing side-entry connectors which represent the subordinate hierarchical levels assigned to the morbidities. These take sensor inputs, which to minimize dissection and achieve the maximum compactness, usually incorporated into the local jacket or connector—and coordinate these within their respective subsystem, or, channel of morbidity control, typically assigned to an organ- or organ system-defined channel of morbidity depicted in FIGS. 37 and 38.

A master control node microprocessor, which takes the precoordinated inputs from the subjacent or penultimate level of control nodes, effects the release of drugs or other agents across the combination of morbidities to accomplish the optimal approximation to an overall normal homeostasis for the patient. Having become available at modest cost, whenever there is a reasonable prospect of the patient, typically elderly, developing an additional morbidity, often sequelary to that or those morbidities evident at the outset, the microprocessor when implanted is overrated to allow subsequent remote reprogramming to include one or more additional channels of morbidity.

Components relegated to a worn control, power, and pump pack, such as the master node microprocessor, need not be overrated to allow expanded function at a later date from the outset, and implemented with less manipulation and at less expense, are replaced as necessary. Overrating the control and power components at the outset precludes a need for much dissection to remove and replace these if invested with tissue by encapsulation, accretions, and/or adhesions, as is likely in an elderly and infirm patient, for example. Within the size and weight constraints (allowing for tissue expansion if necessary) an implanted power source is likewise overrated to accommodate one or more additional morbidities when first implanted.

In this way, overrating at the outset obviates the need for the later addition of one or more channels of morbidity counteraction, or subsystems responsive to a morbidity that arises after the system was first implanted and therefore the need for a second invasive procedure to place the additional jackets or nonjacketing connectors, connecting fluid lines, or feedlines, and sensors. When the emergence of an additional morbidity can be predicted, the jackets and other connectors, fluid lines, and sensors needed to treat the condition are likewise placed at the outset. When not predictable, a second procedure is needed, but recovery of previously implanted components is uninvolved, and endoscopic placement of the additional jacket or other connector with internal or separate sensor or sensors and feedline requires less dissection, less procedural time, and can often be accomplished under regional nerve block if not local anesthesia.

If due to the extent of incision or patient unruliness general anesthesia is necessary, the duration, hence, risk of complications resulting therefrom will be less. Thus, the emergence of another chronic morbidity is not responded to by adding an externally worn waistbelt or backpack. Broadly, an external pack is preferably limited to power, control, and drug storage components, and then for the treatment of relatively short- or medium term conditions resistant to oral or injected medication and/or where the medication provokes adverse side effects. While the intracorporeal jackets, connectors, feedlines and sensors must be implanted, these have been devised to remain stable as not to require removal.

The addition of a magnetized layer as shown in FIGS. 5 and 6 allows a drug bound to a magnetically susceptible carrier particle, magnetized fullerene, microsphere, or nanoparticle to be drawn against and into the wall surrounding the ductus, and when bound to a substance having a natural affinity for the analyte or cell so that the susceptible particle is bound to a particular type analyte or cell in this indirect way, a powerful magnet can be used to extract the analyte or cell targeted.

Long-Term Non-Indwelling and Non-Fistular Vascular Access

Supplantation of central lines and other indwelling catheters for in-hospital use is not contemplated; rather, a far more secure means of vascular access is made available for long-term outpatient use. Where an indwelling catheter limits freedom of movement, disallows participation in activities that could result in dislodgement and injury, and is therefore unsuitable for the practical implementation of automatic ambulatory prosthetic disorder response systems, a ductus side-entry jacket is able to support function thus. With secure junctions to native ductus, such an ambulatory system can be used to target medication to specific segments or levels of any type bodily ductus or the territories or organs those supply. Moreover, the bidirectional capability and volumetric flow rate of junctions created with a side-entry connection jacket is able to exceed that of an indwelling catheter, expanding the potential applications for such a junction.

Ductus side-entry jackets can be made to fit around any type of ductus and are lined with a foam, which highly compliant and variable in thickness, allows ductus of any kind, regardless of intrinsic motility peristaltic or pulsatile, to be jacketed. Jackets applied to ductus belonging to the same or different organ systems deliver drugs under the control of a centralized drug delivery pack suspended from a pants belt, for example. For this reason, the ductus, tissues, and organs treated may belong to different bodily systems, allowing the concurrent and coordinated automatically administered ambulatory treatment under centralized control of different syndromes and comorbidities.

To treat syndromes and comorbid conditions that affect different organ systems, a pump and jacket set might include jackets sized to fit different vessels and a segment along the digestive tract, for example. Adaptive drug release responsive to sensor inputs to a microcontroller in the pack seeks to emulate endogenous adaptive function as exhibited in the release of vasodilators by the endothelial linings of the blood vessels, for example.

A ductus side-entry jacket can be used to minimize if not completely avoid direct connection between a catheter and a native ductus which induces an adverse tissue reaction and to avoid direct anastomoses along the digestive tract, where a segment harvested from the same individual is inserted as a graft elsewhere along the tract only to become infected and rejected if not leak, either resulting in failure or a need for drugs that cause complications. This is the usual result when a section of the small intestine is used as a graft following replacement of a resected or traumatically destroyed esophagus, for example.

An adverse tissue reaction—always an unwanted consequence of placing an implant—results whenever material, even autologous so that an immune reaction is not responsible, is introduced into a location in the body where that type tissue is not normally found. For example a blood patch, whereby a usually small amount of the patient's own blood is injected into the epidural space following a lumbar puncture, or spinal tap, to stop the leaking of cerebrospinal fluid induces inflammation (Gupta, D., Amhaz, H., Mazumdar, A., and Soskin, V. 2014. "Transient Compressive Lumbar Radiculopathy Following Post-epidural Blood Patch," *Journal of Anaesthesiology, Clinical Pharmacology* 30(1): 112-114; Desai, M. J., Dave, A. P., and Martin, M. B. 2010. "Delayed Radicular Pain Following Two Large Volume Epidural Blood Patches for Post-lumbar Puncture Headache: A Case Report," *Pain Physician* 13(3):257-262).

For this reason, even absent infection, hematoma, or adverse sequelae secondary to a hematoma (see, for example, Gupta, D., Amhaz, H., Mazumdar, A., and Soskin, V. 2014, Op cit.; Sorour, M., Krisht, K. M., and Couldwell, W. T. 2014. "Intraventricular Hemorrhage after Epidural Blood Patching: An Unusual Complication," *Case Reports in Neurological Medicine* 2014:406289; Verduzco, L. A., Atlas, S. W., and Riley, E. T. 2012. "Subdural Hematoma after an Epidural Blood Patch," *International Journal of Obstetric Anesthesia* 21(2):189-192; Riley, C. A. and Spiegel, J. E. 2009. "Complications Following Large-volume Epidural Blood Patches for Postdural Puncture Headache. Lumbar Subdural Hematoma and Arachnoiditis: Initial Cause or Final Effect?," *Journal of Clinical Anesthesia* 21(5):355-359; Kardash, K., Morrow, F., and Béïque, F. 2002. "Seizures after Epidural Blood Patch with Undiagnosed Subdural Hematoma," *Regional Anesthesia and Pain Medicine* 27(4):433-436), providing means to make possible the direct delivery to the site of a permanent implant of reaction-ameliorative medication is beneficial.

Another example where an adverse tissue reaction arises in the presence of autologous tissue is a blood patch pleurodesis, where to stop the leaking of air from a secondary spontaneous pneumothorax following a thoracostomy, 50 or so cubic centimeters of the patient's own blood is injected into the chest drain (see, for example, Evman, S., Alpay, L., Metin, S., Kiral, H., Demir, M., and 3 others 2016. "The Efficacy and Economical Benefits of Blood Patch Pleurodesis in Secondary Spontaneous Pneumothorax Patients," *Kardiochirurgia i Torakochirurgia Polska* [Polish Journal of Cardiothoracic Surgery] 13(1):21-25). Equally significant is the fact that when tightly targeted, a drug can be administered in a concentration far higher than would be allowed to circulate. The concentrated delivery of a statin to an atheroma to take advantage of its pleiotropic or non-liver mediated effects is just one example.

Essentially, the means to be described allow the automatic ambulatory infusion of any therapeutic substance and/or the extraction of any substance that can be bound to a magnetically susceptible carrier particle, such conjugation mediated by a substance having a natural affinity for the target analyte. Ideally, such an intermediate can be incorporated into the polymer, such as dextran or polyethylene glycol, coating the nanoparticles (see, for example, Wahajuddin and Arora, S. 2012. "Superparamagnetic Iron Oxide Nanoparticles: Magnetic Nanoplatforms as Drug-carriers," *International Journal of Nanomedicine* 7:3445-3471). A blood patch is a short-term treatment cited for the propensity toward inflammation of any implant, even autologous, and does not justify the application of the means described herein which are meant for the support of permanent implants with anti-inflammatories, antimicrobials, and if necessary, thrombolytics, such as streptokinase, urokinase, or tissue plasminogen activator.

A simple junction type side-entry jacket allows the targeted delivery of a drug or other therapeutic substance as necessary to any shunt, bypass, or graft of immunosuppressive, immunomodulatory, anti-inflammatory, antispasmodic, anticoagulant, or antimicrobial drugs, for example. If the drug is to drawn into the lumen wall, then the jacket or another one or more downstream are radially magnetized, removing these from the simple junction category. Remedial drug delivery is initiated by sensor implants used to supply feedback to the microcontroller in the extracorporeal (non-implanted, external) pump-pack. When not fully taken up within the segment to be treated and the residue would best or must be removed, then a downstream jacket is used to release a reversal or neutralizing agent.

If none exists, then the residual drug is itself targeted for extraction by magnetically susceptible drug-carrier particle scavenging, specialized extraction jackets shown in FIGS. 13 thru 15 and described under Description of the Preferred Embodiments of the Invention. Substantial restriction of the drug, especially those immunosuppressive, antibiotic, or steroidal, even in a higher concentration than would be allowed to continue through the circulation to the target segment or anastomosis, materially reduces if not eliminates the drug from the systemic circulation, and in so doing, reduces if not eliminates adverse side effects, drug-food, and drug-drug interactions.

Attaining Tractive Power with Electromagnets

In stent- and impasse-jackets where electromagnets are used to allow on-off and variation in field strength to attract or allow a particular infused ferrofluid to pass to downstream jackets, the fact that electromagnets, even when wound with silver wire as preferred, to achieve the smallest size possible, are not comparable in tractive force to neodymium magnets, for example, means that nanoparticles and carriers insufficiently susceptible to magnetic traction should incorporate sufficient silicon-iron (Si—Fe) crystal content to achieve the susceptibility required. By varying the amount of Si—Fe crystal bound to different analytes, the relative degree of magnetic susceptibility of each and the order of extraction of that or those most urgently removed is prioritized. Relative susceptibility is then a detectable property.

Analytes to be removed quickly are assigned one or more sensors and the prescription-program written to initiate the extraction of this or these immediately, not after hours in a clinic. In the target analyte magnetic separation scheme depicted in FIG. 39A and that shown in FIGS. 13 thru 15, using double-arm jackets such as that shown in FIG. 7 but with an electromagnet positioned between the arms or within the jacket as in FIG. 39A but without accessory channel, the magnets can be energized according to the master node microprocessor controller prescription-program in a high amplitude pulsed waveform, not only reducing power consumption compared to sustaining the high amplitude but significantly assisting the flush-line in washing away the extractate between pulses.

While the singular or isolated double-arm jacket shown in FIG. 7 includes a water jacket part number 7 and accessory channel part number 11, in applications such as use for intracorporeal dialysis shown in FIGS. 13 thru 15, the double entry arms 70 and 71 can serve to restrain extravasation during placement, and drugs to be dispersed through the dialysate or other fluid in the flush-line can be added to the dialysate flowing through the flush-line 79. In FIG. 39A, accessory channels are essential when a lesion is present or is likely to arise at one of the jackets and the drug or agent used would best be targeted at that jacket.

Delivery through an accessory channel is by injection into the opening in the surface port positioned subdermally in the pectoral region respective of the jacket. The drug, debris solvent, or thrombolytic then enters the extraction jacket outside the substrate ductus in the flush-line in the space occupied by the magnet pole. Where singling out a particular jacket for receipt of the medication or other agent is essential, the pump driving the dialysate is temporarily stopped. Where the drug is to concentrated in the jackets without significant dispersal throughout the dialysate, delivery is thorugh the accessory channel of the highest level or lead jacket in the set (which in a vein is downstream even though the jacket is higher, or craniad).

For delivery of drugs directly into the substrate vessel (as opposed to delivery into the flush-line), here represented as the inferior vena cava, drugs and other agents are injected into a different opening in the same body surface port as is used to access the flush-line, but rather than targeting one or more jackets, the drug flows to a ductus side-entry jacket at a higher level on the substrate vessel and into the target ductus. While drugs delivered to any one of the jackets can be targeted to the substrate vessel at the level of the jacket, the site of disease in renal problems is not the inferior vena cava.

The same applies to the electromagnet shown in FIG. 39B used to draw the cytapheresis or hemodialysis extractate into the bladder. Extraction of the extracted analyte or analytes into the bladder allows the dialysate to recirculate for days or however long the dialysate or other fluid in the flush-line less debris remains usable. In a patient without a bladder, extraction from the dialysate circuit is into a ureteral takeoff diversion confluence chamber such as that shown in FIG. 40. The means for debris extraction shown in FIG. 39B then applies to the confluence chamber. FIG. 7 shows a double-arm electromagnet positioned in the recess between the two arms. In FIGS. 13 thru 15, and 39A, the position of the magnets 74 and flush-line 79 results in maximum turbulence at the head of the magnet pole 75 for flushing away accumulated debris.

In a double-magnet extraction jacket member of an extraction chain-jacket, the magnet to either side is pulsed during the off alternation of the opposing magnet, so that the turbulent flushing away of debris is not resisted by adhesion to an energized magnet. This arrangement allows high continuous high-rate extraction and efficient removal of debris. Double magnet chain-jackets are used where the rate of extraction must be high. Such a position is a debris chamber in a patient whose entire urinary system has been resected. The double magnets are positioned between the dialysate or fluid in the flush-line inflow and outflow lines. Debris is accumulated in the debris chamber until the dialysate or fluid in the flush-line is replaced. Then the magnets are turned off so that turbulent flushing is able to wash away the larger amount of debris accumulated in such a patient.

Intracorporeal extraction of the debris into the urine for expulsion allows the dialysate to be maintained in a substantially untainted condition as allows it to remain in use over a long period comprehending many cycles about the circuit shown in FIG. 39A. If a patient extirpated of the entire urinary system and incapable or urinating is to be spared the need to replenish the dialysate frequently, an intracorporeal means for removing the debris is still necessary, and is described below in the section entitled Chain-jackets. Only spent dialysate not sufficiently cleared of debris need be discarded. Also facilitating the efficient washing away and removal of debris, in FIG. 43, impeller 106, which serves to empty ureteral neoureter 105 confluence chamber 102 when the patient is recumbent, continues to circulate the urine until the pressure within neoureter confluence chamber 102 rises sufficiently to force open chamber outlet elastic slit-valve 108.

Electromagnets are essentially portative rather than tractive, or capable of projection a powerful attractive field at a distance. To take advantage of the on-off and continuously variable control these offer, traction is optimized through the choice of materials not just of the magnet but the objects or analytes to be attracted, addressed below and in the following section. However, electromagnets consume much battery power, adding weight to apparatus intended to be as unobtrusive and function as inconspicuously as possible, automatically, leaving the patient free to move about with few as possible interruptions to insert a fully charged battery, be tethered by a power cord to an electrical outlet, or position oneself in a restricted area for transdermal recharging.

However, suitably configured, sized, and supported magnets materially reduce the problem of encroachment upon neighboring tissue, hence, the potential for annoyance and complications resulting from abrasion and jabbing. Its attractive force provided by an electromagnet rather than a permanent magnet, an impasse or extraction jacket with or without ductus side-entry line offers additional capabilities over jackets using permanent magnets: Augmenting the tractive effect of electromagnets can be accomplished by imparting greater susceptibility to the attractant. Accomplishing increased susceptibility through the incorporation of silicon-iron crystal is addressed above.

Controllable from zero to the maximum field strength, electromagnets allow separate jackets or segmentally defined sectors along a multiple magnet jacket to be turned on or off or varied in field strength in synchrony with the inception of drug delivery by the pump of a magnetically susceptible carrier particle-bound drug or other therapeutic substance. The jackets addressed may be electromagnetic impasse jackets with or without side-entry connector used to detain the carrier-bound drug alongside the wall surrounding the ductus, or with greater field strength, draw the drug into the wall, or extraction-jackets used to remove the carrier-bound drug out of the lumen where it is flushed out of the body.

Use of Silicon-Iron Crystal for Increased Magnetic Susceptibility

For implantation, it is critical that the electromagnets be reduced in mass and power consumption to the minimum. Long known, the value of silicon-iron crystal for improving magnetic susceptibility continues under development. The incorrect use of silicon with iron can impair rather than improve susceptibility (see, for example, Andreeva, Y. I., Drozdov, A. S., Fakhardo, A. F., Cheplagin, N. A., Shtil, A. A., and Vinogradov, V. V. 2017. "The Controllable Destabilization Route for Synthesis of Low Cytotoxic Magnetic Nanospheres with Photonic Response," *Scientific Reports* 7(1):11343).

However, properly employed, silicon-iron crystal significantly increases magnetic susceptibility (see, for example Dostanko, A. P., Korobko, A. O., and Lapchuk, N. M. 2008. *Journal of Applied Spectroscopy* 75(2):203-207; Patrin, G. S., Beletskii, V. V., Velikanov, D. A., Bayukov, O. A., Vershinin, V. V., Zakieva, O. V., and Isaeva, T. N. 2006. "Nonstoichiometry and Low-temperature Magnetic Properties of FeSi Crystals," *Physics of the Solid State* 48(4):700-704; Takeda, L., Ueda, F., Yamaguchi, T., and Tamura, R. 1987. "Crystal Orientation and Magnetic Properties in Thin-gauge Silicon-Iron Sheets," *Institute of Electrical and Electronics Engineers Translation Journal on Magnetics in Japan* 2(5):423-425; Arai, K. I., Ohmori, K., Miura, H., and Tsuya, N. 1985. "Effect of Order☐disorder Transition on Magnetic Properties of High Silicon☐iron Single Crystals," *American Institute of Physics Journal of Applied Physics* 57(2):460 https://doi.org/10.1063/1.334773; Ames, S. L, Houze, G. L. Jr., and Bitler, W. R. 1969. "Magnetic Properties of Textured Silicon☐Iron Alloys with Silicon Contents in Excess of 3.25%," *American Institute of Physics Journal of Applied Physics* 40(3):1577; https://doi.org/10.1063/1.1657778; Taguchi, S. and Sakakura, A. 1969. "Characteristics of Magnetic Properties of Grain☐oriented Silicon Iron with High Permeability," *American Institute of Physics Journal of Applied Physics* 40(3):1539; https://doi.org/10.1063/1.1657752; Nakamura, Y. 1961. "Effect of the Substructure upon Magnetic Properties of Iron-Silicon Single Crystals," *Journal of the Physical Society of Japan*

16(10):1888-1892; Williams, H. J. 1937. "Magnetic Properties of Single Crystals of Silicon Iron," *Physical Review Journals Archive* 52:747).

In some patients, the sequelae of systemic administration may disallow the placement of the graft, posing grave consequences. A simple junction jacket such as shown in FIG. 2 placed just upstream to the anastomosis joining a transplant organ or gland, for example, can be used to target drugs and withdraw diagnostic test samples from the transplant. If uptake within the transplant is not spontaneous, then clasp-magnets are attached about the outer surface of the transplant. When only one such magnet is needed, a permanent clasp-magnet is used.

If comorbid disease recommends the magnetically targeted uptake of drugs at multiple sites or systemically so that using a permanent clasp-magnet would interfere with passage of drugs intended for other sites past it, a clasp-electromagnet is used. The differential energization of these by time offset makes possible any number of mutually noninterfering or nonconflicting uptake sites for particle bound drugs. A graft sustained by means of immunosuppressive and other drugs delivered through the systemic circulation must have its dose limited to avoid systemic consequences; however, systemic consequences such as impaired immunity often appear despite having limited the dose.

Isolation of Drugs Moved in Separate Channels of Control

The means described herein substantially allow only the transplant to be medicated, with the dose optimized for it and kept from exposure to other tissue, not conditioned based upon unrelated contextual factors. If necessary, a second jacket is used to deliver a reversal agent or magnetically extract any objectionable residue. Any of the different drug delivery and/or analyte extraction jackets to be described can be placed under the unified control of the master microcontroller in the pump-pack. This allows the coordinated treatment of related or unrelated disease processes affecting different organs, glands, or organ systems by means of jackets the same or different in type, size, and volumetric flow rate of delivery, for example.

System Adaptation to Changed Pathology

If when the system is implanted, disease sequelary to that immediate is anticipated, the additional prepositioning of sensors, lines, and jackets at the outset eliminates the need for another invasive procedure. While most applications for such jackets are simple, direct, and do not call for subsequent redirection or addition, the ability to redirect or add pump-pair and jacket set pump-pack plug-ins among prepositioned jackets allows presaged complications to be dealt with under coordinated control without surgical reintervention.

Local and Systemic Implications of Automatic Sensor-Driven Targeted Drug Delivery The system is ambulatory and functions around the clock without control by the patient, who may be asleep. In an emergency not programmed for response distant from the clinic, a preplaced pump-pack can transmit the emergency signal to be activated by remote control. The jackets to be described can be placed in encircling relation about ductus along the digestive and/or urogenital tracts, the vascular tree, and/or the airway, to form a continuous passageway through the lumen of a synthetic line and into the native lumen without significant leakage or trauma and with no portion of the junction endoluminal, or projecting into the lumen. This capability has implications for the treatment of disease on a continuous, automatic, sustained, and when necessary, immediately adaptive basis.

This because the body consists of tissue pipelines and the tissues these supply. Except for absorption through the skin and oral mucosa, all intake into the body is through ductus. Any tissue can be accessed through ductus; when a side-entry jacket can be placed at a level that substantially excludes other tissue, the tissue that will be supplied is effectively isolated for targeted delivery of medication. Moreover, because the wall surrounding ductus support many biochemical interactions and discharge sensory feedback signals that modulate the control of numerous functions, the ability to circumscribe only a certain segment along a ductus for the delivery of drugs can have significant physiological implications, the more so when that segment is diseased.

In addition to communication affected by the autonomic nervous system, the luminal wall can release signaling proteins, such as chemokines and interleukins, and the luminal contents can include enzymes, hormones, cells containing cytokine signaling proteins, and so on, so that remote tissues are affected as well. As a result, there is no disease in which bodily conduits are uninvolved. No bodily conduit is analogous to inert plumbing; all are integrated into a hierarchy of negative feedback loops from the individual cells to the brain to actively and appropriately interact with the constitution, pressure, and velocity of passing contents.

Every bodily conduit communicates directly or indirectly with all the tissues in the body not just by transmitting luminal contents, but by signaling local function to higher control centers. In endothelial function, for example, the linings of blood and lymphatic vessels actively secrete vasodilators such as relaxing factor, or nitric oxide, bradykinin, potassium ions, and adenosine and vasopressors or vasoconstrictors such as endothelins, epinephrine, norepinephrine, dopamine, thromboxane, and insulin, all tied into coordinated feedback loops, which continuously adjust the degree of contraction, hence, the systemic blood pressure.

The atrial walls, aortic, and carotid sinus bodies (glomus caroticum, carotid glomus) contain chemoreceptors that detect blood gas and acidity levels, which transmitted to the medulla, signal the autonomic nervous system to adjust the respiratory and heart rates and the stroke volume. Similarly positioned baroreceptors, or pressoreceptors, detect the blood pressure, likewise transmitted to the brainstem, which regulates subsidiary feedback control loops. Placed along an artery, the level at which a simple junction jacket such as that shown in FIG. 2 and described below is positioned sets the supply territory or region.

Advancing the jacket along the artery toward its end supply excludes more proximal branches to neighboring tissue, closing in upon and so narrowing the target zone or supply territory. By the same token, retreating along the artery admits side branches to neighboring tissue, thus expanding the zone. The junction bidirectional, antegrade delivery into the native lumen, whether vascular, digestive, urinogenital, respiratory, for example, is usually of a drug, whereas retrograde delivery from the lumen is usually of a diagnostic test sample.

Accordingly, automated ambulatory systems of pumps able to individually deliver any of a number of different drugs to jackets placed at different levels along a single ductus, different ductus belonging to the same bodily system, or ductus belonging to different bodily systems according to a programmed schedule and mediated by sensor implants have the potential to treat morbidities and comorbidities in a discretionary manner whereby each drug is delivered to the target tissue in a time coordinated sequence. Such treatment has the potential to outstrip any therapy dependent upon the systemic, hence, necessarily indiscriminate, administration of drugs. Susceptible to primary disease, and supplying and draining every part of the body, the treatment of bodily conduits has application to any localized condition.

Drug delivery through a side-entry jacket allows the upstream ductus and tissue it supplies to be avoided. When more effective, the drug can be increased in concentration for the target tissue while substantially reduced in dose compared to the systemic dose that would be needed to achieve the same dose at the target. Whether through the use of a reversal agent or an extraction-jacket, as will be described, if necessary any residue of the drug can be truncated from further circulation at a segment cutoff level. When a bodily conduit or ductus (singular) is itself diseased, effective and efficient treatment requires that medication be actively drawn into, not merely pass by it through the lumen with little uptake.

For disease within the wall of the ductus itself, the junction is extended to incorporate a magnetic collar of which the field strength is incrementally increased in the antegrade direction to achieve a more uniform penetration. Mechanically and magnetically based, the drug targeting spoken of here averts the contingency of discovering a substance that depends upon intrinsic properties and affinities for targeting therapy at the gross anatomical level. A drug must, for example, inhibit a destructive enzyme produced as the result of a genetic defect, such as the tyrosine hydroxylase inhibitor imatinib mesylate (STI-571; Novartis Gleevec®) to selectively target cancer cells.

Or it must take advantage of an inherent affinity of an organ or gland for a substance, such as the thyroid gland for iodine. Here instead, the drug is contained while conducted to the treatment site, where it is forcibly drawn into the surrounding tissue, regardless of its inherent proclivities. Allowing the medication to pass lesions within the wall surrounding the lumen, or ductus-intramural lesions, without uptake wastes medication that if targeted would have contributed to an effective dose, exposes healthy tissue downstream to the wasted dose, and results in complications.

Moreover, increasing the dose to achieve better absorption only increases the waste and the risk. Drug targeting substantially limits exposure to the drug to the tissue intended, isolating the drug from other tissue targeted elsewhere in the body by the same control system. This makes it possible to target a transplant organ without exposing the entire body to immunosuppressive or immunomodulatory medication, and can significantly reduce if not eliminate the damage to the immune system done by chemotherapy and radiation, for example.

The value of drug targeting with respect to the administration of immunosuppressive drugs, nonsteroidal anti-inflammatory drugs such as aspirin, which used to treat arthritis, for example, often produce gastritis and ulcers, statins that induce myositis in susceptible patients, steroids which can produce moon facies and induce diabetes, for example, and the avoidance of adverse side effects, drug-drug and drug-food interactions across the entire array of pharmaceuticals. All bode complications, making directly piped targeting significant in eliminating such adverse sequelae (see, for example, Polyak, B. and Friedman, G. 2009. "Magnetic Targeting for Site-specific Drug Delivery: Applications and Clinical Potential," *Expert Opinion on Drug Delivery* 6(1):53-70).

Conventionally, magnet implants are limited to permanent magnets used to secure dental and maxillofacial prostheses and cochlear implants, and implanted rings used to ligate and atrophy tissue by compression ischemia. Other applications of magnetism require the use of an extracorporeal electromagnet to direct the magnetic field toward the treatment site, which limits such use to the clinic. The importance of drug targeting with respect to preventing rejection in transplantation, for example, will be addressed. Drug targeting can also be of value in averting side effects in drug tolerance and intolerance. Jacket placement assumes that the medication will be required on a long-term basis, would best not be taken orally; by injection, or injection that must be frequent as would promote patient noncompliance, and that accessibility to the site in order to implant the jacket and a port at the body surface to be described will not result in trauma more than negligible and transient.

When the dosage regimen frequent, and/or multiple drugs are needed making self-administration problematic, drug delivery is not dependent upon patient compliance but rather automatic as programmed, through a direct catheteric pipeline to the jacket or through plural lines respective of plural jackets from a port implanted at the body surface. At the same time, the port is available to administer another drug in the clinic from a syringe, for example. In order to realize the benefits of drug targeting, it is essential to possess means for establishing secure connections to ductus. The long-term indwelling of a catheter, needle, endoluminal implant, or prosthesis in a vessel often leads to adverse complications.

Subclavian, femoral, and internal jugular lines, and even peripherally inserted central catheters or PICCs, for example, are susceptible to infection, occlusion, breakage, and leaks (see, for example, Jumani, K., Advani, S., Reich, N. G., Gosey, L., and Milstone, A. M. 2013. "Risk Factors for Peripherally Inserted Central Venous Catheter Complications in Children," *JAMA Pediatrics* 167(5):429-435; Barrier, A., Williams, D. J., Connelly, M., and Creech, C. B. 2012. "Frequency of Peripherally Inserted Central Catheter Complications in Children," *Pediatric Infectious Disease Journal* 31(5):519-521; Shen, G., Gao, Y., Wang, Y., Mao, B., and Wang, X. 2009. "Survey of the Long-term Use of Peripherally Inserted Central Venous Catheters in Children with Cancer: Experience in a Developing Country," *Journal of Pediatric Hematology and Oncology* 31(7):489-492).

Due to the risk of injury, air embolism, or the formation of a hematoma, maintaining multiple such diagnostic sampling and/or drug delivery points in different veins with indwelling catheters is not feasible, certainly not in an ambulatory patient, much less in one who is very young or very old. Moreover, even though direct access to the blood supply to an affected organ or region would afford considerable advantages both diagnostically and therapeutically, this cannot be done with respect to small much less major arteries, wherein the blood pressure is greater. However, the ability to form several secure junctions with arteries, even large ones, opens the way for targeting medication to, taking draws from, and inserting a diagnostic probe into the blood supply of the organs or tissues these supply.

Extended Capabilities

For less power demanding applications, power is obtained by carrying charged button cell batteries to replace the one or more in the surface port. Higher demand on a continuous basis calls for a larger implanted rechargeable battery, the surface port then used to take power from an electrical outlet. The need for more power on an intermittent basis can be satisfied by connection to an external power source with or without recharging a battery. Transdermal energy transfer allows direct tetherless delivery of power whether a battery is simultaneously recharged within a circumscribed area.

Most applications of ductus side-entry connection jackets simple and direct, a secure means for forming a junction with a ductus allows the application of a body area network with wireless transmission, or telemetry, even combined with transdermal energy transfer (see, for example, Mao, S., Wang, H., Zhu, C., Mao, Z. H., and Sun, M. 2017. "Simultaneous Wireless Power Transfer and Data Communication Using Synchronous Pulse-controlled Load Modulation," *Measurement* (London, England) 109:316-325; RamRakhyani, A. K. and Lazzi, G. 2014. "Interference-free Wireless Power Transfer System for Biomedical Implants Using Multi-coil Approach," *Electronics Letters* 50(12) 853-855; Yazicioglu, R. F., Torfs, T., Penders, J., Romero, I., Kim, H., and 4 others 2009. "Ultra-low-power Wearable Biopotential Sensor Nodes," *Conference Proceedings, Institute of Electrical and Electronics Engineers Engineering in Medicine and Biology Society* 2009:3205-3208; Yoo, N. J., Cho, N., and Yoo, J. 2009. "Low Energy Wearable Body-sensor-Network," *Conference Proceedings, Institute of Electrical and Electronics Engineers Engineering in Medicine and Biology Society* 2009:3209-3212; Young, D. J. 2009. "Wireless Powering and Data Telemetry for Biomedical Implants," *Conference Proceedings, Institute of Electrical and Electronics Engineers Engineering in Medicine and Biology Society* 2009:3221-3224; Panescu, D. 2008. "Wireless Communication Systems for Implantable Medical Devices," *Institute of Electrical and Electronics Engineers Engineering in Medicine and Biology Magazine* 27(2):96-101; further references provided below) to afford immediate diagnosis and targeted drug delivery at multiple locations under automatic control.

Intracorporeal Magnetic Apheresis in the Treatment of Myeloproliferative Disorders Magnetic apheresis is dependent upon an intrinsic affinity of the target cell for a certain substance or antigen or of a certain substance or antigen for the target cell. For example, provided immature leukocytes, or blasts, can be restored to phagocytic competence (addressed below in the section on apheresis), an antigen bound to a magnetically susceptible carrier can be used to draw hyperleukocytotic cells out of the bloodstream. The myeloproliferative disorders include polycythemia vera, chronic myeloid or myelocytic leukemia, and chronic idiopathic myelofibrosis (Merck, Op cit. Section 11, Chapter 141).

Energization of the magnets in the treatment of a hypercytotic condition such as hyperleukocytosis or polycythemia vera frequent if not continuous, the system must periodically nullify or cancel remanence. Depending upon the level of current and duration or number of energizations, a pulse or pulses of reversed current can be applied at the end each energization or applied at intervals. The degaussing of electromagnets by current reversal is incorporated into the control program to proceed automatically. If energized at the same time or a moment after the pump, the jacket acts as an impasse jacket with adjustable field strength to control penetration of the magnetically susceptible carrier particle-bound drug or other therapeutic substance into the lumen wall.

Where sludging in the circulation looms, as occurs with certain leukemias and polycythemia vera, sequential extraction jackets with the flush-line coursing through each jacket in sequence, or 'daisy-chained,' the outlet of that upstream connected to the inlet of that downstream are used. Such a train of jackets may be conceived of as a unit, as can the peristaltic jacket shown in FIG. 10. Multiple or compound electromagnet jackets such as the peristaltic jacket shown in FIG. 10 and the extraction chain-jackets shown in FIGS. 13 thru 15 can be centrally controlled as a unit or incorporate a subordinate sequential timing control module analogous to a local ganglion that regulates spinal or digestive function in a subsidiary or hierarchically subordinate relation to higher centers in the brain.

Here the ferrofluid is infused upstream through a simple junction jacket with a series of extraction jackets such as shown in FIG. 14 along the inferior vena cava, for example, to remove the iron oxide-based nanoparticles before these can produce a toxic effect. The nanoparticles are coated with dextran or polyethylene glycol to bind the drug to be carried, and if not incorporated with the initial coating, thereafter recoated with the biologically affinitive substance for the binding in turn of the bound pair with the target cells or analyte, the identity of the affinitive substance or substances depending upon that of the target cell or cells. Examples of inherent or natural affinities include, for example, the thyroid gland for iodine, the myocardium for digoxin, and adipose, or fat, tissue for benzodiazepines.

Similarly, an extraction jacket, hybrid extraction jacket, or chain thereof, all described below under Description of the Preferred Embodiments of the Invention in the section entitled Hybrid Impasse and Extraction Jackets, can extract not just magnetically susceptible bound blood cells passing through the ductus, but any bound analyte, whether previously drawn into the ductus wall and allowed to remain before a toxic effect ensues or can take hold. Moreover, a hybrid clasp extraction-magnet with trap and flush-line or chain thereof can accomplish the same for tissue within the parenchyma of an organ, whether the spleen, a lymph node, or kidney, for example, or an accessible gland, such as the thyroid, thymus, and adrenals. When the capsule of the organ is tough as to necessitate an overly large and heavy electromagnet, the substrate is prepared by stripping away this barrier.

To provide an electromagnetic clasp extraction-magnet, an electromagnetic clasp magnet without flush-line such as shown in FIG. 8 is provided with a debris collecting trap and flush-line such as shown in FIGS. 13 thru 15. A single flush-line can course from the flushing fluid supply or source reservoir in the pump-pack, through each jacket and/or clasp extraction electromagnet placed at different sites along different system ductus, and return to the same waste flushing fluid catch or reservoir in the pump-pack. When, however, the contents of the waste reservoir are to be preserved for analysis, the implant or implants distinguished thus are flushed beginning with a single supply reservoir but separate flush-lines and catch or waste reservoirs.

The availability of iron oxide particle steering and targeting implants which can be used to control the timing of bound particle infiltration into target tissue and the extraction of any residue before it poses a risk toxicity means that the simple fact of potential toxicity in the abstract may be little more than an indiscriminate generalization with little if any practical significance as would legitimately serve to discount such means. Magnetic drug targeting is not an isolated chemical issue but must complement the hardware that will actually be needed to realize its application in optimized form. Foremost in this development is the formulation of magnetically susceptible nanoparticles to selectively bond to cells and bloodborne molecules to be extracted by means of magnetic separation.

Iron oxide particles which are not formulated in response to the capabilities of practical steering and targeting implants will likely have limited application. Efficacy will eventually come down to an inherent reciprocal or dialectical relationship between the pharmacokinetics of the particle-bound drug as formulated and the function of the implants such that formulation would best have contemplated the use of the practical hardware available from the outset, the formulation for plasmapheretic extraction of anomalous antibody-agglutinating or conjugating nanoparticles mentioned above an example.

For this reason, the sooner the desiderata and preferable characteristics of practical implant hardware are clarified, the sooner will the pharmacology be able to follow in the optimal direction for the use of ferrofluid infusant particles to be used with that hardware. Ideally, the practical hardware and the chemistry are developed conjointly, each carrier-bound drug devised to complement the timing characteristics of its delivery as mediated by the hardware. For example, awareness of the ability to eliminate a residue before it can exert a toxic effect imparts significant latitude to the formulation of iron oxide drug carrier particles; the realization that toxicity beyond a certain interval need not be a deterrent is likely to remove a key chemical limitation.

Another consideration is that where the iron oxide would be taken up together with the drug it carries, the bond between the two if not broken spontaneously should be broken by a suitable solvent. As to clinical pharmacokinetics, or the action of the carrier-bound drug in the specific patient with one or more specific lesions, once the jacket implants have been placed, an initial test using the contrast dyed drug can be used to reveal the individual response. Because anatomy dictates the dimensions and disease dictates the positioning of the implants, it is the formulation of the carrier-bound drugs that has the wider latitude and will more often have to adapt for use with the practical steering means available.

For this reason, while the relationship between hardware and drugs is reciprocal, more often the drugs will have to be formulated to complement the hardware rather than the reverse. Electromagnetic extraction jackets, shown in FIGS. 13 thru 15, wherein the jackets are placed in series or a chain with a flush-line connecting the consecutive debris collecting traps can be used to remove leukocytes or an overabundance of blood cells, for example. Such a condition may be the result of a myeloproliferative disorder that would otherwise cause sludging of the blood and interfere with the production in the bone marrow of normal blood cells. In treating polycythemia vera, for example, an upstream simple junction jacket can be used to deliver myelosuppressive drug therapy (see, for example, *The Merck Manual,* 18th Edition, pages 1104-1105) concurrent with extraction.

The treatment of myeloid neoplasias is addressed below in the section entitled Apheresis. The apparatus is not intended for an atypical temporary overabundance of type blood cells as might arise in a transient reduction in relative plasma volume (see, for example, Spivak, J. L 2005. "Polycythemia and Other Myeloproliferative Diseases," in *Harrison's Principles of Internal Medicine,* New York, N.Y.: McGraw-Hill, pages 626-631) or in an infective state, or for essential thrombocytosis or thrombocythemia, for which cytaphersis by means of centrifugation has proven ineffective (ibid., page 631) but rather for chronic myeloproliferative disorders not controlled by an occasional, but not a frequent, phlebotomy and aspirin, for example, for patients with both myeloproliferative, sickle cell, and cardiovascular disease where phlebotomy is contraindicated, and for patients otherwise unable to undergo or not satisfactorily responsive to conventional treatment.

Remanence, or residual magnetization that would interfere with the special value in the use of electromagnets, in that these can be deenergized, effectively eliminating them from the carrier-bound drug steering path, is cleared (degaussed, depermed) by periodically transmitting a pulse or pulses of current through the electromagnet coils, or windings, with revered polarity, that is, in the reverse or nonfunctional direction. As indicated, in an automatic ambulatory system, the magnetically susceptible carrier particle-bound drug is infused through a simple junction jacket such as that shown in FIG. 2 placed upstream, while the flush-line is led from a clean water, flush solution or flush hydrogel supply reservoir in the pump-pack to a waste water reservoir in the pump-pack.

The number of extraction-magnets with trap and flush-line as shown in FIG. 14 required, and type, as to whether these are of the double magnet type shown in FIG. 15, depends upon the rate of residue accumulation. When larger volume extraction is required, as in a leukemia, polycythemia vera, or essential thrombocythemia, two-sided or double magnet extraction jackets such as shown in FIG. 15 are used. The magnets along either side are supplied from the same reservoir but use separate flush-lines to scrub and evacuate the successive poles and traps. Higher volume extraction generally requires supply and waste reservoirs in a pack separate from the pump-pack for less inconvenient replenishment of the flushing fluid and disposal of the effluent Whereas a permanent magnet extraction jacket incorporates a grating so that an external electromagnet can be used to draw out accumulated debris to a safe location, an electromagnetic extraction jacket uses the inmate dc electromagnet to draw the extractate (extractant) into a flush-line. A permanent magnet extraction jacket may or may not be provided with a side-entry line, that is, piped or unpiped. Since electromagnets require a power source, and for ambulatory use this means heavy batteries, the use of these is limited to intermittent applications. Permanent magnets are good for use in impasse jackets to serve as traps for preventing ferrous debris from further passage. That permanent magnets remain energized constantly—elimination of the burden of providing power notwithstanding—has disadvantages, primarily when a drug meant for uptake downstream from the magnet is diverted from its intended target.

While closely related, unpiped impasse jackets using electromagnets and peristalsis prosthesis jackets are not ductus side-entry jackets; however, electromagnetic extraction jackets, which include a side-entry are. Jacket types not covered herein are described in copending applications. Permanent magnets also afford an advantage in that these can be magnetized in any dimension, facilitating conformation to accommodate many anatomical situations. Such function is valuable where stenting miniballs were dislodged in an auto collision, for example, and the downstream prepositioning of two or more impasse jackets eliminated the potential for embolization. However, for applications requiring variability in field strength from virtually zero to the maximum, this constancy, powerless operation notwithstanding, is a detraction that stands in opposition to the controllability of electromagnets.

For applications whereby a microcontroller operates a pump to deliver different magnetically susceptible particle bound drugs intermittently, the ability to energize specific electromagnetic impasse and extraction jackets by location in a time coordinated or sequential way affords a versatility that uncontrollable magnets cannot duplicate. Since any but simple medical conditions can take advantage of this control, the object of adapting electromagnets to such use pertains to the distinct majority of applications. Both types of magnets can be incorporated into a prosthetic disorder response system. In the treatment of comorbidities, for example, the use of permanent and electromagnetic jackets may be separated by bodily system or regionally.

It is also possible to combine permanent and electromagnets in the same system by limiting the magnetic susceptibility of the drug-carrier particles so that these pass the permanent magnets but not the stronger field strength presented by the electromagnets. Rather than requiring a high permeability core with a pole that is limited in area, the permanent magnet consists of material that is intrinsically magnetic, allowing presentation of a continuous attractive surface, which can, moreover, be graduated in magnetic field strength. With either type of magnet, differential delivery to each jacket can be made dependent upon the relative magnetic susceptibility of the drug-carrier intended for each jacket, this attribute distinguishing fractions in the ferrofluid.

Where the field strength of permanent magnets is invariable, requiring varying the susceptibility of the carrier to effect a distribution that is largely statistical, that of electromagnets allows continuous variability in the strength of each magnet for any carrier without varying the carrier susceptibility. Because the permanent magnet is graduated in strength along its length, it satisfies most needs. However, the adjustability in field strength afforded by electromagnets affords greater versatility. The ability of electromagnets to adjust for susceptibility over a large range makes possible the differential distribution of the same or a different susceptible carrier particle-bound drug or other therapeutic substance.

For implantation within the body, a literal application of electromagnets to ductus-encircling jackets has the detractions that the batteries, coils, and cores pose sizes and masses that interfere with the object of incorporation into an ambulatory system. Where constancy is unnecessary and the need for attractive force intermittent as concomitant with collateral action, such as pump delivery of a drug in synchrony with the pulse, electromagnets offer controllability where permanent magnets do not. The energized or on-times of the dc electromagnets used for the various applications delineated herein are brief, so that heat or power consumption inconsistent with the object of embodiment in an ambulatory system are not problematic.

The microprocessor deenergizes the electromagnet a moment before it actuates the pump to flush through the extraction line. A segmentally distributed electromagnetic sphincteric jacket, here for sequential actuation to simulate peristalsis, is shown in FIGS. 10 thru 12. Such a jacket incorporates magnetically susceptible plates opposite each magnet pole 75 and a compressible substrate in place of the hard shell shown in FIGS. 1 thru 5. This is hybridized with an electromagnetic extraction jacket as shown in FIG. 13, used to constrict a large artery would reduce the magnetic gap from the pole 75 to the magnetically susceptible drug-carrier particles to be extracted, causing the particles to pass at a higher velocity.

FIG. 10 shows a sequential formation of electromagnets and draw-plates. Placed in encircling relation to a native esophagus with an esophageal motility disorder, the device functions as a peristaltic assist device. When the native esophagus is missing, the device encircles a pliant tube to function as a prosthetic esophagus. FIG. 11 is a cross section through the device shown in FIG. 10 which can represent one of the contraction jackets in the esophageal device, or as a single contraction jacket, can serve as an artificial sphincter, adaptable to any sphincteric function. Where both esophagus and lower esophageal sphincter are dysmotile, the upper jackets are actuated in sequence to simulate peristalsis, and the lowest (caudad) controlled to duplicate the function of a functional lower esophageal sphincter. The preparatory hiatus hernia herniorrhaphy (hernioplasty) if applicable is essential. Advantages in these electrically actuated devices compared to those passive or inflatable includes control in sequential timing and force of closure and provision of one or more accessory channels for the direct targeting of drugs to the site of treatment.

For this reason, merely applying a draw-plate and compressible substrate tube in lieu of a hard shell to an electromagnetic impasse jacket to make it a hybrid impasse and contraction jacket without at the same time introducing means for reducing the velocity, pressure, and volumetric flow rate at which the luminal contents pass the jacket or jackets is unlikely to improve the carrier particle-bound drug extraction capability. If embedded within a tacky bolus with an opiate administered to slow peristalsis, however, constricting the ductus, here, the gut, to reduce the magnetic gap at the same time that the speed of passing is reduced will increase the extraction rate.

When the drug-carrier-bound substance is a radionuclide, extraction must be thorough. Along the vascular tree (see, for example, Cherry, E. M., Maxim, P. G., and Eaton, J. K. 2010. "Particle Size, Magnetic Field, and Blood Velocity Effects on Particle Retention in Magnetic Drug Targeting," *Medical Physics* 37(1):175-182; Anor, T., Grinberg, L., Baek, H., Madsen, J. R., Jayaraman, M. V., and Kamiadakis, G. E. 2010. "Modeling of Blood Flow in Arterial Trees," *Wiley Interdisciplinary Reviews. Systems Biology and Medicine* 2(5):612-623; Haverkort, J. W., Kenjereš, S., and Kleijn, C. R. 2009. "Computational Simulations of Magnetic Particle Capture in Arterial Flows," *Annals of Biomedical Engineering* 37(12):2436-4248), the choice of a counter-inotropic drug to reduce blood velocity and pressure over an interval no longer than necessary to facilitate extraction with the aid of an impasse, contraction, or extraction jacket is contingent upon the baseline condition of the heart and the presence of collateral disease.

The controller can be programmed to wait over the interval the drug requires to take effect before undertaking any further action. For uncomplicated, that is, normotensive and normorhythmic pulsation, some reduction in the heart-rate can usually be obtained with adenosine, digoxin, and slow kinetic sodium channel blockers, such as the Vaughan Williams Class 1c drugs flecainide and propafenone (*Merck Manual of Diagnosis and Therapy*, 18th Edition 2006, Section 7, Chapter 75, "Arrythmias and Conduction Disorders," pages 677-680).

When a vena cava, for example, is already jacketed much as is the ascending aorta shown in FIG. 21, the control program delivers the drug or drugs through that jacket as a simple junction in advance by the interval before the drug or drugs will take effect before the jacket magnet is energized, whereupon the jacket is used as an electromagnetic impasse-jacket. A sequential arrangement of extraction jackets with flush-line for higher volume extraction is depicted in FIG. 14. In FIGS. 21 and 22, and in any application to a ductus where a sector or portion of the jacket would protrude into neighboring tissue, a non-full round jacket is used, the jacket spring-hinge restorative force, and if necessary suture loops, used to secure the jacket in position. The sector must be completely enclosed off within shell 4.

As shown in FIGS. 16 and 21, accessory channel 11 are available to provide postoperative as well as maintenance medication (see, for example, Sato, H., Hatzakorzian, R., Carvalho, G., Sato, T., Lattermann, R., Matsukawa, T., and Schricker, T. 2011. "High-dose Insulin Administration Improves Left Ventricular Function after Coronary Artery Bypass Graft Surgery," *Journal of Cardiothoracic and Vascular Anesthesia* 25(6):1086-1091; Carvalho, G., Pelletier, P., Albacker, T., Lachapelle, K., Joanisse, D. R., and 5 others 2011. "Cardioprotective Effects of Glucose and Insulin Administration while Maintaining Normoglycemia (GIN [glucose and insulin administration while maintaining normoglycemia] Therapy) in Patients Undergoing Coronary Artery Bypass Grafting," *Journal of Clinical Endocrinology and Metabolism* 96(5):1469-1477; Haga, K. K., McClymont, K. L., Clarke, S., Grounds, R. S., Ng, K. Y., and 4 others 2011. "The Effect of Tight Glycaemic Control, During and After Cardiac Surgery, on Patient Mortality and Morbidity: A Systematic Review and Meta-analysis," *Journal of Cardiothoracic Surgery* 6:3; Albacker, T., Carvalho, G., Schricker, T., and Lachapelle, K. 2008. "High-dose insulin Therapy Attenuates Systemic Inflammatory Response in Coronary Artery Bypass Grafting Patients," *Annals of Thoracic Surgery* 86(1):20-27), although the reasons therefor have been called into question (Hoedemaekers, C. W., Pickkers, P., Netea, M. G., van Deuren, M., and Van der Hoeven, J. G. 2005. "Intensive Insulin Therapy Does Not Alter the Inflammatory Response in Patients Undergoing Coronary Artery Bypass Grafting: A Randomized Controlled Trial [ISRCTN95608630]," *Critical Care* (london, England) 9(6):R790-R797).

Ancillary Function of a Ductus Side-Entry Jacket to Contain an Incipient or Small Aneurysm Depending upon its position, extent, and conformation, a jacket such as that shown in FIG. 21 can be used to gently reduce and medicate an incipient aneurysm of the ascending or thoracic aorta, detaining if not eliminating the need for hybrid open/endovascular reconstruction using a woven polyethylene terephthalate (Dacron®) patch, for example, which poses considerable risks, to include neurological damage which can result in death (see, for example, Voskresensky, I., Scali, S. T., Feezor, R. J., Fatima, J., Giles, K. A., Tricarico, R., Berceli, S. A., and Beck, A. W. 2017. "Outcomes of Thoracic Endovascular Aortic Repair Using Aortic Arch Chimney Stents in High-risk Patients," *Journal of Vascular Surgery* 66(1):9-20.e3; Xydas, S., Mihos, C. G., Williams, R. F., LaPietra, A., Mawad, M., Wittels, S. H., and Santana, O. 2017. "Hybrid Repair of Aortic Arch Aneurysms: A Comprehensive Review," *Journal of Thoracic Disease* 9(Supplement 7):S629-S634; Biancari, F., Mariscalco, G.2, Mariani, S., Saari, P., Satta, J., and Juvonen, T. 2016. Endovascular Treatment of Degenerative Aneurysms Involving Only the Descending Thoracic Aorta: Systematic Review and Meta-analysis," *Journal of Endovascular Therapy* 23(2):387-392; Oskowitz, A. Z., Archie, M., Archie, M., and Quinones-Baldrich, W. 2015. "Hybrid Treatment of Aortic Arch Aneurysms," *Journal of Cardiovascular Surgery* (Turin, Italy) 56(5):719-728; Maurel, B., Sobocinski, J., Spear, R., Azzaoui, R., Koussa, M., and 4 others 2015. "Current and Future Perspectives in the Repair of Aneurysms Involving the Aortic Arch," *Journal of Cardiovascular Surgery* (Turin, Italy) 56(2):197-215; Patel, H. J. and Deeb, G. M. 2013. "Open Aortic Arch. Reconstruction," *Annals of Cardiothoracic Surgery.* 2(2):181-183; Ouzounian, M., LeMaire, S. A., and Coselli, J. S. 2013. "Open Aortic Arch Repair: State-of-the-Art and Future Perspectives," *Seminars in Thoracic and Cardiovascular Surgery* 25(2):107-115; Rana, M. A., Gloviczki, P., and Oderich, G. S. 2012. "Endovascular Stenting with Open Surgery for Reconstructions of the Ascending Aorta and the Aortic Arch: A review of Indications and Results of Hybrid Techniques," *Perspectives in Vascular Surgery and Endovascular Therapy* 24(4):184-192; Szeto, W. Y. and Bavaria, J. E. 2009. "Hybrid Repair of Aortic Arch Aneurysms: Combined Open Arch Reconstruction and Endovascular Repair," *Seminars in Thoracic and Cardiovascular Surgery* 21(4):347-354).

Medication indicated for an abdominal aortic aneurysm no less applicable to an aneurysm of the ascending aorta or arch, medication for an incipient or small aneurysm includes " . . . statins, angiotensin-converting enzyme-inhibitors, antibiotics, and anti-inflammatory agents" (Miyake, T. and Morishita, R. 2009. "Pharmacological Treatment of Abdominal Aortic Aneurysm," *Cardiovascular Research* 83(3):436-443). Where magnetically susceptible micro or nanoparticle-bound drugs are used, a jacket such as that shown in FIG. 21 will additional draw the drug or drugs to the lesion (see, for example, Sivaraman, B., Swaminathan, G., Moore, L., Fox, J., Seshadri, D.1, and 5 others 2017. "Magnetically-responsive, Multifunctional Drug Delivery Nanoparticles for Elastic Matrix Regenerative Repair," *Acta Biomaterialia* 52:171-186; Camardo, A., Seshadri, D., Broekelmann, T., Mecham, R., and Ramamurthi, A. 2017. "Multifunctional, JNK[Jun-N-terminal kinase]-inhibiting Nanotherapeutics for Augmented Elastic Matrix Regenerative Repair in Aortic Aneurysms," *Drug Delivery and Translational Research September* 5; Swaminathan, G., Gadepalli, V. S., Stoilov, I., Mecham, R. P., Rao, R. R., and Ramamurthi, A. 2017. "Pro-elastogenic Effects of Bone Marrow mesenchymal Stem Cell-derived Smooth Muscle Cells on Cultured Aneurysmal Smooth Muscle Cells," *Journal of Tissue Engineering and Regenerative Medicine* 11(3): 679-693; Hu, C., Zhu, K., Li, J.2, Wang, C., and Lai, L. 2017. "Molecular Targets in Aortic Aneurysm for Establishing Novel Management Paradigms," *Journal of Thoracic Disease* 9(11):4708-4722; Jennewine, B., Fox, J., and Ramamurthi, A. 2017. "Cathepsin K-targeted Sub-micron Particles for Regenerative Repair of Vascular Elastic Matrix," *Acta Biomaterialia* 52:60-73; Swaminathan, G., Sivaraman, B., Moore, L., Zborowski, M., and Ramamurthi, A. 2016. "Magnetically Responsive Bone Marrow Mesenchymal Stem Cell-derived Smooth Muscle Cells Maintain Their Benefits to Augmenting Elastic Matrix Neoassembly," *Tissue Engineering. Part C, Methods* 22(4):301-311; Sylvester, A., Sivaraman, B., Deb, P., and Ramamurthi, A. 2013. "Nanoparticles for Localized Delivery of Hyaluronan Oligomers Towards Regenerative Repair of Elastic Matrix," *Acta Biomaterialia* 9(12):9292-9302; Sivaraman, B. and Ramamurthi, A. 2013. "Multifunctional Nanoparticles for Doxycycline Delivery Towards Localized Elastic Matrix Stabilization and Regenerative Repair," *Acta Biomaterialia* 9(5):6511-6525; Assar, A. N. 2009. "Pharmacological Therapy for Patients with Abdominal Aortic Aneurysm," *Expert Review of Cardiovascular Therapy* 7(8):999-1009).

Sequential Contraction Along a Train of Jackets in Simulation of Peristalsis

The jacket shown in FIGS. 11 and 12 is an electromagnetic impasse jacket that with a draw-plate on the opposite side of the ductus and a compressible backing instead of a hard shell such as shown in FIGS. 1 thru 5, has been converted into a contraction-jacket, configured to interact with the contents of the lumen by acting on the wall surrounding the lumen rather than attracting magnetically susceptible carriers passing through the lumen. When fluid lines as necessitate a pump-pack are not required, which is true of a sphincteric and/or peristaltic jacket, the independent module is fully implanted. While in use independently, the local control module, itself a chip microcontroller, and associated components nevertheless represent a single node of the overall prosthetic disorder response system governed by a a central microprocessor as the master control node.

The later addition of another system module, such as requires a pump-pack and fluid lines to deliver synthetic mucus and digestive enzymes, then requires the activation of another node. If the implanted or local control module is so capable, it continues to support the digestive module previously implanted, and has the new node added. When the digestive function need not be coordinated with the added function, it is most expeditious to allow the existing implant to continue to function independently. Otherwise, it is equally expeditious to place the previously implanted local control module as a node under the control of an added microcontroller in the pump-pack, or if the local controller is so capable, assign to it overall control. Later access governs the positioning of components.

Growth Accommodation

For use in prenates, neonates, infants, and small children, measures are instituted to assure that reentry will not be needed for years. This is accomplished by means of the following:

1. The foam lining of the jackets is sufficiently thick to accommodate considerable growth.

2. The spring hinges expand with increased diameter of the substrate ductus to hold the jackets snugly in place without locking, thus fixing the internal diameter.

3. The mainlines conveying blood and accessory channels or sidelines targeting drugs directly to the jacket and lines comprise extendable coiled small-caliber accordion tubes or catheters with restorative force sufficient to find the shortest span without exerting excess tension on the attachment at either end, such tubing, assuring consistency rather than a reduction in the diameter of the tubing when elongated. The routing of these lines is chosen to avoid strangulation of intervening tissue. Any resistance to extension is reported by implant detectors (see, for example, Amjadi, M., Pichitpajongkit, A., Lee, S., Ryu, S., and Park, I. 2014. "Highly Stretchable and Sensitive Strain Sensor Based on Silver Nanowire-Elastomer Nanocomposite," *American Chemical Society Nano* 8(5):5154-5163). Depending upon their detailed chemistry and if not phthalate free, then freedom from residual plasticizer, biocompatible elastic convoluted and accordion-configured tubing are likewise applicable, and 4. Intracorporeal electrical connections are not by hard-wired but rather wireless by means of 'Bluetooth' radio communication among the hierarchical control master node control microprocessor, local implanted biosensors, and microcontrollers.

For application in neonates, the intracorporeal magnetic separation dialysis or apheresis mechanism shown in FIGS. 39A and 39B must incorporate a soft rubbery, accordioned, highly stretchable, flush-line tube compatible with the flush-line peristaltic pump. However, neonates with bilateral renal agenesis, associated with Potter syndrome, or comparable congenital renal malformity are preferably managed with peritoneal dialysis followed by a transplant (see, for example, Thomas, A. N., McCullough, L. B., Chervenak, F. A., and Placencia, F. X. 2017. "Evidence-based, Ethically Justified Counseling for Fetal Bilateral Renal Agenesis,". *Journal of Perinatal Medicine* 45(5):585-594; Haeri, S., Simon, D. H., and Pillutla, K. 2017. "Serial Amnioinfusions for Fetal Pulmonary. Palliation in Fetuses with Renal Failure," *Journal of Maternal-Fetal and Neonatal Medicine* 30(2):174-176; Johnson, A. and Luks, F. I. 2014. "A Cautionary Note on New Fetal Interventions," *Obstetrics and Gynecology* 124(2 Part 2 Supplement 1):411-412; Bienstock, J. L., Birsner, M. L., Coleman, F., and Hueppchen, N. A. 2014. "Successful in Utero Intervention for Bilateral Renal Agenesis," *Obstetrics and Gynecology* 124(2 Part 2 Supplement 1):413-415).

Growth Accommodation in Solid Organ Transplantation

The design features incorporated into all ductus side-entry jackets to include intravascular valves is addressed above in the section entitled Growth Accommodation. In sudden switch organ transplantation, the circulation of the organ recipient is suddenly switched from his own defective organ to the replacement organ in an irreversibly comatose, or 'brain-dead' donor. This capability is imparted by ductus side-entry diversion jackets, or intravascular valves. Where more vessels in the recipient must be connected to the counterpart of each vessel in the donor than the operator can adjust very quickly even with the aid of one or more assistants—as when some vessels underly intervening tissue or the procedure is performed laparoscopically or robotically—each side-entry jacket intravascular diversion valve is actuated from a single switch used to simultaneously energize the plunger solenoid that advances its diversion chute into its respective lumen.

In addition to urinary diversion to an extracorporeal storage bladder, diversion jackets, to include intravascular valves and servovalves as described below in the section entitled Intravascular Valves and Servovalves, make possible solid organ transplantation with zero ischemic time, that is, with no medically significant interruption in perfusion, which is the primary source of complications in conventional transplantation. A sudden switch heart or any other solid organ transplant in a fetus (prenate), neonate, or very young patient is made more challenging than in an adult by the need to accommodate rapid growth—the same factor that limits the durability of a Rastelli procedure in a child.

By the same token, lacking mature immune systems, neonates and infants tend to tolerate heart and other organ transplantation well (see, for example, John, M. and Bailey, L. L. 2018. "Neonatal Heart Transplantation," *Annals of Cardiothoracic Surgery* 7(1):118-125). Significantly, heart transplantation in the very young often requires retransplantation in about a dozen years, but not due to unequal growth between the transplant and the body overall. Usually well short of an adult in size, this is a period over which the accommodation of growth by the means set forth will serve without the need for reentry until retransplantation.

If not, and/or the heart holds, then only the jackets and fluid lines need be replaced. This, however, does not require open surgery. Some hypertrophy of the ventricular walls notwithstanding, transplanted hearts (and organs generally) grow in step with the patient (see, for example, Frazier, O. H., Okereke, O. U., Radovancević, B., Towbin, J. A., Price, J. K., and 4 others 1995. "Heart Transplantation in an 8-month-old Girl. 10th Anniversary Report," *Texas Heart Institute Journal* 22(2):115-118; Addonizio, L. J. and Gersony, W. M. 1992. "The Transplanted Heart in the Pediatric Patient. Growth or Adaptation," *Circulation* 85(4):1624-1626; Bernstein, D., Kolla, S., Miner, M., Pitlick, P., Griffin, M., and 4 others 1992. "Cardiac Growth after Pediatric Heart Transplantation," Circulation 85(4):1433-1439).

That is, the foregoing measures 'buy' sufficient years of growth to accommodate the transplant over the time the transplant will remain functional. Thus, while a five-fold increase in every dimension from neonate to full adult (not until the twelfth year) cannot be complied with by using tubing of any kind—telescoping, accordion, convoluted, coiled, rubbery and stretchable tubing can comply for the time until a new heart will have to be placed in any case. In an adolescent having past the stage of rapid growth, the parts of the prosthetic system are not the limiting factor.

While there are notable exceptions, a heart transplanted into a prenate, neonate, or infant often requires replacement in 10 to 15 years, during which the rate of growth is considerable, leaving relatively little growth to adulthood (see, for example, John, M. ad Bailey, L. L. 2018. "Neonatal Heart Transplantation," *Annals of Cardiothoracic Surgery* 7(1):118-125; Kirklin, J. K., Carlo, W. F., and Pearce, F. B. 2016. "Current Expectations for Cardiac Transplantation in Patients with Congenital Heart Disease," *World Journal of Pediatric and Congenital Heart Surgery* 7(6):685-695; West, L. J. 2016. "Neonatal Tolerance: Applicability to Solid Organ Transplantation," *Current Opinion in Organ Transplantation* 21(1):66-73; Kirklin, J. K. 2015. "Current Challenges in Pediatric Heart Transplantation for Congenital Heart Disease," *Current Opinion in Organ Transplantation* 20(5):577-583; Thrush, P. T. and Hoffman, T. M. 2014. "Pediatric Heart Transplantation—Indications and Outcomes in the Current Era," *Journal of Thoracic Disease* 6(8):1080-1096; Copeland, H., Razzouk, A., Chinnock, R., Deming, D., Hasaniya, N., and Bailey, L. 2014. "Pediatric Recipient Survival Beyond 15 Post-heart Transplant Years: A Single-center Experience," *Annals of Thoracic Surgery* 98(6):2145-2151; Chinnock, R. E. and Bailey, L. L. 2011. "Heart Transplantation for Congenital Heart Disease in the First Year of Life," *Current Cardiology Reviews* 7(2):72-84).

For use in a fetus (prenate), neonate, or an infant, the diversion jackets and lines have therefore been devised to be left in place over this period. However, as clinical judgment determines, during this period, the free transected ends of the arteries and veins closed off at the time of the transplant can be anastomosed. To allow the continued targeting delivery of drugs to the anastomoses, the jackets, drug feedlines, and small port at the body surface are left in place. An advantage in detaining anastomosis is that the size of a heart for orthotopic placement can be slightly smaller or larger as does not allow the vessels to be anastomosed in-line or axially to those of the recipient; instead, the tubing of the valved appliance allows some bending to achieve connection.

As a result, when the need therefor is urgent, the availability of a replacement heart is liberalized to allow use of a somewhat smaller or larger heart or one taken from a patient more discrepant in size and weight (see, for example, Li, P., Dong, N., Zhao, Y., and Gao, S. 2016. "Successful Extracorporeal Membrane Oxygenation (ECMO) Support in Two Pediatric Heart Transplant Patients with Extreme Donor/Recipient Size Mismatch," *Journal of Thoracic Disease* 8(6):1329-1332; Patel, N. D., Weiss, E. S., Nwakanma, L. U., Russell, S. D., Baumgartner, W. A., Shah, A. S., and Conte, J. V. 2008. "Impact of Donor-to-recipient Weight Ratio on Survival after Heart Transplantation: Analysis of the United Network for Organ Sharing Database," *Circulation* 118(14 Supplement):S83-S88; Jeevanandam, V., Mather, P., Furukawa, S., Todd, B., Regillo, T., and 3 others 1994. "Adult Orthotopic Heart Transplantation Using Undersized Pediatric Donor Hearts. Technique and Postoperative Management," *Circulation* 90(5 Part 2):1174-1177; Morley, D., Boigon, M., Fesniak, H., Brubaker, P., Walter, J., and 5 others 1993. "Posttransplantation Hemodynamics and Exercise Function are not Affected by Body-size Matching of Donor and Recipient," *Journal of Heart and Lung Transplantation* 12(5):770-778; Costanzo-Nordin, M. R., Liao, Y. L., Grusk, B. B., O'Sullivan, E. J., Cooper, R. S., and 5 plus others 1991. "Oversizing of Donor Hearts: Beneficial or Detrimental?," *Journal of Heart and Lung Transplantation* 10(5 Part 1):717-730).

Application of Fully and Partially Implanted Systems

Full, or closed-skin, implantation is intended for use in patients with chronic single or multiple morbidities, and following use in organ transplantation, system components are left in place to target and so limit the exposure of other tissue and thus side effects to immunosuppressive and other drugs. Long-term but not lifelong disease warrants the implantation of jacket and/or connectors, drug feedlines, and biosensors, usually incorporated into the jackets or connectors, with the microprocessor, power source, and pumps relegated to a body pack worn about the waist or cinched about a thigh.

When no longer needed, the body pack is removed the intracorporeal components, completely biocompatible if not absorbable, left inside the body. Another circumstance justifying the use of an implanted automatic disorder response system to directly target drugs to lesions or nidi is when the patient suffers adverse side effects from a drug or drugs when are allowed to circulate. Yet another circumstance justifying fully internalized direct pipe-targeting is when a drug is too costly to administer in the dose required when dispersed or dissolved throughout the circulation.

For in-hospital use, a central line such as a central venous catheter, can be placed percutaneously as not to justify even the relatively minor incision and dissection necessary to place a ductus side-entry jacket. For relatively short-term use, the indwelling catheter serves its purpose. However, a long-term central line for recurrent connection for dialysis or to allow the patient to engage in athletics, for example, must be secure and leak-free—not left dangling outside the chest. Once no longer needed, reentry to explant the implanted components is unnecessary. If the term for use is known at the outset, the use of absorbable materials is maximized.

Except for frequent high-volume flow applications such as the need for an opening to pass urine into an external collection bladder, the jacket junction allows the skin to be completely closed, entry and exit openings provided in a subcutaneously, or subdermally, implanted port. Conventional insertion with the aid of ultrasonography notwithstanding, direct visual placement of the jacket and line substantially eliminates the risks associated with conventional placement, to include mispositioning, pneumothorax, infection, thrombosis, hemorrhage and hematoma, as well as dislodgement. Stability and seclusion behind fully closed skin make such a line more resistant to infection from extracorporeal microbiota.

In a patient with one or more chronic morbidities, a prosthetic ambulatory adaptive disorder response system will in most instances be fully implanted, imposing the object then, to so devise the system that it will never require reentry, or revision. Compresent morbidities usually interactive to some extent if not directly related, the overall object is to achieve automatic treatment through an apportionment of therapy among the morbid components as will yield the best overall outcome, that is, as will best reinstate homeostasis across the set of disorders. When morbidity or comorbidty are not expected to persist beyond a certain stage of life, typically youth, the extent of implantation is reduced to the minimum, so that only system components which must be implanted are—jackets, nonjacketing connectors, fluid lines, electrical lines (or wireless intracorporeal radio transmission by Bluetooth), and sensors.

While telemetric or wireless data transmission from the implants will still be of value, eliminated from implantation are the components needed for transdermal drug delivery and power transfer. The relegation of nonimplanted components to an extracorporeal, or external, body pack includes the hierarchical master node microprocessor, subordinate level node microcontrollers along each morbidity channel sent to the microprocessor, the power source, and external drug reservoirs or storage canisters, and pumps. This application focuses on the extracorporeal positioning of these components, while copending application Ser. No. 14/998,495 focuses on intracorporeal positioning, and Ser. No. addresses both.

Transdermal Drug Replenishment and Power Transfer for Full Implantation

Transdermal Drug Replenishment

Full implantation does away with the need for an external (extracorporeal) power, control, and pump pack, attached to the patient waist belt or strapped about a thigh. While such a pump pack little restricts freedom of movement, it still counts as an impediment. Broadly, an external pump pack has the benefit of storing more medication and a higher capacity power source, much reducing the intervals between drug replenishment and recharging of the battery but poses a nuisance weight which may be difficult to keep out of sight. This matters little in a clinic or convalescent center; however, the goal of full implantation is to act as an automatic adaptive disorder response system with little if any imposition upon patient life style.

Full implantation then, requires the expeditious replenishment of drugs and power. Drug replenishment is quickly accomplished with a multiple hypodermic needle or transdermal jet injection head where each injector is connected to a separate source canister. As addressed below in the section entitled Description of the Preferred Embodiments of the Invention. Body Surface Ports, in an epidermal port, an individual injection point is identified on the spring-hinged cap covering the opening. In contrast, in a subdermal port, the injection point or points are indicated by tiny tattooed arrows. Exceptionally, subdermal injection openings can be indicated by holes in an epidermal faceplate.

Multiple hypodermic needle or transdermal jet injection heads are used with subdermal ports and oriented relative to the subdermal openings into the respective fluid lines by a tiny tattooed arrow orientation indicator, or 'key.' Whether epidermal or through a subdermal opening, injection is either directly into an accessory channel or through a short catheteric tube and into a small flat drug reservoir respective of each accessory channel, such reservoirs usually positioned subdermally in the pectoral region. Dosing is either manual according to the calibration on the hypodermic syringe or as metered by the microcontroller implant operating the outlet pump on the drug reservoir. More specifically, in a prosthetic disorder response system, the administration of drugs proceeds automatically under the control of an implanted sensor-driven, prescription-programmed microprocessor, which directs the release of drugs by actuating; the small pump at the outlet of the reservoir.

To assure the accurate release of drugs, the reservoirs are never relegated to gravity feed but rather actively operated by pump energization or activation signals received from the microprocessor. The reservoir outlets are connected to catheters that course to the ductus side-entry and/or impasse-jackets and if required, nonjacketing side-entry connectors as described in copending application Ser. No. 14/998,495, published as 20170197028. These jackets and connectors are essential for such a fully implanted system to automatically treat one or comorbid chronic conditions over an indefinite period. Dose accuracy is also supported by commencing drug delivery with the reservoirs filled.

To accomplish this during replenishment, the pumps at the reservoir outlets are stabilized to prevent outflow, and each injector of the multiple hypodermic needle or transdermal jet injection head is prevented from overfilling its respective reservoir by a cutoff actuated when the supply canister pump meets with the cutoff-triggering level of resistance. The reservoirs are appropriately sized for the dose volume and frequency of each. Use over an indefinite period is made possible by two factors. The first is that fastening to the substrate ductus or tissue surface is by means which do not injure the fine nerves and vessels at the adventitial or tissue surface. Without such means, neuro- and atherodegenerative changes are induced in the substrate tissue and progress quickly, causing serious complications that necessitate prompt removal, or explantation.

The other factor is that the catheters, or fluid drug feedlines, jackets, and connectors are provided with a service or accessory channel, a sideline, (FIGS. 1 thru 6 and 16 thru 22, part number 11) which allow the direct delivery into these of maintenance substances such as anticoagulants, antimicrobials, and anti-inflammatories to keep these parts clean and sterile, as well as adjunctive medication as necessary. The accessory channels supply substances just as do the primary or mainlines—by coinjection into respective situated openings in the subdermally positioned port with reservoirs and outlet pumps where the pump outlet lines are the accessory channels. In most instances, transdermal skin patches are disallowed as not directly controllable in drug delivery and the rate thereof.

Transdermal Power Transfer

While there are numerous methods for providing power by attaching small current-generating mechanisms to moving parts of the body (see, for example, Hannan, M. A., Mutashar, S., Samad, S. A., and Hussain, A. 2014. "Energy Harvesting for the Implantable Biomedical Devices: Issues and Challenges," *Biomedical Engineering Online* 13:79; Mitcheson, P. D. 2010. "Energy Harvesting for Human Wearable and Implantable Bio-sensors," *Proceedings of the Annual International Conference of the Institute of Electrical and Electronics Engineers Engineering in Medicine and Biology Society* 2010:3432-3436), such as the ankles, a fully implanted disorder response system requires complete consistency and dependability of current delivery, and for portability, this means a rechargeable battery or power supply.

Transdermal or transcutaneous power transfer has now acceded to the status of medical dependability (see, for example, Bocan, K. N., Mickle, M. H., and Sejdic, E. 2017. "Tissue Variability and Antennas for Power Transfer to Wireless Implantable Medical Devices," *Institute of Electrical and Electronics Engineers Journal of Translational Engineering in Health and Medicine* 5:2700111; Ahnood, A., Fox, K. E., Apollo, N. V., Lohrmann, A., Garrett, D. J., and 7 others 2016. "Diamond Encapsulated Photovoltaics for Transdermal Power Delivery," *Biosensors abd Bioelectronics* 77:589-597; Bocan, K. N. and Sejdić, E. 2016. "Adaptive Transcutaneous Power Transfer to Implantable Devices: A State of the Art Review," *Sensors* (Basel, Switzerland) 16(3). pii: E393; Ben Amar, A., Kouki, A. B., and Cao, H. 2015. "Power Approaches for Implantable Medical Devices," *Sensors* (Basel, Switzerland) 15(11):28889-28914; RamRakhyani, A. K. and Lazzi, G. 2014. "Interference-free Wireless Power Transfer System for Biomedical Implants Using Multi-coil Approach," *Electronics Letters* 50(12) 853-855; Meng, C., Gall, O. Z., and Irazoqui, P. P. 2013. "A Flexible Super-capacitive Solid-state Power Supply for Miniature Implantable Medical Devices," *Biomedical Microdevices* 15(6):973-983; Poon, A. S. 2009. "Miniaturization of Implantable Wireless Power Receiver," *Conference Proceedings Institute of Electrical and Electronics Engineers Engineering in Medicine and Biology Society:* 3217-3220).

Types of Ductus Side-Entry Jackets

The different types of ductus side-entry jackets are described in greater detail in the section 5 below entitled Description of the Preferred Embodiments of the Invention, which includes jackets used less often, such as double-arm; sphincteric; and choke-jackets. The table below summarizes the types of jackets with direct line feed (piping, side-entry) as addressed herein and those without side entry covered in copending application Ser. No. 13/694,835, published as US 20140163664. Basic vascular and other ductus and impasse side-entry connection jackets conform to any of ten basic configurations with overall dimensions and part sizes proportional to the anatomical structure to be treated.

These are:

1. Simple junction jackets, unmagnetized and without a radiation shield that is, a basic ductus side-entry joining connector or junction with one or more radially and/or longitudinally separated side-entry connectors.

2. Jackets with nonelongated or local nongradient magnet to treat a fully spanned lesion encircled by the jacket.

3. Jackets with elongated or longitudinally extended gradient-magnetized magnet.

4. Jackets with elongated or longitudinally extended gradient-magnetized magnet and overlying tungsten heavy alloy radiation shield.

5. Jackets with radiation shield but without magnet.

6. Sphincteric jackets such as that shown in FIG. 11 place a permanent magnet and electromagnet in opposition to allow a plate to compress the lumen.

7. Peristaltic chain-jackets such as that shown in FIG. 10 queue sphincteric jackets for sequential contraction along a synthetic tube to simulate peristaltic function as a prosthetic esophagus or segment of gut, or for placement about a segment along the native digestive tract to serve as a motor assist device.

8. Choke jackets are continuously adjustable intravascular servovalves which can increase or decrease blood pressure at a level along a vessel.

9. Double-arm jackets expedite the insertion of cabled devices both in the antegrade and retrograde directions and are configured to allow the pole of an electromagnet to be positioned between the arms.

10. Provided with a shield that disintegrates spontaneously or in response to positive action such as the application of heat, a solvent, or both.

While the jackets accord with the caliber of the ductus to be encircled, most other components are kept as standardized as possible. The diameter or caliber of a jacket is dictated by the ductus it is to encircle. Combination (hybrid, special-purpose) jackets with a fluid side-entry line added to an electromagnetic extraction, contraction, or multiple electromagnet contraction or peristaltic jacket, for example, are reserved for sites where the anatomy does not afford sufficient space to place more than a single jacket without encroaching upon neighboring tissue. To place small jackets requires magnification, and those very small a microsurgical stereoscopic or binocular microscope.

As a matter of terminology, impasse-jackets, permanent or direct current electromagnetic, are intended to draw a magnetically susceptible particle-bound drug or other therapeutic substance up against the internal surface of the wall surrounding the lumen, penetration into the wall contingent upon the strength of the magnetic field. Permanent magnet impasse jackets which incorporate an extraction grating allow an extracorporeal dc electromagnet to draw the extractate (extractant) out of the ductus but generally lack sufficient strength to act as extraction jackets without such assistance. Where these can extract the analyte, such jackets may be referred to as extraction-jackets. Extraction jackets proper are electromagnetic, and since the field strength can be varied from zero to a maximum, these can also be used as impasse-jackets. Various combinations of side-entry line and dc electromagnet-incorporating jackets are addressed below.

TABLE 1

Types of ductus side-entry jackets Those magnetic incorporate a permanent magnet layer within the jacket shell, or an electromagnet; or the jackets are molded or machined from a material impregnated with permanent magnets. Ordinarily, all piped jackets incorporate a service, or accessory, channel.

|  |  | Magnetized | |
|---|---|---|---|
|  | Unmagnetized | PERMANENT MAGNET | ELECTROMAGNETIC |
| Unpiped | CLASP-JACKETS<br>DOUBLE-ARM | IMPASSE-JACKETS<br>EXTRACTION JACKETS<br>STENT-JACKETS<br>CLASP- MAGNETS | IMPASSE-JACKETS<br>CONTRACTION-JACKETS<br>DIVERSION JACKETS<br>DOUBLE-ARM<br>CHOKE-JACKETS<br>EXTRACTION JACKETS<br>CHAIN-JACKETS<br>SPHINCTERIC JACKETS |
| Piped | SIMPLE JUNCTION JACKETS<br>DIVERSION JACKETS | IMPASSE-JACKETS<br>PIPED STENT-JACKETS<br>CONTRACTION-JACKETS | IMPASSE-JACKETS<br>EXTRACTION-JACKETS<br>CONTRACTION-JACKETS<br>DIVERSION JACKETS<br>DOUBLE-ARM<br>CHOKE-JACKETS<br>CHAIN-JACKETS<br>SPHINCTERIC JACKETS |

Most involve the detection of a condition or status programmed to automatically initiate the targeted delivery of one or more drugs and/or other therapeutic substances, while others necessitate the continuous extraction of an endogenous or exogenous (iatrogenic) chemical or cellular analyte from the bloodstream, for example. The disease treated may include related comorbidities, such as sequelae or complications which can be anticipated, the polynesic expressions of a single disease, or unrelated intercurrent conditions or superventions. The treatment of dysmotility in the digestive tract, for example, can be coordinated with concurrent treatment of associated symptoms in ancillary digestive organs, such as the pancreas and gall bladder.

A jacket that combines the features of a pliant contraction jacket with an opposing magnetically susceptible drawplate, such as shown in FIGS. 11 and 12, those of the extraction jacket with collection chamber or trap, as shown in FIG. 13, and a side-connector, as shown in FIGS. 1 and 2, represents a triple combination jacket for which, due to their small size, potential applications would likely be limited to neonates and small pets. Magnetized debris adherent to the pole, the trap is mostly for any nonmagnetic debris that enters with the magnetic debris. Since the extractate is drawn to the pole, the trap of an extraction-electromagnet serves primarily to collect fluid drawn out with the extractate, which is then flushed away to a waste reservoir in the pump-pack, as will be addressed.

See pp. 80-100 of pat2a1 search.pdf and Organize all Jacket Types Under this Heading and Add to Table 1.

Combination type jackets may also be justified when drug delivery and another jacket function would best be delivered at the same level or when to place numerous separate, functionally distinct jackets in a frail patient with multiple comorbidities could dangerously extend the intraoperative time under general anesthesia, for example. Radiation shielded but unmagnetized side-entry connection jackets can be used to pass through but are incapable of participating in the uptake of magnetically nonsusceptible therapeutic substances whether radioactive or not. Other than to provide a shielded junction for the radionuclide to pass through, a jacket with a shield but not a magnet is not functional as not serving to draw a radionuclide bonded to a magnetically susceptible carrier into the luminal wall.

A simple junction jacket with radiation shielding but not magnetization assumes that the jacketed conduit will be shielded to an uptake terminus. For example, in FIG. 21, to treat a rare primary unmetastasized tumor within the cardium, lines 11, the jacket, side-connectors 6, and lines 13, here prosthetic right and left coronary end-arteries (but the same would apply in the application shown in FIG. 16 with native vessels), would all require shielding. For uniform uptake of the susceptible particles along the length of the jacket, the magnet is usually increased in magnetic field strength in the antegrade or downstream direction. As an optional alternative, the particulate can be prepared in fractions of varying magnetic susceptibility.

Unless radiation shielded, the jacket can incorporate perforations for adventitial or fibrosal gas exchange with its internal milieu. However, if the radiation shielding is disintegrable as shown in FIG. 6, the perforations are covered over and remain following disintegration. It long known that complete envelopment of an arterial segment within a jacket that lacks perforations immediately induces atherosclerotic degeneration (see, for example, De Meyer, G. R. Y., Van Put, D. J., Kockx, M. M., Van Schil, P., Bosmans, R., Bult, H., Buyssens, N., Vanmaele, R., and Herman, A. G. 1997. "Possible Mechanisms of Collar-induced Intimal Thickening," *Arteriosclerosis, Thrombosis, and Vascular Biology* 17(10):1924-1930) and that a radiation shield for use with radionuclides rules out perforations, the use of a radiation shield imposes requirements as to duration of use and the addition of drugs to suppress atherosclerosis. Shielded side-entry jackets and lines are intended for use with localized tumors in the lumen wall, for example.

Suppression and Extraction of Tumor Shed Malignant Circulating 'Daughter' Cells

However, if detected early, a femoral Ewing sarcoma of a long bone, for example, may be treated by jacketing the diaphyseal nutrient arteries and/or cutting through the compact bone and into the medullary cavity to directly deliver chemotherapeutic drugs to the intramural primary tumor at higher levels than can be circulated, and if the jacket is shielded, a radionuclide; however, due to the pronounced propensity with this diagnosis favoring metastasis, a background systemic dose is imperative. Advantage can also be taken of the graft versus tumor effect by using a simple junction type side-entry jacket without magnet layer such as shown in FIGS. 1 and 2 to deliver harvested hematopoietic stem cells (see, for example, Kolb, H. J. 2008. "Graft-versus-leukemia Effects of Transplantation and Donor Lymphocytes," *Blood* 112(12):4371-4383).

Provided abnormal cells can be differentially bound to a susceptible carrier, an electromagnetic extraction jacket with flush-line as shown in FIGS. 13 thru 15, 39A, and 39B used as for leukapheresis addressed below in the section entitled Ambulatory Magnetic Separation Leukapheresis, or an electromagnetic clasp-magnet with flush-line directed at the central venous sinus can be used to intercept and extract malignant cells from the circulation, thus assisting the circulated drug to suppress metastasis. In such therapy, it is significant that the systemic dose can be reduced. In cytapheresis and hemodialysis, the implanted system promptly initiates the removal of the target analyte upon detection by biosensors incorporated into the jackets, not a day or two later in a clinic.

The systemic approach is to allow a significant reduction in the dose of antineoplastic chemotherapeutics and beamed radiation thus avoiding the bulk of adverse side effects these provoke by directly targeting the mother tumor. In addition to exercising surveillance over the blood flowing past the malignant cell extraction chain and other jackets, the bulk of the chemotherapeutics are pipe-targeted directly at the tumor. The foregoing is thus not limited to premetastatic disease, preserving the value in resection of the primary tumor.

Use of an Extracorporeal Power, Control, and Drug Delivery Body Pack

In a system with an extracorporeal power, control, and drug turret and pump pack rather than one fully implanted and providing a port at the body surface, access to the lumen of the ductus is through the lower of two entry holes at the back of the pump-pack, through the lower arm of the inline port or clean-out shown in FIG. 30, up through the pump line seen as part number 13 in FIGS. 29, 31, and 32, and through the side entry connector. The irrigation continues as a cabled device is passed through or removed from the opening in the side of the ductus. Ordinarily, incremental delivery is apportioned by means of a valve of the type used in a secondary intravenous line intravenous piggyback port, or a one arm inline port or clean-out of the type shown in FIG. 30. Further to minimize leakage, the fluid column in the line leading to the side-entry opening or the water-jacket inlet can include a gelling or thickening agent.

Any of these basic types can be provided with more than a single side-entry connector at any radius about the circumference or separation along the longitudinal axis, and each side-entry connector can have one or more fluid conduction or water-jacket inlets for further use as service channels. In general jackets to be positioned along the vascular tree or other relatively thin-walled ductus, such as the ureters, are placed using only the cutting force of a vacuum, without circle-cutting action, with a medicated tacky hydrogel used to quench bleeding, whereas thick-walled ductus usually require rotation of the side-connector as well, with water or a medicated tacky hydrogel used.

Subsidiary sidelines or conduits, shown as part number 11 in the drawing figures, are not only useful during placement to deliver the fluid used to irrigate the insertion but remain usable thereafter for the delivery of drugs or other therapeutic substances or sensor leads to the synthetic or tissue-engineered conduit generated from autologous cells retained within the side-connector, part number 6 in the drawings. Fluid conduction or water-jacket inlet lines are normally smaller in diameter than the side-entry connector these support. To prevent the entry of fluids passed through the side-entry connector or one of its inlets into the other inlets, the inlets are kept filled with gel until used. Magnetized side-entry connection jackets will pass through without taking up magnetically nonsusceptible therapeutic substances but if any of these are radioactive, the jacket must also incorporate a radiation shield.

To avoid a need to reenter, the selection of a side-entry connection jacket therefore takes into account the prospective scope of type therapeutic substances and the rate of delivery of each that might reasonably become necessary during treatment, and a jacket with the necessary elements to cover the various contingencies, to include the number of water-jacket inlet lines or service channels is placed. The inlets are piped to a port implanted at the body surface that incorporates the number and gauge of the sockets required. Unless a comprehensively configured jacket would encroach on neighboring tissue, overspecification involves only added expense. Distinctions as to shield disintegration that is spontaneous, thermal, chemical, electrical, or combinations thereof are not considered of such import as to define additional jacket types.

The incorporation of a permanent magnet and/or radiation shield is consistent with a need for uniform uptake over the length of the jacket of the magnetically susceptible particle bound drug or radionuclide. A more uniform uptake with electromagnets necessitates the use of more than one. When the magnetism need not be completely stopped, concentrated uptake at the electromagnet pole can be ameliorated by placing the pole through an opening through an otherwise ordinary permanent magnet layer. The outer surface of all jacket types is made as rounded, smooth, and unobtrusive for neighboring tissue as possible. To lend support when the patient is recumbent, jackets that pose a weight problem may require the construction of a horizontally disposed tissue sling or harness. To include extension for prevention, shielded and unshielded magnetized jackets alike are made no longer than is necessary to provide a secure and leak free synthetic-to-native or native-to-synthetic conduit junction.

Ductus-encircling jackets with a radiation shield and with or without a subjacent magnet can also be used to shield a segment of the encircled ductus from radiation directed at neighboring tissue. Shielding is limited by the mass of shielding material which can be incorporated without encroaching upon neighboring tissue or causing the patient discomfort absent means of suspension. The jackets shown in FIGS. 13 thru 15 represent one of four types of electromagnetic ductus jackets, piped and unpiped impasse-jackets, piped extraction jackets, and unpiped contraction-jackets, specifically, the type configured to interact with the contents rather than with the wall surrounding the lumen.

Piped contraction jackets as depicted in FIGS. 11 and 12 and piped extraction jackets as depicted in FIGS. 13 and 14 that deliver susceptible particle bound drugs or other therapeutic substances and constrict the lumen to reduce the gap in the magnetic circuit are not considered to have potential applications as would prompt defining these as separate types of jackets rather than modifications of those so defined. Automatic parenteral administration is usually through an upstream simple junction type jacket as shown in FIGS. 1 and 2 or through the oral route. Another basic type, the electromagnetic impasse jacket without a side-entry line, and therefore, not a side-entry or piped jacket, is configured to draw a ductus contents-borne magnetically susceptible particle bound therapeutic substance into the wall surrounding the lumen.

A third type, analogous to the jackets shown with a permanent magnetic layer in FIGS. 3 and 4, adds a side-entry line to an electromagnetic impasse-jacket. A combination type jacket not mentioned above combines the configuration shown in FIGS. 13 and 15 with an electromagnetic impasse-jacket, allowing take-up into the wall of the magnetically susceptible particle bound therapeutic substance before the more powerful extraction electromagnet removes any residue. In such a jacket, the less powerful impasse section (portion, segment) precedes the extraction magnet. Another type of electromagnetic ductus jacket, used with radiation shielding to expose the lining of the lumen to a radionuclide, for example, combines a side-entry line with an extraction magnet, yet another with proximal side-entry line, and distal extraction magnet interposed by an impasse segment. As to further permutations, permanent and electrical magnets are not used in the same jacket, and the impasse section or segment of a jacket with or without a side-entry line precedes the extraction magnet.

In the train of extraction jackets shown in FIG. 14, only the flush-line is connected in series; to allow the jackets to operate sequentially, the electrical connection of the controller to each jacket must be separate and direct. For most purposes, sequential operation of the jackets is consecutive in line. Otherwise, each can be operated in any sequence vis a vis the others. The sequence in which the magnets are energized can respond to sensor feedback, as will be addressed. Unlike the permanent clasp-magnets addressed in copending application Ser. No. 13/694,835 which draw drug-carrier bound particles continuously, a clasp-electromagnet as shown in FIGS. 8 and 9, fastened to the outer capsule or fibrosal tunic of a target bodily organ, allows the field strength to be turned on, off, or adjusted by the system master microcontroller.

FIGS. 8 and 9 show the clasp-magnet, permanent or electromagnetic, with the pole facing the prongs to engage tissue in facing relation (face-mounted; forward-mounted); however, clasp-magnets, permanent or electromagnetic, can be mounted to face sideways, that is, side-mounted; or backwards to face away from the tissue to which the magnet is engaged (rear-mounted). A compound clasp-magnet mounts multiple magnets on a common mounting. This is done with permanent magnets to adjust the orientation of each magnet by bending the mounting as necessary and with electromagnets for the same reason or to allow a linear array to be energized in a particular sequence. When the clasp-magnet, permanent or electromagnetic, individual or compound, must be mounted at an angle or the individual magnets angled in relation to one another, the mounting plate with integral prongs is metal to allow bending as necessary; otherwise, it is made of polyether ether ketone (PEEK) or a similar tissue compatible polymer.

Electromagnetic clasp-magnets can be used, for example, to detain passage of a superparamagnetic particle carrier-bound drug at a certain level along the ductus thereby increasing uptake in the wall surrounding the lumen, to boost the attractive force of an impasse jacket that cannot be fit into the space available, or to boost and so bias the attractive force in a certain direction to treat an eccentric lesion. Provided an eccentric lesion is near-sided, an electromagnetic clasp-magnet can eliminate the need to encircle a tunneling coronary artery or other ductus which is resistant to dissection and difficult to encircle with an impasse-jacket.

For epicardial application, for example, where the beating heart would cause a proud-standing implant fastened to the visceral pericardium to abrade against the parietal pericardium, the electromagnetic clasp-magnet must be made unobtrusive with a squat core and profile, large number of coil, or winding, turns, and a smooth and rounded cover or cap. At a bifurcation, such as the division of the common into the external and internal carotids or the thoracic aorta into the common iliac arteries, the carriers can be diverted to pass along the one route rather than the other. Such magnets, separate from but under joint coordinated control with drug delivery through the jacket or jackets, allows accelerated penetration into or through the parenchyma or the cessation of attraction as necessary.

With both clasp-magnets and electromagnetic impasse-jackets, the ability to surge the attractive force allows forcible penetration of the carried drug or other affinate into the wall surrounding the lumen on a sudden pulsed or extended basis. The coil (solenoid, winding) can be configured to accommodate different anatomical spaces. The mounting for an electromagnetic clasp-magnet, or patch-magnet is the same as for the permanent magnet shown in FIGS. 25 and 26 of copending application Ser. No. 13/694, 835. Referring now to FIGS. 13 and 14, because the electromagnet-incorporating jackets can be sequentially energized, to include consecutively along the ductus, the same train of jackets can be used for magnetically susceptible carrier bound drug delivery at an inception level along the ductus respective of any in the set without intrinsic nonaffinitive or magnetically coerced uptake until the first energized jacket is approached.

The 'skip lesions' of Crohn's disease can be treated by simultaneously or sequentially energizing the jackets to take up a carrier particle-bound steroid, for example, and the jacket encircling each lesion can be energized to take up the drug or drugs in proportion to the severity of the respective lesion. Adjustment of the field strength allows the drug to be drawn up against the lumen wall, drawn radially outward through the wall to the depth required, or completely extracted. With sequential energization, the same arrangement allows high leukocyte count blood to be remediated by allowing the extractate to be apportioned among the extraction jackets, thus accomplishing ambulatory leukaperesis through magnetic separation while avoiding clogging. 2.

Because such applications are intended to be automatic and ambulatory, upstream infusion of the ferrofluid is through a simple junction side-entry jacket of the kind shown in FIG. Closely related to magnetized ductus side-entry or piped impasse jackets are nonpiped electromagnetic impasse jackets and compound or multi-electromagnet peristalsis jackets. Positioned opposite magnetically susceptible plates as shown in FIGS. 10 and 11, an appropriately positioned set of clasp-electromagnets as shown in FIGS. 8 and 9 can be used to reinstate impaired peristalsis in the capsule of an organ, primarily the kidney. The plates are usually die cut from a thin ferromagnetic stainless steel sheet stock, deburred, and if necessary, edged with a polymeric border to prevent incisions into the substrate ductus, whether native with weakened intrinsic motile function or prosthetic.

FIG. 10 shows a multi-electromagnet jacket mounting magnets without integrated extraction trap and flush-line in an independent jacket as are those depicted in FIGS. 13 thru 15. Spacing and consecutively energizing clasp-electromagnets such as shown in FIGS. 8 and 9 with opposing plates at points along the surface of an organ, or encircling a ductus with a multi-electromagnet jacket such as shown in FIGS. 10 and 11 allows assisting impaired peristalsis or the imparting of peristalsis to a prosthetic or graft ductus. Because both prostheses made of artificial materials and transplanted segments, even autologous, tend to fail at the anastomoses or can be sustained only with immunosuppressant drugs that place the patient at life-long risk for other disease, such prostheses and grafts are better joined to native tissue by means of simple junction jackets of the kind shown in FIGS. 2, 21, and 22.

These not only avoid direct contact between native and prosthetic or graft ductus but allow the direct delivery of medication to the junctions, and if the graft consists of native or engineered tissue, the graft segment. Contraction-jackets are intended for imparting simulated or intrinsic-equivalent normotensive motility to tissue-engineered graft segments of digestive, urinary, and reproductive tract prostheses and native segments which due to disease or innate deficiency, require peristaltic or sphintreric function or functional reinforcement respectively. When generated from autologous cells, normally peristaltic structures elude rejection but fail to develop normal motile function.

Engineered Digestive Tract Segments

While one report is encouraging with respect to lower and not necessarily translatable to higher mammals (Sjöqvist, S., Jungebluth, P., Lim, M. L., Haag, J. C., Gustafsson, Y., Lemon, G., Baiguera, S., and 16 others 2014. "Experimental Orthotopic Transplantation of a Tissue-engineered Oesophagus in Rats," *Nature Communications* 5:3562), tissue engineered esophagi by and large have tended to stenose, and exhibit other deficits (see, for example, Luc, G., Durand, M., Collet, D., Guillemot, F., and Bordenave, L. 2014. "Esophageal Tissue Engineering," *Expert Review of Medical Devices* 11(2):225-241; Maghsoudlou, P., Eaton, S., and De Coppi, P. 2014. "Tissue Engineering of the Esophagus," *Seminars in Pediatric Surgery* 23(3):127-134. Totonelli, G., Maghsoudlou, P., Fishman, J. M., Orlando, G., Ansari, T., Sibbons, P., Birchall, M. A., Pierro, A., Eaton, S., and De Coppi, P. 2012. "Esophageal Tissue Engineering: A New Approach for Esophageal Replacement," *World Journal of Gastroenterology* 18(47):6900-6907; Saxena, A. K. 2014. "Esophagus Tissue Engineering: Designing and Crafting the Components for the "Hybrid Construct" Approach," *European Journal of Pediatric Surgery* 24(3):246-262).

Engineered vascular tissue does, however, exhibit the capacity to regenerate when injured and grow (see, for example, Cummings, I., George, S., Kelm, J., Schmidt, D., Emmert, M. Y., Weber, B., Zünd, G., and Hoerstrup, S. P. 2012. "Tissue-engineered Vascular Graft Remodeling in a Growing Lamb Model: Expression of Matrix Metalloproteinases," *European Journal of Cardiothoracic Surgery* 2012 41(1):167-172; Kelm, J. M., Emmert, M. Y, Zürcher, A., Schmidt, D., Begus Nahrmann, Y., Rudolph, K. L., Weber, B., and 8 others 2012. "Functionality, Growth and Accelerated Aging of Tissue Engineered Living Autologous Vascular Grafts," *Biomaterials* 33(33):8277-8285; Boerckela, J. D., Uhriga, B. A., Willetta, N. J., Huebschb, N., and Guldberga, R. E. 2011, "Mechanical Regulation of Vascular Growth and Tissue Regeneration In Vivo" *Proceedings of the National Academy of Sciences of the United States* 108(37): E674-E680; Cho, S. W., Kim, I. K., Kang, J. M., Song, K. W., Kim, H. S., Park, C. H., Yoo, K. J., and Kim, B. S. 2009. "Evidence for In Vivo Growth Potential and Vascular Remodeling of Tissue-engineered Artery," *Tissue Engineering. Part A* 15(4):901-912; Hoerstrup, S. P., Cummings, I., Lachat, M., Schoen, F. J., Jenni, R., Leschka, S., Neuenschwander, S., and 6 others 2006. "Functional Growth in Tissue-engineered Living, Vascular Grafts: Follow-up at 100 Weeks in a Large Animal Model," *Circulation.* 114(1 Supplement):I159-I166). Until a tissue engineered esophagus is developed, one solution is to engineer esophageal tissue as flat stock or sheeting which can be rolled into a tube and bonded at the free side edges to coalesce by healing, creating a living ductus of the correct strength and pliancy and apply the assist device described herein. Essentially, if the tube is little more than viable, it can be used. For now, such represents a tissue engineered esophagus as the term is used herein.

Motile dysfunction is likewise central to numerous pathological conditions of the native digestive tract whereby the segment has satisfactory structure but motile and probably secretory deficits, so that the lack of a cure and the infeasibility of a fully functional graft preclude resection and replacement. However, deformity that would require a graft in any event, and weakness or dysfunction that would impart motile and secretory function through reinforcement of the native conduit without the need for resection and grafting plainly justify prostheses which impart such function. Whether in a tissue-engineered or a malfunctioning native gut or segment thereof, if the myenteric or Auerbach's plexus, which controls peristalsis, fails to develop normally, then it is probable that neural development is impaired generally, with the submucosal or Meissner's plexus, which controls secretion, and sensation generally, likewise impaired.

While a lack of sensation may be advantageous as reducing or eliminating annoyance during operation, side-entry jackets and suitable timing controls make possible both prosthetic secretory and contractile function, different means therefor addressed below. In prosthetic vessels, prosthetic endothelial function is achieved by delivery of replacement substances through a simple junction jacket placed upstream. Where the segment involved would additionally benefit from a drug or drugs, and the target area for the drug need not be tightly circumscribed, a simple junction jacket such as shown in FIG. 2 placed upstream will serve.

If the graft or native segment is small, the target area for the drug is best restricted to a certain segment whether that equates to the segment to be encircled, or the segment is to be encircled over the least length possible, or the surrounding anatomy allows little clearance, a combination or special-purpose contraction or peristaltic jacket with fluid side-entry, and if appropriate, electrical line or lines added is used. The need for a sphincteric assist device alone in a neonate infrequent, whether applied to a tissue engineered graft or native dysfunctional tract as a jacket, the device will often incorporate both esophageal and sphincteric components with implanted control module as a unit.

For a neonate, the graft is generated from autologous stem or progenitor cells harvested prenatally from fetal sources such as umbilical cord blood, amniotic fluid, and chorionic villi as are cardiovascular tissue engineered graft cells (see, for example, Weber, B., Zeisberger, S. M., and Hoerstrup, S. P. 2011. "Prenatally Harvested Cells for Cardiovascular Tissue Engineering: Fabrication of Autologous Implants Prior to Birth," *Placenta* 32 Supplement 4:S316-S319). Based upon tissue engineered vascular tissue, a perfected tissue engineered esophagus would probably grow in proportion to the rest of the body and heal if injured (Boerckela et al. 2011, Op cit.; Cho et al. 2009, Op cit.).

In an adult, irremediable damage necessitating a functional prosthesis incorporating both components may result from ischemia (see, for example, De Praetere, H., Lerut, P., Johan, M., Daenens, K., Houthoofd, S., Fourneau, I., Maleux, G., Lerut, T., and Nevelsteen, A. 2010. "Esophageal Necrosis after Endoprosthesis for Ruptured Thoracoabdominal Aneurysm Type I: Can Long-segment Stent Grafting of the Thoracoabdominal Aorta Induce Transmural Necrosis?," *Annals of Vascular Surgery* 24(8):1137.e7-e12), compression (see, for example, Ruzmetov, M., Vijay, P., Rodefeld, M. D., Turrentine, M. W., and Brown, J. W. 2009. "Follow-up of Surgical Correction of Aortic Arch Anomalies Causing Tracheoesophageal Compression: A 38-year Single Institution Experience," *Journal of Pediatric Surgery* 44(7):1328-1332; Bonnard, A., Auber, F., Fourcade, L., Marchac, V., Emond, S., and Révillon, Y. 2003. "Vascular Ring Abnormalities: A Retrospective Study of 62 Cases," *Journal of Pediatric Surgery* 38(4):539-543), surgical resection (see, for example, Lerut, T. 2001. "Indications and Outcome of Esophageal Resection," in Tilanus, H. W. and Attwood, S. E. A., *Barrett's Esophagus*, New York, N.Y.: Springer, pages 317-324), or accidental trauma.

Prosthetic Sphincters

A sphincter is normally closed with its smooth muscle lax and opened when the muscle is energized. When the sphincter is too loose, luminal contents reflux, and when stenotic if not atresic (atretic), fails to open when necessary, obstructing the gastric outlet, for example. Because the sphincteric jacket keeps the lumen fully closed until its electromagnet is energized, and fully open when the magnet is energized, conditions both of stenosis and patency are alleviated by the same jacket. Such a jacket may be thought of as an adaptation of a break contact relay, where the living tissue of the ductus is interposed between the contacts. The sphincteric jacket to be described keeps the sphincter closed and opens it only when its respective node as a module or subsystem in the multicore microcontroller is signaled by sensors implanted along the digestive tract that a bolus has entered.

Effective treatments having long existed, the application of individual, or sphincteric contraction-jackets to counteract a sphincter that fails to open the passageway through a hypertrophic or stenotic sphincter as an expansion, dilation, or distension jacket is not ordinarily required. Such a condition as congenital achalasia or hypertrophy of the lower esophageal sphincter is ordinarily amenable to remedial treatment by pneumatic balloon dilation, botulinum toxin injection, or more durably by surgical correction with a Heller myotomy or a variant thereof, and hypertrophic pyloric stenosis (pyloristenosis, pylorostenosis), conventionally resolved by an endoscopic longitudinal pyloromyotomy (Fredet-Ramstedt operation, Ramstedt-Fredet operation, Ramstedt's operation, Ramstedt pyloromyotomy) or a pyloroplasty.

Neither is the placement of a sphincteric jacket proposed where reflux is the result of an hiatal, or hiatus, hernia which can be safely repaired endoscopically (see, for example, Tam, V., Winger, D. G., and Nason, K. S. 2016. "A Systematic Review and Meta-analysis of Mesh vs Suture Cruroplasty in Laparoscopic Large Hiatal Hernia Repair," *American Journal of Surgery* 211(1):226-238; Yang, X., Hua, R., He, K., Shen, Q., and Yao, Q. 2016. "Laparoscopic Hernioplasty of Hiatal Hernia," *Annals of Translational Medicine* 4(18):343; Chang, C. G. and Thackeray, L. 2016. "Laparoscopic Hiatal Hernia Repair in 221 Patients: Outcomes and Experience," *Journal of the Society of Laparoendoscopic Surgeons* 20(1). pii: e2015.00104; Berselli, M., Livraghi, L., Latham, L., Farassino, L., Rota Bacchetta, G. L., and 4 others 2015. "Laparoscopic Repair of Voluminous Symptomatic Hiatal Hernia Using Absorbable Synthetic Mesh," *Minimally Invasive Therapy and Allied Technologies* 24(6):372-376; Priego, P., Ruiz-Tovar, J., and Pérez de Oteyza, J. 2012. "Long-term Results of Giant Hiatal Hernia Mesh Repair and Antireflux Laparoscopic Surgery for Gastroesophageal Reflux Disease," *Journal of Laparoendoscopic and Advanced Surgical Techiques. Part A* 22(2): 139-141).

If this does not completely suppress the hyperacidity, a partial vagotomy will, or will at least allow a significant reduction in the need for omeprazole oral, for example, all antiacids posing risks of adverse side effects (see, for example, Csendes, A., Bragheto, I., Burdiles, P., Smok, G., Henriquez, A., and Parada, F. 2006. Regression of Intestinal Metaplasia to Cardiac or Fundic Mucosa in Patients with Barrett's Esophagus Submitted to Vagotomy, Partial Gastrectomy and Duodenal Diversion. A Prospective Study of 78 Patients with More than 5 Years of Follow Up," *Surgery* 139(1):46-53; Braghetto, I., Csendes, A., Burdiles, P., and Korn, O. 2000. "Antireflux Surgery, Highly Selective Vagotomy and Duodenal Switch Procedure: Post-operative Evaluation in Patients with Complicated and Non-complicated Barrett's Esophagus," *Diseases of the Esophagus* 13(1):12-17; Braghetto, I., Bastias, J., Csendes, A., Acuña, N., Encina, J., Yarmuch, J., and Schutte, H. 1986. "Comparative Reduction of Gastric Acid Secretion after Ranitidine and Supraselective Vagotomy in Patients with Duodenal Ulcer," (in Spanish) *Revista Medica de Chile* 114(12): 1145-1148). Any residual hyperacidity should be readily counteracted with sodium bicarbonate tablets too few to produce adverse side effects such as headache, nausea, muscle pain, or nervousness, for example, or interact with other drugs.

The placement of a functional prosthesis may prove preferable to an open surgical transduodenal sphincteroplasty necessitated by scarring due to repeated endoscopic treatment, dysfunction as the result of a gastric bypass operation, or the resection of an ulcer or tumor, for example. The graft is first anastomosed in position, or the dysfunctional native sphincter sphincteroplastied to allow placement of the jacket endoscopically, the balance of the procedure performed through the same access portal or opening.

The final decision to debulk, incise, or only place the sphincteric jacket assist device to an hypertrophied sphincter is reserved should be made only once the sphincter has been exposed. The jacket is fastened about the sphincter with hook and loop bands wetted on both internal and external surfaces with substances that will forestall if not eliminate an adverse tissue reaction, to include phosphorylcholine, and/or dexamethasone, or curcumin. These should at least make exposure to the polymeric materials gradual, allowing for adaptation.

When the end outer diameter of an hypertrophied sphincter cannot be predetermined or the diameter is irregular or tapered, a sphincteric jacket with magnet pole outside the adventitia as shown in FIG. 12 or an extraction jacket with flap-valve flush thereto such as shown in FIG. 13 is selected for the largest prospective internal diameter is angled to a point about the circumference of the ductus where the diameter is greatest and additional strips of viscoelastic polyurethane foam lining supplied with the jacket used to build up the thickness of the lining of a jacket where the internal surface of the foam falls short of the adventitia. Adhesion of the added layer or layers of foam is by wetting the interface between layers with cyanoacrylate cement.

Foam Lining Degradation, Toxicity, and Prevention Thereof

When situated in a location of moisture, the foam lining of ductus and impasse side-entry jackets and nonjacketing side-entry connectors is subject to gradual breakdown and the release of potentially toxic breakdown products. However, unlike that used in breast implants, the absolute quantity of this substance is tiny, too slight to approximate a burden as would exert a deleterious effect. Nevertheless, to assure that breakdown does not occur, a polyhydrophilic and polyzwitterionic moisture barrier layer of shape compliance equal to that of the material itself is applied to prevent exposure to moisture with consequent breakdown. To serve as a moisture barrier, noble metal plating must be extremely thin to provide shape compliance equal to that of the substrate viscoelastic polyurethane foam and is susceptible to pitting over time, so that plating, if used at all, must be by means of sputtering or vapor deposition of the metal used, or preferably, an encapsulating layer of a chemically stable polymer such as sufficiently plasticized parylene applied.

Susceptible to degradation from exposure to moisture, polyurethane foam implanted in a moist location, especially if immersed in urine, must be encapsulated within by a protective moisture barrier. In order to preserve the properties of the foam, which must invest any tiny nerves and vessels present at the outer surface (tunica externa, tunica fibrosa) of a larger structure, the moisture barrier must comprise a continuous and breach free thin film coating having high elastic compliance. Even though to allow application to the foam in a continuous and breach free film, the coating material must be self-bonding or self-adherent, to least interfere with the shape compliance of the foam, the moisture barrier should be no more than a few molecules thick (see, for example, Zhang, R., Andersson, H. A., Andersson, M., Andres, B., Edlund, H., Edström, P., Edvardsson, S., Forsberg, S., and 9 others 2013. "Soap-film Coating: High-speed Deposition of Multilayer Nanofilms," *Scientific Reports* 3, Article number: 1477).

Unless moisture at the site for implantation is insignificant, a protective moisture barrier is applied to the exposed foam surfaces of the stopper cone, as well as to the foam linings of ductus side-entry jackets and nonjacketing side-entry connectors. Generally, this requires bombardment of the foam with a monomer, such as one of polyethylene or polypropylene, and innoxious plasticizer least likely to leach out over time to no greater a thickness than is essential to isolate the foam from the water of the milieu, and once polymerized, to render the resultant highly elastic continuous thin film unsusceptible to fracture. This thickness achieved, the monomer is polymerized and any residual or free plasticizer removed, as by water flushing. Ortho-phthalate plasticizers identified as potential endocrine disruptors are avoided. The high velocity of bombardment should eliminate the need to minimize subsurface penetration of the foam by freezing.

Sphincteric and Peristaltic Assist Devices

The placement of a sphincteric jacket to alleviate dysfunction as stenosis or patency is reserved for patients not considered good candidates for such a procedure. Patients considered poor risks for the surgery and those who have not benefited from a previous surgical procedure are well served by a fully implanted assist device that functions automatically to meter stomach contents at the entry and/or outlet, and requires a relatively minor laparoscopic procedure under local anesthesia to be placed. Ordinarily, conditions involving inadequacy or the lack of contractive force, such as in Hirschspring's disease, where surgical intervention often leads to adverse sequelae, are addressed.

An independently used sphincteric or peristaltic assist device is a module that can be incorporated in a more comprehensive ambulatory prosthetic disorder response system assigned one of the nodes in the microcontroller. When used alone, the device is fully implanted, with only a connector at the body surface to recharge the battery. The laparoscopic procedure is relatively simple, less susceptible to complications, and with a strain gauge sensor designed to be slid into the outer tunic of the esophagus, for example, less demanding of dissection and surgical expertise than the Ramstedt operation. Sensors suitable for signaling intrinsic motility include piezoresistors, nanoparticle based resistive strain gauges, long life mercury in rubber strain gauges, and fiber optic strain gauges.

Intraoperative time is less, the procedure usually performed under local anesthesia even on a neonate, with less dissection, and the elimination of an accidental duodenotomy or gastrotomy as a distinct risk in a tiny patient (see, for example, Oldham, K. T., Coraqn, Q. G., and Wesley, J. R. 1997. "Pediatric Abdomen," Chapter 103 in Greenfield, L. J., Mulholland, M. W., Oldham, K. T., Zelenock, G. B., and Lillemoe, K. D. (eds.), Surgery: *Scientific Principles and Practice*, page 2067) than even the usually dependable Ramstedt operation. Broadly, such means are intended to apply where disease or malformity which has eluded medical treatment or a previous attempt at surgical correction would otherwise necessitate resection and/or replacement of the native structure.

Contraction and peristaltic jackets and controls are best devised as integral components of a more inclusive disorder response system which collaterally treats unrelated or related coexisting disease, but can be separated as a distinct module within the more comprehensive disorder response system as singular for a patient without collateral disease. When applied by itself, a pump-pack is dispensed with, the controller and battery then also implanted. This is not the case, however, with a patient, primarily one elderly, who is likely to develop other disease as will then require a pump-pack.

Even when a proximal or upstream simple junction jacket is needed to deliver medication or synthetic mucus, for example, or the jacket is to include a ductus side-connector for delivery of a therapeutic substance or substances through a commercially available port or the port described below at the body surface, necessitating the addition of a pump-pack, whenever possible, the procedure is performed endoscopically or laparoscopically under local anesthesia, as is any other procedure contemplated herein. To avoid an unpleasant esthetic result, pump-pack fluid and electrical lines are generally not tunneled subcutaneously.

When fluid support is needed and a separate jacket upstream is not wanted, sphincteric and peristaltic jackets include a side-entry connector with mainline and sideline (service channel, accessory channel). Such fluids typically include synthetic mucus, any deficient digestion hormones, such as cholecystokinin and secretin, and enzymes, such as amylase or a protease. An excessively constrictive or stenotic lower esophageal sphincter such as one hypertrophic is ordinarily correctible through a fundoplication or Nissen fundoplication. However, a weakened one, where the smooth muscle is impaired or a hiatal hernia reduces the available contractive force, leaves the inlet to the stomach partially open. This is a common cause of backwashing or gastroesophageal reflux disease, which can lead to Barrett's esophagus, metaplasia and esophageal cancer.

The means described herein are intended for cases that do not respond well to medical intervention, such as in patients who do not tolerate proton pump inhibitors and histamine blockers well. Other sphincters that cut off rather than properly modulate flow are correctible through relatively safe and simple surgical procedures, such as a pyloromyotomy. However, a weakened pylorus allows duodenogastric reflux and prechymal gastric contents to pass, often leading to ulceration and early dumping syndrome. A dysfunctional ileocecal valve (ileal valve, Tulp's valve) promotes ileocecal incompetence with the return entry (reflux, regurgitation) of colonic contents into the ileum.

When standard of care methods are contraindicated or prove inadequate, a sphincteric or peristaltic contraction-jacket, to include implantable sensors and when drug delivery is necessary, a wearable power pack and control module as described below in the section entitled Description of the Preferred Embodiments of the Invention, or these components implanted may provide a remedy. When used alone and without fluid delivering capability, impaired or, graft sphincter or peristaltic assist devices are packaged separately and fully implanted. When the system must serve collateral disease so that additional modules addressing other dysfunction are required, a pump-pack is used.

Whether a separate module or several are required, each module is preferably controlled within a standardized control regime. It is assigned a respective node and treated and programmed as a semi-independent subsidiary module of a more inclusive prosthetic disorder response system. Supportable with prosthetic distension (expansion, dilation, dilatation) or contractile (constrictive) function no less than tissue-engineered segments are native conduits and segments deficient in contractile function, but which would best be left intact were means available to reinforce or provide the missing contractive force. Jackets applied thus are actuated on the basis of sensors such as strain gauge-based which follow and signal passage of the bolus to the respective control node.

Such deficits, those which result from congenital deformities such as congenital esophageal atresia, congenital intestinal atresia (Christmas tree, maypole, or apple tree deformity), duodenal, jejunoileal, ileal, and colon atresia, defects in neuromuscular development, remedial drug-habituation, as well as the desirability for a functional graft following resection dictated by disease or injury, as when following the removal of a long segment from the gut, responsive to refractory Crohn's disease or ileocolitis, for example. When discovered in utero, the foam lining the tissue-engineered prosthesis with peristalsis multiple electromagnet peristalsis jacket is made as thick as possible to allow for growth.

Following resection for familial adenomatous polyposis, for example, as much of the colon down to the perineum as possible is replaced. With respect to grafts tissue engineered with autologous cells, because the deficits of motor function obtained are due to myenteric plexus and/or associated neural maldevelopment, such grafts are also likely to be associated with deficits in sensory function. Provided neighboring tissue is not encroached upon, irritation if any from the operation of an implanted sphincteric or peristaltic device should not prove prohibitive. Since a tissue engineered or harvested autologous graft is defective in sensory function, the weight of the magnet will not be sensed.

Nevertheless, when considered heavy, the magnet should be suspended with suture or an improvised sling harness. Referring now to FIG. 10, a lower esophageal or a pyloric sphincter that proves untreatable or untreatable without heavy medication can be resected and replaced with a tissue engineered placement. Sphincteric motility is imparted by a single contraction-electromagnet jacket such as shown in FIGS. 11 and 12, briefly described below and more fully described in the section entitled Sphincteric Jackets under Description of the Preferred Embodiments of the Invention. FIG. 11 shows an isolated peristaltic electromagnetic contraction-jacket.

A sphinteric jacket differs from such a peristaltic contraction-jacket magnet, in that the engineered tissue graft ductus is encircled within a hard outer shell having a strong permanent disk magnet mounted to, inlaid or inset into, or embedded within its outer surface. The magnet is magnetized in its long axis or parallel to length, and if not embedded, must be encapsulated within a polymeric outer layer, such as polytetrafluoroethylene, that will not abrade neighboring tissue and is not susceptible to hydrolytic or enzymatic degradation. This permanent magnet is positioned in diametrical opposition to the pole of the electromagnet, and a magnetic stainless steel or iron plate encapsulated with a polymer impervious to hydrolytic or enzymatic dissolution is sutured to the magnet pole side of the graft.

The peristaltic jacket also differs in requiring internal sequential timing control. With both, however, strain gauge sensor implants proximal to the sphincter signal passage of a bolus to the control node. When a prosthetic esophagus includes the lower esophageal sphincter, control of peristalsis and dilatation of the sphincter are controlled as a unit. These sensors can be placed in the pharynx and along the esophagus in sensor-jackets, which must meet the desiderata for a compliant lining and fenestrations, for example. The propulsive action of peristalsis over a distance requires the action of multiple contraction-electromagnets coordinated to step along leap-frog fashion to simulate an advancing wave of constriction or extrusion.

FIG. 10 shows a peristalsis assist device jacket with five contraction-electromagnets to replace a relatively short segment along the digestive, urinary, or reproductive tract, the dimensions of the jacket, its number and spacing apart of magnets dictated by the application. To the extent possible, timing control over magnet energization simulates that normal, the more longitudinal peristalsis of a ureter, for example, different in character than that along the digestive tract. The esophagus, for example, is replaceable or supportable along its entire length distal to the upper esophageal sphincter. When used to bolster intrinsic function, the jacket is placed about the native ductus; when a graft is required, the jacket is placed about the graft, one tissue-engineered using autogenous or autologous cells preferred as least likely to be rejected.

Replacement of the esophagus and pylorus, for example, combines a multiple contraction or peristaltic jacket for the esophagus and an individual peristaltic jacket for the pylorus and places these under the control of a higher control node for jacket to jacket synchronization. When no other microcontroller modules are needed to treat collateral disease in the same patient, control of either or coordinated control of both the peristaltic and sphincteric jackets is relegated to local control, the microcontroller then implanted with only the one node used as a local control module. Otherwise, the multicore microcontroller is housed within the pump-pack, subsidiary or subordinate control nodes of the microcontroller shown in FIGS. 37 and 38.

Absence in peristaltic or sphincteric function results from congenital deformities (see, for example, Pansky, Ben 1982. *Review of Medical Embryology*, Macmillan USA), usually the result of prenatal ischemia, and impairments from nervous and/or muscular deficits due to disease congenital or acquired, or injury, surgical or accidental see, for example, Smout, A. and Fox, M. 2012. "Weak and Absent Peristalsis," *Neurogastroenterology and Motility* 24 Supplement 1:40-47). Provided safe and dependable prostheses are available, irremediably nonfunctional segments can be reinforced, or if unavoidable for collateral reasons, resected and replaced, and congenitally missing segments provided. Whether the native ductus is encircled for reinforcement or a tissue-engineered graft is used, myenteric plexus inadequacy can be compensated for through the delivery of drugs, enzymes and/or synthetic mucus, contraction-synchronized if necessary.

With shorter segments, these can be delivered through an upstream simple junction type side-entry jacket. For short segments, synthetic muciferous, and natural or synthetic enzymatic, and hormonal secreta can be delivered as necessary through a simple junction jacket placed proximally to the affected segment or by adding a side-entry connector to the contraction jacket, which represents a kind of hybrid or combination jacket. When this is inadequate with a peristalsis jacket such as shown in FIG. 10, simple junction jackets can be positioned perpendicularly to the contraction jackets. Exact synchronization rather than simple simultaneity by the control system of the secretory with the contractile function is unnecessary.

Whereas such a condition as comorbid or associated with other symptoms can be treated together with the other symptoms by the control system delineated herein, isolated and uncomplicated contractile dysfunction can be treated with a contraction jacket or shorter peristaltic contraction-jacket with dedicated microcontroller and battery pack. The control program can be adapted to compensate for segmental dysfunction such as to tighten the lower esophageal sphincter. Whether the dysfunction is continuous or intermittent, the introduction of a food bolus, or in a secretory ductus, the buildup of pressure due to accumulation of secretion, causes the strain gauge or equivalent sensors implanted along the ductus to input the activating signal.

Ductus with peristalsis include the ureters, glandular ducts, and gamete transmitting conduits, as well as the gastrointestinal tract, and the renal pelvic wall (Pruitt, M. E., Knepper, M. A., Graves, B., Schmidt-Nielsen, B. 2006. "Effect of Peristaltic Contractions of the Renal Pelvic Wall on Solute Concentrations of the Renal Inner Medulla in the Hamster," *American Journal of Physiology. Renal Physiology* 290(4):F892-F896) and uterus (Kunz, G., Beil, D., Huppert, P., and Leyendecker, G. 2006. "Control and Function of Uterine Peristalsis During the Human Luteal Phase," *Reproductive Biomedicine Online* 13(4):528-540; Kunz, G. and Leyendecker, G. 2002. "Uterine Peristaltic Activity During the Menstrual cycle: Characterization, Regulation, Function and Dysfunction," *Reproductive Biomedicine Online* 4 Supplement 3:5-9).

Applied thus, two or three larger clasp-electromagnets such as shown in FIGS. 8 and 9 can be used to treat gastroparesis, for example. Applied distad along the gastrointestinal tract, a multi-electromagnet jacket as shown in FIG. 10 allows assisting intrinsic function and averting paralytic ileus as the result of a chronically slow wave rate refractory to correction, whether due to ischemia, neuroendocrine, neuroelectrical, enteric neuromuscular, psychosomatic, genetic, environmental, immunological, or iatrogenically induced dysfunction caused by opioids or sedatives, for example. When the intrinsic rate is slow, the consecutive magnets are energized to least interfere with residual intrinsic function by using implanted strain gauge bolus sensors, a timing circuit, and prior art pacing electronics, for example, to interpose an additional contraction midway between those intrinsic.

Intrinsic contractions can be reinforced in transit at the magnet sites. When modified as indicated above, the separate type electromagnet jackets shown in FIGS. 13 thru 16 consolidate the abilities to assist peristalsis mechanically and deliver drugs such as cerulein and neostigmine, established in vitro to be prokinetic (Fruhwald, S., Herk, E., Hammer, H. F., Holzer, P., and Metzler, H. 2004. "Differential Reversal of Drug-induced Small Bowel Paralysis by Cerulein and Neostigmine," *Intensive Care Medicine* 30(7): 1414-1420), where not to directly target these would prove disruptive to other function. Drug delivery through the flush-out line along the train shown in FIG. 14 can be accomplished by pulsing the pump to force open the flap-valves, or if a ferrofluid, then with the aid of a diametrically positioned electromagnet. Discretionary delivery to each side-connector requires that each be provided with a side-connector sideline accessory or service-channel such as appears as part numbers 10 and 11 in FIGS. 1 thru 3 and 16 thru 22.

To date, tissue-engineered esophagi and intestine lack normal neural plexus development and therefore peristaltic function (Totonelli, G., Maghsoudlou, P., Fishman, J. M., Orlando, G., Ansari, T., and 5 others 2012. "Esophageal Tissue-engineering: A New Approach for Esophageal Replacement," *World Journal of Gastroenterology* 18(47): 6900-6907; Saxena, A. K., Baumgart, H., Komann, C., Ainoedhofer, H., Soltysiak, P., Kofler, K., and Höllwarth, M. E. 2010. "Esophagus Tissue-engineering: In Situ Generation of Rudimentary Tubular Vascularized Esophageal Conduit Using the Ovine Model," *Journal of Pediatric Surgery* 45(5):859-864), and autologous grafts harvested from the distal gastrointestinal tract have proven too susceptible to "leakage, infection and stenosis at the implanted site, which leads to severe morbidity and mortality (Kuppan, P., Sethuraman, S., and Krishnan, U. M. 2012. "Tissue-engineering Interventions for Esophageal Disorders—Promises and Challenges," *Biotechnology Advances* 30(6):1481-1492; Shen, Q., Shi, P., Gao, M., Yu, X., Liu, Y., Luo, L., and Zhu, Y. 2013. "Progress on Materials and Scaffold Fabrications Applied to Esophageal Tissue-engineering," *Materials Science and Engineering. Part C, Materials for Biological Application* 33(4):1860-1866; Nakase, Y., Nakamura, T., Kin, S., Nakashima, S., Yoshikawa, T., Kuriu, Y., Sakakura, C. and 5 others 2008. "Intrathoracic Esophageal Replacement by in Situ Tissue-engineered Esophagus," *Journal of Thoracic and Cardiovascular Surgery* 136(4):850-859; Longmire, W. P. and Ravitch, M. M. 1946. "A New Method for Constructing an Artificial Esophagus," *Annals of Surgery* 123(5):819-834).

Rejection the central problem with grafts and end to end anastomoses along the digestive tract, the placement of a simple junction type side-entry jacket as shown positioned for fixation in place in FIG. 1 and fixed in position in FIG. 2 proximally or upstream to the graft can be used to deliver a magnetically susceptible drug-carrier particle bound immunosuppressant and\or adverse tissue response drug or drugs or any combination thereof. Targeted so that uninvolved tissue is not exposed, these drugs can be delivered in higher concentration than might be circulated. Steroids, for example, are used to reduce inflammation, but carry risks such, as the inducement of Addison's disease and moon facies. The proximal magnet-plate pairs deenergized once a bolus passes, a bolus to follow enters the lumen without the need for the prosthetic ductus to incorporate resilient means as would make it elastic so that it self-dilates.

Similarly, statins in higher concentration can induce myopathy, and immunosuppressive drugs leave the patient vulnerable to infection. If necessary, a second jacket to release a reversal agent likewise best targeted, or an extraction jacket such as shown in FIG. 13, positioned distally or downstream to the graft can be used to remove any residue of the bound drug and particulate not taken up within the target segment. This can be applied to the reevaluation of transplants and prosthetic approaches whether tissue-engineered or made of synthetics. Restricting delivery of the drug or drugs to the graft critically reduces if not eliminates side effects, drug food, and drug-drug interactions, which can be especially problematic in comorbid conditions. The control system can regulate the delivery of different drugs through jackets placed at different locations in the body, averting interactions.

Hence, an arrangement such as that shown in FIG. 10, where a peristalsis dysfunctional or tissue-engineered esophagus not yet capable of intrinsic motility but not rejected as are autologous grafts or remediated as indicated above, can function independently of intrinsic motility if any without the need to be synchronized with residual peristaltic function (see, for example, Martinucci, I., de Bortoli, N., Giacchino, M., Bodini, G., and 4 others 2014. "Esophageal Motility Abnormalities in Gastroesophageal Reflux Disease," *World Journal of Gastrointestinal Pharmacology and Therapeutics* 5(2):86-96; Smout, A. and Fox, M. 2012. "Weak and Absent Peristalsis," Op cit.; Bredenoord, A. J., Fox, M., Kahrilas, P. J., Pandolfino, J. E., Schwizer, W., Smout, A. J; and 17 collaborators 2012. "Chicago Classification Criteria of Esophageal Motility Disorders Defined in High Resolution Esophageal Pressure Topography," *Neurogastroenterology and Motility* 24 Supplement 1:57-65; Roman S. and Kahrilas, P. J. 2011. "Challenges in the Swallowing Mechanism: Nonobstructive Dysphagia in the Era of High-resolution Manometry and Impedance," *Gastroenterology Clinics of North America* 40(4):823-835).

Provided esophageal cancer is detected before metastasis, an autologous engineered replacement with motile function that was not rejected would represent a cure. The magnets are situated at intervals along the prosthesis and act upon magnetically susceptible bands on the opposite outside surface. The action while not sensed normally will slightly move adjacent tissue, which should eventually supplant the intrinsic sensation of swallowing, much as the wearer adapts to the quality of sound through a cochlear implant. Despite decades of experimentation, prosthetic esophagi made of metals and plastics have failed over time, dehiscing at the anastomoses, leaking, and becoming infected.

An intestinal prosthesis imposes the additional requirement of appropriate absorption and passage of nutrients through the mesentery or directly into the portal vein (Sugano, K., Nabuchi, Y., Machida, M., and Aso, Y. 2003. "Prediction of Human Intestinal Permeability Using Artificial Membrane Permeability," *International Journal of Pharmaceutics* 257(1-2):245-251). A successful intestinal prosthesis would be tissue-engineered, and would probably require assisted motility until perfected. A prosthetic ureter has been stated to require (Graw, M. and Bahl, H. U. 1986. "An Active Artificial Ureter with Autonomous Energy Supply," *Urologia Internationalis* 41(1):9-15) and not to require (Desgrandchamps, F. and Griffith, D. P. 2000. "The Prosthetic Ureter," *Journal of Endourology* 14(1):63-77) peristaltic function. In vitro fertilization eclipses the need for an artificial fallopian tube.

Since they place their fingers and everything else in their mouths, infection is inevitable in young patients born with a defect replaced with a prosthesis made of alloplastic (nonbiological, synthetic, artificial) materials. Pending the ability to produce autologous tissue-engineered esophagi and intestines with peristalsis, these tissue compatibility sequelae can be averted, while the motive means described herein is used. Prostheses for insertion along the digestive tract made of synthetic materials may be well engineered as stand-alone items; but in end-to end anastomosis with alloplastic materials, the bacteria-laden lumen predisposes to adverse tissue responses that exceed those seen when the lumen is uninvolved, intrinsic defenses as in the bloodstream are numerous, and at sites where remedial substances are easily applied.

This results in rejection (see, for example, Taira, Y., Kamiya, K., Shiraishi, Y., Miura, H., Shiga, T., Hashem, M. O., Yamada, A., Tsuboko, Y., Ito, T., Sano, K. 2014. "Achievement of Peristaltic Design in the Artificial Esophagus Based on Esophageal Characteristic Analysis of Goats' Specimen," 15*th International Conference on Biomedical Engineering IFMBE Proceedings* 43:372-374, New York, N.Y.: Springer; Liang, J. H., Cai, P., Luo, Z. R., Liang, X. L., and Zhou, X. 2012. "Effect of Feeding Regulation Measures for Establishing Esophageal Channel Function in Neoesophagus Created with a Nitinol Artificial Esophagus," *International Journal of Artificial Organs* 35(9):671-678; Liang, J. H., Zhou, X., Zheng, Z. B., and Liang, X. L. 2010. "Long-term Form and Function of Neoesophagus after Experimental Replacement of Thoracic Esophagus with Nitinol Composite Artificial Esophagus," *American Society for Artificial Internal Organ Journal* 56(3):232-234; Miki, H., Okuyama, T., Kodaira, S., Luo, Y., Takagi, T., Yambe, T., and Sato, Y. 2010. "Artificial-esophagus with Peristaltic Motion Using Shape Memory Alloy," *International Journal of Applied Electromagnetics and Mechanics* 33(1-2):705-711; Watanabe, M., Sekine, K., Hori, Y., Shiraishi, Y., Maeda, T., Honma, D., Miyata, G., Saijo, Y., and Yambe, T. 2005: "Artificial Esophagus with Peristaltic Movement," *American Society for Artificial Internal Organ Journal* 51(2):158-161).

Implanted components to include microcontrollers, sensors, and pumps are preferably connected by wireless radio, or Bluetooth, communication. Otherwise, bare electrodes uninvolved, intracorporeal wiring to coordinate the action of the pump or pumps in the pump-pack, connect implanted sensors to the microcontroller, and so on is similar to that used for other electrical implants, the wires passed through a port implanted at the body surface shown in FIGS. 27 and 28, each biocompatibly insulated and through a common outer conduit, once intracorporeal, to be separated as dictated by the anatomy. Variable control over the field strength of a magnet or magnets integral to a side-entry jacket or jackets if often beneficial. Examples include the ability to adjust field strength to achieve the temporary detention or forcibly drawing of a magnetically susceptible particle bound drug through tissue. With contrast and imaging equipment, the depth of penetration of the carrier bound drug into the tissue can be controlled.

Advantages of Electromagnets

In addition to on-off and variable control, electromagnets allow the coordinated release of an accumulated extractate so that it can be flushed through a flushout or purge line without the need for high pump pressure that would increase the rate of battery drainage, necessitating heavier batteries in an ambulatory apparatus. The advantage in electromagnets in allowing superparamagnetic iron oxide nanoparticle drug-carriers that if not extracted would induce toxicological or adverse consequences to be eliminated before toxic sequelae can take hold is addressed above.

FIGS. 13 thru 15 show side-entry jackets with one or more integral electromagnets which by adjusting the magnetic field strength make it possible to detain a magnetically susceptible carrier particle-bound drug or other therapeutic substance at the level of the jacket, draw the drug radially outward through the wall surrounding the lumen, or extract the drug through the wall or the opening made in the side of the ductus.

To allow variability in field strength throughout this range of function, the magnets depicted in these drawing figures, while small and constructed to project the maximum field strength for their size are somewhat larger than were extraction unnecessary. Numerous embodiments of the chain-jacket and its units serve various purposes. Jackets for detaining magnetically susceptible carrier bound drugs against or drawing drugs into the lumen wall use permanent or electromagnets of field strength consistent with such use with no opening in the side of the ductus, whereas jackets for extracting magnetically susceptible carrier bound constituents of the blood have an opening, one spanned by a elastic slit valve to remove constituents larger in diameter such as blood cells, or one spanned by a simple or compound semipermeable membrane as defined above to remove micro- or nanoparticles and excess water.

As addressed below in the section entitled Apheresis, such means open the way to type-cell separation methods. Ambulatory leukapheresis, for example, is but one such prospective application, magnetic separation apheresis, for example, applicable to any analyte that can be bound to a magnetically susceptible drug-carrier for removal to a miniaturized body pack-worn separation machine. Preferably, this process is undergone under the control of implanted sensors and the microcontroller in vivo with the patient oblivious to the process, infusion of the fluid containing the binding particles upstream through a simple ductus junction jacket of the kind shown in FIG. 2.

Such jackets can also be used to remove an analyte before reaching downstream or territory tissue or an organ. Unlike the common shaft or trunk of a double-arm side-connector without an electromagnet as shown in FIG. 7, which round in cross-section, can include a rotary joint, the rotational angle of the double-arm side-connector or connectors and the flap-valve toward its adductal terminus to the long axis of the ductus is not round and not rotated. Instead it is made at different fixed angles and cross-sections appropriate for the site.

A separate clasp-electromagnet as shown in FIGS. 8 and 9 for fastening to the surface or outer capsule of an organ, gland, or lymph node, for example, allows an analyte delivered through an upstream side-entry jacket to be detained or drawn into the parenchyma over a controlled timetable. Provided the organ does not have an outer capsule that is very hard, jackets with an integral electromagnet such as shown in FIGS. 13 thru 15 can, over time, extract the susceptible particles with or without the drug still bound, through the fibrosa, where an accumulation thereof can be flushed away. Alternatively, plural small double-arm side-connectors with electromagnets can be longitudinally arranged in coaxial relation to the long axis of the ductus.

Alternatively, separate microcontrollers can be assigned to each node in the control tree. The object is to optimize drug delivery while least interfering with freedom of movement. The sensors, the positioning of these, and the control desiderata among the nodes signaling a pump-pair depend upon the disease under treatment and vary widely. Once the implanted elements have been placed, only the need to replenish one or more drugs by injection through the body surface port and into a pectoral reservoir or replacement of the vial in the pump pack interrupt the patient in free movement. Such an automated drug delivery system can function as a prosthetic disorder response system to compensate for defects in intrinsic adaptive responses, and where an intrinsic response does not exist, is inadequate, or does not squarely target the etiology, as a bionic disorder response system.

In a tertiary medical center with the patient stationary, this scheme can be expanded so that diagnostic sensor feedback initiates and regulates not only ongoing dosing from among clinician prescribed drugs loaded, but can select as well as deliver drugs from among an unlimited number of drug supply reservoirs. While the drugs delivered must be compatible, which is readily accomplished when delivery is targeted, such a system seeks to detect and return diagnostic information, such as the level of metabolites, antibodies, antigens, and organic or inorganic substances, in relation to homeostatic balance without necessarily ascribing combinations of imbalances to a particular syndrome. Acting directly upon the basis of sensor inputs, such a system is inherently theranostic (individualized, patient-centric) and not susceptible to erroneous presuppositions or errors in treatment to which erroneous presuppositions often lead.

A portable system is loaded with a limited set of specific drugs to treat a diagnosed or predictable condition. By contrast, a stationary system need not be limited thus and does not require a preestablished diagnosis, so that correction expeditious, the risk of misdiagnosis is less. The direct delivery of drugs without relationship to a specific diagnosis allows immediate response to reasonably predictable intercurrent disease, especially valuable when comorbidities are likely. For example, with no change in behavior, metabolic syndrome, or the combination of abdominal obesity, hypertriglyceridemia, lowered high-density lipoprotein serum level, elevated plasma fasting glucose and low-density lipoprotein levels, and hypertension, progression to diabetes and cardiovascular disease is predictable, but not as to time of onset.

Such represents the internalization and rendering immediate of point of care detection (see, for example, Chikkaveeraiah, B. V., Bhirde, A. A., Morgan, N. Y., Eden, H. S., and Chen, X. 2012. "Electrochemical Immunosensors for Detection of Cancer Protein Biomarkers," *ACS* [American Chemical Society] *Nano* 6(8):6546-6561; Rusling, J. F. 2012. "Nanomaterials-based Electrochemical Immunosensors for Proteins," *The Chemical Record* 12(1):164-176; Rusling, J. F., Kumar, C. V., Gutkind, J. S., and Patel V. 2010. "Measurement of Biomarker Proteins for Point-of-care Early Detection and Monitoring of Cancer," *The Analyst* 135(10):2496-2511; Choi, Y. E., Kwak, J. W., and Park, J. W. 2010. "Nanotechnology for Early Cancer Detection," *Sensors* (Basel) 10(1):428-455. Liu, G. and Lin, Y. 2007. "Nanomaterial Labels in Electrochemical Immunosensors and Immunoassays," *Talanta* 74(3):308-317).

For such patients with both portable and stationary systems, prepositioning sensor implants to detect and loading the stationary dispensing system with drugs to treat the additional symptoms associated with congestive heart failure, for example, allows the system to respond to these additional symptoms upon onset. Large in number, with additional drugs appearing often, the complement of drugs dispensed by such a stationary system is reduced to those for each purpose which clinical trials have shown to be safe and effective. The automatic drug selection and delivery control program or prescription data switches the drug reservoir catheters connected to each target ductus from among an unlimited number of drug supply reservoirs. In this, a body area network under 'intelligent' complex or hierarchical adaptive control can also be made to transmit data through a wireless network.

Much as a vaccine confers artificially acquired immunity, such a system effectively serves as an adjunct or nonintrinsic suppressive or negative feedback response loop for adapting to an anomalous condition. By comparison, automatic ambulatory insulin pumps deliver insulin subcutaneously, hence, systemically following a time delay, without targeting ability, and intravenous drug delivery is unsuited to an active life. Implant cardioverter defibrillators deliver electrical current, not fluid drugs, and ventricular assist devices provide mechanical action. Many genetic defects result in a failure to produce an essential enzyme or protein, or to produce the substance in the normal form and/or amount. A disorder response system that supplements or substitutes for a defective intrinsic response constitutes a physiological prosthesis, whereas a system placed to compensate for a genetic defect that evokes no innate adaptive mechanism is bionic.

A metabolic defect such as failure to produce an enzyme in the proper form often results in a failure for a substance to be assimilated so that an innate adaptive mechanism is obstructed, and in some instances, the defective substance produces a chemical imbalance of insufficiency or of excess that accumulates in tissues or the blood, amyloidosis, the tendinous xanthomas of familial hypercholesterolemia, the eyelid and other xanthomas of hypertriglycerinemia (hyperchylomicronemia), and hemochromatosis examples. In some cases, a defect of metabolism can initiate a cascade or chain reaction of chemical failures that if not truncated result in death. In others, such as Tay-Sachs disease, death is more direct and quicker. Prosthetic and bionic disorder response systems with or without diagnostic sensors and programming are intended to reinstate homeostatic balance.

The development of such prosthetic and bionic systems to supplement or replace innate compensatory adaptive feedback loops has been obstructed by the lack of suitable means for securely joining synthetic fluid lines to anatomical ductus. Provided suitable drugs are available, secure and if necessary, targeted delivery can be established. Here means are described for allowing the direct connection and entry into any native lumen through a securely mounted periductal jacket configured to avoid placement of a foreign object in the lumen and having features to avert intra and postoperative complications, to include bleeding and the leaking of luminal contents that if septic, could result in life-threatening infection. Anatomical clearance allowing, a ductus side-entry connection jacket, or simply side-entry jacket, as described herein, can be connected to a ductus at right angles to form a T-joint normal or perpendicular to the ductus.

Where the anatomy affords no clearance and in blood vessels where hemodynamic and coagulative factors must be accommodated, the jacket is attached to the ductus at an angle. A ductus side-entry connection jacket can be extended or elongated in the antegrade direction to present a magnetized gradient and so form a piped impasse-jacket, whereby the inlet catheter or pipe allows delivery of a fluid drug through a port implanted at the body surface to a periductally mounted jacket. At a minimum, an impasse jacket is intended to stop magnetically susceptible particles bound to the drug or other therapeutic substance until an external electromagnet can be used to extract these. Among other factors, notably, the alteration in penetrability caused by the lesion itself, the extent of penetration achievable without the aid of an external magnet depends upon the chemistry of the drug or other therapeutic substance carrier-bound particles, as well as the energy product of the magnet material and its dimensions.

Histological and Cytological Application

Along the vascular tree, penetration at cell depth level to initially treat the intima or where only shallow penetration is wanted can be enhanced through endocytotic methods, such as the binding of lipids or a response-inducing but innocuous virus or virus-mimicking nanocarrier drawn into endothelial caveolar lipid rafts (see, for example, Somiya, M., Liu, Q., and Kuroda, S. 2017. "Current Progress of Virus-mimicking Nanocarriers for Drug Delivery, *Nanotheranostics* 1(4):415-429; López-Ortega, O. and Santos-Argumedo, L. 2017. "Myosin 1 g Contributes to CD44 Adhesion Protein and Lipid Rafts Recycling and Controls CD44 Capping and Cell Migration in B Lymphocytes," *Frontiers in Immunology* 8:1731; de Almeida, C. J. G. 2017. "Caveolin-1 and Caveolin-2 Can Be Antagonistic Partners in Inflammation and Beyond," *Frontiers in Immunology* 8:1530; Murai, T. 2015. "Lipid Raft-mediated Regulation of Hyaluronan-CD44 Interactions in Inflammation and Cancer," *Frontiers in Immunology* 6:420; Kovtun, O., Tillu, V. A., Ariotti, N., Parton, R. G., and Collins, B. M. 2015. "Cavin Family Proteins and the Assembly of Caveolae," *Journal of Cell Science* 128(7):1269-1278; Nassar, Z. D. and Parat, M. O. 2015. "Cavin Family: New Players in the Biology of Caveolae," *International Review of Cell and Molecular Biology* 320:235-305; Chaudhary, N., Gomez, G. A., Howes, M. T., Lo, H. P., McMahon, K. A., and 6 others 2014. "Endocytic Crosstalk: Cavins, Caveolins, and Caveolae Regulate Clathrin-independent Endocytosis," *Public Library of Science Biology* 12(4):e1001832; Head, B. P., Patel, H. H., and Insel, P. A. 2014. "Interaction of Membrane/Lipid Rafts with the Cytoskeleton: Impact on Signaling and Function: Membrane/Lipid Rafts, Mediators of Cytoskeletal Arrangement and Cell Signaling," *Biochimica et Biophysica Acta* 1838 (2):532-545; Joseph, N., Reicher, B., and Barda-Saad, M. 2014. "The Calcium Feedback Loop and T Cell Activation: How Cytoskeleton Networks Control Intracellular Calcium Flux," *Biochimica et Biophysica Acta* 1838(2):557-568; Kirkham, M. and Parton, R. G. 2005. "Clathrin-independent Endocytosis: New Insights into Caveolae and Non-caveolar Lipid Raft Carriers," *Biochimica et Biophysica Acta* 1746 (3):349-363; Parton, R. G. and Richards, A. A. 2003. "Lipid Rafts and Caveolae as Portals for Endocytosis: New Insights and Common Mechanisms," *Traffic* (Copenhagen) 4(11): 724-738). If necessary, a powerful external (extracorporeal) electromagnet is later used to draw the carrier particles radially outward through the lumen wall and/or resituate or extract any residue by force.

Along the vascular tree, primary tumors of the lumen wall are infrequent. However, with susceptible carrier binding and an additional boost through the application of magnetic force, the leaky immature vasculature of tumors along the gastrointestinal tract, for example, allows these to be thoroughly penetrated (see, for example, Holgado, M. A., Martin-Banderas, L., Alvarez-Fuentes, J., Fernandez-Arevalo, M., and Arias, J. L. 2012. "Drug Targeting to Cancer by Nanoparticles Surface Functionalized with Special Biomolecules," *Current Medicinal Chemistry* 19(19):3188-3195; Bertrand, N and Leroux, J. C. 2012. "The Journey of a Drug-carrier in the Body: An Anatomo-physiological Perspective," *Journal of Controlled Release* 161(2):152-163; Arias, J. L., Clares, B., Morales, M. E., Gallardo, V., and Ruiz, M. A. 2011. "Lipid-based Drug Delivery Systems for Cancer Treatment," *Current Drug Targets* 12(8):1151-1165; Taratula, O., Garbuzenko, O., Savla, R., Wang, Y. A., He, H., and Minko, T. 2011. "Multifunctional Nanomedicine Platform for Cancer Specific Delivery of siRNA by Superparamagnetic Iron Oxide Nanoparticles-Dendrimer Complexes," *Current Drug Delivery.* 8Q):59-69; Chen, B., Wu, W., and Wang, X. 2011. "Magnetic Iron Oxide Nanoparticles for Tumor-targeted Therapy," *Current Cancer Drug Targets* 11(2):184-189; Tseng, Y. C. and Huang, L. 2009. "Self-assembled Lipid Nanomedicines for siRNA Tumor Targeting," *Journal of Biomedical Nanotechnology* 5(4):351-363; Koning, G. A. and Krijger, G. C. 2007. "Targeted Multifunctional Lipid-based Nanocarriers for Image-guided Drug Delivery," *Anticancer Agents in Medicinal Chemistry* 7(4): 425-440; Muller, R. and Keck, C. 2004. "Challenges and Solutions for the Delivery of Biotech Drugs—A Review of Drug Nanocrystal Technology and Lipid Nanoparticles," *Journal of Biotechnology* 113 (1-3): 151-170). When an orally administered drug is to be drawn radially outward and into the wall surrounding the lumen without uptake or the need to avoid the lumen upstream, an unpiped magnetized or impasse jacket is placed to encircle the target segment.

To treat the esophagus, the ferrofluid is administered in food; to treat the airway and lungs, administration is in the form of an aerosol where the circumtracheal (peritracheal) or circumbronchial (peribronchial) jacket diverts the magnetically susceptible nanoparticles from the aerosol against and into the lumen wall (see, for example, Tewes, F., Ehrhardt, C., and Healy, A. M. 2014. "Superparamagnetic Iron Oxide Nanoparticles (SPIONs)-loaded Trojan Microparticles for Targeted Aerosol Delivery to the Lung," *European Journal of Pharmaceutics and Biopharmaceutics* 86(1):98-104; Hasenpusch, G., Geiger, J., Wagner, K., Mykhaylyk, O., Wiekhorst, F., and 6 others 2012. "Magnetized Aerosols Comprising Superparamagnetic Iron Oxide Nanoparticles Improve Targeted Drug and Gene Delivery to the Lung," *Pharmaceutical Research* 29(5):1308-1318; Rudolph, C., Gleich, B., and Flemmer, A. W. 2010. "Magnetic Aerosol Targeting of Nanoparticles to Cancer: Nanomagnetosols," *Methods in Molecular Biology* 624:267-280; Dames, P., Gleich, B., Flemmer, A., Hajek, K., Seidl, N., Wiekhorst, F., Eberbeck, D., and 6 others 2007. Targeted Delivery of Magnetic Aerosol Droplets to the Lung," *Nature Nanotechnology* 2(8):495-499).

If uptake is to be along the esophagus, the usually superparamagnetic particle-bound drug (see, for example, Barrefelt, Å., Saghafian, M., Kuiper, R., Ye, F., Egri, G., and 6 others 2013. "Biodistribution, Kinetics, and Biological Fate of SPION [superparamagnetic iron oxide nanoparticle] Microbubbles in the Rat," *International Journal of Nanomedicine* 8:3241-3254. Ling, D. and Hyeon, T. 2013. "Chemical Design of Biocompatible Iron Oxide Nanoparticles for Medical Applications," *Small* 9(9-10):1450-1466; Gu, L., Fang, R. H., Sailor, M. J., and Park, J. H. 2012. "In Vivo Clearance and Toxicity of Monodisperse Iron Oxide Nanocrystals," *ACS* [American Chemical Society] *Nano* 6(6):4947-4954; Wahajuddin and Arora, S. 2012. "Superparamagnetic Iron Oxide Nanoparticles: Magnetic Nanoplatforms as Drug-carriers," *International Journal of Nanomedicine* 7:3445-3471; Xu, C., and Sun, S. 2013. "New Forms of Superparamagnetic Nanoparticles for Biomedical Applications," *Advanced Drug Delivery Reviews* 65(5):732-743; Guo, L., Liu, G., Hong, R. Y., and Li, H. Z. 2010. "Preparation and Characterization of Chitosan Poly(acrylic Acid) Magnetic Microspheres," *Marine Drugs* 8(7):2212-2222) is administered in a bolus of food formulated to avoid breakdown when masticated and mixed with the oral enzymes and bacteria. Any toxic residue incurred with state of the art iron oxide nanoparticles is addressed below in the sections entitled Hybrid Impasse and Extraction jackets and Extraction Jackets under Description of the Preferred Embodiments of the Invention.

If uptake is to take place in the gut, then the bolus must be formulated to withstand breakdown when exposed to the gastric juice. When an orally administered drug is injected or infused for uptake into the wall of a particular segment of a vessel without uptake or the need to avoid the lumen upstream then an impasse jacket is placed about the segment of the blood vessel to be treated. When, however, proximal portions of the ductus ought not to be exposed to the drug, such as when the drug is radioactive or would injure healthy tissue, piping the drug directly to the segment where it is to be taken up is accomplished by means of a side-entry jacket. If uptake within the segment is spontaneous or metabolic without the need for magnetic force, or the jacket is proximodistally positioned to target a particular supply territory, or the jacket is used to form a shunt or bypass, then the addition of a magnetic layer is unnecessary.

Jacket Magnetization and Shielding

The jacket used then is of the kind shown in FIG. 2. When uptake is not spontaneous, a concentric magnetic layer is added to the jacket, creating a piped side-entry impasse jacket as shown in FIGS. 3 thru 6, where FIG. 5 also includes a radiation shield, and FIG. 6 includes a radiation shield made of overlapping bits of tungsten each chemically isolated by encapsulation and bound together by an absorbable adhesive. The usually glycolic acid-based adhesive is formulated to disintegrate over an interval past that requiring the shielding. Depending upon the site, this is accomplished through spontaneous or iatrogenic hydrolytic and or enzymatic degradation that disintegrates the shield once the radiation has abated. Disintegration of the temporary shield then exposes apertures in the jacket shell.

The use of shielding which disintegrates allows the drugs needed to avert the harmful effects of complete ductus enclosure which are targeted to the jacket to be terminated as soon as possible. In contrast to the shielding layer, the magnet layer includes the perforations or apertures. The toxic material of the magnet must, however, be encapsulated within a polymeric coat which lines the apertures. Regardless of the sequence of jacket assembly as to the inclusion of the apertures in the magnet as originally formed, once the jacket has been assembled, the apertures must be recoated to assure that the chemical isolation is complete. Drugs targeted to jackets are formulated to achieve the maximum safe concentration that optimizes efficacy, and thus allows the volume of the drugs to be minimized, extending the period for free movement pending the need for replenishment.

Should, however, a drug in the form of a ferrofluid be required in a larger volume, then provided the rate of accumulation allows it, the magnetized side-entry or piped impasse jacket is provided with an extraction grating or grid, as delineated in copending continuation-in-part application Ser. No. 13/694,835, entitled Integrated System for the Infixion and Retrieval of Implants with or without Drug Targeting. At still larger volumes, continuous evacuation of an analyte, whether endogenous, introduced, chemical, or cellular, for example, is accomplished by means of a double-arm type side-entry connection jacket such as that shown in FIG. 7 with longitudinally elongated side-connector and a bidirectional passive elastic flap type valve at the adductal or distal terminus, as will be described.

Use of Ductus Side-Entry Jackets

FIGS. 1 thru 7 allow that a tacky hydrogel may be used in lieu of pressurized water through water jacket 7 to quench extravasation, or exsanguination, so that valving is by introducing a separate valve. However, any of these jackets will often incorporate a flap-valve as integral with the trepan or die cutter leading edge of the side-connector used to excise a tissue plug from the side of the ductus. To minimize if not eliminate a thrombogenic space increasing the need for an anticoagulant, the flap-valve is no more recessed abductally along the side-connector than is necessary to avoid interfering with the leading trepan or die cutter edge. When an integral flap-valve and trepan are incorporated into the side-connector, recurved prongs shown as part number 20 used to prevent a separate valve-plug from migrating into the native lumen are omitted.

Where a double-arm side-connector will be used to steer a guidewire or cabled device into the native lumen so that recurved prongs would interfere, but a valve at the opening in the side of the ductus is necessary or preferred, the double-arm side-connector incorporates a flap-valve integral with the trepan that serves as its surround. The flap-valve acts as a barrier until the threshold force required to open it, which iatrogenic or responsive to the automatic function of the apparatus, exceeds the physiological or pathological forces present. The force or pressure required to pass through the valve may be directionally biased, so that along the venous tree, for example, extraction requires little more force than that of the blood pressure, whereas the pressure posed by flushing through the line will not be sufficient to drive the tacky hydrogel or flush water used into the ductus.

Obtaining directional bias usually involves little more than scoring the flaps horizontally toward the edge bonded to the die cutter surrounding frame. Ductus side-entry jackets are placed individually, regardless of interconnections established among these once placed. Jackets of the kind shown in FIG. 7 with two or more double-arm side-connectors about the circumference incorporate in each such side-connector a die-cutting or trepan leading edge as the surrounding frame of the flap-valve. When connected in series, jackets with a circumferential or unitized trepan and flap-valve that extended entirely about the circumference could be connected to the aspiration pump to cut a segment out of the lumen wall.

However, even with cutting edges running parallel to the longitudinal axis of the native lumen at intervals about the circumference, the added complexity of extracting the circumferentially divided ring of tissue, and more particularly, the likelihood of eccentricities in hardness as of calcification in different arcs argues for separate placement of each jacket. During placement along the vascular tree, the flap-valve prevents excessive exsanguination despite the use of an anticoagulant to prevent clotting. Both to accommodate the core of the electromagnet and reduce the pressure head-on force of flushing, the angle of the double-arm connector with flap-valve situated toward the imaginary or virtual apex, shown in FIG. 13 thru 15 as eliminated to create a collection chamber or trap for accumulated debris extracted, is made as obtuse as practicable.

Double-arm side-connector jackets as shown in FIGS. 13 thru 15 facilitate:

1. The extraction of magnetic particle-bound analytes or cells.
2. The passing of a guidewire or cabled device into the lumen in either direction, and
3. Expedite jacket to jacket connection in series, or chaining, whereby the outlet arm of the jacket just upstream is connected to the inlet arm of the jacket downstream in a continuous train or 'daisy chain.'

This line can be used to flush through the line or deliver medication to each jacket in sequence. Improbably, if numerous enough to eventually induce iron overload, the soft iron cores of the electromagnets are potentially carcinogenic, necessitating permanent encapsulation to isolate the iron from surrounding tissue (see, for example, Steegmann-Olmedillas, J. L. 2011. "The Role of Iron in Tumour Cell Proliferation," *Clinical and Translational Oncology* 13(2):71-76; Toyokuni, S. 2009. "Role of Iron in Carcinogenesis: Cancer as a Ferrotoxic Disease," *Cancer Science* 100(1):9-16; Galaris, D. and Pantopoulos, K. 2008. "Oxidative Stress and Iron Homeostasis: Mechanistic and Health Aspects," *Critical Reviews in Clinical Laboratory Sciences* 45(1):1-23; Papanikolaou, G. and Pantopoulos, K. 2005. "Iron Metabolism and Toxicity," *Toxicology and Applied Pharmacology* 202(2):199-211; Emerit, J., Beaumont, C., and Trivin, F. 2001. "Iron Metabolism, Free Radicals, and Oxidative Injury," *Biomedicine and Pharmacotherapy* 55(6):333-339).

Double-arm jackets used for low volume analyte extraction on an occasional basis can include a permanent magnet layer to detain the bound analyte, an external (extracorporeal) electromagnet used for extraction. However, for larger volume analyte extraction as cellular in leukapheresis (leukcytapheresis) or erythropheresis (erythrocytapheresis), the jackets incorporate a small electromagnet that faces an elastic slit or flap-valve to be described and shown in FIGS. 13 thru 15. A double-arm extraction electromagnet jacket side-connector is used to facilitate steering of an inserted guidewire or cabled device in either direction, and as shown in FIGS. 13 thru 15, allows the interpositioning of a magnet to allow magnetic separation of selected blood constituents through an elastic slit or flap-valve for cytapheresis or a semipermeable membrane simple or comprised of many fibers for hemodialysis.

Exceptionally, FIGS. 13 thru 15 omit accessory channels to each double-arm jacket on the presumption that a ductus side-entry jacket craniad thereto is available to deliver drugs into the substrate ductus and the vacuum used to incise the ostium into the substrate ductus by the trepan-edged jacket sidestem, or side connector, 6 is passed from the aspirator through the flush-line for application to each jacket in succession; ordinarily, however, at least one accessory channel is provided for each jacket. The debris removed thus is washed away by a flush-line, part number 79 in FIG. 14, which courses through the jackets in sequence. The exact configuration of the jackets depends on the function for which these are used. For cytaphresis, the opening into the vessel—usually the inferior vena cava—is round and covered by an elastic slit-valve.

For dialysis, the opening is extended lengthwise and covered by a semipermeable membrane simple or comprised of many fibers. Generally, for cytapheresis, the flush-line contains water, while for hemodialysis, a dialysate is used. While FIGS. 14 and 15 are sectioned aside from a plane showing apertures 19 for exposing the adventia to the surrounding environment, these are shown in FIG. 13. While much of the potential complications in plasmapheresis are materially reduced if not eliminated with vascular connection by means of a side-entry jacket with accessory channel to allow connection to a port at the body surface by a catheter of relatively fine caliber, plasmapheresis or plasma exchange as such requires the use of an extracorporeal machine.

Tandem application of both apheresis and dialysis in a patient such as one with acute renal injury and leukemia, requiring both (see, for example, Nguyen, R., Jeha, S., Zhou, Y., Cao, X., Cheng, C., and 10 others 2016. "The Role of Leukapheresis in the Current Management of Hyperleukocytosis in Newly Diagnosed Childhood Acute Lymphoblastic Leukemia," *Pediatric Blood and Cancer* 63(9):1546-1551; Douglas, K. W., Parker, A. N., Hayden, P. J., Rahemtulla, A., D'Addio, A., and 14 others 2012. "Plerixafor for PBSC [peripheral blood stem cell] Mobilisation in Myeloma Patients with Advanced Renal Failure: Safety and Efficacy Data in a Series of 21 Patients from Europe and the USA," *Bone Marrow Transplantation* 47(1): 18-23) is by alternating either type configured jacket along the sequence with dialysate in the flush-line. The flush-line empties through a nonjacketing side-entry connector into the urinary bladder, or if the patient has no bladder, then into a prosthetic bladder, or neobladder, for expulsion in the urine.

The internal faces of the flap-valve and that of the collection chamber are given extremely smooth surfaces, the adluminal faces of the flaps cambered, rounded, or bifold angles so as not to trap extractate particles, and made to open only when forced to do so by the magnet. Generally, this is accomplished by the force of the extracted particles against the luminal face of the flaps, although some slight magnetically susceptible material can be incorporated into the flaps. Along the vascular tree, flap opening must be no more than necessary to pull out the extractate or blood will leak into the line necessitating more frequent flushing and reducing battery life.

Flushing with a hydrogel containing heparin, for example ameliorates and complication due to an accumulation of thrombus. Radially asymmetrical, electromagnets must be stabilized in position and add weight, and if, the additional weight of the battery or batteries required. The apparatus preferably functions automatically and constantly, during sleep and while bathing, the need for extraction or flushing limited to the clinic not consistent with this purpose. Division and spacing apart or distributing the jacket and magnets distributes the weight of the magnets and improves the degree of analyte removal. Whether electromagnets are used or used in some positions depends upon the relative weight as well as power consumption.

A single arm inline port or clean-out local to the entry incision as shown in FIG. 22 with the arm directed adductally can serve as a piggyback style port to allow clean-out or the passage of a guidewire or cabled device during placement. Once the access incision is closed, access is through the pump-pack as shown in FIG. 31. Along an artery, the pulse may make it necessary to use two or more impasse jackets at intervals. To allow paths for an external electromagnet to extract a carrier-bound radionuclide once depleted to a level safe for the adjacent tissue, a jacket with such a grid requires a radiation shield that disintegrates when the level of radiation decreases to the safe level. Shielded jackets necessitate the use of shielded lines and other elements of containment such as vials.

Where the positioning within the lumen wall of a magnetically susceptible residue is the primary object, the application of a radiofrequency alternated magnetic field to heat the encircled segment serves to kill the cells of a tumor in the surrounding lumen wall, for example, by thermoplasty. Otherwise, the impasse jacket can be used to align the particulate to an invasive lesion such as a tumor from outside the ductus, while in others still, the opportunity for thermoplasty may arise incidentally, or as a collateral treatment modality. Extravascular patch or clasp-magnets can be placed to increase the field strength or to steer the susceptible particles.

Use of Radiation Shielding

The need for continued delivery of a radioactive substance requires radiation shielding of jacket, fluid lines, and the other parts exposed to the radiation, and demands adjuvant treatment to avert the adverse sequelae of completely enclosing the ductus. Such shielding if permanent induces deterioration of the substrate ductus, necessitating counteracting medication which can itself cause complications. The shielding is ordinarily made to disintegrate following depletion of a low dose rate radionuclide, for example, to a safe level. When the radiation is sent to a side-entry jacket with magnet layer for uptake local to the point of delivery, the supply vial or reservoir, jacket, and piping leading to the jacket must be enclosed within radiation shielding. When delivery is to an upstream level for uptake in the segment of the ductus lying between the entry level and the level where the drug-carrier is extracted, the intervening or treated segment must also be shielded.

Whereas a permanent shield normally consists of a solid layer of tungsten just inside the outer protective shell, which precludes the jacket from including openings, fenestra or apertures, a disintegrating shield consists of overlapping or imbricated particles of tungsten, each encapsulated within a nonbiodegradable polymeric shell applied outside a shell with openings so that complete enclosure-offsetting adjuvant medication need be given only over the period before the shield disintegrates. In the drawing figures, the need for each layer in a given jacket varies independently only to the extent that a simple junction type jacket such as that shown in FIG. 2 does not require a magnet layer, and unless the magnet layer is to attract a radioactive bound drug, neither is a radiation shielding layer.

A radiation shield layer must, however, by accompanied by a magnet layer, since the radioactive substance must not flow through the protected segment within the jacket to irradiate the tissue downstream. A radiation shield is required whenever a radioactive substance is to be delivered, regardless whether the substance is delivered in a ferrofluid that necessitates the use of a magnet layer, for example. In a disintegrating radiation shield, the particles are bonded together with an adhesive blend of polymers of the kind used to make absorbable suture according to the rate of depletion or half-life of the radionuclide. Once a safe level of depletion has elapsed, the particles, outside the outer shell, are free to drop away.

To allow the jacket to open freely, the portion of the shield over the hinges is not bonded, allowing it to bulge out as the jacket is opened. An unmagnetized ductus side-entry jacket can deliver a magnetic carrier bound drug for distribution to a number of separate impasse jackets downstream where each successive jacket presents a somewhat greater field strength. The applicability to the skip lesions of ileocolitis, where steroids, for example, can do havoc, is obvious. Low dose rate radionuclides must be delivered through separate jackets each with magnetized extension and shielded from source vial or reservoir to the point of release.

Such a jacket can be used to attract magnetically susceptible carrier particle-bound drugs radially outward, or centrifugally, from the lumen into and through the lesioned wall. Lesions within the wall are therefore exposed to the drug or drugs. Many conditions require only the systemic, usually subcutaneous, delivery of drugs as typified by insulin pumps long on the market. In more complex situations, where the body affords no intrinsic adaptive response to compensate for a chemical imbalance, for example, several such jackets, each targeting a segment of a ductus, organ, or the region supplied by each segment, can be integrated into a hierarchically hard real time controlled prosthetic compensatory system, predictive or anticipatory as needed, to supplement and parallel that intrinsic, or physiological.

Biosensor Positioning

In a body area network consistent with free movement (see, for example, Darwish, A, and Hassanien, A. E. 2011. "Wearable and Implantable Wireless Sensor Network Solutions for Healthcare Monitoring," *Sensors* (Basel) 11(6): 5561-5595; Konstantas, D. 2007. "An Overview of Wearable and Implantable Medical Sensors," *Yearbook of Medical Informatics* 2007:66-69), diagnostic biosensors provide feedback data used to automatically adjust the dosing and interval for the delivery of each drug. The sensors can be implanted ductus-intramurally, that is, in the wall surrounding the lumen, or inside the jacket or jackets; or to measure transmissivity through the ductus, line the jacket with a gradient array. Sensors at the body surface are usually temporary, most implanted locally to the physiological action or analyte to be monitored.

Situated inside the jacket or connector without immediate incisive insertion as when forcing an electrode or probe into tissue, the formation of cicatricial (scar) tissue or fibrous encapsulation about the sensor, causing its gradual desensitization is lessened if not eliminated (see, for example, Karp, F. B., Bernotski, N. A., Valdes, T. I., Böhringer, K. F., and Rather, B. D. 2008. "Foreign Body Response Investigated with an Implanted Biosensor by in Situ Electrical Impedance Spectroscopy," *Institute of Electrical and Electronics Engineers Sensors Journal* 8(1): 104-112). However, sensors can be implanted anywhere pertinent symptoms can be detected.

This may or may not be within or adjacent to tissue the ductus supplies, adjacent or encircling another type ductus that might exhibit symptoms, or considerably up or downstream from the side-entry jacket supported (see, for example, Vasylieva, N. and Marinesco, S. 2013. "Enzyme Immobilization on Microelectrode Biosensors," in Marinesco, S. and Dale N. (eds.), *Microelectrode Biosensors. Neuromethods*, Volume 80, pages 95-114, New York, N.Y.: Humana Press; Palaniswamy, C., Mishkin, A., Aronow, W. S., Kalra, A., and Frishman, W. H. 2013. "Remote Patient Monitoring in Chronic Heart Failure," *Cardiology in Review* 21(3):141-150; Dey, R. S., Bera, R. K., and Raj, C. R. 2013. "Nanomaterial-based Functional Scaffolds for Amperometric Sensing of Bioanalytes. *Analytical and Bioanalytical Chemistry* 405(11):3431-3448; Kotanen, C. N., Moussy, F. G., Carrara, S., and Guiseppi-Elie, A. 2012. "Implantable Enzyme Amperometric Biosensors," *Biosensors and Bioelectronics* 35(1):14-26; Iost, R. M., da Silva, W. C., Madurro, J. M., Madurro, A. G., Ferreira, L. F., and Crespilho, F. N. 2011. "Recent Advances in Nano-based Electrochemical Biosensors: Application in Diagnosis and Monitoring of Diseases," *Frontiers in Bioscience (Elite Edition)* 3:663-689; Tallaj, J. A., Singla, I., and Bourge, R. C. 2011. "Implantable Hemodynamic Monitors," *Cardiology Clinics* 29(2):289-299; Merchant, F. M., Dec, G. W., and Singh, J. P. 2010. "Implantable Sensors for Heart Failure," *Circulation, Arrhythmia, and Electrophysiology* 3(6):657-667)

This not only places the sensor closer to the tissue eventually affected but alleviates the requirement for extreme miniaturization, crowding, and the risk of clogging (see, for example, Goetzinger, D. J. and Najafi, N. 2010. Delivery System, Method, and Anchor for Medical Implant Placement, U.S. Pat. No. 7,860,579). Moreover, in conformation, dimensions, and principle of operation, situation of sensors apart from the jacket or jackets supported allows sensor implant design freedom and surface treatment to minimize if not avert adverse tissue responses or foreign body reactions (see, for example, Vaddiraju, S., Tomazos, I., Burgess, D. J., Jain, F. C., and Papadimitrakopoulos, F. 2010. "Emerging Synergy between Nanotechnology and Implantable Biosensors: A Review," *Biosensors and Bioelectronics* 25(7):1553-1565). Generally, only the sensing elements of a sensor are implanted, any associated electronics relegated to the pump-pack. Any therapeutic or diagnostic substance in fluid form, to include nanomedical and superparamagnetic, can be targeted to any level of any type ductus which can be jacketed with sensors local or remote.

Implantable sensors and microsensors, under study for decades, are suitable or embody principles of operation suitable for adaptation to allow placement at a distance from the side-entry jacket or jackets whose effect the sensor is used to measure (see, for example, Abraham, W. T. 2013. "Disease Management: Remote Monitoring in Heart Failure Patients with Implantable Defibrillators, Resynchronization Devices, and Haemodynamic Monitors," *Europace* 15 Supplement 1:i40446; Lee, S. H., Sung, J. H., and Park, T. H. 2012. "Nanomaterial-based Biosensor as an Emerging Tool for Biomedical Applications," *Annals of Biomedical Engineering* 40(6):1384-1397; Abraham, W. T., Adamson, P. B., Bourge, R. C., Aaron, M. F., Costanzo, M. R., Stevenson, L. W., Strickland, W., and 7 others 2011. "Wireless Pulmonary Artery Haemodynamic Monitoring in Chronic Heart Failure: A Randomised Controlled Trial," *Lancet* 377(9766): 658-666, erratum 2012 379(9814):412; Adamson, P. B., Abraham, W. T., Aaron, M., Aranda, J. M. Jr., Bourge, R. C., and 4 others 2011. "CHAMPION Trial Rationale and Design: The Long-term Safety and Clinical Efficacy of a Wireless Pulmonary Artery Pressure Monitoring System," *Journal of Cardiac Failure* 17(1):3-10; lost, R. M., da Silva, W. C., Madurro, J. M., Madurro, A. G., Ferreira, L. F., and Crespilho, F. N. 2011. "Recent Advances in Nano-based Electrochemical Biosensors: Application in Diagnosis and Monitoring of Diseases," *Frontiers in Bioscience (Elite Edition)* 3:663-689; Song, H. S. and Park, T. H. 2011. "Integration of Biomolecules and Nanomaterials: Towards Highly Selective and Sensitive Biosensors," *Biotechnology Journal* 6(11):1310-1316; Fritz, B., Cysyk, J., Newswanger, R., Weiss, W., and Rosenberg, G. 2010. "Development of an Inlet Pressure Sensor for Control in a Left Ventricular Assist Device," *American Society for Artificial Internal Organs Journal* 56(3):180-185; Carlson, R. E., Weller Roska, R. L., and Brose, S. A. 2009. Sensors Employing Combinatorial Artificial Receptors, WO 2009073625 A1/US 2009/0203980 A1; Verdejo, H. E., Castro, P. F., Concepción, R., Ferrada, M. A., Alfaro, M. A., Alcaíno, M. E., Deck, C. C., and Bourge, R. C. 2007. "Comparison of a Radiofrequency-based Wireless Pressure Sensor to Swan-Ganz Catheter and Echocardiography for Ambulatory Assessment of Pulmonary Artery Pressure in Heart Failure," *Journal of the American College of Cardiology* 50(25):2375-2382; Bullister, E., Reich, S., D'Entremont, P., Silverman, N., and Sluetz, J. 2001. "A Blood Pressure Sensor for Long-term Implantation," *Artificial Organs* 25(5):376-379; Nitta, S., Katahira, Y., Yambe, T., Sonobe, T., Hayashi, H., and 5 others 1990. "Micro-pressure Sensor for Continuous Monitoring of a Ventricular Assist Device," *International Journal of Artificial Organs* 13(12): 823-829).

Application of Biotelemetry

An implanted body area biosensor network well complements wireless biotelemetry, or medical telemetry service. Feedback sensors can be diagnostic, reporting the level of the metabolite, other analyte, or physiological consequence before and after drug delivery, with or without accompanying sensors to indicate the drug level. Where a sensor or sensors incorporated into the jacket cannot furnish adequate diagnostic information, the apparatus facilitates the drawing and delivery of a sample of the luminal contents for examination with the aid of a larger and analytically more capable device can (see, for example, Marko-Varga, G. A., Nilsson, J., and Laurell, T. 2004. "New Directions of Miniaturization within the Biomarker Research Area," *Electrophoresis* 25(21-22):3479-3491).

The cost in a lack of suitable means for introducing diagnostic reagents and therapeutic substances directly to a selected level along a ductus—which limitation ductus side-entry jackets overcome—has been apparent from a comparable lack of rapid advancement in physiological biosensors and biotelemetry, diagnostic monitoring, and a conspicuous absence of parallel and immediate therapeutic ability through the use of effector, or motor, implants (see, for example, RamRakhyani, A. K. and Lazzi, G. 2014, Op cit; Meng, X., Browne, K. D., Huang, S.-M., Mietus, C., Cullen, D. K., Tofighi, M.-R. and Rosen, A. 2013. "Dynamic Evaluation of a Digital Wireless Intracranial Pressure Sensor for the Assessment of Traumatic Brain Injury in a Swine Model", *Institute of Electrical and Electronics Engineers Transactions on Microwave Theory and Techniques* 61(1) 316-325; Cao, H., Landge, V., Tata, U., Seo, Y.-S., Rao, S., Tang, S.-J., Tibbals, H. F., Spechler, S., and Chiao, J.-C. 2012. "An Implantable, Batteryless and Wireless Capsule with Integrated Impedance and pH Sensors for Gastroesophageal Reflux Monitoring," *Institute of Electrical and Electronics Engineers Transactions on Biomedical Engineering* 59(11):3131-3139; Mahfouz, M., To, G., and Kuhn, M. 2011. "No Strings Attached," *Institute of Electrical and Electronics Engineers Microwave Magazine* 12(7): S34-S48; Zhang, F., Hackwoth, S. A., Liu, X., Li, C., and Sun, M. 2010. "Wireless Power Delivery for Wearable Sensors and Implants in Body Sensor Networks," *Conference Proceedings Institute of Electrical and Electronics Engineers Engineering in Medicine and Biology Society* 692-695; Poon, A. S. 2009, Op cit; Young, D. J. 2009 "Wireless Powering and Data Telemetry for Biomedical Implants," *Conference Proceedings Institute of Electrical and Electronics Engineers Engineering in Medicine and Biology Society* 3221-3224; Valdastri, P., Rossi, S., Menciassi, A., Lionetti, V., Bernini, F., Recchia, F. A., and Dario, P. 2008. "An Implantable ZigBee Ready Telemetric Platform for in Vivo Monitoring of Physiological Parameters," *Science Direct. Sensors and Actuators A Physical* 142(1):369-378).

Instead of ambulatory means for continuously, automatically, immediately and autonomously responding to the condition sensed, readings are transmitted to a specialist for review and the writing of a prescription. The delay in this process is a conspicuous deficiency. Usually, the overall sequence in which the drugs are delivered to each side-entry jacket is maintained whether the jackets are placed along a single ductus, or where interrelated and interdependent organ systems are affected, along ductus belonging to different organ systems. In more complex situations, nested levels of program control, or nodes, each supporting a jacket incorporating symptom and remedial substance delivery and level-measuring sensors, are used.

Control System Options

The nodes can consist of time division multiplexed cores of a multicore microcontroller (see, for example, Schoeberl, M., Brandner, F., Sparsø, J., and Kasapaki, E. 2012. "A Statically Scheduled Time-division-multiplexed Network-on-chip for Real-time Systems," pages 152-160, *Networks on Chip (NoCS)*, 2012 *Sixth Institute of Electrical and Electronics Engineers/ACM International Symposium on*, Lyngby, Denmark, available at http://www.jopdesign.com/doc/s4noc.pdf; Sparso, J. 2012. "Design of Networks-on-chip for Real-time Multi-processor Systems-on-chip," in 12*th International Conference on Application of Concurrency to System Design*, Hamburg, Germany pages 1-5; Paukovits, C. and Kopetz, H. 2008. "Concepts of Switching in the Time-triggered Network-on-chip," in *Proceedings of the* 14*th Institute of Electrical and Electronics Engineers International Conference on Embedded and Real-Time Computing Systems and Applications (RTCSA '08)*, Kaohsiung City, Taiwan, Republic of China, pages 120-129; Schoeberl, M. 2007. "A Time-triggered Network-on-chip," in *International Conference on Field-Programmable Logic and its Applications (FPL* 2007), pages 377-382; Kopetz, H. and Bauer, G. 2003. "The Time-triggered Architecture," Proceedings of the Institute of Electrical and Electronics Engineers, 91(1):112-126; Wiklund, D. and Liu, D. 2003. "SoCBUS: Switched Network on Chip for Hard Real Time Embedded Systems," in *Proceedings of the* 17*th International Symposium on Parallel and Distributed Processing (IPDPS'*03), Los Alamitos, Calif., Institute of Electrical and Electronics Engineers Computer Society, page 78a), which communicate with the higher node or core programmed to function as master or 'supreme' node or controller, and if pertinent, directly with one another.

The distribution of control between the brain and subordinate circuits and ganglions a salient feature of the nervous system, such a hierarchical scheme may be seen as analogous to the relation between the motor cortex and subsidiary or more localized control circuits in the spinal cord, for example. Here such a control tree receives feedback from the sensors associated with each jacket to continuously adjust and coordinate the dosing of the drug delivery program in detail, and overall. Subordinate or 'intimal' nodes closest to their respective sensors feed into a channel of control directed to one morbidity among morbidities, an organ, organ system, lesion, or midus, the sensor readings used by the master node to apportion the release drugs among these targets as best approximates normal homeostasis.

The overall consequence of the combination of drugs released or other therapy applied such as electrostimulatory or thermal entered into memory, the system 'learns' the best combination at a given time and adapts to changes with time, this pattern having diagnostic and prognostic value. Moreover, if automated, the system is able to edit its own prescription-program originally prepared by the pharmacist programmer and thus maintain the optimal time-adjusted therapeutic response to treat the component morbidities or leasions. A ductus or impasse side-entry jacket equipped with the required electromagnets will draw any sufficiently magnetic field susceptible particle-bound drug outward and through the surrounding lumen wall. The position of the side-entry jacket thus targets the level along the ductus, and the magnetic force targets the intramural lesion in that segment. A lesion such as an atheroma is therefore 'washed over' and penetrated by the drug, which can be released continuously or at intervals throughout the day.

Immediacy of Response

This surveillance and therapy continues around the clock, independently of the mental competence or state of wakefulness of the patient, and without the need for a professional attendant. That nonemergency and emergency treatment continues around the clock regardless of the location or mental state of the patient conscious or unconscious, presents benefits deriving from immediacy of symptom detection and initiation of drug delivery. When the number of drugs to be loaded into the pump-pack or implanted drug storage reservoirs based upon the preliminary general diagnosis can be accommodated, the need for a specific diagnosis as to the condition provoking the immediate crisis is eliminated; that is, the symptoms are individually addressed to best affect the cause.

Vasospasm of an epicardial coronary artery, the left anterior descending shown in FIG. 16, for example, can be interdicted coincidently with detection of the initial vasotonic mechanical, electrical, and/or chemical indicators, just as, if not before, overt pain is experienced, nitrates, for example, having already been targeted at the site of spasm when sublingual absorption would just have been initiated. The object is to avert spasm before it is experienced as pain, much less can result in ischemic injury. This immediacy applied to the placement of a side-entry jacket at or near to the source of the disease process can similarly interdict symptoms before or critically before these can take effect. A prosthetic disorder response system best mimics or parallels that innate, and a bionic system best simulates an innate system.

With a drug delivery line connected to a ductus side-entry jacket on the cervical, or extracephalic, internal carotid artery, the detection of an imminent epileptic seizure triggers the release of anticonvulsant medication such as phenytoin, carbamazepine and/or valproate simultaneously if not before the premonitory indications, or aura, is sensed. The system is fully implanted, with a subcutaneously placed portacath leading into a subcutaneously implanted drug reservoir, or which the outlet pump is controlled by the microprocessor. Side effects originating in the brain, such as drowsiness and mood swings, are treated by simultaneous release of counteractive medication, while directly pipe-targeted in doses minute compared to those administered orally or infused, side effects remote from the brain, such as liver toxicity, a rash, and/or aplastic anemia, are avoided.

Depending upon its mechanism and consistent with minimizing trauma, any drug to treat a more serious chronic condition that would be more efficacious were it delivered more closely to an innate response mechanism is a candidate for delivery thus. For example, insulin is delivered as near to the normal source as possible, before processing in the liver. Because it best parallels the natural process, a side-entry jacket applied to the hepatic portal vein to deliver an insulin will best simulate normal function in providing first-pass insulin to the liver. In this, the delivery of the insulin as close to the normal origin as practicable should most quickly avert the inducement of the symptoms associated with an abnormal level of blood glucose.

Glucose sensors implanted in various locations signal an abnormal elevation, whereupon the system initiates insulin delivery. Chronic forms of hepatitis for which effective drugs are available are likewise introduced through the portal vein, thereby reducing side effects and interactions. In this way, the abnormal condition whether due to insulin resistance, nonabsorption, or any other reason for gauging low is detected and responded to instantly, not after a delay to test the blood and disperse from the subcutaneous injection site.

Existing pumps deliver insulin subcutaneously, delaying dispersal throughout the systemic circulation. Since with a prosthetic response system such as that to be described, insulin levels can be monitored continuously, a failure of uptake for any reason, to include lipodystrophy, can be negotiated by programming to effect delivery through an alternative port, which can be placed in anticipation of such an eventuality need should it appear. Using the approach described herein, elevated glucose is detected and responded to as close to the natural location and in the same if not less amount of time as occurs with normal function.

Direct venous infusion also avoids such delay as well as the adverse consequences of injection through the skin into subcutaneous fat (see, for example, Henriksen, J. E., Djurhuus, M. S., Vaag, A., Thye-Rønn, P., Knudsen, D., Hother-Nielsen, O., and Beck-Nielsen, H. 1993. "Impact of Injection Sites for Soluble Insulin on Glycaemic Control in Type 1 (Insulin-Dependent) Diabetic Patients Treated with a Multiple Insulin Injection Regimen," *Diabetologia* 36(8): 752-758; Vaag, A., Handberg, A., Lauritzen, M., Henriksen, J. E., Pedersen, K. D., and Beck-Nielsen, H. 1990. "Variation in Absorption of NPH [Neutral Protamine Hagedorn] Insulin Due to Intramuscular Injection," *Diabetes Care* 13(1):74-76; Vaag, A., Pedersen, K. D., Lauritzen, M., Hildebrandt, P., and Beck-Nielsen, H. 1990. Intramuscular versus Subcutaneous Injection of Unmodified Insulin: Consequences for Blood Glucose Control in Patients with Type 1 Diabetes Mellitus," *Diabetic Medicine* 7(4):335-342; Frid, A., Gunnarsson, R., Güntner, P., and Linde, B. 1988. "Effects of Accidental Intramuscular Injection on Insulin Absorption in IDDM [Insulin Dependent (Type 1) Diabetes Mellitus]," *Diabetes Care* 11(1):41-45) but is unsuited to free movement.

For the purpose of minimizing the risk of insulin lipodystrophy, not just a complication in itself but interfering with absorption of the drug, delivery can be rotated among ports of the type to be described where each port is implanted at a different location at the body surface. The reason is that even though using such a port, the insulin is never in contact with tissue, insulin lipodystrophy can present with continuous insulin infusion, indicating that this complication may not depend upon contact (see, for example, Mokta, J. K., Mokta, K. K., and Panda, P. 2013. "Insulin Lipodystrophy and Lipohypertrophy," *Indian Journal of Endocrinology and Metabolism* 17(4):773-774; Ihlo, C. A., Lauritzen, T., Sturis, J., Skyggebjerg, O., Christiansen, J. S., and Laursen, T. 2011. "Pharmacokinetics and Pharmacodynamics of Different Modes of Insulin Pump Delivery. A Randomized, Controlled Study Comparing Subcutaneous and Intravenous Administration of Insulin Aspart," *Diabetic Medicine* 28(2):230-236; Radermecker, R. P., Piérard, G. E., and Scheen, A. J. 2007. "Lipodystrophy Reactions to Insulin: Effects of Continuous Insulin Infusion and New Insulin Analogs," *American Journal of Clinical Dermatology;* 8(1):21-28; Johansson, U. B., Amsberg, S., Hannerz, L., Wredling, R., Adamson, U., Arnqvist, H. J., and Lins, P. E. 2005. Impaired Absorption of Insulin Aspart from Lipohypertrophic Injection Sites," *Diabetes Care* 28(8): 2025-2027; Raile, K., Noelle, V., Landgraf, R., and Schwarz, H. P. 2001. "Insulin Antibodies are Associated with Lipoatrophy but also with Lipohypertrophy in Children and Adolescents with Type 1 Diabetes," *Experimental and Clinical Endocrinology and Diabetes* 109(8):393-396). Since the drug is piped through the body surface, a lipodystrophic response, although to be avoided as adverse in itself, cannot, however, interfere with delivery and uptake.

Continuously adaptive response with the capability for predictive or anticipatory control is best supported by sensors implanted in different sites and tissues. Numerous glucose sensor techniques are under development (see, for example, Scognamiglio, V. 2013. "Nanotechnology in Glucose Monitoring: Advances and Challenges in the Last 10 Years," *Biosensors and Bioelectronics* 47:12-25. Balaconis, M. K. and Clark, H. A. 2013. "Gel Encapsulation of Glucose Nanosensors for Prolonged in Vivo Lifetime," *Journal of Diabetes Science and Technology* 7(1):53-61; Heo, Y. J. and Takeuchi, S. 2013. "Towards Smart Tattoos: Implantable Biosensors for Continuous Glucose Monitoring; *Advanced Healthcare Materials* 2(1):43-56. Hu, R., Stevenson, A. C., and Lowe, C. R. 2012. "An Acoustic Glucose Sensor," *Biosensors and Bioelectronics* 35(1):425-428; Billingsley, K., Balaconis, M. K., Dubach, J. M., Zhang, N., Lim, E., Francis, K. P., and Clark, H. A. 2010. "Fluorescent Nanooptodes for Glucose Detection," *Analytical Chemistry* 82(9): 3707-3713; Cash, K. J. and Clark, H. A. 2010. "Nanosensors and Nanomaterials for Monitoring Glucose in Diabetes," *Trends in Molecular Medicine* 16(12):584-593; Domschke, A. M. 2010. "Continuous Non-invasive Ophthalmic Glucose Sensor for Diabetics," *Chimia* (Aarau) 64(1-2):43-44).

For immediacy of response, the jacket to deliver the insulin is preferably positioned along the hepatic portal vein, or adopting an orthotopic approach, as close as practicable to the pancreas as the normal source of insulin. The hepatic portal vessels of the mesentery that normally transport nutrients other than amino acids and simple sugars absorbed directly through the gut therefore function normally. However, the blood that flows through these vessels is substantially void of glucose, so that the fact that the insulin is delivered downstream through the jacket is without adverse effect; the pharmacological effect of the insulin not implemented until the liver is entered. A relatively normal position for the release of insulin reduces fluctuations in blood glucose to within normal levels without interfering with first-pass processing of drugs.

This eliminates the need for the subcutaneous injection of an insulin, with a time lag that compared to central release, is considerable. No subcutaneous injection, oral antihyperglycemic drug, or inhaled formulation of insulin, metformin, or any other drug can approximate the ability of an instant response system with multisensor input under hierarchical control to modulate blood glucose to within the normal range. Insulin overdose or overproduction should it arise is remediable by releasing metalloprotease insulin-degrading enzyme (insulysin, insulinase) or glucose directly into the hepatic portal vein or glucose into the bloodstream.

The initiation of such treatment after diabetes mellitus has set in, strictly exemplary and cited for its prevalence, typifies treatment by such means of a disease cascade, here hyperglycemia that would have led to chronic vascular inflammation, nephropathy, retinopathy, medial calcification, and abnormal hematology, leading in turn to thrombosis and cerebral and myocardial infarction. Transient diabetes such as gestational where future pregnancies are not anticipated is not treated thus. If necessary, such treatment when desired due to more than one transient disease process can be implemented using components that are absorbed or disintegrate.

Chronic conditions involving aberrant insulin production, to include insulin rebound (posthypoglycemic hyperglycemia, chronic Somogyi rebound, Somogyi effect), idiopathic postprandial syndrome (reactive hypoglycemia, idiopathic hypoglycemia) are instantly and automatically regulated back to within normal limits, as are comparable transients in any comorbid disease also under treatment by the system. By eradicating the early symptoms of diabetes—glycosuria inducing polyuria, polydipsia, fatigue, blurred vision, hyperinsulinemia, and dyslipidemia; the diverse sequelae that ensue over time, such as peripheral numbness neuropathy, retinopathy, nephropathy, vascular disease (atherosclerosis, angina, cardiomyopathy), venous thrombosis, predisposition to infection, and so on, that often lead to death, are precluded from originating.

Since "An episode of hyperglycemia in a patient with diabetes can require hours or days of intensive therapy to return the blood glucose value to normal," (Klonoff, D. C. 2007. "The Benefits of Implanted Glucose Sensors," *Journal of Diabetes Science and Technology* 1(6):797-800), the ability to prevent the entry of excessive glucose into the systemic circulation under predictive or anticipatory control using sensor implant inputs from different locations and tissues rather than secondarily or reactively having to remedy the excess with medication is especially beneficial.

When the disease process or a sequel induced by it is not focal so that it can be targeted, such as atherosclerosis sequelary to diabetes, a background level of evolocumab, ezetimibe, a statin, and apixaban (see for example, Agnelli, G., Buller, H. R., Cohen, A., Curto, M., Gallus, A. S., Johnson, M., Porcari, A., Raskob, G. E., Weitz, J. I.; with 397 collaborators 2013. "Apixaban for Extended Treatment of Venous Thromboembolism," *New England Journal of Medicine* 368(8):699-708), for example, can be circulated, usually at a lower dose. Multicomponent disease, or comorbidity, whether the components may be ascribed to a distinct causal chain, each is produced by etiologically distinct conditions, or some combination thereof are treated by placement of the jacket or magnetized jacket, with or without clasp-magnet support, at or as close to the origin of each disease component as the avoidance of trauma will allow.

Often, this will involve situating the jacket at the level along the supporting vessel or vessels to target the supply territory where the disease arises or exerts an effect. In this way, the components of comorbidities whether co-original and sequential or substantially unrelated can be treated. As compared to a systemic dose, targeted medication is small, even when more concentrated than might be allowed to circulate. Moreover, in situations where the condition is systemic with only salient lesions targeted, a background dose for circulation can be significantly reduced. The ability to reduce without eliminating a background systemic level of a steroid, for example, can significantly alleviate its adverse side effects.

Moreover, because such a system is able to treat multiple disease conditions related or unrelated, immediately and simultaneously, it is able to suppress not only diabetes and collateral disease for which diabetes is responsible, but to treat disease that induces or facilitates the development of hyperglycemia and diabetes, such as Alström syndrome, Werner's syndrome, acanthosis nigrans, pineal hyperplasia syndrome, ataxia telangiectasia, lipodystrophic disorders that induce insulin resistance, cystic fibrosis, pancreatitis, and hemochromatosis; or, endocrinopathies, such as Cushing syndrome, acromegaly, and pheochromocytoma (see, for example, Kishore, P. 2012. "Diabetes Mellitus (DM)," the Merck Manual online at http://www.Merckmanuals.com/professional/endocrine_and_metabolic_disorders/diabetes_mellitus_and_disorders_of_carbohydrate_metabolism/diabetes_mellitus_dm.htm).

Acting over time, the continuous attraction of a periductally, hence, immediately placed magnetized collar to act upon superparamagnetic drug-carrier nanoparticles or microparticles can replace the need for a powerful and heavier patch-magnet or electromagnet placed subcutaneously or held in position by an extracorporeal harness. Where the anatomy does not afford the clearance required to achieve the field force or pull strength necessary, separate intracorporeal patch-magnets, or neodymium magnets mounted on a tissue clasp or an electromagnet mounted at the body surface are used to support the magnetized jacket.

Ordinarily the collar or jacket is magnetized to present longitudinally and radially symmetrical gradient field strength along the longitudinal axis of the encircled ductus. Hypothetically, the attraction from entirely about the circumference therefore cancels out along the axis, although the asymmetries of real ductus negate this. Due to movement and the imperfect radial symmetry of the lumen, however, magnetic particles never remain centered thus long enough to escape being attracted to one side or the other at every level. However, a separate magnetized collar, or impasse-jacket, or one integrated into a ductus side-entry jacket, can be made to match or complement the eccentricity of the lesion.

For example, an arc can be unmagnetized or magnetized less strongly. This is usually accomplished by introducing an insert made of a nonmagnetic material such as a plastic into the arcuate gap or by magnetizing the arc separately from the rest. When uptake of a magnetically nonsusceptible or nonmagnetic drug is not complete and the residue is to be prevented from flowing past a certain level, provided a reversal agent or antagonist is available, a segment of the ductus can be targeted for treatment by delivering the reversal agent through a second simple junction type ductus side-entry jacket or releasing the agent from an impasse jacket at the level downstream. Such action with an impasse jacket is best spontaneous due to the intrinsic chemical relationship of the reversal agent to the residue, so that it responds to the residue without the need for further action.

When used for the direct targeted delivery of drugs, a primary object in the use of side-entry connection jackets is to align drug delivery with network feedback, if necessary, by means of a hierarchical control system. Thereby, automatic and immediate targeted point drug therapy is achieved—not just diagnostics at one or multiple sites in the body so that the clinician remains limited to drug delivery that is neither immediate nor targeted. If the patient is not to be bedridden or the condition is chronic, a number of needled catheters cannot be used. Ductus side-entry connection jackets afford secure connection to the ductus, and in so doing, enable not just single point direct-to-ductus drug delivery, but the implementation of such a prosthetic supplementary disease-process compensation system.

The ductus side-entry connection pump-pair and jacket sets to be described thus make possible the targeted delivery of drugs through automatic response that is immediate. Were the condition to exceed the range of adjustment for which the system had been set, the exigent readings can be transmitted to a clinician able to adjust the dosing by remote control. Hierarchical control has been available for decades; however, with no means for safely converging with ductus through a secure junction, the relation of hierarchical networked feedback to automatic drug delivery has remained elusive. Because the sensors are associated with collocated means for the targeting of drugs to the location respective of each, immediate and automatic remedial drug delivery, not just information as to the status of the patient, are obtained.

This immediacy of therapy and not just a providing of diagnostics can be a critical factor in the response to a medical emergency Such a system is able to continuously monitor the level of an analyte and initiate and/or adjust the delivery rate of a corrective drug passed through the jacket and into the ductus directly from an ambulatory pump. Many drugs are affected by interaction with constituents of food, other drugs, and circadian factors. The anticoagulant action of warfarin, for example, is reversed in proportion to the intake in food of vitamin $K_1$, necessitating periodic testing of clotting time (prothrombin ratio; international normalization ratio). Implantation allowing extreme miniaturization in sensors over external meters for home use currently available, prothrombin, vitamin $K_1$, and other diagnostic sensor probe readings will be relegated to apparatus small enough to implant rather than to manipulate.

Such a system is able to assess dose sufficiency, and warfarin taking effect after a significant interval, extrapolate from short term deviation to deliver the adjusted dose at or close to the optimal time. Circadian circumstances calling for adjustment in the dose are instantly responded to throughout the day. Such a system is able to 'learn,' making it possible for control over drug delivery to be anticipatory. An unmagnetized or simple side-entry connection jacket can be placed about a native or transplanted tubular anatomical structure (conduit, ductus) to allow a synthetic tube, or catheter, or an artificial or tissue-engineered vessel to open directly into, without entering, a native or graft lumen, thereby significantly reducing the risks of clotting, hemorrhage, leakage, or accidental injury associated with existing means.

Jacket and Nonjacketing Connector Placement

A ductus side-entry jacket seals off potential paths of extravasation or leakage before the ductus wall is breached by excising a small plug of tissue from the ductus wall. A simple drug delivery and lumen and contents withdrawal, or takeout, application is shown in FIG. 16, which depicts a ductus side-entry jacket used to deliver drugs to an endarterial coronary vessel, where entry into the systemic circulation as might result in adverse side effects or a residue that ought not to be released to other tissue is bypassed. The jacket accessory or service channel, part number 11 for targeting drugs through the jacket and into the target ductus, part number 13, is shown entering the jacket underside. The line shown in FIGS. 16 and 22 to a port shown in FIGS. 27 and 28 at the body surface can be tunneled subcutaneously as are ports used with insulin pumps.

Less simple applications involve shunting around or straddling a diseased segment, tumor, or other lesion along the ductus, or the tissue the ductus supplies for exposure or for isolation from a drug or drugs. As shown in FIGS. 17 thru 22, ductus side-entry connection jackets can also be used to join synthetic shunts to native ductus, as will be further addressed. Applied to a coronary artery of a patient lacking a suitable autologous graft, placement thus avoids the need for a direct anastomotic junction between alloplastic and native termini and allows the delivery of anticoagulants.

Restriction of Pumps to the Delivery of Drugs and Dialysate

The pumps are never used to move blood, so that hemolysis and its further complications of organ system injury, anemia, hepatic insufficiency, coagulopathy, and platelet damage or significant gas embolism cannot arise from this source (see, for example, Sapirstein, J. S. and Pierce, W. S. 1997. "Mechanical Circulatory Support," Chapter 66 in Greenfield, L. J., Mulholland, M. W., Oldham, K. T., Zelenock, G. B., and Lillemoe, K. D. (eds.), *Surgery: Scientific Principles and Practice*, page 1554). In an application such as that depicted in FIG. 13, where blood is pumped through synthetic coronary bypasses by the heart, lining the bypasses with a textured surface of sintered titanium microspheres or textured polyurethane, for example, fosters the formation of a physiologically active pseudointima (Sapirstein, J. S. and Pierce, W. S. 1997 Op cit. page 1556; Dasse, K. A., Chipman, S. D., Sherman, C. N., Levine, A. H., and Frazier, O. H. 1987. "Clinical Experience with Textured Blood Contacting Surfaces in Ventricular Assist Devices," *Transactions of the American Society for Artificial Internal Organs* 33(3):418-425).

Enabling the Use of Catheters as Circulatory Bypasses and Shunts

Especially in the elderly and those with a systemic vasculitis (angiitis, arteritis) for whom autologous vessels suitable for transplant or a tissue-engineered conduit are unavailable or the taking thereof would likely result in atrophy of the tissue supplied, the ability to use catheters as replacement conduits is a considerable benefit. The use of catheters in lieu of middle thoracic arteries or saphenous veins for coronary artery bypass grafts is shown in FIGS. 21 and 22, where accessory channels 11 make possible the indefinite use of the catheters by allowing the direct delivery of antithrombotic, anti-inflammatory, and antimicrobial drugs.

If native or engineered vessels are available, these too benefit from the direct targeting of supportive medication. In such use, side-entry jackets need not be used in lieu of anastomosis, which—at least with autologous grafts—allows fused healing by primary intention. Unlike an anastomosis without support by the means indicated, such a jacket allows the nonstop directly targeted delivery of medication directly to the junction at programmed regular intervals or in response to a signal received from a biosensor.

Use of Magnetized Jackets, Clasp-Jackets, and Nonjacketing Connectors

Magnetized jackets are positioned at or antegrade to the sites of lesions within the wall of ductus to draw magnetically susceptible carrier bound drugs radially outward into the wall and any intramural or transmural lesion. More complicated applications involve alternately targeting and withholding a drug or drugs from consecutive segments along a ductus, such as 'skip' lesions along the gut, for example. In the arterial tree, alternation thus is to selectively skip over the ostia leading to an organ or organs or supply territories to be excluded.

A drug to be restricted-thus is delivered at the level desired, and if to be taken up within the surrounding lumen wall, drawn radially outward by a side-entry jacket having a magnet layer extension as shown in FIGS. 4 thru 6, where those in FIGS. 5 and 6 also include radiation shielding. In the vascular tree, extension is ordinarily in the antegrade direction, and for uniform uptake along the jacket and lesion it encircles, gradually increased in field strength. With permanent magnets, this is prepared by magnetizing separate half-cylinders at progressively higher intensities, then sectioning the half-cylinders into half-rings and bonding progressively stronger half-rings into the half cylinders that comprise the jacket magnet. With electromagnets, this is accomplished by positioning the magnets in a linear array wherein each is separately wired, allowing the current transmitted to each consecutive magnet to be adjusted as necessary.

Whereas uptake of a drug delivered through the jacket side-connector is antegrade, for uptake of a carrier bonded drug delivered upstream, the magnet can be extended in either or both the retrograde and antegrade directions. Because the field strength gradient is reversed as well, permanent magnet jackets cannot simply be reversed in direction. Electromagnetic jackets are not limited thus. When the interval separating the entry level from the level for coercive uptake is longer, consecutive magnetized jackets or impasse jackets are placed downstream. If the residue is to be prevented from passing past a certain level, then a second simple junction type jacket as shown in FIG. 2 can be used to release a reversal agent, or antagonist, at the level for cutoff.

The residue must be innocuous to intervening tissue or tissue to which a passed ostium or orifice leads, and where appropriate, extraction by means of an extracorporeal electromagnet if necessary is feasible. If such an agent is unavailable, uptake within the jacketed segment not a factor, and the delivering jacket is unmagnetized, then the drug used is magnetically susceptible particle bound prior to administration and a magnetized jacket used to extract it, the extraction or downstream jacket ordinarily an unpiped, or impasse-jacket, with extraction grid or grating.

Since the local anatomy may not afford adequate clearance for a surrounding collar of the thickness necessary to provide the field strength necessary to draw and hold the susceptible particles against the forces imposed by passing contents, one or more patch or clasp-magnets with rounded edges and corners and situated at angles with minimal encroachment upon the surrounding tissue may be needed to attain the required field strength.

In metastatic renal cancer, the direct targeting of the primary tumor and segments along the great vessels allows any residual distributed disease to be treated with a reduction in the systemic dose and/or other chemotherapeutic means that remain essential to kill tumor-shed malignant circulating 'daughter' cells (see, for example, June, C. H. 2007. "Adoptive T Cell Therapy for Cancer in the Clinic," *Journal of Clinical Investigation* 2007; 117(6):1466-1476; Boldt, D. H., Mills, B. J., Gemlo, B. T. Holden, H., Mier, J., Paietta, E. and 8 others 1988. "Laboratory Correlates of Adoptive Immunotherapy with Recombinant Interleukin-2 and Lymphokine-activated Killer Cells in Humans," *Cancer Research* 48(15):4409-4416; Rosenberg, S. A., Lotze, M. T., Muul, L. M., Leitman, S. Chang, A. E., Ettinghausen, S. E, Matory, Y. L, Skibber, J. M., and 5 others 1985. "Observations on the Systemic Administration of Autologous Lymphokine-activated Killer Cells and Recombinant Interleukin-2 to Patients with Metastatic Cancer," *New England Journal of Medicine* 313:(23)1485-1492). Derivative tumors are treated likewise.

In this context, the ability to straddle each kidney to deliver in vitro-incubated interleukin-2 (Prometheus Laboratories Proleukin®) lymphokine-activated T-cells, or T-lymphocyte killer cells, tumor-infiltrating lymphocytes, or cytotoxic T-lymphocytes (see, for example, *Merck Manual of Diagnosis and Therapy*, 18th Edition 2006, Section 11, Chapter 148, "Tumor Immunology," Immunotherapy, page 1156), into the renal artery or arteries as inlets and extract these at the renal veins as outlets, with another delivery jacket placed about the ascending aorta as shown in FIG. 21 and extraction jacket such as that shown in FIG. 13 applied to the abdominal aorta, with others as necessary applied to the venae cavae, trunk, pulmonary arteries, or pulmonary veins averts side effects of intermittent large dose administration that can result in severe side effects and even death (see, for example, *Merck Manual of Diagnosis and Therapy*, 18th Edition 2006, section 148, "Tumor Immunology," page 1154; Wang, D., Zhang, B., Gao, H., Ding, G., Wu, Q., Zhang, J., Liao, L., and Chen, H. 2014. "Clinical Research of Genetically Modified Dendritic Cells in Combination with Cytokine-induced Killer Cell Treatment in Advanced Renal Cancer," *BMC* [BioMed Central] *Cancer* 14(1):251; Jiang, J., Wu, C., and Lu, B. 2013. "Cytokine-induced Killer Cells Promote Antitumor Immunity," *Journal of Translational Medicine:*11:83; Ostanin, A. A., Chemykh, H. R., Leplina, O Y., Shevela, E. Y., Niconov, S. D., and Kozlov, V. A. 1997. "IL-2-Activated Killer Cells and Native Cytokines in the Treatment of Patients with Advanced Cancer," *Russian Journal of Immunology* 2(3-4):167-176). Moreover, continuous delivery produces better results than does administration by injection every eight hours (Thompson, J. A., Lee, D. J., Lindgren, C. G., Benz, L. A., Collins, C., Shuman, W. P., Levitt, D., and Fefer, A. 1989. "Influence of Schedule of Interleukin 2 Administration on Therapy with Interleukin 2 and Lymphokine activated Killer Cells," *Cancer Research* 49(1):235-240).

The cytotoxic T-lymphocytes or T-lymphocyte killer cells are bound to magnetically susceptible superparamagnetic nanoparticles before loading in the drug vial or reservoir switching turret shown in FIGS. 31, 32, and 36 for infusion through the side-entry jacket or jackets and extraction by means of impasse-jackets. Switching among pump inputs is shown as accomplished by means of a turret for pictorial clarity, alternative means of switching, such as with a relay possible. In any condition whereby a stenosed segment of a major supply artery limits perfusion but allows placement of a synthetic bypass, such a jacket will provide access for the direct delivery of medication in support of the junction itself, to prevent coagulation in the bypass, and/or to treat the territory the bypass supplies, as well as support the junction structurally.

Stenosed vessels with origin at the aortic arch which cause neurologic deficits or paresthesias (see, for example, Messina, L. M. and Zelenock, G. B. 1997. "Cerebrovascular Occlusive Disease," Chapter 80 in Greenfield, L. J., Mulholland, M. W., Oldham, K. T., Zelenock, G. B., and Lillemoe, K. D. (eds.), *Surgery: Scientific Principles and Practice*, page 1757) are no less treatable thus than are aortofemoral or ileofemoral bypasses, for example, as mentioned below. The jacket can provide a simple and secure junction for passing a cabled therapeutic or imaging device through it and into the native lumen. This allows introducing medication or retrieving diagnostic test samples, for example. The jacket as merely a junction can be extended to incorporate a surrounding magnet with a field intensity gradually increased in the antegrade direction to draw a magnetically susceptible carrier bound drug or other therapeutic substance radially outward through the lumen wall.

Radiation Shielding

Cladding the jacket and lines leading to it with radiation shielding further allows the direct delivery through the lines to the jacket of less intensively superparamagnetic drug-carrier bound radionuclide, for example, which are then drawn radially outward through the lumen wall and into contact with any lesion there. Moreover, because the jacket is periductal with the radiation shield the outermost component, the radiation shield can be made of overlapping, or imbricated, particles of tungsten, each encapsulated within a chemically isolating nonabsorbable polymeric casing, for example, and bound to its neighbors with a biodegradable bonding agent so that it disintegrates once the radiation is depleted.

Since layers of the jacket, within or subjacent to a radiation shield if used, can be perforated or fenestrated, the adverse effects of long-term isolation from the internal milieu can be averted. That primary or intrinsic neoplasms and other intramural lesions treated with radiation seldom appear in blood vessels means that the need for radiation shielding is infrequent. Moreover, should such a lesion appear in a vessel, the shielded jacket allows the direct targeting of the affected segment with drugs such as a statin and steroids to suppress the rapid atherosclerotic degradation otherwise seen. In other type ductus, it is the relative half-life and time that the ductus may remain encircled that determines the allowable interval for use and radiation level of the radionuclide.

The jacket is used to establish catheteric, or artificial conduit-to-native end-to-side, rather than native end to native end anastomosis by sutured connection, distinguishing such a junction from most if not all prior art vascular connectors. The synthetic conduit can then be used to deliver therapeutic substances directly from a port implanted at the body surface to the native lumen or to divert contents from one native lumen to the same native conduit downstream as a bypass or to another ductus in the same or a different bodily system as a shunt. As used herein, a 'port' or 'portal' can be of the conventional subcutaneously implanted or portacath (mediport) type used with a central venous catheter.

Body Surface Ports

As shown in FIGS. 27 and 28, when an extracorporeal power, control, and pump pack is used, only the sensors, fluid lines, jackets, and nonjacketing connectors are implanted, only an open type port, or one open to the exterior used. Only the outflow openings in such a port, as in a ureteral urine bypass addressed below must open to the exterior, so that the port is mounted on the skin, or cutaneous rather than subdermally. When the entire system, to include power source, controlling microprocessor, reservoirs, and pumps is fully implanted, the port is closed to the exterior or subcutaneous, access then through the skin by means of a hypodermic needle or jet injector. For increased protection against infection, ports with one or more openings to the outside are usually subcutaneous.

For example, a small (12 millimeters in diameter) port mounted to a side of the mons pubis (to allow ease of visualization for the patient) with outlet to an external collection bag must include an opening to the exterior which is above-skin or cutaneous, while other opening for the injection of drugs are subcutaneous, marked on the surface with tiny tattoo marks. The passageway leading from such an open-type port at the body surface through a connecting tube, usually a catheter, to the side-entry connection jacket used to form a junction with the native conduit or ductus is uniform in diameter throughout, is unobstructed or readily cleared, and can be angled.

This makes it possible not only to move fluids in either direction, to deliver drugs and aspirate diagnostic test samples, but to pass cabled diagnostic and therapeutic instruments through the junction on a regular basis, and allow connection to apheresis—leukapheresis, erythrocytapheresis, thrombocytapheresis, or thrombapheresis-apparatus, as well as allow the use of synthetic tubing to create internal shunts and bypasses. Such a port is no less capable of conventional applications, such as delivering radiopaque contrast agents, chemotherapeutic, antineoplastic, autoimmune suppressive, clotting factor, alpha 1-antitrypsin deficiency replacement, and antimicrobial drugs, and will support total parenteral nutrition as well as hemodialysis and dialysis whether hemodialysis or peritoneal.

Since once placed, routine entry into the lumen involves neither puncturing the skin nor entry into a body cavity, access with such means is effectively noninvasive. Connection directly to the vascular tree thus allows the use of intravascular ultrasound, for example, while connection along the gastrointestinal tract, for example, allows the withdrawal of solid biopsy test samples, for example. Periductal implants avoid the placement of a foreign object within the lumen, invariably associated with the risk of adverse consequences. Such implants can communicate with a port at the body surface, can be used to deliver any therapeutic substance prepared in a flowable form, and when magnetized, can draw magnetic drug-carrier bound drugs radially outward through the tunics to reach inflammation or lesions within the ductus wall.

Drug Penetration and Focus

Indissolubly bound to the carrier and drawn radially outward, the drug will reach the lesion regardless of the axifugal or abaxial depth or distance of the lesion from the lumen. Used to administer chemotherapy along the small intestine, for example, the drug would first reach a primary carcinoma of the mucus epithelium, then an adenoma in the submucosa, then a sarcoma in the outer muscle layers whether primary or incurred by metastatic invasion. No drug eluting stent absorbable or nonabsorbable can approach this depth of penetration. Moreover, uptake is accomplished without dependence upon the presence of receptors for the drug by the target as limits the choice of substance, radionuclide, or monoclonal antibody to one having an intrinsic affinity for the target tissue, such as that of iodine for the thyroid gland.

Application to achieve the targeted treatment of a neoplasms with antimitotic and antiangiogenic drugs that are toxic to all tissue with or without heating, for example, is clear, as is the avoidance of side effects. All drugs can induce side effects, making the ability to limit delivery to only the tissue intended especially beneficial. For example, until a specific gene therapy technique proves successful, every drug given to treat inflammatory bowel disease or regional enteritis (ileocolitis, Crohn's disease, ulcerative colitis), will continue to pose risks for inducing collateral pathology (see, for example, Young, V. B., Kormos, W. A., Chick, D. A., and Goroll, A. H. 2010. *Blueprints: Medicine*, Philadelphia, Pa.: Lippincott, Williams, and Wilkins, page 187).

The systemic circulation of steroids—to treat Cushing's disease, for example—often results in moon facies, and of antimitotic drugs—to treat neoplasms, for example—often results in hair loss. An impasse-jacket can not only directly target a site of disease ordinarily accessible solely through systemic administration—and then weakly, with little of the dose delivered as intended—but the drugs released to or from it can be delivered at concentrations—and if radioactive, at dose rates—with a potency far higher than might be allowed to circulate. Little if any entering the circulation, the drug is concentrated where its effect is intended, exposure to other tissue and the adverse side effects this causes minimized if not eliminated.

With systemic disease that can induce lesions elsewhere, such as atherosclerosis or a vasculitis able to induce localized obstructions, this local focusing does nothing to interfere with administering a background dose of the same or another drug in the circulation. In the treatment of nonsysteruic or localized disease, the inability to closely target drugs to sites within the body where the drugs are intended to take effect, avoiding the general circulation and metabolism by the liver, often disallows, entirely or in concentration, in all or in only certain patients, the use of drugs that would otherwise have potential value. Moreover, numerous drugs exert beneficial local effects when directly applied to the diseased or lesioned tissue.

Limited exposure of more severely atherosclerosed arteries or, segments thereof to statins with or without adjuvants takes advantage of the pleiotropic effects of these drugs, which targeted, can be administered in higher concentration than the risk of myopathic or other side effects would allow (see, for example, West, A. M., Anderson, J. D., Meyer, C. H. Epstein, F. H., Wang, H., Hagspiel, K. D, Berr, S. S. and 7 others 2011. "The Effect of Ezetimibe on Peripheral Arterial Atherosclerosis Depends upon Statin Use at Baseline," *Atherosclerosis* 218(1):156-162; Zhou, Q. and Liao, J. K. 2010. "Pleiotropic Effects of Statins.—Basic Research and Clinical Perspectives," *Circulation Journal* 74(5):818-826; Sastry, P., and Kaski, J. C. 2010. "Atherosclerotic Plaque Regression—The Role of Statin, Therapy". *Drugs Today* (Barcelona) 46(8), 601-608; Araujo, D. B., Bertolami, M. C., Ferreira, W. P., Abdalla, D. S., Faludi, A. A., Nakamura, Y., and Bricharello, L. P. 2010. "Pleiotropic Effects with Equivalent Low-density Lipoprotein Cholesterol Reduction: Comparative Study between Simvastatin and Simvastatin/Ezetimibe Coadministration," *Journal of Cardiovascular Pharmacology* 55(1):1-5; Taylor, A. J., Villines, T. C., Stanek, E. J., Devine, P. J., Griffen, L., Miller, M., Weissman, N. J., and Turco, M. 2009. "Extended-release Niacin or Ezetimibe and Carotid Intima-Media Thickness," *New England Journal of Medicine* 361(22):2113-2122; Zhou, Q. and Liao, J. K. 2009. "Statins and Cardiovascular Diseases: From Cholesterol Lowering to Pleiotropy," *Current Pharmaceutical Design* 15(5):467-478; Wang, C. Y., Liu, P. Y., and Liao, J. K. 2008. "Pleiotropic Effects of Statin Therapy: Molecular Mechanisms and Clinical Results," *Trends in Molecular Medicine* 14(1):37-44; Kastelein, J. J., Akdim, F., Stroes, E. S., Zwinkerman, A. H., Bots, M. L., and 23 others 2008. "Simvastatin with or without Ezetimibe in Familial Hypercholesterolemia," *New England Journal of Medicine* 358(14):1431-1443; Landmesser, U., Bahlmann, F., Mueller, M., Spiekermann, S., Kirchhoff, N., Schulz, S., Manes, C., and 6 others 2005. "Simvastatin Versus Ezetimibe: Pleiotropic and Lipid-lowering Effects on Endothelial Function in Humans," *Circulation* 111(18): 2356-2363; Liao, J. K. and Laufs, U. 2005. "Pleiotropic Effects of Statins," *Annual Review of Pharmacology and Toxicology* 45:89-118; Liao, J. K. 2005. "Clinical Implications for Statin Pleiotropy," *Current Opinion in Lipidology* 16(6):624-629; Wolfrum, S., Jensen, K. S., and Liao, J. K. 2003. "Endothelium-dependent Effects of Statins," *Arteriosclerosis, Thrombosis, and Vascular Biology* 23(5):729-736; Takemoto, M and, Liao, J. K. 2001. "Pleiotropic Effects of 3-Hydroxy-3-Methylglutaryl Coenzyme A Reductase Inhibitors," *Arteriosclerosis, Thrombosis, and Vascular Biology* 21(11):1712-1719; Laufs, U., La, F., Plutzky, J., and Liao, J. K. 1998. "Upregulation of Endothelial Nitric Oxide Synthase by HMG [Hydroxy Methylglutaryl] CoA [Coenzyme A] Reductase Inhibitors," *Circulation* 97(12):1129-1135).

Similarly, the local application of a combination of drugs which includes mammalian target-of-rapamycin, or mTOR, inhibitors, such as sirolimus (rapamycin) and everolimus appears to reduce the vulnerability to rupture of plaque (see, for example, Martinet, W., De Loof, H., and De Meyer, G. R. 2014. "mTOR Inhibition: A Promising Strategy for Stabilization of Atherosclerotic Plaques," *Atherosclerosis* 233(2):601-607; Martinet, W., De Meyer, I., Verheye, S., Schrijvers, D. M., Timmermans, J. P., and De Meyer, G. R. 2013. "Drug-induced Macrophage Autophagy in Atherosclerosis: For Better or Worse?," *Basic Research in Cardiology* 108(1):321; Martinet, W., Verheye, S., De Meyer, I., Timmermans, J. P., Schrijvers, D. M., Van Brussel, I., Bult, H., and De Meyer, G. R. 2012. "Everolimus Triggers Cytokine Release by Macrophages: Rationale for Stents Eluting Everolimus and a Glucocorticoid," *Arteriosclerosis, Thrombosis, and Vascular Biology* 32(5):1228-1235; Croons, V., Martinet, W., and De Meyer, G. R. 2010. "Selective Removal of Macrophages in Atherosclerotic Plaques as a Pharmacological Approach for Plaque Stabilization: Benefits versus Potential Complications," *Current Vascular Pharmacology* 8(4):495-508; Martinet, W., Verheye, S., and De Meyer, G. R. 2007. "Everolimus-induced mTOR [mammalian target of rapamycin] Inhibition Selectively Depletes Macrophages in Atherosclerotic Plaques by Autophagy," *Autophagy* 3(3):241-244).

The gastrointestinal gastritis and ulcers that result from long-term use of nonsteroidal anti-inflammatory drugs such as aspirin and ibuprofen are avoided, as is the risk of urticaria or anaphylaxis responsive to certain drugs such as antibiotics, for example (see, for example, Merck Manual, 18th edition, pages 974 and 1360). Reciprocally, drugs that must be limited in concentration for systemic dispersal because of the side effects and drug-drug interactions that loom when other tissue is exposed can be increased in concentration or potency to the optimal dose for direct delivery from the standpoints not only of efficacy but of portability and power conservation or battery life for use in an ambulatory system.

Without targeting, drugs or other remedial substances that might be used to treat symptoms must sometimes be discounted or limited in strength to avoid conflict with those used to treat the etiology, and those used to treat a disease in one part of the body may conflict with those used to treat another disease in another part of the body. Targeting also makes it possible to eliminate the need for secondary drugs that must be prescribed merely to counteract side effects produced by primary drugs. For example, tightly controlled delivery of drugs that act directly upon a lesion and do not require systemic dispersal to be processed by the liver, for example, minimizes the extent of contact with nontargeted tissue and therefore the opportunities for the drugs to bind covalently with or otherwise affect serum or tissue proteins, identified as a mechanism underlying the iatrogenic inducement of autoimmune disorders.

Where the condition treated is chronic or recurrent as to justify the placement of a direct access feedline, the use of a drug, existing or yet to be developed, to be preferred if it did not induce autoimmune disease when taken systemically, can be sustained (see, for example, Chang, C. and Gershwin, M. E. 2010. "Drugs and Autoimmunity—A Contemporary Review and Mechanistic Approach," *Journal of Autoimmunity* 34(3):J266-J275; Brown, R. J., Rother, K. I., Artman, H., Mercurio, M. G., Wang, R., Looney, R. J., and Cowen, E. W. 2009. "Minocycline-induced Drug Hypersensitivity Syndrome Followed by Multiple Autoimmune Sequelae," *Archives of Dermatology/JAMA Dermatology* 145(1):63-66; Merck Manual of Diagnosis and Therapy, 18th Edition 2006. "Autoimmune Disorders" and "Drug Hypersensitivity," pages 1361-1363; Elkayam, O., Yaron, M., and Caspi, D. 1999. "Minocycline-induced Autoimmune Syndromes: An Overview," *Seminars in Arthritis and Rheumatism* 28(6):392-397).

No endoluminal stent, absorbable or eluting, can restrict delivery so finely as to nearly if not completely eliminate the risk of such sequelae; indeed, the alternative is to administer drugs systemically where exposure to other tissues and organs must be indiscriminate. The use of extravascular implants enlists relatively minor invasive surgery in the service of medical management through the positioning of implants that allow drugs to be precisely targeted rather than administered in higher doses through the systemic circulation, exposing every tissue and organ. Indiscriminate delivery thus is the source of many adverse side effects and drug-drug interactions. Where the use of certain drugs at one anatomical site ordinarily disallows the use of other drugs at another, minimizing if not eliminating drug interaction fundamentally expedites the treatment of regionally concentrated if not distinct comorbidities.

More specifically, the availability of means for substantially isolating certain tissue for the delivery of certain drugs frees the clinician to select the best drugs for treating each of two or more concurrent but separate disease processes, or comorbidities, whether pathophysiologically related or unrelated without much concern for drug-drug interactions. Since clinical trial protocols of new drugs apply criteria that omit comorbidities (Jones, R. 2010. "Chronic Disease and Comorbidity," *British Journal of General Practice* 60(575): 394, the ability to target drugs to a certain lesion preserves the validity of trial findings in eliminating or substantially eliminating the effect of collateral disease. The jackets may be of different sizes, different types, and applied to ductus belonging to different organ systems.

The principle or index diseases seen most often in comorbid conditions are cardiovascular or malignant (Gijsen R., Hoeymans, N., Schellevis, F. G. Ruwaard, D., Satariano, W. A., and van den Bos, G. A. M. 2001. "Causes and Consequences of Comorbidity: A Review," *Journal of Clinical Epidemiology* 54(7):661-674), both having systemic implications and expression, but inducing localized lesions amenable to the targeted delivery of drugs. Studies of comorbidity tend to be relatively few (see, for example, Valderas, J M., Mercer, S. W., and Fortin, M. 2011. "Research on Patients with Multiple Health Conditions: Different Constructs, Different Views, One Voice," *Journal of Comorbidity* 1:1-3; Diederichs, C., Berger, K., and Bartels, D. B. 2011. "The Measurement of Multiple Chronic Diseases—A Systematic Review on Existing Multimorbidity Indices," *The Journals of Gerontology. Series A, Biological Sciences and Medical Sciences* 66(3):301-311; Fortin, M., Lapointe, L., Hudon, C., and Vanasse, A. 2005. "Multimorbidity is Common to Family Practice. Is it Commonly Researched?" *Canadian Family Physician* 51:244-245; Valderas, J. M., Glynn, L., Ferrer-Menuina, X., Johnson, R., and Salisbury, C. 2011. "Diseases that Come in Multiples; A Systematic Review of Multi-morbidity Profiles," *Family Medicine* 43(Supplement 1); Mercer, S. W., Smith, S. M., Wyke, S., O'Dowd, T., and Watt, G. C. M. 2009. "Multimorbidity in Primary Care: Developing the Research Agenda," *Family Practice* 26(2):79-80).

Since a side-entry connection jacket can incorporate more than a single side-entry connector, a catheteric or synthetic drug feed fluid line, or simply line, from the surface can be connected to a side-entry connector used as an inlet into the ductus the jacket encircles, while another, ordinarily larger synthetic outlet catheter is connected to a second side-entry connector to serve as the outlet into a prosthetic bypass that reenters the native conduit distal to or beyond an obstruction. Alternatively, the drug delivery line can be connected by a separate jacket to the native conduit upstream to the bypass outlet jacket or downstream from the synthetic bypass outlet jacket. This versatility makes it possible to differently target segments of the native conduit upstream or downstream to the synthetic-native connection for the delivery of drugs.

For targeting a segment along a conduit, a drug is suitable in proportion to the promptness of its effect at the point or level of and following delivery. A single side-entry connection jacket can incorporate more than one side-connector, any or all of which can be of either type. Whether for diagnostic or therapeutic purposes, when the jacket is to serve primarily for the frequent passage into the native lumen of a cabled device or catheter, a side-entry jacket with a double-arm side-connector as shown in FIG. 7 expedites steering in either direction to the native lumen, a double-arm clean-out or inline port, as shown in FIGS. 30 and 31 affording extracorporeal entry through the pump-pack as shown in FIG. 31.

When the adductal terminus, or distal end, of the side-connector is substantially round, it can be placed using essentially the same procedure to be described for the side-connectors shown in FIGS. 1-6. That is, the side-connector can be rotated as a circle-cutter as well as the application of vacuum force. Such need is substantially limited to the thick walls of lumina along the digestive tract. More often, however, this type of side-connector, elongated along the axis of the ductus at the distal end, is used for the continuous or frequent infusion or extraction of analytes or cells. To deliver medication into the native lumen when the hole, that is, the ostium or stoma, excised from the side of the ductus is covered by a fluid resistor such as elastic flap and slit valves to be described, requires additional exertion by the pump, and therefore added power consumption.

Power Optimization During Ambulatory Use

Battery life is a significant consideration taken up in several sections above, to include those entitled Advantages of Electromagnets, Use of Side-entry Jackets, and Drug Penetration and Focus. Power is conserved by optimizing the efficiency of power consuming components such as drug reservoir pump outlet motors and electromagnets, and by eliminating conditions of obstruction or resistance as necessitates the use of more power. So long as the patient can remain in a limited area, electrical power can be taken directly or by recharging from the city mains or a transdermal energy transfer source indefinitely. However, continuous or frequent intermittent operation during a period of recharging nonavailability, as required by ambulatory apheresis, limits the time the system can continue in use with the patient able to move freely.

To forestall such interruptions while minimizing battery weight, the patient is advised to have fully recharged batteries available. Batteries incorporated into a surface port are generally of the button cell type. Where these are inadequate, a battery pack is worn, as is always the case with a nonfully implanted system where the power, control, and drug storage reservoirs or vials are situated. For simplicity, efficient operation, and long life, the embodiment described below in the section entitled Description of the Preferred Embodiments of the Invention uses an elastic slit membrane, or depending upon the forces involved, extraction trap flap-valve at its distal end.

For extractive use, such as ambulatory apheresis of white blood cells, the jackets, each with electromagnet, are joined in a chain. The magnets are made as small, light in weight, and powerful as possible and include suture eyelets or loops at points about the magnet surfaces to allow the use of suture to fix the magnets in the correct position if necessary. The weight of a magnet chain heavy for a child or frail patient is distributed thus to as many anchoring points as necessary. The same applies to a confluence chamber.

Except for use in a very young or frail patient, the superior conductivity of silver offset by its greater mass and expense, the coil of the electromagnet is wound with copper wire. Subcutaneous placement affords stability for which deeper or periductal placement will usually necessitate stabilization with suture to a pad or patch stitched to neighboring tissue. This insertion may itself require to be stabilized with suture to neighboring tissue. Depending upon the clearance surrounding the substrate ductus, distributing and balancing the weight of a larger magnet is sometimes ameliorable through the use of an extraction jacket having more than one double-arm side-connector, flap-valve, and separate electromagnet at points about the circumference. Connecting the outlet arm of each jacket to the inlet arm of that adjacent with a single flush out line in series simplifies placement and extraction.

Anything which interferes with the free movement of substances through the fluid lines or foam lining the jackets and nonjacketing connectors, whether due to excessive viscosity, adhesion of the drug or agent to the interior of the conduit, kinking, a buildup of debris at a valve, or resistance to the penetration of an anti-inflammatory into the foam lining as to necessitate extended use of the delivery pump, for example, consumes additional energy. To prevent kinking, the sections of piping from jacket to jacket are made thick-walled of a fluoropolymer, usually polytetrafluoroethylene (Teflon® E.I. Dupont de Nemours).

Where discomfort is slight but a distinct power conserving advantage is gained, experience with ventricular assist devices and total artificial hearts indicates that the patient acclimates to the presence of a life-preserving if moderately obtrusive implant, probably with the aid of adaptive tissue development such as toughening or induration of tissue at the points of suspension, attachment, or abutment. Acceptance is promoted by minimizing size and weight and by maximizing stabilization. Subcutaneous placement is therefore expeditious but in increasing the magnetic gap, increases considerably the magnetic strength and power required and thus the weight of the magnet and the battery as power source.

A ductus side-entry jacket with this type of side-connector is placed with the pump generating a vacuum force that draws the tissue plug over the cutting die trepan edge surrounding the slit membrane or flap-valve and pulls the excised plug through the membrane. The magnet remains energized during extraction and is deenergized at the same time that the pump to flush the tissue plug out the line is energized. To prevent the catching of particles on the internal surfaces of flap-valves, these are similarly provided with a smooth surface, usually vapor deposited or laminated polytetrafluoroethylene, special materials such as these used where necessary. To minimize the accumulation of debris, the internal surface of a double-arm side-connector, flap-valve, and fluid line used for extraction on a sustained basis is made of or lined with a slippery substance such as the fluoropolymer polytetrafluoroethylene.

Especially tacky drugs or extracts may necessitate the use of lining surface materials even more slippery (see, for example, Peng, W., Guan, C., and Li, S. 2013. "Ultrasmooth Surface Polishing Based on the Hydrodynamic Effect," *Applied Optics* 52(25):6411-6416; Wong, T.-S., Kang, S. H., Tang, S. K., Smythe, E. J., Hatton, B. D., Grinthal, A., and Aizenberg, J. 2011. "Bioinspired Self-repairing Slippery Surfaces with Pressure-stable Omniphobicity," *Nature* 477 (7365):443-447, comment Nosonovsky, M. 2011. "Materials Science: Slippery When Wetted," *Nature* 477(7365):412-413; Barredo, D., Calleja, F., Nieto, P., Hinarejos, J. J., Laurent, G., Vazquez de Parga, A. L., Farias, D., and Miranda, R. 2008. "A Quantum-Stabilized Mirror for Atoms," *Advanced Materials,* 20(18):3492-3497; Logeeswaran V. J., Chan, M.-L., Y. Bayam, Saif Islam, M., Horsley D. A., Li X., Wu, W., Wang, S. Y., and Williams, R. S. 2007. "Ultra-smooth Metal Surfaces Generated by Pressure-induced Surface Deformation of Thin Metal Films," *Applied Physics A. Materials Science and Processing* 87(2): 187-192).

To avoid the pulse and arterial blood pressure which interfere with the extraction of an analyte and increase the field force required, depleting the battery or batteries more quickly, a continuous analyte extraction and/or delivery jacket such as used for ambulatory apheresis is placed along a major vein (see, for example, Cherry, E. M., Maxim, P. G., and Eaton, J. K. 2010, Op cit.). For any analyte to be extracted before entering the liver, placement along the portal vein affords first-pass interdiction. To prevent injury to the outer tunic (tunica externa, adventitia, fibrosa), the adductal edges of the side ends of the outer shell of the jacket are rounded.

Nevertheless, so that the edges do not come into contact with the outer surface of the ductus, the viscoelastic polyurethane foam lining is made thick enough to accept the radially outward pulsatile or peristaltic excursion due to the intrinsic motility of the ductus. Additionally, so that cutting into the ductus wall to excise the plug of tissue affords sufficient foam around the trepan that the foam will accept the full thickness of the ductus wall as the sharp cutting edge enters, the foam must be no less thick than the thickness of the wall surrounding the ductus lumen. Placement along the pulmonary trunk, pulmonary arteries, and or the superior vena cava addresses the pulmonary circulation, and the inferior vena cava the somatic circulation.

Functionality of Jacket and Nonjacketing Connector Foam Linings

Further increasing the thickness of the foam lining allows for growth in a young patient, as does the compliance of the jacket spring hinges, keyed to the ductus excursive force. Thickening the foam lining also allows the jacket or nonjacketing connector to conform to the shape of a ductus that may be inconsistent in diameter or one that exhibits an irregularity or anomalous or pathological protuberance. The mounting of styloid or miniature cabled devices may also necessitate cushioning over a projection associated with the device. Relief from the need for diametrical uniformity also allows some tissue surrounding the ductus, such as periadventitial fat, to be included in the jacket. The foam lining a ductus side-entry jacket is of a density as to noncompressively invest the tiny nerves and vessels that support the ductus to be treated. The thickness of the foam accommodates changes in diameter along the ductus whether structural or due to intrinsic motility, pulsation, or protrusion of a tumorous lesion in addition to affording considerable latitude in the diameter of the conduit that might be treated with a side-entry connection jacket of given internal diameter.

The sustained permeation of the foam layer through the period intervening in the intermittent delivery of an adverse tissue reaction retardant such as phosphorylcholine through a line from a pump to the foam lining through the jacket shell and magnet and radiation shielding if present is facilitated through the use of an open cell foam, a closed cell foam requiring the introduction of micropores. Gradations in foam density afford yet greater latitude in achieving permeation. To assure that engagement is secure, the outer surface of the jacket side-stem, or side-entry connector, where it enters into the locking collar and the inner surface of the locking collar, or locking nut, in which the ductus side-entry connector is journaled, are raised, roughened, and placed in complementary relation so as to mesh or interdigitate and thus lock the side-entry connector in position when the side stem is inserted.

Connection of the Jacket Sidestem or Jacket Side Connector to the Jacket Barrel

Except for this small area, the side stem, or side-entry connector, slides and rotates freely. Most if not all procedures are performed under local anesthesia without the risks of general anesthesia. Whether before or after the jacket has been placed about the vessel as the operator finds more expeditious, an aspiration line or hose leading to a vacuum pump is attached to the side-entry connector. When the connector is continuous with the catheter leading to it, the catheter serves this purpose. The vacuum is used to hold the outer surface, or adventitia, fibrosa, or serosa, of the tubular structure against the razor-sharp end of the side-entry connector despite intrinsic motility or pulsation, allowing the operator to rotate and gently advance the side-entry connector as a circle-cutter to incise a circular plug from the structure wall.

With adequate vacuum pressure, the razor-sharp adductal edge of the side-entry connector will cut through a thick tissue wall without assistance from the operator; however, if the vacuum is adjusted too high or improperly synchronized to intrinsic movement in the ductus, the sides of the tissue plug may then veer more radially inward with increased depth of cut as the lumen is approached. This can result in the formation of a triangular gutter in the lumen wall surrounding the adductal edge of the connector. Such a gutter is best avoided in the gut, ureters, and other nonvascular ductus as a weak spot not only susceptible to the accumulation of detritus as a trap, but also to the leakage of septic debris. Except in larger muscular arteries, this should seldom occur, and if it does, any accumulation of thrombus in the gap is replaced by intimal tissue.

Nevertheless, if the operator suspects that the risk is present and could result in initiating turbulent, hence thrombogenic, flow, the same precaution should be employed. To prevent this complication, the sides of the side-entry connector are wetted by a swellant formulated to encourage and become supplanted by tissue. Continuity of the side-connector and the supply line tends to make initial placement, substitution, or eventual replacement of the line more awkward, but is not discounted. The connector to a synthetic line is not intended to be applied by the operator or a technician but supplied as a manufactured article. Use of a magnetized side entry connection jacket such as that shown in FIG. 3 to draw the ferrofluid infusate long axifugally outward against, into, and through the lumen wall eliminates the need to perforate the sides of the side-connector apposite the wall to allow direct perfusion into the lumen wall.

The terms 'locking nut,' 'locking collar,' part number 5 in the drawing figures can be a nut with bottom locking washer to achieve rotational fixation when tightened flush down against the subjacent surface, or a self locking collar cap or nut with an internal bushing that ellipsoidal, conical, and/or elastomeric, expands or spreads circumferentially as the collar is rotated. Combined with threading or a side connector 6 friction fitted to the side aperture for receiving the sidestem, tightening nut 5 fixes side connector 6 in position both longitudinally and rotationally along side connector 6 so that it will not pull free of the aperture.

While reverse or hepatofugal flow may necessitate reversing the upstream position of the inlet jacket and the downstream position of the outlet or extraction jacket, the reduced force advantages in venous application are not significantly reduced when idiopathies, individual peculiarities, disease, or surgery induces pulsatile flow (see, for example, Demirtürk, O. S., Güvener, M., Coşkun, I., and Yildirim, S. V. 2013. "Results of Additional Pulsatile Pulmonary Blood Flow with Bidirectional Glenn Cavopulmonary Anastomosis: Positive Effect on Main Pulmonary Artery Growth and Less Need for Fontan Conversion," *Heart Surgery Forum* 16(1):E30-E34; Machare-Delgado, E., Decaro, M., and Marik, P. E. 2011. "Inferior Vena Cava Variation Compared to Pulse Contour Analysis as Predictors of Fluid Responsiveness: A Prospective Cohort Study," *Journal of Intensive Care Medicine* 26(2):116-124; Solhjoo, E., Mansour-Ghanaei, F. Moulaei-Langorudi, R., and Joukar, F. 2011. "Comparison of Portal Vein Doppler Indices and Hepatic Vein Doppler Waveform in Patients with Nonalcoholic Fatty Liver Disease with Healthy Control," *Hepatitis Monthly* 11(9):740-744; Goncalvesova, E., Lesny, P., Luknar, M., Solik, P., and Varga, I. 2010. "Changes of Portal Flow in Heart Failure Patients with Liver Congestion," [in English] *Bratislayské Lekáarske Listy* [*Bratislava Medical Journal*] 111(12):635-639; Neema, P. K., Sethuraman, M., Krishnamanohar, S. R., and Rathod, R. C. 2009. "Superior Vena Cava Syndrome after Pulsatile Bidirectional Glenn Shunt Procedure: Perioperative Implications," *Annals of Cardiac Anaesthesia* 12(1):53-56; Görg, .C, Riera-Knorrenschild, J., and Dietrich, J. 2002. "Pictorial Review: Colour Doppler Ultrasound Flow Patterns in the Portal Venous System," *British Journal of Roentgenology* 75(899):919-929; Görg, C., Wollenberg, B., and Beyer, J. 2001. "Reversed Portal Vein Pulsatility on Doppler Ultrasound Secondary to an Iatrogenic Mediastinal Haematoma," *British Journal of Roentgenology* 74(886):962-964; Rengo, C., Brevetti, G., Sorrentino, G., D'Amato, T., Imparato, M., Vitale, D. F., Acanfora, D., and Rengo, F. 1998. "Portal Vein Pulsatility Ratio Provides a Measure of Right Heart Function in Chronic Heart Failure," *Ultrasound in Medicine and Biology* 24(3):327-332; Gallix, B. P., Taourel, P., Dauzat, M., Bruel, J. M., and Lafortune, M. 1997. "Flow Pulsatility in the Portal Venous System: A Study of Doppler Sonography in Healthy Adults," *American Journal of Roentgenology* 169(1):141-144; Duerinckx, A. J., Grant, E. G., Perrella, R. R., Szeto, A., and Tessler, F. N. 1990. "The Pulsatile Portal Vein in Cases of Congestive Heart Failure: Correlation of Duplex Doppler Findings with Right Atrial Pressures," *Radiology* 176(3):655-658; Hosoki, T., Arisawa, J., Marukawa, T., Tokunaga, K., Kuroda, C., Kozuka, T., and Nakano, S. 1990. "Portal Blood Flow in Congestive Heart Failure: Pulsed Duplex Sonographic Findings," *Radiology* 174(3 Part 1):733-736; Applefeld, M. M. 1990. "The Jugular Venous Pressure and Pulse Contour," Chapter 19 in Walker, H. K, Hall, W. D., and Hurst, J. W. (eds.) *Clinical Methods: The History, Physical, and Laboratory Examinations*, Bethesda, Md.: Butterworth Division, Reed Publishing).

Therapeutic substances and drugs that act quickly without dependency upon the liver for metabolic conversion into the active form are piped directly to a side-entry connection jacket encircling the native conduit at the target level; otherwise, piping must be to a separate jacket positioned upstream. With sustained delivery so that difference in distance to each jacket is insignificant, like kind lesions on multiple ductus or at intervals along a single ductus can be encircled with separate side-entry connection jackets, each supplied by a branch from the same supply line rather than multiple ports. Rather than acting only after having been processed in the liver, the drugs for use thus are direct-acting; drugs that do are delivered in preprocessed form. A drug such as an anticoagulant can be delivered to, or at a distance upstream to, a synthetic bypass at the smallest dose necessary, dispersion in the circulating volume of blood diluting it as to be ineffectual. If necessary, a second jacket can be used to counteract or neutralize any unwanted residue.

Incorporated into the pump-pair plug-in module pump-pack base or receiver, seen as part number 54 in FIG. 19, sensors used to adapt drug delivery through one or more pump-pair and jacket sets can belong to a wireless body area network with a single body central unit (see, for example, Khan, J. Y., Yuce, M. R., Bulger, G., and Harding, B. 2012. "Wireless Body Area Network (WBAN) Design Techniques and Performance Evaluation," *Journal of Medical Systems* 36(3):1441-1457; Chen, M.; Gonzalez, S., Vasilakos, A., Cao, H., and Leung, V. 2010. "Body Area Networks: A Survey," *Mobile Networks and Applications (MONET)* 16(2):1-23; Ullah, S., Shen, B., Islam, S. M., Khan, P., Saleem, S., and Kwak, K. S. 2010. "A Study of MAC [Medium Access Control] Protocols for WBANs [Wireless Body Area Networks]," Sensors (Switzerland).; 10(1):128-145; Ullah, S, Higgins, H., Braem, B., Latre, B., Blondia, C., Moerman, I., Saleem, S., Rahman, Z., and Kwak, K. S 2010. "A Comprehensive Survey of Wireless Body Area Networks: On PHY [Physical], MAC [Medium Access Control], and Network Layers Solutions," *Journal of Medical Systems* 36(3):1-30; Schmidt, R., Norgall, T., Mörsdorf, J., Bernhard, J., and von der Grün, T. 2002. "Body Area Network BAN—A Key Infrastructure Element for Patient-centered Medical Applications," *Biomedical Technology* 47(1):365-368).

Incorporation into the targeted drug delivery system to be described is intended to allow immediate adjustment in the delivery of medication and not just telemetric alerts for followup by remote clinicians. Individual and paired difference-measuring sensors can be positioned within the wall of the ductus, inside the jacket, such as within the inlets to and/or between the foam lining and outer layers of the jacket, or at the surface of the body, and the jackets can be placed along a single ductus, at separate locations along the circulatory system, or to span the inlet and outlet of an organ, for example. Ductus-intramural sensors individual or multiple can be of stay conformation. If necessary, non-stay type microsensors positioned in the jacket foam lining can project a microprobe into or entirely through the ductus wall to extend level and flush with the intima or mucosa.

Use of Sensors

Paired sensors can detect differences in tissue properties such as revealed by heat transmissibility or a small direct current resting potential separating two points. Precautionary positioning of suitable jackets and a drug delivery system in a patient with a known predisposition for a condition distinguished by characteristic tissue degradation such as familial hypercholesterolemia, hypertriglyceridemia, Barrett's esophagus, ileocolitis, and numerous other disorders allows the use of definitive change in temperature, force, or pressure response, transmissivity, conductivity, or chemical indicia to signal the inception and degree of progression in abnormal (nonphysiological) metaplastic transition. Once placed, the prosthetic drug response system can respond immediately and automatically by targeted delivery of appropriate drugs to the reporting site.

Any difference in a blood analyte, intrinsic or introduced, for which the sensor technology is available can be detected at separated points along a ductus, at distances about the circulatory system, or entering and departing an organ. The applicability to the development of suitable sensors of microcantilever immunoassay and microchip sensors, for example, is clear (see, for example, Mohammed, M. I. and Desmulliez, M. P. 2011. "Lab-on-a-chip Based Immunosensor Principles and Technologies for the Detection of Cardiac Biomarkers: A Review," *Lab on a Chip* 11(4):569-595; Osiri, J. K. and Shadpour, H. 2010. "Toward Point-of-care Microchip Profiling of Proteins," *Bioanalysis* 2(10):1745-1754; Tran, N. T., Ayed, I., Pallandre, A., and Taverna, M. 2010. "Recent Innovations in Protein Separation on Microchips by Electrophoretic Methods: An Update," *Electrophoresis* 31(1):147-173). When the jacket cannot accommodate the sensor or sensors, a sample of the lumen contents can be delivered to the pump-pack for analysis therein or retrieval by a laboratory technician.

Metaplastic transition tends to be gradual rather than exigent; however, such a system can respond immediately and automatically to an emergency condition much as an implanted defibrillator can respond to an arrhythmia otherwise likely to result in a sudden arrest. For example, a jacket placed about an internal carotid artery can sense and signal the need for delivery of a drug to the brain as well as deliver the drug through the jacket into the artery, while an outlet jacket about a jugular vein can transmit the blood serum level of the drug in the effluent to indicate uptake in the brain as well as deliver a reversal agent if needed. If the drug would cause adverse side effects in patients generally or in this patient in particular, provided a reversal agent or counteractant is available, a downstream jacket can be used to discharge the reversal agent, substantially withholding entry of the drug into the general circulation.

This can make it possible for drugs not approved due to side effects to be used or used in certain patients. Changes in established conditions to be stressed; however, familial disorders with genomic confirmation may justify intervention prior to materialization. Where the implanted sensor is to be positioned concentrically rather than longitudinally into the ductus wall, and especially where numerous sensors or pickups are to be implanted, better concentricity is obtained through the use of a stay insertion tool, as described in copending application Ser. No. 13/694,835. A periductally mounted magnetized jacket, or impasse-jacket, also described therein, positioned downstream prevents any accidental entry into the circulation of a sensor from resulting in an embolism. Such a jacket incorporates an outer extraction grid allowing extraction of the object to a location outside the lumen. Where the jacket is magnetized, the sensors must be capable of delivering input within the magnetic field.

Numerous implantable sensors usable thus have been developed or remain in development (see, for example, Russell, D. M., Garry, E. M., Taberner, A. J., Barrett, C. J., Paton, J. F., Budgett, D. M., and Malpas, S. C. 2012. "A Fully Implantable Telemetry System for the Chronic Monitoring of Brain Tissue Oxygen in Freely Moving Rats," *Journal of Neuroscience Methods* 204(2):242-248; Sarkar, D. and Banerjee, K. 2012. "Proposal for Tunnel-Field-Effect-Transistor as Ultra-Sensitive and Label-Frees", *Applied Physics Letters* 100(14):143108, Krishnamurthy, V., Monfared, S. M., and Cornell, B. 2010. "Ion Channel sensors—Part I: Construction, Operation, and Clinical Studies, *Institute of Electrical and Electronics Engineers Transactions on Nanotechnology* 9(3):303-312; Part II: Dynamic Modeling, Analysis, and Statistical Signal Processing," *Institute of Electrical and Electronics Engineers Transactions on Nanotechnology* 9(3):313-321; Bazzu, G., Puggioni, G. G., Dedola, S., Calia, G., Rocchitta, G., and others 2009. "Real-time Monitoring of Brain Tissue Oxygen Using a Miniaturized Biotelemetric Device Implanted in Freely Moving Rats," *Analytical Chemistry* 81(6):2235-

2241; Zhou, M., Liu, W., Wang, G., Sivaprakasam, M., Yuce, M. R., Weiland, J. D., and Humayun, M. S. 2006. "A Transcutaneous Data Telemetry System Tolerant to Power Telemetry Interference," *Conference Proceedings Institute of Electrical and Electronics Engineers Engineering in Medicine and Biology Society* 1:5884-5887; Güler, N. F. and Ubeyli, E. D. 2002. "Theory and Applications of Biotelemetry," *Journal of Medical Systems* 26(2):159-178; Vo-Dinh, T. and Cullum, B. 2000. "Biosensors and Biochips: Advances in Biological and Medical Diagnostics," *Fresenius' Journal of Analytical Chemistry* 366(6-7):540-551).

By comparison, ferrofluids taken by mouth for entry into the circulation will remain dependent upon patient compliance. The drug delivery means to be described make possible the targeting of different drugs available now and in the future to different organs, tissues, and vessels with strictly coordinated timing throughout the day, with no attendant present and regardless of patient wakefulness, attentiveness, or mental state, and in a way fundamentally distinct from and more capable than anything allowed by the prior art. Not only is coordinated drug administration under the control of a full time medical professional impracticable under any conditions, but manual control over drug administration employing the means to be described will quickly achieve a complexity to invite human error by trained personnel. The state of pharmacy in part dependent upon the capability to deliver drugs, the availability of such means makes possible advancements in pharmacy not previously possible, not seen before, and unpredictable.

For this reason, the fact that the technology of drug delivery rapidly outstrips what is considered medically practical for the time should not constrain the range of capability that the technology makes possible; rather, the technology should be developed, stimulating the state of pharmacy to advance to the level of sophistication that the new technology makes possible. Furthermore, the fact that the delivery of each drug is timed allows dose delivery to be sequenced, hence coordinated, among different bodily systems, organs, tissues, and vessels. Targeted drugs substantially eliminate adverse drug-drug and drug food interactions as well as side effects. Another area the capability to be described will advance, seen in the INR [international normalization ratio] example, is that of implantable microsensors essential to monitor the level of disease indicia analytes for automated response by the prosthetic response system.

Implantation eliminates manual sampling and the need for apparatus of a size suitable for manipulation, allowing extreme reduction in both the size of the apparatus, and given the immediacy of response, in time to treatment. The fact that each drug is targeted and timed averts the adverse side effects that can result from the dispersal of much larger systemic doses, to include drug-drug interactions and exposure of unintended tissue. These complications often prevent or truncate the use of otherwise preferred drugs whether alone or in combination. Drug targeting seeks to substantially limit medication to the tissue that requires it. When successful, it allows the circumscribed and focused application of a drug to a diseased part or lesion at a concentration, hence potency, that if circulated would prove toxic, damaging to other tissue, or could result in adverse interactions with other drugs.

Drug Targeting

Drug targeting includes not only the direct piping of drugs to lesions or nidi, but the use of magnetic attraction to drive the drug to the tissue depth sought. Targeting applies no less to reversal agents as to drugs, and magnetic blood separation techniques can also be viewed as a form of targeting. The ability to target tissue eliminates systemic dispersal as mandating increased dosing to achieve the dose needed at the site desired at the same time that exposure to other tissues by systemic dispersal limits the drug concentrations that may be used. The waste of greatly diluting costly drugs that might have been restricted to the target thus results in weakened efficacy and increases adverse drug-drug interactions and side effects. Where, as in the treatment of Cushing disease addressed below, limiting the concentration of a drug limits its use to no more than forestalling the need for an adrenectomy, the relatively minor endoscopic surgery needed to allow the dysfunctional tissue to be targeted and the circulation avoided can allow the side effects of the enzyme inhibitors used to be averted, hence, use of these drugs continued, the need for an adrenalectomy long deferred if not negated.

The direct delivery of drugs to limited segments along the middle jejunal or distal ileal segment of the small intestine allows the more proximal portions of the digestive tract to be bypassed. The implications of drug targeting for the practice of medicine are significant and pertain to every bodily system, organ, gland, and region. The body consists of tissue pipelines and the tissues these supply. Nowhere is the potential for drug targeting more relevant than as pertains to vessels and ducts. Every tissue in the body is either part of and therefore directly, or supplied by and therefore indirectly, accessible through vessels and/or ducts. There is no disease in which vascular and other supply and drainage lines are uninvolved and signal the local dysfunction to higher control centers.

Symptoms even appear in bodily systems that would seem qualitatively unlike and remote from that of origin. Regional enteritides can induce arthritis. Osteoporosis and Paget's disease of bone (osteitis deformans), for example, are disorders often secondary to endocrine disease that affect the skeleton. If arterial applications are stressed, it is because of the disproportional involvement of vessels in death from disease. No bodily conduit, to include the smallest, is analogous to inert plumbing; all are integrated into a hierarchy of negative feedback loops from the brain down to the individual cells to actively interact with the passing contents (see, for example, Jameson, J. L. 2005. "Principles of Endocrinology," in *Harrison's Principles of Internal Medicine*, New York, N.Y.: McGraw-Hill, page 2072).

In endothelial function, for example, the linings of blood and lymphatic vessels actively secrete vasodilators such as relaxing factor, nitric oxide, bradykinin, potassium ions, and adenosine and vasopressors or vasoconstrictors such as endothelins, epinephrine, norepinephrine, dopamine, thromboxane, and insulin, all tied into coordinated feedback loops, which continuously adjust the degree of contraction, hence, the blood pressure. That vessel wall, segment, and organ drug targeting has not progressed beyond the drug eluting stent is due to an inadequacy of methods and means for limiting drug delivery to the site that requires treatment and would allow different drugs to be delivered in doses not limited by intolerances beyond the target area. Whether access through 'keyhole' incisions at the body surface is more invasive than transluminal access may not be true.

When a bodily conduit is itself diseased, effective and efficient treatment requires that medication be actively drawn into, not merely pass through the line. Allowing the medication to pass lesions wastes medication that if targeted would have contributed to an effective dose, exposes healthy tissue downstream to the wasted dose, results in complications, and increasing the dose to increase absorption only increases the waste and the risk. When the supply zone or territory or downstream segment becomes diseased, the contents passing through the line should be adjusted or supplemented to promote healing. While therapeutic agents are often best restricted to frankly diseased tissue, the pathways in which the affected tissue participates, and therewith, the far-reaching relations of that tissue to other tissue, means that the propagation of disease from that tissue to other tissue is not so restricted.

For example, the central negative feedback loops that govern angiotension flow along the hypothalamic-pituitary-adrenal axis. The central loops incorporate, integrate, and drive subsidiary loops more and more local in level down to the individual cells. Tied into the neuroendocrine and autonomic nervous systems, the hypothalamic-pituitary-adrenal axis responds to systemic blood volume by continuously regulating the blood serum levels of steroid hormones produced in the adrenal cortex, such as cortisol, and in the kidney, such as angiotensin II. Angiotensin II directly effects vasoconstriction and secondarily effects the release of aldosterone to regulate the balance between sodium and potassium in the blood, thus enlisting osmolar support to regulate water retention.

Collaterally, vasopressin, or antidiuretic hormone, produced in the hypothalamus and released by the pituitary gland in response to a decrease in blood volume exerts a pressor effect and acts as a diuretic by reducing the volume of urine, thereby conserving the volume of blood. That the caliber of blood vessels, for example, is adaptive locally as well as systemically demonstrates that control is effected by a hierarchy of control loops wherein those subordinate interact with those progressively more encompassing until the center just above the brainstem is reached. Central mechanisms initiate the release of circulating vasoconstrictors or vasodilators that cause the linings of blood vessels to contract or relax in response to the condition of the circulatory system, which includes cardiac output, partial pressures of oxygen and carbon dioxide, and the existing concentration of hormones and electrolytes in the blood.

Blood pressure as the product of cardiac output and peripheral resistance subsumes numerous interrelated contributory closed loop actions responsive to emotional state, level of exertion, temperature, metabolism as affected by ingesta, disease, medication, and gas exchange in the lungs effected by cellular level feedback between every cell and its immediate environment. Maintaining normal function in the walls of bodily conduits is thus central to and inseparable from maintaining normal function. Much the same hierarchical integration mutuates between the wider physiological context and any other bodily conduit, whether ureter, gamete transporting duct, the airway, choroid plexus and arachnoid villi, or lymphatic vessel.

Secreting enzymes and mucus, all segments along the digestive tract interact with and actively condition the passing contents—until disease interferes with this process. The linings of vessels, ducts, and other type bodily conduits are properly conceived of as distributed organs and glands that participate in regulatory feedback loops in their own right. A diseased condition of the wall surrounding the channel or the lumen is not just a matter of local structural degradation but signifies disruption in the many important chemical regulatory pathways or loops in which the cells within the wall participate. As a result, no disease in the wall of a bodily conduit is properly viewed as merely local; left untreated, what appears local disease will eventually initiate a cascade of dysfunction that advances to encompass more and more of the body, and as most convincingly exemplified by cancer, can result in death.

While the body is able to compensate for numerous forms of degradation, such as those associated with aging, a failure to produce an essential enzyme or to produce an essential protein as the result of a genetic defect or progressively emerging alteration, for example, is sufficiently anomalous that the body lacks sufficient responsive measures. Thus, up to the degree of deviation that can be accommodated, an atherosclerosed artery is continuously remodeled, preserving its luminal diameter, for example, but the inadequate synthesis of insulin, resulting in diabetes, or tyrosine, resulting in phenylketonuria, for example, demand human intervention.

Such anomalous defects, to which the body has limited if any adaptive or accommodative compensatory response, account for much of internal medical practice. Application to controlled steering of a prosthetic hand has been addressed (Light, C. M., Chappell, P. H., Hudgins, B., and Engelhart, K. 2002. "Intelligent Multifunction Myoelectric Control of Hand Prostheses," *Journal of Medical Engineering and Technology* 26(4):139-146; Chappell, P. H. and Kyberd, P. J. 1991. "Prehensile Control of a Hand Prosthesis by a Microcontroller," *Journal of Biomedical Engineering* 13(5):363-369), but nowhere does there appear the application of hierarchical control to continuous adjustment in the execution of a prescription or any end motion-unrelated medical use.

Where, due to adverse side effects and/or drug-drug interactions, conventional means for overcoming the intrinsic defect prove problematic, the solution will often lie in the targeted delivery of the drug or drugs to the site or sites of the origin and/or symptoms of the disease. A prosthetic adaptive or compensatory system to supplement that intrinsic requires secure means for connecting to ductus, and the ability to deliver drugs automatically according to a program that allows some latitude in the timing and dose of each based upon feedback. A review of copending application entitled Integrated System for the Infixion and Retrieval of Implants with or without Drug Targeting will make clear that the use of ductus side-entry connection jackets, whether simple junction or piped impasse jacket in type, can be coordinated with unpiped magnetic impasse jackets.

Side-entry connection jackets can be used to deliver a drug directly to a certain level along a conduit, and when the side-entry connection jacket incorporates a magnet, the drug can be drawn into the wall of the conduit where it is delivered, or a magnetic jacket downstream can take up the drug after it has passed over the conduit lining. The ability to deliver or release drugs and reversal agents at any level along a conduit means that any segment along the conduit can be targeted, sparing other tissue from exposure to a drug or radionuclide. Placed along an artery, the level of the jacket sets the supply territory or region treated, so that advancing the jacket along the arterial tree closes in on and narrows the distal target supply territory by excluding branches to neighboring tissue, whereas retreating includes other branches and thus expands the target zone.

To avoid encroaching on neighboring tissue, the side-entry jacket selected should be as narrow and short as possible, and positioned to avoid the aortic body or to encroach upon the pulmonary trunk, pulmonary arteries, or the superior vena cava, for example. When clinical judgment is to place greater importance upon avoiding the systemic distribution of the drug, service channel lines, or sidelines, seen as part number 11 in the accompanying drawing figures, accessed through the port or ports implanted at the body surface, are used to deliver heparin and/or other medication to suppress the formation of thrombus and shear stress-induced endothelial dysfunction and intimal hyperplasia.

In adrenocorticotropic hormone or ACTH-independent endogenous (nonpharmaceutical, noniatrogenic) Cushing syndrome, it is essential to selectively lower the production of serum cortisol and not the serum concentration of ACTH or other corticosteroids produced by the adrenal cortex in response to stimulation by ACTH. In this situation, ACTH input to the adrenal cortex itself should not be affected. Therefore, unmagnetized or simple junction piped jackets are placed about the most suitable of the 3 suprarenal artery inlets to the adrenal gland to release metyrapone, ketoconazole, and/or aminogluthimide in higher concentration and potency than might be prescribed for systemic use. The higher concentration of these enzyme inhibitors then more effectively blocks cortisol synthesis without exposure to unintended tissue.

The side effects resulting from this exposure having limited the opportunity for medical management to a brief interval preceding adrenalectomy (see, for example, Young, V. B., Kormos, W. A., Chick, D. A., and Goroll, A. H. 2010. *Blueprints: Medicine*, Philadelphia, Pa.: Lippincott, Williams, and Wilkins, pages 238-239), a need for the more radical and complication prone procedure should be averted. Restriction of ketoconazole for example, to the adrenal gland allows the overproduction of corticosteroid hormone to be suppressed without risk of hepatotoxicity (*Merck Manual*, 18th edition, page 1214). Were no blocking but a reversal agent available, the impasse jacket would be placed at the outlet—proximate to the glands about the suprarenal veins to release a substance selectively neutralizing for the hypersecreted or overproduced cortisol.

In this situation where the Cushing's is pituitary-independent, any increase in ACTH secretion will increase 11-deoxycortisol, which is considerably less potent than cortisol. In systemic doses, metyrapone and ketoconazole can produce adverse side effects. Targeted however, the dose is too low to cause complications. The direct application of a statin to atheromas for the pleiotropic local and nonhepatic benefits and of glucocorticoids, immunosuppressants, and antibiotics to treat a regional enteritis are examples of substances that can be delivered in far higher concentration, hence potency, when directly targeted at lesions while kept from the rest of the body, the drug concentrations used thus toxic if circulated.

However, autoimmune disease genetic and lifelong in accordance with the general guidelines for the use of ductus side-entry jackets to treat long-term or chronic disease, when immunosuppressant drugs can be targeted at circumscribed tissue as by release directly into the ductus, usually an artery, supplying that tissue, immunosuppression that renders the patient susceptible to intercurrent disease is avoided. Since the substance used is drawn into and taken up within the lesion so that absolute amount of the dose in whole-body terms is minute, the need to pre-position a second jacket downstream to release a reversal agent should seldom arise. For intermittent or spaced apart lesions such as the 'skip' lesions in ileocolitis or plaques in atherosclerosis, each jacket is placed to encircle a lesioned segment, any propensity to migrate (move, displace, dislodge), additionally suppressed by connecting the jackets in a train.

Interruption or sectionalization thus achieves not only drug delivery optimization through discriminatory and focused targeting, but allows flexion, leaves intervening segments unenclosed and open to the chemical milieu, and allows reduction in the extent of dissection essential for access and placement. Avoiding bands of connective tissue, mesentery, and the uterine latus or broad ligament, for example, preserves not just mechanical means of support but nerves and vessels. Reducing trauma and disruption to function by avoiding the need to section supporting tissue advances the object of minimizing trauma central to the use of minimally invasive technique. Unshielded jackets about the gut, for example, can straddle small nerves and arteries to avoid Plaque vulnerable to rupture or calcified as would block penetration is treated at the margins.

The addition of a radiation shield to the jacket disallows perforations, cutouts, or division into segments shorter than the lesion for flexion, reduction in weight, and aeration. Were not the radiation shield used formulated to disintegrate, these factors would limit the use of a shielded jacket to conditions where conventional surgery would pose greater risk, such as resection likely to induce paralytic ileus. Jacketing either renal artery targets the kidney to that side; the portal vein, the liver; internal carotid artery, the supply territory on that side of the brain; the internal thoracic artery, the nipple-areola complex on that side; and a coronary artery, its supply territory within the myocardium. To treat pulmonary tuberculosis or asthma, jackets about the bronchi are used with a nebulizer or inhaler that releases susceptible drug-carrier particle-bound drugs to treat the air passages, while a jacket about the pulmonary trunk is used to treat the blood entering the lungs.

The advantage in treating episodic disorders such as cardiac arrhythmias, movement disorders, seizures, headaches, and periodic paralyses with the means described herein is the ability to choke off a flare up or fulmination while incipient. Such conditions, generated in the brain, are treated with ductus side-entry jackets on either or both the internal carotid arteries. When mediated or propagated in the brain but originating remotely, such as in an endocrine gland, the gland or glands too are jacketing proximally along the blood supply. Pulmonary and bronchial disorders such as asthma, emphysema, and tuberculosis intractable to conventional antibiotic delivery is addressed below.

Accessing the bronchi by direct jacketing with or without thermoplasty and terminal bronchioles and alveoli thus and by supply artery, restricting the use of drugs used to treat asthma such as omalizumab to the site intended averts the dizziness, earache, arthralgia, and several other side adverse effects remote from the treatment site associated with the drug. To treat a solitary pulmonary nodule or tumor in a lung, a jacket about the pulmonary artery on that side is used. Jackets can have an arc omitted or include cutouts to gain clearance. Provided a malignant tumor such as a basal cell carcinoma—which does not shed daughter cells spread by hematogenous, or lymphatic dispersal—can be directly targeted with highly toxic chemotherapeutic agents, the adverse side effects associated with conventional chemotherapy will be significantly reduced if not eliminated.

Tumors known to spread by direct extension are treated by corresponding extension of the jacket or jackets. However, metastatic—and micrometastatic disease where malignant cells may have been shed by the tumor that were too small to be detected—demands systemic treatment. Moreover, to destroy daughter cells shed by a primary tumor and any metastases generally requires systemic chemotherapy at the same concentration as is used to treat the primary tumor. In such a situation, targeting to the extent of infusion directly into an end organ, isolated limb perfusion, or external beam radiation likewise require backup systemic chemotherapy; however, as with alternative methods for targeting a lesion expressed by a systemic disease, the higher concentration directed at the primary tumor can reduce the time that the tumor is able to shed daughter cells, and therewith, the duration of treatment.

For disease that is systemic but nonmetastatic such as atherosclerosis or regional enteritis, a background systemic or digestive tract dose is essential but can be much reduced compared to that forced into the lesions by the jackets. Except with metastatic cancer, where treatment must be systemic and uniform, the same or other substances can be differentially delivered to impasse jackets without interfering with the concurrent administration of a background systemic dose administered by infusion, injection, or ingestion. In fact, a fraction of the dose delivered thus can be the carrier bound drug.

That the targeted portion represents a concentrated dose does, however, allow the systemic dose to be less concentrated, averting numerous complications such as adverse drug-drug interactions and dose related side effects. With atherosclerosis or a vasculitis able to induce localized obstructions the qualification stated with respect to metastatic disease, that the systemic dose must be as concentrated as that intended for the primary tumor does not apply; the background dose can be much reduced, eliminating myopathy regardless which statin is used. Limitation to the jacket can substantially isolate a drug from adverse drug-drug interactions with another drug in the general circulation and supplement or reduce the level of any blood constituent that passes.

To minimize return flow and spillage when lines must be disconnected and/or entered to pass through a scope, for example, drug-containing and inert filler materials delivered through a sideline, that is, a side-entry line or a service channel seen in the drawing figures as part number 11, especially when more than one service channel connects to a single side-entry connector, are ordinarily prepared in the form of a viscid flowable substance. Such includes crushed tacky non-alcohol non-acetone hydrogels, or aquagels, sufficiently durable as not to liquify or transition to the sol state when driven or aspirated, jellies, syrups, cellulose gums, slurries, ice slurries, and pressure pumpable semisolids, such as petrolatum, all of which can be formulated to include medication.

Ordinarily, the side-entry connector, shown as 6 in the drawing figures, has two inlet lines, the primary of mainline of the side-connector itself, seen in the drawing figures as 13, and a subsidiary or accessory water-jacket and service channel sideline 11, connected to water-jacket 7. These lines are ensheathed within a common catheter that extends from the paired pumps, packaged as a unit, to the jacket, but can be cut away to part and separately route the lines within the body, that is, distal to the port implanted at the body surface. At a given time, each jacket mainline and sideline is connected to an independently controllable miniature bidirectional or reversible variable speed positive displacement pump. Fluid lines leading from the pump-pack to the port at the body surface are protected by ensheathment within flexible, such as 'gooseneck' conduit.

For lesser volume delivery in relatively simple applications such as the simple junction jacket depicted in FIG. 16, a commercially available syringe driver based infusion pump can be used; however, this assumes placement of the jacket using a separate pump in the clinic and that adjuvant delivery is through compounding the drug delivered through the single line. If a jacket positioned as that depicted in FIG. 16, for example, were to surround a segment of a ductus containing a lesion such as a plaque, then a magnetized jacket such as those shown in FIG. 4 would allow a magnetically susceptible particle bound statin, for example, to be targeted into the arterial wall over the jacketed segment for its anti-inflammatory and other pleiotropic properties.

If the drug or diagnostic agent to be targeted were radioactive, then radioactive shielding would be applied along the delivery path from drug reservoir or refill cartridge to the artery, the long-term administration of a radionuclide by means of a jacket of the kind shown in FIG. 5, and shorter term use with a jacket of the kind shown in FIG. 6, which fenestrated or perforated to allow the adventia to 'breathe,' can remain in place to deliver medication or take test samples as necessary. Similarly, for higher volume medicinal or nutrient delivery in a relatively simple and straightforward application, connection is by insertion of a hose or line from an external reservoir which is inserted into a socket of the turret supplying the rotary peristaltic or roller-head type pump, to be addressed in greater detail.

However, to treat multiple established comorbid and unanticipated intercurrent conditions served by multiple side-entry connection jackets positioned along the same or different type ductus, and to do so in a comprehensive and coordinated manner, the connections between inlet and outlet lines to each pump in each mainline and sideline paired pumps, or pump-pair, are made switchable in timed relation to each of the others. Switching the jacket destination of a given pump in a given pair obviates the relation of the pair to the mainline and sideline of a specific jacket as pertains to the relatively simple application depicted in FIGS. 31 and 32. Since ordinarily, the mainline, or side-entry connected line 13, and the sideline, or water-jacket inlet line 11, are used differently, the ductus side-entry connection jacket, as shown in FIG. 29, is supported by a pump-pair wherein one pump is usually assigned to the one line and the other pump to the other line.

While various relay or valve type switches can be used to switch different therapeutic substances from one jacket to another, for pictorial clarity, the figures depict line switching as effected by means of turrets. These lines are permanently connected to their respective jackets; however, each jacket is provided with as many side-connectors 6 and accessory or water-jacket inlets 10 as necessary. As may be discerned from FIG. 32, which shows line switching turrets at the intake and outlet lines of each pump, either or both inlets to each jacket can be switched to a different drug vial or reservoir. Depending upon the connections made between pumps and jackets, a pump or pump-pair can support one or more jackets, and more than one pump-pair can support a single jacket.

Simple mechanical methods for flushing fluid lines include passing a guidewire with round brush or swab through a clean-out type line port accessed through the pump-pack as shown in FIG. 31 or passing an aspiration catheter connected to a vacuum pump through the line. Provided to do so will not affect a drug in a line, the inmate pump can be used. For the patient not required to return to the clinic on a frequent basis, flushing is better automated. Using the arrangement shown in FIGS. 32 and 36 with successive drug source vials or reservoirs switched while the delivery lines are fixed to the inlets of either jacket, the dose intended for either jacket must take into account any residue left along the internal walls of the lines. Adhesion will vary according to the properties of the substance delivered. When the residue is significant and mixture with a succeeding drug is to be avoided, or when the line is to be left clean, the residue is flushed either forward into jacket inlet 6 or 10 to complete the intended dose or out of the line, usually to a reservoir.

The lines can also be switched to allow a hydrogel, solvent, or wash water, for example, to be recirculated through the closed circuit past the opening in the ductus and into a reservoir. Ordinarily, the relation of pumps to jackets is simple and direct on a one for one basis, but if necessary, a pump or pump-pair can be switched to different jackets, association thus typified in a pump-pair and jacket set wherein a pump-pair support four side-entry jackets. Using the arrangement shown in FIG. 29, to recirculate either pump outlet through a closed circuit past the opening in the ductus in either direction requires the coordinated control over both pumps, the flow passed up through either pump line and back through the other, with completion of the circuit through a reservoir inlet and outlet (not shown).

When the ductus infusion flow rate of two therapeutic substances in fluid form is to be equal or immediacy of tracking in either the antegrade or retrograde direction are paramount, a double-arm or bidirectional side-entry connector similar to the clean-out or inline port shown in FIG. 30 and described below is used. Such a double side entry connector is placed the same way as those shown in the drawing figures but does not require a water-jacket, either of the arms available for this role during placement and for use as an accessory inlet following placement. A double-armed side-entry connector differs from the same general configuration as used in a pump inline port or clean-out, or double-arm bidirectional line lumen access fitting, in that the clean-out is placed inside the line lumen after the line has been die cut to accept it and is connected to a surround used to shield the pipe lumen from gouging in either direction, while the double-arm side-entry jacket side-connector is a part of the jacket.

The jacket, however, because it surrounds a native ductus and an object of the invention is to eliminate the need for any foreign object to remain in the lumen, requires that the tip of a guidewire, cabled device, or catheter be blunt nosed and wetted with a specialty lubricant such as ACS Microslide®, Medtronic Enhance®, Bard Pro/Pel® or Hydro/Pel®, Cordis SLX®, or Rotaglide®. Either a single or double-arm side-connector can be connected to a single pump to obtain closed circuit recirculation. To prevent leakage while allowing a cabled device, guidewire, or fluid drug under pressure to enter a native lumen in either direction without hesitation, a ductus double-armed side-entry connector has a slit elastic membrane as a bidirectional check valve at physiological forces covering the opening into the jacket. Similarly, to allow entry of a guidewire into a pump line in either direction with minimal leakage, a clean-out, or double-armed bidirectional lumen access inline port, as shown in FIG. 30 also uses such a membrane.

The double-arm inline port or bidirectional pump line clean-out or shown in FIG. 30 also allows a fluid to be delivered into the pump line for delivery to the ductus side-entry jacket by an external pump. The external pump is plugged into the opening at the back of the pump-pack for insertion in the pumpward or ductusward direction as desired to deliver or aspirate fluid such as to deliver a drug not included in the turret or obtain a diagnostic test sample of the native lumen contents. With the pump lines leading from the pump-pack disconnected, the port fastened at the body surface with elastic slit membranes covering the loose end and port openings is available as a unidirectional clean-out type inline port distad, toward the jacket. When treatment is of a vessel, whether a tacky gel in the line that resists spilling out when the line is disconnected allows dispensing with slit membranes depends upon whether any gel spills out of the line risking gas embolism when the line is reattached.

Inserting a cabled device, guidewire, or external pump line through the opening at the port leading to side-connector 6 allows access into the ductus. However, the need to disconnect the lines plugged into the port is eliminated by placing double-arm clean-out inline ports in the intake and outlet lines of each pump according to the probability of a tissue plug jam or the accumulation of debris. Since the clean-out type inline port is entered at the side rather than at the end of the line as is the body surface port, it allows the insertion of a cabled device such as a fine endoscope, aspiration catheter, or a special corkscrew-tipped guidewire to extract a tissue plug, for example, in either direction without the need to disconnect the line. Insertion can be in the intracorporeal direction toward the jacket or in the extracorporeal direction toward the pump. Drug concentration often a benefit of targeted delivery, substances to be moved through the lines should be adjusted in viscosity and susceptibility to avoid buildup or clogging.

Lines can be flushed through by recirculating wash water from one reservoir to another through a circuit closed by a line connecting the reservoirs as shown in FIG. 29, for example. This reduces if not eliminates the need to enter lines through a port, whether at the body surface or a clean-out type inline port, in order to flush these through. The need for servicing or maintenance is also reduced through the use of side-entry connection jackets having more than one side-entry connector and/or accessory inlet (service channel, water-jacket, or sideline), through the use of a double-arm type side-connector, or using a jacket with both a conventional side-connector as shown in FIGS. 1-6 and a double-arm type as shown in FIG. 7. Since the double-arm or bidrectional clean-out type inline port shown in FIG. 30 allows insertion directly into the line lumen, there is neither a need nor an advantage in using a port for access to line lumina at intracorporeal levels.

Access through inline ports in the pump-pack to any level up to the native lumen eliminates the need for access to intracorporeal levels of the line that requires entry through the surface port after the lines from the pump-pack have been disconnected. Furthermore, because entry into a line lumen except through the body surface port with pump-lines disconnected must be through the side of the line, direct intracorporeal access would require an additional aperture in the body surface port leading into the space between the lines. And since the sheath enclosing the intracorporeal lines from the surface port can extend no more distally than the level at which the lines diverge, the jacket inlet line and when present, a port situated thus to allow switching between either of two input lines to the same jacket inlet are limited to this distance. By contrast, the clean-out type inline port allows entry into any line to any distance from an insertion point within the pump-pack.

When the application would benefit from frequent endoluminal examination by means of a fine fiberscope or intravascular ultrasound probe, for example, both the line entry port in the pump line within the pump-packet and the side-connector are of the double-arm type. Entering the lower opening at the back of the pump-pack will lead the catheter or cabled device up the pump line. If the pump line is connected to the upper arm of the side-connector, the nose or probe is steered to reverse direction with little if any hesitation. Once the lines emerge from the sheath behind the surface port, tissue may backfill in and around the lines. A packaged single jacket pump-pair and jacket set includes lines permanently connected to either pump outlet and omits pump outlet turrets. A packaged pump-pair and jacket set usually contains a single standardized pump-pair, wherein each pump has intake and outlet turrets to allow switching any drug at the intake turret to any one jacket in the set at a time.

Control System Capability and Standardization

For economy of manufacture, components of the pump-pair and jacket set other than the number of jackets connected at any one time up to the maximum are kept substantially standard, a microcontroller with the same maximum number of cores drawn from the same family and the programming or programming tree written using the same language. Provided the control system is adequate for the medical condition, the action required of the turrets and pumps reduces to so many rotational increments. For this purpose, open loop driven stepper motors, one each per turret and pump, are able to satisfy the most critical applications. Moreover, since the pumps and turrets are fully enclosed and protected from outside contact, the additional cost of closed loop control to allow spontaneous adaptation is not justified.

System Control of Multidrug Delivery System

Control therefore is preferably of sensor response adaptive closed loop control over the delivery of each drug in the turret, control of the pump and turret stepper motors under open loop controlled. While the same degree of complexity and expense is not warranted in less serious cases, in a patient with an unstable life-threatening condition, adaptive response justifies the implantation of sensors tied into closed loops in a wireless body area network with automatic adaptive response in the dosing of each drug by means of a hard real time adaptive hierarchical or nested complex control system.

Such a system, where data is collected as to the best overall outcome across a plurality of morbidities treated with various combinations of drugs administered is analogous to the kind used to control a remote vehicle over uneven terrain, where data concerning the contour of the ground covered and the orientative response thereto is continuously collected for use to adapt for and optimize continued level transit, for example (see, for example, Findeisen, W. 1984. "The Essentials of Hierarchical Control," in Thoft-Christensen, P. (ed.), *System Modelling and Optimization. Lecture Notes in Control and Information Sciences* 59:38-61; Findeisen, W.; Bailey, F. N., Brdys, M., Malinowski, K., Tatjewoki, P., and Wozniak, A. 1980. *Control and Coordination in Hierarchical Systems*, New York, N.Y.: John Wiley and Sons, Issue 9 of the *International Series on Applied Systems Analysis*, Wiley-Interscience; Meystel, A. M. and Albus, J. S. 2002. *Intelligent Systems*, New York, N.Y.: John Wiley and Sons; Albus, J. S. 1995. "RCS: A Reference Model Architecture for Intelligent Systems, Association for the Advancement of Artificial Intelligence Technical Report SS-95-02, available at http://aaai-press.org/Papers/Symposia/Spring/1995/SS-95-02/SS95-02-001.pdf; Albus, J. S. 1993. "A Reference Model Architecture for Intelligent Systems Design," Chapter 2, pages 27-56 in Antsaldis, P. J. and Passino, K. M., eds., *An Introduction to Intelligent and Autonomous Control*, Baltimore, Md.: Wolters Kluwer Academic Publishers; Aguilar, J., Cerrada, M., Mousalli, G., Rivas, F., and Hidrobo, F. 2005. "A Multiagent Model for Intelligent Distributed Control Systems," 191-197; additional references provided below).

That is, with the proper sensors, such a system can be programmed to assimilate or 'learn' events as these are experienced, such as the action of a drug at an interval other than expected (Albus, J., Bostelman, R., Hong, T., Chang, T., Shackleford, W., and Shneier, M. 2006. "The LAGR [Learning Applied to Ground Robots] Project: Integrating Learning into the 4D/RCS [4 Dimensional Remote Control System] Control Hierarchy," *International Conference in Control, Automation and Robotics*—ICINCO 06, Setubal, Portugal, available at http://www.nist.gov/customcf/get_pdf.cfm?pub_id=822702). Unless interrupted by an adverse event, the drug regimen continues unaffected. In such a hierarchical control system, the processors of a monolithic integrated circuit or microchip multicore microcontroller are partitioned to support one control node each, that programmed to function at the highest level of control as the master node sent the inputs from and having a time horizon comprehensive of the subordinate nodes, of which each contributes inputs to the pumps and jackets of the set based upon the sensors that feed it.

More than a single subordinate control level exceptional, a pump-pair and jacket set that includes three jackets, for example, requires a microcontroller with at least four cores (referred to by Parallax, Inc., whose multicore microtroller chips have the individual cores arranged in a circle or 'hub' for access to shared memory, 'cogs'). Magnetic gradient-incorporating side-entry jackets, or piped impasse-jackets, already capable of drawing superparamagnetic carrier bound drugs radially outward through a ductus wall, patch-magnets are placed not to encircle ductus, but attached to the outer capsule of an organ supplied by the ductus and subject to the disease process under treatment. In some instances, the sensors are packaged in the form of stays configured for concentric insertion into the wall of the ductus or parenchyma before the jacket or patch-magnet is applied, so that these sit beneath or within the jacket or patch-magnet.

Minute diagnostic sensor implants respective of each jacket, patch-magnet, or other type implant provide feedback to the lower level nodes respective of each jacket, patch-magnet, or other type implant feedback site, thereby adjusting the dose of the drug respective of each within the prescribed drug delivery context, or the prescription as maintained by the master node. Highly stable conditions may require no more than one sensor closed feedback loop if any. Significant cost reduction may be achieved by limiting control software and hardware to the nonadaptive where more complex control and artificial intelligence are unnecessary. Whether control is nonadaptive or complex, the drivers remain standardized interchangeable pump-pair and jacket set open loop-driven stepper motors. The program automatically and immediately adjusts the delivery of medication for the present condition.

To cover different ranges of disease severity, the multicore microcontroller stores more than one program or prescription. Upon receiving appropriate sensor feedback through one or more subordinate nodes, the master node automatically transfers the program for the out of range node and jacket or the entire set. Should the feedback signals reflect a condition outside the drug delivery response range of the apparatus, a wireless body area network transmits an alarm to the clinic by emergency band or a conventional communication means, such as a text message. Depending upon the urgency, the input can be applied to dispatch an ambulance, alert the patient to return to the clinic, or instruct the patient to connect the pump-pair intake turret lines to higher capacity tabletop drug reservoirs containing the same or different drugs and switch to a different pre-stored control program.

Pump-pair and outlet turrets differing from those implanted only in that relegation to a pump pack removes the size and weight constraints imposed by implantation, the set produced as a unit, a single jacket set omits pump-pair outlet turrets, while multi jacket sets with a reasonable limit of four jackets provide pump outlet turrets to allow switching the pump outlets to any one jacket at any one time. More elaborate line switching as would permit simultaneous outlet switching to more than a single jacket at a time is possible but elusive of practical medical purpose, needlessly complex and costly, and inviting human error. In any such set, the lines connecting the pump-pair to each jacket is permanently fastened to the main and sidelines of each jacket, pump outlet switching among jacket inlets in the set accomplished at the pump outlet turret where any line to any jacket in the set can be rotated into alignment with the pump outlet.

A pump or pump-pair and jacket set thus constitutes a unit apparatus, of which portions proximal to the port implanted at the body surface remain outside the body, or extracorporeal, with those distal to the port implanted, hence, intracorporeal. Since individual jackets in a given standardized pump-pair and jacket set can be different sizes, can be placed along different type ductus in different parts of the body, and the one pump-pair supporting the jacket set allows the delivery of any drug to any jacket in the set in any sequence at any time, to further admit the inter-switching of lines among different pump and jacket sets only causes confusion. Jackets belonging to different pump-pair and jacket sets can be interposed with drug delivery times controlled by the multicore microcontroller in the multipump-pair power and control housing, or base into which the pump-pair plug-in modules insert. However, the need for more than one such set should prove rare and limited to cases of severe multiorgan disease or extensive injury.

At the pump intakes, the individual drug vials or external reseroir inlet pipes insert into an exchangeable rotary magazine that fits onto and is engaged by a turret drive gear. During production and use, each vial and external reseroir inlet hose is identified with a barcode or magnetic stripe running down the side, preloaded cartridges barcoded and sealed. Further to prevent human error, pre-loaded rotary cartridges or sectional trays keyed to prevent incorrect insertion in the turret. While the jackets in a given jacket set can be different sizes and applied along different type ductus, to achieve standardization within the foreseeable scope of medical practicality, the pumps in any given pair are the same, the pumps in different pairs the same, and the drug vial, refill cartridge, or inlet pipe receiving turrets built in and the same. To avoid pump stalls, the spaces or lands separating adjacent vial wells is minimized.

The standardized pump-pair with jacket or jackets in a jacket set plugs into a power and control housing made to accept one or more standardized pump-pair and jacket sets, the power and control housing enclosing a power source and multicore microcontroller commensurate with the number of pump-pair jacket set units it can accept. As shown in FIG. 29, standard or packaged production unit pump-pair and jacket sets that include a single jacket to receive a single drug do not require pump outlet turrets, whereas those with more than one jacket must provide jacket inlet lines leading to each jacket from either pump outlet turret. The pump-pair or pairs and power and control housing are worn in a pump-pack suspended from a waistbelt. Only highly prevalent conditions warrant the production of self-contained standalone units wherein the jacket or jackets are unitized with the power and control housing in a packaged unit.

For the patient provided with more than one pump-pair and jacket set, standardization affords a measure of fail safety in redundancy, different pump characteristics not having to be accounted for as additional variables. In a drug intake turret, the intake of either pump remains stationary as the drug vial or remote drug reservoir inlet line rotates into pump inlet alignment. In a drug outlet turret, the outlet of either pump remains stationary as the jacket inlet lines rotate into pump outlet alignment. This redundancy allows the program to comprehend a larger number of automated responses to inputs, routine or emergency. Because the advantages gained in providing at least one side-entry connector and one accessory line are considerable, and because the flexibility imparted by line switching between the pumps allows noninvasive responses to exigencies, pumps are always paired.

Furthermore, the pumps in a given pump-pair are the same; for all practical purposes, each is assigned to support the same jacket or jackets positioned along the same or a like ductus or to ductus belonging to different bodily systems but having approximately the same diameter, such as one jacket on a renal artery and the other on a ureter. Only differences in the volume and rate of drug delivery to either of two jackets so pronounced that adjustment in concentration and/or the rate of drug delivery to either could not compensate for the different delivery rates would justify the use of a second pump-pair differing in capacity. Such an eventuality is not foreseen. With pump standardization, identification to the program of the relative position of each pump and pump-pair inheres in the electrical connection associated with its socket position, no further distinction required.

This much simplifies programming. When more than one pump-pair is placed under unified control so that the output line of any pump can be redirected to feed into mainline or sideline nominally assigned to another jacket and pump-pair, distinction as a pump-pair becomes one of joint housing, of structure, and often but not always, of function. Since the sideline will often be used to introduce adjuvant medication in relatively small doses and at lower rates than will be delivery through the mainline, and because no application of a side-entry connection jacket may reasonably be expected to eschew the need for this mode of drug delivery, and because the simplest or purest method for allowing different volumetric flow rates and directions is simply to provide two pumps, the pump-pair, rather than the individual pump, is preferred as the unit of pumping componentry manufacture.

As shown in FIG. 29, this allows one pump to be connected to the side-entry connector, of mainline, and the other pump to the water-jacket, or sideline. Provided each pump is provided with a turret, each can, however, be switched between lines to the same or other side-entry connection jacket, allowing, for example, recirculation around a closed circuit driven by a single pump, that on the left-hand side in FIG. 29. The order of increasing utility therefore begins with the pump-pair as effectively irreducible from a practical standpoint; next, optimizing the functionality of each pump in the pair by incorporating means to allow switching inputs from containers, hoses, or other repositories of different drugs or other therapeutic substances; next to incorporating means such as a turret for switching the output of each pump to different lines, therewith realizing the full scope of flexibility obtainable from a single plug-in module pump-pair.

In terms of existing drug regimens, a single pump-pair and jacket set, or jacket supported by a single plug-in module pump-pair, will support any, less complex medical requirement. For this reason, an individual side-entry connection jacket and plug-in module pump-pair as applies to FIG. 16 is considered a standard basic pump-pair and jacket set unit configuration for production. When no more than one plug-in module pump-pair is needed, the power and control module receiver, or base, contains only one pump-pair socket and requires a battery and multicore microcontroller sufficient to control only the one pump-pair. Next in order of increasing utility, physiological sensors, or s, that generate closed loop feedback signals programmed to active adaptive control over drug delivery are incorporated.

Next in order, prompting future developments, comes furnishing more than a single plug-in module pump-pair, both with intake and outlet turrets, and a power and control module able to coordinate the pump and pump turret motions under synchronous control. Survival-dependent applications that require a single pump-pair are usually duplicated in a two pump-pair receiving base for redundancy. In this case, one of the pump-pairs is a standby that takes over when energized by an automatic transfer switch, and the power and control housing need not support more than one pump-pair at a time. Ordinarily, the battery and multicore microcontroller or mixed digital analogue signal field programmable gate array and microcontroller must be capable of powering and controlling the number of pump-pair plug-in modules inserted into it at any given time.

Most to benefit from automatic drug delivery are patients with multiple disorders who are incapable of or inattentive to prescription compliance. Adherence to a more complicated drug regimen, especially one tightly scheduled, when some drugs are to be swallowed, others absorbed through the oral mucosa, and others still injected, for example, can elude even a mentally unimpaired patient. Commercially available automatic infusion and insulin pumps are not designed to do this. Moreover, to wear separate pumps would impede freedom of movement, and the action of each pump would proceed independently of the others, denying the ability to deliver drugs to the different jackets in a strategically coordinated or neoadjuvant manner throughout the day. By contrast, here substance delivery is under the coordinated and synchronized control of an embedded multicore microcontroller which can be overridden, if necessary, remotely by the physician in response to a distress call.

Regardless of the number and type of components used, portable components are housed within a strong, compact, and light in weight wearable, or ambulatory, aluminum alloy or plastic enclosure and provided with connections for the use of stationary apparatus. Light weight pump-packs are suspended from a waist belt. To distribute the weight and dimensions, a combination of mainline and sideline pump-pairs too awkward or heavy to house together are divided among separate smaller pump-packs or unified and carried in a backpack or rucksack, coordination among the pump-pairs remaining under unified control by connection to the microcontroller. Either pump in a given mainline and sideline pump-pair can be a syringe driver or a rotary peristaltic pump, the latter more likely to be supported by automatic line switching.

While negligible advantage is to be gained from the reversibility and variability in speed of each pump in a pump-pair at the current state of pharmaceutical science, this can be expected to change. For example, an advantage in the ability to switch each pump in a pump-pair between mainline and sideline in the single jacket application shown in FIG. 16 would be exceptional, the added complexity of an automated crossover capability only adding to the cost. When only one side-entry connection jacket is required, the pump-pair is made in different sizes with inmate battery and controller as a standard unit. Such a unit, sold with lines of set length and port, diagrammatically represented in FIG. 29, for example, with four jackets provided, requires only that the final overall, or extracorporeal and intracorporeal, length of each line after placement be changed by manual entry of the new values into memory thus changing these values from the preinstallation values that had been based upon the total length of the lines when produced.

More intricate line switching, such as relatively quick changing from the line connections of the kind shown in FIG. 29, depicting instant connections during the recirculation of medicated crushed tacky gel or wash water during installation, to connections of the kind shown in FIG. 31 for the ongoing support of the application shown in FIG. 16, for example, are susceptible to human error and entrusted to the microcontroller. When more than one jacket is required, the number and capabilities of the pump-pairs depends upon whether the nature of the disease, its distribution in the body, or comorbidities require or recommend that each pump-pair be coordinated and synchronized with each of the others. Referring to FIGS. 32 and 36, for example, this synchronization includes the coordinated control over the rotatory indexing of the drug supplying turret that determines the drug to be delivered to the connected jacket and the pumping action of the pump.

If housing two or more pump-pairs in the same enclosure results in a pump-pack that is too heavy, then the pump-pairs are housed separately, or distributed, each with inmate power source; however, to coordinate the action among the pumps when necessary, the separate pump-packs are placed under the centralized and unified control of a microcontroller housed in one of the pump-packs. If each pump-pair in a distributed set can function autonomously, then each has a power and control housing with inmate microcontroller. For treating chronic but stable conditions, a need to adjust the control program might not arise over the lifespan of the patient or the apparatus. However, a change or changes in the medical condition can never be predicted with confidence.

Where the consequences of a change in the condition would be grave, the need for sensors to monitor the pertinent signs and a control program or subroutine and microcontroller able to readily adapt to the change is clear. The program must execute the pump and turret actions essential to carry out the prescription for the unique combination of drugs loaded in the refill cartridges, ampules, or vials at each pump intake turret, that is, coordinate the delivery times and rates of each, hence the speed and runtime of each pump in the combination. Since the possible combinations of drugs is prescribed from among the drugs available at the time for the one or more conditions diagnosed at the outset, the library of available programs is prepared in the order of prevalence and limited to a given disease or combination of diseases, uncommon and rare conditions necessitating adaptation, combination, or revision if not the preparation of a special program.

The length of the lines connecting each pump from each side-entry connection jacket is substantially constant and stored in memory. As shown on the right-hand side of FIGS. 32 and 36, a pump that must deliver multiple drugs is provided with a revolver-cylinder configured turret pump intake mechanism, or loader, which arranges the socket for each drug vial or refill cartridge at intervals about a concentric to the plane of the turret such that paired rotary solenoids or a stepper motor under the control of a microcontroller or multicore microcontroller can index any vial into alignment at the pump intake. To eliminate human errors in administration, the prescription, or instant drug delivery protocol the program is to execute is triggered by the initial load, or combination of drug vials, refill cartridges, or lines led from a separate reservoir inserted in each pump feed mechanism and any changes made, requiring that each vial self-identify upon insertion into its respective socket in the turret.

A similar mechanism at the pump outlet allows the drug to be directed to any of a number of side-entry connectors or water-jacket intake lines, although to reduce the risk of errors, drugs are constrained to the jacket or jackets of the pump-pair and jacket set. For recirculating wash water through a closed circuit to a single jacket whereby the pump outlet is connected to the water-jacket inlet and the pump intake to the side-entry connector, one pump intake turret socket position provides a line permanently connected to the pump intake. Use of the other intake turret socket positions are for drug refills or where the volume is high, an inlet line from an attached reservoir. The dose adjusted for body weight and the specific condition by the control program, common syndromes that call for the same standard of care drug regimen allow packaging the drugs in a preloaded rotational cartridge or sectional tray for insertion in the drug pump intake turret.

Further to reduce the risk of errors during production, drugs and compounded drugs can be identified by an optional QR code reader. Where standardized cartridge vials are loaded into the pump intake turret, the code can be used to set the program automatically. When the patient must not be allowed to adjust the apparatus and the drugs require prompt change, the pump-pack in use is disconnected and an alternative pump-pack preloaded with the prescribed drugs is connected to the jacket lines by a trusted party. An optional alternative means allows for electronic confirmation that the pump intake turret is properly loaded, and if necessary, corrects the identity for the program. FIG. 36 includes a miniature identity code reader positioned alongside the pump intake drug turret. Such a built-in identity code reader can identify a drug set prepackaged in a rotational cartridge or sectional tray.

The cartridge keyed to cause the code bearing vial to face the reader when inserted in the turret, the identity of the drug set and each drug therein can be signaled to the program. Such a built-in reader is not a standard component of the pump-pair and jacket set, however, because the number of conditions that may be responded to with a standardized drug regimen is relatively few, and for an individual patient, the information can be no more than partial, specific doses and dose intervals not broadly generalizable. Implementation of the prescription by a local pharmacist preserves the flexibility of drug dispensing thus. The pharmacist loads the turret sectional trays, or rotational cartridges, with the prescribed drugs, enters the prescription into a routine or program generation terminal, and offloads the routine onto a durable recording medium, such as an optical disc. The program, read into the microcontroller through a conventional data port, controls the action sequence of the pumps and turrets.

Although one or more pump-pair and jacket set plug-in modules may be idle at any given time, the power and control module, or base; into which the pump-pair and jacket set plug-in module or modules insert contains a battery or power source and microcontroller capable of synchronously controlling the pumping and turret actions of the plug-in modules inserted at the time. Since jackets belonging to different sets can be interposed along a ductus, by coordinating these actions, the microcontroller can cause the same or a different drug to be delivered to adjacent segments simultaneously or sequentially, for example. Dispersed jackets allow drug delivery to different type ductus in different parts of the body in any sequence. Patch-magnets fastened onto the outer capsule of an organ allow magnetic carrier bound drugs released into the supply artery of that organ to be drawn radially outward through the parenchyma.

An optional barcode reader included in FIG. 36 confirms that the vial or hose with similar code along its side facing the reader is that specified in the prescription The barcode or stripes may additional encode and confirm the correct flow rate for the viscosity of the substance and the caliber of the line and are read at corresponding reading stripes about the internal surface of the socket, the information transmitted centrally to the microcontroller in the pump-pack to adjust the pump speed. Whereas in a simple embodiment the relation of the drug or gel, for example, to the line remains constant, line switching necessitates that the program, here substantially synonymous with the prescription, adjust control for changes in line length and diameter, along with the flow rate of the drug.

Since microcontroller and multicore microcontroller input pins are needed to set the program, additional pins to input collateral functions such as those from sensors placed to signal changes in medical conditions and outputs to execute the program, and a significant storage capacity needed to record potential changes, the microcontroller in any given pump-pair plug-in pump-pack or the equivalent in a distributed set of pump-packs under unified control must provide a number of pins and performance capacity consistent with industrial multicore microcontrollers. The PICoPLC program ladder logic editing, simulating, and compiling tool that can generate native code for 8-bit and 32-bit microcontrollers, such as the Parallax, Inc. Propeller and Microchip Technology PIC16 central processing units, from a ladder diagram, effectively gaining in a microcontroller a level of integrative capability associated with programmable logic controllers.

For these and other microcontrollers, further reduction in size and power consumption are afforded through discretization, whereby the continuous steam of data is converted into a sequence of data points with sufficient accuracy preserved for control purposes. Sensor inputs that justify proportional-integral-derivative closed loop feedback from implanted sensors may be discretized. Conversion of closed loop physiological or life-sign input data into a sequence of points then overcomes the need for an expensive and larger programmable logic controller able to perform the ongoing calculation essential to control the continuous process as such (see, for example, Uzunovic, T. and Turkovic, I. 2012. "Implementation of Microcontroller Based Fuzzy Controller," 6*th Institute of Electrical and Electronics Engineers International Conference on Intelligent Systems*, Sofia, Bulgaria, available at Institute of Electrical and Electronics Engineersxplore.Institute of Electrical and Electronics Engineers.org; Velagic, J., Kuric, M., Dragolj, E., Ajanovic, Z., and Osmic, N. 2012. "Microcontroller Based Fuzzy-PI [Proportional-Integral] Approach Employing Control Surface Discretization," 20*th Mediterranean Conference on Control and Automation*, Barcelona, Spain, available at Institute of Electrical and Electronics Engineersxplore.Institute of Electrical and Electronics Engineers.org; Avery, S., Gracey, C., Graner, V., Hebel, M., Hintze, J., LaMothe, A., Lindsay, A., Martin, J., and Sander, H. 2010. *Programming and Customizing the Multicore Propeller Microcontroller*: The Official Guide, New York, N.Y.: McGraw-Hill; Nass, M. 2010. "Xilinx Puts ARM [advanced reduced instruction set computation machine] Core into its FPGAs [field-programmable gate arrays]," *Embedded*, available at http://www.embedded.com/electronics-products/electronic-product-reviews/embedded-tools/4115523/Xilinx-puts-ARM-core-into-its-FPGAs; McConnel, T. 2010. "ESC—Xilinx Extensible Processing Platform Combines Best of Serial and Parallel Processing," *Electronic Engineering Times*, available at http://www.eetimes.com/document.asp?doc_id=1313958; Cheung, K. 2010. "Xilinx Extensible Processing Platform for Embedded Systems," available at http://fpgablog.com/posts/arm-cortex-mpcore/; Kanagaraj, N., Sivashanmugam, P., and Paramasivam, S. 2009. "A Fuzzy Logic based Supervisory Hierarchical Control Scheme for Real Time Pressure Control," *International Journal of Automation and Computing* 6(1):88-96; Keckler, S. W., Olukotun, K., and Hofstee, H. P. 2009. *Multicore Processors and Systems*, New York, N.Y.: Springer; Scanlan, D. A. and Hebel, M. A. 2007. "Programming the Eight-core Propeller Chip," *Journal of Computing Sciences in Colleges* 23(1):162-168). Linear stage motors usally steppers, other type motors are not to be excluded.

The 'inertia' and delay in affecting some physiological parameters considerably greater than it is for others, depending upon the application, no individual or composite form of control, to include model predictive, fuzzy, and proportional-integral-derivative can be ruled out. In general, using different controllers in each type pump-pack is more costly than is the use of a standard microcontroller and development environment; nevertheless, provided simple applications and embodiments prevail for a given type pump-pack, the smaller cost of a simple or hobby grade controller is preferable.

However, less feedback adaptive response capability, the requirement placed on the microcontroller as a motion controller consists only of synchronizing the rotatory motion of the pump and pump turret motors. In less critical applications, both the pump and pump turret movers can be open loop controlled direct current stepper motors. The degree of refinement as to the type control but not the motors used rises as the criticality of dose precision and timing (see, for example, Johansson, A. and Stigborg, M. 2013. "Analogue versus Digital Solution for Motor Control," Thesis, Jönköpings Tekniska Högskola [Jönköping School of Engineering, Jonkoping, Sweden] [available at http://www.diva-portal.org/smash/get/diva2: 632203/FULL TEXT01.pdf).

Unless the increased cost for a high capability controller to be embedded in pump-packs used to treat well-defined and predictable conditions is not warranted, a universally applied controller able to support a complex pumping and fluid line switching protocol is used in all pump-packs produced at a time. More specifically, a pump-pack that accommodates a two pump-pairs is used when only a single pump-pair is required, with the hard and software already in place should a second pump-pair be required. Where intercurrent disease or comorbidity necessitate a third pump-pair, this is accomplished by using a second hard and software standardized pump-pack. Preferably, a standardized microcontroller, pump-pairs, and programming method is used across all embodiments from the simplest to the most complex.

This not only affords the greatest flexibility for adapting the program to changing conditions without the need to replace the apparatus, but has the advantage of eliminating the relatively greater cost of nonstandardization in the use of diverse apparatus and control programming, the increased cost for a more versatile microcontroller readily overcoming the added cost per unit and the greater susceptibility to human error. Distributed pump-packs change only in terms of spatial separation or division; each coordinated with the others by joint connection to a central microcontroller housed in one of the pump-packs. The combination of jacket pump-pair plug-in module magnetic barcode or stripe patterns inserted in the power and control pack or packs if distributed, at any given moment sets the microcontroller for coordinated control over the delivery of the combination.

The pump rate of delivery varies with the application, and the duration of battery power varies with the volume. If the dosing does not permit all medication to be delivered from a wearable device, then connection is on an as needed basis to a home tabletop or clinical pump or other apparatus. Additional sidelines connected to the water-jacket allow different adjuvant drugs, for example, to be delivered through the water jacket to enter into the mainline, seen as part number 6 in the drawing figures. Where complete segregation among the drugs is medically insignificant so that these can be delivered in direct sequence through the same line, the drugs can be supplied from vials mounted about a turret, the pump-pack-embedded microcontroller used to control the rotation of the turrets and pumps.

Depending upon the criticality of the application, bidirectional rotation of the turrets can be accomplished two rotary solenoids positioned to turn the turret in opposite directions, a stepper motor, or a sensorless dc motor, the need for tight feedback control applied to the driving paths as opposed to any physiological parametric paths not warranted. While the sequential targeting of different drugs to a certain organ, lesion, or organ system is commonly practiced (see, for example, Calvo, E., Ravaud, A., and Bellmunt, J. 2013. "What is the Optimal Therapy for Patients with Metastatic Renal Cell Carcinoma Who Progress on an Initial VEGFr-TKI [Vascular Endothelial Growth Factor-Tyrosine-Kinase Inhibitor]?," *Cancer Treatment Reviews* 39(4):366-374), as in neoadjuvant therapy, the targeting of organs or tissues belonging to the same or different systems in different locations, such as to stimulate or depress certain pathways in an organ in one part of the body in preparation for the targeted delivery of a drug to an organ or tissue in another part of the body, has been broached barely if at all.

The placement of side-entry connection jackets at different locations in the body makes possible the development of therapy that uses simultaneous or timed sequential targeted delivery of the same or different drugs to the same or different side-entry connection jackets to treat the same or different diseases. Where entry of the drugs into the systemic circulation is at most inconsequential, administration thus can be applied no less to the administration of drugs previously specified as not for simultaneous use. Using the means described herein, the simultaneously or sequentially coordinated delivery of drugs, to include those specified as not for use in the same patient, can proceed frequently in different organs and tissues throughout the day under automatic control.

While the line from a given pump might be divided to supply the mainlines or sidelines of different jackets for treatment of the same or a different condition, or the output of two pumps might be converged into the same line, for example, because errors in the administration of drugs are common under any circumstances, such merging and crossover is discouraged. Numerous hypothetical connections between pumps, lines, ports, and jackets possible, reducing these to the medically pertinent and least costly includes packaging jacket mainline and sideline pump-pairs with lines, port, and jacket as either independent for use of a single jacket or as modules that plug into a receiver pack with shared battery and controller. Within the constraints imposed by miniaturization, dosing, and patient comfort, the pump-pack includes a jacket pump-pair plug-in module for each jacket.

Lines that call for the delivery of medication in small doses continuously or at frequent intervals are relegated to a wearable pump-pack, while lines that call for the delivery of medication in large doses at infrequent intervals may be relegated to a stationary apparatus at home or in the clinic. Ideally, each plug-in module allows not only drug delivery after jacket placement but is used to place the jacket. To assure proper dosing, time coordinated control of the mainline and sideline pumps within each plug-in module inserted in the pump-pack for delivery to one of the differently located side-entry connection jackets is placed under the unified control of a microcontroller embedded within the pump-pack.

Medical pumps in general can deliver medication with precise dosing frequently or continuously even when the dose size is very small, administration thus by a professional in constant attendance impracticable and subject to human error. When, exceptionally, different type pumps are to be inserted into the same pump-pack, human error is avoided through a self-identifying keyed insertion base pin pattern. When plugged into the socket in the pump-pack, the pin pattern of the pump-pair plug-in modules set the microcontroller for coordinated drug delivery from each plug-in module in the combination. With the tissue plug excised, the pump pressure through both the mainline and sideline or sidelines antegrade, and nothing to block the way through it, adjuvant medication converges with that in the mainline to pass through the opening into the ductus.

With antegrade pumping stopped and passage through the opening impeded if not prevented by the blood pressure or luminal contents and a thick and sticky substance to block the opening, the substance takes the course of least resistance by flowing into the side-connector. In excision of the tissue plug from the side of the ductus, the water-jacket is ordinarily started first, and water or a crushed tacky hydrogel, medicinal or medically neutral but usually containing an antimicrobial and anti-inflammatory, is passed through the water-jacket, seen as 7 in the drawing figures, to flush over or irrigate the ductus wall at the prospective opening (ostium, fenestra), to return through the mainline. Only one sideline pump is needed to drive water or a crushed tacky hydrogel through the water-jacket. Irrigation continued, a pulsed vacuum is applied to the side-entry connector along the mainline 13.

A pulsed vacuum is generated by running the pump in reverse or abductally (abcorporeally) and replacing the pump vial or refill cartridge turret cylinder with another having openings spaced about the circumference at intervals to generate the pulses at the frequency desired for the turret rotation speed written into the microcontroller program. The vacuum draws the ductus wall outward, compressing a layer of viscoelastic polyurethane foam lining the jacket, allowing the cutting edge of the side-entry connector to be driven through the lumen wall, excising a plug of tissue. Within the limit set by its thickness, the foam not only allows the cutting edge to be driven through the ductus wall to excise the tissue plug but allows compliance in the internal diameter of the jacket with intrinsic movement in the ductus whether peristaltic or pulsatile.

Where the use of closed cell foam results in a buildup of heat and irritation, or interferes with permeating the lining with a liquid medication, an open cell, hence, porous, viscoelastic polyurethane foam is used. Critically, the lining avoids compression of the fine vessels and nerves about the adventitia or fibrosa that in an artery, for example, would induce atherosclerosis, as addressed below. The lining also compensates for anatomical, inflammatory, or lesion caused deviations in ductus caliber and prevents contact of any part of the jacket from coming into contact with the adventitia or fibrosa. Yet another advantage in the lining is that in a small child, it extends the usable life of the jacket by permitting an increase in ductus diameter due to growth. Should the radially outward excursion of the lumen wall exceed that allowed by the lining, the spring hinges used to fasten the two half cylinders of the jacket will extend the range for expandability.

In a tight location such as that depicted in FIGS. 16 and 21, the combined expandability afforded by the lining and the spring hinges makes it possible to situate the jacket where the normal growth would otherwise interrupt the indwelling time and treatment much sooner (see, for example, Voges, I., Jerosch-Herold, M., Hedderich, J., Pardun, E., Hart, C., and 5 others 2012. "Normal Values of Aortic Dimensions, Distensibility, and Pulse Wave Velocity in Children and Young. Adults: A Cross-Sectional Study," *Journal of Cardiovascular Magnetic Resonance* 14:77; Kaiser, T., Kellenberger, C. J., Albisetti, M., Bergsträsser, E., and Valsangiacomo Buechel, E. R. 2008. "Normal Values for Aortic Diameters in Children and Adolescents—Assessment in Vivo by Contrast-enhanced CMR-Angiography," *Journal of Cardiovascular Magnetic Resonance* 10:56; Machii, M. and Becker, A. E. 1997. "Morphologic Features of the Normal Aortic Arch in Neonates, Infants, and Children Pertinent to Growth," *Annals of Thoracic Surgery* 64(2): 511-515); however, numerous diseases and genetic defects can markedly distort the developing aorta.

The ability to target drugs to specific lesions and thus avoid the circulation and exposure to untargeted tissue is often the more importance in the treatment of small children with radioactive substances; for example. Radiation shielded side-entry connection jackets allow superparamagnetic drug-carried radionuclide nanoparticles for example, to be targeted directly to lesions. To prevent the tissue plug from remaining partially attached or 'hanging up' at the prospective site of the opening, the foam lining must be greater in thickness than the ductus. For this reason, the site should have been well imaged and studied, especially since jacket dimensions are to be kept to a minimum when neighboring tissue would be encroached upon. Placement must control leakage through the opening created even when the tissue plug 'hangs' at the opening.

In general, leakage or extravasation is stopped by denying space outside the opening, by filling the space outside the opening, preferably, with a tacky crushed hydrogel or by forcible restraint using pressure washing or flushing through the water-jacket. The installation process proceeds automatically under a routine stored in the microcontroller read only memory, which outputs prompts for manual intervention if necessary to a separate clinic display. Referring now to FIG. 29, the jacket having been positioned about the ductus before the plug of tissue is removed, the intake of pump 46 if not open is switched from gel drug or wash water reservoir 49 to open, and that of pump 47 from the turret to fill-gel reservoir 54. As will be described, since the output of any pump can be switched to the same or any other pump mainline or sideline, wash water or any therapeutic substance can be recirculated through a closed circuit.

Starting pump 46 in reverse, or counterclockwise, evacuates line 13, drawing the ductus wall over the sharp forward edge or trepan of side-entry connector 6, incising a circular opening. Thicker and harder ductus may require loosening side-entry connector 6 for use as a manual circle-cutter. Even with calcified plaque present, when forced against the razor-sharp front edge of the side-entry connector, the plug should fracture and come away clean. If a thicker plaque does not fracture cleanly and avulses or pulls some tissue about the opening into the side-entry connector, then the foam lining and optionally, the addition of an anti clotting agent to the fill gel in reservoir 54 should still allow a functional junction. A transient or sudden reduction in resistance to the vacuum causes the installation program stored in the controller to start pump 47, driving crushed tacky medicinal or medically inert hydrogel from reservoir 54 through line 11 and the water-jacket.

Two types of valves are suitable for use in lines 13 and 11, each having certain advantages. One type is a polymeric bidirectional elastic slit type, which depending upon the force of the pressure head can range in elasticity and thickness from a membrane to a set of apposite or overlapping flaps having an elasticity consistent with the pressures and fluids used, the other a double winged mechanical throttle and shutoff valve-plug such as that shown in FIGS. 23 thru 25. In most instances, a side-entry connector will have a permanently bonded elastic slit membrane at the adductal or distal terminus. Not properly a valve (which connotes adjustability), such a bidirectional passive and ordinarily nonadjustable terminal fluid resistor simplifies placement or installation by allowing the application of greater vacuum force. Flap-valves used in aperetic applications in particular must have flaps with adluminal surfaces of a very smooth material, usually polytetrafluoroethylene.

Bidirectional Slit and Flap-Valves

A slit type membrane valve is shown in FIG. 33. This valve has more central pie-cut sectors separated by slits, leaving a common frame bonded to the surround. Membrane valves are used to prevent flow or leakage at drug vial, reservoir, and hose connections. By contrast, a flap-valve is placed at the opening made into the lumen of the substrate ductus. The flap type valve to abut upon the adventitia or fibrosa, special measures are taken to prevent harm. The leading (adductal, forward) edge of the flap type valve surround is a cutting die used to excise a plug of tissue from the side of the ductus. This leaves the plug distal to, that is, to the far side, of the valve. The plug is therefore extracted with the same vacuum force used to excise it.

To expedite extraction through the valve, each flap of the flap type valve gives optimal clearance as a rectangular elastic tang or tongue overlapping its neighbors along its unbonded edges, these positioned rectilinearly within and bonded along the outer edge to die surround, which is rectangular with rounded-corners, the long axis parallel to that of the substrate ductus. Both type valves must resist microfractures, fatigue, retain resilience, and remain pliant to allow deflection in either direction when and only when encountering the minimum design force. For vascular applications, achieving the minimal thrombophilic (or thrombofilic, the term in this connection denoting a surface conducive to clotting) propensity of the material in a flap type valve is no less important as achieving the required mechanical properties and endurance.

Anticlotting medication best minimized if not eliminated, various materials and surface treatments are available for reducing if not eliminating this tendency (see, for example, Nilsson, P. H., Engberg, A. E., Bäck, J., Faxälv, L., Lindahl, T. L., Nilsson, B., and Ekdahl, K. N. 2010. "The Creation of an Antithrombotic Surface by Apyrase Immobilization," *Biomaterials* 31(16):4484-4491; Gorbet, M. B. and Sefton, M. V. 2004. "Biomaterial-associated Thrombosis: Roles of Coagulation Factors, Complement, Platelets and Leukocytes," *Biomaterials* 25(26):5681-5703; Spijker, H. T., Graaff, R., Boonstra, P. W., Busscher, H. J., and van Oeveren, W. 2003. "On the Influence of Flow Conditions and Wettability on Blood Material Interactions," *Biomaterials* 24(26):4717-4727; Hong, J., Nilsson Ekdahl, K., Reynolds, H., Larsson, R., and Nilsson, B. 1999. "A New in Vitro Model to Study Interaction between Whole Blood and Biomaterials. Studies of Platelet and Coagulation Activation and the Effect of Aspirin," *Biomaterials* 20(7):603-611).

Such jackets usually permanent, temporary measures as incorporated into drug eluting stents may apply during placement and until endothelialized, but are not adequate over the life of the device (see, for example, Palmerini, T., Biondi-Zoccai, G., Della Riva, D., Stettler, C., Sangiorgi, D., D'Ascenzo, F., Kimura, T., and 12 others 2012. "Stent Thrombosis with Drug-eluting and Bare-Metal Stents: Evidence from a Comprehensive Network Meta-analysis," *Lancet* 379(9824):1393-1402; Aggarwal, R. K., Ireland, D. C., Azrin, M. A., Ezekowitz, M. D., de Bono, D. P., and Gershlick, A. H. 1996. "Antithrombotic Potential of Polymer-coated Stents Eluting Platelet Glycoprotein IIb/IIIa Receptor Antibody," *Circulation* 94(12):3311-3317).

Degradation or failure necessitating invasive reentry, valves of either type must provide a long service life without significant change in mechanical properties (see, for example, Shaw, M. T. and MacKnight, W. J. 2005. *Introduction to Polymer Viscoelasticity*, Hoboken, N.J.: Wiley Interscience; Boresi, A. P. and Chong, K. P. 2000. *Elasticity in Engineering Mechanics*, New York, N.Y.: John Wiley and Sons; Nielsen, S. E. and Landel, R. F. 1994. *Mechanical Properties of Polymers and Composites*, New York, N.Y.: Marcel Dekker). For valves in vascular applications, and flap-valves in particular, long-term repeated abrupt or transient flow at onset and cutoff will eventually induce unfavorable adaptation if not injury.

This is averted by shaping the valve sectors, flaps, or tongues to gradually or incrementally decrease in girth from the outer margin to the center. This method and/or the insertion of narrowed neck or waist sections allow gradual or incremental opening and closing of the flaps, and therewith, control over the rate of delivery or extraction through the valve as a fluid resistor. This not only moderates the volumetric flow rate at onset and cutoff but allows control over this rate by the microcontroller. For this reason as well, the use of materials that are not susceptible to degradation with a loss in resilience over time is important.

When not provided by a single material, the required combination of properties and long life are obtained through lamination, imbrication, overlapping, impregnation, embedment, and combination of various bioinert materials (see, for example, Karbhari, V. M. (ed.) 2013. *Non-destructive Evaluation (NDE) of Polymer Matrix Composites: Techniques and Applications*, Sawston, Cambridge England: Woodhead Publishing Limited; Kaw, A. K. 2006. *Mechanics of Composite Materials*, Boca Raton, Fla.: Taylor and Francis Group, Chemical Rubber Company Press; Abington, Cambridge England: Woodhead Publishing Limited; Owen, M. J., Middleton, V., and Jones, I. A., 2000. *Integrated Design and Manufacture Using Fibre-reinforced Polymeric Composites*, Matthews, F. L. and Rawlings, R. D. 1999. *Composite Materials: Engineering and Science*, Woodhead Publishing Series in Composites Science and Engineering, Boca Raton, Fla.: Chemical Rubber Company Press).

By embedding or laminating magnetically susceptible ferrous matter in the flaps to respond to the field force of an extracorporeal tractive electromagnet under the control of the master microcontroller, for example, such an elastomeric barrier can, however, be made adjustable. Opening the barrier magnetically, however, is usually disqualifying, because lumen contents then extravasate indiscriminately. Thus, in an ambulatory analyte extraction application such as leukapheresis to be described, for example, the incorporation of ferrous matter in the flaps disallows the use of an external electromagnet to differentially extract the susceptible particle bound target analyte. The vacuum force is used to excise a plug of tissue by drawing the ductus wall outward over the cutting die or trepan leading edge-surround of the side-connector.

Once severed, the vacuum pulls the excised tissue plug out through the opened flaps of the membrane, thicker elastomeric flat stock, or sheeting, and the vacuum removed, closes, sealing the opening created in the side of the ductus, substantially truncating further exsanguination. When a cabled device such as a guidewire or fiberoptic scope is passed through such a flexible barrier, the flaps restrict the passable opening to that occupied by the cabled device. Placement thus will be described in reference to the use of a double-arm side-connector as shown in FIG. 7 with longitudinally extended distal terminus and elastic slit membrane for continuous high-volume analyte extraction such as essential for ambulatory apheresis. By comparison, an impasse-jacket with extraction grating is suited to lower volume extraction.

Situated forward and engaged instead by a rubbery surround, elastic slit membrane and mechanical valve-plugs, which are not permanently bonded in place at the distal terminus, offer the advantage that these can be advanced or retracted along the line to any level. Retracted, it allows flow past it into or out of the lumen. A mechanical type valve-plug that is remotely controllable, as addressed below, can be opened and closed to allow antegrade or forward or retrograde or reverse flow as is essential for aspiration through it and the opening in the ductus, for example. Both types of valve-plug will seal off the open end of a line to prevent spillage. The elastic slit membrane, which to be slid along the lumen of the catheter requires to be mounted at the end of a cylindrical annulus or surround much as the head of a drum, easily passes through a cabled device such as an angioscope or laser and is opened by raising the pressure at the pump.

Specified herein for drug vial inlets and outlets and the endings of drug reservoir inlet hoses to be described as well as slidable valve-plugs, the material, thickness, and form of each slit membrane is chosen for the applicable range of threshold opening pressure. Thus, a membrane that due to the intrinsic elasticity of its material and thickness is highly elastic might have a simple diagonal cut, whereas one made of a less elastic material and/or thicker might have a star-shaped cut. The mechanical valve is adjustable, and if remote controlled as addressed below, can be adjusted, fully opened, or fully closed, in flow-through cross-sectional area by a clinician at a remote location in response to an emergency, for example, who can also adjust the pump setting.

A mechanical valve-plug can be repositioned by sliding it along the catheter. This is accomplished by remotely closing and then driving the valve-plug forward or backward at the head of a column of water or gel, which action can be included in the program. When the accuracy of repositioning is significant, the catheter used is ribbed at intervals along the internal surface and the pump pulsed to exceed the threshold pressure for forcing the valve-plug from one such detent to the next. The susceptibility to be driven thus is increased by forming the ends of the rubbery surround to include a circular recess or indentation (depression, trench, trough).

When the valve-plug is positioned as shown in FIGS. 23 and 24, where to seal off the opening in the ductus it has been intentionally restrained by trapping its forward or adductal portion in the space ahead of the forward edge of the water jacket, whether the valve-plus can be dislodged thus depends upon the force of retention associated with its diameter, restorative force and surface friction of the elastomeric surround, and so on. Depending upon the application, valve-plugs are made in different gradations of resistance to dislodgement or retention; however, an alteration in physical properties of the surround over time can necessitate the use of a manual guidewire such as shown in FIG. 26. Valve-plugs reduce the caliber of the cabled devices that can pass and the flow-through cross-section of the lumen; however, when the program controls the valve-plug, it can, if necessary, compute and apply the offsetting increase in pressure to achieve the same flow rate.

Other types of nondiversion valves, or intravascular valves, that use, vane or iris shutters such as those used in cameras are more intricate and subject to malfunction, expensive, and offer no advantage over the types just delineated. The vacuum continued as the gel is delivered, the plug is simultaneously drawn outward, that is, pulled, by the vacuum to its fore and forced outward, that is, expelled, pushed by the gel to its rear, forcing it out through line 13. Any difficulty in extracting the tissue plug is corrected by introducing an aspiration catheter, corkscrew-tipped guidewire, or a hybrid corkscrew-tipped aspiration catheter, through a clean-out type inline port fitting shown in FIG. 30. The fitting is entered at the outer surface of the pump-pack through an upper entry hole affording downward tracking toward the pump, and a lower entry hole affording upward tracking toward the jacket.

Extracorporeal parts, that is, the external parts preceding the port at the body surface, are made of clear, tough, transparent plastic, the pump-pack housing of polycarbonate plastic, for example. When tracking will be frequent, both pump inline port in the pump-pack and side-connector are of the double-arm type. Referring to FIGS. 29 and 32, the additional insertion of an elastic slit membrane in line 13 (not shown) prevents the tissue plug from reaching and clogging or jamming pump 46 in FIG. 29 or pump 56 in FIG. 32. The trapped plug is readily retrieved by means of an aspiration catheter, corkscrew-tipped guidewire, or a hybrid corkscrew-tipped aspiration catheter, introduced through the upper entry arm of the inline port or clean-out, entered through the one of four holes at the back of the pump-pack leading to the upper arm of pump 56, each covered by a spring cap when not in use.

In FIG. 29, pump 46 is stopped and pump 47 continues to force the gel past the opening cut in the ductus, restraining bleeding or leakage and forcing the plug out through the mainline. If the plug hangs at the opening and the side-entry connector is not loosenable for use as a circle-cutter, then a corkscrew-tipped guidewire, or a hybrid corkscrew-tipped aspiration catheter, introduced through the lower entry hole of clean-out type inline port 69, entered through the hole at the back of the pump-pack and any elastic slit membrane in the line to extract the plug. The tacky hydrogel generally includes antimicrobial and anti-inflammatory medication, and by switching the pump intake from the gel reservoir to the vial containing the drug or combination of drugs to be used, can position the initial dose.

Pumping from the fill-gel reservoir is usually to eliminate any voids, that is, to fill segments of the line between drugs. Both pumps are switchable to fill-gel reservoir 54 and when necessary, can be driven at relatively high speeds to deliver the drug at the head of the gel column quickly. Steps in the installation procedure prior to the foregoing, to include implanting and routing the lines and jacket, and steps following the foregoing, to include fixing the port in position are addressed in the detailed description. When the viscosity of the substance to be propelled through the water-jacket line necessitates a force sufficiently larger than that of the vacuum, the flow rates through the lines are regulated by separate pumps under the coordinated control of a microcontroller.

To expedite extraction or washout of the tissue plug and to suppress extravasation, the water or hydrogel pressure through the water-jacket can be increased. When elastic slit membrane valves with a fluid resistance greater than that of the back pressure, here the expulsive force of the blood passing the opening, are placed along the lines, water irrigation can stop with the lines remaining filled with water to deny entry to the native luminal contents, hence, extravasation. Otherwise, irrigation through the sideline and water-jacket is continuous with the delivery of the initial dose of medication in the form of a tacky and thick or viscid syrup or crushed tacky gel, for example. This suppresses bleeding and retrograde flow out through the lines at the same time that the medication is positioned for delivery through the opening once adductal or antegrade mainline pumping is initiated.

Depending upon the specification of the gel or alternative viscid substance, its use may also eliminate the need for an elastic slit or woven membrane to span across the adductal end opening of the side-entry connector. When the medication is less viscid, irrigation can conclude when elastic slit membrane or flap barrier resistors are inserted into each line. Especially in vascular applications, the use of therapeutic substances in the form of variably tacky hydrogels reduces if not eliminates extravasation whether leakage or exsanguination (bleeding) out of the opening in the ductus created, as well as spillage from lines not provided with an elastic slit membrane barrier fluid resistor when the line is disconnected.

To avoid gas embolism and spillage, disconnection is preferably avoided. The formulation of drugs as syrups, jellies, cellulose gums, or hydrogels, for example, to meet mechanical properties of viscosity and tackiness as specified is well understood. Viscous fluids and gels containing or omitting a drug or drugs, and/or other therapeutic or diagnostic substances can be formulated for use with the apparatus described herein to treat any point along an artery with a tissue plug excised, for example, regardless of the expulsive force of the blood. The side-entry connection line or mainline or mainlines 13, but not the sideline or water-jacket supply line or lines 11, can be transited by a cabled device, such as a fine fiberoptic endoscope, laser, or intravascular ultrasound probe.

Access to the line is through a double-arm inline port or clean-out as shown in FIG. 30 and indicated in FIG. 32. The line or clean-out port incorporates an elastic slit membrane that covers the opening into the lumen of the pump line at the junction of the inlet tubes. The membrane allows an inserted device to pass to either arm directing the device in either direction while minimizing leakage as a check valve. For such use, the special guidewire described below and shown in FIG. 26 for retrieving a valve-plug positioned downstream along the catheteric line must have its centering ring 32 slid back and off at the proximal end. During installation of the jacket with lines, port, and pump attached, a valve-plug previously inserted into any line filled with a substance that would leak out the open end is used when the lines are cut off or trimmed flush to the front of the port.

A mechanical valve-plug such as that shown in FIGS. 23 thru 25 and described below, is continuously variable between fully open and fully closed, and can be controlled from outside the line. By contrast, a slit membrane or flap type valve passively opens and closes gradually or incrementally in response to the force of the pressure head. When an elastic slit membrane valve or a valve-plug with its elastic surround engaged by the abductally inclined prongs at the distal end of the side-entry connector has been positioned over the opening created in the side of the ductus, the valve can be retracted so that its distal face is level with the forward edge of the water-jacket to allow flow through the water-jacket. If the valve is a valve-plug, the flow rate can be regulated or metered by adjusting the cross-sectional area of the opening through the plug.

It can therefore be adjusted by the pump microcontroller in coordination with the variable speed pump to throttle the volumetric flow rate through the line. Entry is always with the cabled device or guidewire wetted with an antimicrobial, an anticoagulant or platelet blocker for entry into a blood vessel, for example. One or more valve-plugs can be positioned anywhere along the lines to either side of the port, that is, those extracorporeal connected to the pump and those intracorporeal connected to the jacket, to throttle or shutoff flow through the line. Closing a valve-plug along the mainline accelerates delivery through the opening in the ductus of medication sent-through a sideline, while reversing the bidirectional pump accelerates aspiration therethrough.

As shown in FIG. 31, a valve-plug is extracted by passing the valve guidewire shown in FIGS. 24 and 26 through the lower hole at the back of the pump-pack, which leads through the lower arm of double-arm inline port shown in FIG. 30, and up through pump line 13. Before the local entry wound used to place the jacket has been closed, a proximal single or double-arm clean-out flap-valve type inline port of the kind shown in FIG. 30 can be used to pass through a guidewire or cabled device such a a fiberscope through lines 11 or 13 and into the native lumen. Thereafter, invasive reentry is avoided by routing the guidewire or cabled device as shown in FIG. 31.

When use thus is contemplated, the valve is not of the slit membrane but rather the mechanical, spring-loaded duplex butterfly hemispherical vane or double doors type shown in FIGS. 23 thru 25. The mainline need not be emptied to allow the device to pass through and into the lumen. The clean-out type inline port as a port also allows the intermittent or emergency administration of other drugs. The delivery of medication in the form of viscid gels, jellies, and syrups, for example, eliminates the need to use the water-jacket lines to restrain luminal contents from leaking. Also avoided is the need to use a service channel line to restrain the leakage of luminal contents through pressurized irrigation when the line is already filled with medicinal contents that would result in a sudden overdose.

The formulation of gels that incorporate drugs is well established (see, for example, Peppas, N. A. 2004. "Hydrogels," in Ratner, B. D., Hoffman, A. S., Schoen, F. J., and Lemons, J. E. (eds.), *Biomaterials Science: An Introduction to Materials in Medicine*, New York, N.Y.: Academic Press, pages 35-42, updated in 2012). Passive elastic slit membrane valves allow a cabled device to pass but otherwise act as nonadjustable shutoff valves. In comparison, mechanical shutoff and throttling valve-plugs as shown in FIGS. 15 and 16 limit the diameter and impede passage of cabled devices but can be adjusted from outside the body individually or in groups, different groups adjusted using different radio control frequencies. As many valves of either type can be positioned along a mainline or larger diameter sideline as necessary.

While injectable hydrogels are more often formulated to be liquid at ambient temperature and gel at body temperature to reduce dispersion or diffusion from the injection site or to remain as a tissue-engineered ing scaffold whether to serve as a stem cell culturing matrix (see, for example, Sepantafar, M., Maheronnaghsh, R., Mohammadi, H., Rajabi-Zeleti, S., Annabi, N., Aghdami, N., and Baharvand, H. 2016. "Stem Cells and Injectable Hydrogels: Synergistic Therapeutics in Myocardial Repair," *Biotechnology Advances* 34(4):362-379; Xia, Y., Zhu, K., Lai, H., Lang, M., Xiao, Y., Lian, S., Guo, C., and Wang, C. 2015. "Enhanced Infarct Myocardium Repair Mediated by Thermosensitive Copolymer Hydrogel-based Stem Cell Transplantation," *Experimental Biology and Medicine* (Maywood, N.J.) 240(5):593-600; Ekenseair, A. K., Boere, K. W., Tzouanas, S. N., Vo, T. N., Kasper, F. K., and Mikos, A. G. 2012. "Synthesis and Characterization of Thermally and Chemically Gelling Injectable Hydrogels for Tissue Engineering," *Biomacromolecules* 13(6):1908-1915; Nelson, D. M., Ma, Z., Leeson, C. E., and Wagner, W. R. 2012. "Extended and Sequential Delivery of Protein from Injectable Thermoresponsive Hydrogels," *Journal of Biomedical Materials Research. Part A* 100(3):776-785; Lian, S., Xiao, Y., Bian, Q., Xia, Y., Guo, C., Wang, S., and Lang, M. 2012. "Injectable Hydrogel as Stem Cell Scaffolds from the Thermosensitive Terpolymer of NIPAAm/AAc/HEMAPCL [N-isopropylacrylamide (NIPAAm), acrylic acid and macromer 2-hydroxyethyl methacrylate-poly(ε-caprolactone]," *International Journal of Nanomedicine* 7:4893-4905; Klouda, L. and Mikos, A. G. 2008. "Thermoresponsive Hydrogels in Biomedical Applications," *European Journal of Pharmaceutics and Biopharmaceutics* 68(1):34-45; Yu, L. and Ding, J. 2008. "Injectable Hydrogels as Unique Biomedical Materials," *Chemical Society Reviews* 37(8):1473-1481), for the present purpose, where the drug is contained and directed after it has been introduced, the control problem is extracorporeal, so that the reverse transition is preferred.

Medication delivered in the form of a thermoreversible injectable hydrogel, for example, which sol transitions and flows rather than gels at body temperature allows better control over pump or hypodermic delivery compared to medication delivered as a liquid or in a completely fluid (thin, nonadherent) state (see, for example, Wang, F., Porter, M., Konstantopoulos, A., Zhang, P., and Cui, H. 2017. "Preclinical Development of Drug Delivery Systems for Paclitaxel-based Cancer Chemotherapy," *Journal of Controlled Release* 267:100-118; Singh, N. K. and Lee, D. S. 2014. "In Situ Gelling pH- and Temperature-sensitive Biodegradable Block Copolymer Hydrogels for Drug Delivery," *Journal of Controlled Release* 193:214-227; Morita, C., Kawai, C., Kikuch, A., Imura, Y., and Kawai, T. 2012. "Effect of Amide Moieties for Hydrogelators on Gelation Property and Heating-free pH Responsive Gel-Sol Phase Transition," *Journal of Oleo Science* 61(12):707-713; Nguyen, M. K. and Lee, D. S. 2010. "Injectable Biodegradable Hydrogels," *Macromolecular Bioscience* 10(6):563-579; He, C., Kim, S. W., and Lee, D. S. 2008. "In situ Gelling Stimuli-sensitive Block Copolymer Hydrogels for Drug Delivery," *Journal of Controlled Release* 127(3):189-207). This minimizes running, aids in maintaining dose accuracy, and makes keeping air out of the line less difficult.

Gel-sol transition upon entry into the ductus causing the gel to sol transition and flow at the opening created in the side of the ductus (ostium, vasculostomy opening), can be facilitated through the application of heat or use of a service-channel to deliver a heated pH gel solvent (Nguyen and Lee 2010, Op cit.). The gel can be warmed upon entering the port and along the side-entry connection line by a resistance wire running the length of the line or by a heating coil inside a valve-plug described in the specification to follow at the ostium, while the chemical solvent can be delivered through a service channel, for example.

Use of Pressurized Air during Jacket Side Stem Insertion

Along nonvascular ductus, the nominally designated water-jacket can deliver a pressurized gas, ordinarily air, which can be heated or chilled depending upon which end of a vortex tube or 'cold air gun,' for example, is used as the input. Air can, in fact, replace water or a tacky hydrogel for restraining extravasation from a vessel while the side stem or side-entry connector is inserted into the opening trepaned in the side of the ductus. These properties minimize the outflow of luminal contents through the opening in the side of the ductus to be created and at the access port placed at the body surface. Exceptionally, the opening made in the side of the ductus can be covered over with adherent thin tissue-engineered scaffold seeded with autologous stem cells or treated to encourage overgrowth to replace the tissue that was removed and surgical cement.

Jacket Positioning and Therapeutic Targeting

In some situations, it will be desirable to disconnect a side-entry line filled with medication in order to pass through a cabled device, which as explained below, may also contain a valve-plug that must be retrieved to allow the cabled device to pass through. In this situation, consecutive fluid therapeutic columns to pass through the line are best controlled to assure proper dosing when flow requires the application of propulsive force. A jacket with more than one side-entry connector affords better isolation among more freely flowing drugs. Simple drug targeting by direct delivery can be used to avoid adverse drug interactions. For example, the mechanism of calcium channel blocker function is not dependent upon metabolism in the liver, but can interfere with the metabolism of other drugs when allowed to pass into the liver.

In the case of an end arterial epicardial coronary artery, direct delivery as depicted in FIG. 16 avoids the circulation. Direct delivery into the inferior and/or superior vena cava of a calcium channel blocker, for example, avoids interaction in the liver with drugs administered orally, a trace amount if any recirculated. Placing a side-entry jacket about the inferior and/or superior vena cava allows post-hepatic introduction of any drug in liquid form into the circulation, so that if fully taken up, the drug is not returned to the liver. The use of an impasse jacket allows a superparamagnetic nanoparticle bound drug to be actively removed from the circulation.

In the treatment of hereditary amyloid cardiomyopathy (see, for example, Quarta, C. C., Kruger, J. L., and Falk, R. H. 2012. "Cardiac Amyloidosis," *Circulation* 126(12):e178-82), which is probably far more prevalent in congestive heart failure than is currently diagnosed (Falk, R. H. 2011. "Cardiac Amyloidosis: A Treatable Disease, Often Overlooked," *Circulation* 124(9):1079-1085), direct targeting of the liver can avert the extrahepatic adverse side effects, drug-drug interactions, and certain other problems posed by antisense oligonucleotides and ribonucleic acid interference drugs, for example (see, for example, Rayburn, E. R. and Zhang, R.

2008. "Antisense, RNAi [interference RNA], and Gene Silencing Strategies for Therapy: Mission Possible or Impossible?," *Drug Discovery Today* 13(11-12):513-521; Weyermann, J., Lochmann, D., and Zimmer, A. 2004. "Comparison of Antisense Oligonucleotide Drug Delivery Systems," *Journal of Controlled Release* 100(3):411-423).

Non Val30Met [valine at transthyretin (transporter for thyroxin and retinol) protein position 30 not bound but rather methionine (a mutation)] TTR (transthyretin-related) familial or hereditary amyloid cardiomyophathy, the most prevalent form, in which mutant transthyretin protein binds the amino acid methionine rather than valine at position 30 (see, for example, Siddiqi, O. K. and Ruberg, F. L. 2018. "Cardiac Amyloidosis: An Update on Pathophysiology, Diagnosis, and Treatment" *Trends in Cardiovascular Medicine* 28(1): 10-21; Thenappan, T., Fedson, S., Rich, J., Murks, C., Husain, A., Pogoriler, J., and Anderson, A. S. 2014. "Isolated Heart Transplantation for Familial Transthyretin (TTR) V122I Cardiac Amyloidosis," *Amyloid* 21(2): 120-123; Ruberg, F. L. and Berk, J. L. 2012. "Transthyretin (TTR) Cardiac Amyloidosis," *Circulation* 126(10):1286-1300; van Galen, K. P., van Dijk, J., and Zweegman, S. 2012. "Letter from van Galen et al. Regarding Article, "Cardiac Amyloidosis: A Treatable Disease Often Overlooked," *Circulation* 125(13):e538; author reply e539; Falk, R. H. 2011. "Cardiac Amyloidosis: A Treatable Disease, Often Overlooked," *Circulation* 124(9):1079-1085; Snyder, M. E., Haidar, G. R., Spencer, B., and Maurer, M. S. 2011. "Transthyretin Cardiac Amyloidosis Diagnosed by Analyzing a Prostatic Tissue Sample: A Case Report," *Journal of the American Geriatrics Society* 59(9):1745-1747; Ohmori, H., Ando, Y., Makita, Y., Onouchi, Y., Nakajima, T., Saraiva, M. J., Terazaki, H., and 8 others 2004. "Common. Origin of the Val30Met Mutation Responsible for the Amyloidogenic Transthyretin Type of Familial Amyloidotic Polyneuropathy," *Journal of Medical Genetics* 41(4):e51, available at http://jmg.bmj.com/content/41/4/e51.long or http://www.ncbi.nlm.nih.gov/pmc/articles/PMC1735751/pdf/v041p 00e51.pdf) progresses despite a liver transplant (Benson, M. D. 2013. "Liver Transplantation and Transthyretin Amyloidosis," *Muscle and Nerve* 47(2):157-162).

Transthyretin Amyloidosis can, however, be treated by direct delivery to the liver of:

1. Gene therapy (see, for example, Suhr, O. B., Holmgren, G., and Lundgren, E. 2004. "Gene Therapy: Lessons Learned from Liver Transplantation for Transthyretin-amyloidosis," *Liver Transplantation* 10(12):1551-1553).

2. newer ribonucleic acid interference drugs (see, for example, Guan, J., Mishra, S., Falk, R. H., and Liao, R. 2012. "Current Perspectives on Cardiac Amyloidosis," *American Journal of Physiology. Heart and Circulatory Physiology* 302(3):H544-11552), or 3. Antisense oligonucleotides (see, for example, Benson, M. D., Kluve-Beckerman, B., Zeldenrust, S. R., Siesky, A. M., Bodenmiller, D. M., Showalter, A. D., and Sloop, K. W. 2006. "Targeted Suppression of an Amyloidogenic Transthyretin with Antisense Oligonucleotides." *Muscle and Nerve* 33(5):609-618) for example, using means described herein by delivery from a small port at the body surface directly to the liver.

In fact, the amyloidoses are systemic multi-organ diseases, so that aiming medication at the liver targets the source of the unstable monomers that improperly fold and accumulate in organs and tissues, while systemic circulation of a drug that disintegrates the amyloid should allow deposition to be prevented. At the same time, severely affected organs might benefit from the more concentrated upstream delivery of a successful drug to the arteries supplying the organ if not directly to the organ. The drug regimen for ameliorating the symptoms of an amyloid impaired heart dependent upon the type of amyloid (see, for example, Falk, R. H. 2011 cited above, page 1082), these drugs can be delivered directly to the heart.

Where a particular organ such as the heart is severely affected, the direct and concentrated delivery to and uptake within that organ or the arteries leading to it of prospective systemic medication to accomplish the prevention or even the eradication of existing amyloid deposits (Bodin, K., Ellmerich, S., Kahan, M. C., Tennent, G. A., Loesch, A., Gilbertson, J. A., Hutchinson, W. L., and 13 others 2010. "Antibodies to Human Serum Amyloid P Component Eliminate Visceral Amyloid Deposits," *Nature* 468(7320):93-97; Gillmore, J. D., Tennent, G. A., Hutchinson, W. L., Gallimore, J. R., Lachmann, H. J., Goodman, H. J., Offer, M., and 4 others 2010. "Sustained Pharmacological Depletion of Serum Amyloid P Component in Patients with Systemic Amyloidosis," *British Journal of Haematology* 148(5):760-767; Kolstoe, S. E. and Wood, S. P. 2010. "Drug Targets for Amyloidosis," *Biochemical Society Transactions* 38(2):466-470; Pepys, M. B., Herbert, J., Hutchinson, W. L., Tennent, G. A., Lachmann, H. J., Gallimore, J. R., Lovat, L. B., and 16 others 2002. "Targeted Pharmacological Depletion of Serum Amyloid P Component for Treatment of Human Amyloidosis," *Nature* 417(6886):254-259) should allow much if not all function to be restored.

A successful drug for local interference in the production or removal of existing amyloid deposits would be facilitated were side-entry jackets placed along the internal carotid arteries for concentrated delivery of the drug to the blood shortly before entry into the brain (Moreno, J. A., Halliday, M., Molloy, C., Radford, H., Verity, N., and 6 others 2013. "Oral Treatment Targeting the Unfolded Protein Response Prevents Neurodegeneration and Clinical Disease in Prion-infected Mice," *Science Translational Medicine* 5(206): 206ra138; Halliday, M. and Mallucci, G. R. 2013. "Targeting the Unfolded Protein Response in Neurodegeneration: A New Approach to Therapy," *Neuropharmacology* September pii: S0028-3908(13)00401-00402; Um, J. W., Kaufman, A. C., Kostylev, M., Heiss, J. K., Stagi, M., and 8 others 2013. "Metabotropic Glutamate Receptor 5 is a Coreceptor for Alzheimer aβ oligomer Bound to Cellular Prion Protein," *Neuron* 79(5):887-902; Urn, J. W. and Strittmatter, S. M. 2013. "Amyloid-β Induced Signaling by Cellular Prion Protein and Fyn Kinase in Alzheimer Disease," *Prion* 7(1): 37-41; Kolstoe, S. E., Ridha, B. H., Bellotti, V., Wang, N., Robinson, C. V., Crutch, S. J., Keir, G., and 7 others 2009. "Molecular Dissection of Alzheimer's Disease Neuropathology by Depletion of Serum Amyloid P Component," *Proceedings of the National Academy of Sciences of the United States of America* 106(18):7619-7623). Preventing the diversion of protein essential for normal synaptic function (Moreno et al. 2013, Op cit.) and the binding of soluble amyloid-β oligomers from binding to cellular prion protein (Um et al. 2013, Op cit.) now appear more important for preventing symptoms than does eliminating the accumulated misfolded deposits of prior protein.

Side-entry jackets, patch-magnets, and if necessary, an impasse jacket to eliminate any residue, would critically improve upon systemic distribution of any drug that should be drawn outward toward the adventitia, fibrosa, or outer layer of any vessel or organ treated. Provided the problems of in vivo stability and cellular uptake are overcome, the liver can be targeted as described below with respect to directing immunosuppressive drugs to an organ transplant— by formulating the drugs for superparamagnetic nanoparticle carry with parenchymal penetration by patch-magnets engaged in the hepatic visceral peritoneum. A drug eluting stent has no comparable ability to draw a drug radially outward to the adventitia, nor to sustain the delivery of any drug or drugs prepared in the form of a ferrofluid.

Immunosuppressive drugs are used to prevent the rejection of transplants and to treat autoimmune diseases of localized expression. However, systemic immunosuppression increases the risks of infection, the development of malignancies, adverse drug-drug interactions that interfere with or prevent the treatment of regionally distinct comorbidities, and adverse side effects that would be avoided were the drug or drugs limited to the tissue that required these. The degree to which a given immunosuppressive drug can be targeted or focused to protect an allograft from rejection depends upon its mechanism. Unless reversible at or somewhat in advance of the transplant, immunizing factors that originate systemically, such as in the bone marrow, or remotely, such as in the thymus gland, require that any drugs to reverse these factors if essential be provided as background therapy in the circulation.

However, drugs that in time and distance are progressively more immediate in effect can be delivered less in advance of and closer in proximity to the transplant in the corresponding degree. Existing immunosuppressive drugs for preventing transplant organ rejection include lymphocyte gene expression, cytokine signal transduction, and nucleotide synthesis inhibitors (see, for example, Coico, R., Sunshine, G., and Benjamini, E. 2003. "Transplantation," in *Immunology: A Short Course, Hoboken, N.J.: John Wiley and Sons, page* 265).

For optimal targeting, drugs requiring the least lead time and space to reverse immunizing factors at the inlets to the transplant are selected for delivery in situ. To support organ transplants and their anastomoses, side-entry connection jackets are placed on the inlet and possibly outlet stumps of donor organs before harvesting. Means to secondarily allow the targeting of immunosuppressive drugs to organs that had been transplanted in the past, will alleviate the consequences of systemically immunocompromising transplant patients. Any drug with local action not dependent upon metabolism in the liver can be targeted.

Although portions of side-entry connection jackets not required to prevent leakage following removal can be made absorbable or to spontaneously disintegrate over an interval, side-entry connection jackets are usually intended for long-term or lifelong treatment of chronic conditions and not made for short term use or to be absorbed or removed. For example, placing a side-entry connection jacket on the recipient inlet stump with supply line or lines and surface port before resection of a diseased organ to be replaced by a transplant organ allows delivery to the transplant of immunosuppressive drugs such as cyclosporine, or ciclosporine; nonantibiotic macrolides, such as sirolimus (rapamycin), tacrolimus; azathioprine; mycophenolate mofetil; and glucocorticoids from the moment the transplant is sutured in place.

Since the jacket is upstream to the anastomosis, the transplant organ is medicated in its entirety. Temporary closure where the condition may reemerge is by closing a shutoff and throttle valve-plug as described below. Primarily intended for chronic and incurable conditions and where an alternative approach cannot be used or would pose greater risk, the removal of a side-entry connection jacket and surface port as described below apply only when an adverse tissue reaction or persistent irritation eventuate. Placement of a pump line to periodically deliver adverse reaction palliative or remedial medication depends upon the site of the sensor. Substances indicated are addressed below in the section entitled Clasp-electromagnets under Description of the Preferred Embodiments of the Invention.

Except on the carotids, jugulars, and coronaries, jacket removal if necessary can be accomplished most quickly by endoscopic upstream cross-clamping, excision of the jacketed segment, and end to end anastomosis; however, removal should seldom prove necessary. Removal from a coronary artery such as shown in FIG. 16 necessitates bypass through off-pump or beating-heart distal anastomosis with a pedicled internal thoracic artery or the use a cardiopulmonary bypass machine. Removal from a carotid artery follows the same precautions as for a carotid endarterectomy, to include the use of temporary shunts and bilateral encephalography, for example, to monitor cerebral perfusion (see, for example, Messina, L. M. and Zelenock, G. B. 1997. "Cerebrovascular Occlusive Disease," Chapter 80 in Greenfield, L. J., Mulholland, M. W., Oldham, K. T., Zelenock, G. B., and Lillemoe, K. D. (eds.), *Surgery: Scientific Principles and Practice*, pages 1753-1756).

Unilateral and bilateral carotid jacketing may be undertaken to treat atherosclerosis local to the bifurcation, to set the entry point for targeting the brain with drugs, or both, heparin, aspirin, and apixaban, for example, all deliverable through the jacket. The risk of embolism is greater where plaque is excised; however, any cause of postprocedural stenosis can induce a stroke and must be monitored.

When the drug is bound to a magnetically susceptible carrier, uptake within the brain is with the aid of an external electromagnet over the short term and if necessary over the long-term, by patch-magnet implants, as addressed in copending continuation-in-part application Ser. No. 13/694, 835, entitled Integrated System for the Infixion and Retrieval of Implants with or without Drug Targeting. Any nonradioactive residue that would continue into the systemic circulation will rarely if ever approach a concentration that could cause harm.

Unwanted residues can be eliminated by jackets placed about the jugulars to release a reversal agent. Where a reversal agent remains to be developed, the carrier bound drug is trapped and drawn radially outward by a magnetized jacket with extraction grid to allow the use of a powerful external electromagnet. The presence of a radiation shield such as depicted in FIGS. 5 and 6 obstructs the openings in an open grid essential for extracting a trapped radionuclide, for example. Exceptionally, when accumulation over time and extraction through an extraction grid underlying an outer radiation shield layer that disintegrates to expose the grid is impermissible, to allow immediate extraction, jackets used for radioactive residues omit a radiation shield. Placement of a jacket is expedited in an open field and even through the small albeit preexisting incision to perform an endarterectomy carotid or otherwise.

A side-entry connection jacket offers a means for the direct delivery of food to the gut and gastric aspiration of a neonate with esophageal atresia, a feeding function defect, or a proximal deformity that interferes with feeding, where repair must be deferred, long-term intubation is not possible or contraindicated, and/or total parenteral nutrition should be avoided, for example. Direct connection to the gut bypasses food and airway structures all susceptible to injury and adverse reactions when intubated, the severity proportional to the duration.

The trauma that can result during intubation may be greater than that of placing a side-entry connection jacket with line and port through a small or 'keyhole' incision. These factors are confirmed by the established practice of surgically inserting a feeding tube through an abdominal incision when esophageal varices, severe head trauma, or a proximal obstruction, for example, is present. The use of a side-entry connection jacket and surface port are less susceptible to irritation, infection, and injury. Insertion of a nasogastric, orogastric, or a dubhoff tube in a neonate, even one with normal anatomy, is especially prone to iatrogenic complications, to include mucosal erosions and fistulization (Agarwala, S., Dave, S., Gupta, A. K., and Mitra, D. K. 1998. "Duodeno-renal Fistula Due to a Naogastric Tube in a Neonate," *Pediatric Surgery International* 14(1-2): 102-103).

It has, for example, resulted in irritation anywhere along the route and perforations of the visceral pleura (Thomas, B., Cummin, D., and Falcone, R. E. 1996. "Accidental Pneumothorax from a Nasogastric Tube," *New England Journal of Medicine* 335 (17): 1325), esophagus, posterior wall of the stomach, left lobe of the liver and the spleen hilus. (Gasparella, M., Schiavon, G., Bordignon, L., Buffo, M., Benetton, C.; and 4 others 2011. "Iatrogenic Traumas by Nasogastric Tube in Very Premature Infants: Our Cases and Literature Review," [in English] *Pediatria medica e chirurgica* 33(2):85-88; Sudhakaran, N. and Kirby, C. P. 2001. "Pitfalls of Gastric Intubation in Premature Infants," *Journal of Paediatrics and Child Health* 37(2):195-197), urinary bladder (Mattar, M. S., al-Alfy, A. A., Dahniya, M. H., and al-Marzouk, N. F. 1997. "Urinary Bladder Perforation: An Unusual Complication of Neonatal Nasogastric Tube Feeding," *Pediatric Radiology* 27(11):858-859), cribriform plate (van den Anker, J. N., Baerts, W., Quak, J. M., Robben, S. G., and Meradji, M. 1992. "Iatrogenic Perforation of the Lamina Cribrosa by Nasogastric Tube in an Infant," *Pediatric Radiology;* 22(7):545-546), and rarely, the pericardium (Hanafy, Eel-D., Ashebu, S. D., Naqeeb, N. A., and Nanda, H. B. 2006. "Pericardial Sac Perforation: A Rare Complication of Neonatal Nasogastric Tube Feeding," *Pediatric Radiology* 36(10): 1096-1098).

Accidental perforations usually necessitate the immediate devising of an appropriate strategy to avert death (see, for example, Jackson, R. H., Payne, D. K., and Bacon, B. R. 1990. "Esophageal Perforation Due to Nasogastric Intubation," *American Journal of Gastroenterology* 85(4):439-442; Grünebaum, M., Horodniceanu, C., Wilunsky, E., and Reisner, S. 1980. "Iatrogenic Transmural Perforation of the Oesophagus in the Preterm Infant," *Clinical Radiology* 31(3):257-261). The foam lining of a side-entry connection jacket made deep (thick, broad) for placement along the highly motile gut in any event, considerable room for growth is provided. The use of oral and nasal intubation to meet both respiratory and nutritional requirements can result in human errors leading to significant trauma (Ebenezer, K., Bose, A., and Carl, S. 2007. "Neonatal Gastric Perforation Following Inadvertent Connection of Oxygen to the Nasogastric Feeding Tube," *Archives of Disease in Childhood. Fetal and Neonatal Edition* 92(5):F407), something the distinct placement and markings on the ports used with side-entry-connection jackets would eradicate.

Insertion is prone to complications with patients of all ages (see, for example, Pillai, J. B., Vegas, A., and Brister, S. 2005. "Thoracic Complications of Nasogastric Tube: Review of Safe Practice," *Interactive Cardiovascular andThoracic Surgery* 4(5):429-433). Also problematic are the complications and trauma the tube can impart when left in place on a prolonged basis, as classified and enumerated by Pillai et al., for example (Pillai, J. B., Vegas, A., and Bristera, S. 2005. "Thoracic Complications of Nasogastric Tube: Review of Safe Practice" *Interactive Cardiovascular and Thoracic Surgery* 4 (5): 429-433; Vielva del Campo, B., Moráis Perez, D., and Saldaña Garrido, D. 2010. "Nasogastric Tube Syndrome: A Case Report," [in English and Spanish], *Acta Otolaringologica Española* 61(1):85-86; Brousseau, V. J. and Kost, K. M. 2006. "A Rare but Serious Entity: Nasogastric Tube Syndrome," *Otolaryngology—Head and Neck Surgery* 135(5):677-679; Apostolakis, L. W., Funk, G. F., Urdaneta, L. F., McCulloch, T. M., and Jeyapalan, M. M. 2001. "The Nasogastric Tube Syndrome: Two Case Reports and Review of the Literature," *Head and Neck* 23(1):59-63).

Target organ uptake of drugs prepared for superparamagnetic nanoparticle drug-carrier delivery is optimized for by positioning patch-magnets, described in copending application Ser. No. 13/694,835, about the periphery of the transplant or a diseased native organ or the placement along a native ductus or transplant of an impasse jacket or jackets, likewise described therein. Whether transplantion is orthotopic or heterotopic, placing the side-entry connection jacket or jackets upstream from the inlet anastomosis or anastomoses assures that no portion of the transplant is left outside the medicated zone, as would be the case were the jacket applied to the donor organ when harvested. Targeting the transplanted organ seeks to minimize if not eliminate immunocompromise of the patient as a whole.

When no trace of the drug or drugs should be allowed to circulate, an impasse jacket likewise described in copending application Ser. No. 13/694,835 is positioned upstream of the transplant. If the drug is radioactive, a shielded impasse jacket is used. If depleted over a shorter interval, a disintegrable shield is used. If not, or the unshielded impasse jacket residue is removed endoscopically. This approach is the more valuable when an elderly patient presents comorbidities, for example. In general, immediate delivery of a drug to only the tissue intended optimizes its potency as well as eliminates adverse drug interactions and the complications that result from misapplication of the drug elsewhere.

Superior Security of Long-Term Indwelling Lines with Distal Terminus Jacket Connection Substitution for conventional central catheters or in-hospital central lines placed for relatively brief periods in a nonambulatory patient is unintended. Such jackets can replace central catheters, but should afford significantly improved long-term performance, due both to the stability of the junction and the fact that unlike a central venous such as a Hickman, Groshong®, or Quinton® catheter, for example, the lumen is left clear. Another advantage of a side-entry connection jacket is that the diameter of the line and opening or ostium into the line or conduit can be made larger to support a higher flow rate, which is advantageous for applications such as leukapheresis. For bypassing vessels, luminal uniformity of caliber moving into, through, and past the junction supports laminar flow to lessen thrombogenesis.

A side-entry connection jacket is no less suitable for placement along the gut, renal artery, a ureter, or any other bodily conduit large enough to allow the jacket to be placed, microsurgical methods accepted. Transluminal placement and the use of a guidewire (see, for example, Rupp, S. M., Apfelbaum, J. L., Blitt, C., Caplan, R. A., Connis, R. T., Domino, K. B., and 6 Others 2012. "Practice Guidelines for Central Venous Access: A Report by the American Society of Anesthesiologists Task Force on Central Venous Access," *Anesthesiology* 116(3):539-573) are sources of injury that are avoided. That peripherally inserted catheters and transluminal access is necessarily safer than endoscopic access is misconceived.

Both injuries incurred during placement (see, for example, Amerasekera, S. S., Jones, C. M., Patel, R., and Cleasby, M. J. 2009. "Imaging of the Complications of Peripherally Inserted Central Venous Catheters," *Clinical Radiology* 64(8):832-840; Kusminsky, R. E. 2007. "Complications of Central Venous Catheterization," *Journal of the American College of Surgeons* 204(4):681-696; Eulmesekian, P. G., Perez, A., Minces, P. G., Lobos, P., Moldes, J., and García Mónaco, R. 2007. "Internal Mammary Artery Injury after Central Venous Catheterization," *Pediatric Critical Care Medicine* 8(5):489-491; Hamilton, H. 2006. "Complications Associated with Venous Access Devices," *Nursing Standard* Part One 20(26):43-50; Part Two 20(27): 59-65), while indwelling (see, for example, Gonsalves, C. F., Eschelman, D. J., Sullivan, K. L., DuBois, N., and Bonn, J. 2003. "Incidence of Central Vein Stenosis and Occlusion Following Upper Extremity PICC and Port Placement," *Cardiovascular and Interventional Radiology* 26(2):123-127), and consequences that can follow placement (Ge, X., Cavallazzi, R., Li, C., Pan, S. M., Wang, Y. W., and Wang, F. L. 2012. "Central Venous Access Sites for the Prevention of Venous Thrombosis, Stenosis and Infection," *Cochrane Database of Systematic Reviews* 3:CD004084), to include life-changing restrictions upon movement essential to avoid accidents in which a life-long wearer would be highly vulnerable, should be less than is risked with conventional catheters (see, for example, Children's Mercy Hospital, Kansas City, Miss. 2010. "Central Line at School," care card, available at http://www.childrensmercy.org/content/uploadedFiles/Care_Cards/CMH-11-384p.pdf; Zeigler, S. A. 2007. "Prevent Dangerous Hemodialysis Catheter Disconnections," *Nursing* 37(3):70, available at http://www.fda.gov/MedicalDevices/Safety/AlertsandNotices/TipsandArticlesonDevice Safety/ucm064634.htm).

Catheter insertion into the subclavian vein medial to the border of the first rib is associated with kinking, or pinch-off, which can lead to pinch-off syndrome or pinch-off sign (Mirza, B., Vanek, V. W., and Kupensky, D. T. 2004. "Pinch-off Syndrome: Case Report and Collective Review of the Literature," *American Surgeon* 70(7):635-644; Andris, D. A. and Krzywda, E. A. 1997. "Catheter Pinch-off Syndrome: Recognition and Management," *Journal of Intravenous Nursing* 20(5):233-237), rarely resulting in spontaneous fatigue fracture (Hou, W. Y., Sun, W. Z., Chen, Y. A., Wu, S. M., Lin, S. Y. 1994. "Pinch-off Sign" and Spontaneous Fracture of an Implanted Central Venous Catheter: Report of a Case," (in Chinese with English abstract in Pubmed), *Journal of the Formosan Medical Association* 93 Supplement 1:S65-S69), to which a junction accomplished by placement of a side-entry jacket with direct line to a pectoral port is less quickly established but not susceptible.

Use of a more pliant catheter would prevent fracture but promote kinking, and use of the internal jugular vein alleviates kinking and fracture, but the greater variability in anatomy necessitates the use of ultrasound imaging, undoing some of the advantage in speed of access (Jensen, M. O. 2008. "Anatomical Basis of Central Venous Catheter Fracture," *Clinical Anatomy* 21(2):106-110). Access through the subclavian, internal jugular, or femoral veins pose overall about equal risk (Ge et al. 2012, cited in the preceding paragraph; Ruesch, S., Walder, B., and Tramer, M. R. 2002. "Complications of Central Venous Catheters: Internal Jugular versus Subclavian Access—A Systematic Review," *Critical Care Medicine;* 30(2):454-460) albeit nonidentical as to type, femoral access found by some to be more susceptible to infection (Hamilton, H. C. and Foxcroft, D. R. 2007. "Central Venous Access Sites for the Prevention of Venous Thrombosis, Stenosis and Infection in Patients Requiring Long-term Intravenous Therapy," *Cochrane Database of Systematic Reviews* (3):CD004084) and subclavian to kinking.

Distinction in the rate of infection based upon access route has been brought into question (Marik, P. E., Flemmer, M., and Harrison, W. 2012. "The Risk of Catheter-related Bloodstream Infection with Femoral Venous Catheters as Compared to Subclavian and Internal Jugular Venous Catheters: A Systematic Review of the Literature and Meta-analysis," *Critical Care Medicine* 40(8):2479-2485; Parienti J J, Thirion M, Mégarbane B, Souweine B, Ouchikhe and 12 Others 2008. "Femoral vs Jugular Venous Catheterization and Risk of Nosocomial Events in Adults Requiring Acute Renal Replacement Therapy: A Randomized Controlled Trial," *Journal of the American Medical Association* 299 (20):2413-2422; Deshpande, K. S., Hatem, C., Ulrich, H. L., Currie, B. P., Aldrich, T. K., Bryan-Brown, C. W., and Kvetan, V. 2005. "The Incidence of Infectious Complications of Central Venous Catheters at the Subclavian, Internal Jugular, and Femoral Sites in an Intensive Care Unit Population," *Critical Care Medicine* 33(1):13-20; discussion 234-235).

The tight junction afforded by a side-entry connection jacket is, moreover, no less applicable to systolic pressures and thus usable intra-arterially no less than intravenously. With the venous junction established by means of a side-entry connection jacket, the fixed junction and position of the catheter outside the native conduit prevents erosion when access must be maintained over a long period, much less for to the of life (see, for example, Duntley, P., Siever, J., Korwes, M. L., Harpel, K., and Heffner, J. E. 1992. "Vascular Erosion by Central Venous Catheters. Clinical Features and Outcome," *Chest* 101(6):1633-1638) or migration (see, for example, Oguzkurt, L., Tercan, F., Torun, D., Yildirim, T., Zümrütdal; A., and Kizilkilic, O. 2004. "Impact of Short-term Hemodialysis Catheters on the Central Veins: A Catheter Venographic Study," *European Journal of Radiology* 52(3):293-299; Foust, J. 2004. *Blood Flow Simulation Past a Catheter Positioned in the SVC-IVC-RA Junction: Steady and Unsteady Flow Considerations*, Master's Thesis, Lehigh University, Bethlehem, Pa.).

The need to remove a central catheter is usually due to mechanical problems (see, for example, Darbyshire, P. J., Weightman, N. C., and Speller, D. C. 1985. "Problems Associated with Indwelling Central Venous Catheters," *Archives of Disease in Childhood* 60(2):129-134). That complications are common with entry needle puncture is attributable to the needle, guidewire, and dilator, none of which are used to place a side-entry connection jacket. As a permanent junction, a side-entry connection jacket is safer than an indwelling catheter. A double lumen, fully intracorporeal dialysis or apheresis line leading to a surface port with a switch to open and close the circulation is suitable for use with a home machine.

Not situated, even partially, in the bloodstream as is a conventional central line, a side-entry connection jacket should rarely if ever induce an arrhythmia (Shah, K. B., Rao, T. L., Laughlin, S., and El-Etr, A. A 1984. "A Review of Pulmonary Artery Catheterization in 6,245 Patients," *Anesthesiology* 61(3):271-275). The addition to a side-entry connection jacket of a concentric magnetized layer allows the direct piping of drugs to the jacket as a magnetized collar for drawing of superparamagnetic nanoparticle carrier bound drugs into and through the lumen wall. The caliber of the opening or ostium into the native conduit and the line led to it from the surface of the body can be made larger than that of a central venous catheter.

This not only reduces the risk of vascular complications upon insertion of a larger catheter (see, for example, Wicky, S., Meuwly J. Y., Doenz, F, Uské, A., Schnyder, P., and Denys A. 2002. "Life-threatening Vascular Complications after Central Venous Catheter Placement," *European Radiology* 12(4):901-907), but when the port is not implanted beneath as to be covered over by the skin, allows the passage of narrower catheters and cabled devices and various diagnostic sensors such as a fine fiberoptic endoscope or angioscope in addition to the infusion or injection by syringe of drugs. Unless analog to digital conversion is accomplished within each, the microcontroller must include an analog to digital converter. Similarly, where the motor of each pump in each pump-pair is analog and without an inmate digital to analog converter, the microcontroller must include a digital to analog converter.

Noninjurious Connection to Ductus

Unless given open access to the surrounding environment, a vessel will undergo atherogenesis, or atherosclerotic degreneration (see, for example, De Meyer et al. 1997 cited below), and it is probable that if fully enclosed at the adventitia or fibrosa, any other type native conduits or ductus would likely deteriorate. The literature does address the remedial effect of placing perforations through the jacket but not the amelioration thereof with a foam lining. This makes it advantageous that the side-entry connection jacket for use along the vascular tree not completely enclose the vessel but incorporate perforations entirely through the jacket to include the outer shell, magnet if present, and foam lining. If radiation shielding requires that the vessel be completely enclosed for an indeterminate time, then the foam lining notwithstanding, the same line used to convey the radionuclide to the lesioned segment is used to deliver magnetic drug carrier bound antiatherosclerotic drugs. If the radiation shield and antiatherosclerotic drugs can later be dispensed with, then a disintegrating shield is used.

The perforations can be circular or linear, and if small will not disrupt magnetic performance, certainly not to an extent that cannot be compensated for, even though the outer shell must line the perforations through the magnet to isolate the magnetic material, which is toxic. By the same token, only the enclosed segment is affected thus, and serious lesions may relegate the atherogenic consideration to a secondary status. Atherosclerotic degradation of the encircled native conduit or ductus is averted by lining the jackets with biostable viscoelastic polyurethane foam.

Rather than to place the vasa and nervi vasora, or fine microvasculature and nervelets of the larger ductus, under compression or tamponade, the foam enfolds or ingests to accommodate these. A high-density memory foam, variously referred to as a viscoelastic flexible polyurethane foam, slow recovery foam, or temper foam, of lower indentation force or load deflection and higher phase relaxation or phase change at body temperature in a thickness sufficient to minimize if not eliminate perivascular compression. A properly selected foam shape adapts to accommodate the vasa vasora quickly enough that compression is too brief to initiate the process of degeneration and compensatory neovascularization that can result in hemorrhaging and thromboembolism.

While some of the fine vasa vasorum externae must be broken to encircle the substrate ductus, for others and most of the vasa vasorum intemae, even the temporary compression during placement and adaptation of the foam to the body temperature is avoided, because the jackets are provided with perforations. These are shown in the drawing figures as part number 19, which pass entirely through the layers of the jacket to the adventitial or fibrosal outer surface of the ductus or included periadventitial fat except where the tissue plug is to be removed, so that compression of the vasa vasorum is minimized and gas exchange between the adventitia and the foam and the surrounding body cavity is little if at all affected (see, for example, Sun, Z. 2014. "Atherosclerosis and Atheroma Plaque Rupture: Normal Anatomy of Vasa Vasorum and Their Role Associated with Atherosclerosis," *Scientific World Journal* 2014:285058; Kitman, E. L. and Lerman, A. 2007. "The Dynamic Vasa Vasorum," *Cardiovascular Research* 75(4):649-658; De Meyer et al. 1997 cited below; Williams, J. K. and Heistad, D. D. 1996. "The Vasa Vasorum of the Arteries," (article in French; English abstract at http://www.ncbi.nlm.nih.gov/pubmed/8984146) *Journal des Maladies Vasculaires* 21 Supplement C:266-269).

These properties in an open cell foam facilitate permeation through the foam of a liquid therapeutic substance when wetted at the time the jacket is applied or continued to be delivered inside the jacket shell through a separate line. An open cell structure also less obstructs gas exchange in the interior environment. The condition of compression or tamponade imposed upon these fine structures is therefore brief if it arises at all. Depending upon the application, a side-entry jacket of the kind shown in FIGS. 3 thru 6 with magnet layer can be used to draw an anti-inflammatory, angiogenic, antiangiogenic, anticoagulative, thrombolytic, or antispasmic, or any other magnetically susceptible particle bound drug against or into the wall surrounding the lumen.

While earlier polyurethanes gradually deteriorated in the internal environment (see, for example, Sinclair, T. M., Kerrigan, C. L, and Buntic, R. 1993. "Biodegradation of the Polyurethane Foam Covering of Breast Implants," *Plastic and Reconstructive Surgery* 92(6):1003-1014; Sinclair, T. M., Kerrigan. C L., and Sampalis, J. 1995. "Biodegradation of Polyurethane Foam, Revisited, in the Rat Model," *Plastic and Reconstructive Surgery* 96(6):1326-1335), more recent formulations show good biostability (see, for example, Santerre, J. P., Woodhouse, K., Laroche, G., and Labow, R. S. 2005. "Understanding the Biodegradation of Polyurethanes: From Classical Implants to Tissue-engineered ing Materials," *Biomaterials* 26(35):7457-7470; Stokes, K., McVenes, R., and Anderson, J. M. 1995. "Polyurethane Elastomer Biostability," *Journal of Biomaterials Applications* 9(4): 321-354; Pinchuk, L. 1994. "A Review of the Biostability and Carcinogenicity of Polyurethanes in Medicine and the New Generation of 'Biostable' Polyurethanes," *Journal of Biomaterials Science. Polymer Edition* 6(3):225-267; Szycher, M. and Reed, A. M. 1992. "Biostable Polyurethane Elastomers," *Medical Device Technology* 3(10):42-51). Biostable foams are available from Salviac Limited, Dublin, Ireland. Newer formulations and coatings will further extend the biostability of foams.

The secure connection afforded by the cinching jacket and compliance imparted by the combination of the spring hinges and foam lining accommodate intrinsic motility of the pulse or peristalsis, so that connection to an artery bodes no more risk than does connection to a vein. Side-entry jackets, nonjacketing side-entry connectors, and chain jackets include small suture loops or eyelets to pass through suture for stabilizing the jacket or connector in position by attachment to neighboring tissue at several points. Depending upon whether a large or small ductus is treated, the release of 2,4-toluenediamine (TDA) from the foam lining is small to minute compared to that from a breast implant and too little to act as a carcinogen (see, for example, Vazquez, G. and Pellón, A. 2007. "Polyurethane-coated Silicone Gel Breast Implants Used for 18 Years," *Aesthetic Plastic Surgery* 31(4):330-336; Shanmugam, K., Subrahmanyam, S., Tarakad, S. V., Kodandapani, N., and Stanly, D. F. 2001. "2,4-Toluene Diamines—Their Carcinogenicity, Biodegradation, Analytical Techniques and an Approach towards Development of Biosensors," *Analytical Sciences* 17(12): 1369-1374; Kulig, K. 1998. "Lifetime Risk from Polyurethane Covered Breast Implants," *Environmental Health Perspectives* 106(11):A526-A527; Luu, H. M., Hutter, J. C., and Bushar, H. F. 1998. "A Physiologically Based Pharmacokinetic Model for 2,4-toluenediamine Leached from Polyurethane Foam-covered Breast Implants," *Environmental Health Perspectives* 106(7):393-400; Hester, T. R. Jr., Ford, N. F., Gale, P. J., Hammett, J. L., Raymond, R., Tumbull, D., Frankos, V. H., and Cohen, M. B. 1997. "Measurement of 2,4-toluenediamine in Urine and Serum Samples from Women with Meme or Replicon Breast Implants," *Plastic and Reconstructive Surgery* 100(5):1291-1298).

Progress in the synthesis of polyurethane materials With special endgroups may overcome the release of problematic degradation products without the need for the application of a fine surface film of parylene, for example (see, for example, Ward, R., Anderson, J., McVenes, R., and Stokes, K. 2007. "In Vivo Biostability of Polyether Polyurethanes with Fluoropolymer and Polyethylene Oxide Surface Modifying Endgroups; Resistance to Metal Ion Oxidation," *Journal of Biomedical Materials Research. Part A.* 80(1):34-44; Ward, B., Anderson, J., McVenes, R., and Stokes, K. 2006. "In Vivo Biostability of Polyether Polyurethanes with Fluoropolymer Surface Modifying Endgroups: Resistance to Biologic Oxidation and Stress Cracking," *Journal of Biomedical Materials Research. Part A.* 79(4):827-835; Ward, R., Anderson, J., McVenes, R., and Stokes, K. 2006. "In Vivo Biostability of Shore 55D Polyether. Polyurethanes with and without Fluoropolymer Surface Modifying Endgroups," *Journal of Biomedical Materials Research. Part A.* 79(4):836-845; Ebert, M., Ward, B., Anderson, J., McVenes, R., and Stokes, K. 2005. "In Vivo Biostability of Polyether Polyurethanes with Polyethylene Oxide Surface-modifying End Groups; Resistance to Biologic Oxidation and Stress Cracking," *Journal of Biomedical Materials Research. Part A.* 75(1):175-184).

Significantly, means for encouraging or forestalling hydrolysis, enzymatic breakdown, and attack by the immune system allow the rate of breakdown and persistence of implanted polyurethane to be widely adjusted. Deterioration of foam linings is materially reduced by a cocompliant outer coating intended to prevent breakdown. If any, 2,4-toluenediamine leached from current state of the art polyurethane foams should be too little to affect the adventitia and would be blocked from access to the native lumen by the sides of the side-entry connector. In that TDA is liberated as the material breaks down, biodegradation in vivo and the release of TDA are related, so that a biostable foam can overcome both problems. For this reason, enclosing the foam within an impermeable, biocompatible, and durable metal containing film that nonbrittle, prevents microfractures from forming when the foam is compressed and expands both prevents its disintegration and the release of TDA.

The firm of PFM Medical Aktiengeselshaft, Nürnberg can apply a no-coating free zone composite plastic and metal thin film of niobium, hafnium, zirconium, tantalum, titanium or titaniferous material, or a combination thereof over the surface of the foam by plasma-assisted chemical vapor deposition (Breme, F., Güther, V., and Osten, K-U van 2003. Composite Material, European Patent 0897997, also published as U.S. Pat. No. 6,057,031 and Deutsche Patent 19,736,449). This chemical barrier film must cover all portions of the enclosed foam, to include the sides of the foam bounding the internal surface of the outer shell where it dips down to line any perforations or fenestrations. A sputter coating process that similarly encloses the foam within an outer film of high ductility, hence, flexibility, with little if any alteration in the mechanical properties of the underlying foam could also be used.

Use of Piped Impasse-Jackets

Side-entry jackets which incorporate a concentric magnetized layer, or piped impasse-jackets, part number 8 as shown in FIGS. 3 thru 6, can be used to target superparamagnetic drug-carrier nanoparticles (see, for example, Akbarzadeh, A., Samiei, M., and Davaran, S. 2012. "Magnetic Nanoparticles: Preparation, Physical Properties, and Applications in Biomedicine," *Nanoscale Research Letters* 7(1):144; Frey, N. A., Peng, S., Cheng, K., and Sun, S. 2009. "Magnetic Nanoparticles: Synthesis, Functionalization, and Applications in Bioimaging and Magnetic Energy Storage," *Chemical Society Reviews* 38(9):2532-2542; Wahajuddin, M. and Arora, S. 2012. "Superparamagnetic Iron Oxide Nanoparticles: Magnetic Nanoplatforms as Drug-carriers," *International Journal of Nanomedicine* 7:3445-3471; Silva, A., Silva-Freitas, É., Carvalho, J., Ponte, T., Araújo-Neto, R., Silva, K., Carriço, A., and Egito, E. 2012. "Magnetic Particles in Biotechnology: From Drug Targeting to Tissue-engineered ing, Chapter 13 in Petrie, M. (ed.), *Biochemistry, Genetics and Molecular Biology: Advances in Applied Biotechnology*, New York, N.Y.: InTech Publishing Company; McBain, S. C., Yiu, H. H., and Dobson, J. 2008. "Magnetic Nanoparticles for Gene and Drug Delivery," *International Journal of Nanomedicine* 3(2):169-180; Pankhurst, Q. A. Connolly, J., Jones, S. K., and Dobson, J. 2003. "Applications of Magnetic Nanoparticles in Biomedicine," *Journal of Physics Part D. Applied Physics* 36:R167-R181; Tartaj, P., Morales, M. P., Veintemillas-Verdaguer, S., Gonzalez-Carreno, T., and Serna, C J. 2003. "The Preparation of Magnetic Nanoparticles for Applications in Biomedicine," *Journal of Physics D: Applied Physics* 36, R182-R197; Soppimath, K. S., Aminabhavi, T. M., Kulkarni, A. R., and Rudzinski, W. E. 2001. "Biodegradable Polymeric Nanoparticles as Drug Delivery Devices," *Journal of Controlled Release* 70(1-2):1-20) through the jacketed segment of the lumen wall.

Occlusion of the vasa vasorum is believed to induce a compensatory angiogenic response of neovascularization where the immature microvasculature is especially susceptible to hemorrhage (Galili, O., Herrmann, J., Woodrum, J., Sattler, K. J., and Lerman, L. O. 2004. "Adventitial Vasa Vasorum Heterogeneity among Different Vascular Beds," *Journal of Vascular Surgery* 40(3):529-535; Moreno, P. R., Purushothaman, K. R., Fuster V., Echeverri, D., Truszczynska, H., Sharma, S. K., Badimon, J. J., and O'Connor, W. N 2004. "Plaque Neovascularization is Increased in Ruptured Atherosclerotic Lesions of Human Aorta: Implications for Plaque Vulnerability," *Circulation* 110(14):2032-2038). While antiangiogenic drugs can be delivered through the jacket to suppress neovascularization, occlusion through compression of the intact primary or mature vasa vasorum may well have been the factor that initiated the disease cascade and is best kept to a minimum.

Extraction of Susceptible Drug-Carrier Residues

The potential toxicity of some susceptible drug-carrier residues means that an accumulation thereof small enough and noninjurious if extracted no farther than into the foam lining of the side-entry jacket can be left to remain in the foam. Unless due to disease or a genetic defect the adventitia or fibrosa is sufficiently malacotic for the magnetic layer within the jacket to extract the residue into the foam, the intrinsic magnet, which must conform to the prior constraint that it be lower in mass and thickness than would cause discomfort if not tissue injury, requires an assist from an external electromagnet.

Extraction of susceptible drug-carrier residues into the foam and no farther radially outward, does not necessitate radial through and through perforations through the jacket wall in the form of an extraction grid or grating. Permanent and electromagnet jackets without the field strength to completely extract a toxic residue should be avoided and an electromagnetic extraction jacket such as shown in FIGS. 13 and 15 used in lieu thereof. While the response to an adverse tissue reaction can usually be obtained with the aid pharmaceuticals, toxicity not abolished or reduced to a tolerable level by such means demands extraction.

If toxic, or inducing of an adverse tissue reaction (see, for example, Singh, R. K., Kim, T. H., Patel, K. D., Knowles, J. C., and Kim, H. W. 2012. "Biocompatible Magnetite Nanoparticles with Varying Silica-coating Layer for Use in Biomedicine: Physicochemical and Magnetic Properties, and Cellular Compatibility," *Journal of Biomedical Materials Research. Part A.* 100(7):1734-1742; Hong, S. C., Lee, J. H., Lee, J., Kim, H. Y., Park, J. Y., Cho, J., Lee, J., and Han, D. W. 2011. "Subtle Cytotoxicity and Genotoxicity Differences in Superparamagnetic Iron Oxide Nanoparticles Coated with Various Functional Groups," *International Journal of Nanomedicine* 6:3219-3231; Narayanan, T. N., Mary, A. P., Swalih, P. K., Kumar, D. S., and 5 Others 2011. "Enhanced Biocompatibility of Ferrofluids of Self-assembled Superparamagnetic Iron Oxide-Silica Core-Shell Nanoparticles," *Journal of Nanoscience and Nanotechnology* 2011 11(3):1958-1967; Kunzmann, A., Andersson, B., Vogt, C., Feliu, N., Ye, F., Gabrielsson, S., and 8 Others 2011. "Efficient Internalization of Silica-coated Iron Oxide Nanoparticles of Different Sizes by Primary Human Macrophages and Dendritic Cells," *Toxicology and Applied Pharmacology* 253(2):81-93; Ahamed, M., Akhtar, M. J., Siddiqui, M. A., Ahmad, J., Musarrat, J., Al-Khedhairy, A. A., AlSalhi, M. S., and Alrokayan, S. A. 2011. "Oxidative Stress Mediated Apoptosis Induced by Nickel Ferrite Nanoparticles in Cultured A549 Cells," *Toxicology* 283(2-3): 101-108; Naqvi, S., Samim, M., Abdin, M., Ahmed, F. J., Maitra, A., Prashant. C, and Dinda, A. K. 2010. "Concentration-dependent Toxicity of Iron Oxide Nanoparticles Mediated by Increased Oxidative Stress," *International Journal of Nanomedicine* 5:983-989; Witasp, E., Kupferschmidt, N., Bengtsson, L., Hultenby, K., Smedman, C., Paulie, S., Garcia-Bennett, A. E., and Fadeel, B. 2009. "Efficient Internalization of Mesoporous Silica Particles of Different Sizes by Primary Human Macrophages without Impairment of Macrophage Clearance of Apoptotic or Antibody-opsonized Target Cells," *Toxicology and Applied Pharmacology* 239(3):306-319), or excessive in volume when trapped inside the open cell foam, an extraction-electromagnet such as shown in FIGS. 13 and 15 is used to extract the residue.

To allow a path for an adverse buildup to be removed from the subadvential or subfibrosal harbor with the aid of an external electromagnet, perforations are introduced from the internal surface of the foam lining to the external surface of the side-entry jacket. Extraction when necessary is to the closest location for innocuous deposition. If regardless of the intracorporeal tissue depth to which withdrawn, an unavoidable residue remains toxic or induces an adverse tissue response that does not subside and is irreversible in situ, then extraction is through the extraction grating and entirely outside the body.

This allows access to the chambers of the heart for monitoring, for example, without the need to leave the device in place between readings or the need to reenter every time a reading is needed, a guideway having been prepositioned and the risks of entry not requiring to be confronted each time. When access to the side-entry connection jacket is for no more than conventional injection or infusion, the port implanted at the body surface is ordinarily subcutaneous, or placed beneath the skin.

Radioactive Magnetically Susceptible Drug-Carrier Residue Extracts

As indicated, if radiation shielding requires that the vessel be completely enclosed for an indeterminate time, then the foam lining notwithstanding, the same line used to convey the radionuclide to the lesioned segment is used to deliver magnetic drug carrier bound antiatherosclerotic drugs. If the radiation shield and antiatherosclerotic drugs can later be dispensed with, then a disintegrating shield is used.

In that case, the jacket configuration shown in FIG. 4 without a radiation shield is encircled within a shield of unperforated shielding material such as tungsten in the form of an overlapping particulate shown in FIG. 6 wherein each particle is encapsulated to safely fall away and remain in the body once the absorbable bonding agent breaks down. Where the site of implantation would not afford the hydrolytic and/or enzymatic action required to break down the particle binder over the interval desired, the need for an additional invasive procedure to wet these with a suitable breakdown accelerant should be avoided. Instead, additional ingredients to accelerate breakdown are included in the binder, usually water and/or an enzyme.

The tungsten particles can also include ferrous matter before encapsulation and be bonded together with an organic solder having a low flow or denature temperature so that it disintegrates when placed in a magnetic field alternated at radio frequency. While a radiation shield must not be perforated; to shield low dose rate radionuclides it can, however, be made to safely disintegrate spontaneously due to hydrolysis and enzymatic attack or through the application of a solvent or heat to the particle bonding agent. Shortening the period for shielding is beneficial from the standpoints both of preventing atherosclerotic degradation in the encircled vessel, and targeted delivery notwithstanding, minimizing the period for administering anti-inflammatory drugs such as steroidal, antihyperlasic drugs such as everolimus, and pleiotropically acting antiatherosclerotic drugs such as a statin.

For this reason, a radiation shield that can be disintegrated once the administration of radioactive material is no longer needed is provided. Such a shield, addressed under Description of the Preferred Embodiments of the Invention, consists of tungsten heavy alloy particles encapsulated within an insoluble polymer and compacted so that particles in many layers overlap radially in relation to the ductus long axis. The encapsulated particles can be separated by application of a solvent. For example, if the particles were bonded together by means of a cyanoacrylate cement, wetting the shield with acetone, or dimethyl ketone, would dissolve the bonds. Also, to compensate for the enclosure by the shield, antiatherosclerotic and anti-inflammatory drugs can be included in the medication delivered to the junction and/or vessel through a side-entry connector if available or a service channel.

The synthetic line or lines used to deliver a radionuclide, for example, to the jacket must also be shielded, even though the line itself will usually continued to be needed following radiation treatment to deliver nonradioactive substances. The inducement to eliminate the shielding once treatment has ended is not governed by the considerations pertinent to a native conduit, but rather the alleviation or prevention of discomfort without the need for a second invasive procedure. The outer shielding of jacket delivery lines can be made to disintegrate in the same way as the jacket shield. Preferably, however, a second invasive procedure is avoided by selecting materials that will allow the discretionary disintegration of the shield when examination reveals it can be removed preferably through lithotripsy or alternatively, through the application of heat.

For susceptibility to shock wave lithotripsy, the shield is internally organized into layers bonded by a matrix of low ultimate shear stress (see, for example, Rassweiler, J. J., Tailly, G. G., and Chaussy, C. 2005. "Progress in Lithotriptor Technology," *European Association of Urology Update Series* 3:17-36; Xi, X. and Zhong P. 2001. "Dynamic Photoelastic Study of the Transient Stress Field in Solids during Shock Wave Lithotripsy," *Journal of the Acoustical Society of America* 109(3):1226-1239). The bonding of encapsulated tungsten beads in a disintegrable line shield must afford pliancy as well as disintegrability.

Placing the patient in a radio frequency alternated magnetic field allows heating the magnet to a sub-Curie and sub-injurious temperature that will denature a specially formulated proteinaceous cement, eutectic protein solder, or mucilaginous substance with ferrous content as a binder matrix. The use of a drug-carrier itself magnetized negates such use. Alternatively, when the period over which treatment must continue can be predicted, a biodegradable substance such as one of blended polycaprolactone or polylactide, which can be accelerated to melt through the addition of heat, or of a glycolic acid based polymer can be used.

Use of Mainlines and Sidelines

Referring now to FIG. 16, most often mainline 13 is used to deliver a drug or other therapeutic agent, with sideline 11 available to add another drug or adjuvant substance to merge into that sent through mainline 13. As will be clear from FIG. 1, backflow from mainline 13 into sideline 11 is prevented, as flow through sideline 11 merges unidirectionally with flow through mainline 13. By the same token, when sideline 11 alone is used, flow is still unidirectionally adluminal, the adjuvant not about to reverse direction upon delivery. For this reason, mainline 13 and sideline 11 are not able to reflux or reverse flow either into the other, making the need for valving to open either or both unnecessary.

While ordinarily sideline 11 serves as accessory or subsidiary to mainline 13, by reversing the relative cross sections without changing the rate of flow through either, this relationship might be reversed, and it is clear that the two can be adjusted in relative sized so that inflow into the ductus lumen 1 from either will be equal. With the relative dimensions of the two as depicted in FIG. 1, a cabled device would be passed from the opening in the port at the body surface through mainline 13, sideline 11 available to simultaneously feed in a drug, other therapeutic agent, or a lubricant. The size of the jacket is according to that of the ductus it is to encircle, so that the absolute dimensions of the mainline and sideline passageways is widely variable.

At the large end of the range, a jacket suitable for placement along the colon, for example, with mainline and sideline substantially equal in cross section, should allow ease of steerability through either the mainline or sideline passageway of a miniature cabled device such as a rotary or linear atherectomizer, thrombectomizer, excimer laser, or fiberoptic angioscope, for example. As configured in FIG. 1 to fit a medium sized vessel, steering a cabled device into lumen 1 through mainline 13 may require that the distal end or head of the cabled device if not magnetically susceptible have a highly susceptible bead attached to allow steering with the aid of an extracorporeal magnet. A segment of an artery that requires mechanical or laser angioplasty, stenting, or examination with the aid of a fiberoptic angioscope or intravascular ultrasound probe is thus made accessible.

When a fluid conduction or water-jacket is used as a followup service or accessory channel, that is, as a sideline, to deliver nutrients, for example, the passage of transluminal diagnostic instruments, hemodialysis, or leukapheresis, for example, access is through a surface port with cover removed and antimicrobial precautions applied. The risk of bloodstream infection and the precautions to prevent such an eventuality are less than for a conventional central line. Use of a side-entry jacket fed from an automatic ambulatory, or portable, throughput volume metered pump or syringe driver through a port implanted at the body surface can deliver a vasospasm-suppressing nitrate and/or calcium channel blocker such as nimodopine to the artery immediately and at a higher dose than would be allowed to enter the general circulation.

Microchannel pumps for separately targeting different sites are currently not made in small enough sizes for implantation diagnostics for transmission to a clinic (see, for example, Fu, X., Mavrogiannis, N., Ibo, M., Crivellari, F., and Gagnon, Z. R. 2017. "Microfluidic Free-flow Zone Electrophoresis and Isotachophoresis Using Carbon Black Nano-composite PDMS [polydimethylsiloxane] Sidewall Membranes," *Electrophoresis* 38(2):327-334; Fu, X. and Gagnon, Z. 2015. "Contactless Microfluidic Pumping Using Microchannel-integrated Carbon Black Composite Membranes," *Biomicrofluidics* 9(5):054122).

A multichannel plug and implanted port receptacle or socket expedite the treatment of chronic comorbidities. Such a pump is ideally miniaturized, functionally integrated but not unitized with the port implanted at the body surface as a permanent part thereof which can be worn beneath the clothing, and is not removed, but rather replenished by inserting a new refill cartridge, larger volumes of the therapeutic substance or substances delivered from a separately worn pump. In some patients, targeted drug delivery is recommended due to adverse interaction with other drugs used to treat a comorbidity or adverse side effects.

Automatic Ambulatory Response to Coronary Artery Spasms and Symptoms

Where coronary spasm is chronic, the applicability of drug delivery through the arrangement shown in FIG. 16 is evident. In FIG. 16, body surface port, part number 16, is shown as connected directly to the left anterior descending artery; where the condition is chronic, the port would be used to inject the drug or drugs into small flat bladder reservoirs positioned subdermally in the pectoral region, with drug delivery automatically administered by a sensor-driven microprocessor likewise implanted.

Placement of a side-entry jacket can be used, for example, to alleviate the pain of refractory Prinzmetal's vasospastic, or variant, angina pectoris (see, for example, Cannon, C. P. and Brauwald, E. 2005. "Unstable Angina," in Braunwald's Heart Disease, Philadelphia, Pa.: Saunders; Cannon, C. P. and Brauwald, E. 2005. "Unstable Angina and Non-ST-Elevation Myocardial Infarction," in Harrison's Principles of Internal Medicine, New York, N.Y.: McGraw-Hill, page 1448; Merck Manual of Diagnosis and Therapy, 2006. "Coronary Artery Disease," Chapter 73, page 635; additional references below) in a patient who:

a. Shows a tendency to develop an arrhythmia that could lead to a sudden arrest, and/or b. Shows no evidence of atheromatous obstruction, and/or c. Does not respond to or should not be treated by performing an angioplasty, or d. Is unable to tolerate the long-term use of the drugs commonly prescribed, to include nitrates, such as nitroglycerin; calcium channel blockers, such as the nondihydropyridine drug diltiazem and the phenylalkylamine drug verapamil; rho kinase inhibitors, such as fasudil; and other type drugs, such as amiodarone or papaverine hydrochloride if introduced into the systemic circulation.

All are associated with adverse side effects and drug-drug interactions when introduced into the systemic circulation. Nonvasospastic angina can be treated by this means through the direct delivery of beta blockers, nitrates, calcium channel blockers, ranolazine, verapamil, and amlodipine, for example. Should delivery of a primary drug other than antispasmodic elicit a spasmodic reaction, antispasmodic medication is delivered along with the primary drug.

Targeted drug delivery to the problem coronary artery or arteries not only implements the suppression of myocardial infarction within five years in the twenty percent of patients susceptible thereto, but allows the use of elevated levels of calcium channel blockers and therewith, the effective prevention of spasm while avoiding the risks in long-term use of short acting calcium channel blockers, to include tachycardia, bradycardia, hypotension, dizziness, gingival edema, headache, constipation, leg edema, drowsiness, and associated more with immediate release, or short acting calcium channel blockers, and breast cancer in postmenopausal women (Coogan, P. F. 2013. "Calcium-Channel Blockers and Breast Cancer: A Hypothesis Revived," at "http://archinte.jamanetwork.com/article.aspx?articleid=1723870; Li, C. I., Malone, K. E., Weiss, N. S., Boudreau, D. M., Cushing-Haugen, K. L., and Daling, J. R. 2003. "Relation between Use of Antihypertensive Medications and Risk of Breast Carcinoma among Women Ages 65-79 Years," Cancer 98(7):1504-1513; Sica, D. A. 2006. "Pharmacotherapy Review: Calcium Channel Blockers," Journal of Clinical Hypertenions (Greenwich). 8(1):53-56; Opie, L. H., Yusuf, S., and Kübler, W. 2000. "Current Status of Safety and Efficacy of Calcium Channel Blockers in Cardiovascular Diseases: A Critical Analysis Based on 100 Studies," Progress in Cardiovascular Diseases 43(2):171-196; Gillman, M. W., Ross-Degnan, D., McLaughlin, T. J., Gao, X., Spiegelman, D., Hertzmark, E., Goldman, L., and Soumerai, S. B. 1999. "Effects of Long-acting versus Short-acting Calcium Channel Blockers among Older Survivors of Acute Myocardial Infarction," Journal of the American Geriatrics Society 47(5):512-517; Noll; G. and Lüscher, T. F. 1998. "Comparative Pharmacological Properties among Calcium Channel Blockers: T-channel versus L-channel Blockade," Cardiology. 89 Supplement 1:10-15; Massie, B. M. 1998. "The Safety of Calcium-channel Blockers," Clinical Cardioloogy 21(12 Supplementl 2): II12-II17; Opie, L. H. 1997. "Calcium Channel Blockers for Hypertension: Dissecting the Evidence for Adverse Effects," American Journal of Hypertension 10(5 Part 1):565-577; Thulin, T. 1990. "Calcium Antagonists—Assessment of Side Effects," Scandinavian Journal of Primary Health Care Supplement; 1:81-84; Russell, R. P. 1988. "Side effects of Calcium Channel Blockers," Hypertension 11(3 Part 2):II42-II44; Hedner, T. 1986. "Calcium Channel Blockers: Spectrum of Side Effects and Drug Interactions," Acta Pharmacologica et Toxicologica (Copenhagen) 58 Supplement 2:119-130).

The spasmic contraction of Prinzmetal's angina usually occurs about 1 centimeter distal (antegrade, downstream) to an epicardial coronary artery atheroma but can appear with endothelial dysfunction and abnormalities in vascular smooth muscle cell function in the absence of any treatable lesion, eliminating transluminal intervention as a remedy, such a procedure incapable of eradicating the endothelial dysfunction to which the problem is attributed. The delivery of nitroglycerin and a calcium channel blocker directly to the spastic artery or arteries eliminates the side effects and drug interactions associated with these drugs when introduced at systemic doses into the systemic circulation.

Nontargeted nitroglycerin can induce hypotension, compensatory tachycardia, syncope, flushing, headache, and is subject to a progressive reduction in efficacy, or tolerance, eventually necessitating coadministration with an adjuvant drug such as ranolazine and/or a beta-blocker, or use of another vasodilator such as a calcium channel blocker, which like all drugs, also bodes adverse side effects (see, just below and, for example, Codolosa, J. N., Acharjee, S., and Figueredo, V. M. 2014. "Update on Ranolazine in the Management of Angina," Vascular Health and Risk Management 10:353-362; Muhlestein, J. B. and Grehan, S. 2013. "Ranolazine Reduces Patient-reported Angina Severity and Frequency and Improves Quality of Life in Selected Patients with Chronic Angina," Drugs in Research and Development 13(3):207-213; Wimmer, N. J. and Stone, P. H. 2013. "Anti-anginal and Anti-ischemic Effects of Late Sodium Current Inhibition," Cardiovascular Drugs and Therapy 27(1):69-77; Rognoni, A., Barbieri, L., Cavallino, C., Bacchini, S., Veia, A., and 6 others 2013. "Ranolazine: Effects on Ischemic Heart," Recent Patents on Cardiovascular Drug Discovery 8(3):197-203; Young, J. W. Jr. and Melander, S. 2013. "Evaluating Symptoms to Improve Quality of Life in Patients with Chronic Stable Angina," Nursing Research and Practice 2013:504915; Ferreira, J. C. and Mochly-Rosen, D. 2012. "Nitroglycerin Use in Myocardial Infarction Patients," Circulation Journal 76(1):15-21; Thadani, U. and Ripley, T. L. 2007. "Side Effects of Using Nitrates to Treat Heart Failure and the Acute Coronary Syndromes, Unstable Angina and Acute Myocardial Infarction," Expert Opinion on Drug Safety 6(4):385-396; Ramey, J. T. and Lockey, R. F. 2006. "Allergic and Nonallergic Reactions to Nitroglycerin," Allergy and Asthma Proceedings 27(3):273-280; Thadani, U. and Rodgers, T. 2006. "Side Effects of Using Nitrates to Treat Angina," Expert Opinion on Drug Safety 5(5):667-674).

Side effects of nontargeted calcium channel blockers (see, for example, Humbert, X., Roule, V.; Milliez, P., and Alexandre, J. 2017. "Verapamil and Vasospastic Angina: Underuse in the Elderly Population," Journal of Geriatric Cardiology 14(7):430-435; Slavich, M. and Patel, R. S. 2016. "Coronary Artery Spasm: Current Knowledge and Residual Uncertainties," International Journal of Cardiology. Heart and Vasculature 10:47-53; Hung, M. J., Hu, P., and Hung, M. Y. 2014. "Coronary Artery Spasm: Review and Update," International Journal of Medical Sciences 11(11):1161-1171; Beller, G. A. 1989. "Calcium Antagonists in the Treatment of Prinzmetal's Angina and Unstable Angina Pectoris," Circulation 80(6 Supplement):IV78-IV87) include "1) vasodilatation, 2) negative inotropic effects, 3)

conduction disturbances, 4) gastrointestinal effects, 5) metabolic effects, and 6) drug interaction" (Russell, R. P. 1988. "Side Effects of Calcium Channel Blockers," Hypertension 11(3 Part 2):II42-II44) (see also, for example, Sica, D. A. 2006. "Pharmacotherapy Review: Calcium Channel Blockers," Journal of Clinical Hypertension (Greenwich, Conn.) 8(1):53-56; Thulin, T. 1990. "Calcium Antagonists—Assessment of Side Effects," Scandinavian Journal of Primary Health Care. Supplement 1:81-84; Hedner, T. 1986. "Calcium Channel Blockers: Spectrum of Side Effects and Drug Interactions," Acta Pharmacologica et Toxicologica (Copenhagen, Denmark) 58 Supplement 2:119-130).

Treatment of Kounis syndrome, for example, is with the addition of a nitrate, antihistamine, diphenhydramine, and famotidine, and corticosteroids (see, for example, Ferreira, R. M., Villela, P. B., Almeida, J. C. G., Sampaio, P. P. N., Albuquerque, F. N., and 4 others 2018. "Allergic Recurrent Coronary Stent Thrombosis: A Mini-review of Kounis Syndrome," Cardiovascular Revascularization Medicine March 13. pii: S1553-8389(18)30090-3; Mendoza Vásquez, L. E. 2018. "Allergic Acute Coronary Syndrome (Kounis Syndrome) in a Young Woman during Spinal Anesthesia: A Case Report," Anesthesia and Analgesia Practice March 31; Li, J., Zheng, J., Zhou, Y., Liu, X., and Peng, W. 2018. "Acute Coronary Syndrome Secondary to Allergic Coronary Vasospasm (Kounis Syndrome): A Case Series, Follow-up and Literature Review," BioMed Central Cardiovascular Disorders 18(1):42; Palacios-Zabalza, I., Camino-Rodríguez, E., and Aguirre, C. 2018. "Kounis Syndrome Induced by Ranitidine," Medicina Clinica (Barcelona, Spain) March 7. pii: S0025-7753(18)30081-2; Haddad, A., Smith, T., Bole, A., Shah, M., and Chakravarthy, M. 2018. "Type I Kounis Syndrome Variant: A Case Report and Literature Review," Avicenna Journal of Medicine 8(1):37-39; Mitsis, A., Christodoulou, E., and Georgiou, P. 2017. "Coronary Spasm Secondary to Cefuroxime Injection, Complicated with Cardiogenic Shock—A Manifestation of Kounis Syndrome: Case Report and Literature Review," European Heart Journal. Acute Cardiovascular Care March 1:2048872617701885; Alçay, M. 2017. "Ibuprofen-induced Kounis Syndrome with Diffuse ST Segment Depression and Atrial Fibrillation," Anatolean Journal of Cardiology 18(5): 380-381; Abdelghany, M., Subedi, R., Shah, S., and Kozman, H. 2017. "Kounis Syndrome: A Review Article on Epidemiology, Diagnostic Findings, Management and Complications of Allergic Acute Coronary Syndrome," International Journal of Cardiology 232:1-4; Omri, M., Kraiem, H., Mejri, O., Naija, M., and Chebili, N. 2017. "Management of Kounis Syndrome: Two Case Reports," Journal of Medical Case Reports 11(1):145; Kounis, N. G. 2016. "Kounis Syndrome: An Update on Epidemiology, Pathogenesis, Diagnosis and Therapeutic Management," Clinical Chemistry and Laboratory Medicine 54(10):1545-1559; De Gennaro, L., Brunetti, N. D., Resta, M.1, Rutigliano, D., Tarantini, L., and Caldarola, P. 2016. "Cardiac Arrest and Ventricular Fibrillation in a Young Man Treated with Capecitabine: Case Report and Literature Review," International Journal of Cardiology 220:280-283; Kim, H. I., Cha, K. C., Cha, Y. S., Kim, O. H., Kim, H., and 4 others 2016. "A Subset of Type I Variant Kounis Syndrome: Allergic Angina Syndrome and Persistent Presence of Coronary Spasm," International Journal of Cardiology 223:959-961; Kido, K., Adams, V. R., Morehead, R. S., and Flannery, A. H. 2016. "Capecitabine-induced Ventricular Fibrillation Arrest: Possible Kounis Syndrome," Journal of Oncology Pharmacy Practice 22(2):335-340; Fassio, F., Losappio, L., Antolin-Amerigo, D., Peveri, S., Pala, G., and 6 others 2016. "Kounis Syndrome: A Concise Review with Focus on Management," European Journal of Internal Medicine 30:7-10; Rayner-Hartley, E., Chou, A., Saw, J., and Sedlak, T. 2016. "A Case of Kounis Type I in a Young Woman with Samter's Triad," Canadian Journal of Cardiology 32(10):1261.e1-1261.e3; Memon, S., Chhabra, L., Masrur, S., and Parker, M. W. 2015. "Allergic Acute Coronary Syndrome (Kounis Syndrome)," Proceedings of the Baylor University Medical Center 28(3):358-362; Scherbak, D., Lazkani, M., Sparacino, N., and Loli, A. 2015. "Kounis Syndrome: A Stinging Case of ST-elevation Myocardial Infarction," Heart, Lung, and Circulation 24(4):e48-50; Regis, A. C., Germann, C. A., and Crowell, J. G. 2015. "Myocardial Infarction in the Setting of Anaphylaxis to Celecoxib: A Case of Kounis Syndrome," Journal of Emergency Medicine 49(2):e39-43; Ihdayhid, A. R. and Rankin, J. 2015. "Kounis Syndrome with Samter-Beer Triad Treated with Intracoronary Adrenaline," Catheterization and Cardiovascular Interventions 86(6):E263-E267; Kounis, N. G. 2013. "Coronary Hypersensitivity Disorder: The Kounis Syndrome," Clinical Therapeutics 35(5):563-571; Prajapati, J. S., Virpariya, K. M., Thakkar, A. S., and Abhyankar, A. D. 2013. "A Case of Type I Variant Kounis Syndrome with Samter-Beer Triad," World Journal of Cardiology 5(4):112-114; Fassio, F. and Almerigogna, F. 2012. "Kounis Syndrome (Allergic Acute Coronary Syndrome): Different Views in Allergologic and Cardiologic Literature," Internal and Emergency Medicine 7(6):489-495; "Schwartz, B. G., Daulat, S., and Kuiper, J. 2011. "The Kounis-Zavras Syndrome with the Samter-Beer Triad," Proceedings of the Baylor University Medical Center 24(2):107-109).

Referring now to FIG. 16, surface port 16 can be used by direct connection to the reactive artery or arteries, here shown as limited to the left anterior descending 2. However, when the condition arises more frequently, and especially when not predictable away from a clinic, a small flat drug reservoir in the pectoral region with manually or sensor-driven microprocessor to automatically control the drug reservoir outlet pump can be used. While nitroglycerin oral is effective once the patient has become conscious of the condition, the automatic delivery directly to the affected coronary or coronaries as soon as spasm is detected can avert serious consequences, as when the patient is in traffic.

Most clinicians once approved of injecting adrenalin, or epinephrine, into either the mainline 13 or sideline 11 openings to suppress coronary spasm as a hypersensitive reaction to an allergen, often a drug, such as aspirin (see, for example, Kemp, S. F., Lockey, R. F., and Simons, F. E. 2008. "Epinephrine: The Drug of Choice for Anaphylaxis—A Statement of the World Allergy Organization," World Allergy Organization Journal 1(7 Supplement):S18-S26, and in Allergy 63(8):1061-1070).

This has, however, been brought into question with growing evidence (see, for example, Jayamali, W. D., Herath, H. M. M. T. B., and Kulathunga, A. 2017. "Myocardial Infarction during Anaphylaxis in a Young Healthy Male with Normal Coronary Arteries—is Epinephrine the Culprit?," BioMed Central Cardiovascular Disorders 17(1):237; Zhang, Z. P., Su, X., Yang, Y. C., Wu, M. X., Liu, B., and Liu, C. W. 2015. "Cardiac Arrest with Coronary Artery Spasm: Does the Use of Epinephrine during Cardiopulmonary Arrest Exacerbate the Spasm?," American Journal of Emergency Medicine 33(3):479.e5-e6; Lee, M. G., Park, H. Y., Lee, C. K., Choi, J. H., and Choi, Y. S. 2014. "Coronary Vasospasm Caused by Local Infiltration of Epinephrine after Spinal Anesthesia," Korean Journal of Anesthesiology 67(Supplement):S46-S48; Bhatia, N., Ghai, B., Mangal, K., Wig, J., and Mukherjee, K. K. 2014. "Effect of Intramucosal Infiltration of Different Concentrations of Adrenaline on Hemodynamics during Transsphenoidal Surgery," *Journal of Anaesthesiology, Clinical Pharmacology* 30(4):520-525; Senthilkumaran, S., David, S. S., Jena, N. N., and Thirumalaikolundu-subramanian, P. 2013. "Epinephrine-induced Myocardial Infarction in Severe Anaphylaxis: Is β-blocker a Bad Actor or Bystander?," *American Journal of Emergency Medicine* 31(9):1410; Cunnington, C., McDonald, J. E., and Singh, R. K. 2013. "Epinephrine-induced Myocardial Infarction in Severe Anaphylaxis: Is Nonselective β-blockade a Contributory Factor?," *American Journal of Emergency Medicine* 31(4):759.e1-e2; Kiss, G., Corre, O., Gueret, G., Nguyen Ba, V., and 3 others 2009. "Management of Cardiac Arrest Caused by Coronary Artery Spasm: Eepinephrine/Adrenaline Versus Nitrates," *Heart and Lung* 38(3):228-232; Yang, J. J., Liu, J., Duan, M. L., Zhou, Z. Q., Li, W. Y., and Xu, J. G. 2007. "Lighter General Anesthesia Causes Less Decrease in Arterial Pressure Induced by Epinephrine Scalp Infiltration during Neurosurgery," *Journal of Neurosurgical Anesthesiology* 19(4):263-267; Goldhaber-Fiebert, S. and Grecu, L. 2006. "Postoperative ST-segment Elevation: Was Vasospasm Caused by Anaphylaxis or by Its Treatment with Epinephrine?," *Annals of Allergy, Asthma, and Immunology* 97(4):449-453; Saff, R., Nahhas, A., and Fink, J. N. 1993. "Myocardial Infarction Induced by Coronary Vasospasm after Self-administration of Epinephrine," *Annals of Allergy* 70(5):396-398).

The same connection made with an atherosclerosed coronary artery can be used to directly deliver a statin, proprotein convertase subtilisin/kexin type 9 inhibitor, or any other drug at a concentration in excess of the background or basal dose introduced into the circulation, atherosclerosis, for example, systemic. Diagnosis and automatic targeted treatment for the patient who is asleep, a child, senile, or otherwise incompetent using the means described has many applications exigent and routine, and should not be understood in a limiting sense as pertaining only to the application specified.

As explained in copending application Ser. No. 13/694, 835, treatment of a non end-arterial artery, for example, with a magnetized collar, or impasse-jacket, placed at the antegrade or downstream end of the segment to be treated allows reducing the level or levels to that allowed to circulate at the distal limit of the segment defined, or exit. Where metabolic dysfunction arises in the liver, such a connection can be used to deliver drugs such as apolipoprotein 3C, a protein encoded by the APOC3 gene that is part of very low density lipoprotein, for example, directly into the portal vein. The portable, or ambulatory, pump used to deliver the medication can be manually controlled by the patient.

In Prinzmetal's (variant, vasospastic) angina (see, for example, Slavich, M. and Patel, R. S. 2016, Op cit.; Hung, M. J., Hu, P., and Hung, M. Y. 2014, Op cit.; de Luna, A. B., Cygankiewicz, I., Baranchuk, A., Fiol, M., Birnbaum, Y., and 6 others 2014. "Prinzmetal Angina: ECG Changes and Clinical Considerations: A Consensus Paper," *Annals of Noninvasive Electrocardiology* 19(5):442-453; Kusama, Y., Kodani, E., Nakagomi, A., Otsuka, T., Atarashi, H, Kishida, H., and Mizuno, K. 2011. "Variant Angina and Coronary Artery Spasm: The Clinical Spectrum, Pathophysiology, and Management," *Journal of Nippon Medical School* 78(1):4-12; Acikel, S., Dogan, M., Sari, M., Kilic, H., and Akdemir, R. 2010. "Prinzmetal-variant Angina in a Patient Using Zolmitriptan and Citalopram," *American Journal of Emergency Medicine* 28(2):257.e3-e6; Vandergoten, P., Benit, E., and Dendale, P. 1999. "Prinzmetal's Variant Angina: Three Case Reports and a Review of the Literature," *Acta Cardiologica* 54(2):71-76; additional references above), because the vasospasm tends to occur at rest, often at night, and sometimes when the patient is asleep, increasing the risk of a sudden arrest (Ziccardi, M. R. and Gossman, W. G. 2017. "Angina, Prinzmetal," *StatPearls* online at https://www.ncbi.nlm.nih.gov/books/NBK430776/; Yasue, H., Nagao, M., Omote, S., Takizawa, A., Miwa, K., and Tanaka, S. 1978. "Coronary Arterial Spasm and Prinzmetal's Variant Form of Angina Induced by Hyperventilation and Tris-buffer Infusion," *Circulation* 58(1):56-62, page 61; Voronin, I. M. and Belov, A. M. 2001. "Why Do Prinzmetal's Angina Attacks Occur in Sleep?," (in Russian with English summary), *Klinicheskaia meditsina* [Clinical Medicine] (Moscow); 79(8):64-65; Shappell, S. D. and Orr, W. C. 1975. "Variant Angina and Sleep: A Case Report with Therapeutic Considerations," *Diseases of the Nervous System* 36(6):295-298), drug delivery is best automated.

Where there is the risk of sudden death, an implanted response system with coronary biosensor to signal a condition of spasm to a microprocessor which actuates an implant drug reservoir outlet pump to dispense a remedial drug or drugs such as nitrates directly to the site immediately in coordination with an implanted cardioverter defibrillator—this while the patient is asleep and not yet conscious of the condition—is more likely to save his life (see, for example, Kundu, A., Vaze, A., Sardar, P., Nagy, A., Aronow, W. S., and Botkin, N. F. 2018. "Variant Angina and Aborted Sudden Cardiac Death," *Current Cardiology Reports* 20(4):26; Sueda, S. and Kohno, H. 2018. "Optimal Medications and Appropriate Implantable Cardioverter-defibrillator Shocks in Aborted Sudden Cardiac Death Due to Coronary Spasm," *Internal Medicine* (Tokyo, Japan) January 11; Ahn, J. M., Lee, K. H., Yoo, S. Y., Cho, Y. R., Suh, J., and 27 others 2016. "Prognosis of Variant Angina Manifesting as Aborted Sudden Cardiac Death," *Journal of the American College of Cardiology* 68(2):137-145; Makki, N., Swaminathan, P. D., Hanmer, J., and Olshansky, B. 2014. "Do Implantable Cardioverter Defibrillators Improve Survival in Patients with Chronic Kidney Disease at High Risk of Sudden Cardiac Death? A Meta-analysis of Observational Studies," *Europace* 16(1):55-62; Ruisi, M., Ruisi, P., Rosero, H., and Schweitzer, P. 2013. "A Series of Unfortunate Events: Prinzmetal Angina Culminating in Transmural Infarction in the Setting of Acute Gastrointestinal Hemorrhage," *Case Reports in Cardiology* 2013:641348; Costa, J., Pereira, M. A., Correia, A., Rebelo, A., and Araújo, A. O. 2002. "Sudden Death and Variant Angina," *Revista Portuguesa de Cardiologia* [Portuguese Journal of Cardiology] 21(11):1305-1314; Roberts, W. C., Curry, R. C. Jr., Isner, J. M., Waller, B. F., McManus, B. M., Mariani-Costantini, R., and Ross, A. M. 1982. "Sudden Death in Prinzmetal's Angina with Coronary Spasm Documented by Angiography. Analysis of Three Necropsy Patients," *American Journal of Cardiology* 50(1): 203-210; Maseri, A., Severi, S., and Marzullo, P. 1982. "Role of Coronary Arterial Spasm in Sudden Coronary Ischemic Death," *Annals of the New York Academy of Sciences* 382:204-217).

Much the same treatment applies to Brugada syndrome (see, for example, Gonzalez Corcia, M. C., Sieira, J., Pappaert, G., de Asmundis, C., Chierchia, G. B., and 3 others 2018. "Implantable Cardioverter-defibrillators in Children and Adolescents with Brugada Syndrome," *Journal of the American College of Cardiology* 71(2):148-157; Bayoumy, A., Gong, M. Q., Christien Li, K. H., Wong, S. H., Wu, W. K., and 7 others 2017. "Spontaneous Type 1 Pattern, Ventricular Arrhythmias and Sudden Cardiac Death in Brugada Syndrome: An Updated Systematic Review and Meta-analysis," *Journal of Geriatric Cardiology* 14(10):639-643; Wu, W., Tian, L., Ke, J., Sun, Y., Wu, R., Zhu, J., and Ke, Q. 2016. "Risk Factors for Cardiac Events in Patients with Brugada Syndrome: A PRISMA [Preferred Reporting Items for Systematic Reviews and Meta-Analyses]—compliant Meta-analysis and Systematic Review," Medicine (Baltimore, Md.) 95(30):e4214; Conte, G., Sieira, J., Ciconte, G., de Asmundis, C., Chierchia, G. B., and 12 others 2015. "Implantable Cardioverter-defibrillator Therapy in Brugada Syndrome: A 20-year Single-center Experience," *Journal of the American College of Cardiology* 65(9):839-888; McNamara, D. A., Goldberger, J. J., Berendsen, M. A., and Huffman, M. D. 2015. "Implantable Defibrillators Versus Medical Therapy for Cardiac Channelopathies," *Cochrane Database of Systematic Reviews* (10):CD011168; Dores, H., Reis Santos, K., Adragão, P., Moscoso Costa, F., Galvão Santos, P., and 4 others 2015. "Long-term Prognosis of Patients with Brugada Syndrome and an Implanted Cardioverter-defibrillator," *Revista Portuguesa de Cardiologia* [Portuguese Journal of Cardiology] 34(6):395-402).

To prevent the pain and the risk the spasm may pose, a separate cardioverter defibrillator and/or sensor, electrically and/or strain gauge-based, incorporated into the side-entry jacket is used to detect the vasospasm noninvasively from outside the vessel the instant contraction begins. One or more of the symptoms or indicia associated with vasospasm is used, that addressed below mechanical, a piezoelectric wafer about the foam lining of the jacket used to trigger delivery from the pump of medication the instant the magnitude of the signal from the wafer drops below a threshold level. More specifically, signaled is a reduction in the outer diameter of the artery on the systoles, measured as a threshold reduction in the root mean square force of outward compression when the pressure waves of the pulse pass through the jacket.

The thin and sensitive piezoelectric wafer is interposed between the foam and outer shell, or if present, the magnet layer. The cuff conformation of the jacket allows continuous monitoring of the pulse and blood pressure; however, as indicated above where limitation of sensor positioning to the jacket itself is discounted, this function can be performed anywhere along the same or another vessel by a separate cuff made specifically for this purpose (see, for example, Sideris, D. A., Vardas, P. E., Chrysos, D. N., Toumanidis, S. T., Michalis, L., and Moulopoulos, S. D. 1987. "An Extravascular Hydraulic System to Control Blood Pressure by a Feedback Regulation of the Venous Return," *Cardiovascular Research* 21(5):337-341).

Within the cuff-configured jacket, a networked matrix of minute pressure sensors positioned as a layer between the internal surface of the jacket shell and foam lining can monitor peristaltic forces, velocity, and frequency, or pulsatile action and blood pressure. To allow the measurable transfer of the outward force exerted by the pulse through the foam, compliant projections in the form of small rubbery pillars fastened to the internal face of the wafer pass through the foam to its internal (adluminal, adaxial) surface. The foam lining and spring hinges that join the half-cylinders of the jacket urge the jacket closed about the native conduit or ductus without injury to the small vessels and nerves that enter and depart the adventitial or fibrosal surface while complying with the pulsatile or peristaltic expansion and contraction of the ductus. Once body temperature is reached, placement of the jacket shown in FIG. 21 should not cut off the flow of blood through the pericardiacophrenic artery, for example.

The pillars are contrast marked, such as with tantalum, to allow these to be positioned off to a side of small vessels and nerves supporting the native conduit to be jacketed. Alternatively, a microminiature laser range finder or distance sensor can be used. The pain of ischemia immediate, detecting chemical indicators such as thromboxane or acetylcholine in anticipation of spasm would allow preventing spasm and pain, so that provided testing does not necessitate entry into the lumen, detection thus would be no less effective. The continuous monitoring of oxygen delivery passing through the artery intrinsically provided by the aortic and carotid bodies along with adjustment of the luminal diameter through endothelial function remain the subject of much research. For conditions to which the body is unable to respond on its own, spontaneous response under autonomic intelligent control is sought to be supplemented with a prosthetic response system.

A suitable sensor allows signaling the pump whether the cause is thromboembolic or vasospasmic but shortly after pain has already set in (see, for example, Russell, D. M., Garry, E. M., Taberner, A. J., Barrett, C. J., Paton, J. F., Budget, D. M., and Malpas, S. C. 2012. "A Fully Implantable Telemetry System for the Chronic Monitoring of Brain Tissue Oxygen in Freely Moving Rats," *Journal of Neuroscience Methods* 204(2):242-248; Bazzu, G., Puggioni, G. G., Dedola, S., Calia, G., Rocchitta, G., and 5 Others 2009. "Real-time Monitoring of Brain Tissue Oxygen Using a Miniaturized Biotelemetric Device Implanted in Freely Moving Rats," *Analytical Chemistry* 81(6):2235-2241). Concurrent telemetric warning of hospital staff is likewise enabled.

Where the aortic body is injured or destroyed, the incorporation into large-scale reconstructions such as total arch replacement or various hybrid schemes that add a stent graft (see, for example, Vallabhajosyula, P., Szeto, W. Y., Desai, N., Komlo, C., and Bavaria, J. E. 2013. "Type II Arch Hybrid Debranching Procedure," *Annals of Cardiothoracic Surgery* 2(3):378-386; Appoo, J. J and Pozeg, Z. 2013. "Strategies in the Surgical Treatment of Type A Aortic Arch Dissection," *Annals of Cardiothoracic Surgery* 2(2):205-211, available at http://www.annalscts.com/article/view/1696/2373; Kent, W. D., Herget, E. J., Wong, J. K., and Appoo, J. J. 2012 "Ascending, Total Arch, and Descending Thoracic Aortic Repair for Acute DeBakey Type I Aortic Dissection without Circulatory Arrest," *Annals of Thoracic Surgery* 94(3):e59-e61) of side-entry jackets incorporating oxygen and blood pressure sensors to trigger the direct delivery of drugs such as anticoagulants and nitrates from an ambulatory pump connected to a port or ports implanted at the body surface to prevent clotting and a lead to stimulate the respiratory centers in the medulla and pons allows approximation of normal dynamic functional response, or aortic reflex, to increase oxygenation.

Needle type oxygen microsensors, for example, made by Precision Sensing GmbH are adaptable for incorporation into the side-connector. By extension, any condition that generates anticipatory or prodromal chemical, such as enzymatic, hormonal, or cytokine, and/or mechanical symptoms at the jacket for which a sensor is available to register the change can be applied to control an ambulatory pump to preclude, suppress, or truncate upon onset, what would otherwise have been the ensuing crisis. This approach assumes a serious if not life-threatening chronic episodic condition that justifies implantation of the jacket and port at the surface.

Any such condition, to include severe migraine, variant angina, arrhythmia, or regional enteritis, for example, where a detectable marker is present for which a microminiature sensor to detect an anticipatory blood chemical marker (Ngoepe, M., Choonara, Y. E., Tyagi, C., Tomar, L. K., du Toit, L. C., Kumar, P., Ndesendo, V. M., and Pillay, V. 2013. "Integration of Sensors and Drug Delivery Technologies for Early Detection and Chronic Management of Illness," *Sensors* (Basel) 13(6):7680-7713; Lalauze, R. (ed.) 2012. *Chemical Sensors and Biosensors*, Hoboken, N.J.: John Wiley and Sons; Sadana, A. and Sadana, N. 2011. *Handbook of Sensors and Kinetics*, Oxford, England: Elsevier; Rosen, Y. and Gurman, P. 2010. "MEMS [Micro-Electro-Mechanical-Systems] and Microfluidics for Diagnostics Devices," *Current Pharmaceutical Biotechnology* 11(4):366-375; Elman, N. M. and Upadhyay, U. M. 2010. "Medical Applications of Implantable Drug Delivery Microdevices Based on MEMS [Micro-Electro-Mechanical-Systems]," *Current Pharmaceutical Biotechnology* 11(4):398-403; Staples, M. 2010. "Microchips and Controlled-release Drug Reservoirs," *Wiley Interdisciplinary Reviews. Nanomedicine and Nanobiotechnology* 2(4):400-417; Comeaux, R. and Novotny, P. 2009. Biosensors: Properties, Materials and Applications, Commack, N.Y.: Nova Science Publishers; Joshi, R. 2006. *Biosensors*, Delhi, India: Isha Books; Eggins, B. R. 2002. *Chemical Sensors and Biosensors*, West Sussex, England: John Wiley and Sons; Turner, A. P. F., Karube, I., and Wilson, G. S. 1987. *Biosensors: Fundamentals and Applications*, Oxford, England: Oxford University Press), for example, for incorporation into the side-entry jacket can be provided may be used thus to avert an impending onset or exacerbation before the absolute threshold of sensation is reached.

Such a marker or markers are likely to be detectable in only a subset of each population, need only appear before the experiential correlates do, and may or may not go to the ultimate etiological basis for the condition. By comparison, an unpiped impasse jacket while preloaded and made to discharge automatically, is limited to a lower rate volume of drug delivery. The signal whether used to initiate remedial drug delivery can also be used to alert local emergency medical services or if used for the latter purpose alone, does not require a line leading from the jacket to a port at the body surface with an ambulatory pump connected. When the cause is unknown, the pump can deliver a thrombolytic drug as well as a vasodilator. The volume of these drugs in relation to that of the circulatory system is minute and incapable of inducing problem bleeding should an interventional procedure or surgery become necessary.

The microminiature oxygen, or lambda, sensor must be washed over by the passing blood and therefore positioned to a side of the opening or ostium of the side-entry connector. Such a sensor can be used to initiate drug delivery regardless of the cause of the ischemia. Eventually, chemical and/or electrical sensors for detecting aortic, para-aortic, and carotid body outputs indicating hypoxia, used by the body to increase the respiration rate, or out of normal range acidity, can be applied to the immediate delivery of drugs to reverse thrombus or vasospasm as causes of the hypoxia in patients with chronic conditions. Less preferred is the detection of creatine kinase or troponin when the patient is already in pain; ideally, the patient if asleep is not awakened. Even when shutoff and throttle valve-plugs to be described is inserted in the line, the same catheter as is used to deliver the medication can run wires between the sensor or sensors and the pump.

However, feedback devices, sensors, and sensors mounted to shutoff and throttle valve-plugs are generally monitored telemetrically, and control adjustments to the openings through valves preferably accomplished by radio remote servo control, thus eliminating the need to slide the valve-plug along the side-entry connection line catheter containing a wire. Wires are generally reserved for higher current demand requirements, such as to heat a coil within a valve-plug to warm the passing medication and stringent space constraints disallow providing a local or inmate source of power. Since a previously positioned valve-plug would block the extraction of the tissue excised from the side of the ductus, a side-entry connector continuous with the line connected to it cannot also have a valve inserted in the line prior to placemen. Therefore, when the need or benefit of a valve-plug is evident before placement, the plug is still positioned immediately after the side-entry jacket has been applied.

Valve-Plugs and Cable Insertion

Certain procedures, to include the passage of a cabled device, such as a narrow endoscope, laser, or a linear or rotary thrombectomizer or atherectomizer, for example, may be difficult to accomplish with fluid, or sol state medication already in the line, especially when a valve-plug must first be retrieved to clear the way. If the cabled device is narrow enough and the valve openings relatively large in cross-sectional area, then the cabled device can pass through the valve-plug. This maneuver is best reserved for devices such as an endoscope that allow passage through the valve to be observed. Medication which for better control, is pumped as a thermoreversible gel which liquifies at higher than body temperature and must be warmed upon approaching the vasculostomy is liquified by a heating element within a valve-plug.

Where a nichrome or other resistance wire coated for internal use is used to warm the medication flowing through the catheteric line not within a valve-plug but rather along the entire length of the line, so that the elastomeric seal surround of the valve-plug addressed below slides over it, the wire is stiff and taut. For this purpose, the elastomer surround of the valve-plug should have a lower coefficient of friction. A surround less resistant to being slid along the line is also used when the valve-plug must allow expeditious extraction from the line in order to pass a cabled device through the side-entry connector and into the native lumen. When the side-entry connection jacket is applied to a blood vessel, extraction thus without the need to insert a guidewire is by using the water-jacket to force the valve-plug out of the line.

In that case, the valve-plug has a less frictional surround which to clear the way from the water-jacket has been trimmed back at the vessel end. A hydrogel prepared drug not welling down the internal surface of the line tubing, then depending upon the frictional values required, the line can be made of a low friction fluoroplymer, usually polytetrafluoroethylene. To avert leakage or extravasation through the side-entry opening, the force to extract the valve-plug must be greater than the blood pressure to a magnitude that allows forcing the valve-plug out of the line but not so great as to cut off or significantly reduce flow through the vessel.

By reserving the use of wire for a valve-plug-inmate heating coil and instead using a stiff wire that enters the valve-plug at the rear, the problem of jamming by seizing and snagging the wire when run through the catheter and the valve-plug is moved is eliminated. A stiff wire connected to the back of the plug to deliver power to a component within the valve-plug to adjust the vanes or to warm a resistance wire inside the valve-plug eliminates the need for a wire affixed to the internal surface of the catheter wall as a continuous sliding contact or 'hotrail.' The hotrail is not also usable to warm the fluid line contents, which necessitates high resistance wire. For warming line contents, such as a thermoreversible drug hydrogel to flow all along the length of a side-connector or service channel line, a nichrome or other resistance wire is used, and can be run adjacent to the hotrail conductor.

Since the medication delivered through side-entry connector and service channel lines is usually in the form of a thermoreversible gel, the ability to warm the valve-plug or the line from end to end, peripherally liquid filming the gel, often expedites repositioning the valve-plug or passing a cabled device down the line and into the ductus. If delivery of electrical power to the valve-plug is through a wire that enters the valve-plug at its rear and trails behind it rather than through contact between a hotrail and sliding boot or shoe on the side of the valve-plug, then a keyhole at the center bottom of the valve-plug seen as part number 28 in FIG. 24 for insertion of a guidewire must be kept clear. Such a trailing wire must therefore be inflexible enough as not to jam the valve-plug when withdrawn and enter the rear of the valve-plug off to a side of the keyhole.

Except to warm the medication along the entire length of the catheter line when warming within the pump is not possible, wires used other than to power components within valve-plugs are seldom needed. In the clinic, placement of the patient in a radiofrequency alternated magnetic field can be used to warm magnetically susceptible matter in the drug and/or the side-entry jacket. With the aid of a sensor, response to acute cardiac events are supplemented by the immediate and direct delivery of drugs when signaled by an implanted cardioverter defibrillator. Reference to vascular applications should not be understood in a limiting sense, the potential uses of side-entry connection jackets pertaining to bodily conduits of any kind. The number of drugs separately delivered from an ambulatory pump depends upon the diagnostic comprehension afforded by the sensors used, delivery of several drugs independently and automatically controllable.

Use of Prosthetic Vessels

For patients lacking suitable graft vessels, the direct continuous delivery of anticoagulant and, if necessary, antihyperplastic drugs makes possible the use of catheters, tissue engineered, and existing synthetic blood vessels as coronary or other vascular bypass conduits, or ductus (see, for example, Lin, P. H., Chen, C., Bush, R. L., Yao, Q., Lumsden, A. B., and Hanson, S. R. 2004. "Small-caliber Heparin-coated ePTFE Grafts Reduce Platelet Deposition and Neointimal Hyperplasia in a Baboon Model," *Journal of Vascular Surgery* 39(6):1322-1328; Chen, C., Lumsden, A. B., and Hanson, S. R. 2000. "Local Infusion of Heparin Reduces Anastomotic Neointimal Hyperplasia in Aortoiliac Expanded Polytetrafluoroethylene Bypass Grafts in Baboons," *Journal of Vascular Surgery* 31(2):354-363).

Another area where elimination of any presence within the lumen, safe and stable mechanical connection with the conduit, and the ability for drug delivery targeted at the junction improve upon the long-term use of a central venous catheter pertains to venous shunts such as peritoneovenous shunts used to drain peritoneal and pleural fluid into the circulation, to include those considered improved (see, for example, Kawaratani, H., Tsujimoto, T., Kubo, T., Aihara, Y., Takaya, T., and 5 Others 2013. "Liver Abscesses after Peritoneal Venous Shunt," *Case Reports in Gastroenterology* 7(2):245-250; Martin, L. G. 2012. "Percutaneous Placement and Management of Peritoneovenous Shunts," *Seminars in Interventional Radiology* 29(2):129-134; Perera, E., Bhatt, S., and Dogra, V. S. 2011. "Complications of Denver Shunt," *Journal of Clinical Imaging Science* 1:6; White, M. A., Agle, S. C., Padia, R. K., and Zervos, E. E. 2011. "Denver Peritoneovenous Shunts for the Management of Malignant Ascites: A Review of the Literature in the Post LeVeen Era," *American Surgeon* 77(8):1070-1075; Tomiyama, K., Takahashi, M., Fujii, T., Kunisue, H., Kanaya, Y., and 5 Others 2006. "Improved Quality of Life for Malignant Ascites Patients by Denver Peritoneovenous Shunts," *Anticancer Research* 26(3B):2393-2395; Hu, R. H. and Lee, P. H. 2001. "Salvaging Procedures for Dysfunctional Peritoneovenous Shunt," *Hepatogastroenterology.* 48(39):794-797).

Ductus side-entry connection jackets and the catheteric lines the jacket accessory channel make possible allow or improve body surface-to-ductus, ductus-to-surface, ductus-to-ductus shunting, and ductus segment bypass connections. The delivery of drugs these afford is direct, immediate, and targeted, minimizing entry into the systemic circulation, and thus avoiding exposure to other tissue and adverse interactions with drugs used elsewhere in the body. Junctions with relatively thick-walled conduits or ductus such as the gut or with blood vessels for the delivery of drugs from outside the body (but not those used to channel the circulation) through a narrow vasculostomy, can be joined through a T-joint configured junction perpendicular or normal to the long axis of the receiving or discharging vessel. Although of value along thick-walled conduits rather than vessels, rectilinear junction of the side-entry connector and native conduit means that the adluminal end of the connector is usable as a manual tissue plug circle-cutter.

However, to least disrupt the laminar flow of blood and thus minimize thrombogenesis and shear stresses through the junctions of vascular bypasses and shunts that would induce endothelial dysfunction and atherosclerotic degradation in the tissue—and if in the arterial tree promote restenosis and the formation of atheromatous plaque—the points at which vascular branches converge and diverge are suitably angled (see, for example, Reneman, R. S. and Hoeks, A. P. 2008, "Wall Shear Stress as Measured in Vivo: Consequences for the Design of the Arterial System," *Medical and Biological Engineering and Computing* 46(5):499-507; Stroev, P. V., Hoskins, P. R., and Easson, W. J. 2007. "Distribution of Wall Shear Rate throughout the Arterial Tree: A Case Study," *Atherosclerosis* 191(2):276-280; Reneman, R. S., Arts, T., and Hoeks, A. P. 2006. "Wall Shear Stress—An Important Determinant of Endothelial Cell Function and Structure—in the Arterial System in Vivo. Discrepancies with Theory," *Journal of Vascular Research* 43(3):251-269; Painter, P. R., Eden, P., and Bengtsson, H. U. 2006. "Pulsatile Blood Flow, Shear Force, Energy Dissipation and Murray's Law," *Theoretical Biology and Medical Modeling* 3:31).

Combining a reduction in turbulence with the administration of heparin or other such drug allow a plastic catheter to serve as a vascular bypass. This means for averting the formation of thrombus is probably enhanced through the application of new surface treatments to the synthetic tube used (see, for example, Breme, F., Güther, V., and Osten, K-U van 2003. Composite Material, European Patent 0897997, also cited above). Junction at an acute angle is also less radially protrusive and therefore more readily accommodated without encroachment upon and irritation to neighboring tissues. Moreover, when the caliber of the catheter is large enough, the avoidance of right angular junctions makes it possible to pass catheteric diagnostic and therapeutic instruments, such as a Swan-Ganz catheter and cabled devices such as a fiberoptic angioscope, through the junction.

The need to exit and reenter a native vessel such as an obstructed coronary artery at suitable divergent and convergent angles is no less significant when the segment bypassed is totally occluded. Intended to connect synthetic to native conduits for drug delivery or to withdraw diagnostic test samples, and native to synthetic to native to bypass or shunt rather than the direct connection by anastomosis of native conduits where no synthetic or catheteric line is involved, side-entry connection jackets are not limited to blood vessels and differ from vascular connectors devised to allow direct and sutureless end to end anastomosis between blood vessels, for example (see, for example, Tozzi, P., Corno, A. F., and von Segesser, L. K. 2002. "Sutureless Coronary Anastomoses: Revival of Old Concepts," *European Journal of Cardiothoracic Surgery* 22(4): 565-570).

Because it allows flow in either direction, the bidirectionality of junctions provided by side-entry connection jackets can be used to withdraw blood upstream and return it downstream or the reverse between any takeoff or origin and outlet or insertion large enough in caliber to be jacketed and situated to allow access without significantly traumatizing dissection. For example, surface ports, whether adjacent or separated, implanted for the purpose of introducing medication can be connected to an extracorporeal pump to shunt blood between these in either direction over a range of volume transfer rates limited only by the calibers of the lines and speed of the pump. If the flow rate is high enough, the majority of the blood passing through the circulation will be shunted from the intake to the outlet. Shunting can be passive by direct connection of the shunt takeoff and outlet jackets, but shunting from a small to a large vessel can be assisted by interposing a pump between inlet and outlet jackets.

This is usually with the pump extracorporeal by connection between the surface ports, but with the implantation of a miniature inline pump, can be intracorporeal. Shunting may serve only to redirect flow to bypass the intervening sections of the circulatory system or to apply an apheretic or hemodialytic function extracorporeally at the shunt, the rate of this process then a determinant of a suitable shunt flow through rate. The shunting of blood flow between distant points has the potential to further expand the use of drugs otherwise contraindicated due to adverse drug-drug interactions. For example, the concentration of a drug can be reduced over a segment of the circulatory system whether occupied by an organ or gland, by shunting a significant fraction of the blood around the segment, organ, or gland.

When a nondiseased vessel for grafting is unavailable, the ability of the patient to withstand a longer procedure requiring that a suitable graft first be harvested, or the longer time under anesthesia would best be minimized, side-entry connection jackets allow the connection of lines from the body surface and interpositioning of segments to be joined with optimized luminal continuity, minimal leakage, and if a vessel, angularly configured for minimal endothelial damage and exposure to the blood of nonintimal surface area (Gummert, J. F., Opfermann, U., Jacobs, S., Walther, T., Kempfert, J., Mohr, F. W., and Falk, V. 2007. "Anastomotic Devices for Coronary Artery Bypass Grafting: Technological Options and Potential Pitfalls," *Computers in Biology and Medicine* 37(10):1384-1393). Because atherosclerosis is systemic, autologous vessels may be suspect in any event. Currently, when a native graft would be unusable, the condition of the patient militates against harvesting it, or a catheter must be joined to a native conduit, synthetic materials must be used.

For use in the vascular tree, however, synthetic conduits tend to encourage coagulation as to require anticoagulant serum levels in proportion to their narrowness. Until synthetic materials become available that will function more like the equivalent native conduits, the use of these materials will be limited to larger prostheses not requiring the use of anticoagulants at dangerous levels. At the same time, a homograft or allograft not harvested from an identical twin, or an isograft, requires immunosuppressive medication for life. If to a downstream point along the same ductus to bypass the intervening segment, or to another ductus as a shunt, the synthetic conduit or pipeline used will usually be made of polytetrafluoroethylene (Teflon®, E.I. duPont de Nemours and Company) or polyethylene terephthalate (Dacron®, Invista, Incorporated). While incipient and not filled with clot, a side-entry connection jacket can prevent continued enlargement and deliver medication.

Conduits of these materials in expanded or woven form (Stollwerck, P. L., Kozlowski, B., Sandmann, W., Grabitz, K., and Pfeiffer, T. 2011. "Long-term Dilatation of Polyester and Expanded Polytetrafluoroethylene Tube Grafts after Open Repair of Infrarenal Abdominal Aortic Aneurysms," *Journal of Vascular Surgery* 53(6):1506-1513; Walker, T. G., Kalva, S. P., Yeddula, K., Wicky, S., Kundu, S., Drescher, P., d'Othee, B. J., Rose, S. C., and Cardella, J. F.; 2010. "Clinical Practice Guidelines for Endovascular Abdominal Aortic Aneurysm Repair," *Journal of Vascular and Interventional Radiology* 21(11):1632-1655), chemically treated, and/or synthetic/native composite forms (see, for example, Naoum, J. J. and Arbid, E. J. 2012. "Bypass Surgery in Limb Salvage: Polytetrafluoroethylene Prosthetic Bypass," *Methodist Debakey Cardiovascular Journal* 8(4): 43-46; Khalil, A. A., Boyd, A., and Griffiths, G. 2012. "Interposition Vein Cuff for Infragenicular Prosthetic Bypass Graft," *Cochrane Database of Systematic Reviews* 9:CD007921; Bastounis, E., Georgopoulos, S., Maltezos, C., Alexiou, D., Chiotopoulos, D., and Bramis, J. 1999. "PTFE-vein Composite Grafts for Critical Limb Ischaemia: A Valuable Alternative to All-Autogenous Infrageniculate Reconstructions," *European Journal of Vascular and Endovascular Surgery* 18(2):127-132) all fall within the scope of the type catheters and prostheses to which the use of side-entry connection jackets applies.

In vascular applications where discontinuities of wall compliance results in adverse shear forces with consequent intimal hyperplasia, this material can be used in less stiff, expanded forms (Li, L., Terry, C. M., Shiu, Y. T., and Cheung, A. K. 2008. "Neointimal Hyperplasia Associated with Synthetic Hemodialysis Grafts," *Kidney International* 74(10):1247-1261; Loth, F., Jones, S. A., Zarins, C. K., Giddens, D. P., Nassar, R. F., Glagov, S., and Bassiouny, H. S. 2002. "Relative Contribution of Wall Shear Stress and Injury in Experimental Intimal Thickening at PTFE End-to-side Arterial Anastomoses," *Journal of Biomechanical Engineering* 124(1):44-51; Ojha, M. 1994. "Wall Shear Stress Temporal Gradient and Anastomotic Intimal Hyperplasia," *Circulation Research* 74(6):1227-1231; Bassiouny, H. S., White, S., Glagov, S., Choi, E., Giddens, D. P., and Zarins, C. K. 1992. "Anastomotic Intimal Hyperplasia: Mechanical Injury or Flow Induced," *Journal of Vascular Surgery* 15(4): 708-717).

The " . . . flow stagnation point along the arterial floor resulting in a region of low and oscillating shear where the second type of intimal thickening developed . . . " described by the last of the references cited may prove unavoidable with mechanical means as to necessitate the continued administration of hyperplasia-suppressive medication, such as sirolimus and everolimus. The delivery of such medication through a second side-entry connector, second jacket, or a water-jacket inlet used as a service channel should alleviate this problem as a potential cause of bypass failure. The targeted delivery of these drugs in what corresponds to a minute dose in systemic terms averts the many side effects these can produce.

A silicone coating has been reported to lessen hyperplasia (Lumsden, A. B., Chen, C., Coyle, K. A., Ofenloch, J. C., Wang, J. H., Yasuda, H. K., and Hanson, S. R. 1996. "Nonporous Silicone Polymer Coating of Expanded Polytetrafluoroethylene Grafts Reduces Graft Neointimal Hyperplasia in Dog and Baboon Models," *Journal of Vascular Surgery* 24(5):825-833). The targeting by direct delivery of an anticoagulant to tubing made of existing materials at concentrations that would not be circulated makes practicable the use of these materials as vascular conduits in narrower calibers. Metal tubing is thrombofilic (thrombophilic) and lacks pliancy, and expanded polymeric fabrics remain less compliant than the walls of native vessels.

While suture, clips, and staples (see, for example, Garitey, V., Rieu, R., and Alimi, Y. S. 2003. "Prostheto-prosthetic and Aorto-prosthetic Anastomosis Using Stents, Threads, Clips and Staples. In Vitro Comparative Study," (English abstract in Pubmed), *Journal des Maladies Vasculaires* [Journal of Vascular Diseases] 28(4):173-177), can pose problems of leaking and hyperplasia, direct native to native conduit surgical anastomoses with suture allow healing. However, means for achieving more natural tissue integration of prostheses made of expanded polymerics without hyperplastic hindrance, currently limited to larger caliber reconstructions (Appoo, J. J et al. 2013 and Kent, W. D. et al. 2012 cited above) where direct synthetic to native conduit anastomoses with suture can perpetuate the problems posed by suture (as well as destruction of the aortic body and the dynamic oxygenation response it provides), remains under investigation.

While the junction itself must be inconsistent in compliance, the use of side-entry connection junctions in lieu of surgical anastomoses avoids certain pitfalls associated with suture in general and as regards post-junction or post-anastomosis continuity of wall compliance (see, for example, Hollier, L. H. and Towne, J. B. (eds.) 2004. "Anastomic Aneurysms," in *Complications in Vascular Surgery, Chapter 6*, pages 155, 156 New York, N.Y.: Marcel Dekker; Tiwari, A., Cheng, K. S., Salacinski, H., Hamilton, G., and Seifalian, A. M. 2003. "Improving the Patency of Vascular Bypass Grafts: The Role of Suture Materials and Surgical Techniques on Reducing Anastomotic Compliance Mismatch," *European Journal of Vascular and Endovascular Surgery* 25(4):287-295; Ballyk, P. D., Walsh, C., Butany, J., and Ojha, M. 1998. "Compliance Mismatch May Promote Graft-artery Intimal Hyperplasia by Altering Suture-line Stresses," *Journal of Biomechanics* 31(3):229-237; Dobrin, P. B., Mirande, R., Kang, S., Dong, Q. S., and Mrkvicka, R. 1998. "Mechanics of End-to-end Artery-to-PTFE Graft Anastomoses," *Annals of Vascular Surgery* 12(4):317-323).

Blood vessels representing but one type of native conduit contemplated, numerous types of artificial blood vessels and other conduits are under development. Producing artificial blood vessels poses formidable complications (see, for example, Fink, H. 2009. *Artificial Blood Vessels: Studies on Endothelial Cell and Blood Interactions with Bacterial Cellulose*, Doctoral Dissertation, University of Gothenburg, Güteborg, Sweden). Existing smaller caliber synthetic lines such a those for replacement of diseased coronary arteries tend to induce coagulation and clog. Equally problematic, over time, implanted catheters used thus will be inevitably be exposed to contaminated blood and develop biofilm. A third source of catheter clogging is the agent itself, which intact or degraded, can congeal and/or coat the internal walls of the catheter. The accessory or service channel allows a diluent such as heparin for blood, an antibiotic for biofilm, or normal saline for insulin, for example, to be delivered into the catheter and terminal jacket or connector.

As shown in FIGS. 1 thru 6 and 16 thru 22, part number 11, smaller ductus side-entry jackets for the receipt of substances through smaller caliber tubing such as a catheter incorporate an accessory channel (service channel, sideline) that gives direct access to the line lumina and jackets for the direct delivery of anticoagulants and antimicrobials, for example, with little if any release into the general circulation. For this reason, ductus side-entry jackets make possible fully implanted disorder response systems. That is, the remotely controlled directly piped targeting of drugs and therewith, an implanted automatic ambulatory adaptive disorder response system, necessitates non-clogging, non-dislodging, and biofilm-free catheters and ductus connectors, as an accessory channel (service channel, sideline) with entry portal at the body surface makes possible.

To administer an anticoagulant systemically in order to prevent this renders the patient susceptible to problem bleeding; plainly, to restrict the anticoagulant to the conduit intended, especially with minimal if any entry into the wider circulation of little more by volume than a trace dose, would confer an element of safety. For narrower conduits to convey blood, the side-entry connection jackets described will be available for a prospective synthetic vascular material. Tending to become clogged due to coagulation, these and related materials have proven disappointing as replacements for smaller caliber vessels. That a synthetic coronary bypass catheter, for example, can have anticlotting drugs piped directly to it in a targeted way should overcome this limitation until better artificial vessels become available.

Coronary artery bypass surgery can thus be made practicable for patients without vessels suitable for use as grafts or unable to withstand conventional autologous transplantation without the risk of deferring bypass surgery until permanent and functionally sufficient artificial vessels become available. Placement of a side-entry jacket just upstream or close to the retrograde margin of a synthetic coronary bypass to release an anticoagulant and/or platelet blockade can enable the use of existing catheters as bypasses. The advantages and disadvantages of the physiological conduit are replaced with those of a synthetic conduit; however, a native graft can remain less predictable and so pose as great if not greater a risk of adverse complications than would an artificial bypass or replacement.

Magnetized jackets for encircling a conduit to trap or release drugs bound to magnetically susceptible particles, or impasse-jackets, piped to the surface allow drug replenishment when an unpiped impasse-jacket cannot be preloaded to deliver the volume of the drug or drugs required and continued delivery jacket would otherwise necessitate the use of reinvasive means in a clinic each time the drug had to be replenished. Side-entry connection jackets used to join conduits afford capabilities for communicating with the junction so formed not obtained with native to native anastomoses. Conventional suture when properly applied with or without a surgical adhesive or tissue cement is superior to nonabsorbable vascular connectors for joining natural vessels.

However, conduits joined with a side-entry jacket are not both native; rather, that jacketed is native, while that retained within the connector is synthetic or tissue-engineered but whether due to disease or trauma, lacking in a secure base to connect with suture. In contrast, known vascular connectors seek to join one natural vessel to another. Side-entry connection jackets are secure when placed, are not contingent for long-term dependability upon successful healing after the patient has been closed, and can be used to make end-to-side junctions between native and synthetic or tissue-engineered bypass conduits where an autologous graft is unobtainable or its secure healing not assured.

The establishment of a secure, nonleaking junction between synthetic and natural conduits is valuable when the use of an homologous graft in place thereof would impose a lifelong burden of having to take immunosuppressive drugs, and thus, to confront the constant vulnerability associated with being immunocompromised. Drug targeting by the means described should, however, substantially restrict the immunosuppression to the graft and tissue in contact with it, averting the need to immunocompromise the patient as a whole. A side-entry connection jacket allows direct delivery to an autologous graft of the immunosuppressive medication, and a magnetized collar, or impasse-jacket, as described in copending application Ser. No. 13/694,835 allows the medication to be drawn into and taken up within the lumen wall of the graft. The delivery side-entry connection jacket can itself incorporate a magnet, so that the medication is drawn into the lumen wall upon arrival, or a separate impasse jacket can be positioned downstream.

Moreover, provided a reversal agent is available, any residue that passes beyond the level for cutoff can be neutralized or counteracted. Whether the agent is delivered through another side-entry jacket or is released by an impasse jacket depends upon the amount of the agent to be made available. In most instances, the drug will have-been taken up within the graft, and if not brought down to zero residue or close enough to zero as has no medical significance, a reversal agent will not be needed. Attachment of the conduit to the connector is by pushing the conduit over the free end of the connector. To prevent disconnection of an elastic or rubbery catheter, the outer surface of the connector is provided with recurved prongs, and the joint additionally secured by pushing the end of the catheter over the connector; if necessary, banding or lashing it about.

Since the side-entry connector is synthetic and connected to a synthetic conduit and the angles and calibers of the side-entry connectors are selected to minimize shear stresses, shear stress at the entry to and exit from the bypass where the native and synthetic components meet is much reduced. When the angle at the insertion is favorable and the caliber of the lumen consistent, the synthetic line can be bonded to the internal surface of the side-entry connector by secure means to include plastic welding and adhesives. Sudden step-ups or step-downs in luminal diameter due to a ledge presented by the free edge of the inner tube is eliminated by using thin stock to make the side-entry connector and the synthetic line to be bonded to it, any ledge that could induce turbulent flow or damage blood cells progressively thinned or feathered out into the internal surface of the outer tube.

Deviations in luminal diameter along a service channel and the jacket used to join it to a native vessel have little if any medical significance; however, junctions that join synthetic to native or native to synthetic lines through which the bloodstream is redirected must, to the extent possible, be undisruptive of flow therethrough. That is, these should be uniform in internal or luminal diameter, properly angled, and without internal in- or outstepping ledges or protrusions that would cause turbulent flow (see, for example, Melih Guleren, K. 2013. "Numerical Flow Analysis of Coronary Arteries through Concentric and Eccentric Stenosed Geometries," *Journal of Biomechanics* 46(6):1043-1052; Tan, F. P., Wood, N. B., Tabor, G., and Xu, X. Y. 2011. "Comparison of LES of Steady Transitional Flow in an Idealized Stenosed Axisymmetric Artery Model with a RANS Transitional Model," *Journal of Biomechanical Engineering* 133(5): 051001; Avila, K., Moxey, D., de Lozar, A., Avila, M., Barkley, D., and Hof, B. 2011. "The Onset of Turbulence in Pipe Flow," *Science* 333(6039):192-196; Varghese, S. S. and Frankel, S. H. 2003. "Numerical Modeling of Pulsatile Turbulent Flow in Stenotic Vessels," *Journal of Biomechanical Engineering* 125(4):445-460).

By comparison, native vessels have adaptive responses that allow flow into the coronary arteries from the far larger aorta, for example, so long as the person is otherwise healthy; should hyperlipidemia enter the picture, however, and an unmistakable underlying, covert intolerance for the shear stresses produced will quickly reveal itself, making the coronary arteries among the most common sites for the inducement of atherosclerotic lesions. A synthetic tube is not susceptible to lesioning, but is to the formation of thrombus, clogging, and causing damage to blood cells, any 'adaptation' necessitating the use of drugs, here delivered through a service channel or channels.

This is true at both the origin, or takeoff; and the flow rejoining or insertion jackets. At the same time, the delivery of an anticoagulant through a fluid conduction or water-jacket inlet used as a followup service channel suppresses coagulation and the formation of thrombus within the bypass and the delivery of sirolimus (rapamycin), or everolimus (Cagiannos, C., Abul-Khoudoud, O. R., DeRijk, W., Shell, D. H. 4th, Jennings, L. K., Tolley, E. A., Handorf, C. R., and Fabian, T. C. 2005. "Rapamycin-coated Expanded Polytetrafluoroethylene Bypass Grafts Exhibit Decreased Anastomotic Neointimal Hyperplasia in a Porcine Model," *Journal of Vascular Surgery* 42(5):980-988), through the same or another jacket inlet reduces any propensity toward the formation of intimal hyperplasia.

Where disconnection would bode hemorrhaging or the leaking of septic contents, the synthetic line is made continuous with the side-entry connector, or no one means for establishing such connections between lines and side-entry connector are depended upon; rather, a cement is used with synthetic conduits, and prongs and/or banding, tying about, or lashing used to assure that the joint will be permanent. When a radiation shield of woven tungsten heavy alloy can be slid with little resistance over the underlying outer shell enclosing the magnet, a unitized or continuous line and jacket allow removal of the shield when no longer needed by disconnecting the surface port and pulling the shield out.

A woven sheath of fine tungsten wire in the number of layers required affords pliancy for routing the line for least discomfort due to any significant weight. Since a valve-plug would block the way to allow extraction of the tissue removed from the side of the ductus, a side-entry connection line continuous with the line connected to it cannot also have a valve inserted in the line prior to placement. The weave can tie in loops or eyelets at points along the periphery for passing suture to distribute any significant weight by apposition and suspension at several points.

The distal end of the woven sheath abuts upon the side-stem, or side-connector locking nut, which the proximal end abuts against the rear of the port membrane, front plate, or equivalent internal surface. Use of a compacted encapsulated tungsten bead shield eliminates the need for even this superficially invasive procedure, and to avoid deeper reentry, the jacket itself is bead shielded. The encapsulated tungsten beads in a disintegrable line shield must be bound together to yield pliancy as well as disintegrability. Since the shield ensheaths a synthetic conduit, the means for effecting disintegration are less stringent as to the temperature or chemicals that can be used.

Generally, connection to a catheter made of a nonelastic and slippery polymeric, such as polytetrafluoroethylene, polyethylene terephthalate, or these in expanded or woven form is by inserting the ends of the side-connector and the catheter in an elastic or rubbery sleeve that clings to the slippery material so that the edges of each meet flush. End to end connection of the side-entry connector or the distal end of a catheter connected to the side-connector to a native conduit is similar to that used to join the side-connector to a nonelastic catheter, in that an external elastic connecting sleeve is used. The side of the sleeve to go over the native conduit is lined with viscoelastic foam and if disconnection is a concern, has recurved prongs protruding through the foam from a surrounding shell to undercut the adventitia, fibrosa, or serosa.

Delineation of the procedure for placement of a side-entry connection jacket, lines, and port is deferred until the need for various components has been made clear. Ordinarily, line connections to a jacket are made before the jacket is positioned along the ductus or a jacket with integral connector and line used; since once positioned the lines must be connected to the side-entry connector to allow excision of the tissue plug, reversing these steps gains nothing. Connection to the lines of the jacket allows the correct length to port of each line to be determined with confidence and eliminates the difficulty of connecting the lines to the jacket when placed at an awkward angle in relation to the approach.

FIG. 5 shows a side-entry jacket extended in the antegrade direction with a magnet layer that incorporates a tungsten radiation shield for use as a piped impasse-jacket, while FIG. 6 shows such a jacket with shielding formulated to disintegrate once the radiation has been depleted. As with all side-entry jackets, those smaller for placement along thinner walled ductus, do not require a rotatable side-connector with lock bushing for use as a circle-cutter. Radiation shielding must completely envelop the jacket and the line leading to it. In larger jackets such as those for use along the digestive tract, the screw lock bushing used to tighten the side-connector in position after use as a circle-cutter is bonded to the surrounding layers so that this segment at the jacket end of the line rotates together as a unit knob.

As depicted in FIG. 16, the most basic installation includes two lines, the side-entry connector line, or mainline 13, and a fluid conduction or water-jacket line, sideline 11 as a subsidiary or accessory line.

Were the sideline only used after placement to deliver supplementary doses of an additional drug or drugs, an adjuvant, or a reversal agent, for example, these could usually be added to the medication delivered through the side-entry connector line and thus eliminated. However, the water-jacket line is essential during placement of the jacket along a blood vessel, for hemostasis and to assist in washing out the tissue plug, and during placement along another type ductus, to deliver immediate pressure irrigation, preventing septic contents from leaking into the surrounding cavity, which is important during installation in an emergency with no opportunity to purge the ductus.

After placement, the service channel remains available for the suppression of bleeding or leakage by pressure irrigation if the side-entry connection line is wanted emptied; the immediate delivery of a second medication that would otherwise not reach the ductus until it had passed entirely through the line with the medication already filling it; and to allow the aspiration of diagnostic test samples, for example. Immediately present in encircling and facing relation to the opening in the ductus, the delivery of any other medication is immediate rather than by travel through the side-entry connection line. The water-jacket line also aids in the quick evacuation of the side-entry connection line at the same time that it prevents a vacuum at the opening in the ductus. The water jacket inlet line, available after placement as a service channel, is relatively flexible as to orientation, and is led to the entry port at the body surface as best routed to avoid encroachment on neighboring tissue.

Vessels pose a greater risk of complications than do other type ductus which pose less of a leakage problem, are usually larger, and more accessible. Nonmanipulative or passive circle cutting (trephination) of the entry plug for a side-entry connection jacket along the vascular tree not only reduces the risk of trocar gouging, but makes it possible for junctions at convergences and divergences to be set at the proper angle, the elliptical cutting edge not rotatable, and allows the jacket to be placed with lines already attached, further reducing the need for manipulation. Connection is never by means internal to the lumen, or channel. A central desideratum pertaining to the connectors and related ductus jackets is elimination from the lumen: left clear, the normal physiology of the ductus is far less if at all affected, and should a transluminal intervention become necessary, the lumen will be unobstructed.

Importance of Vascular Connection with No Presence Inside the Native Lumen

That situation within the bloodstream of any implement, whether an indwelling catheter or a conventional intraluminal stent induces turbulent flow inviting an accumulation of thrombus, hence, the need for an anticoagulant is well established. By avoiding the placement of a foreign object in the lumen, extraluminal jackets as described herein, to include those incorporating a side-entry connector, avoid a central drawback of conventional means of intervention. While the side-entry jacket as a means for joining a synthetic to a native ductus pertains to all ductus, there are some distinctions in the application of this concept to vessels as opposed to other type ductus such as the gastrointestinal tract.

Placement of a side-entry jacket along a nonvascular ductus is by suction through the side connector, or side stem 6, while manually circle-cutting with the front razor edge of the side-entry connector, and usually, irrigation or flushing the opening created with water fed through the water-jacket rather than a tacky crushed hydrogel to prevent leaking. If clearance of the surrounding anatomy demands that the side-entry connector join at an angle, then water is still used although placement follows the vascular procedure, a more powerful vacuum needed to incise through the thicker ductus wall. In contrast, placement of a side-entry jacket along the vascular tree is by ductus wall plug removal using suction without manual circle-cutting and a tacky viscid crushed hydrogel rather than water fed through the water-jacket.

Whereas nonvascular side-entry connectors may be angled to avoid encroaching upon neighboring tissue, vascular side-entry connectors must be set at an angle to converge with the native lumen with minimal shear stress. When nonvascular side-entry jackets must be angled, placement is the same as it is for vascular jackets. The angular junction elliptical, the side-entry connector cannot be rotated as a circle-cutter (plug cutter, trephine), so that extraction of the tissue plug must be left to the sharp cutting edge of the side-entry connector and the sudden application of vacuum pressure, followed by the outward force of the blood and continued wash water, which restrains extravasation and reverses direction to flow out through the mainline or side-entry connection line driving the excised plug of tissue before it.

Lines with an elastic membrane slit remain filled, denying entry by luminal contents. The initial dose delivered in the form of a crushed tacky hydrogel then stops any bleeding as well as positions the drug for delivery when antegrade pumping through the mainline is begun. When the access port implanted at the body surface that leads through the connecting line and side-entry jacket into the native lumen is of the open type described below, valve-plugs and cabled devices such as a fiberoptic angioscope, intravascular ultrasound probe, or laser, for example, can be passed through to examine or treat the lumen. Slightly tacky hydrogel that adheres to the far end of a cabled viewing device is easily brushed away, even without first wetting the outer surface of the device with a lubricant such as ACS Microslide®, Medtronic Enhance®, Bard Pro/Pel® or Hydro/Pel®, Cordis SLX®, or Rotaglide®.

Once the tissue plug has been extracted, the line can be closed leaving it filled to deny entry into the line of luminal contents or extravasation prevented by inserting a valve-plug. A valve-plug if used is of the active type in open position. To minimize impeding the continued outflow of the crushed tacky hydrogel or liquid used to prevent extravasation and prevent a buildup of pressure that would force the gel or liquid into the opening made in the side of the ductus, the valve-plug is slowly advanced through the line outflow until positioned. To allow the operator to observe the position of the valve-plug through the endoscopic incision with an endoscope, the line must be transparent. Regardless of the type ductus to be jacketed, the endoscope also allows the use of a long handled pliars to loosen and tighten the lock bushing.

In conventional use, the diameter of the opening through the valve-plug can be equal to the internal diameter of the line proximally and distally to the valve-plug, because the valve itself can be larger in diameter overall; here, however, the valve must be placed inside and toward or at the distal end of the supply line catheter, so that no such latitude is available. When incorporation of a spring-loaded ball type valve-plug untenably reduces the luminal or internal diameter of a line that must be small in caliber to begin with, the terminal valve-plug consists of either a duplex disc or wafer style butterfly valve or an elastic polymer woven fabric or spandex like weave that will yield to column pressure over a threshold level which is fit over the adductal or ductus-adaxial end of the delivering line and side-entry connector to cover over the distal end, proximal portions of the slit membrane valve bonded to the outer surface of the line by means of a suitable adhesive. Of these types, that mechanical is shown in FIGS. 15 and 17 with a passive slit elastic membrane type shown in FIG. 25.

When the drug is administered by pump, the volumetric flow rate can be set at the pump; however, the valve can function as a throttle whether delivery is by infusion or injection and not limited to the bistable, that is, either fully open or fully closed. For use along the gastrointestinal tract, the entry of air into the ductus lumen is inconsequential, so that the valve alone can be used to check inflow through a side-entry or if sufficiently large in diameter, a service channel line. However, along the vascular tree whether the drug is fluid or in the form of a gel, any unoccupied segment of the line is filled with a nondrug or neutral gel or water or a liquid therapeutic to prevent the introduction of air into the vessel. In some instances, a nonwoven or continuous sheeting material or fabric of suitable elasticity with a slit or slits over the distal end can be used if a sock is continued back over and bonded to the outer surface of the delivery line.

Along the gastrointestinal tract where the shear forces of peristalsis might part the weave or slits of the elastic retaining valve to allow seepage into the delivery line, the antibiotic containing water can be preceded at the distal end by a column of stable but readily gel-converted or dissolved blocking material, such as a biocompatibly disintegrating aerogel or hydrogel (see, for example, Lutolf, M. P. 2009. "Biomaterials: Spotlight on Hydrogels," *Nature Materials* 8(6):451-453; Jeon; O., Bouhadir, K. H., Mansour, J. M, and Alsberg, E. 2009. "Photocrosslinked Alginate Hydrogels with Tunable Biodegradation Rates and Mechanical Properties," *Biomaterials* 30(14):2724-2734; Peppas, N. A. 2004. "Hydrogels," in Ratner, B. D., Hoffman, A. S., Schoen, F. J., and Lemons, J. E. (eds.), *Biomaterials Science: An Introduction to Materials in Medicine*, New York, N.Y.: Academic Press, pages 35-42) until needed.

Medication for delivery into a vessel should not be formulated as an aerogel when the accumulation of liberated gas can become sufficient to constitute a gas embolism. If offsetting factors override this generalization, then the dose is adjusted to compensate for the change in volume. Any jacket can be directly fed different drugs timed together or separately through a multiluminal catheter entered through a port at the body surface and connected to a single side-entry connector delivery from an automatic ambulatory pump with timing controls, for example. Jackets must be suited to the proposed site for placement, so that a jacket for placement about the ascending aorta to connect synthetic coronary artery bypass conduits, for example, must be positioned and configured to minimize encroachment upon the pulmonary trunk and superior vena cava.

It is therefore minimized in outer diameter, achieved primarily by reducing the thickness of the foam layer but not to a thickness less than that of the ductus wall as would not allow the tissue plug to be cut through entirely, compliance with intrinsic movement in the encircled ductus then more dependent upon the restorative force of the spring hinges. By contrast, a side-entry connection jacket for use with a long bone such as mentioned above in connection with Ewing sarcoma must adapt for a cross-sectional radial asymmetry of the bone, accomplished by using a jacket with a thicker foam lining. The variability in jacket proportions and configuration, to include the number of side-entry connectors, and the ability to variably apportion jackets to the aorta and its large derivatives is such that the highly variable anatomy is readily accommodated. The placement of the jacket and the positions, angles, and length of the connectors are taken into account.

Given that the input or body surface-to-ductus lines or catheters can be plural, can be each multiluminal, and that plural side-entry jackets can be positioned along a given ductus to receive plural catheters, it is apparent that the possibilities for ductus interconnection thus outstrip, much less satisfy, medical necessity. For example, dividing the outflow of a ductus between two other like type ductus through separate side-entry connectors of a single jacket has uses, but except for a line from the surface to a ductus, for either line to include more than a single lumen does not. The practicality of multiple or multiluminal lines from the body surface may be justified when each drug is best targeted to certain tissue and substantially kept out of the systemic circulation, as will be addressed, and/or the different drugs can be used only because the targeting sufficiently isolates the drugs from one another that adverse drug-drug interactions are avoided. The capability should stimulate implementation.

When the ductus is a blood vessel, an additional line from the surface is connected from a pump to a water-jacket in the side-entry connector which is used to irrigate the plug excision entry wound under pressure, restraining bleeding and assisting to remove the plug. Once the side-entry connector is placed, the water-jacket, not limited to the one entry line used to assist in vasculostomy, can be used to deliver drugs independently or to withdraw test samples from the lumen. Not only can multiple lines deliver fluids to and from the water-jacket, but any line connected to the connector or water jacket can connect subsidiary lines through side-entry connection jackets, for example.

Whether between native vessels or catheters connected by side-entry jackets, secondary or supporting surface-to-ductus connections can be used to maintain or monitor primary ductus-to-ductus junctions. For example, anticlotting drugs can be delivered directly to junctions between vessels prone to thrombose. Used to secure a synthetic bypass or one tissue-engineered where additional support is essential to form a secure junction, the jackets can be sent anticlotting medication, and if necessary, a bactericide, viricide, and/or anti-inflammatory drug, for example. To support organ transplant end to end anastomoses, the inlet and outlet stumps, or stubs, of donor organs are provided with side-entry jackets before harvesting, or excision.

This allows the direct delivery to the transplanted organ and anastomoses of anticlotting, antiatherosclerotic, and if homologous, immunosuppressive drugs to the substantial exclusion of the rest of the body. The use of synthetic or otherwise tissue-engineered catheters that require secure connection not obtainable with suture alone as bypass grafts joined by side-entry connection jackets may eliminate tissue reactions, reducing the need for medication to that anticlotting. Drug targeting seeks to limit medication to the tissue that requires it. Where achieved, drug targeting allows the circumscribed and focused application of a drug to a diseased part or lesion at a concentration that if circulated could prove injurious if not toxic to other tissue, result in unwanted side effects, and/or adverse interactions with drugs intended for other tissue.

The ability to target tissue not only eliminates systemic limitations on concentration and thus the efficacy of a drug where needed, but eliminates the waste of greatly diluting costly drugs throughout the circulatory system to achieve the dose intended for the target tissue when this concentration can even be permitted. There is no disease in which the circulatory system is uninvolved and local dysfunction not signaled to higher control centers, often initiating a cascade of dysfunction. Direct-to-lumen side-entry connection as described herein allows the targeting of drugs to a definable segment of a tubular anatomical structure, or ductus, and therewith, the tissue supplied from or drained through the segment.

Medication piped directly to a specific level along the tubular structure bypasses the lumen upstream and any tissue branches thereof supply, and is limited in extent by positioning complementary or counterpart means downstream for taking up and/or neutralizing the drug. A reversal agent can be delivered to the ending level through a second side-entry jacket, so that only the intervening segment is exposed to the drug. When bound to magnetically susceptible drug-carrier particles, a magnetized jacket, or impasse-jacket, encircling the ductus downstream at the level for uptake can be used to draw the medication into and through the lumen wall.

An especially potent or radioactive drug that could injure nontargeted tissue can be eliminated by placing a backup side-entry or impasse jacket to eliminate any of the drug not neutralized by the jacket positioned at the first ending level. The structures can be entering or departing vessels, ducts, or any other type of tubular channel along the circulatory, digestive, genitourinary system, or upper airway. Likewise, the omission of a segment specifically eliminates that segment and the tissue supplied by its branches from exposure to the drug. Drug targeting by such means can fulfill a central role in the treatment of disease. A side-entry connector is a small tube open to an anatomical lumen. The connector extends out from the lumen through the side of the side-entry connection jacket which attaches and positionally stabilizes the ductus side-entry connector without leakage while complying with the motility intrinsic in any tubular anatomical structure.

Accessed through a port implanted at the body surface, the connector serves as an entry point for connection of a drug delivery catheter, passageway for a diagnostic sensor (see, for example, Hu, W., Lu, Z., Liu, Y., Chen, T., Zhou, X., and Li, C. M. 2013. "A Portable Flow-through Fluorescent Immunoassay Lab-on-a-chip Device Using ZnO Nanorod-decorated Glass Capillaries," *Lab on a Chip* 13(9): 1797-1802; Patel, S., Park, H., Bonato, P., Chan, L., and Rodgers, M. 2012. "A Review of Wearable Sensors and Systems with Application in Rehabilitation," *Journal of Neuroengineering and Rehabilitation* 9:21; Pantelopoulos, A. and Bourbakis, N. G. 2010. "A survey on Wearable Sensor-based Systems for Health Monitoring and Prognosis," *Institute of Electrical and Electronics Engineers Transactions on Systems, Man, and Cybernetics, Part C: Applications and Reviews* 40(1):1-12; Yilmaz, T., Foster, R., and Hao Y. 2010. "Detecting Vital Signs with Wearable Wireless Sensors," *Sensors* (Basel) 10(12):10837-10862), or as a pathway for withdrawing diagnostic testing samples.

For ease of manipulation and because connection of the line will necessitate the clearing of neighboring tissue in any event, the ductus side-entry connector is made as long but no longer than necessary. Connection of the line after the jacket has been placed is expedited when the jacket has been marked with contrast to allow its quick location. To allow use of the side-entry connector as a manual circle-cutter to expedite plug removal or vasculotomy, side-entry connectors to or from relatively thick-walled conduits such as the gut are perpendicular (normal, at right angles) to the long axis of conduit and jacket. Right angular entry and exit side-connection are used when bloodstream confluence or splitting are uninvolved.

With blood vessels, the side-entry connector is attached to the jacket at an acute angle as most attenuates shear stress, so that when the delivery line is round in cross-section as affords optimal omnidirectional flexibility to expedite subcutaneous tunneling during placement, the sharp adluminal edge will be elliptical. In a vascular bypass or shunt application such as shown in FIGS. 21 and 22, the elliptical forward die-cutting edge of side-connector 6 prevents its rotation, and thus the creation of breaches at the apices about the cut that would allow exsanguination, or seepage, more problematic with anticoagulants.

However, the combination of the razor-sharp front edge of the side-entry connector, application of suction, outward force exerted by the blood pressure, and that of the water ejected from the fluid-conducting or water-jacket will usually excise and extract the tissue plug without the need for the operator to loosen a rotatable side-connector. If the plug 'hangs,' then it is pulled away by a hook ended guidewire passed through a proximal clean-out or inline port such as that shown in FIG. 30. A proximal clean-out or inline port is usually one armed and unidirectional. Highly calcified or hydroxyapatite-capped lesions are often self contained, stable, not vulnerable or prone to rupture, and best left alone.

The roughened surfaces on the outside surface of side-entry connector 6 and inside surface of locking bushing or collar 5 are therefore arranged vertically to detent connector 6 at the cutting forward (adaxial) and installed positions. In a side-entry connected line where a future need to extract a valve-plug to be described, such as to pass through a narrow endoscope or laser, can be ruled out with confidence, the valve-plug can be of the nominally permanent type and the internal surface of the side-entry connector configured to retain the valve-plug in place indefinitely. Thus, when the valve-plug is to remain in place, the internal surface of the side-entry connector also has small prongs or dentations on its internal surface distal or adaxial to the native lumen-adaxial front cutting edge of the side-connector.

These dentations assist in retaining a valve-plug as described below in position when the junction must be sealed, the means for doing so addressed toward the end of this specification. When the valve-plug is to recoverable noninvasively through the application of water pressure, the portion of its peripheral surround of rubbery material at its forward (adductal, ductus-adaxial) end is snipped away so that it will not lodge thus between the free (forward, ductus adaxial) edge of the water-jacket and the prongs. By contrast, the round conformation of side-connector 6 in a jacket intended for use along a thick-walled conduit such as the gut allows rotation as a trephine to assist in excising the enterostomy plug. A narrow connector for joining a catheter of fine caliber to a vessel to admit medication rather than to divert flow through a vessel can enter at right angles and be rotated as a trepan or circle-cutter so that the entry plug can be actively removed.

Side-entry connectors for use along the vascular tree are fixed in rotatory angular position by the elliptical shape at the adluminal end. The degrees and freedom of movement of the side-entry connector set by the locking collar or bushing at the base of the connector, reciprocating movability of the side-entry connector is limited to that little greater than the thickness of lumen wall essential for complete excision of the plug. When passage through the jacket is at an angle so that the cutting edge of the side-connector is elliptical and its use as a circle-cutter is denied, the greater thickness of the foam lining over that of the lumen wall allows the vacuum pressure to be increased effecting tissue plug excision. Turning now to FIG. 1 thru 7, 13 thru 15, 17 thru 19, 21 thru 23, 29, 31, and 32, viscoelastic polyurethane foam lining 3 is incorporated to protect small vessels and nerves that support the wall surrounding the ductus, is beneficial if not essential in almost every application.

To protect the small vessels and nerves, the foam envelops or wraps around these tiny structures investing them in a fairly static relationship relative to the compression and expansion in the jacket as a whole. The two sources of jacket compliance to expansion and contraction of the encircled conduit are spring-hinges 14 used to join the half-cylinders along meeting inner edges or joint 15 comprising the jacket and foam lining 3. In an artery, for example, a significant difference in excursion of the foam and the adluminal end of side-connector 6 as the pulse entered the retrograde or upstream end of the jacket and traveled to connector 6 and then moved out the antegrade end of the jacket would tend to wrench away and separate the adluminal end of side-connector 6 from the adventitia.

Except in a young patient treated for a chronic condition, the traveling swell of the pulse is probably never, and the bulge of peristalsis as seen in the esophagus, rarely, defined so sharply by an abrupt rise and fall as to make sudden jerking at the side-entry connector/foam interfaces of more than passing concern. The means described should not pose a problem of intimal hyperplasia that would lead to failure; however, where this contingency is a concern, a water-jacket inlet or service channel is available to deliver antihyperplastic drugs. Side-entry connection jackets used to deliver these drugs at surgical or conventionally sutured anastomoses use the side-entry connector for drug delivery. To allow for growth without the need for a second invasive procedure, a side-entry jacket or an impasse jacket for use in a child is increased in the width of foam lining to the extent the anatomy allows.

Protrusion of the adluminal end of the side-entry connector 6 into the lumen would disrupt laminar flow and its separation would result in bleeding into the foam about the connector. Separation of side-entry connector 6 from the surrounding foam is prevented by bonding the outer surface of connector 6 to surrounding foam lining 3. To avoid this contingency, the jacket is limited in length so that differences in excursion along its length as the traveling wave passes through are minimal and lining 3, usually viscoelastic polyurethane foam, is selected in a density, usually higher, as responds to pulsatile or peristaltic compression with a delay or lag time equal or greater than the intervals of the passing expansions and contractions.

Also to achieve a compressibility that best resists forces that would separate the adluminal end of connector 6 and the adventitia, foams of different densities and chemistry can be used or combined as concentric layers. Locking collar or bushing 5, outer shell 4, foam lining 3, and lumen wall 2 are substantially locked together and move as a unit, riding up and down with the jacket as it expands and contracts with the encircled conduit. As shown in FIG. 3, to the extent that the end caps of shell 4 cannot encroach upon the adventitia, shell 4 is made to wrap around the sides of foam lining 3. Magnet 8 must be isolated thus, foam lining 3 made thicker as necessary.

Side-entry connector 6 is fixed to shell 4 by locking collar or bushing 5, so that when shell 4 rests against the adventitia or fibrosa, the adluminal edge of side-entry connector 6 expands or contracts with the margins of the jacket. The shell substantially inflexible the shell then expands and contracts as a whole, so that connector 6 reciprocates together with the antegrade or upstream and retrograde or downstream ends of the jacket. The jacket ends are then made thicker and rounded as to be nonincisive. Extension lengthwise of the jacket to ensheath more than one passing pulsatile or muscular wave and variation in the foam density in coordination with this change in dimensions will also alter the forces seen by side-entry connector 6.

Side-entry connectors used to form bypass or shunt divergences and convergences where the angles for optimal flow characteristics through the junction are acute and which must function as plug circle-cutters or plug-cutters are provided with a locking collar or bushing having an internal bore complementary to the angle of the connector but no different in structure and function than the locking bushing of a side-connector at right angles. Thinner walls are drawn against and pass over the cutting edge, vacuum pressure, the blood pressure, and pressure washing through the water-jacket, removing the plug even should it briefly hang or adhere as a flap.

Vascular junctions are therefore angled to minimize shear stress and least interfere with streamline or laminar flow through the junction (see, for example, Loth, F., Fischer, P. F., and Bassiouny, H. S., 2008, "Blood Flow in End-to-Side Anastomosis," *Annual Review of Fluid Mechanics* 40:367-393; Freshwater, I. J., Morsi, Y. S., and Lai, T. 2006. "The Effect of Angle on Wall Shear Stresses in a LIMA to LAD Anastomosis: Numerical Modelling of Pulsatile Flow," *Proceedings of the Institution of Mechanical Engineers Part H Journal Engineering in Medicine* 220(7):743-757; Leva, C. and Engström, K. G. 2003. "Flow Resistance over Technical Anastomoses in Relation to the Angle of Distal End-to-side Connections," *Scandinavian Cardiovascular Journal* 37(3): 165-171).

To avoid the superfluous aspiration of blood as well as to preclude trocar type gouging or incision into the lumen wall opposite the point of entry, vessels are entered using the least functional vacuum pressure. The instant the wall is breached, the vacuum pressure is transferred from the wall to the blood, which is also expelled due to the blood pressure, so that the vacuum is then eliminated as a cutting force. These factors and the use of contrast dye as necessary substantially eliminate the risk of gouging injury. A hanging flap due to a lesion of unanticipated physical properties in the lumen wall at that point is forced out by the blood pressure and pulled off by the pressurized irrigation of the water-jacket, which can be increased in pressure briefly for the purpose.

Like other lumina introduced, the water jacket can be used to aspirate diagnostic samples. Side-entry connectors at junctions with vessels for connection to a port at the body surface to infuse drugs through a tiny ostium can join the vessel normal to or at right angles (perpendicularly). The fluid-conducting or water-jacket can be used to deliver or withdraw a liquid or gas. Since the fluid-conducting or water-jacket and the side-entry connector can be used as separate channels in either direction or to create a circuit, the water-jacket is not divided into independent channels. Use along the gut does not require a side-entry connector with a fluid-conducting or water-jacket at the time of placement.

However, the potential uses for the fluid-conducting or water-jacket for postoperative maintenance and to deal with sequelae makes including the fluid-conducting or water-jacket in every side-entry connection jacket prudent. Uniformity thus also serves to reduce the cost of production. The front edge of the ductus side-entry connector, then not needed as a manual circle or plug cutter or trephine (trepan) and punch, can be angled to avoid encroachment upon neighboring tissue, the opening or ostium into the lumen then likewise angled, hence, ellipsoidal with the edge honed in the long axial direction of the connector.

Ductus side-entry connection jackets may be magnetized and used in combination with impasse-jackets, which placed in encircling relation about a tubular anatomical structure, apply magnetic force to magnetically susceptible carrier particle-bound drugs in a passing ferrofluid (see, for example, Ruuge, E. K. and Rusetski, A. N. 1993. "Magnetic Fluids as Drug-carriers: Targeted Transport of Drugs by a Magnetic Field," *Journal of Magnetism and Magnetic Materials* 122(1-3):335-339), for example. Drugs indissolubly bound to the carrier are drawn against or through the lumen wall, whereas those dissolubly bound are released to pass downstream. A side-entry jacket can define the starting, and if necessary, another side-entry jacket or an impasse-jacket, the ending level, along a tubular anatomical structure, thus describing the intervening segment for receiving medication or that level wherein drugs dissolubly bound to the carrier particles will be released to pass downstream.

Side-entry connection jackets can also be used to deliver, and impasse jackets to set the point for releasing a reversal agent along the lumen. The distinction between side-entry and impasse jackets actually represents the extremes along a spectrum wherein many combine the features of either type in pure form as both piped to an entry port implanted at the body surface and magnetized. Any side-entry or impasse jacket that incorporates ferrous matter can be heated by placing the patient in a radiofrequency alternated magnetic field to affect the physiology of the ductus or the chemistry of the medication and/or other therapeutic substances employed. Side-entry connection can also be used to connect like or different type conduits internally without an entry port at the body surface.

For example, side-entry jackets allow off-pump, or beating-heart, coronary artery bypass using synthetic or tissue-engineered conduits, without the need to harvest and injure uninvolved tissue even when useable autologous conduit is available, as well as to reduce the durations of the overall procedure, anesthesia, and when employed, cardiopulmonary bypass, hypothermia, and cardioplegia, or circulatory arrest. Jacket placement can be on the ascending aorta with bypasses taken off from the same or different jackets, and an additional bypass taken. Once outside the polyether ether ketone or similar tough polymer jacket shell or casing, the angled connectors curve to avoid encroachment upon surrounding tissue. A common longitudinally narrow side-entry jacket with radially arranged side-entry connectors, or more than one jacket, can be placed about the ascending aorta, each synthetic coronary artery bypass catheter connected to side-entry jackets at both the origin and insertion, or destination.

Depending upon the anatomy, a second jacket is positioned on the aorta or the near brachiocephalic (innominate) trunk, for example. Optionally, to allow direct access to the side-entry connected junctions with drugs such as clopidogrel and/or aspirin in an artery or warfarin, heparin, or apixaban in a vein, a fluid-conduction or water-jacket inlet or a second side-entry connector to any such side-entry connection jacket can be led to a port implanted at the body surface. Such drugs not only suppress clotting but clogging due to ingrowth and hyperplasia (see, for example, Lin, P. H., Chen, C., Bush, R. L., Yao, Q., Lumsden, A. B., and Hanson, S. R. 2004. "Small-caliber Heparin-coated ePTFE Grafts Reduce Platelet Deposition and Neointimal Hyperplasia in a Baboon Model," *Journal of Vascular Surgery* 39(6):1322-1328).

An anatomically or extra-anatomically positioned aortofemoral or ileofemoral bypass to relieve the ischemia of advanced (Type 4) atherosclerotic aortoiliac obstructive, or aortoiliofemoral occlusive disease (see, for example, Koksal, C., Kocamaz, O., Aksoy, E., Cakalagaoglu, C., Kara, I., Yanartas, M., and Ay, Y. 2012. "Thoracic Aorto-bifemoral Bypass in Treatment of Juxtarenal Leriche Syndrome (Midterm Results)," *Annals of Vascular Surgery* 26(8):1085-1092; Capoccia, L., Riambau, V., and da Rocha, M. 2010. "Is Femorofemoral Crossover Bypass an Option in Claudication?," *Annals of Vascular Surgery* 24(6):828-832)," *Annals of Vascular Surgery* 26(8):1085-1092) in a patient without a suitable autologous graft is an example of an arterial application, while a crossover saphenous vein bypass graft (see, for example, Haas, G. E. 1989. "Saphenofemoral Vein Crossover Bypass Grafting in Iliofemoral Vein Obstruction," *Journal of the American Osteopathic Association* 89(4):511-518; Jorgensen, P. E., Lundsgaard, C., Jelnes, R., and Frimodt-Møller, C. 1986. "Iliofemoral Bypass Surgery for Lower Limb Ischaemia. A Follow-up of 62 Patients," *Annales chirurgiae et gynaecologiae* 75(3):155-159; Ehrenfeld, W. K., Levin, S. M., and Wylie, E. J. 1968. "Venous Crossover Bypass Grafts for Arterial Insufficiency," *Annals of Surgery* 167(2):287-291) is an example of a venous application.

These patients are normally elderly with distributed atherosclerotic disease that discourages the additional surgery required to harvest autografts likely to prove poor prospects for continued patency in any event (see, for example, Davidović, L. B., Lotina, S. I., Kostić, D. M., Cinara, I. I, Cvetković, S. D., and 5 others 1997. "Factors Determining Late Patency of Aortobifemoral Bypass Graft." [in Serbian; English abstract in Pubmed] *Srpski Arhiv za Celokupno Lekarstvo* 125(1-2):24-35; Davidović, L. B., Lotina, S. I., Kostić, D. M., Cinara, I. I, Cvetković, S. D., and 5 others 1997. "Dacron and Polytetrafluoroethylene Aorto-bifemoral Grafts," [in Serbian; English abstract in Pubmed] *Srpski Arhiv za Celokupno Lekarstvo* [Serbian Archives of All Medicine] 125(3-4):75-83). This combination of circumstances makes a viable alternative which allows the use of synthetic tubing with means for averting occlusion appropriate.

Side-entry connection jackets can serve as a useful adjunct whether native grafts or synthetic prostheses are to be targeted with drugs. When a polymeric synthetic is used as a bypass, targeting the bypass for an anticoagulant and/or other drugs using a bypass entry jacket to deliver the drug and if necessary, a bypass exit jacket to deliver a reversal agent or counteractant restrains a systemically small dose from circulating. Several fluid-conduction passages or water-jacket passages can be incorporated into a side-connector and used together to aspirate, or to deliver the same, or separately to deliver different drugs. The water-jacket in a side-entry jacket used to divert blood from a vessel is not made of metal as would promote the accumulation thrombus necessitating the use of an anticoagulant but rather polymeric.

Solid objects requiring a clear path such as diagnostic catheters or sensors are threaded or 'snaked' through the conduit to the junction through the side-connector from a port implanted at the body surface. This allows the use of a fiberoptic angioscope to examine the junction and view the delivery of the drug through the fluid-conduction or water-jacket, for example. Provided the angle of the side-entry connector to the jacket is acute or steep enough, the same path can be used to pass through a rotational thrombectomizer or a rotational or linear atherectomizer, for example, significantly expediting the possibilities for preventing, diagnosing, and treating any later acute event.

Using fluid-conduction or water-jackets, accessory fluid inlets and outlets can be led from a port at the body surface to the native-to-synthetic and synthetic-to-native junctions. The targeted administration of medication to each of several systemically unrelated side-entry junctions will usually be different as to drugs used and scheduling. Since the catheter used as a bypass or shunt is synthetic, delivery at the junction of origin will treat the junction itself and the blood flowing past the junction, but the lumen wall will only once the destination junction is crossed. That anticlotting or antibiotic medication, for example, will be of benefit throughout the course to include that synthetic is clear.

However, because not only thrombus but atherosclerotic plaque tends to develop at sites of increased shear stress such as branches, the anti-inflammatory or pleiotropic effects of statins should be exploited by delivering the statin to the junction of origin, not that of insertion however distant, if not upstream, atherosclerosis systemic as to recommend a lesser background dose in the systemic circulation at all times. A downstream side-entry jacket or side-entry impasse jacket having its fuid-conduction or water-jacket inlets connected to a port at the body surface, or if needed only briefly, an unpiped impasse-jacket, can be used to neutralize any residue of a drug and thus prevent it from further circulation.

This allows the use over a circumscribed segment of a statin at a dose that if circulated would induce myopathy. Incorporating one or more fluid-conduction or water-jacket inlets on each side-entry connector affords flexibility in allowing different joints and segments or stretches to be medicated differently as well as alike as the need arises. Bypass grafts using harvested vessels anastomosed with suture are preferable to the use of synthetic materials. Where such a graft would benefit from the direct delivery of medication, means set forth herein can prove of value in a subsidiary, supportive role. A side-entry connection jacket receiving a catheter from a port at the body surface placed to precede a bypass graft can deliver drugs for uptake within the bypass.

Any residue to be prevented from passing downstream can be neutralized by a reversal agent delivered through a downstream line or by release from an impasse jacket just past the bypass outlet or insertion anastomosis. Targeted delivery of drugs in higher than circulated concentration is intended to suppress restenosis, shrinkage, sclerosis, and the formation of thrombus. Autologous vascular grafts used in the arterial tree are targeted primarily with a platelet blockade and a statin, whereas those used in the venous tree are primarily targeted with an anticoagulant such as warfarin, preference given to those for which an effective reversal agent is available. The ability to target anticoagulants is of value, because the use of these drugs must often precede the need for surgery, and the risk of problem bleeding is also alleviated should the patient suffer accidental trauma.

The ability to substantially restrict medication, such as immunosuppressants and antibiotics, to an homologous graft considerably reduces the risk of systemic complications, to include adverse drug-drug interactions and side effects. When the drug acts upon contact, the side-entry connection jacket can be placed on the vascular and functional inlet stumps of transplant organs when harvested and before placement, or insertion of the graft; when the drug requires some lead before acting, the jacket is placed upstream in the recipient, delivery through the same jacket as that used to make the transplant junction then downstream thereof. In a parallel manner, an outlet jacket needed to delivery a reversal agent can enter the transplant exit jacket, or if lead time is required, downstream thereto.

Because the overall dose is small compared to dosing for systemic circulation, targeting substantially eliminates the advantage of warfarin over direct Factor Xa inhibitors such as apixaban (Eliquis®, Bristol-Myers Squibb/Pfizer), dabigatran etexilate (Pradaxa®, Boehringer Ingelheim), and rivaroxaban (Xarelto®, Bayer HealthCare AG) as reversible with vitamin K. Reversal agents for Factor Xa inhibitors such as PRT4445 (Portola Pharmaceuticals) (see, for example, Lu, G., DeGuzman, F. R., Hollenbach, S. J., Karbarz, M. J., Abe, K., and 7 others 2013. "A Specific Antidote for Reversal of Anticoagulation by Direct and Indirect Inhibitors of Coagulation Factor Xa," *Nature Medicine* 19(4):446-451; Rupprecht, H. J. and Blank, R. 2010. "Clinical Pharmacology of Direct and Indirect Factor Xa Inhibitors," *Drugs* 70(16):2153-70) for systemic dosing are currently undergoing trials.

In the unlikely circumstance that a drug would have to be limited to a defined segment of a native conduit whether intrinsic or used as a bypass or shunt, a second jacket at the cutoff level can be used to remove any residue from the circulation. Once a reversal agent is available, conversion from the oral form for the Factor Xa inhibitor and its reversal agent should pose little difficulty. Targeting in different situations can spare numerous complications such as muscle impairment, problem bleeding, and the risks associated with immunocompromising the patient as a whole. An unwanted residue for which a reversal agent is unavailable can be prevented from further passage by bonding it to magnetically susceptible micro or nanoparticles, if not directly, then to an affinitive substance that will seek it out.

Provided the drug works locally and need not be processed by the liver, a bypass graft to divert or shunt around a site of chronic venous insufficiency, such as a crossover saphenous vein bypass (see, for example, Greenfield, L. J. 1997. "Chronic Venous Insufficiency," in Greenfield, L. J., Mulholland, M. W., Oldham, K. T.; Zelenock, G. B., and Lillemoe, K. D. (eds.), *Surgery: Scientific Principles and Practice*, page 1965) to avert and compensate for affected side deep vein thrombosis, for example, may similarly be targeted for medication. A side-entry jacket upstream to, or one with two side-entry connectors at the inlet connection to a synthetic venous bypass can target an anticoagulant such as apixaban to the bypass, thus overcoming the thrombotic propensity of a catheteric (synthetic, prosthetic) venous bypass that is the primary deterrent to such application. The prevention of subarachnoid hemorrhage alone makes this approach advantageous.

b. Apheresis and Hemodialysis, Stationary With or Without an Attendant, or Carryable, or Implanted Magnetic While implanted magnetic separation apheresis or hemodialysis on a continuous bases can be implemented with permanent magnets, the use of electromagnets affords on-off, intermittent, and field strength variability that affords greater versatility. Field strength variability allows the field strength to be periodically reduced so that the accumulated debris is sweep away at the attracting pole without the need to increase the flush-line flow rate, thus conserving power. For this reason, references to magnets in the specification and in the drawing figures are to electromagnets; this should not, however, be construed to exclude the use of permanent magnets in every case. With magnetic separation apheresis and dialysis, only the target analyte or analytes are removed, so that fluid replacement is not necessary to avoid hypovolemia.

Intracorporeal Ambulatory Magnetic Separation Leukapheresis

Most disorders either pertain to or have representation in the blood as to call for the extraction of endogenous or intrinsic substances dispersed throughout the bloodstream. Where the blood must be kept from sludging—leukocytes in leukostasis, or erythrocytes in polycythemia vera—to prevent obstruction of the microvasculature that if not stopped would lead to multiple organ failure, blindness, and eventually death, the rate of removal must be high (see, for example, Matheson, N. A. 1969. "The Microcirculation in Shock," *Postgraduate Medical Journal* 45(526):530-533). The value in more intensive, that is, protracted and/or frequent hemodialysis using conventional means of separation is documented below.

In many if not most neurological (see, for example, Loschiavo, C., Grecò, M., Polo, A., and Del Colle, R. 2015. "The Use of Therapeutic Apheresis in Neurological Diseases and Comparison between Plasma Exchange and Immunoadsorption)," (in Italian with English abstract at Pubmed), *Giornale Italiano di Nefrologia* 32(1). pii: gin/32.1.10; Kaya, E., Keklik, M., Sencan, M., Yilmaz, M., Keskin, A., and 10 others 2013. "Therapeutic Plasma Exchange in Patients with Neurological Diseases: Multicenter Retrospective Analysis," *Transfusion and Apheresis Science* 48(3): 349-352; Chhibber, V. and Weinstein, R. 2012. "Evidence-based Review of Therapeutic Plasma Exchange in Neurological Disorders," *Seminars in Dialysis* 25(2):132-139; Gwathmey, K., Balogun, R. A., and Burns, T. 2011. "Neurologic Indications for Therapeutic Plasma Exchange: An Update;" *Journal of Clinical Apheresis* 26(5):261-268) disorders, the need to remove substance is exigent, making the need for quick removal the usual case.

The same may be said of:

Autoimmune neurological disease such as "myasthenia gravis, Guillain-Barré syndrome, multiple sclerosis, and Reye's syndrome" (Mascarella, J. J. and Hudson, D. C. 1991. "Dysimmune Neurologic Disorders," *American Association of Critical Care Nurses Clinical Issues in Critical Care Nursing* 2(4):675-684) (see also, for example, Stork, L., Ellenberger, D., Beißbarth, T., Friede, T., Lucchinetti, C. F., Brück, W., and Metz, I. 2018. "Differences in the Reponses to Apheresis Therapy of Patients with 3 Histopathologically Classified Immunopathological Patterns of Multiple Sclerosis," *Journal of the American Medical Association Neurology* 75(4):428-435; Ehler, J., Koball, S., Sauer, M., Mitzner, S., Hickstein, H., Benecke, R., and Zettl, U. K. 2015. "Response to Therapeutic Plasma Exchange as a Rescue Treatment in Clinically Isolated Syndromes and Acute Worsening. of Multiple Sclerosis: A Retrospective Analysis of 90 Patients," *Public Library of Science One* 10(8):e0134583), Autoimmune disease that directly targets or secondarily affects the nervous system (see, for example, Soyuöz, A., Karadağ, Ö., Karaağaç, T., Kihç, L., Bilgen, Ş. A., and Özcebe, O. İ. 2018. "Therapeutic Plasma Exchange for Refractory SLE [systemic lupus erythematosis]: A Comparison of Outcomes between Different Sub-phenotypes," *European Journal of Rheumatology* 5(1):32-36; Rypulak, E., Borys, M., Piwowarczyk, P., Fijalkowska, M., Potrec, B., and 6 others 2016. "Successful Treatment of Anti-NMDA [N-methyl-d-aspartate] Receptor Encephalitis with a Prompt Ovarian Tumour Removal and Prolonged Course of Plasmapheresis: A Case Report," *Molecular and Clinical Oncology* 5(6):845-849; Khair, A. M. 2016. "Utility of Plasmapheresis in Autoimmune-mediated Encephalopathy in Children: Potentials and Challenges," *Neurological Research International* 2016:7685807; Magro-Checa, C., Zirkzee, E. J., Huizinga, T. W., and Steup-Beekman, G. M. 2016. "Management of Neuropsychiatric Systemic Lupus Erythematosus: Current Approaches and Future Perspectives," *Drugs* 76(4):459-483; Ehrlich S1, Fassbender C M, Blaes C, Finke C, Günther A, and 12 others 2013. "Therapeutic Apheresis for Autoimmune Encephalitis: A Nationwide Data Collection," (in German with English abstract at Pubmed), *Nervenarzt* 84(4):498-507; Mazzi G1, Roia D D, Cruciatti B, Matá. S, Catapano R. 2008. "Plasma Exchange for Anti GAD [glutamic acid decarboxylase] Associated Non Paraneoplastic Limbic Encephalitis," *Transfusion and Apheresis Science* 39(3):229-233), and Autoimmune disease generally (see, for example, Sharwood, E. F., Hughes, I. P., Pretorius, C. J., Trnka, P., Peake, J., and Huynh, T. 2018. "Therapeutic Plasma Exchange Normalizes Insulin-mediated Response in a Child with Type 1 Diabetes and Insulin Autoimmune Syndrome," *Pediatric Diabetes* 19(1):171-179; Garla, V., Kovvuru, K., Ahuja, S., Palabindala, V., Malhotra, B., and Abdul Salim, S. 2018. "Severe Hyperthyroidism Complicated by Agranulocytosis Treated with Therapeutic Plasma Exchange: Case Report and Review of the Literature," *Case Reports in Endocrinology* 2018:4135940; Kobayashi, T., Matsuoka, K., Yokoyama, Y., Nakamura, T., Ino, T., 5 others 2018. "A Multicenter, Retrospective, Observational Study of the Clinical Outcomes and Risk Factors for Relapse of Ulcerative Colitis at 1 Year after Leukocytapheresis," *Journal of Gastroenterology* 53(3):387-396; Iizuka, M., Etou, T., Kumagai, M., Matsuoka, A., Numata, Y., and Sagara, S. 2017. "Long-interval Cytapheresis as a Novel Therapeutic Strategy Leading to Dosage Reduction and Discontinuation of Steroids in Steroid-dependent Ulcerative Colitis," *Internal Medicine* (Tokyo, Japan) 56(20):2705-2710; Candoni, A., De Marchi, F., Vescini, F., Mauro, S., Rinaldi, C., and 4 others 2017. "Graves' Disease Thyrotoxicosis and Propylthiouracil Related Agranulocytosis Successfully Treated with Therapeutic Plasma Exchange and G-CSF [granulocyte—colony-stimulating factor] followed by Total Thyroidectomy," *Mediterranean Journal of Hematology and Infectious Diseases* 9(1):e2017058; Bambauer, R., Latza, R., Burgard, D., and Schiel, R. 2017. "Therapeutic Apheresis in Immunologic Renal and Neurological Diseases," *Therapeutic Apheresis and Dialysis* 21(1):6-21; Imperiali, G., Amato, A., Terpin, M. M., Beverina, I., Bortoli, A., Devani, M., and Viganò, C. 2017. "Granulocyte-Monocyte Apheresis in Steroid-dependent, Azathioprine-intolerant/Resistant Moderate Ulcerative Colitis: A Prospective Multicenter Study," *Gastroenterology Research and Practice* 2017:9728324; Benjegerdes, K. E., Hyde, K., Kivelevitch, D., and Mansouri, B. 2016. "Pustular Psoriasis: Pathophysiology and Current Treatment Perspectives," *Psoriasis* (Auckland, New Zealand) 6:131-144; Bambauer, R., Latza, R., Burgard, D., and Schiel, R. 2016. "Therapeutic Apheresis in Hematologic, Autoimmune, and Dermatologic Diseases with Immunologic Origin," *Therapeutic Apheresis and Dialysis* 20(5): 433-452; Takayama, T., Okamoto, S., Hisamatsu, T., Naganuma, M., Matsuoka, K., and 4 others 2015. "Computer-aided Prediction of Long-term Prognosis of Patients with Ulcerative Colitis after Cytoapheresis Therapy," *Public Library of Science One* 10(6):e0131197; Saniabadi, A. R., Tanaka, T., Ohmori, T., Sawada, K., Yamamoto, T., and Hanai, H. 2014. "Treating Inflammatory Bowel Disease by Adsorptive Leucocytapheresis: A Desire to Treat without Drugs," *World Journal of Gastroenterology* 20(29):9699-9715; Olsen, H. H., Muratov, V., Cederlund, K., Lundahl, J., Eklund, A., and Grunewald, J. 2014. "Therapeutic Granulocyte and Monocyte Apheresis (GMA) for Treatment Refractory Sarcoidosis: A Pilot Study of Clinical Effects and Possible Mechanisms of Action," *Clinical and Experimental Immunology* 177(3):712-719; Bambauer, R., Latza, R., Bambauer, C., Burgard, D., and Schiel, R. 2013. "Therapeutic Apheresis in Autoimmune Diseases," *Open Access Rheumatology: Research and Reviews* 5:93-103; Takayama, T., Kanai, T., Matsuoka, K., Okamoto, S., Sujino, T., and 6 others 2013. "Long-term Prognosis of Patients with Ulcerative Colitis Treated with Cytapheresis Therapy," *Journal of Crohn's and Colitis* 7(2):e49-e54; Suzuki, A., Haruna, K., Mizuno, Y., Kuwae, Y., Ono, Y., and 7 others 2012. "Successful Treatment of Three Cases of Generalized Pustular Psoriasis with Granulocyte and Monocyte Adsorption Apheresis," *Therapeutic Apheresis and Dialysis* 16(5):445-448; Itagaki, M., Saruta, M., Iinuma, T., Arihiro, S., Kato, T., and Tajiri, H. 2012. "Infliximab- and Immunosuppressant-resistant Crohn's Disease Successfully Treated with Adsorptive Granulocyte Apheresis Combined with Prednisolone," *Case Reports in Gastroenterology* 6(1):118-123; Sanchez, A. P. and Ward, D. M. 2012. "Therapeutic Apheresis for Renal Disorders," *Seminars in Dialysis* 25(2):119-131; Fujisawa, T., Murase, K., Okumura, Y., Kanoh, H., Doi, T., and 3 others 2011. "Generalized Pustular. Psoriasis Successfully Treated with Granulocyte and Monocyte Adsorption Apheresis," *Therapeutic Apheresis and Dialysis* 15(4):374-378; Shukuya, R., Hasegawa, T., Niwa, Y., Okuma, K., and Ikeda, S. 2011. "Granulocyte and Monocyte Adsorption Apheresis for Generalized Pustular Psoriasis," *Journal of Dermatology* 38(12):1130-1134; Lew, W. H., Chang, C. J., Lin, J. D., Cheng, C. Y., Chen, Y. K., and Lee, T. 2011. "Successful Preoperative Treatment of a Graves' Disease Patient with Agranulocytosis and Hemophagocytosis Using Double Filtration Plasmapheresis," *Journal of Clinical Apheresis* 26(3):159-161; Ibargoyen-Roteta, N., Gutiérrez-Ibarluzea, I., Rico-Iturrioz, R., López-Argumedo, M., Reviriego-Rodrigo, E., Cabriada-Nuño, J. L., and Schünemann, H. J. 2010. "The GRADE [Grading of Recommendations, Assessment, Development and Evaluation] Approach for Assessing New Technologies as Applied to Apheresis Devices in Ulcerative Colitis," *Implementation Science* 5:48; Pineda, A. A. 2006. "Developments in the Apheresis Procedure for the Treatment of Inflammatory Bowel Disease," *Inflammatory Bowel Diseases* 12 Supplement 1:S10-S14; Roth, S. H. 2006. "Role of Apheresis in Rheumatoid Arthritis," *Drugs* 66(15):1903-1908; Sanmartí, R., Marsal, S., Valverde, J., Casado, E., Lafuente, R., and 5 others 2005. "Adsorptive Granulocyte/Monocyte Apheresis for the Treatment of Refractory Rheumatoid Arthritis: An Open Pilot Multicentre Trial," *Rheumatology* (Oxford, England) September; 44(9):1140-1144; Nydegger, U. E. and Sturzenegger, T. 2001. "Treatment of Autoimmune Disease: Synergy between Plasma Exchange and Intravenous Immunoglobulins," *Therapeutic Apheresis* 5(3): 186-192; Koo, A. P. 2000. "Therapeutic Apheresis in Autoimmune and Rheumatic Diseases," *Journal of Clinical Apheresis* 15(1-2):18-27).

Responsive thereto, ambulatory magnetic separation apheresis (or dialysis) can proceed continuously, and rather than to require the removal of blood into an extracorporeal machine and then return it to the bloodstream, ambulatory magnetic separation apheresis and dialysis extract the objectionable analyte or analytes directly from the bloodstream. That removal is continuous reduces if not eliminates the likelihood of an acute relapse (see, for example, Ehler, J., Blechinger, S., Rommer, P. S., Koball, S., Mitzner, S., and 4 others 2017. "Treatment of the First Acute Relapse Following Therapeutic Plasma Exchange in Formerly Glucocorticosteroid-unresponsive Multiple Sclerosis Patients—A Multicenter Study to Evaluate Glucocorticosteroid Responsiveness," *International Journal of Molecular Sciences* 18(8). pii: E1749).

The implant prosthetic disorder control system able to administer systemic corticosteroids, adrenocorticotropic hormone automatically, as well as perform plasmapheresis, or plasma exchange on a continual basis, relapse is a characteristic of multiple sclerosis best eliminated (see, for example, Berkovich, R. R. 2016. "Acute Multiple Sclerosis Relapse," Continuum (Minneapolis, Minn.) 2016 22(3):799-814; Kalincik, T. 2015. "Multiple Sclerosis Relapses: Epidemiology, Outcomes and Management. A Systematic Review," *Neuroepidemiology* 44(4):199-214; Kalincik, T., Buzzard, K., Jokubaitis, V., Trojano, M., Duquette, P., and 43 others 2014. "Risk of Relapse Phenotype Recurrence in Multiple Sclerosis," Multiple Sclerosis (Houndmills, Basingstoke, England) 20(11):1511-1522).

By contrast, conventional blood removal methods usually require the patient to appear at a clinic several days a week for several hours, which circumstance in itself is predisposing to avoiding the use of such methods when possible, and compliance failure, and this consideration trumps the relatively nugatory distinctions in treatment time using different conventional means (see, for example, Hafer, C., Golla, P., Gericke, M., Eden, G., Beutel, G., and 4 others 2016. "Membrane Versus Centrifuge-based Therapeutic Plasma Exchange: A Randomized Prospective Crossover Study," *International Urology and Nephrology* 48(1):133-138; Kes, P., Janssens, M. E., Bašić-Jukić, N., and Kljak, M. 2016. "A Randomized Crossover Study Comparing Membrane and Centrifugal Therapeutic Plasma Exchange Procedures," *Transfusion* 56(12):3065-3072).

Provided means for bonding the superparamagnetic nanoparticle or microparticle drug-carrier to the target analyte are available, magnetic separation, which comprehends chemical properties, exceeds forms of separation based upon size and mass. Continuous analyte delivery and extraction for ambulatory apheresis is accomplished by means of a special higher volume analyte extraction jacket and a powerful magnet held in position at the body surface by a harness, such a jacket and if necessary, a suspension harness created by passing suture through suture loops or eyelets integral with the jacket or jackets for fixation to neighboring tissue at numerous points to distribute and balance the weight thereof.

A relatively static means for extracting the targeted substance or cells without filtration or centrifugation, for example, significantly increases the potential for miniaturization essential for embodiment in an ambulatory system. In some instances, the targeting agent can be synthetic (see, for example, Zhang, M., He, X., Chen, L., and Zhang, Y. 2011. "Preparation and Characterization of Iminodiacetic Acid-functionalized Magnetic Nanoparticles and its Selective Removal of Bovine Hemoglobin," *Nanotechnology* 22(6):065705; Zhang, M., Cheng, D., He, X., Chen, L., and Zhang, Y. 2010. "Magnetic Silica-coated Sub-microspheres with Immobilized Metal Ions for the Selective Removal of Bovine Hemoglobin from Bovine Blood," *Chemistry Asian Journal* 5(6): 1332-1340; Thomas, L., Mansour, V., Jain, R., Kulcinski, D., Loefler, K., Carter, C., and Hardwick, A. 1995. "Use of the CS-3000 Plus to Prepare Apheresed Blood Cells for Immunomagnetic Positive Cell Selection," *Journal of Hematotherapy* 4(4):315-321).

While technologically distinct from the separation apparatus to be described, which uses ductus side-entry jackets to make possible the intracorporeal removal of selected blood constituents in an unattended ambulatory patient, the concepts of extracorporeal magnetic hemoextraction, magnetic-activated cell sorting (MACS® Miltenyi Biotec, Bergisch Gladbach, Germany) have precedence (see, for example, Huang, L., Bian, S., Cheng, Y., Shi, G., Liu, P., Ye, X., Wang, W. 2017. "Microfluidics Cell Sample Preparation for Analysis: Advances in Efficient Cell Enrichment and Precise Single Cell Capture," *Biomicrofluidics* 11(1):011501; Zhao, W., Cheng, R., Jenkins, B. D., Zhu, T., Okonkwo, N. E., and 6 others 2017. "Label-free Ferrohydrodynamic Cell Separation of Circulating Tumor Cells," *Lab on a Chip* 17(18): 3097-3111; Rampini, S., Li, P., and Lee, G. U. 2016. "Micromagnet Arrays Enable Precise Manipulation of Individual Biological Analyte-superparamagnetic Bead Complexes for Separation and Sensing," *Lab on a Chip* 16(19): 3645-3663; Wu, W. T., Martin, A. B., Gandini, A., Aubry, N., Massoudi, M., and Antaki, J. F. 2016. "Design of Microfluidic Channels for Magnetic Separation of Malaria-infected Red Blood Cells," *Microfluidics and Nanofluidics* 20(2). pii: 41; Murlidhar, V., Rivera-Báez, L., and Nagrath, S. 2016. "Affinity Versus Label-free Isolation of Circulating Tumor Cells: Who Wins?," *Small* (Weinheim an der Bergstrasse, Germany) 12(33):4450-4463; Rampini, S., Kilinc, D., Li, P., Monteil, C., Gandhi, D., and Lee, G. U. 2015. "Micromagnet Arrays for On-chip Focusing, Switching, and Separation of Superparamagnetic Beads and Single Cells," *Lab on a Chip* 15(16):3370-3379; Hejazian, M., Li, W., and Nguyen, N. T. 2015. "Lab on a Chip for Continuous-flow Magnetic Cell Separation," *Lab on a Chip* 15(4):959-970; B. D., Murthy, S. K., and Lewis, L. H. 2015. "Fundamentals and Application of Magnetic Particles in Cell Isolation and Enrichment: A Review," *Reports on Progress in Physics* 78(1):016601; Kim, J., Massoudi, M., Antaki, J. F., and Gandini, A. 2012. "Removal of Malaria-infected Red Blood Cells Using Magnetic Cell Separators: A Computational Study," *Applied Mathematics and Computation* 218(12): 6841-6850).

Combined with chemotherapy, the ability to selectively bind cells or Auer rods of an acute myeloid leukemia, or of polycythemia vera for extraction from the bloodstream and replace these with cells or stem cells not so affected using a portable or ambulatory system rather than intermittently through use of a stationary leukaphersis machine, as addressed below in the section entitled Apheresis, may well improve the treatment of the myeloid neoplasias. High volume cellular removal as in a leukemia or polycythemia vera is by permanent or electromagnetic chain extraction jackets as shown in FIGS. 13 thru 15 which incorporate a magnet, shown as part number 8 in FIGS. 4 thru 6 or electromagnets shown as part numbers 74, 75, and 84 in FIGS. 11 and 12.

Magnetic leukapheresis, or leukocytapheresis is intended to supplement, not to replace or reduce the use of primary chemotherapeutic medical and radiation treatment to decrease the production of leukocytes, especially where leukostasis, or symptomatic hyperleukocytosis, poses the risk of life-threatening occlusion of the microvasculature (see, for example, Makroo, R. N., Kakkar, B., Chowdhry, M., Agrawal, S., Seth, S., and Thakur, U. K. 2017. "Therapeutic Leukapheresis in a Tertiary Care Hospital: A Case Series," *Asian Journal of Transfusion Science* 11(1):65-68; Pastore, F., Pastore, A., Wittmann, G., Hiddemann, W., and Spiekermann, K. 2014. "The Role of Therapeutic Leukapheresis in Hyperleukocytotic AML [acute myeloid or myelogenous leukemia]," *Public Library of Science One* 9(4):e95062).

When the patient is free of urological disease with intact lower urinary tract, flush-line 79 is run to empty through a nonjacketing side-entry connector with extraction jacket into the urinary bladder, expulsion then normal, that is, urethral. When the lower urinary tract is diseased, malformed, or missing, bilateral ureteral takeoff lines leading through a small port positioned subdermally to a side of the mons pubis allows emptying directly into a bathroom fixture or an external collection bag, a urine confluence chamber as shown in FIGS. 39B and 43 interposed only when necessary, as when the patient is bed-ridden and unable to stand. Provided with the mechanical means for effecting extraction intracorporeally, any constituent of the blood which can be bound to a magnetically susceptible microparticle to the exclusion of other type cells can be selectively, or differentially, extracted from the blood.

Required are In eliminating the need for extracorporeal removal of the blood and return of healthy blood cells to the circulatory system, leukapheresis through magnetic separation significantly reduces if not eliminates the contamination with large platelets and erythrocytes, which due to inadequately resolved separation, impairs conventional leukapheresis—"Moreover, platelets and red blood cell were contaminated in the product of leukapheresis. It is an urgent problem to be solved in order to realise higher efficacy and higher purity of WBC collection to improve the survival of patients with HLL [hyperleukocytic leukaemia] through optimising instruments." (Jin, Y., Guo, S., Cui, Q., Chen, S., Liu, X., and 12 others 2018. "A Hospital Based Retrospective Study of Factors Influencing Therapeutic Leukapheresis in Patients Presenting with Hyperleukocytic Leukaemia," *Scientific Reports* 8(1):294).

As to the incidental inclusion of erythrocytes in the extract fraction, the rate of erythrocyte replenishment at two million per second (see, for example, Higgins, J. M. 2015. "Red Blood Cell Population Dynamics," *Clinics in Laboratory Medicine* 35(1):43-57), and subject to increase when cells are lost (see, for example, Patel, H. H., Patel, H. R., and Higgins, J. M. 2015. "Modulation of Red Blood Cell Population Dynamics is a Fundamental Homeostatic Response to Disease," *American Journal of Hematology* 90(5):422-428; Dzierzak, E. and Philipsen, S. 2013. "Erythropoiesis: Development and Differentiation," *Cold Spring Harbor Perspectives in Medicine* 3(4):a011601; Higgins, J. M. and Mahadevan, L. 2010. "Physiological and Pathological Population Dynamics of Circulating Human Red Blood Cells." *Proceedings of the National Academy of Sciences of the United States of America* 107(47):20587-20592) is more than sufficient to accommodate a small loss incidental to the magnetic extraction when trapped amid aggregated leukocytes.

The same may be said for platelets, likewise replaced continuously, the overall mass rather than the number thereof physiologically conserved (Kuter, D. J. 1996. "The Physiology of Platelet Production," *Stem Cells* 14 Supplement 1:88-101). By comparison with conventional, such as centrifuge, separation, magnetic leukapheresis substantially reduces if not eliminates the incidental extraction of non-phagocytic cells and platelets not bound to a magnetically susceptible microparticle or of aggregated nanoparticles. The transfusion of healthy leukocytes only after a span of magnetic leukapheresis has been completed and current through the electromagnets has been reversed to degauss residual magnetism, or remanence, assures that few if any healthy leukocytes are extracted.

This includes immature leukocytes, or blasts, which recent insight indicates may be medically prompted to develop immune to include phagocytic function, as addressed below. Until such methods are instituted, transfusion of healthy and not primary dependence upon 'cured' leukocytes will continue to be necessary. In cases of leukostasis where the blood becomes thickened and clogs the microvasculature, the removal of leukocytes is not a cure but rather imperative to sustain proper oxygenation; the primary cause in a leukemia is not the overproduction of leukocytes, which is but one symptom of a bone marrow cancer.

The value in an ambulatory automatic leukocyte extraction system is that this process is coordinated with the automatic release of chemotherapeutics and, if necessary, radiotherapeutic agents, to strike at the diseased marrow as the nidus of disease. The direct targeting of radioactive agents into the bone nutrient artery, or blood supply, or if appropriate, by drilling through the periosteum, compact bone, and endosteum into the modularity cavity to position a ductus side-entry jacket along the diaphysis requires radiation shielded lines and jackets as shown in FIGS. 5 and 6, Significantly, magnetic separation leukapheresis is not limited to the clinic, but rather automatic, ambulatory, adaptive, and continuous, reduces if not eliminates delay in the alleviation of microvascular obstruction, to include retinal, renal, hepatic, and coronary, and those precipitative of serious vascular accidents, as well as renal, pulmonary, and neurological impairment (see, for example, Makroo, R. N., Kakkar, B., Chowdhry, M., Agrawal, S., Seth, S., and Thakur, U. K. 2017, Op cit.; Awh, C. C., Miller, J. B., Wu, D. M., and Eliott, D. 2015. "Leukostasis Retinopathy: A New Clinical Manifestation of Chronic Myeloid Leukemia with Severe Hyperleukocytosis," *Ophthalmic Surgery, Lasers and Imaging Retina* 46(7):768-770; Gong, J., Wu, B., Guo, T., Zhou, S., He, B., and Peng, X. 2014. "Hyperleukocytosis: A Report of Five Cases and Review of the Literature," *Oncology Letters* 8(4):1825-1827; Ganzel, C., Becker, J., Mintz, P. D., Lazarus, H. M., and Rowe, J. M. 2012. "Hyperleukocytosis, Leukostasis and Leukapheresis: Practice Management," *Blood Reviews* 26(3):117-122; van Haelst, P. L., Schot, B., Hoendermis, E. S., and van den Berg, M. P. 2006. "Acute Myeloid Leukaemia as a Cause of Acute Ischaemic Heart Disease," *Netherlands Heart Journal* 14(2):62-65).

If left untreated, hyperleukocytosis results in the death of almost half of these patients within a week (see, for example, Giammarco, S., Chiusolo, P., Piccirillo, N., Di Giovanni, A., Metafuni, E., and 3 others 2017. "Hyperleukocytosis and Leukostasis: Management of a Medical Emergency," *Expert Review of Hematology* 10(2):147-154). Leukapheresis is but one means available for reducing the number of circulating blasts of which the implant system described herein is capable, and claims as to its insufficiency compared to induction and low-dose chemotherapy, for example, may reflect a slower rate or overall percentage of removal, and/or contamination with other blood components, to which the implant system described is less susceptible than are conventional extracorporeal machines (see, for example, Korkmaz, S. 2018. "The Management of Hyperleukocytosis in 2017: Do We Still Need Leukapheresis?," *Transfusion and Apheresis Science* February 20. pii: S1473-0502(18)30040-30045; Jin, Y., Guo, S., Cui, Q., Chen, S., Liu, X., and 12 others 2018, Op cit.).

That the system makes it possible to remove leukocytes around the clock means that a higher proportion of leukocytes than 40 percent can be removed (see, for example, Tendulkar, A. A., Jain, P. A., Gupta, A., Sharma, N., Navkudkar, A., and Patle, V. 2017. "Therapeutic Leukocyte Reduction for Acute and Chronic Myeloid Leukemias: A 4-year Experience from an Oncology Center in India," *Asian Journal of Transfusion Science* 11(2):156-161; Berber, I., Kuku, I., Erkurt, M. A., Kaya, E., Bag, H. G., and others 2015. "Leukapheresis in Acute Myeloid Leukemia Patients with Hyperleukocytosis: A Single Center Experience," *Transfusion and Apheresis Science* 53(2):185-190). At least in part, insufficiency in number and rate of blast removal and contamination with other type blood cells may be responsible for the shortcomings of leukapheresis accomplished with conventional machines (Korkmaz, S. 2018, Op cit.).

No less important than relative freedom from the risks of infection, problem bleeding, hematoma, and injury associated with repeated vascular access (see, for example, Dogra, K., Fulzele, P., Rout, D., Chaurasia, R., Coshic, P., and Chatterjee, K. 2017. "Adverse Events During Apheresis Procedures: Audit at a Tertiary Hospital," *Indian Journal of Hematology and Blood Transfusion* 33(1):106-108; Eder, A. F., Dy, B. A., DeMerse, B., Wagner, S. J., Stramer, S. L., O'Neill, E. M., and Herron, R. M. 2017. "Apheresis Technology Correlates with Bacterial Contamination of Platelets and Reported Septic Transfusion Reactions," *Transfusion* 57(12):2969-2976) is the impact upon patient quality of life: conventional blood exchange techniques take at least three hours in a clinic.

The application of nonmagnetized vascular connection jackets as described herein advances extracorporeal blood component extraction techniques in making possible three steps in the advancement of blood extraction. These are:

1. Immediacy and complication-free machine connection to existing clinic-bound, technician operated machines without exposed catheters and the risk of complications these bode.
2. The implementation of existing machines for use in the home without the aid of a technician, and
3. Blood extraction techniques made automatic and ambulatory in a miniaturized and lightweight machine carried in a body pack. In all three cases, only system components which must be implanted—sensors, fluid and electrical lines, side-entry jackets, nonjacketing connectors, and connecting port at the body surface are implanted; diagnostic and therapeutic calculations are performed by a microprocessor within the machine.

The application of magnetized vascular connection jackets and nonjacketing side-entry connectors with a separation electromagnet makes possible intracorporeal magnetic blood component extraction with expulsion of the extracted components in the urine, and therewith, elimination of an extracorporeal machine. In such an ambulatory automatic disorder response system, all system components are implanted. The advisability for using any of these four methods varies as the duration and severity of the disorder; patients within ready reach of the clinic who require treatment only occasionally are not the target population. Apheresis and dialysis addressed below in section 1 h, entitled Apheresis and Hemodialysis, Stationary with or without an Attendant, Carryable, or Implanted Magnetic, reference here will be to intracorporeal magnetic leukapheresis as exemplary.

The system delineated herein is capable of treating a leukemia by conventional chemotherapeutic and radiochemotherapeutic means, mechanical apheretic treatment appropriate as adjuvant to primary chemotherapy and/or radiotherapy to the extent that leukostasis (symptomatic hyperleukocytosis, acute hyperleukocytic leukemia, sludging) must be prevented and therewith "ultimate neurological, pulmonary, gastrointestinal complications, coagulopathy, and tumor lysis syndrome [which] cause increased morbidity and mortality" (see, for example, Berber, I., Kuku, I., Erkurt, M. A., Kaya, E., Bag, H. G., and 4 others 2015, Op cit.) (see also, for example, Abla, O., Angelini, P., Di Giuseppe, G., Kanani, M. F., Lau, W., and 3 others 2016. "Early Complications of Hyperleukocytosis and Leukapheresis in Childhood Acute Leukemias," *Journal of Pediatric Hematology and Oncology* 38(2):111-117; Nguyen, R., Jeha, S., Zhou, Y., Cao, X., Cheng, C., and 10 others 2016. "The Role of Leukapheresis in the Current Management of Hyperleukocytosis in Newly Diagnosed Childhood Acute Lymphoblastic Leukemia," *Pediatric Blood and Cancer* 63(9):1546-1551; Oberoi, S., Lehrnbecher, T., Phillips, B., Hitzler, J., Ethier, M. C., Beyene, J., and Sung, L. 2014. "Leukapheresis and Low-dose Chemotherapy Do Not Reduce Early Mortality in Acute Myeloid Leukemia Hyperleukocytosis: A Systematic Review and Meta-analysis," *Leukemia Research* 38(4):460-468; Pastore, F., Pastore, A., Wittmann, G., Hiddemann, W., and Spiekermann, K. 2014. "The Role of Therapeutic Leukapheresis in Hyperleukocytotic AML [Acute myeloid, or myelogenous, Leukemia]," *Public Library of Science One* 9(4): e95062; Giles, F. J., Shen, Y., Kantarjian, H. M., Korbling, M. J., O'Brien, S., and 6 others 2001. "Leukapheresis Reduces Early Mortality in Patients with Acute Myeloid Leukemia with High White Cell Counts But Does Not Improve Long-term Survival," *Leukemia and Lymphoma* 42(1-2):67-73), where the different experience of the Oberoi and Giles teams may be attributable to improvement in therapy between the two.

In fact, hyperleukocytosis not having had sufficient time to significantly interfere with microcirculation, initial treatment of an acute myeloid leukemia in children is claimed by some to be little if at all dependent upon leukapheresis but rather chemotherapy (Chen, K. H., Liu, H. C., Liang, D. C., Hou, J. Y., Huang, T. H., Chang, C. Y., and Yeh, T. C. 2014. "Minimally Early Morbidity in Children with Acute Myeloid Leukemia and Hyperleukocytosis Treated with Prompt Chemotherapy without Leukapheresis," *Journal of the Formosan Medical Association* 113(11):833-838), which circumstance should be short-lived.

However, the opposite view has also been expressed, possibly because microvascular obstruction had already set in (Korkmaz, S. 2018, Op cit.; Tendulkar, A. A., Jain, P. A., Gupta, A., Sharma, N., Navkudkar, A., and Patle, V. 2017, Op cit.; Thiébaut, A., Thomas, X., Belhabri, A., Anglaret, B., and Archimbaud, E. 2000. "Impact of Pre-induction Therapy Leukapheresis on Treatment Outcome in Adult Acute Myelogenous Leukemia Presenting with Hyperleukocytosis," *Annals of Hematology* 79(9):501-506), probably because prompt leukaperesis imposed no adverse effect.

Another myeloproliferative disorder, sometimes distinct but often associated with essential thrombocythemia, analogous in that the microvasculature becomes clogged with a bone marrow malignancy-induced overabundance of red blood cells, polycythemia vera (see, for example, Tefferi, A. and Barbui, T. 2017. "Polycythemia Vera and Essential Thrombocythemia: 2017 Update on Diagnosis, Risk-stratification, and Management," *American Journal of Hematology* 92(1):94-108; Aruch, D. and Mascarenhas, J. 2016. "Contemporary Approach to Essential Thrombocythemia and Polycythemia Vera," *Current Opinion in Hematology* 23(2):150-160; Falchi, L., Newberry, K. J., and Verstovsek, S. 2015. "New Therapeutic Approaches in Polycythemia Vera," *Clinical Lymphoma, Myeloma, and Leukemia* 15 Supplement:S27-S33; Griesshammer, M., Gisslinger, H., and Mesa, R. 2015. "Current and Future Treatment Options for Polycythemia Vera," *Annals of Hematology* 94(6):901-910; Raedler, L. A. 2014. "Diagnosis and Management of Polycythemia Vera: Proceedings from a Multidisciplinary Roundtable," *Ameridan Health and Drug Benefits* 7(7 Supplement 3):S36-S47; Tibes, R. and Mesa, R. A. 2013. "Emerging Drugs for Polycythemia Vera," *Expert Opinion on Emergency Drugs* 18(3):393-404), would be treated in an analogous manner, the method for rendering the target cells magnetically susceptible then other than that specified for phagocytes.

Provided overproduced leukocytes and/or platelets can also be bound to magnetically susceptible micro- or nanoparticles, the implanted system can be used to extract these cells as well (see for example, Masarova, L., Alhuraiji, A., Bose, P., Daver, N., Pemmaraju, N., and 4 others 2018. "Significance of Thrombocytopenia in Patients with Primary and Postessential Thrombocythemia/Polycythemia Vera Myelofibrosis," *European Journal of Haematology* 100(3): 257-263; Masarova, L., Bose, P., Daver, N., Pemmaraju, N., Newberry, K. J., and 4 others 2017. "Patients with Post-essential Thrombocythemia and Post-polycythemia Vera Differ from Patients with Primary Myelofibrosis," *Leukemia Research* 59:110-116; Rotunno, G., Pacilli, A., Artusi, V., Rumi, E., Maffioli, M., and 19 others 2016. "Epidemiology and Clinical Relevance of Mutations in Postpolycythemia Veia and Postessential Thrombocythemia Myelofibrosis: A Study on 359 Patients of the AGIMM [Associazione Italiana per la Ricerca sul Cancro (AIRC)-Gruppo Italiano Malattie Mieloproliferative (Italian Cancer Research Association—Myeloproliferative Disease Group]," *American Journal of Hematology* 91(7):681-686; Boiocchi, L., Gianelli, U., lurlo, A., Fend, F., Bonzheim, I., and 3 others 2015. "Neutrophilic Leukocytosis in Advanced Stage Polycythemia Vera: Hematopathologic Features and Prognostic Implications," *Modern Pathology* 28(11):1448-1457; Michiels, J. J., Bernema, Z., Van Bockstaele, D., De Raeve, H., and Schroyens, W. 2007. "Current Diagnostic Criteria for the Chronic Myeloproliferative Disorders (MPD) Essential Thrombocythemia (ET), Polycythemia Vera (PV), and Chronic Idiopathic Myelofibrosis (CIMF)," in French with English abstract at Pubmed *Pathologie et Biologie* (Paris, France) 55(2):92-104).

Provided with the mechanical means for effecting extraction intracorporeally, any constituent of the blood which can be bound to a magnetically susceptible microparticle to the exclusion of other type cells can be differentially extracted from the blood. In addition to magnetic extraction, rendering problematic blood cells susceptible to a magnetic field makes it possible to bind these to superparamagnetic carrier-bound chemotherapeutic, radiotherapeutic, and other agents of cellular destruction, such as natural killer cells, allowing the implant system to treat the different type cells of the compound disorder; otherwise, diseased cells extractable thus would be treated by the implant system, with those not so treated conventionally. Accordingly, the system can accomplish all phases of treatment less transfusions.

Immature leukemic cells with chemical and phagocytic immune function imparted by means such as that indicated just below should be removed only to the extent that leukostasis, or sludging, is alleviated, blood fluidity restored, and a normal number of functional leukocytes remain to support immune function (see, for example, Ali, A. M., Mirrakhimov, A. E., Abboud, C. N., and Cashen, A. F. 2016. "Leukostasis in Adult Acute Hyperleukocytic Leukemia: A Clinician's Digest," *Hematological Oncology* 34(2):69-78; Berber, I., Erkurt, M. A., Kuku, I., Kaya, E., Gozukara Bag, H., and 4 others 2016. "Leukapheresis Treatment in Elderly Acute Leukemia Patients with Hyperleukocytosis: A Single Center Experience," *Journal of Clinical Apheresis* 31(1):53-58; Berber, I., Kuku, I., Erkurt, M. A., Kaya, E., Bag, H. G., and 4 others 2015, Op cit.).

Significantly, the system can administer substances not only to allow the attainment by circulating immature leukemic blast cells of immune function and reduce the number of blast cells through magnetic separation leukapheresis, but can also reduce the number by administering induction chemotherapy, hydroxyurea, and low-dose chemotherapy, thus enabling hyperleukocytosis amelioration through both medicinal and mechanical means (Korkmaz, S. 2018, Op cit.), the removal of supernumerary leukocytes from the bloodstream but one of many applications for apheresis.

While the transfusion of hematopoietic stem cells can precede or succeed magnetic separation leukapheresis, since magnetic separation leukostasis indiscriminately extracts all types of phagocytically functional leukocytes, the transfusion of healthy allogeneic bone marrow, usually followed by leukocytes, which may be necessary to attain a proper balance in the relative number of different type leukocytes, should always follow extraction (see, for example Silla, L., Dulley, F., Saboya, R., Kerbauy, F., de Moraes Arantes, A., and 4 others 2017. "Brazilian Guidelines on Hematopoietic Stem Cell Transplantation in Acute Myeloid Leukemia," *European Journal of Haematology* 98(2):177-183; Cornelissen, J. J. and Blaise, D. 2016. "Hematopoietic Stem Cell Transplantation for Patients with AML [acute myeloid leukemia] in First Complete Remission," *Blood* 127(1):62-70; Cannas, G. and Thomas, X. 2015. "Supportive Care in Patients with Acute Leukaemia: Historical Perspectives," *Blood Transfusion* [Trafusione del Sangue] 13(2):205-220; Silla, L. M., Dulley, F., Saboya, R., Paton, E., Kerbauy, F., Arantes Ade, M., and Hamerschlak, N. 2013. "Bone Marrow Transplantation and Acute Myeloid Leukemia: Brazilian Guidelines," *Revista Brasileira de Hematologia e Hemoterapia* 35(1):56-61; Kolb, H. J. 1998. "Donor Leukocyte Transfusions for Treatment of Leukemic Relapse after Bone Marrow Transplantation. EBMT [European Group for Blood and Marrow Transplantation] Immunology and Chronic Leukemia Working Parties," *Vox Sanguinis* 74 Supplement 2:321-329; van Rhee, F. and Kolb, H. J. 1995. "Donor Leukocyte Transfusions for Leukemic Relapse," *Current Opinion in Hematology* 2(6):423-430).

Any means for bonding magnetically susceptible matter to phagocytes or their precursor cells, such as monocytes, will render these directly separable from whole blood—for the present purpose, blood flowing through the inferior vena cava past a chain extraction jacket. For example, in chronic lymphocytic leukemia, if maturable or restorable to phagocytic function, such as through disrupting programmed cell death protein 1-programmed cell death protein ligand 1 (PD-1/PD-L1); and/or possibly lymphocyte-activation gene 3 (LAG-3); hepatitis A virus cellular receptor 2 (HAVCR2) or T-cell immunoglobulin and mucin-domain containing-3 (TIM-3); or V-domain immunoglobulin suppressor of T cell activation (VISTA) protein signaling, phagocytes will respond to the infusion of superparamagnetic iron oxide microparticles or iron oxide-coated autologous dead cells, for example, by ingesting these.

Phagocytosis of magnetically susceptible particles then renders the phagocytes themselves magnetically separable, hence, retrievable (see, for example, Annibali, O., Crescenzi, A., Tomarchio, V., Pagano, A., Biancandhi, A., Grifoni, A., Avvisati, G. 2018. "PD-1/PD-L1 [programmed cell death protein 1-programmed cell death protein ligand 1] Checkpoint in Hematological Malignancies," *Leukemia Research* 67:45-55; Pianko, M. J., Goldberg, A. D., and Lesokhin, A. M. 2018. "Clinical Development of PD-1 Blockade in Hematologic Malignancies," *Cancer Journal* (Sudbury, Mass.) 24(1):31-35; Tomuleasa, C., Fuji, S., Berce, C., Onaciu, A., Chira, S., and 11 others 2018. "Chimeric Antigen Receptor T-Cells for the Treatment of B-Cell Acute Lymphoblastic Leukemia," *Frontiers in Immunology* 9:239; Yoon, D. H., Osborn, M. J., Tolar, J., and Kim, C. J. 2018. "Incorporation of Immune Checkpoint Blockade into Chimeric Antigen Receptor T Cells (CAR-Ts): Combination or Built-in CAR-T," *International Journal of Molecu-* lar Sciences 19(2). pii: E340; Qorraj, M., Bruns, H., Böttcher, M., Weigand, L., Saul, D., and 3 others 2017. "The PD-1/PD-L1 [programmed cell death protein 1-programmed cell death protein ligand 1] Axis Contributes to Immune Metabolic Dysfunctions of Monocytes in Chronic Lymphocytic Leukemia," *Leukemia* 31(2):470-478; Ok, C. Y. and Young, K. H. 2017. "Checkpoint Inhibitors in Hematological Malignancies," *Journal of Hematology and Oncology* 10(1):103; Qorraj, M., Böttcher, M., and Mougiakakos, D. 2017. "PD-L1/PD-1: New Kid on the "Immune Metabolic" Block," *Oncotarget* 8(43):73364-73365; Gravelle, P., Burroni, B., Péricart, S., Rossi, C., Bezombes, C., and 5 others 2017. "Mechanisms of PD-1/PD-L1 Expression and Prognostic Relevance in Non-Hodgkin Lymphoma: A Summary of Immunohistochemical Studies," *Oncotarget* 8(27): 44960-44975; Giuliani, M., Janji, B., and Berchem, G. 2017. "Activation of NK Cells and Disruption of PD-L1/PD-1 Axis: Two Different Ways for Lenalidomide to Block Myeloma Progression," *Oncotarget* 8(14):24031-24044; Pianko, M. J., Liu, Y., Bagchi, S., and Lesokhin, A. M. 2017. "Immune Checkpoint Blockade for Hematologic Malignancies: A Review," *Stem Cell Investigation* 4:32; Nishimori, A., Konnai, S., Okagawa, T., Maekawa, N., Ikebuchi, R., and 8 others 2017. "In Vitro and In Vivo Antivirus Activity of an Anti-programmed Death-ligand 1 (PD-L1) Rat-bovine Chimeric Antibody against Bovine Leukemia Virus Infection," *Public Library of Science One* 12(4):e0174916; Rupp, L. J., Schumann, K., Roybal, K. T., Gate, R. E., Ye, C. J., Lim, W. A., and Marson, A. 2017. "CRISPR/Cas9-mediated PD-1 Disruption Enhances Anti-tumor Efficacy of Human Chimeric Antigen Receptor T Cells," *Scientific Reports* 7(1):737; Yu, M. G. and Zheng, H. Y. 2017. "Acute Myeloid Leukemia: Advancements in Diagnosis and Treatment," *Chinese Medical Journal* (English edition) 130(2):211-218; Brusa, D., Serra, S., Coscia, M., Rossi, D., D'Arena, G., and 7 others 2013. "The PD-1/PD-L1 Axis Contributes to T-cell Dysfunction in Chronic Lymphocytic Leukemia," *Haematologica* 98(6):953-963; Kearl, T. J., Jing, W., Gershan, J. A., and Johnson, B. D. 2013. "Programmed Death Receptor-1/Programmed Death Receptor Ligand-1 Blockade after Transient Lymphodepletion to Treat Myeloma," *Journal of Immunology* 190(11):5620-5628).

Additionally, following allogeneic hematopoietic stem cell transplantation, the reinstatement of immune function by means other than the incorporation of immune checkpoint blockade into chimeric antigen receptor T cells is indicated (see, for example, Litjens, N. H. R., van der Wagen, L., Kuball, J., and Kwekkeboom, J. 2018. "Potential Beneficial Effects of Cytomegalovirus Infection after Transplantation," *Frontiers in Immunology* 9:389; Takenaka, K., Nishida, T., Asano-Mori, Y., Oshima, K., Ohashi, K., and 12 others 2015. "Cytomegalovirus Reactivation after Allogeneic Hematopoietic Stem Cell Transplantation is Associated with a Reduced Risk of Relapse in Patients with Acute Myeloid Leukemia Who Survived to Day 100 after Transplantation: The Japan Society for Hematopoietic Cell Transplantation Transplantation-related Complication Working Group," *Biology of Blood and Marrow Transplantation* 21(11):2008-2016).

Another method is to diminish the use of immunosuppressives following allogeneic hematopoietic stem cell transplantation (see, for example, Yang, J., Cai, Y., Jiang, J., Wan, L., Bai, H., and 4 others 2018. "Early Tapering of Immunosuppressive Agents after HLA-matched Donor Transplantation Can Improve the Survival of Patients with Advanced Acute Myeloid Leukemia," *Annals of Hematology* 97(3):497-507; Liu, Q. F., Fan, Z. P., Zhang, Y., Jiang, Z. J., Wang, C. Y., and 4 others 2009. "Sequential Intensified Conditioning and Tapering of Prophylactic Immunosuppressants for Graft-versus-host Disease in Allogeneic Hematopoietic Stem Cell Transplantation for Refractory Leukemia," *Biology of Blood and Marrow Transplantation* 15(11): 1376-1385).

Yet other methods for the recovery of immune function have emerged (see, for example, Piras, F., Riba, M., Petrillo, C., Lazarevic, D., Cuccovillo, I., and 6 others 2017. "Lentiviral Vectors Escape Innate Sensing but Trigger p53 in Human Hematopoietic Stem and Progenitor Cells," *European Molecular Biology Organization Molecular Medicine* 9(9):1198-1211; Servais, S., Hannon, M., Peffault de Latour, R., Socie, G., and Beguin, Y. 2017. "Reconstitution of Adaptive Immunity after Umbilical Cord Blood Transplantation: Impact on Infectious Complications," *Stem Cell Investigation* 4:40).

Leukocytes produced and entering the venous tree throughout the body, removal is most efficient along the channel of maximum confluence, the inferior vena cava. As shown in FIGS. 13 thru 15 and 39A, the chain of extraction jackets with flush-line position entry portals along the substrate vessel, here the inferior vena cava. The entry portals are entered through a one-way elastic slit-valve such as that shown in FIG. 33, forced open when the accumulated magnetically tagged analytes, here leukocytes, to be removed become sufficiently numerous to present a responsive attraction strong enough to push through the valve into the flush-line under a resting field strength.

The flush-line itself is a continuously recirculated 'endless loop' which releases the unwanted cells through a like 'separation magnet/conveyor belt' mechanism as is used to draw the cells into the flush-line; that is, by exceeding the resistance of a one-way slit-valve with a nonjacketing side-entry connector mounted electromagnet set at a resting'field strength at the bladder or confluence chamber. The level and duration of current is adjusted for the degree of leukostasis as detected by a flow rate biosensor in the flush-line. If leukostasis is so pronounced that the flush-line at the slit-valves along the chain extraction jackets and/or attached to the urinary bladder clog, a flow rate biosensor in the flush-line signals the system microprocessor to send a surge pulse to the extraction jackets.

If one pulse is not adequate to extract the accumulated leukocytes from the flush-line, current is delivered through a fine nichrome filament coursing through the leaves of each slit valve, such a filament included as standard in these valves. This then warms and so softens, the polymeric material of the valves, reducing the resistance to passing. A second pulse with the valve warmed should clear the flush-line as detected by the flow rate biosensor. If not, a stronger surge pulse is sent. Since the caliber of the flush-line and other components are prescribed based upon the degree of leukocytosis, the flush-line should clear under the force exerted by the electromagnets in the resting mode without the need for either pulsing or warming, which are backup options in the microprocessor prescription-program.

Once in the bladder, expulsion is through a small port positioned subdermally to a side of the mons pubis, which provides the orifice for urine outflow through a tube into either a collection container, typically cinched about a thigh, or into a bathroom receptacle. In a patient with intractable urinary incontinence, or enuresis, nocturia, or when the lower urinary tract is diseased or missing, side-entry diversion jackets on the ureters direct the urine into a confluence chamber as shown in FIG. 40. Once released into the confluence chamber, the removal path for the detritus is the same as that described below for a ureteral takeoff and urine evacuation arrangement.

Magnetic separation apheresis avoids the removal of healthy blood cells along with those wanted removed from the bloodstream and therefore eliminates the need for a second step of returning undiseased components of the blood back into the circulatory system, and the extraction of untargeted cells as contaminates diagnostic results is much reduced if not eliminated (Jin, Y., Guo, S., Cui, Q., Chen, S., Liu, X., and 12 others 2018, Op cit.). To effect magnetic apheresis, as described below in section entitled Aphersis, portable and magnetic, where only the cells targeted for extraction are removed from the bloodstream with the balance of blood continuing through the vascular tree, the side-entry jackets for extracting defective blood cells incorporate an electromagnet and the removed cells are conveyed into and expelled with the urine as shown in FIGS. 39A and 39B.

When the patient is able to void normally, the apheresis or dialysis extractate is delivered directly into the native urinary bladder, whereas in a patient with a diseased or missing lower urinary tract, delivery is into a prosthetic substitute bladder or a kind of neobladder, with forcible expulsion means to assure prompt voiding when the patient in recumbent as shown in FIG. 43. In a patient with diseased or missing lower urinary tract, the apheresis or dialysis circuit shown in FIG. 39A delivers the extractate into the same kind of prosthetic substitute bladder, or, neobladder, as that shown in FIG. 40, the means of delivery differing from that into a native bladder in omitting the need for a flexible connection between flush-line and neobladder.

The ductus side-entry chain extraction jackets shown in FIGS. 13 thru 15 are modified double-arm ductus side-entry jackets, one such shown in FIG. 7, while those shown in FIG. 39A are modified side-entry jackets. The ureteral takeoff jackets such as shown in FIGS. 40 thru 42 are intravascular valve diversion jackets and are uninvolved in apheresis or dialysis. Depending upon the status of the urethra, the course from the native or neobladder is either by emptying through the urethral meatus or into a urine collection bladder cinched about a thigh. Rather than to incorporate magnetic separation system sufficiency self-checking into the prescription-program—which may involve the evaluation of numerous indicia, not just white blood cell count—adding much code, requiring additional biosensors—to be miniaturized for implantation, an increasing system complexity and expense, this is best confirmed by conventional microscopic and chemical urinalysis.

While dialysis is performed with a higher blood flow rate as prompts the creation of a surgical fistula, the means described herein can be used for dialysis or apheresis with a flow rate one quarter that of dialysis (see, for example, Adeel Ebad, C., Davitt, S., Gnanasekaran, R., Khan, A., and Moran, A. M. 2016: "Application of Hong's Technique for Removal of Stuck Hemodialysis Tunneled Catheter to Pacemaker Leads," *Radiology Case Reports* 12(1):97-101; Ding, Y., Francis, J., Kalish, J., Deshpande, A., and Quillen, K. 2016. "Recurrent Focal Segmental Glomerulosclerosis Apparently Resistant to Plasmapheresis Improves after Surgical Repair of Arteriovenous Fistula Aneurysms," *Clinical Kidney Journal* 9(3):408-410; Wang, L., Wei, F., Jiang, A., Chen, H., Sun, G., and Bi, X. 2015. "Longer Duration of Catheter Patency, but Similar Infection Rates with Internal Jugular Vein Versus Iliac Vein Tunneled Cuffed Hemodialysis Catheters: A Single-center Retrospective Analysis," *International Urology and Nephrology* 47(10):1727-1734; Vellanki, V. S., Watson, D., Rajan, D. K., Bhola, C. B., and Lok, C. E. 2015. "The Stuck Catheter: A Hazardous Twist to the Meaning of Permanent Catheters," *Journal of Vascular Access* 16(4):289-293; Santoro, D., Benedetto, F., Mondello, P., Pipitò, N., Barillà, D., and 4 others 2014. "Vascular Access for Hemodialysis: Current Perspectives," *International Journal of Nephrology and Renovascular Disease* 7:281-294; Hingwala, J., Bhola, C., and Lok, C. E. 2014. "Using Tunneled Femoral Vein Catheters for "Urgent Start" Dialysis Patients: A Preliminary Report," *Journal of Vascular Access* 15 Supplement 7:S101-S108; Murea, M., James, K. M., Russell, G. B., Byrum, G. V. 3rd, Yates, J. E., and 4 others 2014. "Risk of Catheter-related Bloodstream Infection in Elderly Patients on Hemodialysis," *Clinical Journal of the American Society of Nephrology* 9(4):764-770; Golestaneh, L. and Mokrzycki, M. H. 2013. "Vascular Access in Therapeutic Apheresis: Update 2013," *Journal of Clinical Apheresis* 28(1):64-72; Okafor, C. and Kalantarinia, K. 2012. "Vascular Access Considerations for Therapeutic Apheresis Procedures," *Seminars in Dialysis* 25(2):140-144; Kalantari, K. 2012. "The Choice of Vascular Access for Therapeutic Apheresis," *Journal of Clinical Apheresis* 27(3):153-159; Kalantari, K. 2012. "The Choice of Vascular Access for Therapeutic Apheresis," *Journal of Clinical Apheresis* 27(3):153-159; Okafor, C. and Kalantarinia, K. 2012. "Vascular Access Considerations for Therapeutic Apheresis Procedures," *Seminars in Dialysis* 25(2):140-144; Okafor, C. and Kalantarinia, K. 2012. "Vascular Access Considerations for Therapeutic Apheresis Procedures," *Seminars in Dialysis* 25(2):140-144; Kovač, J., Premru, V., Buturović-Ponikvar, J., and Ponikvar, R. 2011. "Two Single-lumen Noncuffed Catheters in the Jugular Vein as Long-term Vascular Access: A Preliminary Report," *Therapeutic Apheresis and Dialysis* 15(3):311-314; Matsuura, J., Dietrich, A., Steuben, S., Ricker, J., Barkema, K., and Kuhl, T. 2011. "Mediastinal Approach to the Placement of Tunneled Hemodialysis Catheters in Patients with Central Vein Occlusion in an Outpatient Access Center," *Journal of Vascular Access* 12(3):258-261; Di Iorio, B. R., Mondillo, F., Bortone, S., Nargi, P., Capozzi, M., and 3 others 2006. "Fourteen Years of Hemodialysis with a Central Venous Catheter: Mechanical Long-term Complications," *Journal of Vascular Access* 7(2):60-65; Quarello, F., Fomeris, G., Borca, M., and Pozzato, M. 2006. "Do Central Venous Catheters Have Advantages over Arteriovenous Fistulas or Grafts?," *Journal of Nephrology* 19(3):265-279).

Apheresis machines described herein are of three types: the first, or Type 1 machines, are conventional, that is, fully extracorporeal, only the advantages in improved vascular access employed; the second, or Type 2 machines implant or internalize in the patient the components essential to compensate for the absence of a technician to evaluate the diagnostic data and set the machine controls. Type 2a machines for use in the home and Type 2b machines miniaturized to be carried in a body pack, include the physiological or diagnostic sensors with the controlling microprocessor and blood processing components enclosed in the extracorporeal housing. In a Type 3 system, all of these components are implanted as well as the diagnostic and controlling components extracorporeal; and the third, fully implanted.

Type 1 and Type 2 machines use vascular access through a small port connected to ductus side-entry jackets and thus benefit from quick and complication-free connection to the extracorporeal apheresis or dialysis machine or intracorporeal equivalent without the risks and complications associated with conventional means of vascular access. In Type 3 machines, an external machine is not connected to the patient; rather vascular access is internalized, the port at the body surface used to communicate with the implanted system, whether by adding drugs or other agents, or withdrawing test samples, or inserting cabled devices.

Type 2 machines implant or internalize the biosensors and a machine for use in the home necessitating quick and complication free connection to the machine and diagnostics-responsive self-adjustment, and one carryable necessitating miniaturization. While quick connection to an apheresis or dialysis machine with little concern for injury or infection represents a basic improvement, the objective here is not to improve apheresis or dialysis machines as such but rather to set forth the groundwork to make possible automatic ambulatory blood separation technology through the implementation of intracorporeal magnetic apheresis.

Staged Advancements:

1. Clinic—Only vascular access is improved, the extracorporeal machine plugged into a small subdermally implanted port connected to the vessels through ductus side-entry jackets, sensors and controlling circuitry housed in the extracorporeal machine. With a conventional clinic-bound, stationary, such as centrifugation, sedimentation, and/or filtration-based apheresis machine, only the intracorporeal components for blood delivery to and return from the machine are implanted, the advantage gained being immediacy and catheter and fistula complication-free machine connection. Such an arrangement, suited to intermittent use requires intravascular valve diversion jackets to divert blood through fluid lines to and from a port at the body surface. The port has blood outflow and return openings and electrical jacks for connecting the external machine to the intravascular valves. With a technician operating the machine, the invention relates to improved vascular access.

2. Self use at home—Vascular access is improved, and the physiological biosensors to indicate the condition of the patient to the therapy-controlling microprocessor in the extracorporeal apheresis machine are implanted. A stationary machine for use in the home differs from a machine in the clinic in the need for additional diagnostic biosensors and machine control circuitry to compensate for the absence of a trained technician in setting the machine controls and establishing the treatment parameters. Components which can be incorporated into the machine are not implanted in the patient. The implanted components remain the same for use with such an upgraded machine as with a machine for use by a technician, only the intracorporeal components for blood delivery to and return from the machine implanted, the advantage gained being immediacy and complication-free machine connection.

3. Pack-carried—Vascular access is improved, with physiological biosensors to indicate the condition of the patient to the therapy controlling microprocessor in the extracorporeal apheresis machine implanted, thus allowing the machine to be much reduced in size and weight. With a miniaturized, lightweight, hence, readily carryable centrifugation, sedimentation, filtration, optical detection, or other separation process-based apheresis machine carried in a body pack, where connection of the implanted system to the machine and its use is frequent if not continuous, connection of the implant system to the machine is the same as that used with a stationary machine upgraded for use in the home. No components which can be housed in the pack are implanted; only components which must be implanted—sensors, fluid lines, and magnets—are implanted. Miniaturization of the extracorporeal machine is largely enabled by relegation of the therapeutic parameters to the implant microprocessor and sensors. The lack of miniaturized machines attests to the lack of vascular connectors and means of automatic control without which readily carryable machines for self-use cannot be implemented.

4. Full implantation, only the small port at the body surface is visible from the outside. No apheresis machine is used. Instead, the implant sensor-driven microprocessor directs the release into the bloodstream of a magnetically susceptible carrier with an affinity for the type cell targeted to bond with it for magnetic extraction from the bloodstream and any drugs needed, from one or more subdermally implanted storage reservoirs, or bladders positioned subdermally, usually in the pectoral region. The implant microprocessor energizes extraction or piped chain double-arm type extraction-jackets (FIGS. 13 thru 15) which feed the cell extract debris into the urinary bladder or an collection chamber with impeller the same as the confluence chamber shown for the ureteral takeoff of urine.

The flush-line is run to and washes the extracted cellular debris into the confluence chamber for expulsion with the urine through a small body surface port mounted to a side of the mons pubis. Takeoff from the ureters is with diversion chute intravascular valves. If the patient is urge-sentient, the valves are manually controlled at the surface body port for voluntary use. If not, expulsion is automatic. Expulsion under the control of the patient is through a small hose into a bathroom receptacle or through a longer hose into a collection bag cinched about a thigh, for example. Automatic expulsion is according to the latter. Magnetic separation of red blood cells from whole blood is hardly new, but implementation in a fully implanted apheresis system cannot proceed without a means for providing permanently secure connection to the substrate vessel made possible by ductus side-entry jackets.

Where magnetic susceptibility is:

a. Inherent in the type cell to be extracted (see, for example, Blue Martin, A., Wu, W. T., Kameneva, M. V., and Antaki, J. F. 2017. "Development of a High-throughput Magnetic Separation Device for Malaria-infected Erythrocytes," *Annals of Biomedical Engineering* 45(12):2888-2898; Leong, S. S., Yeap, S. P., and Lim, J. 2016. "Working Principle and Application of Magnetic Separation for Biomedical Diagnostic at High- and Low-field Gradients," *Interface Focus* 6(6):20160048; Plouffe, B. D., Murthy, S. K., and Lewis, L. H. 2015, Op cit.; Hejazian, M., Li, W., and Nguyen, N. T. 2015. "Lab on a Chip for Continuous-flow Magnetic Cell Separation," *Lab on a Chip* 15(4):959-970; Nam J1, Huang H, Lim, H., Lim, C., and Shin, S. 2013. "Magnetic Separation of Malaria-infected Red Blood Cells in Various Developmental Stages," *Analytical Chemistry* 85(15):7316-7323; Bhakdi, S. C., Ottinger, A., Somsri, S., Sratongno, P., Pannadapom, P., and 4 others 2010. "Optimized High Gradient Magnetic Separation for Isolation of Plasmodium-infected Red Blood Cells," *Malaria Journal* 9:38; Hackett, S., Hamzah, J., Davis, T. M., and St Pierre, T. G. 2009. "Magnetic Susceptibility of Iron in Malaria-infected Red Blood Cells," *Biochimica et Biophysica Acta* 1792(2):93-99; Zborowski, M., Ostera, G. R., Moore, L. R., Milliron, S., Chalmers, J. J., and Schechter, A. N. 2003. "Red Blood Cell Magnetophoresis," *Biophysical Journal* 84(4):2638-2645), or b. Imparted to cells or pathogens by selectively rendering these magnetically susceptible (see, for example, Myklatun, A., Cappetta, M., Winldhofer, M., Ntziachristos, V., and Westmeyer, G. G. 2017. "Microfluidic Sorting of Intrinsically Magnetic Cells under Visual Control," *Scientific Reports* 7(1):6942; Yung, C. W., Fiering, J., Mueller; A. J., and Ingber, D. E. 2009. "Micromagnetic-microfluidic Blood Cleansing Device," *Lab on a Chip* 9(9):1171-1177; Owen, C. S. 1978. "High Gradient Magnetic Separation of Erythrocytes," *Biophysical Journal* 22(2):171-178) or c. Scarcely adumbrated in the literature, rendering endogenously produced stem cells of the type to be extracted during formation in the marrow magnetically susceptible upon reaching unipotency, that is, at the stage in development where the precursory hemocytoblasts, or multipotential hematopoietic stem cells, or common myeloid or lymphoid progenitor cells have just lost pluripotent and oligopotent capacity (see, for example, Shen, W. B., Anastasiadis, P., Nguyen, B., Yarnell, D., Yarowsky, P. J., Frenkel, V., and Fishman, P. S. 2017. "Magnetic Enhancement of Stem Cell-targeted Delivery into the Brain following MR-guided Focused Ultrasound for Opening the Blood-brain Barrier," *Cell Transplantation* 26(7):1235-1246; Jin, X., Abbot, S., Zhang, X., Kang, L., Voskinarian-Berse, V., and 5 others 2012. "Erythrocyte Enrichment in Hematopoietic Progenitor Cell Cultures Based on Magnetic Susceptibility of the Hemoglobin," *Public Library of Science One* 7(8): e39491), but not sufficiently susceptible to allow seizure by an electromagnet—even one optimized in field strength, size, and weight for implantation—apheresis by means of implanted magnetic separation may necessitate an increase in the susceptibility of the target cell type. This is accomplished by bonding a substance with an inherent or an imparted selective affinity for the target cell type to a superparamagnetic iron oxide micro- or nanoparticle released into the bloodstream in a ferrofluid.

Provided means for bonding the superparamagnetic nanoparticle or microparticle drug-carrier to the target analyte are available, magnetic separation, which comprehends chemical properties, exceeds forms of separation based upon size and mass. Continuous analyte delivery and extraction for ambulatory apheresis is accomplished by means of a special higher volume analyte extraction jacket and a powerful magnet held in position at the body surface by a harness, such a jacket and suspension harness.

A relatively static means for extracting the targeted substance or cells without filtration or centrifugation, for example, significantly increases the potential for miniaturization essential for embodiment in an ambulatory system. Where analysis of harvested biopsy samples necessitates equipment too large even to house within a body pack, connection thereto is through a socket in a small port at the body surface.

In some instances, the targeting agent (see, for example, Contini, P., Negrini, S., Bodini, G., Trucchi, C., Ubezio, G., and 3 others 2017. "Granulocytes and Monocytes Apheresis Induces Upregulation of TGFβ1 [transforming growth factor beta-1] in Patients with Active Ulcerative Colitis: A Possible Involvement of Soluble HLA-I [human leukocyte antigen-I]," *Journal of Clinical Apheresis* 32(1):49-55; Mehta, J., Singhal, S., Gordon, L., Tallman, M., Williams, S., and 6 others 2002. "Cobe Spectra is superior to Fenwal C S 3000 Plus for Collection of Hematopoietic Stem Cells," *Bone Marrow Transplantation* 29(7):563-567; Thomas, L., Mansour, V., Jain, R., Kulcinski, D., Loefler, K., Carter, C., and Hardwick, A. 1995. "Use of the CS-3000 Plus to Prepare Apheresed Blood Cells for Immunomagnetic Positive Cell Selection," *Journal of Hematotherapy* 4(4):315-321).

When the endogenous or intrinsic substance or analyte eschews direct binding to magnetically susceptible carrier particles, binding is to a substance having an inherent selective affinity for the target endogenous substance. When introduced or reintroduced into the body, the magnetically susceptible carrier particle bound substance with an inherent affinity for a particular biological target or intracorporeal analyte seeks out and latches onto the target, making possible its extraction with the aid of a magnet. Substances that can be extracted from the blood by this means include cell types, inorganic atoms, and organic molecules, to include enzymes, hormones, other proteins, nucleotides, peptides, polypeptides, and introduced contrast, stain, dye, any of which may occasionally be radioactive.

The extracorporeal or in vitro binding of endogenous or other biological substances to magnetically susceptible particles in order to extract these or to extract analytes to which these bind with the aid of an external magnet as in immunomagnetic separation has been in use for decades and has undergone much progress, warranting ambulatory implementation (see, for example, Chen, P., Huang, Y. Y., Hoshino, K., and Zhang, X. 2014. "Multiscale Immunomagnetic Enrichment of Circulating Tumor Cells: From Tubes to Microchips," *Lab on a Chip* 14(3):446-458; Magbanua, M. J. and Park, J. W. 2013. "Isolation of Circulating Tumor Cells by Immunomagnetic Enrichment and Fluorescence-activated Cell Sorting (IE/FACS) for Molecular Profiling," *Methods* [San Diego, Calif.] 64(2):114-118; Herrmann, I. K., Schlegel, A., Graf; R., Schumacher, C. M., Senn, N., Hasler, M., Gschwind, S., and 5 others 2013. "Nanomagnet-based Removal of Lead and Digoxin from Living Rats," *Nanoscale* 5(18):8718-8723; Hoeppener, Swennenhuis, J. F., and Terstappen, L. W. 2012. "Immunomagnetic Separation Technologies," *Recent Results in Cancer Research* 195:43-58; Brimnes, M. K., Gang, A. O., Donia, M., Thor Staten, P., Svane, I. M., and Hadrup, S. R. 2012. "Generation of Autologous Tumor-specific T Cells for Adoptive Transfer Based on Vaccination, in Vitro Restimulation and CD3/CD28 Dynabead-induced T Cell Expansion," *Cancer Immunology Immunotherapy.* 61(8):1221-1231; Hermann, I. K., Bernabei, R. E., Urner, M., Grass, R. N., Beck-Schimmer, B., and Stark, W. J. 2011. "Device for Continuous Extracorporeal Blood Purification Using Target-specific Metal Nanomagnets," *Nephrology, Dialysis, Transplantation* 26(9):2945-2954; Yoshino, T., Maeda, Y., and Matsunag, T. 2010: "Bioengineering of Bacterial Magnetic Particles and Their Applications in Biotechnology," *Recent Patents in Biotechnology* 4(3):214-225; Takahashi, M., Akiyama, Y., Ikezumi, J., Nagata, T., Yoshino, T., Iizuka, A., Yamaguchi, K., and Matsunaga, T. 2009. "Magnetic Separation of Melanoma-specific Cytotoxic T Lymphocytes from a Vaccinated Melanoma Patient's Blood Using MHC/Peptide Complex-conjugated Bacterial Magnetic Particles," *Bioconjugate Chemistry* 20(2):304-309; Takahashi, M., Yoshino, T., Takeyama, H., and Matsunaga, T. 2009. "Direct Magnetic Separation of Immune Cells from Whole Blood Using Bacterial Magnetic Particles Displaying Protein G," *Biotechnological Progress* 25(1):219-226; Yoshino, T., Hirabe, H., Takahashi, M., Kuhara, M., Takeyama, H., and Matsunaga, T. 2008. "Magnetic Cell Separation Using Nano-sized Bacterial Magnetic Particles with Reconstructed Magnetosome Membrane," *Biotechnology and Bioengineering* 101 (3):470-477; Witzens-Harig, M., Hellmann, C., Hensel, M., Kornacker, M., Benner, A., Haas, R., Fruehauf, S., and Ho, A. D. 2007. "Long-term Follow-up of Patients with Non-Hodgkin Lymphoma Following Myeloablative Therapy and Autologous Transplantation of CD34+-selected Peripheral Blood Progenitor Cells," *Stem Cells* [Dayton, Ohio] 25(1): 228-235; Chen, H., Bockenfeld, D., Rempfer, D., Kaminski, M. D., and Rosengart, A. J. 2007. "Three-dimensional Modeling of a Portable Medical Device for Magnetic Separation of Particles from Biological Fluids," *Physics in Medicine and Biology* 52(17):5205-5218; Chen, H., Ebner, A. D., Bockenfeld, D., Ritter, J. A., Kaminski, M. D., Liu, X., Rempfer, D., and Rosengart, A. J. 2007. A Comprehensive in Vitro Investigation of a Portable Magnetic Separator Device for Human Blood Detoxification," *Physics in Medicine and Biology* 52(19):6053-6072; "Chen, H., Kaminski, M. D., Liu, X., Mertz, C. J., Xie, Y., Torno, M. D., and Rosengart, A. J. 2007. "A Novel Human Detoxification System Based on Nanoscale Bioengineering and Magnetic Separation Techniques," *Medical Hypotheses* 68(5):1071-1079; Gu, H., Xu, K., Xu, C., and Xu, B. 2006. "Biofimctional Magnetic Nanoparticles for Protein Separation and Pathogen Detection," *Chemical Communications* [Cambridge, England] 9:941-949; Ito, A., Shinkai, M., Honda, H., and Kobayashi, T. 2005. "Medical Application of Functionalized Magnetic Nanoparticles," *Journal of Bioscience and Bioengineering* 100(1):1-11; Kuhara, M., Takeyama, H., Tanaka, T., and Matsunaga, T. 2004. "Magnetic Cell Separation Using Antibody Binding with Protein A Expressed on Bacterial Magnetic Particles," *Analytical Chemistry* 76(21): 6207-6213; Hardwick, R. A., Kulcinski, D., Mansour, V., Ishizawa, L., Law, P., and Gee, A. P. 1992. "Design of Large-scale Separation Systems for Positive and Negative Immunomagnetic Selection of Cells Using Superparamagnetic Microspheres," *Journal of Hematotherapy* 1(4):379-386).

The ability to form secure junctions with vessels and miniaturization make possible the incorporation into a wearable pump-pack of apheretic techniques that allow magnetically nonsusceptible target substances to be bound to susceptible carriers endogenously in response to implanted sensor feedback under predictive control without the need for periodic return to the clinic for an invasive procedure. If the biological substance is bound to superparamagnetic nanoparticle or microparticle carriers, then once connected to the affinate, the analyte will have been rendered susceptible to a magnetic field. This makes it susceptible to seizure and resituation within the body by an impasse jacket and extraction from the body with the aid of a periductal electromagnet. A local extraction jacket incorporating an electromagnet can accomplish either or both actions.

Miniaturization and the ability imparted by ductus side-entry jackets to form secure junctions with vessels make possible apheretic techniques that facilitate connection to conventional apheresis and dialysis machines and open the way for the development of magnetic apheresis and dialysis, whereby endogenous magnetically nonsusceptible target substances bound to exogenous susceptible carriers are rendered magnetically extractable from the bloodstream. In such an implanted system, when extraction is not continuous, sensor feedback signals an implant microprocessor to initiate extraction without the need for periodic revisits to the clinic.

When the prognosis is for eventual recovery, only components that must be implanted are so, the rest incorporated into a wearable pump-pack. Binding the blood constituent in apheresis or type molecule in hemodialysis to a superparamagnetic nanoparticle or microparticle carrier renders the target cells or substance susceptible to a magnetic field. As described below, the extractate is flushed into the bladder or if the patient has no bladder, then into a kind of neobladder referred to as a confluence chamber for expulsion in the urine. Also in this manner, an errant miniball is made susceptible to seizure and resituation within the body by an impasse-jacket, or extraction from the body with the aid of a periductal electromagnet. A local extraction jacket incorporating an electromagnet can accomplish any of these actions.

Numerous substances have been prepared for such application (see, for example, Barbucci, R., Giani, G., Fedi, S., Bottari, S., and Casolaro, M. 2012. "Biohydrogels with Magnetic Nanoparticles as Crosslinker: Characteristics and Potential Use for Controlled Antitumor Drug-delivery," *Acta Biomaterialia* 8(12):4244-4252; Paulino, A. T., Pereira, A. G., Fajardo, A. R., Erickson, K., Kipper, M. J., Muniz, E. C., Belfiore, L. A., and Tambourgi, E. B. 2012. "Natural Polymer-based Magnetic Hydrogels: Potential Vectors for Remote-controlled Drug Release," *Carbohydrate Polymers* 90(3):1216-1225; Marszall, M. P. 2011. "Application of Magnetic Nanoparticles in Pharmaceutical Sciences," *Pharmaceutical Research* 28(3):480-483; Marszall, M. P., Moaddel, R., Kole, S., Gandhari, M., Bernier, M., land Wainer, I. W. 2008. "Ligand and Protein Fishing with Heat Shock Protein 90 Coated Magnetic Beads," *Analytical Chemistry* 80(19):7571-7575; Ito, A., Shinkai, M., Honda, H., and Kobayashi, T. 2005, Op cit.; Gupta, A. K. and Gupta, M. 2005. "Synthesis and Surface Engineering of Iron Oxide Nanoparticles for Biomedical Applications;" *Biomaterials* 26(18):3995-4021). Ultimately, drug-carrier particle binding, performed in vitro at the outset, will also be internalized with the use of extravascular jackets.

The magnet may be local in the form of an impasse jacket encircling the ductus, or if the anatomical clearance does not allow sufficient field strength, then an impasse jacket with support from patch-magnets, a powerful external tractive electromagnet, obtainable by connection to the $B_0$ magnet of a tomograph, for example, or these in combination. When the implanted jacket and any other magnets have sufficient field strength to hold the analyte, the completion of analyte resituation or extraction by an external neodymium iron boron permanent or an electromagnet can follow after an interval. The magnetically susceptible carrier varies in number according to the mass of the intracorporeal target, so that to target a certain type of blood cell so that it can be manipulated while intact on a one for one carrier to target basis requires a larger number per target than does the extraction of a nucleotide, for example.

A few examples of such counter-specific pairing, essentially pertinent to any situation wherein one substance effectively neutralizes or cancels out, or selectively fastens onto the receptors of another, to inactivate it are, the flow rate through the ductus and reaction time allowing, antigen-antibody, such as virus antibody, antibody-antigen, enzyme-substrate, substrate-enzyme, enzyme inhibitor-reversible enzyme inhibitor, hormone-receptor protein, and the relation mutuating between Type 1 and Type 2 cytokines. These same relations, along with reversal agents to neutralize drugs delivered through a jacket upstream, can be released from a downstream jacket to reverse the effect of endogenous substances or drugs.

Severe and intractable hypercholesterolemia such as familial, especially in instances of statin intolerance (see, for example, Zodda, D., Giammona, R., and Schifilliti, S. 2018. "Treatment Strategy for Dyslipidemia in Cardiovascular Disease Prevention: Focus on Old and New Drugs," *Pharmacy* (Basel, Switzerland) 6(1). pii: E10; Wang, A., Richhariya, A., Gandra, S. R., Calimlim, B., and Kim, L., and 3 others 2016. "Systematic Review of Low-density Lipoprotein Cholesterol Apheresis for the Treatment of Familial Hypercholesterolemia," *Journal of the American Heart Association* 5(7). pii: e003294; Lui, M., Garberich, R., Strauss, C., Davin, T., and Knickelbine, T. 2014. "Usefulness of Lipid Apheresis in the Treatment of Familial Hypercholesterolemia," *Journal of Lipids* 2014:864317; McGowan, M. P. 2013. "Emerging Low-density Lipoprotein (LDL) Therapies: Management of Severely Elevated LDL Cholesterol—The Role of LDL-apheresis," Journal of Clinical Lipidology 7(3 Supplement):S21-S26; Robinson, J. G. 2013. "Management of Familial Hypercholesterolemia: A Review of the Recommendations from the National Lipid Association Expert Panel on Familial Hypercholesterolemia," *Journal of Managed Care Pharmacy* 19(2):139-149; van Buuren, F., Kreickmann, S., Horstkotte, D, Kottmann, T., and Mellwig, K. P. 2012. "HELP [heparin-induced extracorporeal LDL precipitation] Apheresis in Hypercholesterolemia and Cardiovascular Disease: Efficacy and Adverse Events after 8,500 Procedures," *Clinical Research in Cardiology Supplements* 7:24-30; Health Quality Ontario 2007. "Low-density Lipoprotein Apheresis: An Evidence-based Analysis," *Ontario Health Technology Assessment Series* 7(5):1-101; Vella, A., Pineda, A. A., and O'Brien, T. 2001. "Low-density Lipoprotein Apheresis for the Treatment of Refractory Hyperlipidemia," *Mayo Clinic Proceedings* 76(10):1039-1046; Thompson, G. R. and Kitano, Y. 1997. "The Role of Low Density Lipoprotein Apheresis in the Treatment of Familial Hypercholesterolemia," *Therapeutic Apheresis* 1(1):13-16), can be ameliorated if not alleviated by ambulatory plasmapheresis that removes low and very low density lipoprotein refractory to conventional medication through the gradual automatic continuous infusion and extraction of magnetized C60 (fullerenes, buckminsterfullerenes) and/or other superparamagnetic iron oxide nanoparticles carrying ligands for these targets.

Diseased cells and analytes in the blood are usually a result, rather than the cause, of disease. Even when apheresis is used to remove diseased constituents of the blood such as malaria-infected red blood cells, the procedure is not remedial but rather symptomatic. Leukapheresis, for example, does not go to the source of leukocyte overproduction and therefore, while essential to treat leukostasis, cannot in itself be a cure (see, for example, Pastore, F., Pastore, A., Wittmann, G., Hiddemann, W., and Spiekermann, K. 2014, cited below in the section entitled Apheresis and Hemodialysis, Stationary with or without an Attendant, or Carryable, or Implanted Magnetic). Apheresis is usually intended to clear the bloodstream of an overburden of type cells such as leukocytes or erythrocytes, or of analytes, such as low density lipids and triglycerides and alleviate the further symptomatic consequences of such an excess.

With familial hypercholesterolemia, for example, these further consequences include rapidly progressive atherosclerotic degeneration and the need for a portocaval shunt, ileal bypass, or liver transplantation, all carrying risks and subject to procedural and later complications (see, for example, Bambauer, R., Olbricht, C. J., and Schoeppe, E. 1997. "Low-density Lipoprotein Apheresis for Prevention and Regression of Atherosclerosis: Clinical Results," *Therapeutic Apheresis* 1(3):242-248) and is not represented as going to the etiological cause of the disorder (see, for example, Ballard, K. D., Mali, E., Guo, Y., Bruno, R. S., Taylor, B. A., and 3 others 2016. "Single Low-density Lipoprotein Apheresis Does Not Improve Vascular Endothelial Function in Chronically Treated Hypercholesterolemic Patients," *International Journal of Vascular Medicine* 2016:4613202).

Because extraction can continue around the clock, the patient may be spared the need for a portocaval shunt or partial ileal bypass, both of which can result in adverse sequelae, if not the need for a liver transplant (see, for example, Schwartz, J., Padmanabhan, A., Aqui, N., Balogun, R. A., Connelly-Smith, L., and 5 others 2016. "Guidelines on the Use of Therapeutic Apheresis in Clinical Practice—Evidence-based Approach from the Writing Committee of the American Society for Apheresis: The Seventh Special Issue," *Journal of Clinical Apheresis* 31(3):149-162; Health Quality Ontario 2007, Op cit.; *The Merck Manual,* 18th Edition, 2006, page 1305), which necessitates the administration of immunocompromising drugs for life with the patient placed at risk of infection. Therapeutic plasmapheresis and hemapheresis subsume numerous cellular and autoimmune protein targets for extraction—essentially all those responsible for autoimmune disease. The extraction ferrofluid is pumped from its respective reservoir, infused through a simple junction jacket placed about the blood supply to the target organ or gland.

Unlike conventional plasmapheresis, replacement plasma is not needed, because only the target analyte or analytes are extracted, the rest of the plasma continuing to flow through the circulation. An infusate, such as a ferrofluid containing a substance with a natural affinity for the target analyte, or affiliate, bound to a magnetically susceptible carrier if needed, would be pumped from another reservoir through another such jacket. Potentially, any analyte which can be directly or indirectly bound to magnetically susceptible nanoparticles through an intermediary or mutually conjugative or agglutinative substance with a natural affinity for an innate target cell or molecule that causes disease can be used to scavenge the affinate and extracted from the passing blood by extraction-electromagnets with the strength to attract the particles.

With an autoimmune condition that attacks a particular organ or gland, such as type 1 diabetes, hemolytic anemia, myasthenia gravis, or Hashimoto thyroiditis, for example—dozens of serious disorders fall under this category—extraction jackets placed at the blood supply or in an array over the organ or gland removes the mutein or anomalous hemoglobin which is replaced with hemoglobin containing the normal form of the analyte through a simple junction jacket placed upstream. The brief interval and limited distance over which these scavenger particles are allowed to circulate substantially reduces if not eliminates any toxic consequences that would otherwise ensue were these allowed to remain in the bloodstream.

This factor fundamentally liberates the formulation of these particles. The corticosteroids, autoimmune medication, and anti-inflammatory drugs conventionally prescribed all pose significant problems. To extract an anomalous hemoglobin responsible for autoimmunity selective of a certain organ, gland, or type tissue, the intermediary conjugate, or natural affiliate for delivering the susceptible nanoparticle to the target may comprise a molecular substituent sufficient to effect bonding or an amount of the native target insufficient to neutralize the selectivity of the anomalous hemoglobin.

Where the endogenous substance cannot be used, the fact that the process is transient as to elude toxicity makes it possible to use any exogenous or synthetic substance that mutually bonds to the carrier and target analyte despite toxicological convention. Provided this can be extended to include immunoglobulin antibodies in plasma, automatic ambulatory intracorporeal plasmapheresis, whereby blood is not removed and then returned or replaced but continues to flow through the bloodstream during extraction without leaving the body is possible. Cytapheresis that delivers the cells to a reservoir allows the cells to be harvested and examined.

The period over which the apparatus can continue to deliver platelets and erythrocytes concurrent with leukapheresis by means of magnetic separation while a leukemic patient able to do so is free to move, for example, depends upon the rate volumes of extraction and delivery. These determine the volumes of infusates (infusants) that will require safe and portable reservoir storage for replenishment, as well as the volumes of any extractates accumulated by system flushing. This burden is reduced through the use of the same reservoir or reservoirs to accept all of the extractates as the infusate is depleted whether or not allowing the extractates to mix.

Siderophilous, or having an inherent affinity for the iron in erythrocytes or red blood cells, in polycythemia (erythrocytosis, polyemia, polyhemia), to include polycythemia vera, the superparamagnetic magnetite or maghemite predisposes the nanoparticles to bond with heme containing cells directly, rendering the erythrocytes susceptible to extraction erythrocytapheresis by means of magnetic separation. To extract cells not directly bound thus using one or more extraction-jackets to be described requires the bonding to the carrier of an intervening or interloper substance to which the cell does have a natural affinity. When introduced into the bloodstream in vivo, the target cells attach the natural affinate and therewith, the drug-carrier, and having been made magnetically susceptible, can be extracted. Automatic ambulatory apheresis using extraction-jackets such as shown in FIG. 15 can be applied to several different type target cells.

Automatic ambulatory magnetic extraction cytapheresis such as thrombocytapheresis (thrombapheresis, plateletpheresis, platelet apheresis, platelet separation), leukapheresis, and plasmapheretic processes which seeks to bind an analyte other than a type cell to a biological affinate bonded to a magnetically susceptible nanoparticle allows the nanoparticles to remain in the bloodstream over too small an interval and leave little if any potentially toxic residue. Because of this transience, analyte extraction by such means should not pose problematic toxicity as attributed to iron oxide-based nanoparticles when used as presumed in literature cited herein to any significant degree.

Where the volume of leukocytes is high but the patient is still able to function, an automatic ambulatory assist should allow a reduction in the frequency of visits to the clinic for centrifugation apheresis. In a leukemia, the malignant transformation of progenitor blood cells leads to anemia, thrombocytopenia, granulocytopenia, infiltration of tissue with diseased cells, and therewith, enlargement of the liver, lymph nodes, meninges, and other organs (see, for example, *The Merck Manual,* 18th Edition, page 1105). The flush-line is fed from a supply reservoir and pump in the pump-pack which is activated at the interval programmed to deliver the treated flushing fluid, wash water, or a hydrogel and carries off the cellular or other debris to a dump reservoir also in the pump-pack.

Leukapheresis is but one example of therapeutic cytapheresis which can be relegated to an automatic ambulatory system. Sickled erythrocytes and those affected by malaria, for example, can be extracted through noncentrifugal sedimentation erythrocytapheresis and replaced by normal cells (see, for example, *The Merck Manual,* 18th Edition, page 1143) infused through a simple junction jacket positioned upstream. Other type blood cells such as platelets or plasma can be extracted and/or infused in the same way. In an ambulatory system with leukocyte-detecting sensors under automatic control, the object is to liberate an ambulatory patient from frequent visits if not confinement to the clinic. Apheretic processes that require connection of a currently nonimplantable console are connected at the body surface port.

If necessary, the extractant (extractate) is withdrawn from such an impasse jacket through an extraction grating by a powerful external (extracorporeal) electromagnet. Low toxicity permitting, extraction is normally into adjacent tissue. However, since permanent magnets continue to hold the extractate, and higher volume extraction or apheresis generates debris that must be periodically purged, that is, flushed out through an expulsion line, jackets used thus incorporating an electromagnet. Encapsulation of the potentially carcinogenic exposed pole of an electromagnet in an implant is essential. The electromagnet is rigidly connected to the jacket shell with its proximal pole nuzzled in the fork of the double-arm type side-entry jacket with extraction trap flap-valve to be described used.

When intended primarily for higher volume magnetic apheresis such a leukapheresis, the chain of double-arm jackets, as shown in FIGS. 13 thru 15, will usually truncate the inner sides of the arms to create a collection chamber or trap along the flush-line that affords more space for the accumulation of debris as well as a landing for the small electromagnet, which can be deenergized when the flush pump is actuated. The use of an outer body vest or harness to position one or more magnets in facing relation to each jacket, thereby drawing higher volume extractates such as leukocytes in leukaperesis into the flush-line (wash out line, flush out line, flush through line, purge-line) line to the reservoir should be considered only when incorporation of a magnet into each jacket would pose too great a weight to implant in the patient.

Ambulatory Magnetic Intracorporeal Hemodialysis

While more intensive, that is, protracted and/or frequent hemodialysis appears to prolong life, patients resist self-treatment at home that would facilitate more intensive treatment. The reasons for this are primarily anxiety at the agitating sight of connection for vascular access to an extracorporeal machine and concern as to whether the machine settings are correct (see, for example, Ermer, T., Kopp, C., Asplin, J. R., Granja, I., Perazella, M. A., and 6 others 2017. "Impact of Regular or Extended Hemodialysis and Hemodialfiltration on Plasma Oxalate Concentrations in Patients with End-stage Renal Disease," *Kidney International Reports* 2(6):1050-1058; Cornelis, T., Eloot, S., Vanholder, R., Glorieux, G., van der Sande, F. M., and 4 others 2015. Protein-bound Uraemic Toxins, Dicarbonyl Stress and Advanced Glycation End Products in Conventional and Extended Haemodialysis and Haemodiafiltration," *Nephrology, Dialysis, Transplantation* 30(8):1395-1402; Cornelis, T., van der Sande, F. M., Eloot, S., Cardinaels, E., Bekers, O., and 3 others 2014. "Acute Hemodynamic Response and Uremic Toxin Removal in Conventional and Extended Hemodialysis and Hemodiafiltration: A Randomized Crossover Study," *American Journal of Kidney Diseases* 64(2): 247-256; Stokes, J. B. 2011. "Consequences of Frequent Hemodialysis: Comparison to Conventional Hemodialysis and Transplantation," *Transactions of the American Clinical and Climatological Association* 122:124-136) (see also, for example, Mathew, A., McLeggon, J. A., Mehta, N., Leung, S.2, Barta, V., McGinn, T., and Nesrallah, G. E. 2018. "Mortality and Hospitalizations in Intensive Dialysis: A Systematic Review and Meta-analysis," *Canadian Journal of Kidney Health and Disease* 5:2054358117749531; Nesrallah, G. E., Li, L., and Suri, R. S. 2016. "Comparative Effectiveness of Home Dialysis Therapies: A Matched Cohort Study," *Canadian Journal of Kidney Health and*

*Disease* 3:19; Palmer, S. C., Palmer, A. R., Craig, J. C., Johnson, D. W., Stroumza, P., and 5 others 2014. "Home Versus In-centre Haemodialysis for End-stage Kidney Disease," *Cochrane Database of Systematic Reviews* (11): CD009535).

Another deterrent to self-treatment is the time required for and risk of complications, to include infection and access failure, associated with a surgically created arteriovenous fistula to mature to the point of usability (see, for example, Tordoir, J. H. M., Zonnebeld, N., van Loon, M. M., Gallieni, M., and Hollenbeck, M. 2018. "Surgical and Endovascular Intervention for Dialysis Access Maturation Failure during and after Arteriovenous Fistula Surgery: Review of the Evidence," *European Journal of Vascular and Endovascular Surgery* 55(2):240-248; Siddiqui, M. A., Ashraff, S., and Carline, T. 2017. "Maturation of Arteriovenous Fistula: Analysis of Key Factors," *Kidney Research and Clinical Practice* 36(4):318-328; Bylsma, L. C., Gage, S. M., Reichert, H., Dahl, S. L. M., and Lawson, J. H. 2017. "Arteriovenous Fistulae for Haemodialysis: A Systematic Review and Meta-analysis of Efficacy and Safety Outcomes," *European Journal of Vascular and Endovascular Surgery* 54(4): 513-522; Allon, M. 2017. "Arteriovenous Grafts: Much Maligned but in Need of Reconsideration?," *Seminars in Dialysis* 30(2):125-133; Jeong, H. Y., Ko, E. J., Kim, S. H., Lee, M. J., Cho, H. J., Yang, D. H., and Lee, S. Y. 2017. "Administration of a High-dose Erythropoietin-stimulating Agent in Hemodialysis Patients is Associated with Late Arteriovenous Fistula Failure," *Yonsei Medical Journal* 58(4):793-799; Hu, H., Patel, S., Hanisch, J. J., Santana, J. M., Hashimoto, T., and 7 others 2016. "Future Research Directions to Improve Fistula Maturation and Reduce Access Failure," *Seminars in Vascular Surgery* 29(4):153-171; Bashar, K., Conlon, P. J., Kheirelseid, E. A., Aherne, T., Walsh, S. R., and Leahy, A. 2016. "Arteriovenous Fistula in Dialysis Patients: Factors Implicated in Early and Late AVF [arteriovenous fistula] Maturation Failure," *Surgeon* 14(5): 294-300). Here vascular access through a small port at the body surface in communication with dictus side-entry jackets at the artery and vein is established at the outset. Yet another deterrent to conventional dialysis is the time required; an ambulatory system that functions continuously eliminates the need for treatments that take hours of time that could otherwise have been used productively.

Responsive to these concerns, provision of a small port at the body surface which directly communicates with the venous tree through a ductus side-entry jacket little different than inserting a plug into an electrical outlet, and control by an implanted sensor-driven microprocessor, materially lessen if not eliminates these deterrents. Intracorporeal hemodialysis is accomplished with ductus side-entry jackets lacking a magnet and elastic slit-membrane but incorporating a semipermeable membrane simple or comprised of many fibers, so that the venous blood in the inferior vena cava flows craniad, while the dialysate in the flush-line, pressurized by an implanted pump, flows caudad. The means for releasing drugs and replacing minerals removed from the blood during dialysis are the same as for drugs and other substances covered above and below.

The average largest diameter of leukocytes 6 to 8 micrometers or microns, that of red blood cells 6.2-8.2 micrometers, and that of platelets 2 to 3 micrometers; blood cells are much larger than molecular constituents in the blood. At 0.26 nanometers, urea molecules, for example, are much smaller, so that when the kidneys fail, these must be removed by means of dialysis. The system is directed to intracorporeal hemodialysis; for continuous ambulatory peritoneal dialysis, the exit site is capped off with a small cutaneous port positioned to a side of the mons pubis, eliminating the need for a dressing and frequent cleaning to prevent infection.

Magnetic dialysis is dependent upon the ability to target blood constituents for bonding to or compounding with magnetically susceptible carriers delivered into the blood in a ferrofluid introduced through a small port at the body surface. Magnetic dialysis differs from magnetic apheresis in the use of a semipermeable membrane or large assemblage of tiny semipermeable fibers. Membranes with apertures large enough to pass blood cells would pass blood nonselectively, that is, would also allow plasma, to include molecular constituents not bonded to a magnetic carrier, to pass into the flush-line.

By comparison, an elastic slit-valve opens only when the accumulated pull on the blood cells drawn to the magnet is great enough to allow the cells bonded to a magnetic carrier to push through and into the flush-line, after which the slit-valve immediately closes, cutting off all but trace amounts of plasma from entry. Thus, as in conventional modes of dialysis, the means of separation must depend upon a semipermeable membrane or large assemblage of tiny semipermeable fibers. Plasma exchange is by binding all constituent for removal to a susceptible carrier and introducing the donor plasma through the body surface port.

Convective modalities to include haemofiltration, haemodiafiltration, and acetate-free biofiltration more complex, difficult and costly to miniaturize, and not established as superior to conventional hemodialysis (see, for example, Buchanan, C., Mohammed, A., Cox, E., Köhler, K., Canaud, B., and 4 others 2017. "Intradialytic Cardiac Magnetic Resonance Imaging to Assess Cardiovascular Responses in a Short-term Trial of Hemodiafiltration and Hemodialysis," *Journal of the American Society of Nephrology* 28(4):1269-1277; Ermer, T., Kopp, C., Asplin, J. R., Granja, I., Perazella, M. A., and 6 others 2017, Op cit.; Nistor, I., Palmer, S. C., Cornelis, T., Eloot, S., Vanholder, R., Glorieux, G., van der Sande, F. M., and 4 others 2015, Op cit.; Craig, J. C., Saglimbene, V., Vecchio, M., Covic, A., and Strippoli, G. F. 2015. "Haemodiafiltration, Haemofiltration and Haemodialysis for End-stage Kidney Disease," *Cochrane Database of Systematic Reviews* 2015 (5):CD006258; Nistor, I., Palmer, S. C., Craig, J. C., Saglimbene, V., Vecchio, M., Covic, A., and Strippoli, G. F. 2014. "Convective Versus Diffusive Dialysis Therapies for Chronic Kidney Failure: An Updated Systematic Review of Randomized Controlled Trials," *American Journal of Kidney Diseases* 63(6):954-967; Wang, A. Y., Ninomiya, T., Al-Kahwa, A., Perkovic, V., Gallagher, M. P., Hawley, C., and Jardine, M. J. 2014. "Effect of Hemodiafiltration or Hemofiltration Compared with Hemodialysis on Mortality and Cardiovascular Disease in Chronic Kidney Failure: A Systematic Review and Meta-analysis of Randomized Trials," *American Journal of Kidney Diseases* 2014 63(6):968-978; Rabindranath, K. S., Strippoli, G. F., Daly, C., Roderick, P. J., Wallace, S., and MacLeod, A. M. 2006. "Haemodiafiltration, Haemofiltration and Haemodialysis for End-stage Kidney Disease," *Cochrane Database of Systematic Reviews* (4):CD006258), the preferability of adapting conventional hemodialysis to the conditions of extreme space constraint is plainly indicated.

In a patient requiring both leukapheresis and dialysis (see, for example, Bojanic, I., Mazic, S., Rajic, L., Jakovljevic, G., Stepan, J., and Cepulic, B. G. 2017. "Large Volume Leukapheresis is Efficient and Safe Even in Small Children Up to 15 Kg Body Weight," *Blood Transfusion* 15(1):85-92; Tapper, E. B., Luptakova, K., Joyce, R. M., and Tzachanis, D. 2014. "A 78-year-old Man with Acute Myeloid Leukemia (AML) and Acute Renal Failure," *American Journal of Case Reports* 15:364-367; Pastore, F., Pastore, A., Wittmann, G., Hiddemann, W., and Spiekermann, K. 2014, Op cit.), chain extraction jackets for apheresis and dialysis are usually separate, jackets of either type not alternated along the same chain.

The flush-line for apheresis usually circulates water, that for dialysis a dialysate. In such a patient, electromagnet and slit valve-equipped individual magnetic separation-type extraction jackets for apheresis do not alternate with those for hemodialysis in the same chain. Instead, a separate chain of membrane jackets, more numerous than those needed for apheresis, running along the contralateral side of the inferior vena cava is needed to achieve the overall blood-dialysate interface permeable membrane surface area essential for dialysis. Both empty through a nonjacketing side-entry connector into the urinary bladder, or if the patient has no bladder, then into a confluence chamber serving as a neo-bladder for expulsion through a drainage line into a conventional bathroom receptacle or a collection bottle cinched about a thigh, for example.

Replacement of flush-line fluid is from a flat reservoir positioned subdermally in the pectoral area or if a larger volume is needed, then from a storage container cinched about a thigh, for example. Conventional means for dialysis cannot simply be reduced in size for implantation and intracorporeal function. To significantly increase the surface area of the semipermeable membrane separating the bloodstream from the dialysate following through the jacket along the flush-line, ductus side-entry jackets with electromagnet for hemodialysis are elongated parallel to the axis of the ductus and multifiber compound membranes used. FIGS. 13 thru 15 omit accessories channels on the presumption that the function thereof during placement and to deliver drugs to the site can be performed by the dialysate; where this is not the case, accessory channels connected to the port at the body surface are provided.

For example, the surface area of the semipermeable membrane in extracorporeal dialyzers is or exceeds 1.2 square meters in area. A surface area of this size cannot be achieved using even a large number of simple small diameter flat membranes (see, for example, Chowdhury, N. S., Islam, F. M. M., Zafreen, F., Begum, B. A., Sultana, N., Perveen, S., and Mahal, M. 2011. "Effect of Surface Area of Dialyzer Membrane on the Adequacy of Haemodialysis," *Journal of Armed Forces Medical College of Bangladesh* 7(2):9-11).

To compensate for this diffusion or filtration surface area, too large to be implanted, magnetic separation hemodialysis continues as long as necessary and uses multiple membrane extraction jackets in a chain, each membrane having a relatively small surface area but supported by magnetic traction as a means for forcibly pulling the target analytes or solutes through the membrane. Such requires bonding or compounding the analytes to be extracted—primarily urea and creatinine—with magnetically susceptible carrier nano- or microparticles.

While the goal in placing a fully implanted automatic adaptive means of hemomdialysis is to fully support the function of renal replacement, restriction in surface area that restricts this but significantly increases the duration, and therewith, the intensity of treatment and reduces the size of dips and peaks in the blood concentration levels of toxic substances, as well as the frequency and time a patient must spend in the clinic constitutes a material improvement in the quality of life. Intensity can be further increased combination with continuous ambulatory peritoneal dialysis where much of the risk of infection is avoided through the use of a cutaneous port, which should significantly reduce peritonitis.

Continuous ambulatory dialysis is limited in the time it can remain in use, primarily by noninfectious complications such as dialysate leakage, catheter dysfunction, and rarely, sclerosing encapsulating peritonitis, which can lead to secondary bowel obstruction. Where complications associated with continuous ambulatory peritoneal dialysis inevitably interfere with peritoneal dialysis (see, for example, Obaid, O., Alhalabi, D., and Ghonami, M. 2017. "Intestinal Obstruction in a Patient with Sclerosing Encapsulating Peritonitis," *Case Reports in Surgery* 2017:8316147; Candido Pde, C., Werner Ade, F., Pereira, I. M., Matos, B. A., Pfeilsticker, R. M., Silva, R. F. 2015. "Sclerosing Encapsulating Peritonitis: A Case Report," *Radiologia Brasileira* 48(1):56-58; Stuart, S., Booth, T. C., Cash, C. J., Hameeduddin, A., Goode, J. A., Harvey, C., and Malhotra, A. 2009. "Complications of Continuous Ambulatory Peritoneal Dialysis," *Radiographics* 29(2):441-460; Xu, P., Chen, L. H., and Li, Y. M. 2007. "Idiopathic Sclerosing Encapsulating Peritonitis (or Abdominal Cocoon): A Report of 5 Cases," *World Journal of Gastroenterology* 13(26):3649-3651), intracorporeal magnetic dialysis can serve as a substitute.

Where other noninfectious complications arise which are remediable in less time than sclerosing encapsulating peritonitis but prohibits continuous ambulatory peritoneal dialysis, such as hernia, dialysate leakage, and catheter dysfunction, fully implanted automatic magnetic hemodialysis can serve as a bridge to reduce the frequency and/or duration of conventional dialysis. Regardless of any such combination, the system sensors and microprocessor inherently record pertinent data which can be read out during visits or transmitted to the clinic, and, can signal a significant deviation from normal blood solute concentration values at any time.

For implantation, the material of the semipermeable membranes used—especially given the forcible means employed—must have great strength, a long service life, and allow many washing cycles. An alternative implantable microdialysis concept, which microfluidic channel-based is otherwise completely different to include the overall conformation of the membrane, has found water-permeable nanoporous filtering membranes which eliminate the need for a dialysate made of polyethersulfone to be effective (Ota, T., To, N., Kanno, Y., and Mild, N. 2016. "Evaluation of Biofouling for Implantable Micro Dialysis System," *Proceedings of the Institute of Electrical and Electronics Engineers Engineering in Medicine and Biology Society Annual International Conference* 2016:1942-1945; To, N., Sanada, I., Ito, H., Prihandana, G. S., Morita, S., Kanno, Y., and Miki, N. 2015. "Water-permeable Dialysis Membranes for Multi-layered Microdialysis System," *Frontiers in Bioengineering and Biotechnology* 3:70; To, N., Sanada, I., Ito, H., Morita, S., Kanno, Y., and Mild, N. 2015. "Development of Implantable Hemodialysis System Using PES [polyethersulfone] Membranes with High Water-permeability," *Proceedings of the Institute of Electrical and Electronics Engineers Engineering in Medicine and Biology Society Annual International Conference* 2015:1194-1197).

Another concept using a hollow fiber polymer and silicon nanopore membrane, also of different conformation, has established the utility of silicon nanoporous membranes with a highly monodisperse pore size distribution (Kim, S., Fissell, W. H., Humes, D. H., and Roy, S. 2015. "Current Strategies and Challenges in Engineering a Bioartificial Kidney," *Frontiers in Bioscience* (Elite edition) 7:215-228;

Fissell, W. H., Fleischman, A. J., Humes, H. D., and Roy, S. 2007. "Development of Continuous Implantable Renal Replacement: Past and Future," *Translational Research* 150 (6):327-336). Another membrane material stated to protect against protein-bound plasma toxins (addressed below) has been reported (Pavlenko, D., van Geffen, E., van Steenbergen, M. J., Glorieux, G., Vanholder, R.4, Gerritsen, K. G., and Stamatialis, D. 2016. "New Low-flux Mixed Matrix Membranes that Offer Superior Removal of Protein-bound Toxins from Human Plasma," *Scientific Reports* 6:34429).

Also important for patients with impaired cardiovascular function, or cardiorenal syndrome, is the ability of the membrane to reduce elevated levels of protein-bound uremic toxins (Yamamoto, S., Sato, M., Sato, Y., Wakamatsu, T., Takahashi, Y., and 9 others 2018. "Adsorption of Protein-bound Uremic Toxins through Direct Hemoperfusion with Hexadecyl-immobilized Cellulose Beads in Patients Undergoing Hemodialysis," *Artificial Organs* 42(1):88-93; Saum, K., Campos, B., Celdran-Bonafonte, D., Nayak, L., Sangwung, P., and 3 others 2018. "Uremic Advanced Glycation End Products and Protein-bound Solutes Induce Endothelial Dysfunction through Suppression of Krüippel-like Factor 2," *Journal of the American Heart Association* 7(1). pii: e007566; Lai, J., Akindavyi, G., Fu, Q., Li, Z. L., Wang, H. M., and Wen, L. H. 2018. "Research Progress on the Relationship between Coronary Artery Calcification and Chronic Renal Failure," *Chinese Medical Journal* (English edition) 131(5):608-614; Pavlenko, D., Giasafaki, D., Charalambopoulou, G., van Geffen, E., Gerritsen, K. G. F., Steriotis, T., and Stamatialis, D. 2017. "Carbon Adsorbents with Dual Porosity for Efficient Removal of Uremic Toxins and Cytokines from Human Plasma," *Scientific Reports* 7(1):14914; Deltombe, O., de Loor, H., Glorieux, G., Dhondt, A., Van Biesen, W., Meijers, B., and Eloot, S. 2017. "Exploring Binding Characteristics and the Related Competition of Different Protein-bound Uremic Toxins," *Biochimie* 139:20-26; Maheshwari, V., Thijssen, S., Tao, X., Fuertinger, D., Kappel, F., and Kotanko, P. 2017. "A Novel Mathematical Model of Protein-bound Uremic Toxin Kinetics during Hemodialysis," *Scientific Reports* 7(1):10371; Pavlenko, D., van Geffen, E., van Steenbergen, M. J., Glorieux, G., Vanholder, R.4, Gerritsen, K. G., and Stamatialis, D. 2016, Op cit.; Deltombe, O., Van Biesen, W., Glorieux, G., Massy, Z., Dhondt, A., and Eloot, S. 2015. "Exploring Protein Binding of Uremic Toxins in Patients with Different Stages of Chronic Kidney Disease and during Hemodialysis," *Toxins* (Basel, Switzerland) 7(10):3933-3946; Ito, S. and Yoshida, M. 2014. "Protein-bound Uremic Toxins: New Culprits of Cardiovascular Events in Chronic Kidney Disease Patients," *Toxins* (Basel, Switzerland) 6(2): 665-678; Rossi, M., Campbell, K. L.2, Johnson, D. W., Stanton, T., Vesey, D. A., and 6 others 2014. "Protein-bound Uremic Toxins, Inflammation and Oxidative Stress: A Cross-sectional Study in Stage 3-4 Chronic Kidney Disease," *Archives of Medical Research* 2014 45(4):309-317).

In intracorporeal magnetic dialysis, blood is not removed from the body, and no extracorporeal machine is used, so that a blood pump and other components of a dialyzer needed to condition the blood is not used. Instead, the blood is pumped by the heart, so that when the chain extraction jackets to be described are connected to the abdominal aorta, for example, the blood pressure would be systolic-variable and when connected to the inferior vena cava, for example, would be diastolic-variable. Because the larger variation in pressure in the aorta would tend to interfere with passage through the membrane, the lower pressure in the inferior vena cava is usually preferable.

Pressurization of the dialysate can only be increased to the point where magnetic separation is overcome by sweeping the analyte targeted for extraction past the openings in the membrane. Optimization of the surface area depends upon the type dialysis as the choice of haemodiafiltration, haemofiltration, and haemodialysis; pressurization of the dialysate; and conformation of the permeable membrane or multifiber filter. A surgical fistula for vascular access requiring weeks if not months to mature to usability, necessitating delay until hemodialysis can commence in a normal manner, a quick plug-in connection means eliminates this impediment.

c. Intravascular Valves and Servovalves

Intravascular, or endoluminal, valves and servovalves, or diverion jackets, are ductus side-entry jackets which incorporate a reciprocable, that is, retractable and advanceable, or extendable, tongue, or diversion chute, to draw off all or a part of the flow through the substrate ductus, or that to which the jacket is attached. Such valves can be used, for example, to divert flow through a ureter into a drainage line and prosthetic bladder, or neobladder, or into a collection bag usually cinched about a thigh. Numerous shunting and bypass applications involve the controllable diversion or partial diversion of blood from a vessel through a length of tubing and into another vessel. To prevent injury to or leaks from the substrate ductus, the diversion chute must be completely enclosed within the ductus side-entry jacket.

Overall, ductus-side entry jackets are essential for long term secure and leak-free connection to ductus for any purpose requiring direct access to the lumen of the ductus. This is true from a basic central line to the implementation of an automatic ambulatory adaptive disorder response system and the provision of intravascular valves and servovalves. In intracorporeal magnetized hemodialysis as depicted in FIGS. 13 thru 15, 39A, and 39B, pole-facing target analyte magnetic extraction jackets are more efficient; nevertheless, where space does not allow, an intravascular valve diversion jacket such as that shown in FIG. 41 equipped with an electromagnet having its pole aligned to the long axis of the valve and magnetic separation elastic slit valve or semipermeable fiber bundle and flush line allows magnetized analytes targeted for extraction to be diverted to an extracorporeal collection bottle, or urinal, or to a ureteral takeoff confluence chamber such as that shown in FIGS. 40 and 43 when the magnet is deenergized.

The controlling microprocessor must reverse current flow to the electromagnet frequently enough to eliminate any remanence, or residual magnetization. This is not so, however, for leukapheresis, where the volume of cells to be extracted will clog the valve. Intravascular valves adjust the cross section of the native lumen for flow-through by adjustably occlusive diversion into another vessel, or if the diversion path is intentionally blocked (plugged, blind-ended), then by restricting flow, whereas a sphincteric, that is, perivascular, or periductal rather than intravascular, jacket such as that shown in FIG. 11, compresses the vessel from without, round and about. Both are provided with sufficient protective foam, part number 3, to prevent injurious compression of the adventitia.

An intravascular valve or diversion-type jacket or a sphincteric jacket additionally provides at least one accessory channel which can be used to directly target drugs or an anticoagulant into the jacketed vessel. For example, insulin can be delivered directly into the portal vein. Of the following three basic types of intravascular valves, only those solenoid actuated are limited to bistable or binary operation, that is, allow movement only from the fully open to the fully closed position and the reverse. Continuously variable, the manual and linear motor-driven valves can also be used to move the chute all the way in or out.

Intravascular valve-type ductus side-entry jackets acting as manually adjusted diversion valves can be made to adjust and divert all or a portion of the flow through a ureter or vessel, and by closing off the diversion path, act as choke valves, or servochokes to adjust hemotension:

1. Manually in a continuously variable, or from an all open to an all closed position or the reverse, usually by means of a push/pull or Cowden cable with a control incorporated into the body surface port. Control thus is suitable for allowing a patient with nocturia, for example, to switch and thus divert normal ureteral flow away from the native urinary bladder and into a collection bladder cinched about a thigh, or if the lower urinary tract is malformed, deformed, or missing, then into a collection bladder or a prosthetic, or neobladder, instead.

Applied along the vascular tree, continuously variable control of an intravascular valve allows adjustment in hemotension, either by diverting a portion of the flow into another usually larger vessel or by extension of the tongue or chute into the vessel lumen to reduce the cross section available for flow. Sphincteric jackets can accomplish a banding type function, but by adjustably constricting the substrate vessel rather than partially obstructing flow-through. This may be to reduce shear stress, expedite healing, adjust the apportionment of blood to different portions of an organ in preparation for a surgical procedure, or reduce the flow rate and increase the pressure to increase the uptake of a magnetically susceptible micro- or nanoparticle-carried drug by a magnetized ductus side-entry jacket.

In a constant perfusion/zero ischemic time sudden switch solid organ transplantation, for example, simultaneous manual switching by the operator and one or two assistants of intravascular diversion valves on the supply and drainage vessels of the recipient's organ from fully open to fully diverted causes the circulation of the recipient to be switched from the defective organ of the recipient to that of an irreversibly comatose, or 'brain-dead,' donor. Where the donor cannot be positioned beside the recipient, more recent means for transporting organs without significant interruption in perfusion or extended refrigeration are used. Sudden switch heart and liver transplantation in prenates and adults are cited as functions allowed by intravascular valves to be elaborated upon in greater detail.

The highly elastic accordioned tubing used to connect the diversion jacket intravascular valves to the recipient and corresponding donor vessels is additionally coiled to assume the shortest length, or contract, once the donor organ is positioned in the recipient. Then, because these, as do all ductus side-entry jackets, have as the primary object the safe, secure, and long-term if not lifelong connection to the substrate ductus, the jacket-vessel connections can either remain connected through the diversion jackets and the stumps anastomosed, or if the recipient vessels are diseased or have been avulsed due to an injury, the synthetic lines and connections are left in place and the patient closed.

Once the anastomoses are completed, the fluid lines connecting the jackets can be removed and the jackets left in place permanently to support the anastomoses with medication injected through the accessory channels, each with respective opening in the surface port; which will usually be positioned subcutaneously in the pectoral region. Allowing permanence, the subdermally positioned port allows the injection of antimicrobials, anti-inflammatories, anticoagulants, and/or thrombolytics, for example, for direct targeting to the treatment site through the accessory channel or channels of each side-entry valve jacket. The same technique is used to perform a constant perfusion/zero ischemic time carotid endarterectomy, carotid aneurysmal repair, or an extracardiac transposition of the great vessels, for example, where the jackets and hypoallergenic tubing likewise contracts to the shortest length short of pulling at the ends and so can remain.

2. From fully open to fully closed and the reverse by means of plunger solenoids actuated with a common switch by the operator or an assistant. This is used when more diversion valves on several vessels, some deep, or running beneath another organ and more difficult to access must be switched simultaneously than the operator, even with the aid of one or more assistants, will be able, or 3. By means of a microminiature linear motor or tiny piston, usually as an intravascular servovalve under the direct control of the system master node microprocessor in response to hemotension detecting sensor input.

Exemplary Applications

Urinary Diversion by Ureteral Takeoff

The advantages of intravascular valve diversion jackets largely derive from the ability to directly target medication through the jacket mainline and sideline (accessory channel, service channel) or sidelines (accessory channels, service channels) to the treatment site. The overall arrangement of a urinary diversion system with takeoff at the ureters is schematically depicted in FIG. 40, with a diversion valve shown in FIG. 41. As seen in FIG. 41, to commit a larger cross section through the mainline for flow through the substrate ductus, here a ureter, the accessory channel 11 courses along the bottom center of the diversion chute 111 and ends at the distal tip of the diversion chute just short of the ostium obturator 116 to empty into the substrate ductus just beneath the diversion chute. To reach the urothelium above the level of the chute, a basic ductus side-entry jacket with one or more accessory channels is used.

Accessory channels allow immediate treatment of adverse tissue and stenotic reactions upon placement as well as direct access to treat infection and clear clogging as long as the valve remains in use. While medication can also be delivered to the site through the mainline, this results in significant dilution of the drug, which may be costly. The valve shown in FIG. 41 is readily adapted to incorporate one or more additional accessory channels to reach the outside of the substrate ductus and not just the ureteral lumen and urothelium. Larger accessory channels can also be used to pass through cabled devices such as fiberoptic into the native lumen for diagnosis or therapy.

Ureteral takeoff pertains to obstruction in the lower urinary tract; percutaneous nephrostomy remains the recommended procedure when obstruction is intrarenal. Diversion valves have at least one accessory channel available to deliver medication and/or a crystal solvent into the line leading from the valve to the small outlet port positioned to a side of mons pubis. In this case, the inferior position of the port requires that a second port, typically in the pectoral region be that used to inject management agents. If only a urinary diversion requires treatment, a conventional porta-cath or mediport can be used.

In a patient with impaired or missing urinary bladder, distal segment of the ureters, or a portion of the lower urinary tract distal to the bladder, for example, nonadjustable intravascular, or endoluminal, valves allow the diverted drainage of urine directly from the ureters into a prosthetic bladder, or neobladder, or into an external collection-bag. In a patient with intractable nocturia, for example, where diversion is sought only during sleep, the patient can extend the valve chutes into the ureteral lumen for diversion with a simple turning knob on the cutaneous port positioned to a side of the mons pubis to which the drainage hose is connected leading to the collection bag.

Applications for ureteral takeoff range from a relatively innocuous nocturia in a patient who can void normally but wishes not to be aroused during sleep, where the patient uses a switch to divert urine from the lower tract before retiring for the night, to cases of severe bodily injury and surgical exenteration, or evisceration for pelvic cancer which has metastasized to neighboring structures, a radical cystectomy responsive to an intractably painful interstitial cystitis (bladder pain syndrome), or a bladder exstrophy, the anatomy to allow normal elimination then having been lost or unusably malformed. Ureteral takeoff can replace a percutaneous nephrostomy, or diversion directly from one or both kidneys regardless where disease, obstruction, or loss has occurred caudally along the urinary tract, or a urostomy, or drainage from the ureters into a harvested and tubulated length of ileum leading to a surface stoma when the kidneys and upper ureters are intact.

A nephrostomy poses a significant maintenance burden, to include changing the dressing at least weekly, or whenever it becomes wet, the latter interfering with normal bathing, and while major complications are relatively uncommon, poses some risks (see, for example, Lessne, M. L., Holly, B., Huang, S. Y., and Kim, C. Y. 2015. "Diagnosis and Management of Hemorrhagic Complications of Interventional Radiology Procedures," *Seminars in Interventional Radiology* 32(2):89-97; Degirmenci, T., Gunlusoy, B., Kozacioglu, Z., Arslan, M., Ceylan, Y., Ors, B., and Minareci, S. 2013. "Utilization of a Modified Clavien Classification System in Reporting Complications after Ultrasound-guided Percutaneous Nephrostomy Tube Placement: Comparison to Standard Society of Interventional Radiology Practice Guidelines," *Urology* 81(6):1161-1167; Carrafiello, G., Laganà, D., Mangini, M., Lumia, D, Recaldini, C., and 5 others 2006. "Complications of Percutaneous Nephrostomy in the Treatment of Malignant Ureteral Obstructions: Single-centre Review," *Radiologia Medica* 111(4):562-571; Lewis, S and Patel, U. 2004. "Major Complications after Percutaneous Nephrostomy—Lessons from a Department Audit," *Clinical Radiology* 4 59(2):171-179; Radecka, E. amf Magnusson, A. 2004. "Complications Associated with Percutaneous Nephrostomies. A Retrospective Study," *Acta Radiologica* 45(2): 184-188; Kaskarelis, I. S., Papadaki, M. G., Malliaraki, N. E., Robotis, E. D., Malagari, K. S., and Piperopoulos, P. N. 2001. "Complications of Percutaneous Nephrostomy, Percutaneous Insertion of Ureteral Endoprosthesis, and Replacement Procedures," *Cardiovascular and Interventional Radiology* 24(4):224-228).

A urostomy poses a long term risk of degenerative transition or metaplasia to a cancerous condition of the ileal conduit and neobladder, also fabricated from gut, which not lined by urothelium, is irritated by urine, such as an Indiana pouch, and the peristoma is easily irritated (see, for example, Bell, M. A., Wright, E. J., Fang, S. H., Johnson, M. H., and Sopko, N. A. 2018. "Management of Advanced Adenocarcinoma in Indiana Pouch Urinary Diversion," *Urology Case Reports* 17:53-55; Sherman, B. and Taylor, F. 2017. "Adenocarcinoma in a Koff Urinary Ileal Diversion," *Urology Case Reports* 13:126-127; Prcic, A. and Begic, E. 2017. "Complications after Ileal Urinary Derivations [Diversions]," *Medical Archives* (Sarajevo) 71(5):320-324; Jian, P. Y., Manka, M. G., Santoni, C., Wright, E. J., and Gearhart, S. L. 2015. "Tubular Adenoma in the Indiana Pouch of a Patient with a History of Bladder Exstrophy," *Urology Case Reports* 3(5):141-142; Godoy, G., Coburn, M., Lynch, G., Ro, J. Y., and 3 others 2012. "Adenocarcinoma Following Urinary Diversion," *Canadian Urological Association Journal* 6(2): E77-E80; Szymanski, K. M., St-Cyr, D., Alam, T., and Kassouf, W. 2010. "External Stoma and Peristomal Complications following Radical Cystectomy and Ileal Conduit Diversion: A Systematic Review," *Ostomy/Wound Management* 56(1):28-35; Rolstad, B. S. and Erwin-Toth, P. L. 2004. "Peristomal Skin Complications: Prevention and Management," *Ostomy/Wound Management* 50(9):68-77; Simeone, C., Antonelli, A., Tonini, G., and Cunico, S. C. 2003. "Ileal Conduit and Urinary Stoma Complications," (in Italian with English abstract at Pubmed), *Archivio Italiano di Urologia, Andrologia* 75(1):6-9; Yamada, Y., Fujisawa, M., Nakagawa, H., Tanaka, H., Gotoh, A., and 3 others 1998. "Squamous Cell Carcinoma in an Ileal Conduit," *International Journal of Urology* 5(6):613-614; Banigo, O. G., Waisman, J., and Kaufman, J. J. 1975. "Papillary (Transitional) Carcinoma in an Ileal Conduit," *Journal of Urology* 114(4):626-627).

Cardiovascular procedures such as the first three listed below should be accomplished with manually operated ductus side-entry intravascular diversion valves if and only if the valves can be switched quickly as to approach simultaneity, such as when the operator and an assistant coordinate their action. Otherwise, simultaneous operation is accomplished through the use of valves incorporating a tiny plunger solenoid controlled from the same switch. By contrast, intravascular valves used to adjust hemotension as addressed by the fourth type procedure listed below are usually equipped with a microminiature linear motor capable of precise shifts in position and are servovalves controlled by the master node microprocessor on the basis of negative feedback received, for example, from strain gauge biosensors.

In the vascular tree, intravascular valves make possible temporary and permanent controllable shunts and bypasses to allow, for example:

1. Bypassing the carotid bifurcation so that full flow through both the internal and external carotids is substantially uninterrupted and oxygenation unreduced throughout a carotid endarterectomy or aneurysmal repair. When the native vessels are incompetent, the bypass is left in place indefinitely or only the jackets left in place to directly target medication to the treatment site introduced through a port at the body surface.

2 Extracardiac transposition of the great vessels with zero ischemic or interrupted perfusion time.

3. Sudden switch solid organ transplantation with zero ischemic or interrupted perfusion time 4. Modulating the volume, rate, and pressure of flow through a vessel by partial diversion of flow to another proximal vessel, usually one of larger caliber.

1. Bypassing the Carotid Bifurcation

In a conventional carotid endarterectomy, a shunt inserted midprocedurally into the common carotid and through the internal carotid artery to sustain blood flow and thereby avoid an ischemic stroke diverts blood from the external carotid and obstructs the operative field by overlying plaque on the far or reverse side of the shunt (see, for example, Chung, J. and Dodson, T. F. 2011. "Surgical Treatment of Carotid and Peripheral Vascular Disease," in Fuster, V., Walsh, R. A., Harrington, R. A. (eds.), *Hurst's The Heart*, 13th edition, New York, N.Y.: McGraw-Hill; pages 2347-2354, FIG. 110-1).

By comparison, a bifurcation-configured bypass allows blood to flow past the plaque from the common through both the internal and external carotids without interruption in perfusion or obstruction of the surgical field. To achieve continuous flow throughout the procedure, such a bypass incorporates an intravascular diversion switch on the common carotid. When an endarterectomy would place the patient at risk, the bypass, made of optimally biocompatible materials, is applied where it can remain indefinitely and the patient closed with the bypass left.

All ductus side-entry jackets and diversion jackets, or intravascular valves, are provided with at least one accessory or service channel through which drugs, other therapeutic agents, and fluid line, jacket, and connector maintenance solutions, such as antimicrobials and crystal solvents, can be introduced through the body surface port. Initial irritation if not an adverse tissue reaction arising following the procedure, at least one accessory channel to the intravascular valve on the common carotid is provided to directly pipe medication to the treatment site. The accessory channel is fed an anti-inflammatory injected through a subcutaneous portacath or mediport into a subcutaneous reservoir with outlet pump switched remotely by the patient by means of an extracorporeal keyless entry switch.

2. Extracardiac Transposition of the Great Vessels

Extracardiac transposition of the great vessels (see, for example, Goor, D. A., Dische, R., and Lillehei, C. W. 1972. "The Conotruncus. I. Its Normal Inversion and Conus Absorption," *Circulation* 46(2):375-384) with no significant disruption in flow and oxygenation is cited as an application of plunger solenoid-controlled ductus side-entry intravascular valve diversion jackets, detailed description of the placement procedure deferred to a divisional application. To least disrupt bloodflow, intravascular valve diversion jackets used to accomplish extracardiac transposition use connecting tubes matched to the caliber of the substrate vessel, which factor determines the size of the jackets, and the tubing of the diversion shunts and accessory channels to each lower jacket are made of nonkinking material, the course of each smoothly curved from the origin to the destination vessel.

Synthetic shunts and bypasses are made with tubing of the same gauge as the vessels these connect, and to avoid the inducement of turbulence and the accumulation of thrombus or debris, the junctions and turns must be smooth and gradual. Briefly, the jackets are positioned on each vessel at an inferior and a superior level, those inferior inverted to divert flow craniad into the lines leading to those superior, which are not inverted. Once the secure and leak-free connection of each valve has been confirmed, the operator or an assistant switches all four jackets from fully open with no blood diverted to fully closed with all blood diverted to cross over to the opposite vessel at the same instant, as in a sudden switch solid organ transplantation.

The procedure, considerably less traumatizing than conventional correction, allows the immediate termination of systemic circulatory underoxygenation and ensuing left ventricular hypoplasia which if not corrected immediately would result in the maldevelopment of every organ system and short life expectancy. In a frail neonate not able to tolerate conventional surgical correction, this means that immediate correction is achieved at birth and the defect prevented from further injury. The same applies to a sudden switch heart transplantation in a prenate, neonate, or infant.

3. Sudden Switch Solid Organ Transplantation

A sudden switch transplantation applies ductus side-entry diversion valves to instantly divert and so bypass the circulation of the recipient from his own defective organ to and through the donor organ thus incorporating the transplant into his own circulatory system. Such a bypass includes the several individual vessels of the organ, so that the bypass is compound; for clarity, the representation of such a bypass in FIGS. 44A and 44B summarizes all arterial or excurrent and all venous or incurrent vessels as unit vessels. The citation of heart transplantation responds to the frequency of the need therefor and to stress the capability for zero ischemic time when the blood driver itself is transplanted. Any solid organ can be sudden switch transplanted without ischemia or reperfusion injury.

Synthetic shunts and bypasses are made with tubing of the same gauge as the vessels these connect, and further to avoid the inducement of turbulence and the accumulation of thrombus or debris, the junctions and turns are made smooth and gradual. Sudden switch solid organ transplantation is cited as an application of plunger solenoid-controlled ductus side-entry intravascular valve diversion jackets, which incorporate a deployable and retractable flow-diversion chute wherewith a single depression of the control switch instantly actuates all of the valves, switching the donor organ to the recipient. A more than cursory treatment of sudden switch solid organ transplantation is deferred to another patent application.

In sudden switch transplantation, the replacement organ is harvested from an irreversibly comatose, or 'brain-dead,' donor after circulation through the organ has been switched from the supply and drainage vessels of the donor to the corresponding vessels of the recipient, thus instantly transferring the donor organ from the circulatory system of the donor to that of the recipient. Significantly, this results in zero ischemic time and eliminates crossclamping, the shock of sudden excision, unperfused chilling, and reperfusion injury. When the donor is not located in the same center, the donor heart or heart and lungs are transported to the recipient center by normothermal continuous perfusion beating-heart means already available.

In sudden switch organ transplantation, where the ductus to be connected are those of different individuals side by side but at a distance from one another, the lines are coiled and stretchable to self-contract when placed within the recipient at which time the stumps of donor and recipient can be anastomosed, or the connecting lines and jackets can remain in place as a prosthesis in lieu of anastomosis, or the stumps can be anastomosed and the lines and jackets left in place to allow the direct targeting to the treatment site of supportive agents. Ideally, patients requiring different organs are transported to the irreversibly comatose donor (not the reverse) who has been maintained on life support and ideally, whose heart is harvested last. If the urgency of a prospective heart recipient warrants, the heart is removed but immediately replaced with an artificial heart; in organ transplantation, perfusion discontinuity and anoxia are the main sources of complications such as reperfusion injury and pulmonary hypertension.

Conventional organ transplantation also involves the transection and anastomosis of vessels which does not allow the seamless switching of circulation from a defective recipient to a competent donor organ as does sudden switching. In a sudden switch transplant, the lines and jackets connecting recipient and donor can remain in place as bypasses while anastomosis is performed, or if the native vessels of the recipient are considerably diseased, then the lines and diversion jackets can be left in place indefinitely as a prosthesis, or if the native vessels are not significantly diseased and/or the operator wishes direct access to the site after closing, then the jackets and accessory channels are left in place to support the anastomosed vessels.

In heart transplantation, for example, the minimum number of arteries to be reconnected depends upon whether all are transected close to the origin or beyond the level at which these branch, but always includes the aorta and pulmonary trunk or right and left pulmonary arteries, and the minimum number of veins includes the superior and inferior venae cavae and the right and left pulmonary veins. Each vessel in the recipient and the donor has one valve. In a sudden switch transplant, generally eight to ten vessels in the donor heart are suddenly switched from the circulatory system of the donor to that of the recipient with at most an instantaneous transient interruption in flow, disruption in flow minimized not just by the abruptness, but by the simultaneity of the switch. Even when the side-entry jacket intravascular diversion valves to accomplish this are easily accessible, to achieve simultaneous switching of ten valves is likely to prove difficult for an operator, even with the aid of assistants.

For this reason, synchrony is accomplished by remotely switching all of the valves simultaneously from the same electrical switch. The valve driver is a damped plunger solenoid or a tiny piston. When recipient pretransplantation pulmonary vascular resistance is too pronounced, the sudden switch technique is extended to include the lungs in a heart-lung transplant. In liver transplantation, since the diversion valve jackets and connecting lines need never be removed, or can be left in place until the anastomoses have been completed, the sudden switch technique eliminates problem bleeding as the main complication. The same applies to a sudden extracardiac transposition of the great vessels in a prenate, neonate, or an infant.

Sudden switch transplantation using the total orthotopic rather than the conventionally preferred bicaval technique (see, for example, Jungschleger, J. G. M., Boldyrev, S. Y., Kaleda, V. I., Dark, J. H. 2018. "Standard Orthotopic Heart Transplantation," *Annals of Cardiothoracic Surgery* 7(1): 169-171; Rivinius, R., Helmschrott, M., Ruhparwar, A., Erbel, C., Gleissner, C. A., and 5 others 2017. "The Influence of Surgical Technique on Early Posttransplant Atrial Fibrillation—Comparison of Biatrial, Bicaval, and Total Orthotopic Heart Transplantation," *Therapeutics and Clinical Risk Management* 13:287-297; Kara, I., Ay, Y., Yanartaş, M., Köasal, C., Toker, M. E., Yildirim, T., and Balkanay, M. 2012. "Does the Surgical Technique Used in the Orthotopic Heart Transplant Affect the Results Regarding the Rhythm?," *Anadolu Kardiyoloji Dergisi* [Anatolian Journal of Cardiology] 12(3):255-260) allows the deferment of more extensive anastomosis of the atria—a major deterrent to solid organ transplantation in a fetus due to the minuteness of the stitches required.

The total orthotopic technique is also associated with the lowest rate of postransplantion arrhythmia (see, for example, Rivinius, R., Helmschrott, M., Ruhparwar, A., Erbel, C., Gleissner, C. A., and 5 others 2017. "The Influence of Surgical Technique on Early Posttransplant Atrial Fibrillation—Comparison of Biatrial, Bicaval, and Total Orthotopic Heart Transplantation," *Therapeutic and Clinical Risk Management* 13:287-297; further references cited shortly below). This technique also offers somewhat greater latitude as to the exact positioning of the new heart within the chest of the recipient, and eliminates the need for lengthy microsurgery over a significant interval when anastomosis becomes essential to assure growth. For a heart transplant, the chests are opened, and the diversion valves placed on the corresponding vessels in recipient and donor connected by suitable stretchable and coiled tubing, the general scheme of these connections schematically summarized in FIGS. 44A and 44B.

FIGS. 44A and 44B are schematic representations of the diversion jacket orientations in a sudden switch transplant. Shown for a heart transplant, the arrangement applies to any solid organ transplant. For clarity, the accessory channels, clearly shown in FIG. 41 have been omitted, and all vessels arising from the top of, that is, cranially and rising superior to the heart, or supercardial, and all those arising from the bottom of the heart, that is, caudally, infracardially, inferior to and descending subcardially, to the heart are shown as having been gathered into or summarized in unit channels. The diversion valves in both donor and recipient are first all retracted so that the integrity of either circulatory system is sustained. When switched so that all of the valves are extended into the lumen, the heart of the recipient is suddenly replaced by the heart of the donor.

Using the orientation of the diversion valve shown in FIG. 41 as the reference or index orientation, the supercardial jacket of the donor shown retracted in FIG. 44A and extended into the lumen in FIG. 44B is inverted, or upside down, and reversed in direction. The supercardial jacket of the recipient shown as retracted in FIG. 44A and extended in FIG. 44B is the same in orientation as the diversion valve shown in FIG. 41. The infracardial jacket of the donor shown retracted in FIG. 44A and extended into the lumen in FIG. 44B is right side up, or noninverted, and reversed in direction, and the infracardial jacket of the recipient shown retracted in FIG. 44A and extended into the lumen in FIG. 44B is inverted and not reversed in direction.

In an adult heart transplant where macro-reentrant atrial tachyarrhythmia arises from surgical anastomosis lines (Bulut, M., Evlice, M., Celik, M., Eren, H., Savluk, Ö. F., and 7 others 2017. "Atrial Electromechanical Delay in Patients Undergoing Heart Transplantation," *Journal of Arrhythmia* 33(2):122-126) (see also, for example, Wdowczyk, J., Makowiec, D., Gruchala, M., Wejer, D., and Struzik, Z. R. 2018. "Dynamical Landscape of Heart Rhythm in Long-term Heart Transplant Recipients: A Way to Discern Erratic Rhythms," *Frontiers in Physiology* 9:274; Ko, S. B. 2018. "Perioperative Stroke: Pathophysiology and Management," *Korean Journal of Anesthesiology* 71(1):3-11; Guan, L., Collet, J. P., Mazowita, G., and Claydon, V. E. 2018. "Autonomic Nervous System and Stress to Predict Secondary Ischemic Events after Transient Ischemic Attack or Minor Stroke: Possible Implications of Heart Rate Variability," *Frontiers in Neurology* 9:90; Acampa, M., Lazzerini, P. E., Guideri, F., Tassi, R., and Martini, G. 2016. "Ischemic Stroke after Heart Transplantation," *Journal of Stroke* 18(2): 157-168; Thajudeen, A., Stecker, E. C., Shehata, M., Patel, J., Wang, X., and 3 others 2012. "Arrhythmias after Heart Transplantation: Mechanisms and Management," *Journal of the American Heart Association* 1(2):e001461), anastomosis can be deferred or avoided altogether by leaving the intravascular valves and connecting tubes in place as a permanent prosthesis.

Where anastomosis is deferred or discounted so that the synthetic lines and jackets to be left in place as a prosthesis, any generation of arrhythmogenic discharges from the cut ends of the stumps is treated by targeting an anesthetic to the cut ends through the accessory channel or channels 11. The same applies where anastomosis is immediate. While less problematic with the total orthotopic than alternative techniques, this may alleviate the aberrations in rhythm that induce post-transplantation atrial fibrillation and stroke as the deterrents to the otherwise preferable total orthotopic technique.

At the same time that the replacement heart is placed in the chest, the use of synthetic lines and jackets facilitates the correction of any donor congenital anomalies such as the tunneling or anastomosis of the heart supply or drainage vessels. Once the donor organ is positioned in the recipient, the tubing spontaneously assumes its shortest nonpulling length. The diversion valves serving to bypass and give access to medicate each prospective anastomosis, the corresponding vessels can then be anastomosed and the tubing removed. This allows medication to be directly targeted to each vessel and anastomosis by injection into the respective opening in the body surface port.

To the extent that time allows and as appropriate, solid organ transplantation is preceded or accompanied by interrelated processes, to include:

a. Induction therapy (see, for example, Bocedi, A., Noce, A., Rovella, V., Marrone, G., Cattani, G., and 8 others 2018. "Erythrocyte Glutathione Transferase in Kidney Transplantation: A Probe for Kidney Detoxification Efficiency," *Cell Death and Disease* 9(3):288; Briasoulis, A., Inampudi, C., Pala, M., Asleh, R., Alvarez, P., and Bhama, J. 2018. "Induction Immunosuppressive Therapy in Cardiac Transplantation: A Systematic Review and Meta-analysis," *Heart Failure Reviews* March 13; Dhamidharka, V. R., Naik, A. S., Axelrod, D. A., Schnitzler, M. A., Zhang, Z., and 11 others 2018. "Center Practice Drives Variation in Choice of US Kidney Transplant Induction Therapy: A Retrospective Analysis of Contemporary Practice," *Transplant International* 31(2):198-211; Hill, P., Cross, N. B., Barnett, A. N., Palmer, S. C., and Webster, A. C. 2017. "Polyclonal and Monoclonal Antibodies for Induction Therapy in Kidney Transplant Recipients," *Cochrane Database of Systematic Reviews* 1:CD004759; Raj, S., Ruiz, P., and Rusconi, P. 2017. "Early Primary Graft Failure after a Pediatric Heart Transplant and Successful Rescue with Plasmapheresis, Immunoglobulins, and Alemtuzumab," *Annals of Pediatric Cardiology* 10(1):69-71; Butts, R., Davis, M., Savage, A., Burnette, A., Kavarana, M., and 3 others 2017. "Effect of Induction Therapy on Graft Survival in Primary Pediatric Heart Transplantation: A Propensity Score Analysis of the UNOS [United Network for Organ Sharing] Database," *Transplantation* 101(6):1228-1233; Ruan, V., Czer, L. S., Awad, M., Kittleson, M., Patel, J., and 7 others 2017. "Use of Anti-thymocyte Globulin for Induction Therapy in Cardiac Transplantation: A Review," *Transplantation Proceedings* 49(2):253-259; Webster, A. C., Wu, S., Tallapragada, K., Park, M. Y., Chapman, J. R., and Carr, S. J. 2017. "Polyclonal and Monoclonal Antibodies for Treating Acute Rejection Episodes in Kidney Transplant Recipients," *Cochrane Database of Systematic Reviews* 7:CD004756; Kittipibul, V., Tantrachoti, P., Ongcharit, P., Ariyachaipanich, A., Siwamogsatham, S., and 3 others 2017. "Low-dose Basiliximab Induction Therapy in Heart Transplantation," *Clinical Transplantation* 31(12); Sarwal, M. M. 2016. "Fingerprints of Transplant Tolerance Suggest Opportunities for Immunosuppression Minimization," *Clinical Biochemistry* 49(4-5):404-410; Yao, X., Weng, G., Wei, J., and Gao, W. 2016. "Basiliximab Induction in Kidney Transplantation with Donation after Cardiac Death Donors," *Experimental and Therapeutic Medicine* 11(6):2541-2546; Barten, M. J., Schulz, U., Beiras-Fernandez, A., Berchtold-Herz, M., Boeken, U., and 10 others 2016. "A Proposal for Early Dosing Regimens in Heart Transplant Patients Receiving Thymoglobulin and Calcineurin Inhibition," *Transplantation Direct* (6):e81; D'Addio, F., Margonato, D., Pensato, U., Borgese, L., Potena, L., and Fiorina, P. 2015. "Novel Therapeutic and Diagnostic Management of Heart Transplant Patients," *Heart, Lung, and Vessels* 7(3):198-207; Wiseman, A. C. 2015. "Induction Therapy in Renal Transplantation: Why? What Agent? What Dose? We May Never Know," *Clinical Journal of the American Society of Nephrology* 10(6):923-925; Turner, A. P. and Knechtle, S. J. 2013. "Induction Immunosuppression in Liver Transplantation: A Review," *Transplant International* 26(7):673-683; Aliabadi, A., Grömmer, M., and Zuckermann, A. 2011. "Is Induction Therapy Still Needed in Heart Transplantation?," *Current Opinion in Organ Transplantation* 16(5):536-542).

b. Tolerogenic therapy (see, for example, Thomson, A. W., Humar, A., Lakkis, F. G., and Metes, D. M. 2018. "Regulatory Dendritic Cells for Promotion of Liver Transplant Operational Tolerance: Rationale for a Clinical Trial and Accompanying Mechanistic Studies," *Human Immunology* 79(5):314-321; Marin, E., Cuturi, M. C., and Moreau, A. 2018. "Tolerogenic Dendritic Cells in Solid Organ Transplantation: Where Do We Stand?," *Frontiers in Immunology* 9:274; van der Zwan, M., Baan, C. C., van Gelder, T., and Hesselink, D. A. 2018. "Review of the Clinical Pharmacokinetics and Pharmacodynamics of Alemtuzumab and Its Use in Kidney Transplantation," *Clinical Pharmacokinetics* 57(2):191-207; Domogalla, M. P., Rostan, P. V., Raker, V. K., and Steinbrink, K. 2017. "Tolerance through Education: How Tolerogenic Dendritic Cells Shape Immunity," *Frontiers in Immunology* 8:1764; Lynch, K., Treacy, O., Gerlach, J. Q., Annuk, H., Lohan, P., and 4 others 2017. "Regulating Immunogenicity and Tolerogenicity of Bone Marrow-derived Dendritic Cells through Modulation of Cell Surface Glycosylation by Dexamethasone Treatment," *Frontiers in Immunology* 8:1427; Behnam Sani, K. and Sawitzki, B. 2017. "Immune Monitoring as Prerequisite for Transplantation Tolerance Trials," *Clinical and Experimental Immunology* 189(2):158-170; Wekerle, T. 2017. "Immune Tolerance in Transplantation," *Clinical and Experimental Immunology* 189(2):133-134; Lee, J. H., Park, C. S Jang, S., Kim, J. W., Kim, S. H., and 3 others 2017. "Tolerogenic Dendritic Cells are Efficiently Generated Using Minocycline and Dexamethasone," *Scientific Reports* 7(1):15087; Ezzelarab, M. B., Raich-Regue, D., Lu, L., Zahorchak, A. F., Perez-Gutierrez, A., and 7 others 2017. "Renal Allograft Survival in Nonhuman Primates Infused with Donor Antigen-pulsed Autologous Regulatory Dendritic Cells," *American Journal of Transplantation* 17(6):1476-1489; Obregon, C., Kumar, R., Pascual, M. A., Vassalli, G., and Golshayan, D. 2017. "Update on Dendritic Cell-induced Immunological and Clinical Tolerance," *Frontiers in Immunology* 8:1514; Moreau, A., Alliot-Licht, B., Cuturi, M. C., and Blancho, G. 2017. "Tolerogenic Dendritic Cell Therapy in Organ Transplantation," *Transplant International* 30(8):754-764; Zhou, Y., Shan, J., Guo, Y., Li, S., Long, D., Li, Y., and Feng, L. 2016. "Effects of Adoptive Transfer of Tolerogenic Dendritic Cells on Allograft Survival in Organ Transplantation Models: An Overview of Systematic Reviews," *Journal of Immunology Research* 2016:5730674; Xia, M. J., Shan, J., Li, Y. P., Zhou, Y. N., Guo, Y. J., and 3 others 2014. "Adoptive Transfusion of Tolerogenic Dendritic Cells Prolongs the Survival of Liver Allograft: A Systematic Review," *Journal of Evidence-based Medicine* 7(2):135-146), and c. Chimerization of the donor and the recipient to include the use of stem cells (see, for example, Zhang, M., Racine, J. J., Lin, Q., Liu, Y., Tang, S., and 4 others 2018. "MHC-mismatched Mixed Chimerism Restores Peripheral Tolerance of Noncross-reactive Autoreactive T Cells in NOD

[nonobese diabetic] Mice," *Proceedings of the National Academy of Sciences of the United States of America* 115(10):E2329-E2337; Lin, J., Chan, W. F. N., Boon, L., and Anderson, C. C. 2018. "Stability of Chimerism in Nonobese Diabetic Mice Achieved By Rapid T Cell Depletion is Associated with High Levels of Donor Cells Very Early after Transplant," *Frontiers in Immunology* 9:837; Wang, L., Jiang, Z., Huang, D., Duan, J., Huang, C., and 7 others 2018. "JAK/STAT3 [Janus kinase/signal transducer and activator of transcription 3] Regulated Global Gene Expression Dynamics during Late-stage Reprogramming Process," *BioMed Central Genomics* 19(1):183; Cross, A. R., Glotz, D., and Mooney, N. 2018. "The Role of the Endothelium during Antibody-mediated Rejection: From Victim to Accomplice," *Frontiers in Immunology* 9:106; Wang, J. W., Fontes, M. S. C., Wang, X., Chong, S. Y., Kessler, E. L., and 8 others 2017. "Leukocytic Toll-like Receptor 2 Deficiency Preserves Cardiac Function and Reduces Fibrosis in Sustained Pressure Overload," *Scientific Reports* 7(1):9193; Shin, J. E., Jung, K., Kim, M., Hwang, K., Lee, H., and 4 others 2018. "Brain and Spinal Cord Injury Repair by Implantation of Human Neural Progenitor Cells Seeded onto Polymer Scaffolds," *Experimental and Molecular Medicine* 2018 50(4)39; Gosset, C., Vigletti, D., Rabant, M., Vérine, J., Aubert, O., and 6 others 2017. "Circulating Donor-specific Anti-HLA Antibodies are a Major Factor in Premature and Accelerated Allograft Fibrosis," *Kidney International* 92(3):729-742; Yang, Y., Liu, B., Xu, J., Wang, J., Wu, J., and 30 others 2017. "Derivation of Pluripotent Stem Cells with In Vivo Embryonic and Extraembryonic Potency," *Cell* 169(2):243-257.e25; Guichard-Romero, A., Marino-Vazquez, L. A., Castelán, N., López, M., González-Tableros, N., and 4 others 2016. "Impact of Pretransplant Exposure to Allosensitization Factors Generating HLA Antibodies in the Luminex Era, *Transplant Immunology* 38:33-39; Wu, L., Li, N., Zhang, M., Xue, S. L., Cassady, K., Lin, Q., Riggs, A. D., and Zeng, D. 2015. "MHC-mismatched Mixed Chimerism Augments Thymic Regulatory T-cell Production and Prevents Relapse of EAE [experimental autoimmune encephalomyelitis] in Mice," *Proceedings of the National Academy of Sciences of the United States of America* 112(52):15994-15999; Rezaee, F., Peppelenbosch, M., and Dashty, M. 2013. "Donor Chimera Model for Tolerance Induction in Transplantation," *Human Immunology* 74(5): 550-556; Daley, G. Q. 2010. "Stem Cells: Roadmap to the Clinic," *Journal of Clinical Investigation* 120(1):8-10; Windrem, M. S., Schanz, S. J., Guo, M., Tian, G. F., Washco, V., and 7 others 2008. "Neonatal Chimerization with Human Glial Progenitor Cells Can Both Remyelinate and Rescue the Otherwise Lethally Hypomyelinated Shiverer Mouse," *Cell Stem Cell* 2(6):553-565; Starzl, T. E., Demetris, A. J., Murase, N., Trucco, M., Thomson, A. W., and Rao, A. S. 1995. "The Changing Immunology of Organ Transplantation," *Hospital Practice* 30(10): 31-34, 37-42).

In a prenate or neonate with a severely malformed heart, such preparation is attenuated according to the premature state of the immune system.

4. Modulating the Volume, Rate, and Pressure of Flow through a Vessel

An intravascular servovalve can be used to divert a portion of the flow to another vessel, or by directing the diversion into a blind outlet line or use of a sphinteric jacket such as that shown in FIG. 11, act much as a vessel-encircling band (see, for example, Nezafati, M. H., Nezafati, P., and Kahrom, M. 2017. "Pulmonary Artery Banding Using Polytetrafluoroethylene; Choice of Material," *ARYA* (advanced research yields in atherosclerosis) *Atherosclerosis* 13(5):202-204; Como, A. F. 2005. "Pulmonary Artery Banding," *Swiss Medical Weekly* 135(35-36):515-519) controllable from a small port at the body surface to slow flow and increase the hemotension below, or retrograde to the level of the valve. When made adjustable thus, the valve jacket, diversion or sphincteric control at the port is keyed to prevent accidental or inexpert adjustment.

Such a body surface port is therefore both cutaneous and subcutaneous, the loosening and tightening control cutaneous or above the skin and keyed, the opening or openings to inject medication subcutaneous and marked on the skin by tiny tattooed, easily removable by laser if and when the port can be removed. Moreover, the substrate vessel or its branches do not undergo fibrous degeneration, scarring, erosion if not cut-through, and stenosis as when banding is performed in an effort to alleviate "intractable heart failure secondary to large pulmonary flow," requiring angioplastic treatment to alleviate the stenosis, at least in part cicatricial (Davis, Z., McGoon, D. C., Danielson, G. K., and Wallace, R. B. 1975. "Removal of Pulmonary Artery Band," *Israel Journal of Medical Sciences* 11(2-3):110-115) (see also Danilowicz, D., Presti, S., and Colvin, S. 1990 "The Disappearing Pulmonary Artery Band," *Pediatric Cardiology* 11(1):47-49).

Such degeneration is attributable to the compression of the vasa vasora and vasa nervora addressed above in the section entitled Types of Ductus Side-entry Jackets, ductus side-entry jackets, of which an intravascular valve is but one type, embodying a basic design conceived of precisely to eliminate compression and complete enclosure from the surrounding environment. No less important, unlike a band, however, the valve can be adjusted from outside the body, eliminating the need for revision that requires reopening the patient.

Arterial banding must be closely monitored for the provocation of anomalous arterial developments (see, for example, Davies, R. R., Radtke, W. A., Klenk, D., and Pizarro, C. 2014. "Bilateral Pulmonary Arterial Banding Results in an Increased Need for Subsequent Pulmonary Artery Interventions," *Journal of Thoracic and Cardiovascular Surgery* 147(2):706-712; Arnold, R. R., Loukanov, T., and Gorenflo, M. 2014. "Hypoplastic Left Heart Syndrome—Unresolved Issues," *Frontiers in Pediatrics* 2:125; Alsoufi, B. 2013. "Management of the Single Ventricle and Potentially Obstructive Systemic Ventricular Outflow Tract," *Journal of the Saudi Heart Association* 25(3):191-202; Kawamura, A., Oshima, Y., Maruo, A., and Matsuhisa, H. 2012. "Compression of an Anomalous Single Coronary Artery from Pulmonary Artery by Banding," *European Journal of Cardiothoracic Surgery* 41(4):e59-e61; Honjo, O. and Caldarone, C. A. 2010. "Hybrid Palliation for Neonates with Hypoplastic Left Heart Syndrome: Current Strategies and Outcomes," *Korean Circulation Journal* 40(3): 103-111; Daenen, W., Eyskens, B., Meyns, B., and Gewillig, M. 2000. "Neonatal Pulmonary Artery Banding Does Not Compromise the Short-term Function of a Damus-Kaye-Stansel Connection," *European Journal of Cardiothoracic Surgery* 17(6):655-657). In a fully implanted system, sensors provide the master control microprocessor with hemotensive data, and the microprocessor affects adjustment in the intravascular or sphincteric valve used automatically in accordance with the prescription-program where the patient is not likely to even notice the adjustment.

Band adjustment is always necessary following initial placement, and the recent advent of percutaneous band adjustability, only applicable up to two month, percutaneous band adjustability regarded as an improvement over the conventional or nonadjustable banding prior art (see, for example, Talwar, S., Kamat, N. A., Choudhary, S K., Ramakrishnan, S., Saxena, A., and 3 others 2016. "Mid-term Outcomes of Patients Undergoing Adjustable Pulmonary Artery Banding," *Indian Heart Journal* 68(1):72-76; Changizi, A., Yaghoubi, A., Azarasa, M., Ghaffari, S., and Montazerghaem, H. 2014. "A Study on the Mortality and Complication Rates following Percutaneously Adjustable Pulmonary Artery Banding," *Journal of Cardiovascular and Thoracic Research* 6(4):253-255; Choudhary, SK1, Talwar S, Airan B, Mohapatra R, Juneja R, and 3 others 2006. "A New Technique of Percutaneously Adjustable Pulmonary Artery Banding," *Journal of Thoracic and Cardiovascular Surgery* 131(3):621-624; Higashidate, M., Beppu, T., Imai, Y., and Kurosawa, H. 1989. "Percutaneously Adjustable Pulmonary Artery Band. An Experimental Study," *Journal of Thoracic and Cardiovascular Surgery* 97(6):864-869).

Since neither an intravascular valve nor a sphincteric jacket do not compress the vasa vasora and vasa nervora, and medication can be directly targeted to either type jacket, the constriction can continue over a finite interval during which the substrate vessel will not undergo degenerative change. In addition to the direct targeting of medication to the treatment site, if necessary, the accessory channel is used to prevent an accumulation of thrombus by delivering an anticoagulant, usually heparin. A more recent form of banding allows adjustment telemetrically without reentry or percutaneous access, representing and improvement over the prior art that still affords no way to target medication directly to the treatment site.

In small patients, the device is likely to encroach upon neighboring tissue and cause discomfort if not tissue erosion, which should not be taken to detract from its demonstrated utility over a limited period of months during which septal defects might spontaneously close, radical surgery be deferred, and experience gained in the correct degree of tightness to apply in various circumstances (see, for example, Como, A. F., Kandakure, P. R., Dhannapuneni, R. R., Gladman, G., Venugopal, P., and Alphonso, N. 2013. "Multiple Ventricular Septal Defects: A New Strategy," *Frontiers in Pediatrics* 1:16; Durandy, Y. 2013. "Pulmonary Artery Banding is Still a Valuable Option," *Frontiers in Pediatrics* 1:17; Dhannapuneni, R. R., Gladman, G., Kerr, S., Venugopal, P., Alphonso, N., and Como, A. F. 2011. "Complete Atrioventricular Septal Defect: Outcome of Pulmonary Artery Banding Improved by Adjustable Device," *Journal of Thoracic and Cardiovascular Surgery* 141(1): 179-182; Bonnet, D., Como, A. F., Sidi, D., Sekarski, N., Beghetti, M., and 6 others 2004. "Early Clinical Results of the Telemetric Adjustable Pulmonary Artery Banding FloWatch-PAB [pulonary artery banding]," *Circulation* 110 (11 Supplement 1):II158-II163).

As with continuous variability accomplished by manual means, this may be to reduce shear stress, expedite healing, or reduce the flow rate and increase the pressure to increase the uptake of a magnetically susceptible micro- or nanoparticle-carried drug by a magnetized ductus side-entry jacket. Where variable adjustment using manual control is for rough apportionment of flow between the straightaway and a shunt or bypass, the linear motor is controlled by a microprocessor, usually implanted, to achieve precise apportionment.

More precise control thus is also applicable, for example, when fine adjustment is required in the diversion of blood flow from a small to a large vessel or from a large vessel to multiple smaller vessels to adjust the blood pressure. Such pertains, for example, to the main pulmonary artery where a nonadjustable band is conventionally used to ameliorate pulmonary hypertension, or to the portal vein, where liver disease poses impedance to the inflow of blood resulting in portal hypertension and its sequelae such as esophageal varices.

One circumstance calling for reducing the pressure in the portal vein arises following resection of the liver, where the resulting want of sufficient liver tissue, or small size hepatic remnant, results in portal hypertension due to the disproportionately large volume of blood arriving. Overcoming this problem imparts the ability to provide multiple donor grafts from a single healthy donor liver, while averting the risks of sepsis and ischemia-reperfusion injury, often the cause of post-hepatectomy liver failure (see, for example, Jia, C., Dai, C., Wang, H., Wan, Y., Qiao, Y., and 5 others 2018. "Differential Effects of Three Techniques for Hepatic Vascular Exclusion during Resection for Liver Cirrhosis on Hepatic Ischemia-reperfusion Injury in Rats," *Gastroenterology Research and Practice* 2018:5309286; Eshkenazy, R., Dreznik, Y., Lahat, E., Zakai, B. B., Zendel, A., and Ariche, A. 2014. "Small for Size Liver Remnant following Resection: Prevention and Management," *Hepatobiliary Surgery and Nutrition* 3(5):303-312; Reyal, J. and Uemoto, S. 2009. "Percutaneously Adjustable Portal Vein Banding Device Could Prevent Post-operative Liver Failure—Artificial Control of Portal Venous How is the Key to a New Therapeutic World," *Medical Hypotheses* 73(5): 640-650).

Either a sphincteric jacket or an intravascular valve diversion jacket can substitute for a right or left portal vein embolization to favor the side of the liver desired preparatory to a partial hepatectomy (see, for example, Li, D. and Madoff, D. C. 2016. "Portal Vein Embolization for Induction of Selective Hepatic Hypertrophy Prior to Major Hepatectomy: Rationale, Techniques, Outcomes, and Future Directions," *Cancer Biology and Medicine* 13(4):426-442; May, B. J. and Madoff, D. C. 2012. "Portal Vein Embolization: Rationale, Technique, and Current Application," *Seminars in Interventional Radiology* 29(2):81-89). However, when conventional embolization or a sphincteric jacket would induce portal hypertension which the condition of the patient makes preclusive of the procedure, use of a diversion jacket with the diversion path used to draw away a proportion of the flow allows flow reduction without hypertension. Diversion is usually through a ductus side-entry jacket into a large vein such as the inferior vena cava, but can also be terminated in other tissue as in a Vineberg procedure.

Whereas current means of embolization are permanent or absorbable, a diversion jacket is continuously variable, with a small linear motor to advance and retract the chute which can be radio remote controlled. Control thus represents a significant advantage when the condition of the patient changes or the future liver remnant does not develop as anticipated. Another benefit of the diversion jacket is the ability to directly target drugs into the vein and liver—avoiding all other tissue—through one or more accessory channels where the release of drugs can be controlled by an implanted sensor-driven microprocessor operating the outlet pump of a drug storage bladder or reservoir replenished through a subdermally positioned surface port. Placement of the diversion jacket is through a 'keyhole' incision.

While the jacket itself replaces therapeutic embolization, clamping, and less versatile forms of banding to reduce post resection portal hypertension, the accessory channel of either type jacket, intravascular valve ductus side-entry jacket diversion valve or sphincteric can be used to deliver any fluid therapeutic substance, to include:

Antioxidants and antioxidant gene transfer (see, for example, Schwarz, C., Fitschek, F., Bar-Or, D., Klaus, D. A., Tudor, B., and 7 others 2017. "Inflammatory Response and Oxidative Stress during Liver Resection," *Public Library of Science One* 12(10):e0185685; Manzanares, W., Dhaliwal, R., Jiang, X., Murch, L., and Heyland, D. K. 2012. "Antioxidant Micronutrients in the Critically Ill: A Systematic Review and Meta-analysis," *Critical Care* 16(2):R66; Chen, C. F., Hsueh, C. W., Tang, T. S., Wang, D., Shen, C. Y., and Pei, J. S. 2007. "Reperfusion Liver Injury-induced Superoxide Dismutase and Catalase Expressions and the Protective Effects of N-acetyl Cysteine," *Transplantation Proceedings* 39(4):858-860; He, S. Q., Zhang, Y. H., Venugopal, S. K., Dicus, C. W., Perez, R. V., and 4 others 2006. "Delivery of Antioxidative Enzyme Genes Protects against Ischemia/Reperfusion-induced Liver Injury in Mice," *Liver Transplantation* 12(12):1869-1879; Jaeschke, H. 2002. "Antioxidant Gene Therapy and Hepatic Ischemia-reperfusion Injury," *Hepatology* 36(1):243-245; Cerivenka, H., Khoschsorur, G., Bacher, H., Werkgartner, G., El-Shabrawi, A., and 3 others 1999. "Normothermic Liver Ischemia and Antioxidant Treatment during Hepatic Resections," *Free Radical Research* 30(6):463-469; Cerwenka, H., Bacher, H., Werkgartner, G., El-Shabrawi, A., Quehenberger, F., Hauser, H., and Mischinger, H. J. 1998. "Antioxidant Treatment during Liver Resection for Alleviation of Ischemia-reperfusion Injury," *Hepatogastroenterology* 45(21):777-782).

Insulin in relatively large doses (see, for example, Okabayashi, T. and Shima, Y. 2014. "Are Closed-loop Systems for Intensive insulin Therapy Ready for Prime Time in the ICU?," *Current Opinion in Clinical Nutrition and Metabolic Care* 17(2):190-199; Amrein, K., Kachel, N., Fries, H., Hovorka, R., Pieber, T. R., and 4 others 2014. "Glucose Control in Intensive Care: Usability, Efficacy and Safety of Space GlucoseControl in Two Medical European Intensive Care Units," *BioMed Central Endocrine Disorders* 14:62; Hassanain, M., Metrakos, P., Fisette, A., Doi, S. A., Schricker, T., and 5 others 2013. "Randomized Clinical Trial of the Impact of Insulin Therapy on Liver Function in Patients Undergoing Major Liver Resection," *British Journal of Surgery* 100(5):610-618; Fisette, A., Hassanain, M., Metrakos, P., Doi, S. A., Salman, A., and 6 others 2012. "High-dose Insulin Therapy Reduces Postoperative Liver Dysfunction and Complications in Liver Resection Patients through Reduced Apoptosis and Altered Inflammation," *Journal of Clinical Endocrinology and Metabolism* 97(1): 217-226; Okabayashi, T., Ichikawa, K., Namikawa, T., Sugimoto, T., Kobayashi, M., and Hanazaki, K. 2011. "Effect of Perioperative Intensive Insulin Therapy for Liver Dysfunction after Hepatic Resection," *World Journal of Surgery* 35(12):2773-2778; Okabayashi, T., Nishimori, I., Maeda, H., Yamashita, K., Yatabe, T., and Hanazaki, K. 2009. "Effect of Intensive Insulin Therapy Using a Closed-loop Glycemic Control System in Hepatic Resection Patients: A Prospective Randomized Clinical Trial," *Diabetes Care* 32(8):1425-1427), or Mesenchymal stem cells (see, for example, Cao, Y., Zhang, B., Lin, R., Wang, Q., Wang, J., and Shen, F. 2018. "Mesenchymal Stem Cell Transplantation for Liver Cell Failure: A New Direction and Option," *Gastroenterology Research and Practice* 2018:9231710; Kwak, K. A., Cho, H. J., Yang, J. Y., and Park, Y. S. 2018. "Current Perspectives Regarding Stem Cell-based Therapy for Liver Cirrhosis," *Canadian Journal of Gastroenterology and Hepatology* 2018:4197857; Li, Y. W., Zhang, C., Sheng, Q. J., Bai, H., Ding, Y., and Dou, X. G. 2017. "Mesenchymal Stem Cells Rescue Acute Hepatic Failure by Polarizing M2 [inflammation-decreasing] Macrophages," *World Journal of Gastroenterology* 23(45): 7978-7988; Huang, B., Cheng, X., Wang, H., Huang, W., la Ga Hu, Z., 10 others 2016. "Mesenchymal Stem Cells and Their Secreted Molecules Predominantly Ameliorate Fulminant Hepatic Failure and Chronic Liver Fibrosis in Mice Respectively," *Journal of Translational Medicine* 14:45; Wang, Y., Yu, X., Chen, E., and Li, L. 2016. "Liver-derived Human Mesenchymal Stem Cells: A Novel Therapeutic Source for Liver Diseases," *Stem Cell Research and Therapy* 7(1):71; Cen, P., Chen, J., Hu, C., Fan, L., Wang, J., and Li, L. 2016. "Noninvasive In-vivo Tracing and Imaging of Transplanted Stem Cells for Liver Regeneration," *Stem Cell Research and Therapy* 7(1):143; Wang, K., Chen, X., and Ren, J. 2015. "Autologous Bone Marrow Stem Cell Transplantation in Patients with Liver Failure: A Meta-analytic Review," *Stem Cells and Development* 24(2): 147-159; Margini, C., Vukotic, R., Brodosi, L., Bernardi, M., and Andreone, P. 2014. "Bone Marrow Derived Stem Cells for the Treatment of End-stage Liver Disease," *World Journal of Gastroenterology* 20(27):9098-9105).

The terms intravascular valve and intravascular servo-valve do not apply to passive, that is, not actively controlled, elastic slit valves as used in chain extraction side-entry jackets for accomplishing ambulatory intracorporeal cytapheresis or as flow resistors in drug pump turrets or functionally equivalent parts in miniaturized form for carrying in a pack or implantation. The terms apply rather to valves actively actuated, whether individually by hand, multiply by energization from a common manually operated switch, or in the case of servovalves, in a proportional manner, either manually with a synchro, resolver, or digital or optical equivalent, or by automatic response to an implanted master controller microprocessor executing a prescription-program responsive to biosensor input signals.

Chain Jackets

Examples of chain-jackets are shown in FIGS. 13 thru 15, 39A, and 39B. Segmental sequentially actuated jackets such as the peristaltic prosthesis or assist device with sequentially timed sphincteric jackets shown in FIG. 10 are not chain-jackets but rather queued sphincteric jackets sequentially timed to simulate peristalsis in esophageal and intestinal prostheses and assist devices placed about the native conduit when dysfunctional or exhibiting a motility disorder such as intestinal paralysis and intractable spasm. FIGS. 39A, and 39B show the arrangement of double-arm chain jackets used for ambulatory implanted cytapheresis or hemodialysis, cyapheresis using a slit-valve positioned between the vessel and magnet as the magnetic separation filter whereas dialysis uses a semipermeable membrane or assemblage of a large number of semipermeable fibers.

FIG. 39A depicts four chain-jackets applied to the inferior vena cava, and FIG. 39B is a more detailed view of the caudal end of the circuit where the magnetically separated target analyte is delivered into the urinary bladder for normal elimination in the urine. The process is described below in the section entitled Description of the Preferred Embodiments of the Invention. The peristaltic pump-driven flush-line contains water or a dialysate circulated about the circuit and periodically removed and replenished through the access lines connected to the port positioned to the right-hand side of the mons pubis in FIG. 39B.

Flush-line 79 is simultaneously emptied and replenished with fresh dialysate or apheresis fluid through fluid exchange lines 97 and 99. For this purpose, a separate component shown in FIG. 39C with dialysate or apheresis fluid reservoir and a peristaltic pump such as that shown toward the top of FIG. 39A is used. In a patient requiring dialysis due to impaired kidney function but not missing any part of the urinary system, ambulatory magnetic separation dialysis is as shown in FIG. 39B where the extracted debris is drawn into the urinary bladder for expulsion, the device shown in FIG. 39C used to replenish the dialysate when the need therefor is indicated by the small turbidometric sensor-driven lamp on port 16.

When the patient is missing the lower urinary tract, the system shown in FIG. 40, which depicts application in a patient without the need for dialysis, is used. In the absence of a bladder, the extraction of debris from flush-line 79 is into the neoureteral confluence chamber 102 by the same method as is shown for a patient with a bladder in FIG. 39B. Expulsion is through port 16 and into collection bag 101 As with the patient having a complete urinary system, the device shown in FIG. 39C is used to replenish spent fluid when a small lamp on port 16 comes on.

As addressed shortly below, for use with patients whose entire urinary tract has been or is likely to be bilaterally removed, leaving them wholly dependent upon dialysis, nothing seen in FIG. 40 applies. Rather, the expulsion of extracted target analyte debris must be not by extraction into urine but directly from the flush-line 79. In this case, there is no urine; the only medium available being the dialysate or aphereses fluid itself at the time of replacement. As addressed below, the component shown in FIG. 39C replaces a urine collection bag. The patient either wears it in a carrying pack or must keep it close at hand should the turbidometric sensor driven lamp on port 16 come on to signal the need for fluid replacement.

Referring now to FIG. 39B, filling of the bladder gradually compresses a dacron squeezebox, or accordion-type folding tube, bringing a flush-line-to-bladder crossover window set in the lower loop of the flush-line into flush contact with the slit-valve or semipermeable membrane likewise set in a ring-surround window in the superior surface of the bladder. The dacron tube supports the slit-valve or semipermeable membrane in preventing urine from leaking. A relatively powerful electromagnet enclosed within a housing having smooth edges and rounded corners positioned down on the inferolateral surface of the bladder close to the neck, hence, effectively beneath the bladder on the left hand side of the patient (right hand side of the drawing) draws the magnetically susceptible micro or nanoparticle-bound target analyte through the window interface and into the bladder, the target analyte expelled in the urine.

Referring to FIGS. 39A and 40, when the patient has or requires a radical cystectomy as well as dialysis, the window semipermeable membrane surround in flush-line 79 is permanently bonded to the corresponding window surround in neoureteral 105 confluence chamber 102 (see, for example, Wang, Y., Jin, B., and Yao, X. 2016. "Metachronous Urothelial Carcinoma of Whole Urinary Tract in a Dialysis-dependent Patient: A Case Report," *Oncology Letters* 11(6):4027-4029; Tseng, S. F., Chuang, Y. C., and Yang, W. C. 2011. "Long-term Outcome of Radical Cystectomy in ESDR [sic ESRD-end stage renal disease] Patients with Bladder Urothelial Carcinoma," *International Urology and Nephrology* 43(4):1067-1071;

If the patient has undergone a complete extirpation of the urinary tract (radical cystectomy and bilateral nephroureterectomy with discretionary lymphadenectomy) pending a transplant or is contemplated or predictable to progress thus (see, for example, Han, Y., Shou, D., Wen, L., Shi, J., Ding, J., Gong, P., and Gong, W. 2016. "Interplay between Chronic Kidney Disease (CKD) and Upper Tract Urothelial Carcinomas (UUC): Foe or Friend?," *Oncotarget* 7(33):53951-53958; Vtorenko, V. I., Trushkin, R. N., Lubennikov, A. E., Podkorytova, O. L., and Motin, P. I. 2015. "Bilateral Nephroureterectomy with Cystoprostatectomy Ad Bloc and Lymphadenectomy in a Patient with End-stage Renal Failure and Cancer of the Urinary Bladder T2bn0m0 [the TNM (tumor/node/metastasis) malignant tumor classification for T2b—ulcerated, n0—no regional metastases detected, and m0—no detectable evidence of distant metastases]," (in Russian with English abstract at Pubmed), *Urologiia* (Moscow, Russia) (2):126-129; Wang, L. J., Lee, S. Y., Teh, B. T., Chuang, C. K., and Nortier, J. 2014. "Upper Tract Urothelial Carcinomas in Patients with Chronic Kidney Disease: Relationship with Diagnostic Challenge," *Biomed Research International* 2014:989458; Chung, S. D., Tsai, Y. C., Wang, S. M., Hung, S. F., Huang, C. Y., Chueh, S. C., and Yu, H. J. 2013. "Laparo-endoscopic Single-site (LESS) Bilateral Nephroureterectomy for Patients with End-stage Renal Disease," *Minimally Invasive Therapy and Allied Technologies* 22(1):61-64; Green, D. A., Rink, M., Xylinas, E., Matin, S. F., Stenzl, A., and 4 others 2013. "Urothelial Carcinoma of the Bladder and the Upper Tract: Disparate Twins," *Journal of Urology* 189(4):1214-1221) so that the patient will be left completely dependent upon dialysis, the use of a conventional convergence chamber 102 as shown in FIGS. 40 and 43 with debris removal window is no longer an option.

Absent urine to flush away the debris, expulsion is by the flush fluid as it is expelled when replaced. To this end, a separate debris accumulation chamber comprising an enclosure with semipermeable fivers for dialysis or slit-valve for apheresis in a transit window and opposing electromagnet continuously draw the debris out of the flush-line. Not shown in FIG. 39A, which depicts an intracorporeal dialysis of apheresis system in a kidney impaired patient who produces urine, the accumulation chamber would be positioned where the dialysate or other fluid outlet line coupling 96 shown in FIG. 39A is positioned.

FIG. 39C shows a dialysate (or apheresis fluid) disposal and replenishment chamber used in lieu of a collection bag by a patient who has undergone the complete removal of his urinary system, which includes a radical bilateral nephroureterectomy with cystoprostatectomy and discretionary lymphadenectomy. Like a collection bag, the disposal and replenishment chamber plugs into surface port 16, but unlike a collection bag, the chamber need not be worn constantly. It should be within easy reach for use when a turbidometric sensor signals the need to change the fluid by turning on a small lamp on body surface port 16. Only the extracorporeal component is shown in this application. The intracorporeal component comprises a debris collection chamber positioned where exit line coupling 96 is shown.

This chamber incorporates a bay of semipermeable fibers for dialysis or an elastic slit-valve for apheresis in a separation transit window and an electromagnet to draw the toxic debris or cells that had been extracted from the bloodstream. Exchanging the spent dialysate or apheresis fluid 98 for fresh is by actuating pump 119, which flows fresh fluid through inflow line 122 through port 16 through coupling 100, and through the debris collection chamber situated where exit line coupling 96 is shown to wash over the pole of the electromagnet. The debris is thus flushed out with the spent dialysate through intracorporeal outflow line 97, the outflow opening in port 16, and the chamber extracorporeal outflow line 121 at the same time that fresh dialysate 101 (or apheresis fluid) is pumped through chamber outflow line 122, port 16 inflow opening, and intracorporeal inflow line 99 through coupling 100 into flush-line 79. In this manner, spent dialysate or apheresis fluid is used to flush out toxic debris in lieu of urine.

Power-conserving measures such as pulsed traction, energy optimized electromagnets, and silicon-iron crystal bonded to the analyte or analytes to be extracted, or extractate, notwithstanding, the completely ambulatory system still requires more frequent recharging of button cells in port 16, a small implanted battery pack, or direct connection to an electrical outlet. Recharging in any stationary location is facilitated with the aid of transdermal energy transfer. Clearly, even if the system treatment is not fully adequate, the patient is still spared the onerous imposition of visiting a clinic many days a week or spending as much time connected to an extracorporeal machine.

d. Body Surface Ports, Cutaneous, Subcutaneous, and Both

Body surface ports represent the points of ingress into the lines, jackets, and connectors of systems that implement the direct pipe-targeting of drugs and other therapeutic and system maintenance agents to the respective target treatment sites. As such, the incorporation of effective design measures for preventing microbial intrusion are vital.

1. A cutaneous, or epidermal, port is fastened onto the skin and provides one or more protectively covered openings to the outside. Epidermal ports serve, for example, to allow the insertion of cabled transcatheteric or transluminal devices, such as angioscopes and lasers, and to provide an outlet, or egress, for a relatively high volume effluent, such as urine or the dialysate in an intracorporeal hemodialysis system. For optimal sterility, port openings for injecting drugs or other agents for direct targeting through fluid lines and ductus side-entry jackets or nonjacketing side-entry connectors to nidi or treatment sites are usually not positioned epidermally. Instead these use openings positioned subdermally, making these combination epidermal and subdermal. All ports provide means for facilitating the application of antimicrobials or antiseptics to the foam layers lining the tissue-port interfaces.

2. A subcutaneous, or subdermal port is positioned beneath to be covered over by the skin. Where more than one opening is provided, the position for insertion of the hypodermic needle or jet injector is indicated by clearly marked tiny tattoos or by holes in a plate or protective cover above the skin. Where only one injection path is needed, a conventional portacath or mediport leading to a ductus side-entry jacket or side-entry connector can be used. However, as various drugs, other therapeutic agents, and system maintenance solutions are usually needed, a single point of entry will seldom prove adequate. Like a portacath, the port includes a subcutaneous cover membrane. No more than two small dot tattoos or cover holes can serve to rotationally align, or key, a multi-headed injector to simultaneously replenish various substances, each through its assigned opening, which may enter into a mainline or sideline (accessory channel).

3. Body surface ports cutaneous, or epidermal, and subcutaneous, or subdermal.

One type of cutaneous body surface port described in parent application Ser. No. 14/121,365 and herein as well is shown in FIGS. 27 and 28. The port is epidermal and provides four openings for the passage of electrical conductors, inflow of drugs, other therapeutic agents, and system maintenance solutions, the insertion of cabled devices such as flexible punch biopsy forceps, angioscopes, intravascular ultrasound probes, and lasers, and the outflow of urine, and in an intracorporeal hemodialysis or apheresis system, the replenishment of spent dialysate or apheresis fluid. Description of a combination epidermal and subdermal port including both types, the section below entitled Description of the Preferred Embodiments of the Invention describes and illustrates a combination epidermal and subdermal port.

SUMMARY OF THE INVENTION

A biocompatible, viscoelastic polyurethane foam-lined polymeric jacket or collar comprising complementary spring-hinged half cylinders and incorporating a radially extending ductus lumen side entry connector for attaching a catheter or hose is placed through a small endoscopic incision to surround a segment of a tubular anatomical structure or the territory (region, area) supplied or drained by a branch from or to the segment to be treated. Thickness of the ductus wall widely variable, the razor-sharp forward or adductal die-cutting edge of the side-entry connector is generally one third the outer diameter of the ductus or the diameter of its lumen. With the jacket encircling the ductus and cutting off any path of leakage or exsanguinations into the surrounding cavity or tissue, a vacuum is used to draw a plug of tissue from the side of the ductus wall.

When the wall is too thick for suction alone to excise the plug, the jacket side-connector can be used as a trepan or circle-cutter and locked in position. When the disease warrants, the pump or pumps connected to the ductus side-entry jacket or switchable among multiple jackets are tied in a closed loop control system. Comorbidities are treated concurrently with different types and sizes of jackets according to the sizes of the different system ductus to be jacketed, the drugs used for each targeted and isolated from the others and other tissue as the situation requires.

When necessary, the control system is programmed to simulate 'learning' ability, delivering drugs in response to sensor-detected symptoms in anticipation or predictively with the objective of suppressing critical events before these appear as pain or discomfort. Ductus side-entry jackets incorporating a diversion chute allow use as intravascular valves and servovalves of which only the chute enters the lumen. Solenoid-driven valves are bistable in completely diverting or passing flow, whereas manually and linear motor-driven valves can divert any fraction of flow.

Such valves make possible urinary diversion, reduction in blood pressure through a vessel, off-pump or beating-heart solid organ transplantation, extracardiac transposition of the great vessels, and arterial switching, without interruption in perfusion. Of special importance in neonates and the very young, in solid organ to include heart transplantation, the donor organ is harvested after circulation through it has been switched to the recipient, eliminating ischemic time, cross-clamping, sudden excision, unperfused chilling, and reperfusion injury.

The irreversibly comatose, or 'brain-dead,' donor—not the recipient—is machine supported, eliminating the sequelae associated with blood cell damage and microemboli. Intravascular valves also allow local adjustments in blood pressure, quick connection to apheresis and dialysis machines, implement the prospect of carriable and eventually, implantable apheresis and dialysis machines, and incorporate accessory channels for the direct targeting to the treatment site or sites of drugs and passage of cabled devices from a small port at the body surface.

OBJECTS OF THE INVENTION

1. A primary object of the invention is to provide a means for joining smaller caliber synthetic or tissue-engineered conduits or catheters to native ductus which leaves the lumen of this tubing free and clear of thrombus, biofilm, and accretions, shows no medically significant leakage, reverse flow, or dislodgement, and can therefore be fully implanted over an indefinite period.

2. Another object of the invention is to provide remotely controlled, piped targeting of drugs through an accessory channel (service channel, sideline) from an entry portal at the body surface directly to lesions and treatment sites generally where the non-clogging, non-dislodging, and biofilm-free performance of the catheters and ductus connectors used is essential to an implanted disorder response system.

3. An associated object of the invention is to provide means for the direct and continuous connection of a catheteric tube entered through a port at the body surface to the lumen of a tubular gastrointestinal, circulatory, respiratory, or genitourinary structure, allowing the delivery of drugs, radionuclides, or other therapeutic substances through a jacket fastened to the ductus while avoiding the upstream lumen and tissue supplied by branches thereof or the release of drugs into the circulation, as essential to provide, a fully implanted automatic adaptive disorder response system.

4. A central object of the invention is to provide the patient with a means of ambulatory therapy that functions automatically, least interferes with freedom of movement, and in particular, spares the patient from being tethered to a therapeutic apparatus, hence bedridden, or confined to treatment as an in-patient.

5. Yet another object of the invention is to allow the direct and immediate translation of chemical, electrical, and immunoassay feedback diagnostics into automatic drug delivery around the clock, constituting no more than a slight impediment to free movement, whether to the locus of detection, the site of the symptom, and/or the etiological origin, under the control of a hierarchical or complex control system capable of predictive or anticipatory control and further adaptable through 'learning' ability, and in so doing, apply such control to the practice of internal medicine.

6. Another object of the invention is to make possible the coordination, and usually the collocation, of drug need detection and delivery means so that drugs can be targeted directly to the anatomical point of detection or a point functionally related thereto, thereby enabling the implementation of prosthetic disorder response systems, to include those employing hierarchical control.

7. Yet another object is to provide a kind of joint or junction that also allows forming synthetic or tissue-engineered bypasses and shunts between native conduits which can, but need not, communicate with a port implanted at the body surface, averting the need for, or the need to harvest, a suitable autologous graft.

8. Another object is to allow a safe and secure connection of a synthetic to a native conduit that unlike an indwelling catheter, provides a ready-made direct path into the native conduit for treatment and testing to allow the patient complete freedom of movement while connected to an automatic portable pump or diagnostic testing instrument.

9. Another object is to provide a connection to an anatomical ductus that fully compliant with the intrinsic motility of the ductus, secure, and less prone to infection, affords better opportunity for healing without complications.

10. Whether placed as a precaution to deliver drugs in the event of a medical emergency or to allow the use of testing equipment, the connection is usually meant to be permanent. For this reason, periodic diagnostic testing or treatment does not require the reintroduction of an indwelling needled catheter for each treatment or test, the risk associated with placing such a catheter and the need to immobilize the patient therefore averted.

11. A related object is to allow the use of a magnetized side-entry jacket to draw a magnetically susceptible carrier bound drug into the lumen wall at the side-entry junction, jacket magnetization is generally circumferential with the strength increased in the downstream or antegrade direction for more uniform uptake along the entire length.

12. Another related object is to provide a junction that will serve as the level at which the lumen is entered in relation to a magnetized jacket encircling the structure downstream used to truncate further transport of magnetically susceptible carrier particles. In this way, the segment for exposure to medication introduced in the form of a ferrofluid can be limited.

13. A related object is to allow the use of the downstream jacket to suspend a reversal agent in the lumen, so that depending upon whether the drug-carrier bond is soluble, the drug can be restricted to the segment designated and the territory supplied by any side branches to or from the segment. Jackets that interfere with flexion if too long are divided, that downstream continuing in strength of magnetization where that upstream had left off. For treating eccentric lesions, magnetization is limited to the arc requiring treatment. Such a lesion might be, for example, a benign tumor, or if malignant, then one itself palliated or the site of its resection medicated.

14. Other objects are to accomplish connection to the structure through a junction that places nothing, such as an indwelling catheter, in the lumen, so that—consistent with stent jacket and impasse jackets of like object disclosed in copending application Ser. No. 13/694,835—the lumen is completely unobstructed, little if at all affected in normal flow past the junction while not in use, and any transluminal interventional procedure that may be needed, especially one exigent, will have a clear pathway.

15. Another object is to situate all parts of the jacket and its supply pipeline extraluminally so that parts of the jacket no longer needed to prevent leakage through the ostium created can be made disintegrable or absorbable.

16. Yet another object is to provide a junction that allows equality of luminal diameter between the synthetic or tissue-engineered and natural lines, allowing bidirectional application with consist volumetric flow rate between synthetic and native conduits or the reverse, and, if necessary, the entire flow to be cross-clamped and shunted.

17. Yet another object is to provide a direct channel for withdrawing diagnostic testing samples or for passing cabled devices such as angioscopes, excimer lasers, atherectomizers, thrombectomizers, or analytical sensors from outside the body, introduced endoscopically or by insertion through a port at the body surface.

18. Yet other objects are to accomplish the foregoing by means and methods that allow endoscopic application with minimal invasiveness under local anesthesia with anticlotting medication substantially limited to the entry site, and little if any in the systemic circulation.

19. Another object of the invention is to allow on-off and proportional flow through a ductus such a blood vessel to be adjusted, thereby making possible numerous surgical procedures otherwise degraded due to ischemia or inadequate or excessive blood pressure, for example.

20. Yet another object of the invention is to provide ports for the injection of drugs and retraction of biopsy test samples, for example, which are positioned subcutaneously, cutaneously, or a combination thereof.

21. Another object of the invention is to make possible implanted hemodialysis and apheresis by means of magnetic separation.

22. Yet another object of the invention is to provide ductus side-entry jackets which incorporate controllable diversion chutes to serve as intravascular valves which make possible urinary diversion with takeoff at the ureters, and zero ischemic time carotid endarterectomy, extracardiac transposition of the great vessels, solid organ transplantation, to include that of the heart itself, and the modulation of flow rate through a vessel by partial diversion of the flow therethrough to another vessel of large caliber.

DESCRIPTION OF THE DRAWINGS

FIG. 8 shows a side view of a clasp-electromagnet with its pole directed away from, rather than facing, the tissue attaching base as would apply to a clasp impasse electromagnet or a clasp extraction electromagnet.

FIG. 9 shows an overhead view of the clasp-electromagnet shown in FIG. 8.

FIG. 11 is a cross-sectional view through an electromagnetic impasse jacket that by adding a magnet draw-plate on the opposite outer surface of the ductus, functions as a contraction or sphincteric jacket equivalent to a segment in a peristalsis jacket such as shown in FIG. 10, which can compress the ductus interposed between the electromagnet-plate pairs in an advancing sequence.

FIG. 12 shows a longitudinal section through an electromagnetic impasse jacket to which a draw-plate has been added on the opposite side of the ductus to function as one of the electromagnet-plate pairs along a tissue-engineered ductus as shown in FIGS. 10 and 11.

FIG. 13 is a longitudinal section through an extraction double-arm electromagnetic ductus side-entry jacket for analyte exchange with the lumen rather than the wall surrounding the ductus, with integral trap or collection chamber and flush-through or purge line, the magnet with bent around core and coil beneath the plane of the drawing.

FIG. 14 shows a series of extraction electromagnet jackets spaced along a ductus with common flush-through line connected in series.

FIG. 15 is a longitudinal section through a ductus with an extraction jacket having two or four extraction electromagnets positioned circumferentially about the jacket, the bent around cores and coils unseen outside the plane of the drawing but configured as that of the individual electromagnet-plate pairs of the multi-paired jacket shown in FIGS. 10 and 11.

FIG. 19 shows the side-entry connection jacket of FIG. 17 placed about the ascending aorta diagrammatically, FIG. 21 providing a more anatomical view.

FIG. 20 is a left side view of the side-entry connection jacket shown in FIGS. 17 and 19 represented as level to its horizontal or transverse plane.

FIG. 21 is an anterior or facing view of the heart with the jacket shown in FIGS. 17, 19, 20, and 22 placed proximal to the root of the ascending aorta to join synthetic or tissue-engineered epicardial coronary artery bypass conduits for insertion distal to the blockages in the left anterior descending or anterior interventricular branch artery to the right and the right coronary artery to the left, through smaller single arm ductus side-entry connection jackets shown without accessory or side lines.

FIG. 28 is a side view partially in section of the port with base plate fastened to the body surface for connection of one or more side-entry connection mainlines and water jacket or sidelines, shown to a side of a plane passing through the suture holes, with the port cap screwed on.

FIG. 33 shows the elastic slit membrane at the junction of a therapeutic substance supply reservoir hose where the hose connects by means of a lip undercutting or click-on collar to the top of the system standardized vial used to insert the hose into one of the vial receiving receptacles in the pump intake turret.

FIG. 34 is a side view of a system standardized therapeutic substance turret vial, here used as a reservoir hose connector, for insertion into one of the vial receiving receptacles in the pump intake turret.

FIG. 35 shows a longitudinal sectional view of a system standardized therapeutic substance vial connected to the end of a drug reservoir supply hose for engaging the hose in one of the vial receiving receptacles in the pump intake turret as both the connector and starting dose.

FIG. 36 is a diagrammatic representation of a pump with pump intake drug turret.

FIG. 37 is a diagrammatic schematic diagram of the control train when a single pump-pair and jacket set is inserted in the pump-pack, shown in the abstract as to the positioning of the parts as inside or outside the body, the train constituting a hierarchical control system.

DESCRIPTION OF THE PREFERRED EMBODIMENTS OF THE INVENTION

Simple Junction Side-Entry Jackets

Figure 1:
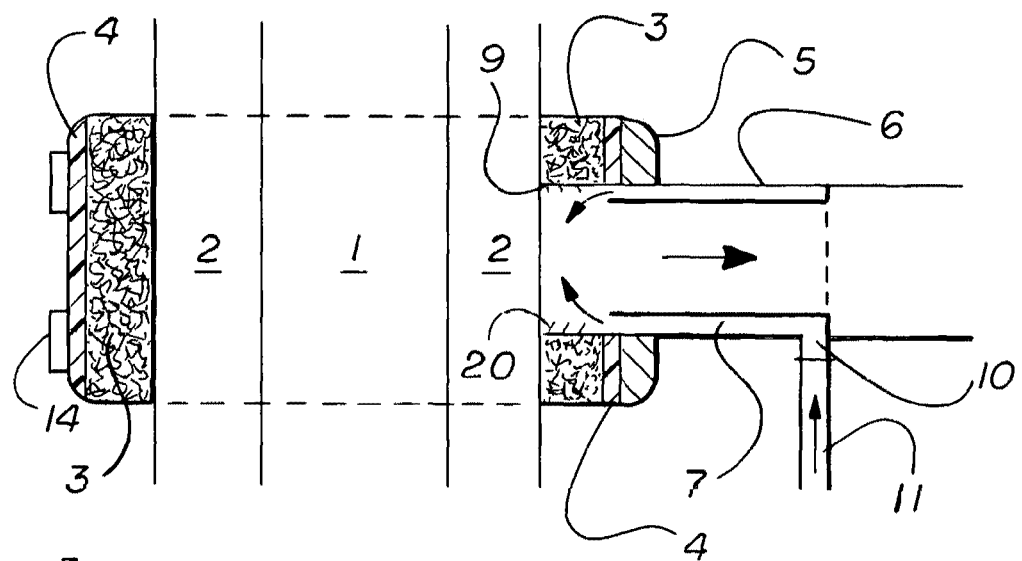
FIG. 1 shows a longitudinal section through a segment along a tubular anatomical structure with a magnetized and unshielded, or simple junction type, side-entry connection jacket having an internal fluid-conducting or water-jacket, shown placed about a ductus before the side of the lumen wall is drawn under vacuum pressure past the sharp leading edge of the side-entry connector to cut and extract therefrom a plug of tissue.
Figure 2:
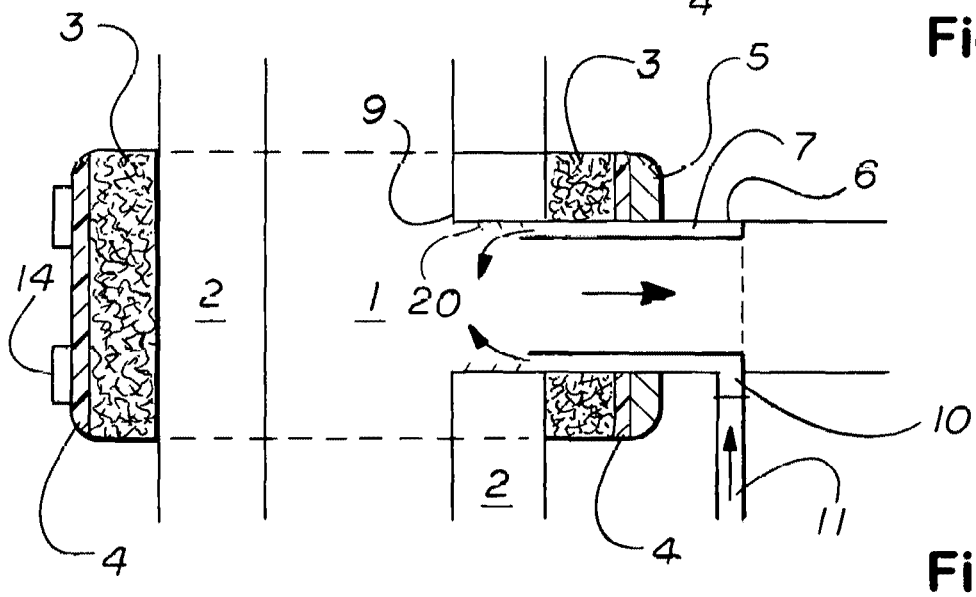
FIG. 2 shows the side-entry connection jacket of FIG. 1 after the sharp leading edge of the side-entry connector has been used to cut a plug from the side of the lumen wall and the plug extracted so that the leading edge has been advanced to be planar with the internal surface of the lumen.

Simple junction side-entry jackets are intended to replace indwelling catheters for long-term use. Simple junction jackets omit a magnetic layer, and except when used to convey a radioactive substance, radiation shielding. FIGS. 1 and 2 depict ductus side-entry jackets, with side-connector 6 and accessory or water-jacket inlet 10, which, as shown in FIGS. 16, 21, 29, 31, and 32, respectively serve to connect mainline 13 and side-connector sideline or accessory 11. Whereas—as shown in the application depicted in FIG. 16—sideline 11 goes to a port 16 at the body surface 18, mainline 13 may go to the port, or as shown in the application depicted in FIG. 21, it may be used instead to connect a prosthetic line used to replace a bodily conduit. Connection of mainline 13 to port 16 denotes its use to transmit medication to or withdraw diagnostic test samples from the native lumen through the side-entry jacket to which line 13 is connected.

By contrast, connection of mainline 13 other than to port 16 denotes its use as a prosthetic conduit to convey the materials of the ductus it replaces. In the simple junction jacket shown in FIGS. 1 and 2, part number 1 is a native lumen, 2 the wall surrounding the lumen, 3 a viscoelastic polyurethane foam lining, and 4 a strong outer shell, or casing, 4 made of polyether ether ketone (PEEK) or another biocompatible nonallergenic material. All types of jackets—with or without side-connector, permanent magnet or electromagnet based, contraction, extraction, and the variants of these—have a viscoelastic polyurethane foam lining, and unless radiation shielding prohibits it, the jacket is fenestrated throughout its thickness. All such jackets are urged shut by spring hinges 14 which are chosen to apply sufficient closing force to minimize if not eliminate the need for suture eyelets 118 to prevent migration but not so much force that sufficient opening to accommodate inflammation or growth is prevented.

Figure 5:
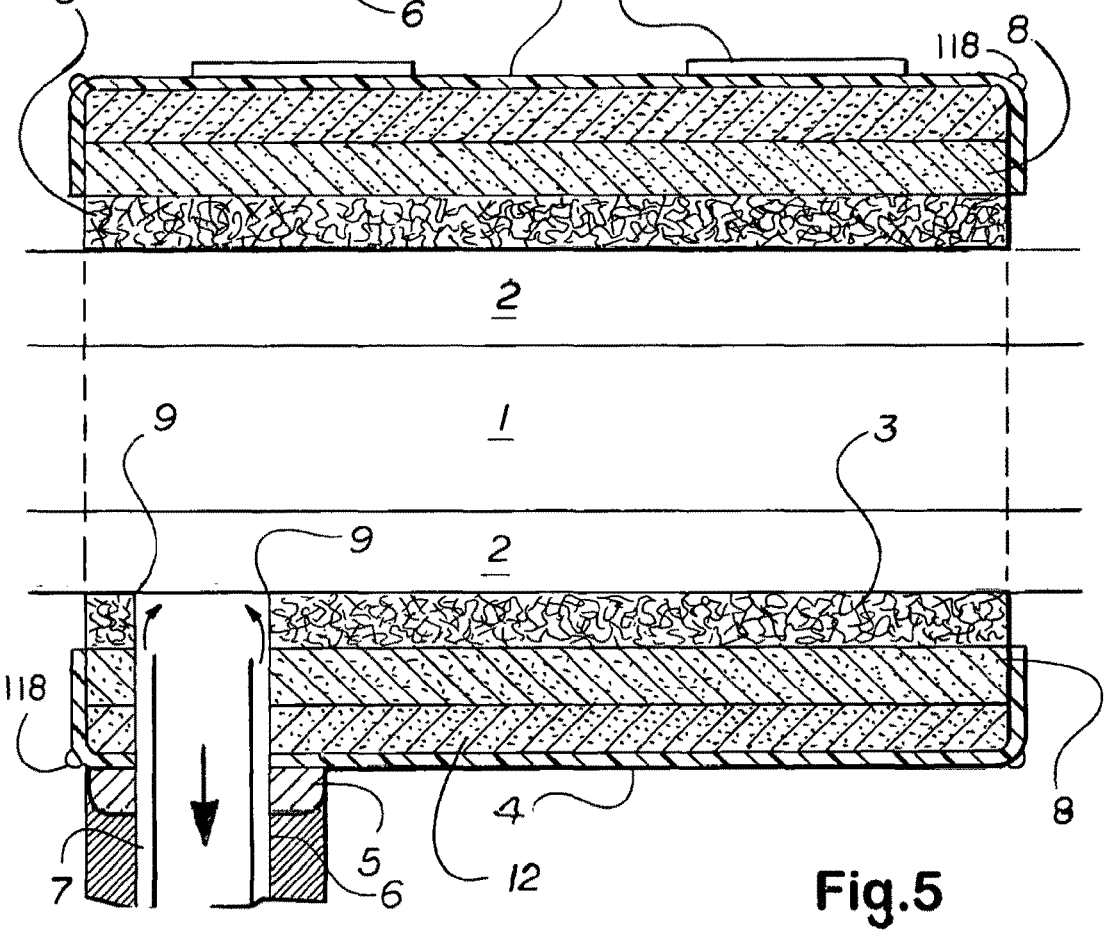
FIG. 5 shows a side-entry connection jacket of the same kind as that shown in FIG. 4 with the addition of a wrap-around tungsten 'heavy' alloy radiation shield for use with a relatively low dose-rate short half-life radionuclide for use along a vascular or nonvascular ductus when provided with a magnet layer and a nonvascular ductus when not.
Figure 6:
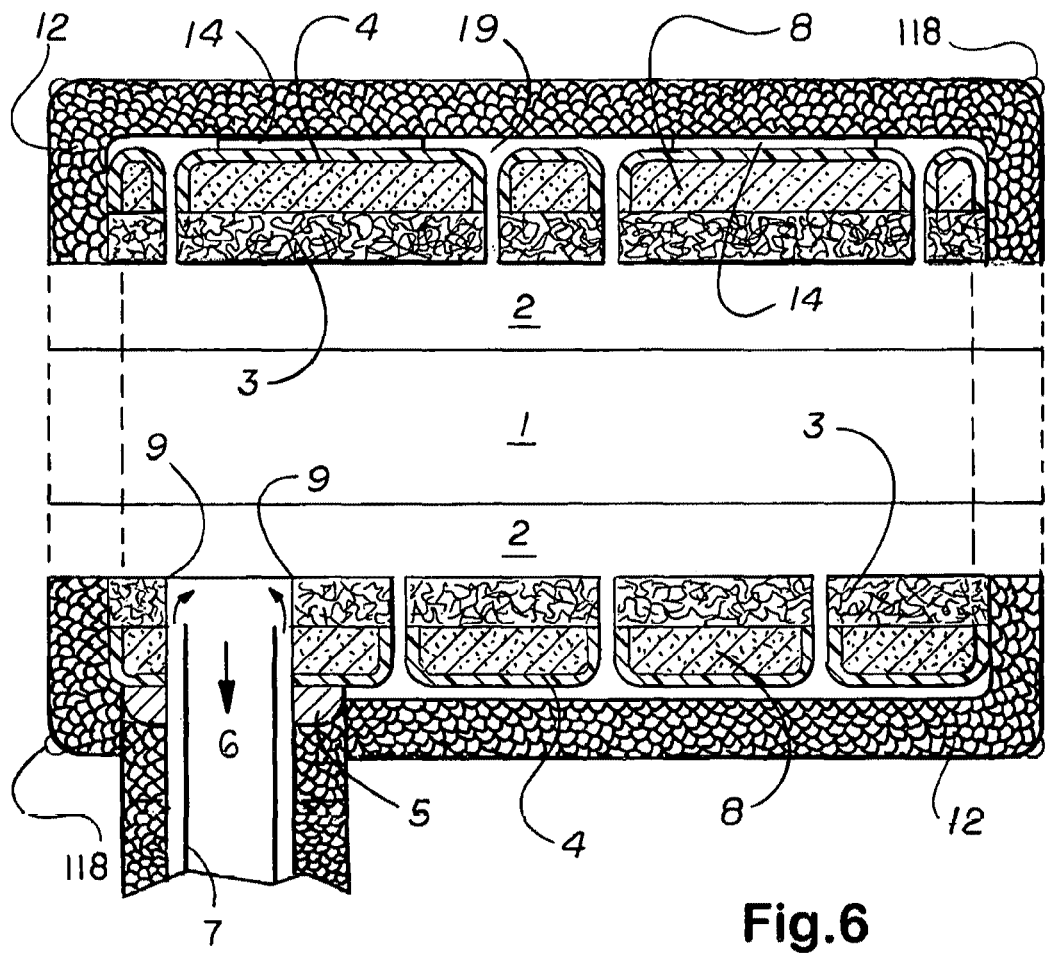
FIG. 6 shows a disintegrating radiation shield as the outermost layer of the jacket, applied outside the perforated shell surrounding the magnet layer seen in FIG. 4.

This factor promotes the disintegrable shielding shown in FIG. 6 which once dispersed, exposes perforations 19 previously encircled over that nondisintegrable shown in FIG. 5 when possible. In FIG. 1, the ductus side-entry jacket has been placed to encircle the structure before the razor-sharp trepan or die-cutting leading edge of the side-entry connector 6 has cut through the wall so that it is flush planar with the internal surface of the lumen with the plug having been extracted from the side of the ductus. Viscoelastic foam lining 3 serves to protect fine vessels and nerves at the interface with the substrate conduit, provide motional compliance or depth of excursion according to the intrinsic motility of the conduit encircled, and accommodates an irregularity in the diameter of the ductus such as caused by the lesion treated.

Figure 16:
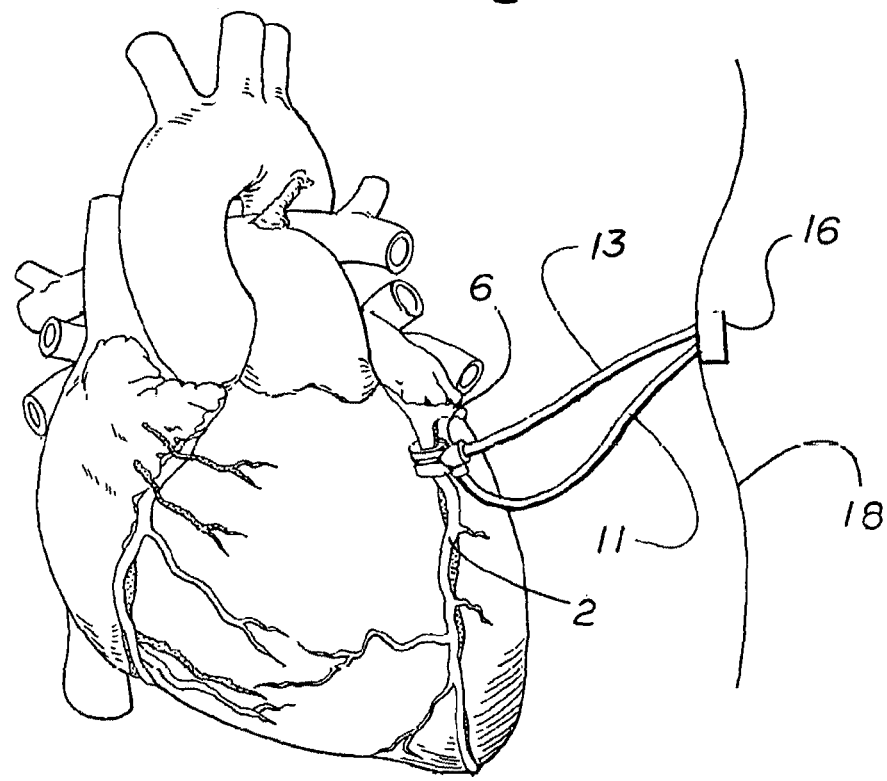
FIG. 16 shows a catheteric or tissue-engineered line from a port such as shown in FIGS. 27 and 28 at the body surface and schematically shown in FIGS. 21, 22, 29, 31, 32, and 38 to a native conduit, such as a vasospasm-susceptible (angiohypertonic, angiospasmic) artery, depicted here as the left anterior descending epicardial coronary.

FIG. 16 shows the application of a side-entry jacket for gaining access to a native lumen, where both lines connect to the native lumen, here to allow one-way epicardial coronary infusion through mainline 13 with collateral or intermittent adjuvant medication delivered through accessory or sideline 11, the administration of drugs contemplated as proceeding automatically under programmed sensor input-prompted control. To prevent a passive slit-membrane or flap-valve or a mechanical valve-plug described below from protruding into the native lumen despite the intrinsic pulsation or peristalsis, side-entry connector 6 is provided on its internal surface in front of or ductus-adaxial to the forward edge of water-jacket 7 with small recurved or backward directed or ductus-abaxially bent prongs 20.

Thus, accessory Or sideline 11 almost always connects a native ductus through port 16 at the body surface 18, to an extracorporeal pump contained in a wearable pump-pack. Side entry connector 6 slidably and rotationally friction fits through the journal formed by outer shell of casing 4 and the raised interdigitating landings between it and locking collar or bushing 5 and a round hole through foam ling 3 in the side of and entirely through the jacket. When jacket shell 4 is extruded, collar 5 or bushing 5 is fused with or bonded to it as to allow a right angular side-entry connector 5 to be rotated for use as a trepan. Locking collar or bushing 5 has circumferentially spaced apart, raised, and roughened areas oriented in the long axis of connector 6 on its inner surface as the complement to corresponding or mating areas on the outer surface of side-entry connector 6.

These areas are positioned to mesh and lock the connector in the radial position required when front circle-cutting edge 9 of side-entry connector 6 is planar (flush, even, level) with the internal surface of the lumen so that these areas overlap. To radially redirect inlet 10, side-entry connector 6 is pulled out of the jacket and reinserted at the radial angle needed to allow as direct as possible a line 11 to the port 16 at the surface 18. Any additional inlets 10 will then be rotated likewise, different orientation among lines 11 only beneficial when each must be connected to a surface port at a different location, which improbable, can be accommodated by producing side-connector 6 with inlets 10 positioned thus. Because a later need for direct access to the jacket in order to provide medication, for example, is not predictable, it is preferable to install the jacket with lines led to the surface.

The line connecting a given side-entry jacket to a port at the body surface can be a service channel as 11 or a synthetic conduit 13 connected to a second side-entry connector 6 of the same side-entry connection jacket. The incorporation of fluid conduction or water-jacket 7 with inlet 10 for connection of irrigation line 11 during placement and as service channel thereafter as standard means that in use to connect one native lumen or segment thereof to another via a catheter, both of the side-entry jacket connectors 6 will incorporate means for connection of a service channel or bypass junction supply catheter leading to the port 16 implanted at the body surface 18.

Internal fluid-conducting or water-jacket 7 may be visualized as comprised of a top-hat configured insert within side-entry connector 6, with brim ductus abluminally disposed to create a closed off fluid-tight cylindrical collar shaped space within and in concentric relation to the adluminal or circle-cutter ended segment of side-entry connector 6. The internal diameter of the passageway or channel through side-entry connector 6 is thus reduced to the internal diameter of water-jacket 7 over the ductus adluminal segment occupied by fluid-conducting or water-jacket 7, so that a catheter passed through side-entry connector 6 to position its distal tip in the lumen must be narrower than a hose fit over side-entry connector 6 by the difference in the two internal diameters.

Fluid-conducting or water-jacket 7 can be used to pass any fluid in either direction and is ordinarily connected to a pump capable of propelling a hydrogel, air, or water through it in either direction. Any fluid introduced through fluid-conducting or water-jacket 7 hose or catheter 11 attached to fluid-conducting or water jacket 7 connector or inlet 10 flows around and then up through the concentric cylindrical space of fluid-conducting or water jacket 7 to discharge through the circular gap formed by the outer surface of ductus side-entry connector 6 and fluid-conducting or water-jacket 7. The pressure and temperature of the fluid, usually water, is set externally at the pump. The parts of the side-entry connection jacket are generally molded of polyether ether ketone (PEEK), graphene, or if fabricated from nonmagnetic stainless steel tubing, then bonded together by continuous-bead, or non-spot, resistance welding.

Usually used in a subsidiary role to minimize lumen spillage when the conduit wall plug is cut during placement and to deliver adjuvant medication whether under automatic control thereafter, water-jacket and service channel 7 with inlet 10 and line 11 serve in a subsidiary or secondary support role with a flow volume smaller than that of the primary channel flowing through side-entry connector 6. However, depending upon the application, the service channel line comprised of water-jacket proper 7, inlet thereto 10, and line 11 might be equal if not larger in diameter than the primary flow though side-entry connector 6. This is also the case with the alternative double-arm side-connector jacket shown in FIG. 7, configured to allow expeditious passage of a guidewire or cabled device into the native lumen in either direction.

When the side-entry connection jacket is to be placed along the gut of a larger vertebrate, such as a human adult, a vacuum pump hose attached to the proximal or free end of the side-entry connector is used to draw the outer surface of the lumen wall against the razor-sharp front or adluminal edge of the connector, thereby maintaining the tissue in contact with the cutting edge to assist the operator in using the side-entry connector as a circle-cutter to cut a plug through the side of the ductus wall. Since unlike the situation with tubular anatomical structures other than the gut, the plug can be disposed of by pushing it into the lumen, the pump is reversed to blow or forcibly wash the plug into the lumen under air or water pressure.

Figure 22:
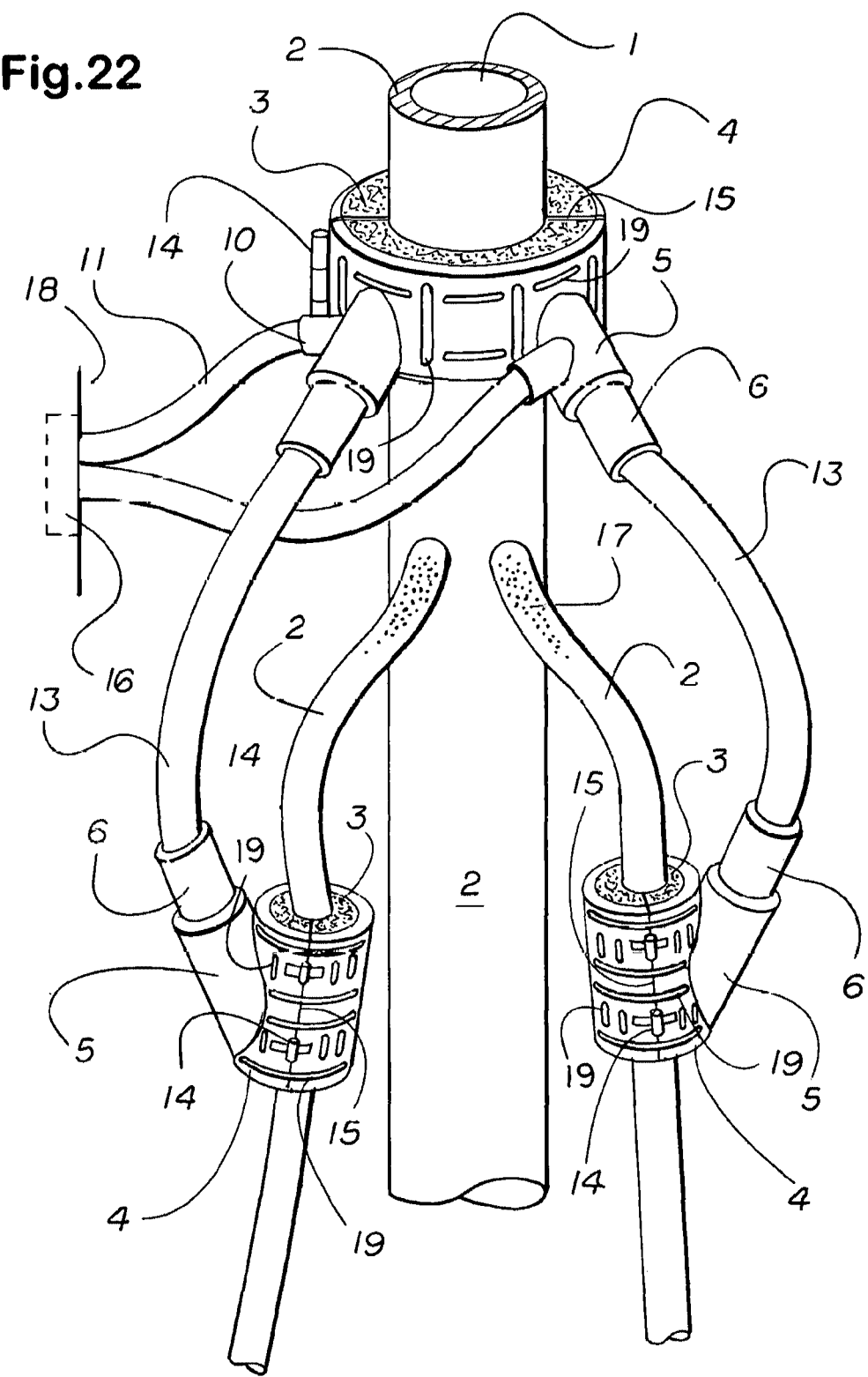
FIG. 22 is a pictorial schematic or circuit diagram of the side-entry connection jacket shown in FIG. 21 in greater detail, showing the connection of each side-connector to a synthetic or tissue-engineered native artery bypass line from the ascending aorta to smaller single arm ductus side-entry connection jackets shown without accessory or side lines but with each bypass connected by accessory or water-jacket inlets to a port at the body surface, thereby to deliver an anticoagulant, essential to prevent current state of the art catheters and synthetic blood vessels from thrombosing.

In FIGS. 16, 21, 22, 29, 31, 32, and 38, accessory or sideline 11 is connected to a native ductus, which occupies the jacket lumen. In FIGS. 21 and 22, however, side-connector 6, rather than used to hold mainline 13 for connection to port 16 at the body surface 18, is used instead to connect a prosthetic shunt or bypass for connection in turn to a native ductus, whether by anastomosis or as shown here, by distal side-entry jackets. FIGS. 21 and 22 show such an application, with side-connector 6 used to secure both the left and the right anterior descending prosthetic coronary artery tissue-engineered or synthetic bypasses.

Unlike the applications depicted in FIGS. 17 thru 22, in this application, so long as any adjuvant medication is not to be delivered separately, the water-jacket and its supply line (sideline, accessory line) 11 will be needed only during placement. Since accessory lines 11 are provided to the aortic jacket, drugs can be delivered through the replacement arteries at a distance close enough that the distal or end-arterial jackets need not retain lines 11 after these have been used to place the arterial jackets. While not all applications require an internal fluid-conducting or water-jacket, the significant post-implantation expansion in versatility of emergency responses it affords and the offsetting economy of avoiding different embodiments is considered to outweigh the negligible reduction in cost of omitting it.

For this reason, the port implanted at the body surface is routinely provided with two openings, one communicating with the side-entry connector, the other with the fluid-conducting or water-jacket. In internal ductus-to-ductus, or native lumen to native lumen use as a bypass or shunt—depicted in FIG. 16 as used to bypass the stenosed proximal segments of the left anterior descending, or anterior interventricular descending branch of the left, and the right coronary arteries—by connection of the ascending aorta to each artery distal to the obstruction, side-entry connectors 6 are attached to tissue-engineered prosthetic arteries or catheters leading to the side-entry connectors 6 at the arteries. Interluminal use is not limited to interconnection between ductus of like type such as arteries or veins but can include arteriovenous connection, for example.

Even with the expectation of uncomplicated healing in the placement of tissue-engineered graft arteries using suture, accessory lines 11 to automatically detect the need for and target medication directly to the grafts under closed loop adaptive control with the patient ambulatory will continue to increase the odds for successful healing with less physical discomfort and distress. As shown in FIGS. 1 thru 6, side-connector 6 incorporates a hydrogel, fluid conduction or water-jacket 7 entered through line 11 and inlet 10 to assist in its placement. Thereafter it remains available to serve as an accessory or service channel for aspiration or the delivery of medication directly to the jacket from the pump through port 16 at the body surface 18.

When the side-entry jacket shown in FIG. 2 is used before (upstream, or proximal to) a cross-clamp to initiate, or after (downstream or distal to), a cross clamp to terminate, a bypass to the same or a shunt to another ductus, connector 6 will have been used to attach the catheteric line to serve as the bypass or shunt and will therefore no longer be available for surface-to-ductus connection for the purpose of piping medication or communicating directly with lumen 1. In such use, water-jacket side branch 10 is used as a secondary or accessory side-entry connector or connector 6 is provided with additional secondary or accessory side-entry connectors similar to water jacket side branch 10. These secondary side-connectors can pass through water-jacket 7 and directly into the lumen of primary connector 6. Delivery to this jacket, which lacks a surrounding magnet as would make it an impasse jacket rather than a simple junction jacket, excludes drug-carrier particle bound drugs.

Side-entry jackets not made for magnetic use can incorporate ferrous materials. Catheters or artificial vessels used to shunt the flow of blood such as shown in FIGS. 21 and 22 should be the same in caliber as the native vessel, fed a fractionated, or low molecular weight, heparin drip and/or another anticoagulant or anticoagulants through a service channel shown as part number 11, any additional medication through the same or another service channel, and angled for streamline or laminar flow with minimal thrombogenic turbulence or churning of the blood. The instillation of heparin through synthetic lines avoids injection site reactions. Lines not used to conduct native luminal contents are used to deliver therapeutic substances. FIG. 16 shows catheteric line 13 from port or port 16 at the body surface 18 to a native ductus, here a vasospasm-susceptible left anterior descending coronary artery. Such a line can be used to immediately target the artery with a vasodilator, such as nitroglycerin, when, as is usual, the spasm is of atherosclerotic inducement, a statin, as well as preventive medication such as a calcium channel blocker.

Where such a line had previously been placed, the central infusion of saline ice or Ringer's lactate slurry, for example, at a higher rate of delivery can be promptly initiated should the need arise (see, for example, Arrich, J., Holzer, M., Havel, C., Milliner, M., and Herkner, H. 2012. "Hypothermia for Neuroprotection in Adults after Cardiopulmonary Resuscitation," *Cochrane Database of Systematic Reviews* 9:CD004128; Knapik, P., Rychlik, W., Siedy, J., Nadziakiewicz, P., and Cieśla, D. 2011. "Comparison of Intravascular and Conventional Hypothermia after Cardiac Arrest," *Kardiologia Polska* 69(11):1157-1163; Taccone, F. S., Donadello, K., Beumier, M., and Scolletta, S. 2011. "When, Where and How to Initiate Hypothermia after Adult Cardiac Arrest," *Minerva Anestesiologica* 77(9):927-933; Polderman, K. H. and Herold, I. 2009. "Therapeutic Hypothermia and Controlled Normothermia in the Intensive Care Unit: Practical Considerations, Side Effects, and Cooling Methods," *Critical Care Medicine* 37(3):1101-1120; Polderman, K. H., Rijnsburger, E. R., Peerdeman, S. M., and Girbes, A. R. 2005. "Induction of Hypothermia in Patients with Various Types of Neurologic Injury with Use of Large Volumes of Ice-Cold Intravenous Fluid," *Critical Care Medicine* 33(12): 2744-2751; Vanden Hoek, T. L., Kasza, K. E., Beiser, D. G., Abella, B. S., Franklin, J. E., Oras, J. J., and 7 others 2004. "Induced Hypothermia by Central Venous Infusion: Saline Ice Slurry Versus Chilled Saline," *Critical Care Medicine* 32(9 Supplement):S425-S431; Kasza, K., Fisher, B., Shareef, F., Oras, J., Chang, J., Tentner, A., Fischer, P., and 7 others 2008. "Medical Ice Slurry Coolants for Inducing Targeted-Organ/Tissue Protective Cooling," at http://www.ne.antgov/capabilities/sinde/biomed/IceSlurry Cooling.pdf; Shikanov, S., Wille, M., Large, M., Razmaria, A., Lifshitz, D. A., Chang, A., Wu, Y., Kasza, K., and Shalhav, A. L. 2010. "Microparticulate Ice Slurry for Renal Hypothermia: Laparoscopic Partial Nephrectomy in a Porcine Model," *Urology* 76(4):1012-1016, at http://www.ne.anl.gov/capabilities/sinde/biomed/Lapar Kidney-SurgerySlurryCoolingAUA.pdf.

The medication can be administered manually from a syringe when the patient feels pain or automatically from the portable (ambulatory, wearable) pump-pack when a chemical or mechanical sensor associated with the jacket signals the pump through conductors passed through the same catheteric line 13 to the pump at port 16 before the threshold of pain sensation is reached. The coronary artery end-arterial, the targeting is complete, thereby minimizing adverse side effects and drug-drug interactions associated with drug delivery through the systemic circulation. With the scheme shown in FIG. 16, drug delivery can be initiated manually by the patient at the onset of pain or automatically by a sensor connected by a wire passed through delivery line 13, for example, to a miniature portable (ambulatory, wearable) pump.

Preferably, however, a blood gas or mechanical sensor in the jacket signals the pump preemptively or prodromally, that is, before the patient senses pain. Targeting minimizes adverse side effects, addressed above under Background and drug-drug interactions associated with drug delivery through the systemic circulation. Here, avoiding the liver minimizes if not eliminates interactions of calcium channel blockers such as diltiazem and verapamil, with other drugs meant to treat a comorbid condition elsewhere in the body. Any vessel or other bodily conduit of adequate caliber to allow application of a side-entry connection jacket can be made to deliver any fluid medicinal substance. A larger jacket placed about the pulmonary artery can be used to deliver decongesting drugs to the pulmonary capillaries.

Smaller jackets placed about the internal carotid arteries of a patient showing signs of vascular dementia can be used to deliver platelet blockers, antiatherosclerotic medication, other cholesterol reducing drugs, and antihypertensives at a concentration higher than would be allowed to circulate to treat systemic atherosclerosis. Where the disease is systemic, a background dose is circulated as well. Delivery directly to the brain of an antihypertensive might aid in suppressing an advancing subcortical hypertensive leukoencephalopathy or Binswanger disease. Disorders involving the carotid and coronary arteries are cited as exemplary; by this means, the vascular and/or luminal inlets and if necessary outlets of any discrete organ can be jacketed for treatment to the substantial exclusion of the rest of the body. If necessary, a downstream jacket is used to deliver a reversal or neutralizing agent if available to eliminate any residuum from further circulation.

FIG. 21 is an anterior view of the heart with the double side-connector with water-jacket inlets shown in FIGS. 17, 19, 20, and 22 having been placed about the ascending aorta to join synthetic coronary artery bypass conduits for distal insertion at the respective coronary arteries. The distal connection is made with smaller side-entry connection jackets distal to the occluded segments represented in FIG. 22 as 17. Connection to a port 16 at the body surface 18 through lines 11 connected to the side-entry connector 6 accessory or water-jacket inlets 10 allows delivery of an anticoagulant essential to prevent state of the art synthetic blood vessels from clogging with thrombus. Whereas in FIGS. 21 and 22 the proximal jacket secures synthetic catheters 13 used as coronary artery bypasses, in the application depicted in FIG. 16, the jacket encircles the coronary artery, and the vasodilator is fed through side-entry connector 6 line 13.

More specifically; in FIG. 16, the flow is through a catheter or synthetic line and the junction created with the side-entry connection jacket to a coronary artery, where the angle and caliber of the lumen expedite laminar flow of the blood stream. In FIG. 16, line 11 is essential to minimize if not prevent exsanguination during placement of the jacket, but the native artery is not so prone to become obstructed by clot as is the synthetic artery depicted in FIG. 21, where an anticoagulant and possibly antihyperplastic drugs must continue to be fed to the synthetic bypasses by lines 11 from the surface through the water-jacket inlets 10 of each side-entry connector 6 continued in use as a post implantation service channel. Nevertheless, because a need for drug delivery separately from that delivered through mainline 13 might always arise, line 11 is never made absorbable.

In FIG. 21, flow is through a tissue-engineered artery or catheter, and the junction made by the side-entry connection jacket into a coronary artery, where the angle of entry for the small volume delivered allows perpendicular junction without the need for approach through a side-connector of the proper angle or a caliber equal to that of the artery. Essentially then, the configuration of FIG. 21 replaces the aorta for the surface port implanted at the body surface as the source of flow. The coronaries end-arterial, the segment targeted starts at the jacket, here of the kind without magnet shown in FIGS. 1 and 2, and ends within the myocardial supply area or territory of the artery.

Where bidirectional flow is contemplated, a side-entry connector 6 line 13 is generally preferred to a water-jacket inlet line 11 for the larger caliber and greater flow rate. When an eventual need for additional side-entry connectors 6, side-entry connector lines 13, water-jackets 7, water-jackets inlets 10, and water-jacket inlets lines 11 cannot be predicted, the number potentially required are prepositioned in one procedure. Primary lines such as those shown in FIGS. 16 and 21 are often dedicated and committed to a specific constant use. By contrast, additional lines can usually be used to deliver different drugs or to withdraw samples, for example, in a consecutive manner, so that the number added is small. FIGS. 16 and 21 are exemplary and not to be interpreted in a limiting sense as to conclude that analogous treatment might be less applicable along the digestive tract, urinogenital system, or the airway, for example.

Types of Electromagnet Jackets

Electromagnet jackets are of four basic types:

1. Impasse electromagnet jackets without pipe or a side-entry, analogous to permanent magnet impasse-jackets described in copending application Ser. No. 13/694,835, published as US 20140163664.

2. Impasse electromagnet jackets with a side-entry or access into the native lumen, analogous to the permanent magnet impasse-jackets shown in FIGS. 3 and 4; which except for a hard outer shell and the lack of a draw-plate are the same in essence as the contraction electromagnet jackets shown in FIGS. 11 and 12.

3. Extraction jackets, shown in FIGS. 13 thru 15, with an entry into the native lumen used primarily to extract magnetically susceptible, commonly, superparamagnetic nanoparticle carrier-bound drugs into an integral collection chamber or trap; and 4. Contraction-electromagnets proper, such as those shown in FIGS. 10 thru 12, used to compress interposed tissue, which controlled in an iterative sequential pattern function as the peristalsis simulation jacket shown in FIG. 10.

Figure 39A:
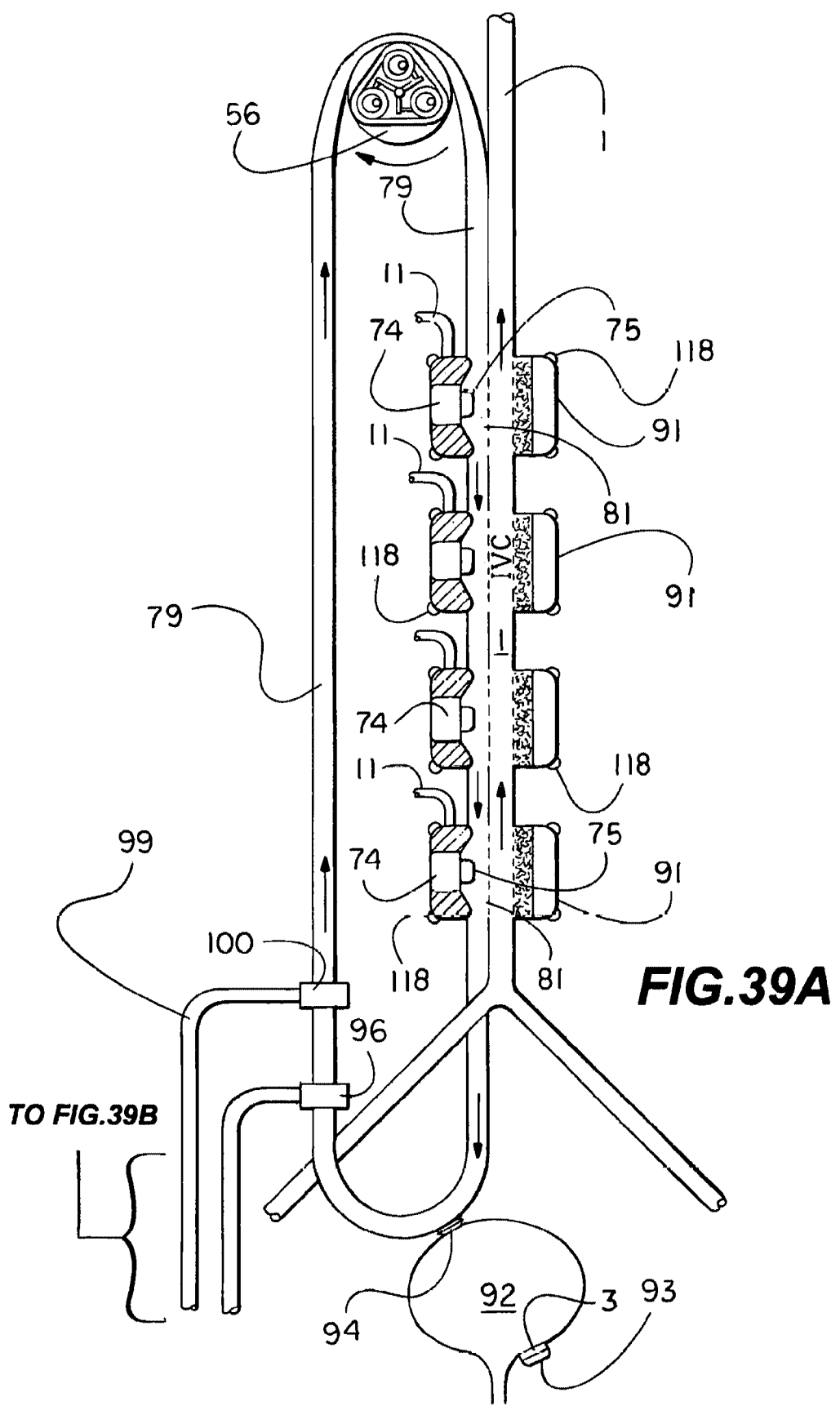
FIG. 39A shows a chain of hemodialysis magnetic separation jackets with bundled semipermeable fibers, or for cytapheresis, slit-valve at the extraction transit window applied to the inferior vena cava and water or dialysis flush-line circuit for drop-off of the magnetically separated extractant into the urinary bladder under the tractive force applied by a subcystic electromagnet.
Figure 39B:
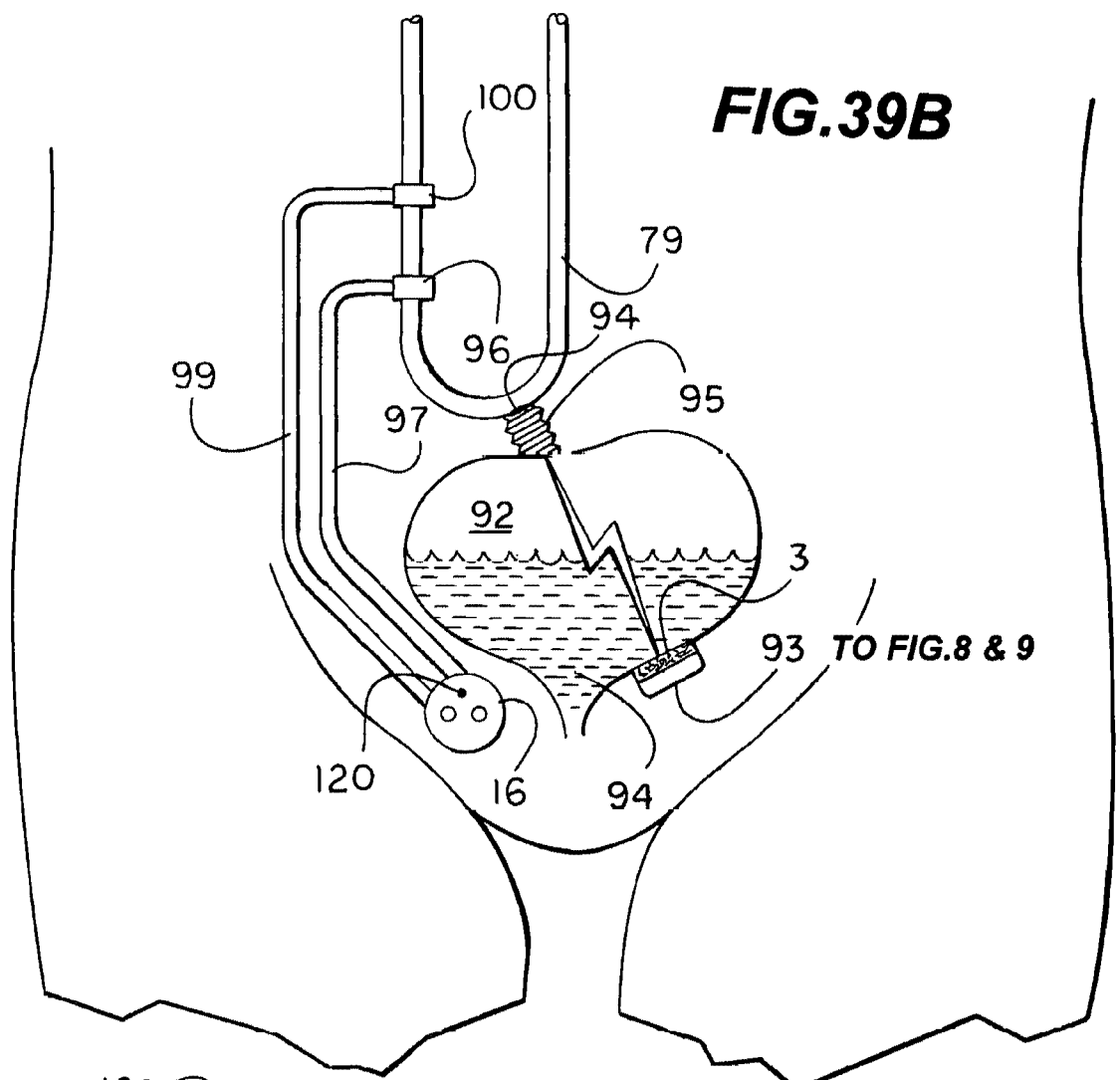
FIG. 39B shows drop-off of the magnetically separated extractant into the urinary bladder.
Figure 39C:
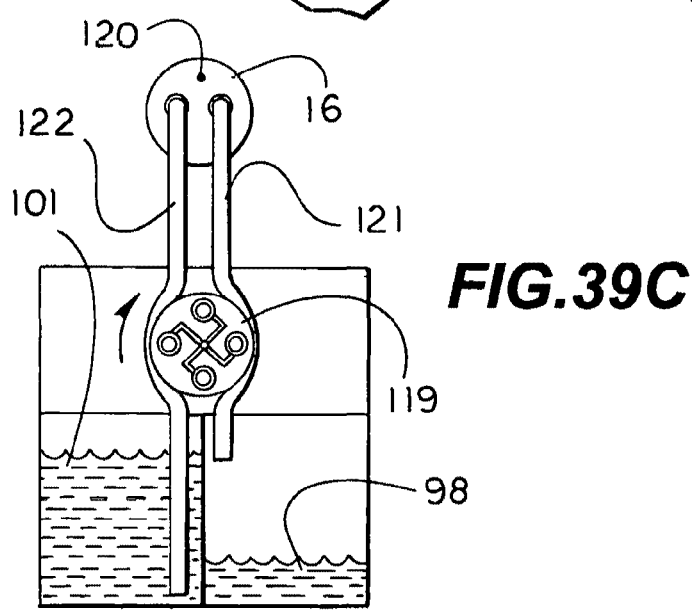
FIG. 39C shows a dialysate disposal and replenishment chamber used to replace spent dialysate or apheresis fluid, and for use in conjunction with a debris collection chamber in lieu of a urine collection bag by a patient who has undergone complete removal of the urinary system, or a radical bilateral nephroureterectomy with cystoprostatectomy and discretionary lymphadenectomy.

To these basic types can be added permanent radiation shielding, individual contraction-jackets, used to simulate sphinteric function, and extraction jackets with an integral collection chamber or trap, and modified double-sided double-arm side connector, as shown in FIG. 15, with interposed electromagnets applied to the extraction of high-volume debris. In FIGS. 39A and 39B, more compact jackets suitable for use in small patients for intracorporeal magnetic separation hemodialysis or cytapheresis are shown connected in series by a common flush-line which empties into the urinary bladder.

Figure 40:
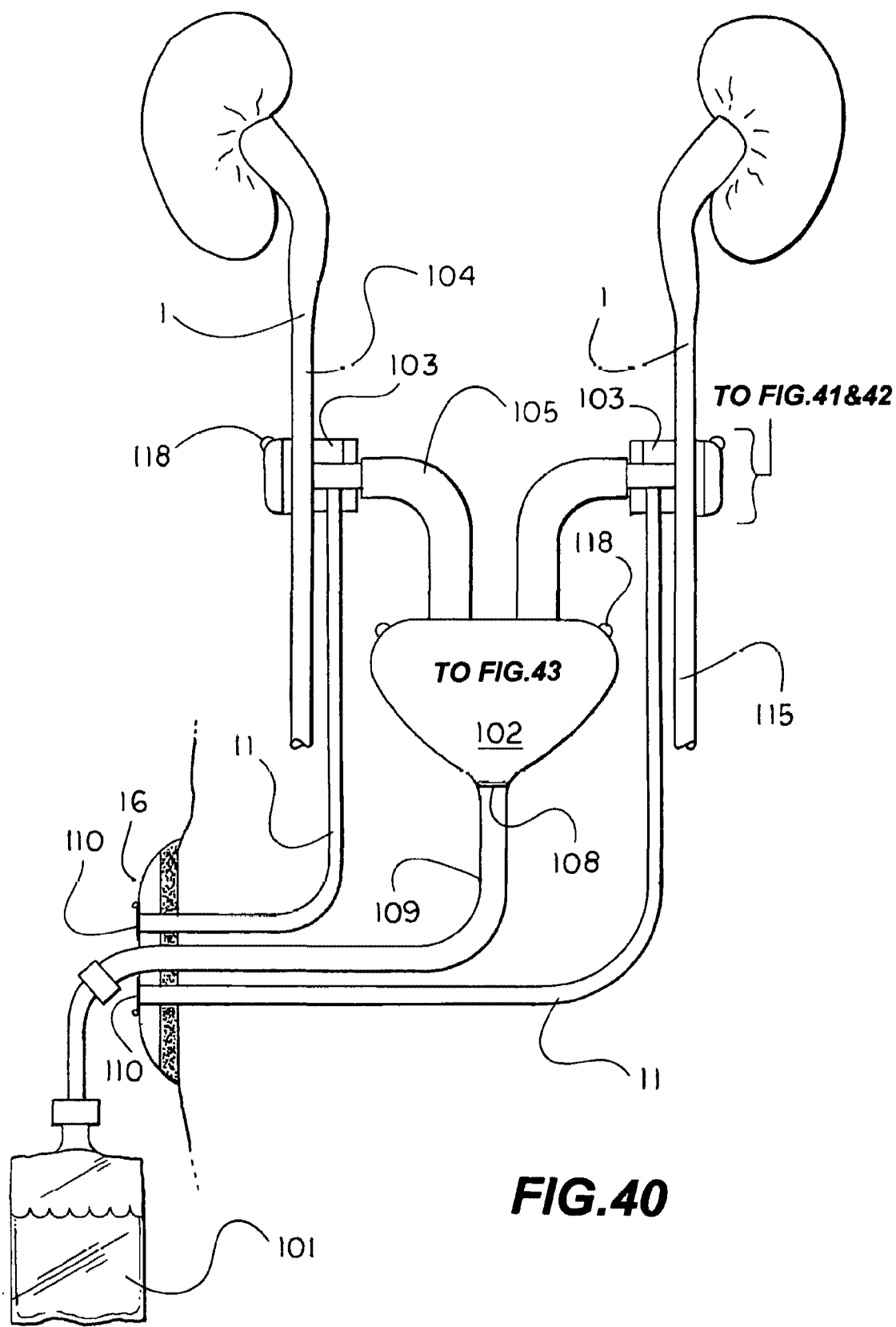
FIG. 40 shows the layout of nonadjustable intravascular (endoluminal) diversion valves and drainage path prosthesis to allow a patient following exenteration, for example, to eliminate without the need for a urostomy or a nephrostomy.

If the bladder is missing, then as shown in FIG. 40, takeoff is with the aid of diversion jackets through synthetic neoureters 105 into a collection or confluence chamber 102 from which the debris of separation is extracted in the same manner as it were a native bladder. When the patient is ambulatory, either the native bladder or confluence chamber empties into a collection bag typically cinched about a thigh. Various combination jackets serve exceptional purposes.

For example, a contraction and extraction electromagnet jacket combining the features of the contraction jacket shown in FIGS. 11 and 12 having a pliant shell and draw-plate and the extraction jacket shown in FIG. 13 would constrict the ductus to extract magnetically susceptible particle-bound drugs from the lumen. This is done with adjuvant medication administered systemically to slow down the volumetric flow rate through the lumen during the process.

Magnetized Side-Entry Jackets, or Piped Impasse-Jackets

Piped Impasse-Jackets Using Permanent Magnets

Ductus side-entry or piped impasse jackets with magnetization may incorporate permanent or electromagnets, to incorporate both types exceptional. When the side-entry connection jacket is not just piped but provided with a permanent or dc electromagnet to draw drug-carrier particles delivered through the pipe into the lumen wall, outer shell 4 is wrapped completely around magnet 8, magnetized in separate segments and bonded together, to isolate the toxic and brittle magnetic material. Since the side-entry connection jacket shown in FIG. 1 has neither magnetic nor radiation shielding layers interposed, foam lining 3 and outer shell or casing 4 are in direct contact. For clarity, the ductus is shown stripped of adherent tissue; in fact, some perivascular fat, serosa, or mesentery, for example, can be encircled within the fenestrated jacket if the microcirculation is not cut off.

Figure 4:
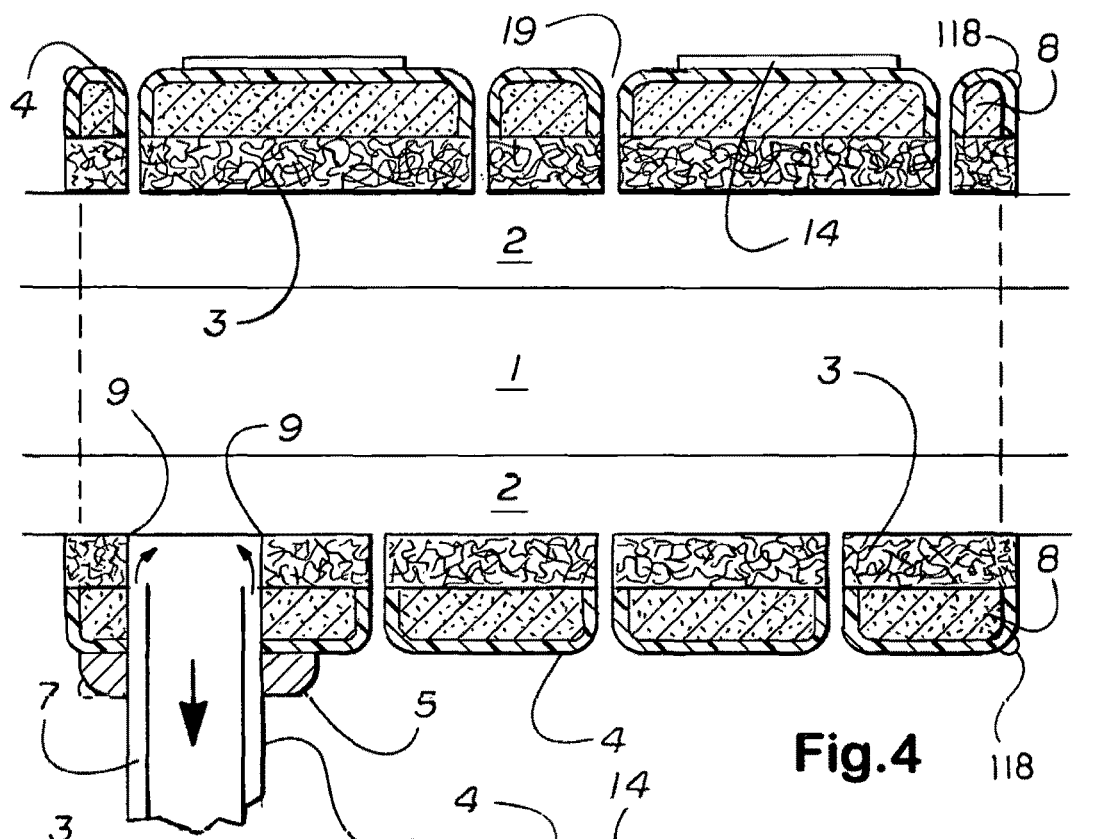
FIG. 4 shows a longitudinal sectional view of a segment along a tubular anatomical structure encircled by a longitudinally extended, field strength-graduated, or magnetic gradient-type side-entry connection jacket, or piped impasse-jacket.

Longitudinal extension or elongation essentially integrates a simple junction side-entry jacket with an impasse-jacket for the purpose of acting upon the drug or other therapeutic substance delivered through the native lumen and carried forward by the lumen contents immediately upon delivery. As shown in FIG. 4, longitudinal extension is usually to add a permanent magnet which for uniformity of uptake is usually magnetized in separate segments which are then bonded together to present a long central axis axifugally directed field intensified in a graduated manner in the antegrade or downstream direction. The actuability and adjustability of electromagnets affording superior functional versatility, most practical applications for extension using electromagnets also call for the inducement by each consecutive magnet of a field stronger than that of the magnet preceding or upstream to it.

Longitudinal extension is embodied in jackets such as shown in FIGS. 4 thru 6 and/or jackets connected together into a train, with strong polymeric or stainless steel wire, and radiation shielding added, shown as part number 12 in FIGS. 5 and 6 if treatment involves the use of a radionuclide. Fixed in the direction of its graduated field strength, a permanent side-entry magnet jacket cannot simply be reversed in direction to take up a carrier bonded drug delivered upstream whereas an electromagnet jacket can. While a single jacket can incorporate both a side-entry antegrade antegrade-directed gradient to take up a carrier-bound drug arriving from upstream and a retrograde-directed gradient to take up a carrier-bound drug arriving through the side-entry, the use of separate jackets is preferred as affording flexibility and a break in ensheathment.

Figure 3:
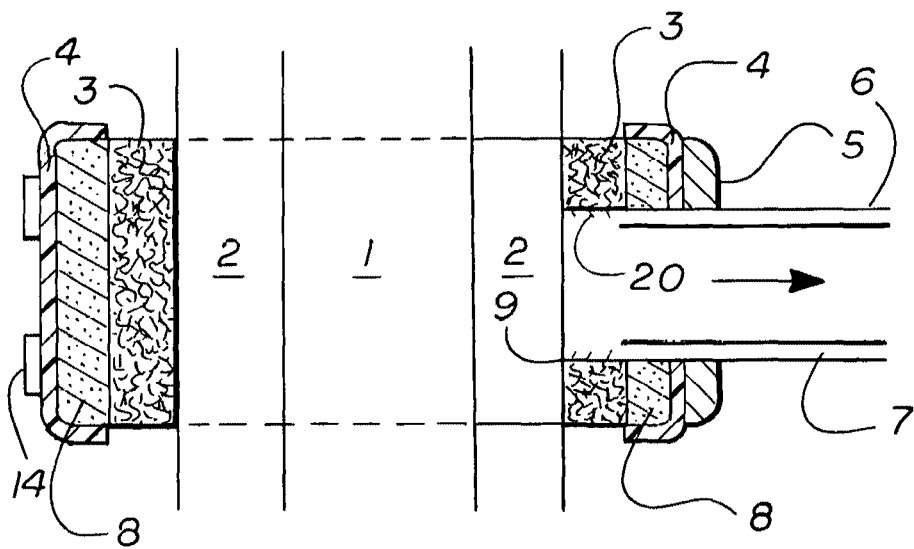
FIG. 3 shows a longitudinal sectional view of a segment along a tubular anatomical structure with a side-entry connection jacket as that shown in FIG. 1 but with the addition of a magnet layer outside of and concentric to the long axis of the jacket.

The jackets shown in FIGS. 3 and 4 differs from the simple junction jacket shown in FIGS. 1 and 2 in having a magnetized layer 8 outside concentric to foam lining 3. Rather than uniformly magnetized through the thick dimension to direct the field radially toward the long axis of the lumen without change in field strength from one end of the jacket to the other, layer 8 is assembled from adjacent segments from separately magnetized high energy product neodymium iron boron paired half-cylinders. Each half-cylinder pair is magnetized through its thick dimension to direct the field radially toward what will be the long axis of the lumen with progressively greater intensity and sectioned into half-rings. One half-ring from each pair is then bonded to the next in order of increased field strength to reconstitute half-cylinders, but now with increasing field strength directed toward the long axis of the lumen from one to the next segment or section along the length of the sectional half-cyliner. The half-cylinders are then joined into an openable cylinder by bonding to spring-hinges 14.

The openable cylinder produced thus presents a magnetic field which is graduated by sectors from one end of the cylinder to the other. This gradient is intended to facilitate uniform uptake against, into, or through the subjacent lumen wall of a drug or other therapeutic substance delivered through ductus lumen 2 or jacket connector 6 or 10 as a ferrofluid wherein the medicinal substance is bound, such as molecule to molecule, to a magnetically susceptible carrier particle, such as a superparamagnetic nanoparticle. Unlike an impasse jacket without a, side-entry connector which must be marked to indicate the direction of increasing field strength, the side-entry of the completed jacket serves to indicate the end of lesser field strength. The jacket is placed with the increasing force directed downstream, that is, in the forward or antegrade direction of flow through the native lumen.

Such a magnetized jacket with side-entry connector, or piped impasse-jacket, is placed to encircle a lesion to be treated in order to draw the medication against or into the lesion. The jacket side-entry connector can receive magnetically nonsusceptible or ordinary drugs and superparamagnetic particle-bound drugs together or as mixed, or delivery of the different drugs can be offset, only the magnetically drug bound fraction detained at the jacket. Drugs or other therapeutic substances that should not mix before entry into the native lumen under treatment can be delivered to the side-entry connector through a multiluminal catheter simultaneously or at intervals. Separate catheters can be led to different side-entry connectors on any one jacket, each catheter can be multiluminal, and different water-jacket inlet or service channels used for further segregation, the primary object in this being to allow for future pharmaceutical developments.

Alternatively, a single line to conduct drugs to be kept separate during delivery is flushed through with Water or a solvent, an intervening pump turret refill cartridge, several of these, or insertion of a hose feeding into the turret socket used to separate these substances. Were the segment to be treated instead limited to a length along an artery that can be encircled within one continuous jacket, then the jacket shown in FIG. 4 is used, and if radioactive then a jacket with radiation shield as shown in FIG. 5 as permanent and FIG. 6 as disintegable. FIG. 4 shows a longitudinal section through a ductus with side-entry connection jacket before the side-connector has been advanced to cut a plug out of the structure wall with its leading sharp edge brought into level alignment with the internal surface of the lumen wall. The jacket has a concentric layer of high energy product neodymium iron boron with the magnetic strength gradually increased in the downstream or antegrade direction. Such a jacket constitutes a piped impasse-jacket.

Perforations 19 may be circular, slits, or slots not so extended as would significantly interrupt the magnetic gradient. Outer shell 4 lines the perforations down to the foam, but not more adaxially or closer to the adventitia as would allow the inner edge of shell 4 to encroach upon the adventitia. In FIG. 4, the radially inner or adaxial edges at the ends of shell 4 have been brought down into contact with the outer surface of foam lining 3, whereas in FIG. 5, the foam is kept clear of shell 4, the plastic and metal composite film used to chemically enclose and isolate foam 3 assumed in FIG. 5 as lacking sufficient puncture or shear resistance to avoid its perforation, even were the edges rounded. The bond of the drug to the carrier particles can be dissoluble or indissoluble. When the bond is broken, the drug is released to flow downstream and the carrier taken up in the lumen wall. When the bond persists, the drug is drawn with the carrier into the wall.

Different formulations can thus be used to cause the drug and/or other therapeutic substance or substances to flow past, penetrate for a distance into, or completely perfuse through the segment wall. For example, where uptake into the lumen wall is not sought, nonmagneted jackets such as those shown in FIGS. 1 and 2, each connected to its respective socket in the port implanted at the body surface define the starting and ending levels with delivery by the upstream jacket of the drug and the downstream jacket of the counteractant (reversal agent, neutralizing agent, antidote). When not accomplished automatically during the prodromal phase as addressed above under the section entitled Background, introduction of the drug through port 16 can be through syringe injection by the patient when experiencing anginal pain attendant upon vasospasm induced ischemia. Provided the patient is awake and mentally competent, manual actuation thus may be satisfactory.

Figure 17:
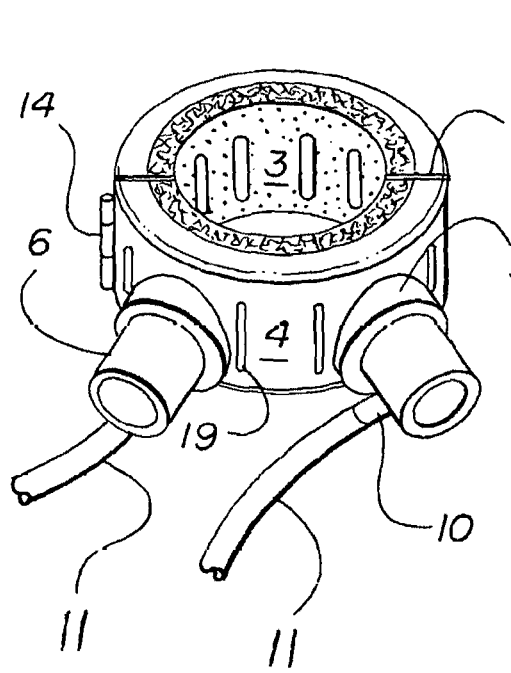
FIG. 17 is a perspective cross-section through a simple junction, or unmagnetized and nonelongated, thin-walled, side-entry connection jacket such as shown in FIGS. 1 and 2, with two side-connectors everted and inclined caudally in relation to the transverse plane of the jacket, for placement about a native conduit to accept synthetic catheters or artificial arteries as shown in FIGS. 21 and 22.

Otherwise, such function is best automated to accomplish drug delivery as soon as a measurable parameter indicates spasm. Such means were briefly addressed in the section above entitled Background. FIG. 17 shows an unelongated, unmagnetized, and unshielded, relatively thin-walled side-entry connection jacket of the simple junction type shown in FIGS. 1 and 2, but with two side-entry connectors 6. The jacket shown in FIG. 17 is suitable for placement toward the aortic root to allow the connection of coronary artery synthetic bypass lines as shown in FIGS. 21 and 22, where the great vessels are juxtaposed limiting jacket thickness, and dissection to gain access best minimized. Existing synthetic tubes, especially those of a caliber suitable for use as artery bypasses, require the delivery of an anticoagulant to prevent clotting. Line 11 allows the anticoagulant and any other drug or drugs heeded, to be targeted to the end arterial coronary artery so that entry of the drug or drugs into the general circulation is avoided.

Viscoelastic polyurethane foam lining 3 conforms to and reduces trauma to the fine nervelets and vessels that support the ductus, and when thick enough, is compliant as to alleviate shaping the site, reducing the need for dissection and secondarily, the procedural duration. The foam lining allows the jacket to conform to irregularities in external diameter of the ductus and according to the thickness allowed by the clearance available, allows some periadventitial or other adherent tissue to be included for encirclement when physiologically desirable or fine dissection would significantly extend the procedural duration. Such jackets are longitudinally extended to incorporate the magnetic layer, which according to the field strength applied, are used to detain or draw the drug-carrier bound affinate against or into the wall surrounding the lumen.

Detention may pend delivery of a second substance that acts upon the first to break the carrier bond or to modify the drug, for example. A drug-carrier remaining bonded to the drug draws the drug against, and dependent upon the magnetic field strength, into the wall. When the bond is broken, the susceptible carrier is drawn alone, freeing the drug to continue through the circulation. FIG. 3 shows a side-entry connection jacket such as that shown in FIG. 2 with concentric magnet layer 8 interposed between viscoelastic polyurethane foam lining 3 and outer protective and magnet isolating shell or casing 4 of polyether ether ketone, for example, after sharp adluminal edge 9 of connector 6 has been brought to level alignment with the internal surface of lumen wall 2. At this time, the magnet would be made of high energy product neodymium iron boron.

Casing or shell 4 is wrapped about the sides of the jacket not only to protect, but to isolate the brittle magnetic material, and if incorporated, a tungsten heavy alloy radiation shield which are toxic, from the neighboring tissue. Depending upon the volume of delivery required, when, as shown in FIGS. 17 thru 22, jacket side-entry connector 6 is taken up to attach a synthetic bypass or shunt, a second side-entry connector or water-jacket side-branch connector 10 is used as the inlet for drugs in fluid form to include drug-carrier ferrofluids. Water-jacket inlet 10 and its line 11 are normally smaller in diameter than side-entry connector 6 but can be made as large as the application requires.

Magnet 8 is magnetized over the lesioned area in the segment jacketed whether radially symmetrical or encircling and can be omitted over an arc in which it is not essential and to reduce jacket thickness assists in the avoidance of neighboring tissue. The magnetized area of magnet 8 is that over which the magnetically susceptible particle bound drug is to be drawn from lumen 1 radially outward against, and when the field strength is sufficient, through native conduit wall 2, making the jackets shown in FIGS. 3 and 4 not just infusion junctions but piped impasse-jackets, and those in FIGS. 5, and 6 with radiation shielding, usually for the susceptible particle bound infusate; however, the infusate can be unmagnetized, another susceptible particle bound substance detained.

Side-connector 6 is generally positioned opposite the lesion, such as a tumor along the gut, with the magnet or portion of the magnet layer in fact magnetized on the opposite side to draw superparamagnetic drug-carrier nanoparticles delivered through connector 6 into the lesion. Foam layer 3 accommodates the lesion according to its thickness. Intended for uptake immediate to side-entry connector or native lumen inlet tube 6, magnetization is not of a segment along the lumen as recommends progressively increasing the strength of magnetization in the antegrade direction to obtain more uniform distribution of uptake along the length of a longitudinally extended jacket. Alternatively, the susceptibility of the drug-carrier particles can be varied spectrally.

Magnetization can, however, be graduated about the circumference to increasingly concentrate drug delivery to the center of the lesion, a sector of the magnet can be omitted, or the magnet otherwise configured or magnetized to match the lesion to be treated. When the magnetizer or the size of the jacket prohibit finer distinctions in field strength, the magnet is assembled from separately magnetized rings, arcs, or segments as necessary, these pieces bonded to constitute the half-cylinders joined by spring loaded hinges 14. A need to compose the magnet of different magnetic materials is not contemplated. When connector 6 can be positioned diametrically or opposite to the lesion, a side-entry jacket is selected in which magnet layer 8 is increased in strength of magnetization moving radially or about the circumference away from connector 6 to the opposite side where it is at the maximum in superjacent relation to the lesioned tissue.

Omission of an arc in the otherwise concentric magnet layer or graduation in the magnetic field strength is attained by proportional graduation in magnet thickness only when necessary to avoid encroachment upon neighboring tissue with patient discomfort. Using suture to impart lifting force will often serve to avert discomfort. Otherwise, standardization in general and uniformity of thickness in the magnet and other layers is less costly. Magnetic side-entry connectors must not themselves be magnetically susceptible; however, this does not exclude the use of nonmagnetic stainless steels. FIGS. 3 and 4 show side-entry connection jacket with surrounding concentric magnet layer 8 but not radiation shielding as shown in FIGS. 5 and 6.

When applied to a jacket for use on a blood vessel, the strength of magnetization is gradually increased in the antegrade or downstream direction in proportion to the blood pressure and susceptibility of the particles. The uptake of superparamagnetic drug-carrier nanoparticles delivered into the circulation through the side-entry connector is then as uniform as the volume of ferrofluid, blood pressure, susceptibility of the particles, and strength of magnetization allow. For treating radially asymmetrical or eccentric lesions, side-entry jacket magnets such as shown in FIGS. 3 thru 6 can be made to complement the eccentricity, or radial asymmetry, of the leasion by situating nonmagnetic blank sectors in the magnet layer.

In FIGS. 3-6, toxic neodymium iron boron magnet 8 is completely enclosed within shell 4, which also protects the brittle material in the event of a direct blow in an accident, for example. The native adluminal or adaxial surface of magnet 8 is covered by foam lining 3. In FIG. 5, showing the side-entry jor acket before side-entry connector 6 has been advanced to cut a plug out of the ductus wall 2 and its leading cutting edge 9 brought to level alignment with the internal surface of the lumen wall, radiation shield 12 allows the delivery of a drug-carrier bound low dose rate radionuclide for drawing into the lumen wall 2, likewise toxic, has shell 4 extended about the jacket ends to enclose it with the inner surface of radiation shielding 12 surrounding magnet 8.

Side-entry connection jacket connector subsidiary fluid conduction or water jacket inlet pipelines 11 can be accessed through a conventional membrane port or port 16 implanted subcutaneously or onto the fascia at the body surface 18 to administer the anticoagulant and/or other drugs directly to the bypasses by injection or release by an ordinary syringe, automatic ambulatory syringe driver, or an infusion pump, thus avoiding the systemic circulation. Such a membranous port for leakless perforation by an injection needle eliminates problems of spillage out of the line should it require to be opened at the proximal end, and for that reason, is to be preferred whenever the application permits. However, a port that must allow insertion and removal of a cabled device or a valve cannot be of the conventional subcutaneous membrane type but must be configured to minimize spillage when opened.

If discontinuous or unextended in length or width, slit or slot-shaped perforations to allow gas exchange between adventitia and the interior milieu need not significantly interfere with uniformity of drug-carrier uptake by the magnet. To fully enclose the toxic magnetic material, outer shell 4 must line any perforations to the same depth as at the axial ends of the jacket, meaning from the external surface of the side-entry connection jacket up to the internal surface of foam lining 3. A jacket with radiation shield 12 is not perforated. To allow the use of a radiation shield that need not be recovered in a second invasive procedure, a shield is used that will safely disintegrate to expose the adventitia, fibrosa, or serosa through perforations through the more central magnet and foam layers. A shield that will spontaneously disintegrate can be made, for example, of biocompatible or chemically inert polymer encapsulated tungsten heavy alloy beads compacted to overlap in multiple layers bonded together with a thin coating of an absorbable adhesive, such as one of polyglycolic acid.

Such a jacket effectively isolates the tungsten heavy alloy by encapsulation without the need for a continuous outer shell but must incorporate a shell subjacent or long axially central to the magnet to fully enclose it once the radiation shield has disintegrated. The shell must not only enclose the magnet concentrically but line the perforations incorporated to allow the adventitia to 'breathe.' Since enclosure-induced atherosclerosis probably involves obstruction of the minute vasa supplying the artery treated, should perforations along prove inadequate to suppress atherosclerotic deterioration, a service channel is used to deliver anti-inflammatory and antihyperplasia medication.

The application of a side-entry connection jacket interrupts the internal surface of a native conduit—in an artery, the endothelium—by no greater an area than the opening or ostium leading into the side-entry connector, the impairment to endothelial function thus small and focal. No distal end of a catheter is suspended within the lumen to disrupt flow, to irritate the entry rim, or erode the intima over time, and there is no transition in the internal surface moving through the jacket and past the connector. Unless the opening into the lumen is too large, flow is not significantly disturbed or endothelial function disrupted briefly and not so that drugs cannot alleviate the temporary local trauma.

Connection of neither the side-entry connector to the conduit nor a water-jacket inlet to the line connected to it is fastened end-to-end with suture. The ductus is completely enclosed so that it cannot 'breathe' only when radiation shielding necessitates and then during the shortest effective duration of treatment and with the administration of anti-atherogenic medication. The use of a synthetic conduit becomes necessary when no autologous vessel is suitable and when an autologous stem cell generated tissue-engineered replacement is unavailable or cannot be secured in position with suture. Surface-to-ductus pipeline catheters routinely incorporate more than a single lumen and can be used bidirectionally to deliver medication, draw diagnostic samples, pass testing sensors to the junction, or contain wires as necessary.

Enabling the use of synthetic materials to form bypasses and shunts and thus eliminate the need to harvest native tissue or stem cells to tissue-engineer a replacement, side-entry jackets placed beside native-native end to end anastomoses can also be used to target medication to the anastomosis and angled, allow a fiberoptic angioscope, for example, to be passed through the jacket to monitor the anastomosis, for example. The advantage compared to a conventional transluminal approach is that the prepositioned conduit with entry through a port implanted at the body surface eliminates the need for entry by incision and the risks of the transluminal method. It is not suggested that such a line is placed where the prospective uses therefor do not justify placement.

Side-entry and impasse-jackets seek to advance medical surgery, or medical management assisted by minor surgery, whereby a relatively low risk invasive procedure is used to position implants that make it possible to access and target, or substantially limit, medication to certain tissue while avoiding exposure to other tissue or drugs. A primary area for the application of such treatment is lifelong episodic severe disease, whereby detection of onset markers is applied to trigger delivery of counteracting medication, thus suppressing symptoms before these start. Junction by means of side-entry jackets is amenable to robotic placement and allows followup access not allowed by sutured anastomoses.

Whereas surface-to-ductus lines can be multiluminal, side-entry jackets used in ductus-to-ductus connections in lieu of bypass and shunt grafts and anastomoses are usually monoluminal. To allow different drugs or other therapeutic substances to be administered independently or simultaneously to a ductus, a line from the body surface to the side-entry connection jacket encircling the target ductus can be multiluminal, entry into the jacket through a side-entry connector and/or a fluid, conducting or water-jacket inlet line, a jacket able to incorporate a number of either or both type inlets where the pathology along a ductus differs in different segments, different jackets positioned along the ductus to treat each condition can be accessed through the same or different entry points at the body surface.

A side-entry connection jacket retains a synthetic bypass or shunt in its side-entry connector. The bypass or shunt is always monoluminal. Because the conduit or line is synthetic, the need for supportive medication through a supply line from a port at the body surface is substantially reduced to an anticoagulant and an antimicrobial ordinarily delivered though a water-jacket inlet used as a followup service channel rather than through another side-entry jacket placed on or upstream to the bypass or shunt. Venous insufficiency that uses a synthetic conduit or ductus to divert blood from a diseased to a competent vein or to bypass an occluded segment along the vein is normally from a side-entry connector on the source vein, usually one of larger caliber, to a side entry connector on the destination vein or distal segment.

A side-entry jacket is not limited to a single connector. Rather, multiple connectors can be radially and/or longitudinally separated along the jacket. Thus, by connecting catheteric conduits to two or more side-entry connectors on a single jacket, the flow through the jacketed ductus can be diverted to two or more receiving ductus, and a ductus with two or more side-entry connectors can receive flow from two or more source ductus. Moreover, any one side-entry connector can be provided with more than one water-jacket inlet that can be used as a service channel to deliver drugs or aspirate biopsy samples, for example, once the jacket has been placed. Jacket supply lines from a port implanted at the body surface are catheteric, preferably synthetic.

In the drawing figures, a line connected to a side-entry connector, or mainline, appears in the drawing figures as part number 13, while a line connected to a fluid conduction or water-jacket, which can be continued in use once the jacket has been positioned as a service channel, or sideline, appears as part number 11. The water-jacket is used to minimize if not prevent spillage through the opening created just after the plug of tissue has been cut from the side of the ductus. Along the gastrointestinal tract, this is usually by flushing or irrigating the opening with pressurized water. Along a blood vessel, leakage is usually accomplished not with water but rather a tacky crushed hydrogel, which like the water, can incorporate drugs such as a broad-spectrum antibiotic or antiseptic.

In subsequent use, mainlines and sidelines can be used to deliver the same or different therapeutic substances, which can be separated by segments of broad-spectrum antibiotic-containing or inert nondrug containing crushed tacky hydrogel. With a blood vessel, a drug hydrogel is advanced by applying pressure to it, allowing control at the pump without the need for local valving. If the delivery medium is a slightly tacky crushed gel that does not flow unless driven, then control over leaking and dosing is much improved. Gels are more suitable for delivery into blood vessels as these expedite hemostasis. With such a delivery medium, if necessary, an actively controlled butterfly shutoff and throttle valve-plug is used.

If the delivery medium is a free flowing fluid, then control is attained with the aid of a passive elastic slit membrane or fine fiber spandex stretch valve-plug at the adductal end of the side-entry connector, thus covering over the opening into the ductus. Passage through the valve-plug requires a threshold minimum pressure. Along the gastrointestinal tract or a ureter, for example, leakage of septic or potentially septic contents must be prevented, and this can be accomplished by flushing the opening with antimicrobial containing water or a gel. With a backup valve-plug positioned with its adductal face level with the edge of the water-jacket and its vanes open, a drug or drug hydrogel under antegrade pressure and delivered through the mainline advances into the ductus.

Depending upon the viscosity of the crushed hydrogel or syrup, for example, its tackiness, the size of the opening into the water-jacket, and the resistance posed by a slit or elastic weave membrane or sieve type valve-plug if present, some of the drug will enter into the water-jacket or sidelines if these are not already filled. Provided the drug is in the form of a tacky crushed gel, the water-jacket or sideline will quickly clog, so that dosing will substantially equate to that delivered through the mainline. Opening the valve-plug allows delivery of the same or different drugs through the mainline and sidelines. Under these same conditions with the valve-plug open, a drug delivered through a sideline or the water-jacket as a service channel only will back up, that is, flow into the mainline at the head of the column of the primary drug hydrogel to follow, where it can serve as neoadjuvant or preparatory adjuvant.

Closing the backup valve-plug allows drug delivery through the sidelines alone. In aspirative or retrograde flow, closing the valve-plug limits aspiration to the water-jacket, whereas opening it allows aspiration through both the mainline and sidelines. When present, a valve used to throttle flow through the line is fully opened when the rate of delivery is controlled by a pump; otherwise, when hard wire powered or remote controlled as described below, such a valve can be used as a rate of delivery trimmer throttle. Multiple lumen lines serve to separate components that become active when combined or are best kept apart during delivery up to the valve-plug, which may be situated at the distal terminus of line 13 or 11 just where the native lumen or water-jacket inlet respectively are entered.

Another option is to flush through the line between components or fractions to be kept separate until delivered by placing water or solvent cartridges or connecting a hose feed into the pump turret between the components. For example, the side-entry connector line is flushed outward by pumping water through the water-jacket. A single valve is used with a double or larger number multiple lumen line, but the valve itself must be lodged within a single lumen segment along the line; however, to prevent directional reversal at the valve where the hydrogel drug moves through one vane and returns through the other, the delivery lumen or lumina must be aligned to one of the two vanes or leafs of the valve and return lumen or lumina the other vane.

A valve-plug for use within a side-connection line having two lumina where either lumen must be aligned to a respective vane incorporates an internal medial septum to the outer or ductus abaxial side of the vanes that clears the leadscrew or servo connector and keying the distal end of the dual lumen line to the septum. However, since spanning a valve-plug across more than one lumen prevents its removal or repositioning, the use of a dual-lumen line can be applied only where it is known with confidence that the valve-plug will not have to be removed or resituated. Since as described below, adjustment of the vane angles can be by wired or remote electrical means volumentric flow rate through such an immobilized valve-plug is not prevented.

Where the port is not of the subcutaneous membrane type but rather configured to allow the passage of devices wider than an injection needle, the water-jacket is used to irrigate the opening in the ductus under pressure. A valve cannot be used because the plug of tissue excised or a cabled device must be passable, and a valve would block the way from the line into the ductus. To restrain luminal contents from spilling out into the surrounding cavity, either the water jacket is used to irrigate the opening in the ductus under pressure, or the pressure of the fluid medication itself accomplishes this; both side-entry and water-jacket lines are not used at the same time. To prevent medication from entering the water-jacket thus cycling around and flowing out through the service channel line or lines, water-jacket lines are kept filled with water or if already in use as service channels, then the therapeutic fluid these conveyed.

Conversely, when the water-jacket is used to pressure irrigate the opening in the ductus, the side-entry connection line must be clear to allow the wash water to flow out. Antegrade or adductal flow can consist of fluid medication with or without adjuvant medication delivered through a service channel or channels, in which case all lines remain connected to the pump. Some pumping arrangements will require that for the opening in the ductus to be irrigated, the main or side-entry connection line must be vented to the exterior or opened at the pump end to allow the wash water to flow out. In addition to the need to restrain lumen content from leaking when the opening is incised in the side of the ductus, the need for a clear passageway arises whenever a throttle or shutoff valve-plug or a cabled device must be inserted or withdrawn.

To minimize its size in general and to avoid puncturing through aortic bodies in particular, the jacket is kept short in axial length. When applied as shown in FIGS. 21 and 22 to rechannel the flow of blood in double vessel disease, adjuvant medication is delivered through subsidiary (fluid conduction, water-jacket) service channel lines 11. Side-entry connector lines 13 are usually larger in caliber than service channel lines 11, which convey blood only when used to draw a blood sample. Use of a double side-entry connector jacket to allow synthetic bypass in single vessel disease would allow use of the second side-entry connector 6 for the delivery of medication from a port implanted at the body surface.

Along a straight ductus, extension in the long axis proportionally suppresses any tendency for angling or levering relative to the long central axis of the native conduit encircled. In the application depicted in FIGS. 21 and 22, however, the simple junction double side-connector jacket shown in FIG. 17 is positioned along the arch just above the root of the aorta and therefore nestled amid surrounding structures that spare it from levering of any significance. The foam lining must have sufficient thickness and compressibility, and the jacket a spring hinge closing force that complies with the pulse instantly. Because foam lining 3 affords additional protection from levering stresses, the jacket is used only to provide a secure junction with the aorta, and avoiding extension up and around the aorta would injure important baroreceptors and chemoreceptors, the jacket shown in FIG. 17 is made shorter.

Figure 18:
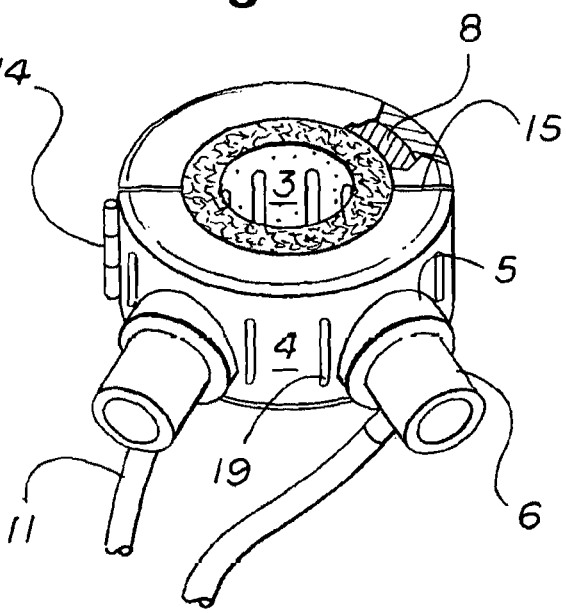
FIG. 18 is a perspective cross-section through a jacket of the kind shown in FIG. 3 configured as the jacket without magnet layer shown in FIG. 17 with two arms and the addition of a concentric magnet layer.

The double side-connector jacket shown in FIG. 18 is not used only to provide a secure junction with a native conduit as shown in FIGS. 19, 21, and 22, but incorporates magnet 8 for the purpose of drawing a magnetically susceptible particle-bound drug or other therapeutic substance into the wall surrounding the lumen. Any jacket with a magnet layer must span across the lesion and then some as 'extension for prevention;' unless the diseased segment of the conduit is much smaller in length than the jacket must be to provide the junction, it will be greater in length than a jacket in the same location only used to form a junction. The simple junction type double side-connector jacket shown in FIG. 19 does not require magnet or radiation shield layers. However, a jacket with both magnet layer, concentric or eccentric, and a radiation shield, like that shown in FIG. 5 or 6 but with two or more side-connectors is considered one of numerous variants according to the medical requirements.

Unpiped Electromagnet Impasse-Jackets

Unpiped electromagnet impasse-jackets lack a side-entry connector. Such jackets are able to generate greater magnetic field force focused at a circumscribed area. Multiple electromagnets, small as possible to minimize the size and dimensions of the jacket, are positioned at intervals along the jacket to achieve a graduated increase in field strength from the retrograde to the antegrade end. The magnets can be arranged in a helical pattern to distribute the weight. Helically arranged jackets also allows the core and coil of each magnet to be oriented longitudinally rather than circumferentially in relation to the long central axis of the native lumen and jacket. Unpiped electromagnet impasse jackets are used where an intervening permanent magnet impasse jacket would interfere with movement past it of magnetically susceptible particle-bound drugs meant to target tissue downstream therefrom, for example, and where very strong attractive force is needed to attract a susceptible particle or affinate carrying a drug or analyte to the tightly circumscribed area of the magnet pole.

Where a permanent magnet-based impasse-jacket is usually preferable for uniform uptake over the length of the jacket, an electromagnet-based impasse jacket is preferable for uniform uptake confuted to a small segment. With the exceptions that a hard outer shell and no draw-plate is used, unpiped electromagnet impasse-jackets are configured as is the peristalsis jacket shown in FIG. 10, with individual magnet cross sectional views provided in FIGS. 11 and 12. When better to distribute the weight, the magnets are positioned in a helical pattern, the cores and coils will be offset, allowing these to be aligned to the long axis of the ductus and jacket. Situating the magnet pole in an opening or each of several magnets in openings respective of each in the jacket wall to reach down to the outer surface of the adventitia as shown in FIG. 12 reduces the magnetic gap, allowing some reduction in the size and weight of the magnet or magnets.

Piped Electromagnet Impasse-Jackets

Figure 10:
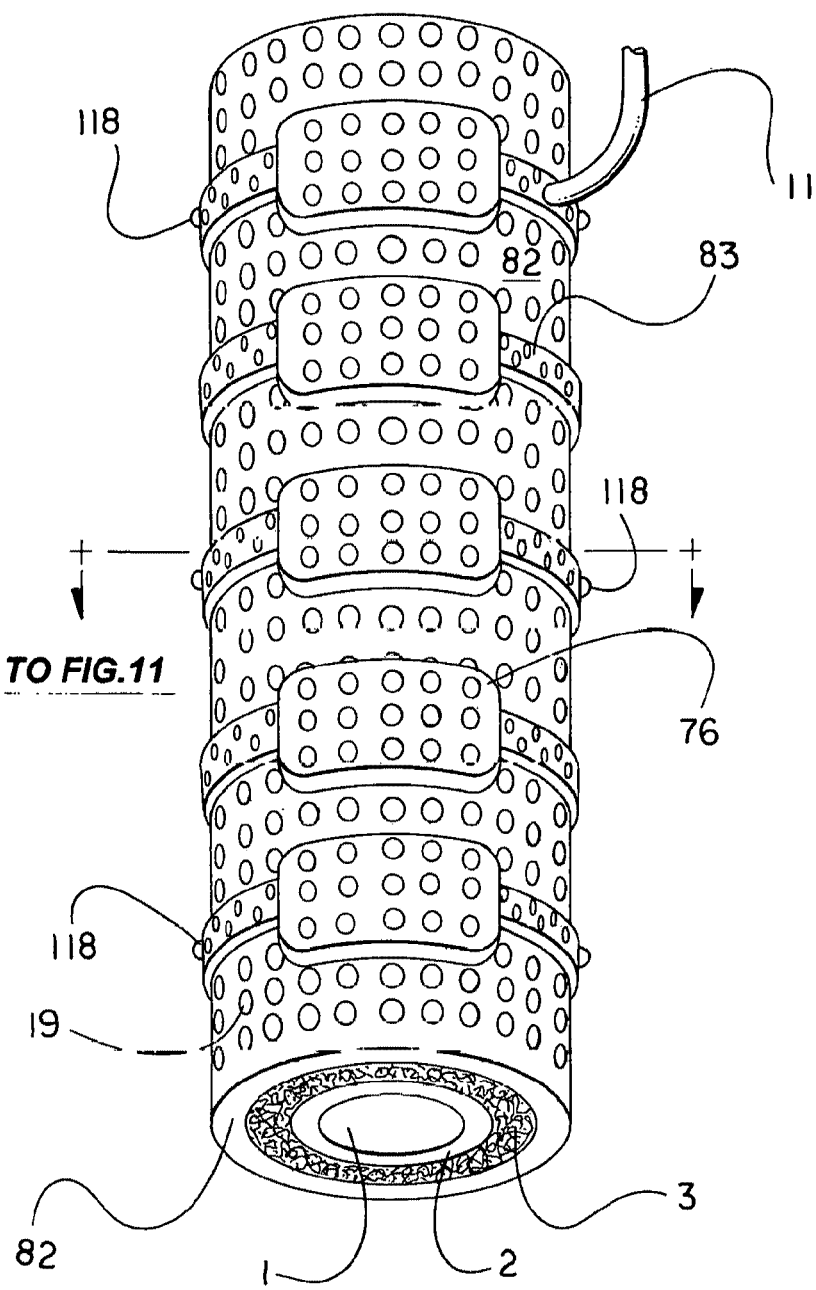
FIG. 10 is an outer perspective view of a tissue-engineered ductus with magnetically susceptible plates mounted on a thick spandex or similar stretchable rubber backing 82 lined with viscoelastic polyurethane foam 3, the opposing magnet poles directed at the center of each draw-plate seen in the cross-section shown in FIG. 11, such a formation used to compress successive segments of the ductus interposed between the magnets and plates in a coordinated sequence to simulate peristalsis.

Piped electromagnet impasse jackets are configured as is the train of contraction-electromagnets depicted in FIGS. 10 thru 12, except that the mounting substrate is a hard shell as shown for permanent magnet jackets in FIGS. 1 thru 6, and no draw-plate is used. The various medical desiderata specified in the preceding section for piped impasse jackets using permanent magnets—such as the need to avoid completely enclosing the ductus by incorporating spaced openings (apertures, fenestra) that pass entirely through the jacket from its outer surface to the outer surface of the native ductus, and in the section that follows for clasp-magnets—such as the preventive and palliative use of adverse tissue reaction substances—apply no less to piped electromagnet-jackets. Absorbable and permanent radiation shielding if necessary is also the same as shown for permanent magnet side-entry jackets in FIGS. 5 and 6.

For simplicity of control as a unit, gradual intensification in the field strength of each successive series-wired identical magnet in the antegrade (anterograde) direction from one magnet to the next along the linear array can be accomplished by inserting resistors between each. In an apparatus to be worn, however, this poses factors of needless mass and wasted power consumption, in that every magnet in the array must match that of the one magnet which must present the strongest field. With larger jackets where these considerations become significant in terms of the size and weight of the battery and each implant, patient comfort, and wearing time (meantime to discharge), it is preferable to use non-identical magnets which differ in the number of coil turns and/or core permeability from one series-wired magnet to the next. In either case, the average field strength of the array as a whole is then adjusted as a unit. While different affiliates may require different field strengths, separate wiring to allow adjusting the amperage to each magnet should not be necessary.

Radiation Shielded Jackets

Shielded jackets generally call for shielded supply lines; however, if the radioisotope is weak and immediately flushed through, this is sometimes avoided. Depending upon the placement and type medication to be administered, shielded jackets can be flushed for this purpose alone. Jacket shielding 12 is no thicker or extended about the jacket than the dose-rate of the radionuclide makes necessary. Delivery of a radionuclide is usually direct to the side-entry jacket through a line leading to port 16 implanted at the body surface 18, thus avoiding the circulation.

Tungsten heavy alloy radiation shielding 12 like neodymium iron boron magnet layer 8, is toxic, so that both are completely enclosed within chemically isolating and protective outer shell 4, typically made of polyether ether ketone, or PEEK, polymer and prospectively, of graphene. Complete enclosure of vessels promotive of atherosclerotic change, shell 4 wraps around perforations through the jacket down to the outermost layer of the vessel, or adventitia. To prevent noncompliant contact of the edges of shell 4 with the outer surface of native conduit wall 2 as would reduce the compliant excursion allowed by foam lining 3 and risk incisional or gouging injury, shell 4 must not extend adluminally adaxially past magnetic 8 and radiation shield 12 layers.

The jacket shown in FIG. 5 is suitable for the long-term delivery of lower dose-rate radioisotope or radionuclide along a ductus less susceptible to deterioration when enclosed thus, where the line is flushed with water to clear any significant radioactive residue. The jacket is also used to deliver drugs such as a steroid, statin, calcium channel blocker, or nitrates to counteract degradation the result of enclosure. By contrast, the jacket shown in FIG. 6 has a shield layer formulated to disintegrate once the radiation has been depleted, clearing 'breathing slits' 19 to allow normal gas exchange in the internal environment. A side-entry jacket for a blood vessel must not completely enclose the vessel for more than a brief time or atherosclerotic degradation will ensue. If clinical judgment favors irradiating the lesion over permitting this consequence, then sideline 7 is used to deliver antiatherosclerotic medication.

Alternatively, where radiation therapy will be short term and the jacket by its weight or diameter causes discomfort, shielding layer 12 consists of overlapping tungsten particles encapsulated for chemical isolation and bound with an adhesive having a spontaneous hydrolytic and enzymatic breakdown time matched to the radiation exposure time. In such a jacket, the particulate shield is without an outer shell as shown in FIG. 5. Shielding 12 is formulated to disintegrate once the radiation is depleted or removed, exposing perforations 19 through underlying jacket shell 4. That is, shielding 12 encloses a jacket of the kind shown in FIG. 4, so that once the shielding has disintegrated, the exposed jacket shell 4 relieves the obstruction to the vasa and nervi vasora and allows the adventitia or fibrosa to 'breathe,' permitting the level of degradation counteracting drugs to be reduced if not eliminated.

Higher dose rate materials necessitate corresponding increase in the thickness of shielding 12 and shielding of the line leading up to the side-entry connection jacket. Provided sharp edges about the periphery of the jacket have been eliminated, the jacket will usually be couched amid tissue that will support and stabilize it without abrasive contact, even when the mass of the shielding 12 is significant. To minimize sliding movement against surrounding tissue, outer shell 4 is given a nonabrasive uneven surface. Heavier shielded jackets may require additional support with a polymeric halter or harness that may be provided with eyelets to pass through suture.

To preclude the need for a second invasive procedure to recover the jacket, the radiation shield, which must not include perforations (apertures, fenestrations) essential to prevent atherosclerotic degeneration in the substrate vessel, is normally formulated to disintegrate, the shielding in the supply line or lines, whether subsidiary or service channel or side-entry connector lines allowed to remain. Due to the mass of tungsten heavy alloy, jackets fed from shielded lines are minimized in weight to prevent patient discomfort. If higher dose rate radioisotopes necessitate the use of a thicker shield, suture is used to suspend and distribute the load. More heavily shielded jackets provide eyelets that extend from the outer surface of the shield to pass suture.

The radiation shield for long-term use shown in FIG. 5 is nondisintegrating. To prevent atherosclerotic degeneration in the substrate vessel which remains enclosed necessitates the delivery of anti-atherosclerotic, antihyperplasic, and/or anti-inflammatory drugs. In FIG. 16, line 11 remains following use to place the jacket and thereafter remains available as an accessory line for the separate transmission of substances to the target ductus. The side-connector conducts drugs toward the target vessel, not blood away from it as in FIG. 21, both lines 13 and 11 flowing into the target ductus. By contrast, the jacket shown in FIG. 21 is not placed about the target vessel but rather uses lines 13 to shunt blood away from the aorta as the source to which it is mounted for delivery of the shunted blood to the jackets placed distad about the target vessels.

In FIG. 21, drugs for delivery to the distal jackets is passed through lines 11. While placed, the distal jackets also required lines 11, which then sealed off, do not appear in the figure, drawn for pictorial clarity rather than optimal functionality. Radiation shield 12 is therefore enclosed within outer shell 4. In contrast, the shield in a shield disintegrable jacket encloses the magnet, that is, is interposed between the magnet and the shield of compacted encapsulated beads, chemical isolation already afforded by the polymeric coating applied to each bead. Whether in a jacket with nondisintegrating shield as shown in FIG. 5 or one with a disintegrating shield as shown in FIG. 6, locking bushing 5 is coplanar with surrounding portions of the shield and consists of solid or continuous, not particulate, heavy tungsten alloy.

In a shielded jacket, to allow side-connector 6 to be used as a trepan or circle cutter, the shielding bonded to side-connector lock bushing 5 is discontinuous with the shielding surrounding it as a rotatable knob. FIGS. 19 and 20 show the double side-connector jacket of FIG. 17 placed about a vessel where the side-entry connectors 6 have been set at a downward angle for optimized or least turbulent flow-through within the space available. The jacket is of the simple junction type shown in FIG. 2 without a magnet to constitute an impasse jacket as shown in FIGS. 3 and 18 for the purpose of drawing medication outward into and/or through the luminal wall. In FIG. 21, the same jacket, used to form a secure junction with the aorta, is used to give origin to synthetic coronary arteries in a patient unable to provide suitable autografts and/or for whom the bypass procedure must be accomplished with minimal anesthesia or trauma, so that the additional procedure of harvesting grafts is avoided.

Double-Arm Side-Entry Connector Jackets

Figure 7:
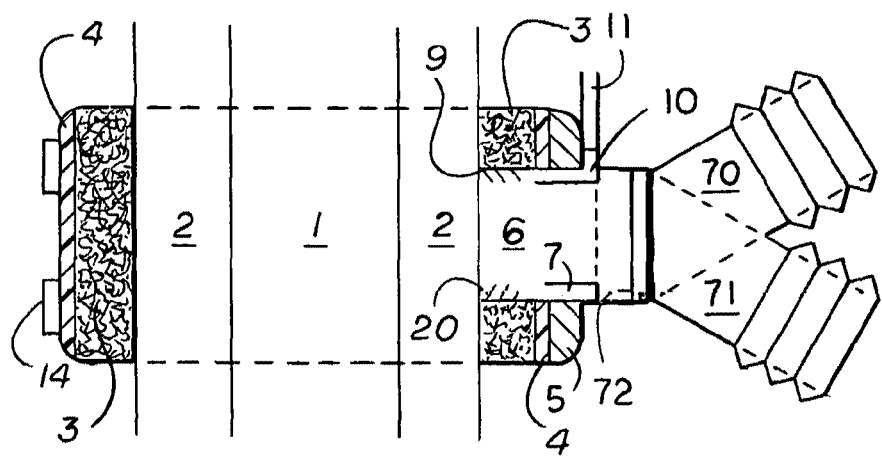
FIG. 7 shows a ductus side-entry jacket with a double-arm or branched side-entry connector before the sharp leading edge of the side-entry connector has been used to cut a plug from the side of the lumen wall and the plug extracted, which configuration expedites the steering of a cabled device into the native lumen in either direction and allows the infusion of drugs or a ferrofluid or transfusion at a higher flow rate.

Rather than a simple junction type side-entry jacket such as shown in FIGS. 1 and 2 with a side-connector and an accessory inlet, a dual or double-arm side-connector as shown in FIG. 7 is one with two connecting arms 70 and 71 that diverge at an angle from a common adductal shaft where either connecting arm can connect the mainline or sideline. While the arms are shown as equal in diameter, no such limitation applies. The differences between ordinary and double-arm jackets are limited to the side-connector, other embodiments to include the addition of magnetization permanent or electromagnetic nand shielding no less applicable.

The ductus-encircling or ensheathing portions of a double-arm side-entry jacket and the part numbers shown in FIG. 7 are the same as for the simple junction jacket described above and are no different than those described for permanent and electromagnet impasse jackets shielded or unshielded. The embodiment shown in FIG. 7 allows disconnection of double-arm 70 and 71. One adaptation of double-arm jackets is shown in FIGS. 13 thru 15 for an intracorporeal magnetic separation cytaperesis or hemodialysis circuit such as that shown in 39A, where electromagnet poles are positioned in the reentrant toward the vertex where the arms meet. The part numbers in FIG. 7 are the same as those in FIGS. 1 thru 6.

Figures 29, 30:
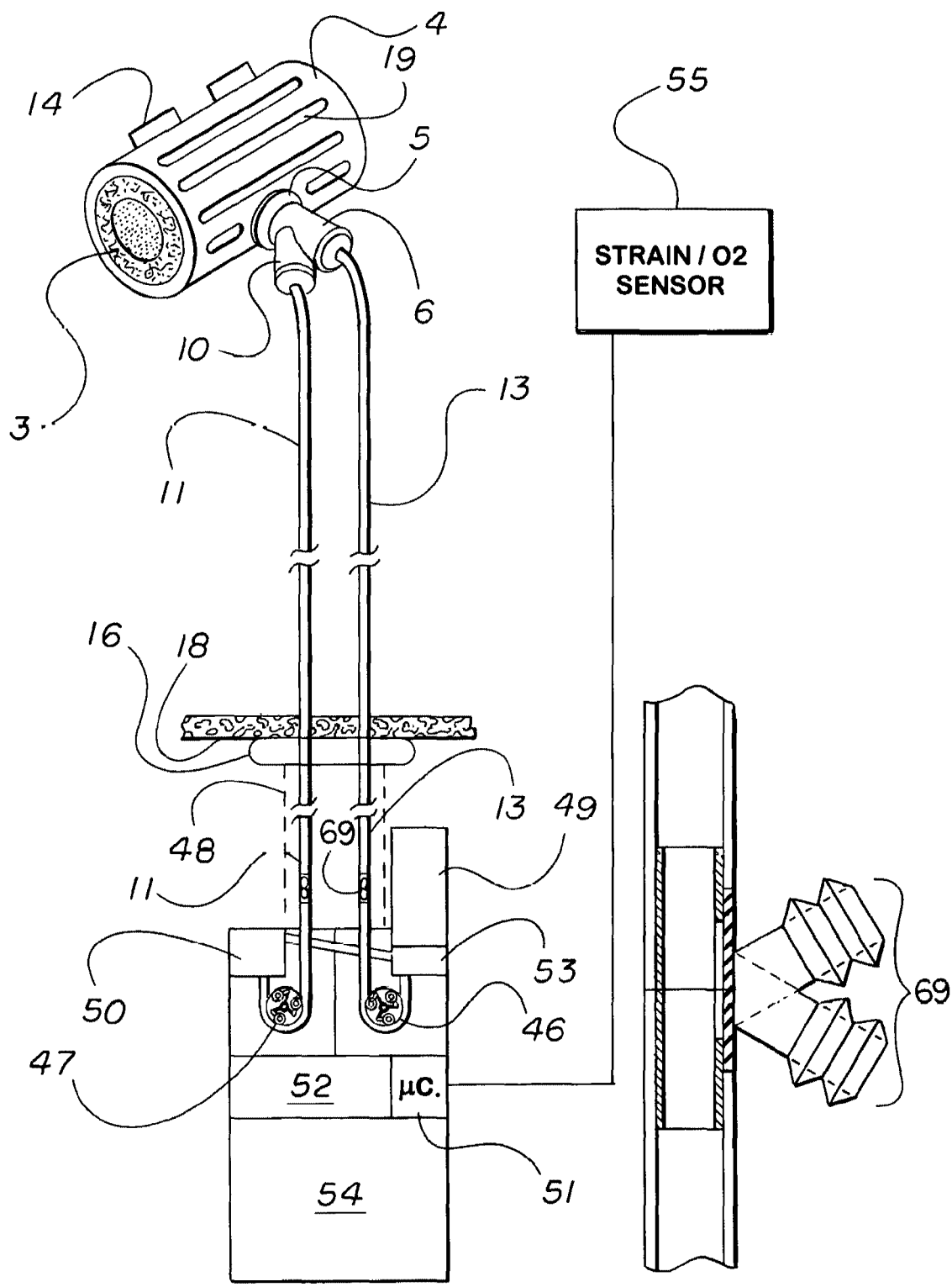
FIG. 29 is a diagrammatic representation of a pump-pair plug-in module without inlet or outlet line switching turrets inserted into a single pump-pair power and control module, wherein one pump is connected to the side-connector and the other pump to the accessory inlet or water-jacket of the same single side-entry connection jacket.
FIG. 30 is a detailed view of a double-arm, branching or forked type inline port or clean-out used to facilitate the bidirectional insertion of a cabled device such as a fiber endoscope or laser, or a debris extraction aspiration catheter or hook-tipped guidewire into the lumen of a catheteric fluid line, as shown in FIG. 31.

In FIG. 30, a double arm inline port is shown as a permanent part of a synthetic shunt or bypass tube. When applied to a native ductus such as an artery, the double arm port is incorporated into a ductus side-entry jacket with leak-free placement as explained for ductus side-entry jacket generally. Any cabled device, whether fiberoptic endoscope, laser, intravascular ultrasound probe, linear or rotatory atherectomizer, thrombectomizer, aspiration catheter, or guidewire, is effortlessly directed into either the antegrade or retrograde direction by insertion through the line, whether treated as the mainline or sideline, which leads that way.

An inline port double-arm conformation side-connector thus serves to expedite frequent fiberoptic or angioscopic inspection or therapy of the junction or translauminal or catheteric examination or treatment of the native lumen which the jacket encircles. More than one double arm side-connector can be incorporated into a single jacket, where except for this, the jacket is constructed no differently. While the double arm devices shown in FIGS. 7, 13 thru 15 and 30 depict the arms as being equal in size, no such limitation should be inferred.

Using a larger arm as the accessory or sideline allows easier passage of larger caliber cabled devices and higher volumetric flow rates. In FIG. 7, the double-arm side-connector is shown in mid-longitudinal section, rotary joint 72 indicating that shaft or trunk 6 is round, allowing it to be rotated to whatever angle is best accommodated by the anatomy. In the embodiment shown in FIG. 7, double arms 70 and 71 are connectable and disconnectable and can be used as an attachment to a basic ductus side-entry jacket.

Double-arm side-connectors with elliptical or rectangular ductus side-entry openings or ostia, with or without flap-valve, such as shown in FIGS. 13 thru 15, cannot rotate unless the shaft encircling the ostium is circular; however, where the trepan edge and vacuum allow cutting the opening or ostium into the substrate ductus without the need to rotate the sidestem, the ability to create an oval or rectangular opening into the ductus can provide a significantly greater area, significant in an intracorporeal magnetic separation hemodialysis system such as shown in FIGS. 39A and 39B.

Clasp-Electromagnets

Clasp-electromagnets and extraction-electromagnets are configured to attach to the surface of nonductal tissue and cannot where a collar or jacket configuration cannot be used. Rather, these are attached by means of prongs treated to avert adverse tissue reactions and formed to encourage tissue infiltration. FIG. 8 shows a side view and FIG. 9 an overhead view of a clasp-electromagnet suitable for use as indicated just above or for positioning about the outer surface of a gland or organ to draw a bloodborne magnetically susceptible particle-bound drug radially outward through the parenchyma, for example. The mounting of a clasp-electromagnet is preferably molded in a single piece in polyether ether ketone (PEEK), graphene, or another polymer likely not to evoke an adverse tissue reaction. Various orientations of the electromagnet in relation to its mounting are addressed in the section above entitled Background of the Invention. The use of a clasp-electromagnet or an array thereof with a magnetically susceptible plate or plates-applied to the far side of tissue across a gap from the array can be used to place that tissue in tension as a reverse type contraction magnet. Such an array can take any shape. Contraction magnets are addressed below in the section of like title.

Mountings other than that shown, which provides an opening for the magnet pole, consist of a simple plate with rounded and blunted edges configured to avoid abrasive contact with neighboring tissue. If necessary, the mounting can be placed in a hot sand box and bent to the exact shape needed in the catheter laboratory or clinic. To minimize procedural time, the clasp-electromagnet is configured to be pushed down against tissue to which it is to be attached and self-engage without further effort. In FIGS. 8 and 9, mounting magnet pole-surround face-plate 70 is continuous with and branches radially outward into a number of flexible prong-arms 71 terminating in prongs 72. To encourage tissue infiltration and integration, prongs 72 are textured and include a central perforation.

Clasp-electromagnets can be used where the ductus to be treated cannot be dissected free for encirclement with a jacket or where an eccentric lesion is on the facing side of the ductus. Clasp-electromagnets can also be placed to temporarily, periodically, or permanently supplement and boost the field force of a primary extraction-electromagnet with or without a flush-through line when the anatomy does not afford the clearance needed for a primary electromagnet to not encroach upon neighboring tissue. Abrasive and gouging encroachment must be avoided as the potential cause of incisions, fistulae, and ulcers. For this reason, the electromagnets are made as squat and unobtrusive as possible, housed in a smooth enclosure, and mounted for minimal obtrusion. The prongs are textured and perforated to encourage tissue infiltration and integration and are passivated by wetting with substances that suppress adverse tissue responses.

Substances typically used for this purpose include dexamethasone (see, for example, Vacanti, N. M., Cheng, H., Hill, P. S., Guerreiro, J. D., Dang, T. T., and 5 others 2012. "Localized Delivery of Dexamethasone from Electrospun Fibers Reduces the Foreign Body Response," *Biomacromolecules* 13(10):3031-3038; Bhardwaj, U., Sura, R., Papadimitrakopoulos, F., and Burgess, D. J. 2010. "PLGA/PVA Hydrogel Composites for Long-term Inflammation Control Following S. C. [Subcutaneous] implantation," *International Journal of Pharmaceutics* 384(1-2):78-86; Patil, S. D., Papadmitrakopoulos, F., and Burgess, D. J. 2007. "Concurrent Delivery of Dexamethasone and VEGF for Localized Inflammation Control and Angiogenesis," *Journal of Controlled Release* 117(1):68-79; Patil, S. D., Papadimitrakopoulos, F., and Burgess, D. J. 2004. "Dexamethasone-loaded Poly(lactic-co-glycolic) Acid Microspheres/Poly(vinyl alcohol) Hydrogel Composite Coatings for Inflammation Control," *Diabetes Technology and Therapeutics* 6(6):887-897).

The adverse tissue reaction retardant can be prepared in the form of implant-coated or embedded particles, microspheres, or nanorods (see, for example, Mercanzini, A., Reddy, S. T., Velluto, D., Colin, P., Maillard, A., Bensadoun, J. C., Hubbell, J. A., and Renaud, P. 2010. "Controlled Release Nanoparticle-embedded Coatings Reduce the Tissue Reaction to Neuroprostheses," *Journal of Controlled Release* 145(3):196-202; Bhardwaj, U., Papadimitrakopoulos, F., and Burgess, D. J. 2008. "A Review of the Development of a Vehicle for Localized and Controlled Drug Delivery for Implantable Biosensors," *Journal of Diabetes Science and Technology* 2(6):1016-1029; Bhardwaj, U., Sura, R., Papadimitrakopoulos, F., and Burgess D. J. 2007. "Controlling Acute Inflammation with Fast Releasing Dexamethasone-PLGA [poly(lactic-co-glycolic acid] Microsphere/PVA [cross-linked polyvinyl alcohol] Hydrogel Composites for Implantable Devices," *Journal of Diabetes Science and Technology* 1(1):8-17; Patil, S. D., Papadimitrakopoulos, F., and Burgess, D. J. 2004. "Dexamethasone-loaded Poly(lactic-co-glycolic) Acid Microspheres/Poly(vinyl alcohol) Hydrogel Composite Coatings for Inflammation Control," *Diabetes Technology and Therapeutics* 6(6):887-897; Hickey, T., Kreutzer, D., Burgess, D. J., and Moussy, F. 2002. "In Vivo Evaluation of a Dexamethasone/PLGA Microsphere System Designed to Suppress the Inflammatory Tissue Response to Implantable Medical Devices," *Journal of Biomedical Materials Research* 61(2):180-187).

Another adverse tissue reaction retardant is phosphorylcholine (see, for example, Goreish, H. H., Lewis, A. L., Rose, S., and Lloyd, A. W. 2004. "The Effect of Phosphorylcholine-coated Materials on the Inflammatory Response and Fibrous Capsule Formation: in Vitro and in Vivo Observations," *Journal of Biomedical Materials Research. Part A* 68(1):1-9; Chen, C., Lumsden, A. B., Ofenloch, J. C., Noe, B., Campbell, E. J., Stratford, P. W., Yianni, Y. P., Taylor, A. S., and Hanson, S. R. 1997. "Phosphorylcholine Coating of ePTFE Grafts Reduces Neointimal Hyperplasia in Canine Model," *Annals of Vascular Surgery* 11(1):74-79; Whelan, D. M., van der Giessen, W. J., Krabbendam, S. C., van Vliet, E. A. Verdouw, P. D., Serruys, P. W., and van Beusekom, H. M. M. 2000. "Biocompatibility of Phosphorylcholine Coated Stents in Normal Porcine Coronary Arteries," *Heart* 83(3):338-345).

A coating of zinc oxide, especially in the form of nanorods, can moderate an inflammatory immune response (see, for example, Zaveri, T. D., Dolgova, N. V., Chu, B. H., Lee, J., Wong, J., Lele, T. P., Ren, F., and Keselowsky, B. G. 2010. "Contributions of Surface Topography and Cytotoxicity to the Macrophage Response to Zinc Oxide Nanorods," *Biomaterials* 31(11):2999-3007). Hydrogel polymers incorporating phosphorylcholine can be used as a bioinert medium for this medication (Lewis, A. L. 2006. "PC [Phosphorylcholine] Technology as a Platform for Drug Delivery: From Combination to Conjugation," *Expert Opinion on Drug Delivery* 3(2):289-298).

Clasp Extraction-Electromagnets

Where most clasp-electromagnets are mounted with the pole fastened to the mounting and directed away from the subjacent tissue as is clear from FIGS. 8 and 9, a clasp-extraction-electromagnet is secured to its mounting base at the rear, opposite its working pole. That is, a clasp-electromagnet usually looks away from its mounting in assisting a piped impasse jacket with additional attractive force. Also, whereas a clasp electromagnet as shown in FIGS. 8 and 9 corresponds in function to an unpiped electromagnetic impasse jacket, a clasp extraction-electromagnet corresponds to an extraction jacket such as shown with a single magnet in FIG. 13. Unless the organ is enclosed within a capsule or rind that significantly increases the field force necessary to extract the unwanted residue, no opening or window is made through the capsule into the subjacent tissue.

Since there is no flap-valve to close the flush-line at the adductal end of the side-connector and tissue interface or contact area, the flushing fluid comes into direct contact with and washes over this tissue, allowing its treatment by including therapeutic substances in the flushing fluid. When the outer surface of the organ is fenestrated, the adductal edge of the side-connector is made to protrude into the fenestration to aid in maintaining the margin free of tissue ingrowth. If also necessary to prevent regeneration of the excised capsule by second intention, which would have the effect of increasing the magnetic field strength needed to effect extraction, then the flushing fluid has added to it a substance to counteract this process. Provided it is safe to do so, a small proportion of the flushing fluid can be replaced with sodium hypochlorite which is then itself promptly flushed away with plain water, for example.

Since flushing fluid must not be allowed to leak about the edges of the adductal end of the side-connector despite its pressure, the side-connector is not allowed to lift away. The prongs are therefore of a size and penetrate to a depth as will prevent leakage. When such treatment is exclusive of other extraction jackets and clasp-electromagnets, a separate supply reservoir, flush-line, and catch reservoir are used. When exclusive thus, the contents of the waste flushing fluid are available for diagnostic testing. Otherwise, a single flush-line can course through extraction jackets and clasp extraction-electromagnets at different sites. Ordinarily, the same flush-line courses through a circle of clasp extraction-electromagnets positioned about the surface of an organ, for example.

When the subjacent outer surface of the organ is not fenestrated, to provide the extractive force required, the magnet must be powerful enough to extract the residue before it can exert a toxic effect. Formulation of the drug-carrier particulate to retard this consequence thus bears directly upon the size and weight of the electromagnet or electromagnets needed. An impasse jacket or clasp-electromagnet is ordinarily placed to draw a carrier particle-bonded analyte, or extractate, against and through the ductus wall, and extraordinarily—when the debris to be accumulated will be small and innocuous or can be neutralized with the addition of a followup substance—out through the adventitia to adhere to the pole until the magnet is turned off.

Since at the current state of iron oxide-based drug carrier particle formulation, the debris may be toxic or become toxic after an interval, it is more common for the debris to be completely extracted from the tissue and purged or expunged from the body. With a permanent magnet impasse-jacket, a powerful extracorporeal electromagnet is used to pull out the susceptible particles through an extraction grating. However, an automatic ambulatory system must be able to purge the debris without a need to visit the clinic. With an extraction electromagnet jacket or clasp extraction electromagnet, a pole flush-line is provided to carry away the accumulated debris to a remote tank or waste reservoir in the pump-pack. Accordingly, the pole of the clasp-electromagnet is withdrawn from the surface of the tissue to no greater a distance than is essential to interpose the flush-line path, which passes through the magnetic gap.

Sphincteric Jackets

Sphincteric dysfunction involves a condition of laxity or constriction along the digestive tract. Until its electromagnet is energized, a prosthetic sphincter assist device keeps the lumen fully closed. When energized, the magnet fully opens the lumen. It is therefore able to remedy a condition of either laxity or constriction. Unless so hypertrophied and stenosed that an assist device would have to be excessively large and heavy, a stenosed sphincter in a neonate, for example, should not require preparatory surgery. This notwithstanding, the device is not preferred over surgical correction that would impart a permanent cure.

Ductus chokes—not intravascular valves used as chokes or servochokes; see section of like title below—are not sphincteric, prosthetic, or physiological, but rather contraction jackets used to facilitate system placement and maintenance by clamping the ductus from outside. When sphincteric and/or peristaltic jackets with control electronics are applied to the treatment of isolated motile dysfunction rather than as one module in a system used to treat multiple disorders, the omission of fluid lines allows implantation without the need, for a waist belt borne pump-pack. A local control module and rechargeable battery can be implanted to assist only peristalsis or a sphincter, or the native or a tissue engineered graft esophagus together with the lower esophageal sphincter, or the pyloric sphincter and portion of the gut, for example, as a unit.

Native or Tissue Engineered Graft Sphincter Assist Device

When the condition of weakness or the absence of contractive function is irremediable and the sphincter muscle thick, if and only if necessary to allow reduction in the magnetic gap and therewith, the need for a more powerful and heavier magnet, a lower esophageal or pyloric sphincteroplasty, for example, is performed to prepare the native segment for placement of the jacket. While a larger electromagnet will increase the weight and rate of battery drainage, within the functional magnetic gap, greater tolerance for deviations from cylindrical can be accommodated by increasing the thickness of the foam lining. If for any reason placement of an assist device or graft is preferred over surgical treatment for a stenotic sphincter, the permanent magnet is omitted. A sphincter that is lax requires the permanent magnet.

A native sphincter such as the lower esophageal, pyloric, or ileocecal maintains the lumen closed at rest and opened when stimulated by the autonomic nervous system; that is, contraction of the smooth muscle of the sphincter opens the lumen. A sphincter assist device must therefore open (distend, dilate, expand) the lumen when energized. A lapband sized for placement about a sphincter with port at the body surface not only works in reverse to contract the substrate structure, but cannot respond within the response time required. This stands in contrast to the action of peristalsis, a traveling wave of contraction produced by contraction of the circular and longitudinal smooth muscles in the wall of the conduit; however, a series of lapbands is likewise unadaptable to serve as an assist device for an impaired native or a graft segment.

A prosthetic sphincter best mimics a native sphincter in limiting the expenditure of energy to the exceptional condition, that of opening the lumen only following ingestion, conserving energy. That is, a contraction jacket that kept the lumen closed at all times except when deenergized following ingestion, allowing the lumen to open, would soon drain even a large and heavy battery. Peristalsis is likewise exceptional, in that it is activated only during ingestion. In a prosthesis, emulation of this energy conserving means optimizes the consumption of battery power, allowing the apparatus to function while portable over a much longer period, with a pump-pack that is smaller and lighter in weight, and less an impediment to free movement.

An impaired native and graft sphincter assist device is generally produced as a component in and for immediate incorporation into a prosthetic disorder response system of more encompassing scope as necessary. A prosthetic sphincteric jacket has a hard polymeric, such as polyether ether ketone (PEEK), outer shell with viscoelastic foam lining and perforations such as shown in FIG. 17 which pass through both shell and foam lining to expose the outer surface of the native or tissue engineered sphincter to the surrounding environment. A neodymium magnet is bonded to, inlaid into the outside, or embedded within the hard jacket shell at one side. Diametrically opposite thereto, an electromagnet capable of inducing greater field strength than the permanent magnet is mounted at the outside of the shell as shown for the contraction jacket in FIG. 12. As other jackets and clasp-electromagnets described herein, the jacket is lined with high density open cell viscoelastic polyurethane foam.

A perforated magnetically susceptible stainless steel draw-plate is sutured to the side of the ductus opposite the permanent magnet to face the electromagnet, its center along the diametrical line passing through the center of the permanent magnet and electromagnet so that the three components are coaxial. Provided the perforations in the draw-plate are monolithically or continuously lined with the encapsulating layer that encloses the rest of the draw-plate, a draw-plate of iron can be used. The permanent magnet has sufficient attractive force that so long as the electromagnet is not energized, the draw-plate, sutured at the opposite or far side of the ductus in relation to it, is pulled toward the permanent magnet. The tissue-engineered or native ductus is therefore collapsed between the two against the foam lining of the jacket.

To allow the subjacent ductus to 'breathe,' perforations are made through the jacket and draw-plate. So long as the electromagnet is not energized, the ductus is held closed passively with no expenditure of battery power. When energized, the electromagnet overpowers the retentive ability of the permanent magnet, causing the lumen of the ductus to open (expand, dilate). The perforated plate, made of magnetically susceptible stainless steel, is positioned in diametrical opposition to the pole of the electromagnet. Further to reduce the overall magnetic gap separating the magnet pole from the plate, the magnet pole is positioned within an opening in the side of the jacket, that is, through the hard shell and foam lining. To minimize encroachment upon neighboring tissue, the electromagnet coil or winding is bent around the jacket.

Ductus Chokes

System chokes are individual contraction jackets used to facilitate prosthetic disorder response system placement and maintenance by briefly suppressing intrinsic motility and preventing the continued movement of luminal contents into or out of the segment addressed. A ductus choke is a contraction-jacket equivalent to one of the segmental draw-plate and multiple electromagnet pair peristaltic magnets shown in FIG. 10, wherein the draw-plates are shown above the compound peristaltic jacket and in view while the electromagnets are below in diametrical opposition thereto and out of sight. These are, however, shown in the cross-sectional views of FIGS. 11 and 12.

However, whereas the individual draw-plate magnet pairs of the peristalsis-jacket shown in FIG. 10 function as a unit, the independent contraction jacket or system choke is individually actuated. FIG. 11 shows such a jacket in encircling relation to a native ductus in diametrical and FIG. 12 in longitudinal cross section, with lumen 1 and surrounding tissue wall 2. The control system applies the input from proximally positioned strain gauge bolus sensors to the control of the magnet. A contraction-jacket has pliant tube 77 made of a rubbery implantable polymeric material rather than a hard shell 4, perforated through to the outer surface of the naïve ductus or graft.

Pliant tube 77 is lined with viscoelastic polyurethane foam 3 and elastic, with restorative force to reopen the lumen when the lumen-contracting attractive force of electromagnet 74 on draw-plate 76, coaxial with electromagnet 74 mounted at the opposite outer surface of the pliant tube is released. Perforated plate 76, made of magnetically susceptible stainless steel is positioned in diametrical opposition to electromagnet pole 75. As shown in FIG. 12, further to reduce the overall magnetic gap separating magnet pole 75 from plate 76, magnet pole 75 is positioned in an opening in the jacket side. To minimize encroachment upon neighboring tissue, electromagnet coil or winding 74 is bent around the jacket.

Compound, or Peristalsis, Contraction Jackets

Peristalsis jackets position individual contraction electromagnet jackets at intervals along a common substrate tube of the same kind as an individual contraction jacket. When mounted to a common substrate as a linear array and controlled to contract in advancing paired consecution leapfrog style with strictly coordinated timing, the set of contraction-jackets mounted, such as a tissue-engineered esophagus incapable of peristalsis, can be made to simulate peristalsis. As shown in FIG. 10, the common jacket mounting the set is termed the electromagnet-jacket, the component magnets then controlled as a unit. In a prosthetic disorder response system directed to more than one disease condition, timing control of the jacket as a unit can be accomplished either locally by a timing module mounted to the jacket or remotely by the respective control node.

Except that a hard shell without draw-plate is used, and the magnets are energized to present equal rather than progressively greater field strength from the retrograde to the antegrade end of the jacket, peristalsis jackets are the same in general structure or homologous with electromagnet impasse-jackets. Ductus obtained through tissue-engineering with autologous cells currently incapable of intrinsic peristalsis to provide a prosthetic esophagus, for example, peristaltic function can be imparted by applying impasse-jackets at intervals along the ductus with a magnetically susceptible plate positioned in diametrical opposition to each magnet. Unless means for withdrawing the plates are provided, the impasse jacket can no longer function as other than a contraction or peristalsis jacket.

Addition of the plates 76 thus changes the function of each magnet from an impasse-jacket, used to detain a passing superparamagnetic nanoparticle-bound drug, to a contraction or peristalsis jacket. Such a compound jacket differs from a more conventional impasse jacket magnet also in that its energization by the microcontroller is sequential within the set rather than independent A peristalsis jacket, with paired electromagnet and ferromagnetic plates arranged diametrically at intervals along its length, is shown in FIGS. 10 thru 12. Peristaltic action is simulated by energizing each consecutive magnet and plate pair while that preceding continues energized under the sequential timing control of a microcontroller. Such a jacket can be applied anywhere along the digestive tract, for example, where peristalsis of the native ductus is impaired or missing.

Autologous grafts and prostheses along the digestive tract having a history of failure, the application of such a jacket is substantially limited to instances of weakened peristalsis. Prosthetic esophagi of autologous gut, alloplastic, or nonbiological, materials having a record of rejection at the anastomoses, and those tissue-engineered not developing peristaltic function, a jacket mounting electromagnets in a sequential formation under coordinated control can serve to impart motility until a better tissue-engineered replacement ductus is developed. Whether a tissue-engineered replacement would be less susceptible to failure than an autologous graft remains to be seen.

The magnetically susceptible draw-plates 76 shown in FIG. 10 are fastened to a thick spandex or similar stretchable rubber backing 82, a reinforcing band 83 with hook and loop ends binding about each draw-plate 76. Thick spandex or similar stretchable rubber backing 82 is lined with an inner layer of viscoelastic polyurethane foam 3. Only the foam comes into contact with the outer surface of the dysfunction native or tissue-engineered ductus with lumen 1 and surrounding wall 2. The encircled ductus consisting of living tissue whether native dysfunctional or tissue-engineered, plates 76 and jacket or wrap 82 include perforations 19, which extend entirely through draw-plates 76, thick spandex or similar rubber backing 82, and high density viscoelastic polyurethane foam lining 3 to expose the surface of the ductus.

Fastening of the magnets with coils 74, cores, 84, and poles 75 and draw-plates 76 to spandex or similar rubbery backing 82 is by means of bands 83. Draw-plates 76 can be fastened with small rivets (not shown) and a strong cement made for internal (intracorporeal) use, whereas the magnets are bonded along the side of the coil proximate to the band by means of a strong nonbiodegradable cement. Electromagnet-jackets are thus distinct from clasp-electromagnets in fastening to the substrate tissue on a backing that wraps the tissue about nonincisively, rather than by means of inserting prongs.

While shown in a linear arrangement, plates 76 can distribute the weight of the jacket by positioning these in a spiraling or helical arrangement about the substrate jacket, or the weight offset by esophagopexy or suspension of the prosthesis with suture. The jacket contains perforations 19 to allow exposure of the outer tunic to the internal environment. When sequentially energized in the distal direction, each electromagnet compresses the tissue interposed between plates 2 and pole 75 of the magnet.

To prevent regurgitation, the magnet proximal (cephalad, superior) to each magnet remainis energized until the magnet distal to it is energized. Alternative applications can employ one or more separately jacketed electromagnets to compress intervening tissue or simulate peristalsis in nonductal organs, such as along the renal capsule. As shown in the cross-section of FIG. 11, the core and coil have been bent around to least encroach upon neighboring tissue and more evenly distribute the weight while standing.

Unpiped Electromagnet Impasse-Jackets

Unpiped electromagnet impasse-jackets function as do permanent magnet impasse jackets to draw a magnetically susceptible particle-bound drug, drugs, or other therapeutic substances passing through the ductus lumen against the lumen wall until a second substance arrives, for example, or into the lumen wall. Where the permanent magnet jacket will attract any magnetically susceptible particle bound substance, the electromagnet does so only when energized. For this reason, any number of susceptible particle-bound substances can pass the jacket until that to be attracted arrives. An unpiped electromagnet impasse jacket shown in FIGS. 11 and 12 but has a hard outer shell and no draw-plate.

The multiple electromagnets are small as possible, usually arranged in a helical pattern to better distribute the weight, and identical, but graduated in amperage, hence, field strength from the upstream to the downstream end. Another type of electromagnet-jacket, the extraction jackets shown in FIGS. 13 thru 15, 39A, and 39B used for magnetic separation ambulatory hemodialysis or cytapheresis as described below where a ferrofluid infused upstream through a simple junction jacket binds with the type analyte to be extracted is described below.

In FIG. 39A, where a chain of magnetic separation jackets are shown attached to inferior venal cava, the term upstream pertains to levels caudal, or inferior, to that of the chain. To the extent that intrinsic motility assist jackets serve only to replace dysfunctional or missing sphincteric, and multimagnet contraction jackets weak or missing peristaltic function, only electrical, not fluid, connections are necessary. In FIGS. 39A and 39B, the choice of a peristaltic, or roller, pump 56 is to take advantage of the pulsatent flow of the output, which incremental and slightly hesitant, hence, periodically slowed, allows more effective magnetic extraction of the superparamagnetically carrier bound microparticles or nanoparticles.

This allows the entire prosthesis to be implanted. When a simple junction jacket is needed upstream to supply synthetic mucus or other digestive substances, an extracorporeal pump-pack must be added. When fluid delivery is needed from the outset, the control and power components are relegated to a pump-pack, allowing access without an invasive procedure. Fluid delivery may be direct to a sphinteric or peristaltic jacket that is piped, or indirect, to simple junction jacket placed upstream. However, when synthetic mucus and enzymes, for example, are to be delivered, the jacket must be provided with one or more side-connectors and fluid lines led from a supply reservoir and pump in the pump-pack under the control of the microcontroller.

Power Source

A central object to confer freedom of movement, the tethering and detention of a power cord is reserved for recharging. Added weight notwithstanding, the battery compartment in the pump-pack should include a fully charged spare battery. For direct power, to recharge batteries, and avert fouling of the battery compartment due to battery leakage should it occur, the pump-pack includes an internal power supply with ac power cord. In general, because it introduces contingency of availability, the use of an external power supply or ac adapter is not preferred despite the reduction in weight.

Hybrid Impasse and Extraction-Jackets

If allowed to remain within the lumen wall or other target tissue, current superparamagnetic iron oxide nanoparticles for use as drug-carriers may pose a problem of toxicity (see, for example, Wahajuddin and Arora, S. 2012. "Superparamagnetic Iron Oxide Nanoparticles: Magnetic Nanoplatforms as Drug-carriers," *International Journal of Nanomedicine* 7:3445-3471). With continued research into the formulation of drug carriers, this should prove less a problem, but means must be available for dealing with such a contingency. An unpiped electromagnet impasse jacket as described in the preceding section can be used to draw the carried drug into the wall using an initial range of field strengths, any toxic residue then drawn entirely out of the wall with the average field strength of the magnets from one end of the jacket to the other increased.

Since the residue will accumulate at the magnet poles 75, this is satisfactory only when a small amount of the affiliate is drawn out, as in some noncytapheretic extraction. One type of jacket that allows the drug to be drawn into the lumen wall and then extracted is a permanent magnet impasse jacket with extraction grating as described in copending application Ser. No. 13/694,835, published as US 20140163664. Such a jacket requires the use of a powerful external electromagnet to draw the unwanted residue out of the wall. This requires a visit to the clinic, and must be repeated where treatment is on a continued basis and/or the amount of the residue necessitates its frequent removal. With a chronic myeloproliferative disease, missing a visit to the clinic can bode grave consequences, recommending the use of an automatic ambulatory apparatus.

The type of hybrid extraction jacket used depends upon the rate volume of extractate removal and accumulation. For small volumes, an electromagnetic impasse jacket with magnets having poles outside the adventitia such as shown in FIG. 12, and with sufficient strength to extract the bound analyte can be used if the buildup and remaining of residue at the poles poses no risk. The jacket fixes the magnetic gap separating the magnet pole from the motile adventitia; however, a residue toxic for the ductus wall will usually be equally toxic for surrounding tissue, and unless adherent to the pole or poles, the residue will drop away and drift off when the magnet is turned off. Moreover, when the accumulation is more than negligible, magnets able to generate the field strength required will tend to be larger and heavier.

These will necessitate additional dissection to place, suture or harness to stabilize, limiting the use of such jackets to sites that afford the necessary clearance, and adding to intraprocedural duration and the added risk of encroachment upon neighboring tissue. For these reasons, a more practical form of hybrid impasse and extraction jacket for most applications alternates electromagnets mounted as shown in FIG. 12, where the magnet poles remain outside the wall of the ductus, with those mounted as shown in FIG. 13 or 15 with trap and flush-line that passes through the consecutive extraction-magnet traps interposed between the magnets mounted as shown in FIG. 12, where a plug of tissue has been removed from the ductus wall.

Thus, whereas the flush-line in such a train of extraction jackets suitable for automatic ambulatory hemodialysis or cytapheresis as shown in FIGS. 13 thru 15 and 39A and described below in the section that follows passes from magnet pole 75 and associated traps 78 of one separate consecutive extraction jacket to the next, the flush-line passing through a hybrid jacket passes from one trap to the next within the length of a single jacket, passing over the intervening impasse electromagnets.

Another type of hybrid jacket facilitates the extraction of a potentially harmful magnetically susceptible residue. Since native lumen wall 2 is fenestrated to position flap-valve 81 in face to face relation with magnet pole 75, wall 2 facing magnet pole 75 is missing. Extraction of a potentially harmful residue from within lumen wall 2 is by a permanent magnet impasse-jacket such as shown in copending application Ser. No. 13/694,835, FIGS. 16A, 16B, and 16C with extraction grating and, if necessary, the aid of an external (extracorporeal) electromagnet, or by an extraction jacket with magnets able to generate the tractive force necessary to pull the residue through wall 2.

Such a jacket mounts magnets as shown in FIG. 12, where ductus wall 2 is intact but unlike the embodiments depicted in FIGS. 13 thru 15 in that each jacket has flush-line connection arms 80 allowing flush-line 79 to pass through and over magnet pole 75 each jacket. The space separating the face of magnet-pole 75 from elastic slit-valve for cytapheresis and bundled semipermeable fibers for hemodialysis 81 in a magnetic separation extraction jacket or the outer surface of the ductus in a hybrid impasse and extraction jacket is positioned directly in the path of flush-line 79 and is therefore continuously flushed clean Referring to FIG. 39A, with peristaltic pump 56 temporarily off, the volume of debris accumulated before flushing becomes necessary depends upon the magnetic tractive force, the rate at which the residue is accumulated, and the flow rate through flush-line 79 upon recovery of pump 56. Periodic cytapheresis performed continuously over an interval allows the use of multiple extraction jackets such as shown in FIG. 14, wherein each of the several magnets can be reduced in size and weight. Addressed here and in the section to follow, further to implement automatic intracorporeal magnetic separation hemodialysis or cytapheresis, another type of hybrid electromagnet jacket uses multiple smaller electromagnets such as those chained in FIGS. 13 and 15.

Extraction Jackets

Extraction jackets, shown in FIGS. 13 thru 15 and 39A allow analytes bound to or carried by magnetically susceptible particles such as superparamagnetic iron oxide microparticles or nanoparticles to be withdrawn from a native lumen 1 and accumulated in a collection chamber, the pole of an electromagnet along a flush line as shown in FIGS. 13 thru 15 and 39A, and the magnet-associated trap 78, for removal. In profile, the jacket of FIG. 13 resembles that of FIG. 11 with the magnet core 84 and coil 74 bent around to minimize its protrusion. However, unlike the contraction-jacket shown in FIG. 11, the jacket is not pliant and no draw-plate is used. In FIGS. 13 thru 15, magnets 74 do not protrude to the extent the drawings imply: for descriptive purposes, the components of the extraction jackets, which wrap around and out of sight, have been laid relatively flat to the plane of the drawings and enlarged. In FIG. 14, trap 78, situated along flush-line 79, is connected to flush-line 79 by means of inlet and outlet connecting arms with convoluted fluid line or hose retentive ends 80.

Flush-line 79 conducts a flushing solution, wash water, or a flushing hydrogel from a clean supply reservoir in the pump-pack, through trap 78, to a waste reservoir in the pump-pack when periodically directed to do so by the control system program, which is based upon the rate of accumulation. FIG. 14 shows that when more than a single extraction jacket is used, flush-line 79 consecutively passes through each successive trap in the series, which is functionally bidirectional and geometrically symmetrical. An advantage in the use of electromagnets is that other type jackets addressed herein, such as electromagnetic impasse-jackets, can be interposed between the extraction jackets shown in FIG. 14 for use independently of or coordinated with the use of the extraction jackets.

In a compound jacket such as the peristaltic jacket shown in FIG. 10 or a series (chain, train) of jackets meant to function as a unit, such as the extraction jackets shown in FIG. 14, the magnets are wired in series and not separately adjustable. Interposed magnets when not components in another series are separately controllable. Individual magnet control makes possible the discretionary targeting of the carrier bonded drug or drugs delivered upstream to a specific jacket or subset of jackets and the type lesion these encircle at a given time. For any drug or drugs delivered by infusion through a simple junction jacket located upstream, administration is fully automatic, the patient unaware of the continuous process whereby condition-specific sensors signal the respective node to initiate drug delivery.

Optimally, this takes place before symptoms emerge. The single magnet extraction jacket shown in FIG. 13 has hard outer shell 4, made of a polymer well tolerated in the internal environment, such as polyether ether ketone, is made with rounded edges, minimal protrusion of magnet 74, compact as the thickness of viscoelastic polyurethane foam shell lining 3 will allow to avoid encroachment upon neighboring tissue, and includes perforations 19 which expose the outer surface of ductus wall 2 to the environment. Extraction jacket flap-valve 81 as shown in FIG. 13 is addressed above in the section entitled Background of the Invention. Flap-valve 81 is biased in pliancy to be more resistive to the entry into native ductus lumen 1 of fluid from line 79 than the extraction past its flaps of magnetically susceptible particles.

This bias is the product of flap geometry and the mechanical properties or deformation moduli of the material or materials, such as laminated, of which the flaps are made. The internal surface of flap-valve 81 is in direct contact with the contents of lumen 1 and must be constituted of a material or materials such as synthetic least likely to induce an adverse reaction. Flap-valve 81 at the adductal end of the passageway (throat, corridor) leading up to the adventitial or fibrosal outer tunic is flush planar to it along the outer surfaces of the ductus wall and foam lining flap-valve, or if falling short thereof, the sides of the passageway isolate the foam from the opening in the ductus wall.

Jacket Placement

Figure 27:
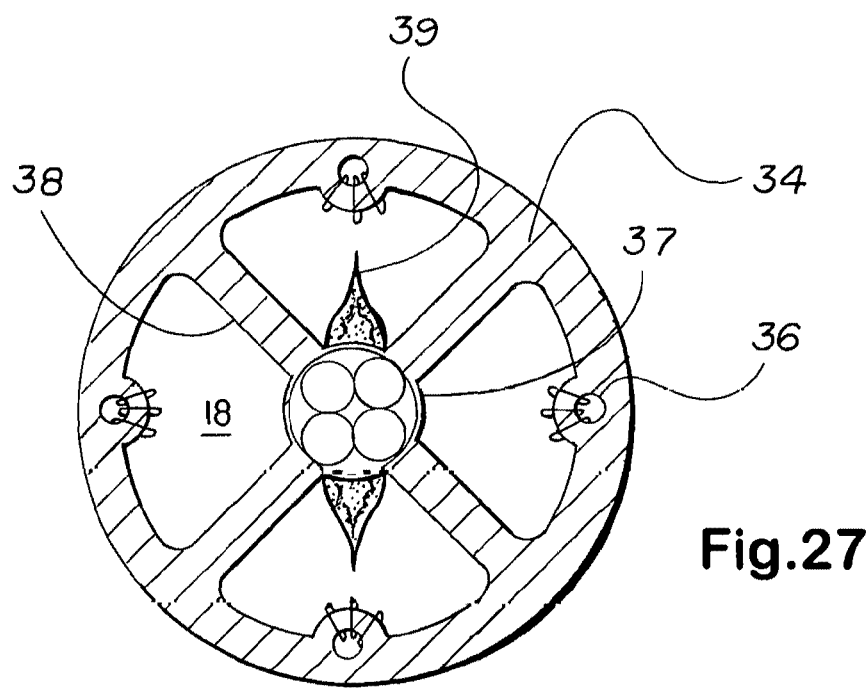
FIG. 27 is a full-face view of the upper surface of the base plate of the body surface port shown in FIG. 28 for positioning at the body surface for connection of electrical, fluid mainlines, and side-entry connection mainlines and water-jacket sidelines also used as accessory or service channel lines.

As shown in FIGS. 16 and 21, for example, the jackets with fluid and electrical lines connected are introduced through surface port 16 via an incision at the body surface shown in FIG. 27. To minimize trauma and the risk of infection, this incision is made no larger than is necessary to pass through the jackets and lines without excessive force. At the leading end of its lines, each jacket is then subcutaneously tunneled over the subjacent fascia to the site overlying that for its placement. Deeper or plunging dissection to gain access to the site for placement is limited to that essential. Whether periadventitial or fibrosal fat is left substantially intact depends upon its functional relation to the ductus, the avoidance of needless trauma, and the availability of the greater field force necessary to support the specific application over the wider magnetic gap that results. To allow for unanticipated contingencies, the magnets and battery are always somewhat overrated.

Once the plug is cut from the vessel wall, the connector is locked in position with its front edge level with the internal surface of the lumen. Used along the gut, the vacuum pump is then reversed to force the plug into the lumen. In a vessel, the plug must be extracted. This is accomplished with the vacuum. Should the tissue plug hang or resist extraction due to circumferential enclosure by surrounding tissue, a guide wire with hooked front tip is passed through an inline port as described below. When the combination of the foam lining and vacuum pump are not sufficient to hold the outer wall of the structure against the internal surface of the jacket, preliminary administration of polyethylene glycol-electrolyte solution for evacuation and opiates to truncate peristalsis is routine, as is the administration of antihypertensives to reduce the blood pressure.

As soon as the plug is excised, the vacuum pump is shutoff as promoting bleeding, and the pump switched to pump inlet hose 11 to ductus side-entry connector-internal fluid-conducting or water-jacket inlet 10, ductus side-entry connector-internal fluid-conducting or water-jacket 7 used to direct pressurized water against the breach, thereby suppressing bleeding (exsanguinations, extravasation) and forcing the plug out through side-entry connector 6. If necessary, a suction catheter is passed through side-entry connector 6 or the hose connected to side-entry connector 6 to pull out the plug.

The hemostatic or bleeding suppressive irrigation is stopped, the catheteric line leading to the automatic portable pump delivering medication through port 16 implanted at the body surface 18 quickly connected to side-entry connector 6, and fluid medication started with the object of establishing continuous flow, eliminating the entry of air into the line. Because it will have been prepositioned for any number of routine foreseeable and unforeseeable contingencies, a second catheteric line is always connected between fluid-conducting or water-jacket 7 connector or inlet 10 and its respective socket in port 16 implanted at the body surface 18.

When the vacuum is applied to the outer surface of the ductus, the sharp trepan front edge of the side-connector is drawn through the lumen wall, compressing the surrounding foam. This action effectively seals the jacket from native lumen contents, minimizing leakage. Once the forward sharp edge of the side-connector is aligned to the internal surface of the ductus wall, the foam decompresses, removing the brief compression on the fine nervelets and vasa vasora which the foam serves to protect. To prevent leakage of septic contents into the surrounding body, or peritoneal, cavity, journaling of the connector in the side of the jacket is tight.

Blood instantly spurting out of a breach in an artery on the systoles and continuing to drain on the diastoles to initiating clotting, the connector may be wetted with heparin lock flush, or 'hep-lock,' solution and provided with an internal circumferential fluid-conducting or water-jacket open at the front which irrigates the opened plug hole with pressurized and medicated tacky hydrogel, water, or heparinized water, for example, to restrain bleeding and reduce the risks of infection or inflammation. Once the front or adluminal trepan edge of the connector has been advanced to be level with the internal surface of the lumen, the fluid-conducting or water-jacket remains as a second lumen for other uses addressed below in this section.

The medicated tacky hydrogel or water, pressurized to minimize bleeding without significant entry into the bloodstream, is turned on an instant after the plug has been cut, and assists the vacuum to force the plug out through the side-entry connector. The combination of expulsive forces assures that the plug is safely extracted and cannot enter the lumen as an embolism. To assure that the plug does not catch on the distal or adluminal free edge of the fluid-conducting or water-jacket, the edge is rounded or rolled to form a rim and sufficiently receded in relation to the edge surrounding it as not to clog or interfere with cutting the plug.

A simple catheter, narrow hose connected to a vacuum pump or larger diameter thrombus aspiration catheter, the aspiration line serves first to retain the adventitia against the razor front edge of the side-entry connector, and is therefore introduced through the connector and turned on before the plug is cut.

The vacuum line then cuts or assists the operator in cutting and withdrawing the plug, so that it is left on throughout plug cutting and extraction. Should the vacuum overpower the fluid or water pressure so that some blood issues from the vessel, the duration of the operation, hence, the absolute amount of blood loss is medically insignificant. When application under vacuum pressure of the sharp front or adductal edge of the connector to a thin walled vessel is sufficient to cut the plug, the need for the operator to manipulate the connector as a circle-cutter is eliminated, so that a locking collar or bushing is unnecessary.

The aspiration line and water ejected from the fluid-conducting, flushing solution, tacky hydrogel, or water jacket are then used to withdraw the plug from the side-entry connector. Shutting off of the plug removal aspiration pump and turning on of the fluid-conducting or water-jacket pump are controlled with the same switch. The side-entry connector water-jacket ringing around to line the distal interior of the connector and its feed line attached to the connector at right angles, the connector lumen is clear. Irrigation is continued as and after the plug removal aspiration line has been withdrawn. Water spilling into the body cavity is removed with an ordinary aspiration line.

Connection of the multilumen water or medication-filled catheter leading to the port implanted at the body surface to the side-entry connector at the same time that the fluid-conducting or water-jacket pump is turned off prevents air from entering the line and completes the procedure. To prevent gas from entering, lines are kept filled, usually with a medicated tacky hydrogel. Each line has a small one-way bleed valve to eliminate gas from the line. Any seepage of sterile wash water through such a valve is reabsorbed into the body and without medical significance. The pieces of crushed tacky hydrogel, fill or medicated, are generally too large to exit thus and could rarely if ever result in complications.

Separating doses of water-insoluble or immiscible medication with water, for example, additionally assures dose accuracy, as well as prevents extravasation. A hypodermic syringe, infusion catheter, automatic infusion or similar ambulatory (wearable, portable) automatic pump is connected at the port to deliver medication directly to the jacketed segment. To assure that each dose is accurate, doses are separated along the queue by water or a hydrogel, for example. Provided a method is available to bond the target analyte or analytes to a superparamagnetic micro or nanoparticle carrier, magnetic separation is suitable for apheresis, such as stem cell removal, leukapheresis or for hemodialysis.

Circulation between the lumen and pump at one level, which can be accomplished with a dual lumen catheter, or from side-entry jackets at different levels, the connection is suitable for apheresis, such as leukapheresis or dialysis, for example. Circulation after the cutting edge has been brought level to the lumen wall and the connector locked in position can continue from one level with the fluid-conducting or water-jacket and the channel or passageway through the connector used in either direction. For this purpose and when the fluid-conducting or water-jacketway is to be used to withdraw diagnostic testing samples and the passageway through the connector to deliver drugs or the reverse, the relative diameters of fluid-conducting or water-jacket and passageway are chosen with this purpose in mind when the side-entry connection jacket is selected.

To avert backup inflow, when water rather than a tacky crushed hydrogel—which can also position the initial dose—is used to prevent leaks or extravasation during placement, lines can be filled with a higher viscosity substance such as a hydrogel without being capped off as would necessitate invasive reentry to recover their use. When the formation of a lesion is anticipated, unused jackets and lines ending at the port, without insertion of a corresponding pump-pair plug-in module in the pump-pack, can be prepositioned at points such as just downstream to the bifurcation in the common carotid artery. To attach or remove a hose or catheteric supply line, side-entry connector 6 can either be temporarily locked in position in the side-entry connection jacket or removed. FIG. 2 depicts the same side-entry jacket as that shown in FIG. 1 after the adluminal end of side-entry connector 6 has been advanced into level planar alignment with the internal surface of lumen wall 2.

Valve Plugs

Should for any reason the side-entry connection jacket require to be disabled, prongs 20 shown in FIGS. 1 thru 3 are configured to engage and securely retain the forward or ductus adaxial portion of the silicone or other suitable elastomeric full length outer cylindrical surround or full length annulus of a shutoff and throttle valve-plug against the forward edge of water-jacket 7, thus covering over the opening made in the side of the ductus. This plug, especially when engaged thus, is never a solid mass of rubbery material as would hinder quick response to an exigent circumstance. From the moment the tissue plug is removed from the side of a blood vessel in particular, the plug must be extracted at the same time that leakage, if not eliminated, must be kept to a minimum.

Since the plug must be extracted through the side-entry connection line, keeping the line filled is not an option. The opening is therefore irrigated with water delivered at greater than the blood pressure through the water-jacket while the tissue plug is extracted. Because the side-entry connection line is needed to allow the irrigation water or other fluid to escape, the line cannot be filled while irrigation continues, although closing off the outlet at the instant irrigation is stopped will leave the line filled. However, introduction into the line of a valve-plug affords not only control over hemostasis but the rate of drug delivery. Valve-plugs are either passive, using an elastic membrane with slits, slats, or pinholes, or spring-loaded ball or vanes that open in response to the applied pressure to determine the volumetric flow rate therethrough, or are active, that is, mechanical and adjustable, so that the rate can be varied independently of the applied pressure by opening and closing a gate, such as in a butterfly valve.

Either type of valve-plug can be used with a side-entry connection jacket whether the jacket is of the simple junction, magnetized junction, or shielded and magnetized junction type. An active or vane adjustment type shutoff and throttling valve-plug is continuously variable between fully closed and fully open positions, so that in combination with the setting at the pump, for example, such a valve-plug can be used to throttle the volumetric flow rate through the line. Elastic membrane valves are suitable for use with fluids but not crushed hydrogels. Elastic membrane slit-valves such as shown in FIG. 33 are used on small caliber catheteric lines that would otherwise empty of costly medication when the line was disconnected, for example. Provided the material of the valve is surface treated to minimize clotting, preferably without necessitating the infusion of anticlotting medication, elastic membrane valves can be made suitable for use with blood; however, these are generally without an incisive forward edge and limited to use in apparatus not in direct contact with native tissue.

The use of washing fluid and drugs in the form of slightly tacky hydrogels rather freely flowing liquids also reduces spillage, preventing lines from emptying when disconnected. When slid past the forward edge of water-jacket 7, the forward portion of the elastomeric surround 33 expands to the wider internal diameter of side-connector 6 to become pierced and engaged by recurved prongs 20. A wire passed through the line to supply current to a heating coil inside should be sufficiently inflexible as not to be overridden by the retreating valve-plug causing it to jam along the line within the gamut moved. The operator views the tantalum coated plug and drives it flush against the opening in the side of the ductus. Now the elastomeric surround is caught between the front edge or ledge of water-jacket 7 but prevented from moving forward by prongs 20, thus firmly fixing it in position. This prevents the plug from migrating into the lumen of the ductus.

Valve-plugs are either active mechanisms that regulate flow-through regardless of the applied fluid pressure or passive fluid resisters that respond to the applied pressure. It is also possible to combine these principles of operation in a single plug where the diameter of the slit elastic membrane that passively responds to the applied pressure is adjusted by the incorporation thereof within a mechanical operation 1 type plug. Closing openings in the plug essential to move it through the fluid column partially rather than fully allows such a plug, shown in FIGS. 23 thru 25 and described below, to be used as a throttle as well as a shutoff valve-plug. Used as a throttle, the valve-plug can be positioned anywhere along a side-entry connector line 13 or a service channel line 11. Elastomeric valve-plug surround 33 is, however, sufficiently compressible that a plug held securely as indicated can be retracted by an operator applying the required pulling force at the end of the guidewire to remove it.

The stopper and valve-plug is long and snugly fitting as to prevent veering from the long axis of the line in which it is inserted, cocking and jamming, or migrating. The plug pushed into the lumen, the pump is disconnected from and the permanent line leading to the port 16 implanted at the surface 18 connected to side-entry connector 6. The medicinal fluid is then passed into the lumen. Larger muscular arteries excepted, when placed along a blood vessel, the ductus wall will usually be thin enough that suction and the razor-sharp front edge of the connector alone will be sufficient to cut the plug with no effort on the part of the operator. The blood pressure prevents the plug from reentering the vessel where it would embolize but is not adequate to force the plug entirely through the vacuum line with the pump off.

Since side-entry connection jackets are used to articulate a native conduit, lines 13 connected thereto convey native luminal contents unidirectionally. By contrast, flow through subsidiary or service channel lines 11 is often bidirectional. FIGS. 21 and 22 show a side-entry connection jacket applied to the ascending aorta to allow blood to be diverted into catheters or artificial arteries that bypass occluded segments of the intrinsic coronary arteries in a patient who lacks adequate native grafts and/or could not withstand the lengthier surgery and anesthetization to complete a conventional bypass harvesting and grafting procedure. FIG. 21 provides an anatomical overview of the jacket shown in FIGS. 17, 19, and 20 in use to attach catheters as coronary artery bypasses, while FIG. 22 provides a nonanatomical schematized view of the repair shown in FIG. 21.

To bypass endoluminal obstructions 17, catheters 13 are joined to the ascending aorta above and to respective distal segments of the native coronary arteries below by insertion of either end into side-entry connectors 6. Since the segment of the arteries shown sd bypassed in FIGS. 21 and 22 change little in caliber, upper and lower side-entry connectors are shown as equal in diameter, although the use of tapering or progressively narrowed catheters would allow mimicking the anatomy. While the upper and lower side-entry connectors are depicted as alike, the jackets differ in overall diameter and in that the delivery from a port 16 implanted at the body surface 18 of adjuvant medication, here an anticoagulant, through service channel lines 11 has been applied only at the upper jackets.

Placement thus allows sizing and joining of side-entry connectors 6 at either end of catheters 13 before or after endoscopic entry, the choice based upon patient anatomy. Whereas the lines that connect to side-entry connectors 6 and water-jacket inlets 10 from surface port 16 are synthetic, the jackets encircle native conduits 2, here the large aorta and the narrow coronaries. That is, whether the line from the port 16 at the body surface 18 is directly to a native conduit or indirectly to a synthetic conduit, bypass, or shunt by connection to and/or for junction with a native conduit, it is normally a native conduit 2 that is encircled by the jacket and the synthetic line that is connected to side-connector 6, any accessory or subsidiary lines 11 connected to water-jacket inlet 10 synthetic as well.

Whether used to unidirectionally conduct luminal contents through a bypass or shunt or to communicate with the surface bidirectionally, lines 13 connected to side-entry connectors 6 are synthetic with the jacket applied to a native conduit. Fluid conduction or water-jacket inlet service channel or subsidiary lines 11 are also synthetic but used to channel native luminal contents only exceptionally when used to draw test samples. The use thereof is normally unidirectional to deliver medication to a bypass or shunt jacket junction from a port 16 implanted at the body surface 18. When water-jacket lines 11 lack sufficient caliber to move contents directly to and from the native conduit, either a jacket with larger inlets 10 or a jacket with an additional side-entry connector is used to connect a line of larger caliber. In that instance, the line from the first side-entry connector joins the synthetic bypass, while the line connected to the second side-entry connector is connected at the surface.

Coagulation a deterrent to the use of current synthetic materials as bypasses or shunts shown in the accompanying drawing as part number 13, the side-entry connector water-jacket inlets 10 are used to connect the synthetic bypasses 13 to a port 16 implanted at the body surface 18 for the delivery of an anticoagulant and/or other liquid medication over water jacket inlet lines 11 shown in FIGS. 21 thru 22. The bypasses and distal or insertion jackets are usually connected to the connectors before the jackets are placed, the lines from the body surface to the proximal or epicardial jackets for the delivery of the anticoagulant and any other liquid medication through a water-jacket inlet lines 11 connected thereafter. Placement about the ascending aorta is usually more expedient when bypass catheters 13 are attached to side-entry connectors 6 after the jackets have been placed. This may not be so for other locations.

Figure 23:
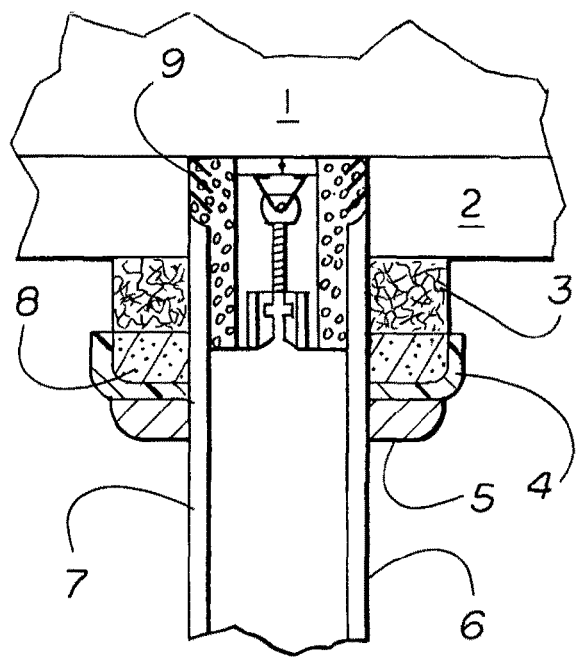
FIG. 23 is a longitudinal sectional view through an adjustable obturator type or stopper shutoff and throttle valve-plug in use to close off or to adjust the volumetric flow rate through the opening or ostium in the side of a native ductus created when placing a side-entry connection jacket, shown in place within the side-entry connection jacket.

Mechanical Valve-Plugs Manually Translatable and Adjustable and/or Radio Remotely Adjustable Should for any reason the opening into the opening or ostium made in the side of the native conduit or ductus require to be closed off, a mechanical occlusion device in the form of a shutoff obturator or stopper and throttle valve-plug is used. FIG. 23 is a longitudinal section through a shutoff and throttle valve-plug in use to completely seal off the passageway through the passage created between the jacket and the native conduit, wherein lumen 1 is bounded by surrounding wall 2 and the side entry connector 6. The plug, shown in fully closed position, is seated at the ductus end of side-entry connector 6 to close off the opening into the ductus. One or more valve-plugs introduced into a line during placement of a jacket with lines and pump attached, as addressed below, may be positioned anywhere along the line, whether intra- or extracorporeally.

Figure 24:
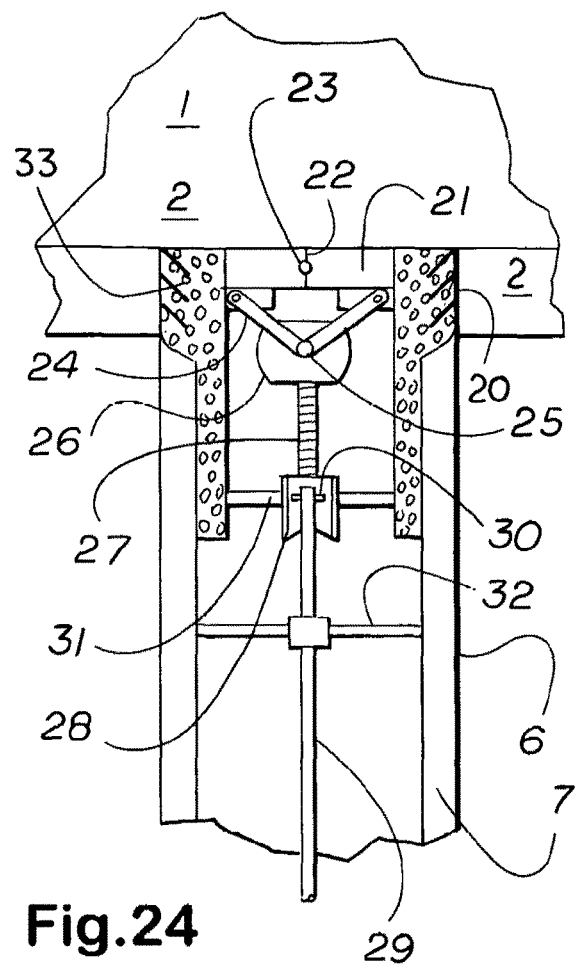
FIG. 24 is a longitudinal sectional view through an adjustable obturator or stopper shutoff and throttle valve-plug in use to close off or to adjust the volumetric flow rate through the opening or stoma in the side of a native ductus created when placing a side-entry connection jacket, with the distal segment of the guidewire shown in FIG. 26 used to place, advance, remove, and in this mechanical embodiment, adjust the valve-plug.

Once the operator has determined the best anatomical path or routing—and therewith the best lengths for the intracorporeal mainline and sideline between jacket and port—which need not be adjoined, or tunneled and routed together, this shutoff ability allows the port to be slid up to the skin and the lines cut flush at the port faceplate without medically significant spillage, for example. If remotely controlled as described below, flow through the valve-plug or plugs can be throttled or stopped at any distance from the patient, allowing the clinician to affect the rate of flow-through in response to a call from a distant wearer. Midline as opposed to endline valving that uses an elastic slit membrane requires spanning the membrane across the longitudinal is not remotely controllable thus and less common than electromechanical valve-plugs.

Where the side-entry connection jacket must be removed or is no longer needed, complete removal of the jacket, lines, and port requires a second invasive procedure in which the ductus if a vessel is cross-clamped upstream long enough to place a graft or several turns with a hydrogel adhesive tape coated to encourage regrowth over the opening. The special treatment required for the carotid and coronary arteries is addressed above under Background. If the opening is small enough, tape is used with an absorption rate slower than that of endothelial regrowth. Referring now to FIGS. 23 and 24, valve-plugs can be configured to permanently close off the opening made in the side of the ductus, to do so while allowing in- and outflow through the side-entry connector but not the water-jacket, or to allow continued flow through the water-jacket as well as the side-entry connector, and can be made only so retentive in level that the program can reposition a valve-plug by sliding it at the head of a column of water or gel as programmed or as the clinician chooses.

Since line 13 must be kept filled with fluid to deny entry into line 13 by any contents of lumen 1 that would leak through the opening, the obturator must be advanceable, and if necessary retractable or withdrawable, through a fluid column. Special handling and viewing equipment needed at very small calibers, a slit membrane valve or mechanical shutoff obturator or stopper and throttle valve-plug is no less usable in a service channel as shown in FIGS. 1, 2, and 17 thru 22 as it is in a line 13 connected to a side-entry connector. As a throttle, even when used to temporarily stop flow, the plug can be situated anywhere along the line. Use in a side-entry connector attached line is with the front of the plug flush against the opening in the ductus to seal the ductus with no fluid between the plug and opening. When used as a long-term or permanent shutoff valve-plug to seal off the opening, the front of the plug must fit flush over the opening in the ductus with no fluid between these.

Effecting shutoff involves no invasive procedure as would placing a graft over the opening, which would begin to leak luminal contents were the jacket removed. If the jacket is to be removed, then the ductus is cross-clamped upstream, the special requirements pertaining to the carotid and coronary arteries addressed above under Background. Once the plug has been seated in position to cover the opening at the ductus-adluminal end of side-entry connector 6, completely closing continuously adjustable vanes (shutters, leaves, wings) 21 of the miniature duplex butterfly valve closes off flow-through. Whereas a valve-plug leaves open the possibility for inflow or outflow, covering over the opening or ostium created in the side of the ductus can also be with an autograft or absorbable hydrogel breach tape, the internal surface of which is treated to encourage the regeneration of tissue that closes the breach.

When opened, semicircular discs or vanes 21 allow fluid to pass through the plug in either direction, allowing the antegrade delivery of medication or the withdrawal of laboratory test samples. Continuously variable adjustment in elevation of the vanes, hence, the cross-sectional area of the apertures through the plug, allows continuous adjustment in the volumetric flow through the plug in either direction as a throttle. The throttle feature is pertinent to drug self-administration with a manually operated syringe, especially by an elderly patient with impaired motor control. When a pump is used to deliver medication through a side-entry connector-line 13 or service channel 11, the dosing and rate of delivery can be set at the pump, averting the risks of drug delivery that is too fast or too slow.

In FIGS. 23 and 24, semicircular vanes or duplex butterfly valve discs 21 are tantalum contrast coated for improved fluoroscopic visibility and to prevent leakage when fully closed, edged with a durable watertightening rubbery or compressible elastomeric material, such as silicone. When fully elevated and thus closed, the outer edges of valve discs or vanes 21 are in contact with the internal surface of side-entry connector 6. Valve discs or vanes 21 meet flush at common midline watertight folding hinge joint 22 by rotation about axle 23, which is a pin fastened with no external presentation to the sides of side-entry connector 6. Valve discs or vanes 21 are pushed upwards into closed position and pulled downwards into open position by links 24.

Like vanes 21, links 24 are not strips but rather flats extending entirely across the semicircular space each extends over or subtends, edged with an elastomer where these are in contact with adjacent surfaces for watertightness, and joined for rotation at axle 25, which passes through follower block 26 and is fixed by resistance welding at either end to without extension outside side-entry connector 6. Links 24 therefore deflect and cause to diverge ductus-adaxially advancing, or in the orientation depicted in FIGS. 23 and 24, upwards flowing fluid, to either semicircular outer side edges of links 24, directing the fluid toward the side openings cleared by vanes 21. At their opposite or ductus-adaxial ends, links 24 connect to the underside of either respective vane 21 by rotatory joints toward the central outer edge which are able to slide from side to side within an enclosed way.

In a mechanical embodiment, links 24 are driven forward, or ductus adaxially, and pulled backward, or ductus-abaxially, when threaded shaft or leadscrew follower block 26, to which axle 25 is mounted, is advanced, or raised in FIGS. 23 and 24, by rotating leadscrew 27 clockwise and retracted or lowered by rotating leadscrew 27 counterclockwise. To maintain watertight contact between the outer surface of follower block 26 and the inward or medial edges of links 24, follower block 26 is oblate, so that its sides extend into the increasing space that would be opened between links 24 and the sides of follower block 26 as the central level in elevation of links 24 is approached were the sides of follower block 26 straight vertical.

Figure 26:
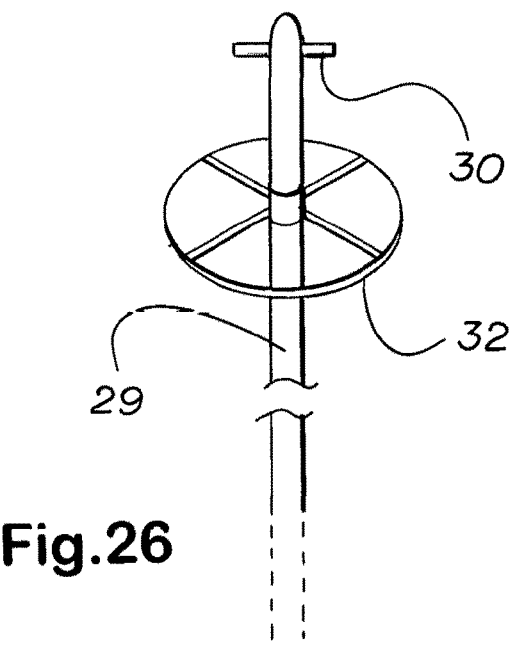
FIG. 26 is a detailed view of the distal end of the guidewire shown in FIG. 24 for advancing, retracting, and adjusting the cross-sectional area for flow-through of a shutoff obturator or stopper and throttle valve-plug.

At its ductus-abaxial or outer end, leadscrew 27 is fixedly inserted into journaled rotary bearing 28, having keyed entry hole 29 with entry opening into the keyhole at its ductus-abaxial or lower end as seen in FIGS. 23 and 24. FIG. 26 shows the distal or keyed end of guidewire 29, configured to fit into the opening or keyhole and the vertical and circumferential ways cut or molded into the internal wall of valve-plug journaled rotary bearing 28. In a valve-plug that is mechanically adjusted in vane elevation, hence, the volumetric flow rate, by rotating leadscrew 27, the sidewise or circumferentially extending keyways or tracks within rotatory bearing 28 allow rotation as well as advancement and withdrawal of the valve-plug.

In a remotely controlled servo embodiment, a leadscrew is not used. Instead, the direct drive armature of a linear servomotor or a rod connected to it and the bottom of follower block 26 replaces leadscrew 27 and rotatory bearing 28 to adjust vanes 21, a keyed guidewire and insertion keyhole still needed to advance or withdraw the valve-plug but not to adjust vanes 21. Thus, even though the rod extending from the armature or the ductus-adaxial end of the direct drive linear armature is itself fixedly connected to the keyed receptacle in lieu of a journaled bearing 28, the side or circumferential tracks or keyways remain essential to engage the sidewise extensions or side pieces of guidewire key crosspiece 30 for valve-plug advancement and withdrawal through side-entry connector 6 and line 13 connected to it, or along a service channel line 11.

Whenever a line is entered at the port so that luminal matter would be ejected and flow back through the opening or stoma and out through the line to cause the hydrogel to spill out at the port, the water-jacket lines should be used to forcibly irrigate the stoma, restraining luminal contents from exiting. If following placement, the water-jacket line or lines had been used as service channels to deliver medication, and to feed water through the line or lines would cause the medication in the service channel or channels to enter the lumen resulting in an overdose, then the side-entry line or lines is plugged with a stopper and the medication aspirated from the service channel or channels so that they can be used again as a water-jacket.

Figure 25:
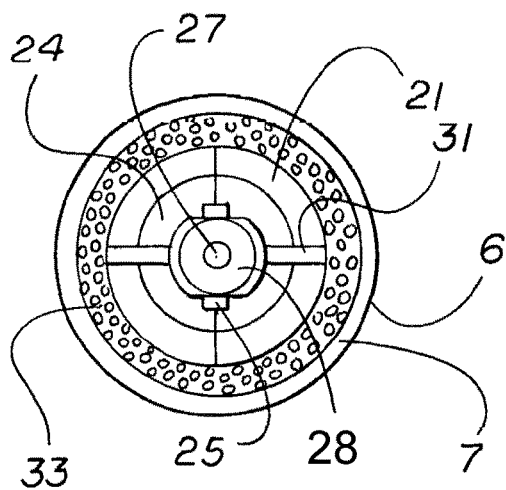
FIG. 25 is a full face cross-sectional partially ghost view of the rear, that is, the underside or proximal end, of the shutoff obturator or stopper and throttle valve-plug shown in FIG. 13.

As seen in the proximal (rear, underside, ductus abaxial) view of a valve-plug in FIG. 25, rotary bearing in journal 28 is suspended by frame 31 at the center toward the valve-plug bottom, the valve-plug otherwise open below. The distal end of guidewire 29, shown in FIG. 26 is rounded or domed and has centering ring 32 with a diameter equal to the internal diameter of the catheteric line, so that the key at the distal tip of guidewire 29 slides into the underside keyhole of journal bearing 28 without hunting. Once the tip of guidewire 29 enters journal 28, it is stopped and must be rotated to admit crossbar key 30 before it can fully seat within the cavity at the bottom of journal 28. Leadscrew 27 and rotary bearing in journal 28 are self-locking, so that the rotary angle to which leadscrew 27 is set is held until intentionally changed.

A plug inserted along a double lumen or multiluminal line preserves segregation of the contents of the lumina to pass through either vane and to prevent delivery contents from reversing direction with concurrent outflow through the return vane and lumen by separating entry into either vane by means of a septum. In a mechanical embodiment, rotary bearing in journal 28, hence, leadscrew 27, is rotated by inserting a guidewire with keyed tip into a cavity open at the bottom of rotary bearing in journal 28. The key at the distal end of the guidewire consists of a small crossbar that fits into the complementary female notching within the cavity. The two longitudinal notches or ways are diametrically opposed and allow the tips of the crossbar 30 to slide up and down. Links 24 are connected together by common axle rotatory joint 25 at the center of leadscrew follower block 26.

Threaded shaft or leadscrew follower block 26 is raised by rotation of leadscrew 27 clockwise and lowered by rotation of leadscrew 27 counterclockwise. At the distance from the closed end of the cavity equal to the distance between the tip and crossbar on the guidewire, the longitudinal notch to either side is extended to either side by a notch at right angles. Rotating the guidewire when fully inserted within the cavity thus causes the tips of the crossbar to slide within these side notches until the ends of the notches prevent further rotation that does not also rotate rotary bearing within journal 26, thus rotating leadscrew 27, raising or lowering follower block 26 and therewith links 24 and vanes 21. The plug can thus be moved with two degrees of freedom, consisting of longitudinal advancement or withdrawal (retraction) and rotation to either side.

Access to a side-entry line 13 or service channel 11 by hypodermic needle is through a conventional subcutaneous or fascia set membrane port. For insertion or removal of a plug to serve as a shutoff or throttle valve or for passing through a fine caliber cabled device such as a fiberoptic angioscope, such a conventional port is not usable. An alternative port that affords the patency essential must provide an open passage into the body with minimal risk of infection. Since a plug if not a fine cabled device the same diameter as is the lumen of the line, means must be provided so that a wire or wires passed through the line from a sensor or heating coil inside a shutoff valve or throttle plug do not interfere with or become damaged by passage through the lumen.

While it still requires entry into the line with a guidewire to insert or retrieve a shutoff and throttle valve, a remotely controlled valve eliminates the need to insert a guidewire into the line in order to adjust the valve, making it possible to effect make the adjustment while the patient remains upright and the competent patient to do so on the basis of guidance over the phone. Another advantage in remote closed loop servo control is that the feedback signal is clearly displayed, so that the vanes need not be visually confirmed to have been set to the angle wanted by viewing the tantalum contrast coated vanes with the aid of imaging equipment. In a remotely controlled embodiment, a pulse width modulated microminiature linear remotely controlled servo with a linear potentiometer as the feedback device is used. Alternatively, a valve-plug inmate vane mover can be powered by a conductor run down a side of the fluid line, usually a side-entry connected line.

In a remotely controlled embodiment, the leadscrew and follower are replaced by a shaft connected directly or to a rod connected to the servo armature. Completely avoiding the need to reenter when the valve is in use, such as to pass through a cabled device, is accomplished by placing a second jacket and line along the same ductus. To use the same line and jacket, the valve must be removed to clear the way, leakage out of the opening in the side of the ductus prevented by using the water-jacket to irrigate the opening under pressure, just as is done when placing a side-entry connection jacket. Removal and insertion of a remotely adjustable shutoff and throttle valve-plug is by means of a guidewire, as described for a manually adjusted valve.

When not required for passing through cabled devices or to support high-volumetric flow use, the surface port for a vascular side-entry jacket line can be of the portacath or conventional subcutaneously coursed or 'tunneled' central venous catheter type with implanted septum or membrane accessed through the skin with a hypodermic needle. However, for greater volumetric flow rate, to pass through cabled devices such as a fiberoptic angioscope or laser, and to expand the scope of applications beyond the vascular tree, the line is usually made patent from end to end. A side-entry jacket placed for the purpose of providing a passageway for cabled devices is positioned to allow the farthest travel through the lumen.

When a need for periodic visual examination by fiberoptic angioscope or intravascular ultrasound probe, for example, is anticipated, or when the probability is high that a transluminal procedure such as an angioplasty will become necessary, a second line and jacket can be placed and valved or kept filled with a durable hydrogel, for example, to prevent backflow. When the need to use a cabled device or devices is unanticipated, so that placement of a separate jacket or side-entry line for this purpose was not accomplished, a second invasive procedure is averted by passing the cabled device through the existing side-entry mainline. Provided the line is suitably valved, the cabled device can be passed through a piggyback port and the substance in the line, and provided an ambulatory pump-pack is securely fastened to the patient when moved between upright and recumbent positions, lines uninvolved in the procedure can continue to function without interruption.

Body Surface Port

Figure 28:
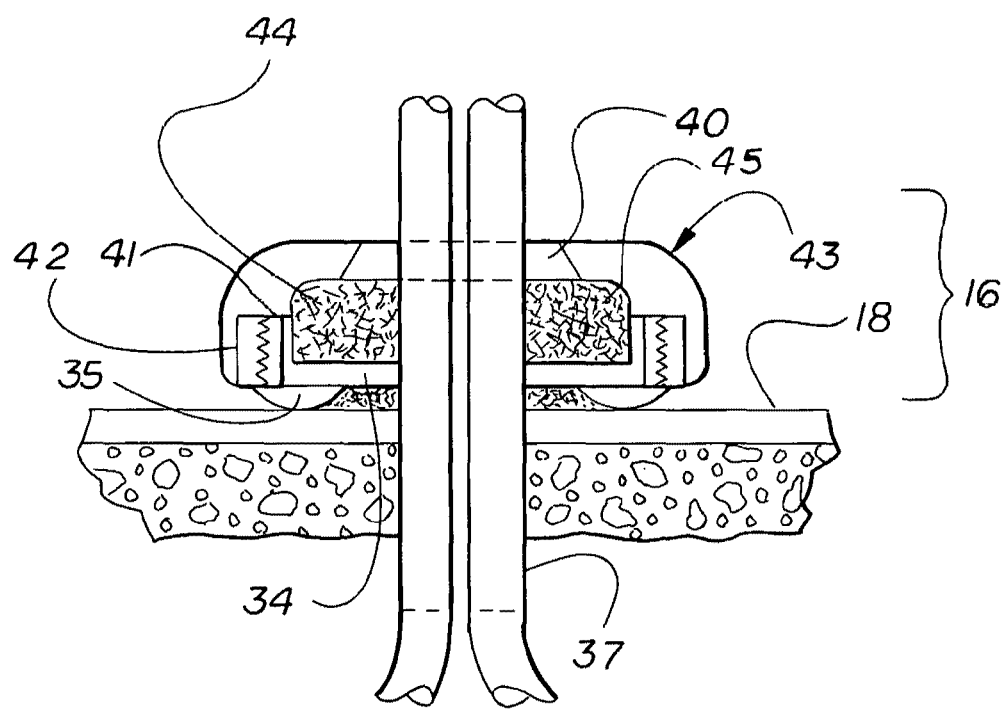

FIGS. 27 and 28 show a port for placement at the body surface, usually positioned pectorally as is a portacath, with lines of uniform diameter from end to end, allowing the passage therethrough of cabled devices as well as fluid pharmaceuticals. When use for cabled devices is not the primary or an initial purpose, the inability of a conventional subcutaneously placed port, or 'portacath,' for example, is properly disregarded only when an eventual need for more versatile function can be discounted with confidence. The lightweight port is minimized in size and number of parts, simplifying placement, reducing the opportunities for malfunction and complications, to include infection and adverse tissue reactions, making simple home maintenance by patients, and preventing pulling or pushing of the lines inside the body.

To avoid interference with clothing, least draw notice, and minimize the risk of collision, the port has a low pancake or squat truncated cone profile with rounded edges. A wide base minimizes depression of the body wall when pushed from the front, and inclined sides deflect collisions from any side. Essential sutures are internal and blanketed beneath antimicrobial and anti-immune agent wetted gauze. These features may make possible self-sufficient care by the very young and old. Turning now to FIG. 27, shown is a port baseplate 34, made, for example, of nylon-carbon or nylon-glass fiber composite titanium or a nonmagnetic stainless steel.

That the port is shown with four lines through lines conduit 37 is purely exemplary, the same arrangement used for any number of lines, the diameter of the port adjusted to accommodate a larger number. The most elementary or basic configuration, suitable for the application depicted in FIG. 16, for example, requires but one mainline and one sideline, each connected to a bidirectional pump. Port baseplate 34 is surface coated with an antimicrobial compound, such as one silver-based, and rests against the skin on cushion 35, made of a suitable rubbery plasticizer-free nonallergenic material such as silicone so that no portion of baseplate 34 can come into contact with the skin.

Cushion 35 must encircle to the outer side of suture holes 36 to fully encircle baseplate 34 thereby closing off the space overlying the skin to deny access to environmental pathogens, and should include openings or fenestrations sufficiently large to allow gauze 44 to protrude down between brace arms 38, but not extend over portions of the underside of baseplate 34 through which suture must be passed, or present angled edges as would cause irritation. Rather than to completely close off the suture points from the surrounding air, at least one of the perforations should admit a fine hypodermic needle to inject an antimicrobial if necessary. Suture holes 36 can pass through suture that to allow full enclosure of the wound by port cap 43 wraps inward around baseplate 34.

Suture can be passed through each local suture hole independently or made to cross over a neighboring brace arm 38 and/or lines conduit 37 suspension brace arm 38. Some combination and overlap of these three suture patterns provides the most stable and secure fastening of the port down to the integument. To expedite eventual removal of the port if necessary, bonding of lines conduit 37 to lines 13 and 11 and any other lines to the same side-entry connection jacket together by means of cyanoacrylate cement is accomplished only after the operator correct has found the optimal length and is limited to the more outward portions of the interfaces where these are in contact with one another and the internal surface of lines conduit 37. This allows the port to be removed by crushing the lines and conduit closer to the skin with a pliers before cutting the suture used to attach the port to the body Where it passes through single small incision 39, lines-conduit 37 is coated to promote healing of the cut edges, hydrogen peroxide, povidone iodine, chlorhexidine gluconate, and hexachlorophene suitable antimicrobial agents. The binding of port components surrounding lines-conduit 37 is by compression cinching when port cap 43 is screwed down to baseplate 34. Incision 39 is completely enclosed by port cap 43 and can be protected by a small antiseptic soaked temporary dressing. How best to encourage the prompt healing of incision 39 by second or third intention depends upon its absolute size and is achieved by conventional means, to include the use of surgical cement. The central ends of lines-conduit 37 suspension brace arms 38 are bonded to the sides of lines-conduit 37 with an adhesive such as a cyanoacrylate cement.

Lines-conduit 37 made of polyether ether ketone (PEEK) or another implantable plastic binds together side-entry connector lines 13 and/or service channel lines 11 and extend through incision 39 into the internal cavity. Final fitting is least complicated when port, lines 11 and 13 encircled by lines-conduit 37, and jacket or jackets are preassembled and lines 11 and 13 and jacket or jackets are passed through incision 39 from the outside. Ports, lines, and jacket or jackets for common applications over a range of common sizes sold as preassembled are passed through the incision jacket first and moved into position endoscopically. As shown in FIG. 18, the proximal or outer end of lines-conduit 37 is encircled by port faceplate flange 40 having a downwardly expanding (inclined, beveled) outer edge complementary to the reversely inclined internal-side of the center hole in port cap 43 when port cap 43 has been removed.

Faceplate flange 40 is sufficiently elastic that screwing on port cap 43 progressively places the lines (catheters, tubes) it encircles under greater compression as a compression fitting. Screwing port cap 43 onto port base plate 34 thus seals off gauze compartment 45 from air and waterborne microbiota about the outer surface if the port, while cushion 35 provides antimicrobial sealing at the bottom or skin contact surface. To allow the length of the intrracorporeal lines to remain freely adjustable during placement, port 16, which includes lines conduit 37, must remain freely slidable along lines 13 and 11 until cinched by screwing down port cap 43. To this end, lines conduit 37 is permanently and strongly bonded only to baseplate 34.

Lines made of a material amenable to roughening surface deformation by mechanical abrasion or chemical etching, for example, are prepared for retention by compressive cinching thus. When the lines or catheters passed up through and bound to or fused with faceplate flange 40 are made of a low friction fluoropolymer, for example, the internal surfaces of these lines parallel to faceplate flange 40 have bonded along the internal surface thereof ferrules with a denticulated or serrated internal surface. Inelastic tubes or plugs for insertion into the open ends of the lines have bonded or fused about the outer surface a corresponding ferrule of complementary denticulations or serrations that mesh with the corresponding internal projections of the intracorporeal lines when these opposed surfaces are forced flush into apposition.

When the port is not in use, the entry of microbiota or debris into the port lines is prevented by inserting a rubbery plug to cover over the port top center opening, thus sealing the port off from the environment. This is done by partially unscrewing port cap 43 and inserting a rubbery plug with peglike projections that insert into the open end of each line. The back of the plug overextends and roofs over the top center opening of the port lines conduit 37. Screwing down port cap 43 then compresses port faceplate flange 40, cinching about each projection within its respective line. When fewer in number than the port lines, lines from a pump or syringe driver to be connected to the port pass through a hole in such a plug, which otherwise is the same as the rubbery plug just described.

When no line would be left open to the environment, multiple pump lines can each insert directly into their respective port line on a short-term basis; otherwise, the lines pass through a rubbery plug to seal the top center opening of port lines conduit 37. It being crucial for the delivery of medication that pump and port lines be correctly aligned, keying is imparted by making the port lines slightly different in internal diameter so that the pump lines will fit into the port lines only when correctly aligned. If necessary, differences in line caliber can be compensated for by adjustment in the delivery rate of the respective line pump in the pump-pack.

Separate insertion of the pump lines without a plug is discouraged not only for increased susceptibility to contamination but because joint insertion of pump lines in a plug improves correct alignment of pump and port lines, since keying is of the group, not each pump line, which may appear to fit the wrong port line when the diameters of the port lines differ only slightly. Since a rubbery plug with all line positions in use has no projection that would insert into a port line to become cinched about when port cap 43 is screwed down, means must be provided to ensure that the plug will be held down tightly to cover over and seal the top center opening of port lines conduit 37. This is accomplished simply by causing the plug to cling strongly to the pump lines by making the holes in the plug through which each pump line passes slightly smaller in diameter than its respective line.

Insertion of lines leading from a pump or syringe driver, for example, is by loosening port cap 43, removing the plug seal, inserting the pump lines and securely screwing down port cap 43. Since patients will differ considerably in thickness of subcutaneous fat and muscle, when sold as already assembled, lines-conduit 37 is provided with additional length and a tube cutter. When passed through incision 39, the distal jacket or jackets are closed but the protrusion of side-entry connectors and lines connected thereto will necessitate cautious angling of the jacket or jackets through incision 39. The outside wall of baseplate 34 is raised in height to provide an encircling thread 41 complement to thread 42 circling about the inside base end of port cap 43.

To expedite screwing it on and off, port cap 43, made of polyether ether ketone (PEEK) or another strong and lightweight plastic, is ribbed about the periphery, and screws down to baseplate 34 by engagement of thread 41 about the perimeter of baseplate 34 and thread 42 complementary thereto, running about the inner surface of port cap 43 along the bottom thereof. Shaped gauze pads 44 are easily replaced by the wearer, who need only unscrew port cap 43, press gauze pad 44 in gauze compartment 45 over faceplate 40, which retains it. To fill port cap 43 so as to reach down between lines conduit 37 suspension brace arms 38 to disinfect incision 39, gauze pads 44 are sufficiently thicker while uncompressed and preferably dispensed in individually wrapped hermetically sealed sterile plastic packages.

The pads are preferably dispensed having been wetted or permeated with antimicrobial and anti-inflammatory solutions and a healing promoting substance, such as a 20% solution of zinc oxide, as appropriate. Alternatively, the wearer wets the gauze with solutions from separate drip-top bottles. Provided medication is conveyed from the pump to the side-entry connection jacket in the form of a gel with adequate colligative strength or hardness, leakage out the proximal end of the line when disconnected should pose no problem. The use of a cabled device may necessitate clearing the line of medication or a neutral line filler in the form of a gel. This is most readily accomplished by using the water-jacket alone to drive the gel out of the line with the pressure of the backflow through the side-entry connection line.

The water pressure directed at the opening in the side of the ductus then restrains ductus lumen contents from leaking as it forces out the gel or liquid medication from the side-entry connection line. Since only continued water pressure restrains the ductus lumen contents, the opening must be sealed as soon as irrigation is stopped, usually by queuing an inert or medical gel in immediate succession to the water or by advancing a valve-plug with vanes fully open up against the opening and then closing the vanes. Alternatively, if not already present and so positioned, a valve-plug is inserted and positioned flush against the opening in the ductus. Resituating the valve-plug along the line is normally with the vanes open. To clear the line of proximal, or abaxial, gel to the pump side of the valve-plug, the vanes are shut and the valve-plug withdrawn to act as a plunger that expels the gel.

Along the vascular tree, water pressure is not applied with the valve-plug vanes closed when the medicinal gel is tenacious, since depending upon the relative magnitude of the water and blood pressure, the back-pressure could force water into the native lumen. In combined use of a valve-plug and water-jacket with or without heat to clear the line, provided no injury would result, the pressure from the water-jacket is allowed to force out the valve-plug as well as wash down the inside of the line, no guidewire then needed to retract the valve-plug. Resistance by the gel is reduced when the valve-plug or a resistance wire running along the inside of the side-entry connection line is used to warm the gel.

Combining water pressure, heat, and mechanical plunger action clear the line, leaving it free of a residue. The valve-plug, heated or unheated, can also be used first as a plunger, with the inside of the line thereafter washed down by the outflow from the water-jacket. A submersible pump-pack can continue to operate during bathing or swimming.

Installation consists of 1. Preparing the lines, usually before the jacket and lines are placed endoscopically or robotically; 2. Placement anatomically, that is, positioning the jacket about the ductus and finding the most favorable route for the lines from the jacket to the port to be positioned at the body surface; 3. Extraction of the tissue plug from the side of the ductus; and 4. Instituting postprocedural and ongoing main and sideline flow by the pumps under manual and/or microcontroller control. Port 16 must be situated for maximum comfort, convenience, and serviceability. This is usually in a higher pectoral location, requiring that lines 13 and 11 be tunneled from the body surface to the ductus. To assure quick identification, lines 13 and 11 are clearly marked and contrast coated.

The application depicted in FIG. 16, with one mainline 13 and one sideline, or water jacket and service channel 11, without additional sideline represents the simplest case condition for pump configuration and control. Where the prospective use is limited thus, the apparatus can be unitized. A line with a single jacket includes the jacket, intracorporeal and extracorporeal main and sidelines, the port where the external lines are plugged into the internal lines, and a pump-pair with one pump for each line, within a dedicated pump-pack that contains the battery and microcontroller. Such a unitized pump-pack would seldom if ever include pumps that would be switchable to serve more than one jacket mainline or sideline.

Where the prospective need should be flexible to allow for the addition of one or more jackets, the pump-pack is preferably of the pump-pair plug-in module receiving type that is not tied to or unitized with any particular type or number of pump-pair plug-in modules and not limited to a program that is less adaptable if not fixed. Instead, the pump-pack is a separate plug-in module pump-pair receiver with battery, controller, and program that adapts to a range of coordinated functions that might be required to support the different number of plug-in pump-pairs inserted in the pump-pack at any one time.

The use of pump-pair plug-in modules that include pumps provided with a switching turret as will be described to allow delivery through any jacket mainline or sideline of any in a number of jackets is more appropriate in such a more capable system. Within the constraints of patient comfort and freedom of movement, a wearable pump-pack can be configured to support a single jacket or a number of jackets, less frequently used pumps relegated to stationary or tabletop equipment in the home or clinic. Wearable pump microcontroller selection is based upon low power consumption for extended battery life and wearing time, consistent with programmability that allows the range and precision of operation required. In jacketing a vessel to depicted in FIG. 16, for example, each line terminates proximally or at the extracorporeal end passes through a separate pump toward it's.

The vials are mounted on a turret with detents rotated by a rotary solenoid. Before the operator has determined the most favorable route, setting the tunnel length requires that port 16 freely slide along the lines that pass through it, bonding of the port to the lines therefore deferred until after this length has been determined. Due to the need to minimize bleeding and avoid gas embolism, placement along the vascular tree under local anesthesia with the circulation uninterrupted is more demanding than is placement along a ureter or the gastrointestinal tract, where either can be temporarily anesthetized to suppress peristalsis, cross-clamped, and flushed clear of debris by irrigation through a fine hollow needle or hypotube.

If the ductus would collapse during circle-cutting to remove the tissue plug, the temporary placement of one cross-clamp upstream and another downstream to the prospective opening allows the intervening segment to be injected with a crushed tacky hydrogel, for example, so that it poses sufficient resistance to the side-entry connector during use as a circle-cutter or trephine to allow quick and clean excision of the plug. By contrast, in treating a vessel, especially a coronary or a carotid artery, endoscopically as will normally be the case, rather than in an open field, confirming that the lines are correctly primed will be critical.

While the use of transparent lines and side-entry connector allow direct viewing to expedite examination with a lit boroscope or endoscope, correct priming and making any adjustments if necessary is more readily accomplished before rather than after entry and routing. Regardless of the type ductus jacketed, the lines appurtenant of the same jacket will usually be routed together; however, where this would encroach upon neighboring tissue, the lines can be routed separately between the port and the jacket. Lines to move together are jointly ensheathed or cinched at intervals. To allow immediate identification whether viewed directly or imaged, each line must be clearly marked. Placement in an open field to treat the same or a different condition avoids the manipulative impediments of placement endoscopically. However, placement does not require an open field.

Endoscopic placement is through two small incisions, the first close to the prospective entry level along the ductus to be jacketed, the other for the port. If superficial, the routing can also be followed through palpation. When the overall distance from port to jacket necessitates, an intervening incision or two is made to route the jacket to the ductus. Provided the jacket has corners and edges rounded and passes through without abrading the port incision, the jacket with lines attached is passed through the port incision, led to, and placed to encircle the ductus. Once the operator is satisfied that the routing and tautness of lines 13 and 11 is optimal, port 16 is slid flush up against the skin, baseplate sutured in position, cement applied to bond the proximal segments of the lines 13 and 11 and other points to be fixed in position, and port-cap 43 screwed down, cinching together the components passed through faceplate 40.

The turret line switching means to be described can readily outstrip any legitimate need for complexity based upon evidence based medical benefit, and the use of the simplest and least costly effective embodiment is always to be preferred. While added complexity increases the chances for malfunction, the drug routing scheme using turrets to be described keeps all moving parts in the pump-pack outside the body, allowing expedited servicing. For patients with simple embodiments remote from a repair technician, redundancy is used to allow for safe failure. Because the pump and turrets are more susceptible to failure, two identical pump-pairs are worn in a double socket power and control housing able to support either at a time. If the risk warrants, then each pump-pair is provided with an independent power source and microcontroller.

Figure 31:
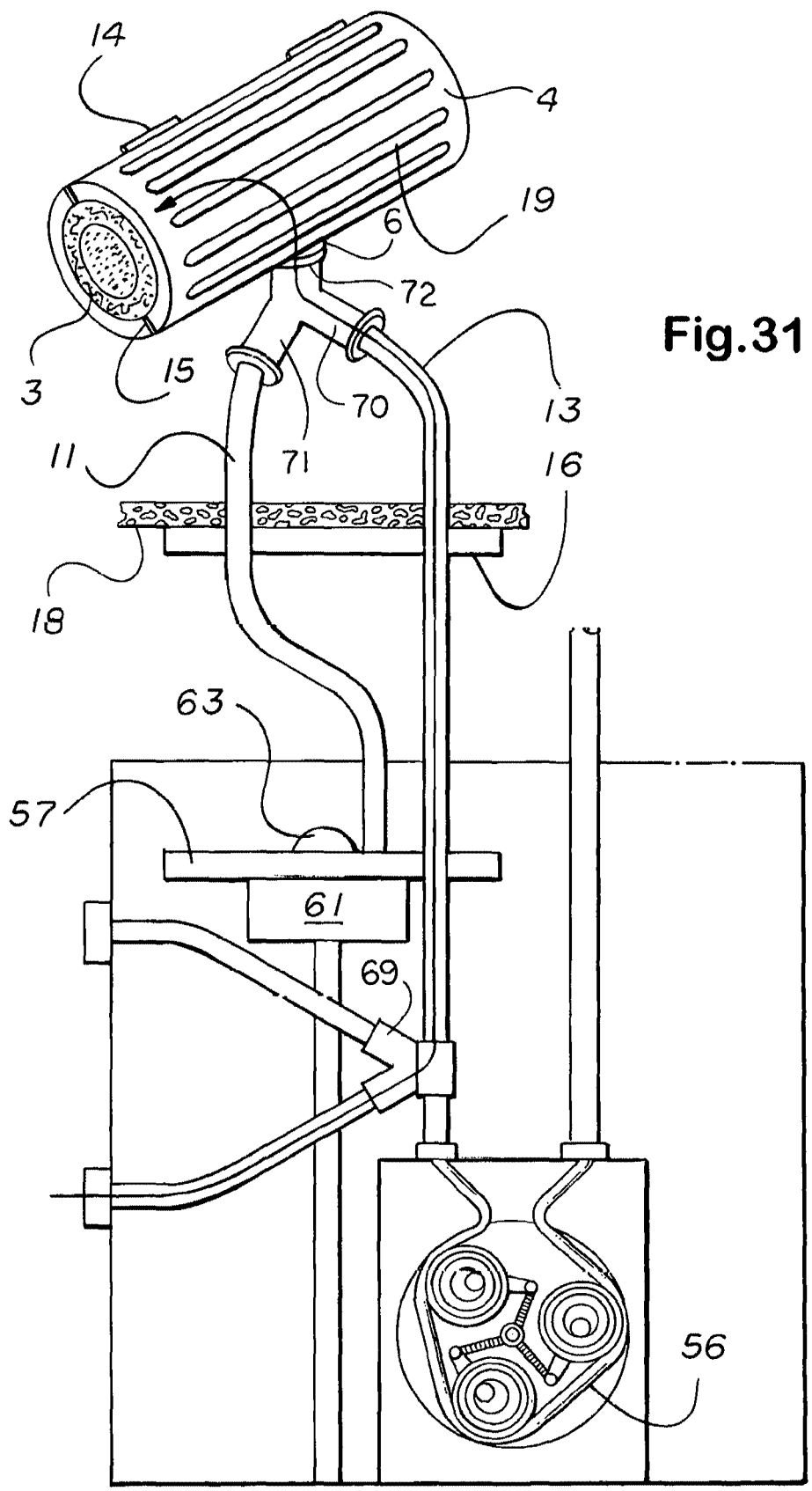
FIG. 31 shows a double-arm or forked type inline port connector or clean-out as shown in FIG. 30 placed along a pump-line inside the pump-pack for extracorporeal access that allows the insertion into the pump line of a cabled or catheteric device such as an aspiration catheter, guidewire, laser, intravascular ultrasound or ablation probe, or a fiber endoscope, for example, through the pump line in either direction, with a double-arm side-connector as shown in FIG. 7 at the jacket to allow insertion and passage through the lumen of the cabled device into the ductus in either direction, as well as for drug delivery purposes.
Figure 32:
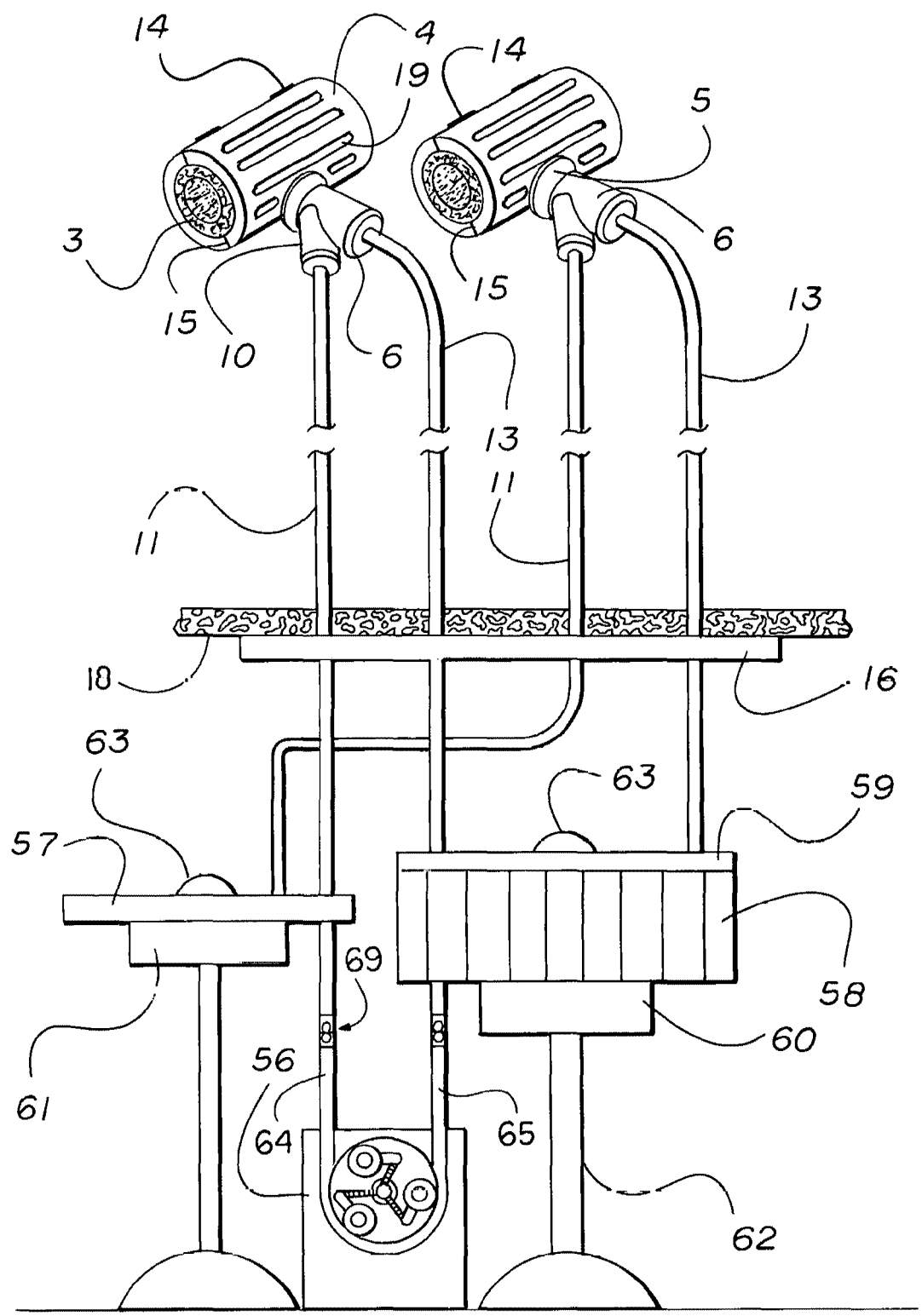
FIG. 32 shows right-hand pumps in a standardized pump-pair wherein line switching using turrets allows any drug or line rotated into alignment with the pump intake by the pump intake line switching means shown as a turret to be delivered through any one line rotated into alignment with the pump outlet by the pump outlet switching means also shown as a turret but without drug vials for simplicity.

Whether an automatic transfer switch is used depends upon the probability of consciousness during malfunction. Referring now to FIGS. 29, 31, and 32, the jackets in a set supplied from the same or either of two pumps, for example, might be placed at intervals along a single ductus or distributed to different ductus of the same or different systems, and may be interposed by jackets connected to another pump or pumps, this versatility facilitating the treatment of comorbid conditions. Unplugging one pump-pack at the port and immediately connecting another allows uninterrupted drug delivery during servicing. FIG. 29 shows a plug-in module pump-pair inserted in a single pump-pair power and control module that includes microcontroller 51, battery 52, and optional hydrogel auxiliary reservoir 54.

FIG. 29 assigns the right-hand pump of the pair to drug intake and the left-hand pump to pump output. The module also includes variable speed reversible peristaltic pump 46, shown as rotating clockwise and switched to side-connector 6 through mainline 13, reversible pump 47, shown as rotating counterclockwise through water-jacket line or sideline 11, a miniature armoured flexible 'gooseneck' or BX electrical type cable conduit protective sheath 48 enclosing mainline 13 and sideline 11 to protect these up to the port 16. This simplified view omits pump intake and outlet turrets to allow switching any drug to any jacket inlet.

Bidirectional Inline Port

FIG. 30 provides a detailed view of a bidirectional inline port fitting for insertion in a pump line to allow bidirectional entry into the line as a clean-out type inline port or cabled transcatheteric or transluminal device access point. This fitting can also incorporate a one-way valve to expel air from the line. As shown in FIG. 30, the integral connecting arms are usually male with a smooth bore and ribbed or convoluted outer surface to retain an elastic, hose passed over it. Whether the connecting arms are male with ends presenting internal ledges facing outward into a connecting hose or female with the reverse conformation depends upon whether the fitting is used to pass a fluid not delivered through a catheter, so that the ledge would accumulate material. The latter circumstance is responded to by using external or female connecting arms as shown in FIG. 31.

To prevent gouging or seizure (catching) of a guidewire or cabled device introduced into the line, the bidirectional clean-out type inline port fitting is made of a hard polymeric material such as polypropylene or nylon and formed to extend from the opening in the pump line to line the line as an annulus. The fitting is configured to steer the distal tip of the introduced device either up or down and through a slightly elliptical rather than true circular elastic slit membrane covering the opening or ostium into the pump line, the slightly ellipsoidal shape of the opening and membrane resulting from and varying with the angle of the intersection of the two inlet tubes. In manufacture, insertion of the fitting shown in FIG. 30 in a pump line, ordinarily proximal to a pump intake or outlet, is by sliding the line over a mandrel and applying a surrounding die that transects the line and cuts the complementary cutouts usually parabolic semicircular, in either free end.

The halves of the line are then pulled off of the mandrel and the free ends thereof slid over the top and bottom tubular extensions of the separately cast bidirectional clean-out type inline port fitting. The fitting and lines can be bonded together by fusion bonding, laser welding, ultrasonic welding, or by means of a suitable adhesive (see, for example, Zhou, Y. N. and Breyen, M. D. (eds.) 2013. *Joining and Assembly of Medical Materials and Devices*, Cambridge, England: Woodhead Publishing Ltd.; Ratner, B. D., Hoffman, A. S., Schoen, F. J., and Lemons, J. E. 2012. *Biomaterials Science: An Introduction to Materials in* Medicine, Waltham, Mass.: Elsevier-Academic Press). In FIGS. 29, 31, and 32, 69 are clean-out type inline ports which to prevent gouging and seizure of the extraction guidewire corkscrew tip or jamming at the nose end of cabled devices such as a fine endoscope or angioscope, necessitate that the material of the pump intake and outlet pipes or the segments thereof containing the clean-out type inline ports respective of each pipe be made of a hard and strong polymer such as polypropylene or nylon.

Shown in FIG. 32 is a pump intake switching turret to the right and a pump outlet turret to the left. The intake turret and parts used to connect the source of the drug or other substance to be delivered, such as a medicated flushing water or hydrogel, are shown in greater detail in FIGS. 33 thru 36. When too small to provide the volume of medication required, the standardized drug vial shown in FIGS. 33 thru 36 for insertion into a turret drug vial receptacle serves as the connector attached to the end of a hose from the drug reservoir for engagement in the turret. The vial also provides the initial dose of the drug or another drug preparatory to delivery of the primary drug. The arrangement shown in FIG. 29 is practicable but simplified for illustrative clarity.

A more usual and versatile arrangement is shown in FIG. 32, wherein one of the pumps in a pump-pair and jacket set is furnished with turrets at both its intake and outlet to allow any drug delivered through the intake turret to be sent to any jacket in the set. The two jackets represented in FIG. 32 as equal in size and distance from the pump might be placed along the same ductus, or ductus differing not only in size and/or distance from the pump but belonging to different bodily systems. This might, for example, consist of a jacket placed along the digestive tract and another placed about the artery that supplies that segment of the tract, or each jacket might treat different diseases related or coincidental. Flexibility and speed in reconnection of the lines to and from each pump are often significant when line switching must be reconfigured quickly as during installation.

While the pump-pack provides controls to override the switching arrangement controlled by the microcontroller in the even of a malfunction, the detailed disconnections and connections required to treat complex diseases and combinations thereof make automatic control responsive to sensor implants distinctly preferable if not essential for averting human error. Closed circuit recirculation with the arrangement shown in FIG. 29 necessitates connecting the pump intake and outlet lines. The circuit is completed by connecting the pump reservoirs together. The arrangement shown in FIG. 29 allows each pump to recirculate through a jacket via a closed circuit. While the jackets may vary in size according to the ductus each is to encircle, a pump-pair and jacket set unit can be standardized as to size, with the intake to either pump served from an infusate-switching source vial or hose, here depicted as a turret.

More complex arrangements, whereby the pumps are reversed as intake and outlet, intakes are interchangeable between a separate drug reservoir and the turret used to consecutively rotate vials of different drugs into the inline pumping position, the pump intake and outlet turrets of the same pump are functionally reversed, the outlet line of one pump is inserted into the intake turret of its partner pump or a pump in a different pump-pair, and so on, are avoided as exceeding practical needs and promoting human error. In FIG. 29, the drug on the right is stored in a reservoir so that more frequent and/or larger doses can be delivered, whereas that on the left must deliver its drug in small doses. The pump arrangement shown in FIG. 29 might be used, for example, to support the application shown in FIG. 16, wherein the side-entry connection jacket is used to form a simple junction without extension as a magnetized layer of increasing field strength in the antegrade direction to attract a superparamagnetic particle-bound drug radially outward through the lumen wall as a piped impasse jacket such as those shown in FIGS. 3 and 4.

Multiple drugs are then supplied to the pump by a switching means such as a turret, wherein the loading positions or sockets can accept a vial such as shown in FIG. 34, which can also be used as the connector to a hose leading to a reservoir. With respect to FIG. 31, when lines 13 and 11 have elastic slit membrane valves proximal to the pump intake and outlet; indexing the turrets as appropriate and reversing the direction of rotation of the pump allows the alternate delivery of medication through either line. Indicated as part number 48 in FIG. 29, the distance to port 16 once placed widely variable so that the pump and electrical lines would be exposed to the risk of damage from a snag or impact the longer these are, protective BX type conduit ensheathing guard 48, extending to port 16 protects the lines.

The length of the lines as sold having been entered into memory by the maker for the jacket placement process, the length of each line following placement must be manually entered to change the original values in memory. Here the pump-pack supports just one side-entry connection jacket with drug or wash water or flushing fluid reservoir 49 on the right-hand side to supply the inlet to mainline pump 46, rotating clockwise as shown, and sideline pump outlet or vial or refill cartridge holding turret 50 feeding the inlet of sideline pump 47, rotating counterclockwise. The intake to pump 46 is not limited to a static drug or wash water supply reservoir as shown in FIG. 29, but can include a supply turret containing circumferentially arranged compartments for inserting drug refill vials or for coupling inlet lines from other pumps or reservoirs internal, that is, intracorporeal, or external.

Neither is the drug radioactive as would require radiation shielding such as shown in FIG. 5. Mainline drug or wash water reservoir 49 and sideline drug reservoir, or if different drugs are to be delivered, turret feed 50, allow use of a microcontroller 51. Mainline pump 46, sideline pump 47, and microcontroller 51 draw power from battery 52. When supplementary or adjuvant drugs are likewise best targeted rather than taken orally, the drug reservoirs are replaced with a turret having sockets for holding drug vials or refill cartridges. In such a standardized jacket with support pump-pack unit, replacement of either reservoir with a turret necessitates sockets that will receive either a reservoir or a turret.

Since the unit must accept turrets so that the time and rate of feed can change with each indexing of the turret, the reservoir and turret sockets must include sensors and conductors for relaying vial or refill cartridge control or prescription data to microcontroller 51, and the program must respond to the data. While a basic standardized embodiment might call for changing drugs and adjusting controls mounted to the pump-pack by hand, this would not only negate the advantage or dependability conferred by automatic control but severely limit the range of use. Few disease conditions requiring but a single drug, and limitation to a single standard basic embodiment allowing the cost of production to be minimized, the standard basic unit includes reservoir-or-turret sockets with supporting sensors, conductors, processor, and program.

Successive refills can contain the same or different drugs, each turret indexed by actuation of opposing rotary solenoids or a quick response stepper motor. Different drugs may require adjustment in the speed of pumps 46 and 47, increasing the complexity of control, possibly necessitating a more capable microcontroller. Due to the prevalence and number of disorders such unitized embodiments can be used treat, the unit is suitable for production in different standardized sizes, significantly reducing costs. Further to reduce the cost, over a midrange of sizes, a single type embodiment with loosenable side-entry connector can serve both vascular and nonvascular application. At the lower end of the size range, the side-entry connector is not adjustable further reducing the cost.

At the high end of the size range, those nonvascular are provided with a side-entry connector that can be loosened to allow its use as a trephine. Standalone integral units made in different sizes may be adequate where little if any benefit would be gained from additional complexity and cost, typically, in the maintenance of conditions that are common but pose little threat of sudden decline or death. In a single pump-pair with the mainline pump connected to a single side-entry connector and the sideline pump connected only to the sideline or water-jacket connector, providing a turret at the intake to each pump allows the sequential delivery of any drug through the side-entry connector or its sideline inlet. The ability to direct the outflow from a given pump to different jackets, or line switching, is not required of a single pump-pair with single jacket unit.

Pump-packs for relatively simple applications to treat a stable condition generally support a pump-pair with two jackets and are self-constrained or integral, whereas more complex applications use one or more pump-pairs where each plugs in as a module into a pump-pack receiver. Although most lines connecting pumps and jackets will be small in caliber, the length of the lines may be considerably greater than that of a conventional automatic insulin pump, for example. For this reason, because much tacky gel may be required for jacket placement, especially when these are multiple, when each successive dose is dispersed through or separated by it, a filler substance is usually required to take up any drug-intervening spaces in the line. As shown in FIG. 29, this need is satisfied by connecting a large filler gel reservoir 54 at the bottom of the pump-pack to a pump intake line, usually through a flip flop or turret switching mechanism 53.

In FIG. 29, the hose leading from filler reservoir 54 to one of the intake pipe positions provided by the pump intake switching mechanism 53 is not shown as able to follow any of numerous paths. For use during placement of the jacket, drug reservoir switch 53 can also connect the intake of pump 46 to the outlet of pump 47 feeding into water-jacket line 11 and fill-gel reservoir 54. Similarly, the intake to pump 47 can be switched fill-gel reservoir 54. Filler reservoir 54 can also be used for storing ductus tissue opening irrigation and line flushing water. Portability not a factor in the clinic, the hose leading from pump-pack filler reservoir 54 can be disconnected at switching mechanism 53 for connection to stationary sources of hydrogel or water. Nominally indicated in FIG. 19 is control feedback sensor 55, typically for reporting blood gas levels or physiological parameters such as smooth muscle tension, many types and positioning possible.

For conditions that require treatment less simple than that depicted in FIG. 16, the pump-pair shown in FIG. 29 is increased in capability by incorporating a turret at the pump intake and/or outlet. As shown in FIG. 29, lines 11 and 13 are independent as to disallow recirculation through a closed circuit that must include both. Recirculation not only allows the periodic flushing through of lines automatically by the microcontroller 51 to remove residues, but as a part of or to expedite installation. To form a continuous loop and thus allow recirculation, the in-line drug vial or refill cartridge socket in turret 50 is connected by a pipe to drug or wash water reservoir 49. Admittance into the pipe is by a solenoid driven drop gate or swing-over obturator open/close valve under the control of microcontroller 51. Completion of the circuit by direct communication thus eliminates the greater complexity and expense of interconnecting lines 13 and 11 by means of in line switching valves.

Forming a closed circuit for flushing lines, for example, can be accomplished using both pumps in a pair as shown in FIG. 29 or a single pump as shown in FIG. 32. In FIG. 29, pumps 46 and 47 are configured for function as a coordinated pump-pair, pump 46 drug intake supply reservoir 46 and pump 47 outlet drug supply and line coupling turret 50 assigned not to both but rather to either pump in the pump-pair. In the arrangement depicted in FIG. 32, one of the pumps in a given pump-pair is used independently. The outlet of the other pump in the pump-pair could be plugged into the intake or outlet turret of the other pump; however, the need for such cross-feeding between pumps in a pair is exceptional. Cross-feeding to pumps belonging to other pump-pair and jacket sets is avoided as needlessly complicated as to invite errors.

The utility of pump outlet line switching between jackets is beneficial when, for example, a very small dose of a costly drug must be delivered to two or more jackets, and especially, when the consecutive time of delivery to each jacket is significant. Equally important is that the capability supports the development of new drug regimens, to include the automatic targeting of drugs to different parts of the body in strategically timed succession throughout the day, not previously amenable to practical implementation. In dual or double pump-pair embodiments, increasing the number of side-entry connectors and sidelines of each jacket to match the number of pump inputs eliminates the need to place a second line switching means. Such include a turret at a single side-entry connector or branching the main and sideline entering a side-entry connection jacket toward the pump outlets so that each of two drugs accordingly move through separate lines.

Whereas lines supporting side-entry connection jackets placed along the vascular tree or the urogenital tract are small enough in caliber that placement should seldom encroach upon neighboring tissue as to cause pain by compression of a nerve or vessel, jackets placed along the gastrointestinal tract or airway might do so. Where anatomical or operative considerations discourage the placement of multiple lines to access a given jacket, the input line to each jacket is provided with a conventional miniature piggyback port with valve. FIG. 32 shows one of the two pumps in a pump-pair with switching mechanisms at both the pump intake and outlet to allow the sequential delivery of any drug to the mainline or sideline of any jacket.

In FIG. 32, crushed tacky hydrogel, drugs, drug hydrogels, and/or wash water for separate consecutive delivery to different jackets are delivered from one of the pumps in a pump-pair through the lines 13 and 11 and side-entry connector 6 of either jacket. Pump outlet flow lines (arms, runs) 11 are connected at intervals about outflow indexing turret plate 57, and pump intake lines 13 are connected at intervals about turret drug vials and/or vials used as drug reservoir hose connectors to pump intake sectional tray consisting of sectional tray 58 and hold-down plate 59. Each turret rotates one inlet vial or line into the in-line position at the same time that it rotates the preceding line out of the in-line position. Lines 13 and 11 are given enough slack that these do not interfere with rotation of the turrets.

FIG. 32 depicts the side-entry connection jacket at the top left as currently connected to pump 56, pump to turret outlet line 64 indexed, or switched by turret 57 motor 61 to the inline position, with accessory or sideline 11 connected to water-jacket or accessory inlet 10 of that jacket. The lines of the jacket to the top right are not currently indexed to the pump inline positions and are therefore disconnected from pump 56. Pump 56 is continuously adjustable in speed and reversible, allowing outflow to and inflow from either jacket over the range of drug volumetric flow rates without the need to switch to lines of different caliber.

Pump 56 is usually one of a pair, one usually connected to the sideline, the other to the side-connector as shown in FIG. 29. When more than one pump-pair is present, the connection of these to either jacket is through lines connected to the turret respective of each jacket. Reciprocally, jackets not shown in FIG. 32 may communicate with pump 56. The foregoing degrees of flexibility attest to a potential versatility able to respond to extraordinarily complex medical conditions. Pump and jacket relations are ordinarily simple. As shown in FIG. 29, means of switching such as turrets may not be necessary. The simplest functional arrangement is always to be preferred.

To prevent air from entering the lines in vascular applications, turrets 57 and 59 omit blank vial positions that leave a line open-ended; rather, pumping is stopped once the amount of the infusate has passed when the hose can be disconnected. As shown, the left-hand turret lacks a vial and reservoir hose plug in table seen at 58 on the right, indicating that in this application, only the right-hand turret loads drug vials or receives medicated hydrogel or other therapeutic substance reservoir hoses. Were, however, drugs to be supplied from the turret to the left or a tacky medicinal hydrogel, for example, to be recirculated through the closed pump circuit with pump 56 when rotated clockwise, then the turret on the left would be of the same kind as that on the right. If to fill the line then stop or recirculate the gel, a reservoir hose as shown in FIG. 36 would supply the gel necessary to fill the line.

Recirculation may be used during placement and during the flushing of a series of jackets such as shown in FIG. 10 flushing, however, ended by running the accumulated flush fluid out of the system. In FIG. 32, to allow pump inline positioning of either jacket mainline 13 as well as any drug in drug vial turret 58, right-hand turret top-plate 59 to which jacket mainlines 13 are connected and drug vial turret 58 must be independently rotatable. As depicted, a single turret motor 60 is engageable with line rotating top plate 59 and drug vial turret at 58, a conventional latching or intromitting pawl mechanism internal to turret stile or mounting shaft 62 used to effect switching engagement. Alternatively, a second turret motor can be placed directly beneath motor 60. In this application, the drug supply turret has lines connected to it because drugs are recirculated through the closed circuit.

When turret 58 is to receive a drug reservoir hose as shown in FIG. 36, line connection top-plate 59 and turret 58 must move together, and line 13 to the left will then be rotated out of the pump line, preventing recirculation through the closed circuit to the left. Because a hose from or to a reservoir supplying a drug or other therapeutic substance as shown in FIG. 36 necessitates insertion through top or hold-down plate 59 and into a vial receptacle, the hose, top-plate, and receptacle must move together. Positioning a reservoir hose inline with a pump intake or outlet denies that position for a sideline 13 or mainline 11. Such conflicts are minimized by standardizing a dual pump or pump-pair configuration to include turrets at the intake and outlet of either pump thereby providing an additional path. The configuration of FIG. 32 is simplified to allow treatment of an uncomplicated condition at less expense.

This limits any lines 13 and 11 also inserted to a single turret drug position. Placement of a jacket requiring both recirculation and reservoir feed is therefore expedited by providing each pump with an intake and an outlet turret and recirculating through the one pump while feeding from a reservoir through the other pump. The elimination of topplate 59 eliminates the ability to reposition lines 13 and 11 in relation to the drug vials. Rotating pump 56 counterclockwise sends the inline drug in the right-hand turret through line 13 of whichever jacket has been rotated into the pump intake inline position. When pump 56 is rotated clockwise, the drug in the turret drug vial or hose receptacle to the right of FIG. 21 is drawn downward into pump 56 and pumped through sideline 11 of whichever jacket accessory or water jacket inlet 10 is connected thereto and rotated into the inline pump outlet position.

Pump reversibility can serve to avoid the need for a symmetrical turret and switching scheme, that even with only one pump would considerably increase the cost of the pump-pack and jacket set. Referring to FIGS. 32 and 36, the receptacles in turret 58 can each receive a vial containing a drug or other therapeutic substance. As depicted in FIGS. 33 thru 36, the larger of the two differently sized standardized vials 66 and 85 is also used as a connector or coupling to engage a hose led from a drug, drug gel, fill gel, or other therapeutic substance reservoir such as 49 or 54 in FIG. 29. Standardized vial 66 also provides an initial or preparatory dose, is therefore filled when removed from the sterile wrapping as dispensed, and to prevent the loss of contents, has slit membrane valves 67 and 68 to close off its upper and lower ends.

To prevent the loss of contents, membrane valves 67 and 68 remain closed except when forced open under pump pressure to allow the passage of contents therethrough. Connection to a reservoir is necessary, because an amount of the tacky gel used to quench bleeding immediately after the plug of tissue from the side of the ductus is extracted, or wash water, for example, is larger than fits into a vial. Line connection and drug refill insertion plate 59 has concentric openings that allow the insertion therethrough of drug vials into subjacent turret drug vial or reservoir loaded sectional tray 58 and are threaded or incorporate other conventional means for coupling or fastening the end of a fluid line from a fluid reservoir or another pump thereto.

The openings through connection and drug refill insertion plate 59 generally either connect a line from a remote reservoir or a different pump or contain a drug vial; for a pipe to flow through an interposed vial or reservoir of another drug in the sectional tray is exceptional. In FIG. 32, the turret to the right-hand or pump intake side includes upper line coupling or connection and drug refill insertion and hold-down plate 59, which to position any line connected thereto into the pump intake position in any sequence, must be capable of rotating both clockwise and counterclockwise.

At the same time, to rotate any drug vial or reservoir inserted within turret drug vial or reservoir loaded sectional tray 58 into the pump intake position in any sequence, turret drug vial or reservoir loaded sectional tray 58 must also be capable of rotating in either direction, and must do so independently of line connection and drug refill insertion plate 59. Independent rotator indexing of plate 59 and turret drug vial or reservoir loaded sectional tray 58 is accomplished through the use of separate direct current stepper motor 60, used to rotate line connection and drug vial turret sectional tray 58, used to rotate turret drug vial or reservoir holding sectional tray 58. In FIG. 32, drivers 60 and 61 are depicted as through-bore or direct drive-configured for visual clarity, the use of a gear train not disallowed.

Line connection and drug refill insertion plate 59 may be fastened to turret mounting shaft or stile 62 by pressing and so expanding the upper end of stile 62 into an end cap that retains and allows plate 59 and turret drug vial or reservoir holding sectional tray 58 to rotate freely and independently between it and motor 60 beneath it; however, use of a removable fastener such as a screw in cap or flange allows plate 59 and turret drug vial or reservoir holding sectional tray 58 to be replaced and therewith extending the sizes of the drug refills and lines that can be accommodated. However, most such apparatus is intended to treat chronic conditions that are generally stable over the long-term, so that this additional degree of flexibility exceeds most practical needs.

Ordinarily, when the side-entry connectors belong to different jackets, it is the pump nominally assigned to each jacket that would deliver the drug to either jacket. However, when this is the same drug and a number of drugs must be administered, relegation to one pump spares duplication of the drug in the turret position of the other pump allowing an additional drug to be loaded therein. Consecutive delivery from one pump to two side-entry connectors on the same jacket, delivery to either of the side-entry connectors on the same jacket from pumps respective of each side-entry connector, delivery from one pump to one or both side-entry connectors on a different jacket are equally possible.

With line switching, the distance from the pump outlet to the side-entry connector of each jacket must be manually entered into the controller one time. To segregate drugs that should not be mixed before arrival, a pump outlet turret can switch to different lines that deliver the drug to different side-entry connectors of the same jacket. For delivery from a single pump to multiple jackets where the mixing of drugs is insignificant, the line switching mechanism is used to successively deliver different drugs through the same line to the same side-entry connector and jacket. Line switching may be used to change the drugs successively delivered to a given jacket or to isolate drugs for delivery to the same jacket by directing each through a different delivery line and jacket entry point.

Placing additional jackets, and when the drug is bound to a drug-carrier, magnetized jackets, or impasse-jackets, and capsula-fastened patch-magnets at different locations in the body to coordinate the targeted receipt of drugs according to a timed sequence, for example, opens a new field for the development of coordinated drug strategies, those elucidated implementable in the form of standardized pump-pack and jacket package units. Even in a relatively simple embodiment such as that depicted in FIG. 6, drugs best not compounded to be targeted directly to the jacket can be kept apart for timed consecutive delivery under central control. This is done by replacing a singular fixed position pump inlet or entry line vial or refill cartridge receptacle with a turret feed mechanism to be described.

Also to isolate successive drugs, intervening boli of a drug compatible with those preceding and succeeding it in delivery or of an inert substance in the form of a crushed tacky hydrogel can be interposed to minimize if not eliminate premature mixing of the principle drugs as the result of delivery through the same line. A similar turret at the pump outlet would allow delivery to be switched to other jackets; however, for economy, the incorporation of a pump outlet turret in a single pump-pair and power and control module is generally limited to common conditions for which a benefit to be gained in synchronous delivery to different jackets is well established. Otherwise, the strategically timed delivery of multiple medications to multiple jackets is relegated to a pump-pair receiver pump-pack to be described.

Alternatively, the turret feed can direct the output of either pump in the pair through a second pair of main and sidelines to a second side-entry connector connected to the same jacket. The use of two or more side-entry connectors with a single jacket should seldom be needed and impedes placement. Rather than multiple side-entry connectors, it is preferable to position another jacket or jackets at small intervals along the ductus. The relation among jackets placed thus can be made clear by passage to the same port, although numerous lines leading to numerous jackets can be connected to the same port. That with a turret the outlet of either pump in a single pump-pair could be directed to any number of side-entry connectors on any number of side-entry connection jackets is obvious.

FIGS. 33 thru 36 provide a detailed view of the two differently sized standardized drug or other therapeutic substance vials 66 and 85 for insertion in a turret. Of the two, that larger, 85, is received in a turret receptacle or well which can also be used to insert a hose from a drug or other therapeutic supply reservoir in the pump-pack during ambulatory use or from another source in the clinic. To admit and discharge fluid, the smaller of the two standardized drug or other therapeutic substance vials, 66, has elastic membrane valve 86 with slits 87 at both its top and bottom. For use of the larger standardized sized vial 85 as the insert end of a drug reservoir inlet hose in a turret well or recess, one end of vial 86 has lip 67 to engage the end of hose 88.

Connection of lip 67 to the end of hose 88 is by secure friction fit, cutting engagement by slip-on or click-over engagement. Except for connecting lip 67, vial 85 is the same whether used alone or to serve as the turret end segment and connector of a drug reservoir hose for insertion into and secure connection to one of the vial receptacles or wells in the turret. In FIG. 36, QR matrix or conventional barcode 89 on the side of drug vial 66 identifying the drug or other therapeutic substance contained seen through a window cut through turret wall 90 makes it possible for an optical reader to detect any error in turret loading or insertion.

Ambulatory Adaptive Prosthetic Disorder Response System Control

Figure 38:
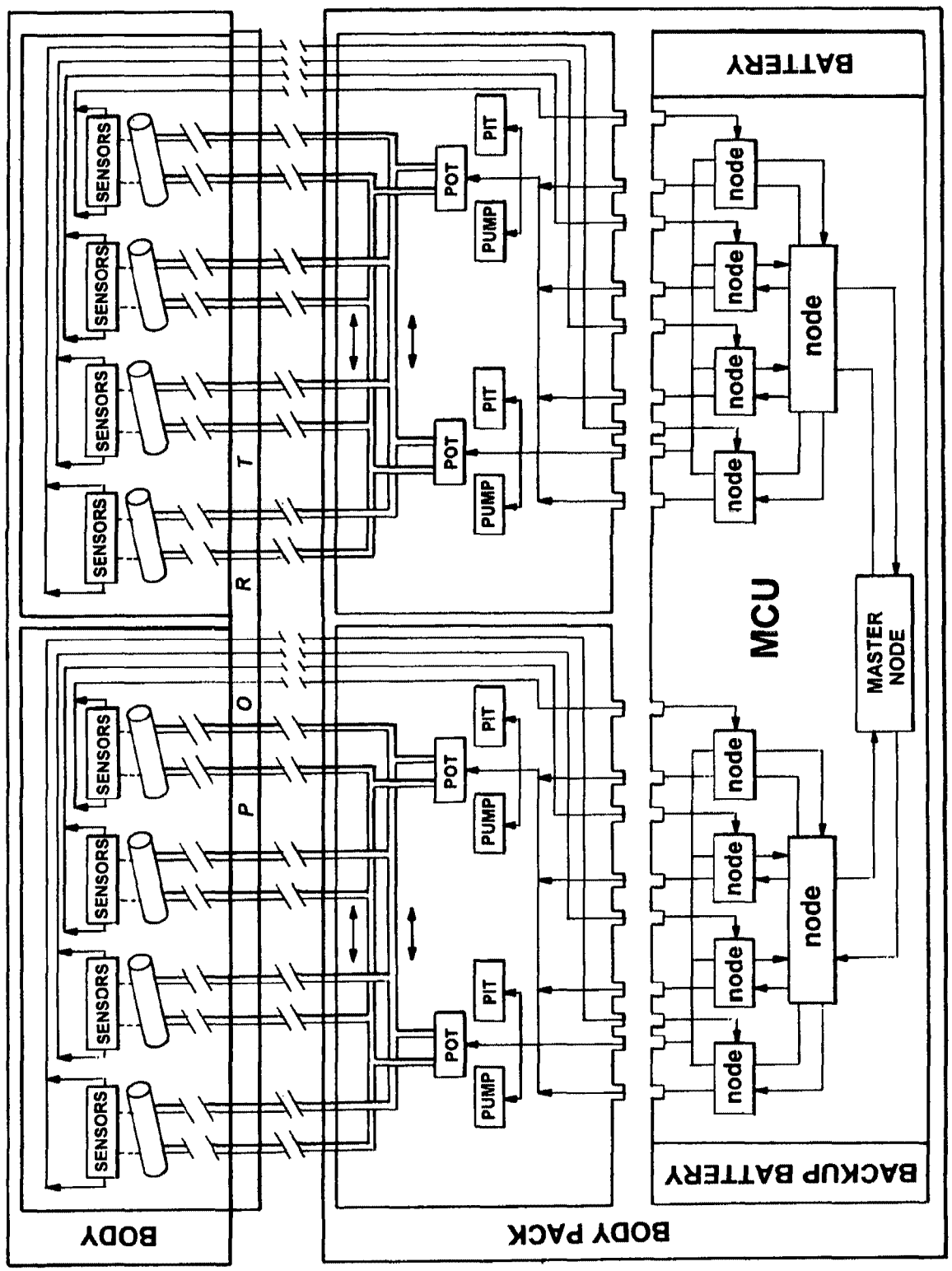
FIG. 38 is a simplified diagrammatic schematic diagram of the interconnections within a hierarchical control system and positioning as inside or outside the body when a second pump-pair and jacket set is added to the first in the pump-pack.

FIG. 37 provides a schematic of the control hierarchy for a single pump-pair in support of four jackets in the pump-pair and jacket set, the control program, that is, the prescription-program, of the master node, a microprocessor, determined by the specific or comorbid conditions to be treated. Nodes subordinate to the master node are generally microcontrollers. FIGS. 37 and 38 provide a schematic of the pump-pack, jacket set, and control system. Unlike FIG. 38, in FIG. 37, only the control train is represented, the distinction between intra and extracorporeal elements omitted. An extracorporeal pack affords considerably more space and can hold a larger volume of numerous drugs, other therapeutic agents, and equipment maintenance solutions. While shown as carried in a body pack, the control hierarchy is implantable with the impediment of a pack eliminated.

When implanted, the contents labelled body pack at the lower left in FIG. 38 are miniaturized; otherwise, FIG. 38 applies no less to a fully implanted as to a body pack carry system. Also when implanted, to preclude complications due to encroachment upon or strangulation of tissue by wires, data intercommunication from the sensors and subordinate nodes and control signals from the master node are preferably by wireless, or Bluetooth transmission. For pictorial clarity, where the electrical and fluid lines between nodes and jackets are actually separate and distinct, those between nodes and jackets are shown as consolidated until finally led to each jacket, and remote sensors and auxiliary drug supply reservoirs have been omitted. Electrical connectors, more remote sensors, drug supply reservoirs and outlet pumps controlled by the master node have been omitted.

If provided with the requisite switching and valving, the fluid and electrical lines shown as shared could support each jacket independently but not simultaneously, the utility thereof contingent upon the condition or conditions to be treated; simultaneous capability is accomplished by furnishing the components necessary. In FIGS. 37 and 38, single lines are electrical, or if it is found difficult to route the electrical lines without the risk of strangulating intervening structures, then connected by wireless Bluetooth transmission rendered selective by difference in carrier frequency. If virtually simultaneous operation cannot be achieved with a single carrier transmitter switching among the jackets, the microprocessor is provided with more than one transmitter.

The lines serve to independently energize the electromagnet or electromagnets in each jacket, implant, or pack-carried drug reservoir outlet pump, and/or return sensor data arriving from the jacket performance monitoring sensor or sensors to the node respective of that jacket. The double lines and pumps are fluidic and bidirectional. These electromagnets might be electromagnetic impasse-jackets, contraction-electromagnets, peristalsis contraction-electromagnets and/or extraction-electromagnets individual or dual as shown in FIG. 15 for high-volume extraction as in leukapheresis, as shown in FIG. 14, used in combination and coordinated for relatively high volume target analyte uptake.

The implanted system can usually hold the same number of agents but in smaller volume as will necessitate more frequent replenishment by injection through the body surface port. The lines could be shared, however, were the requisite switching and valving provided. The different jackets and biosensors can be placed along the same ductus, different ductus belonging to the same organ system, or ductus belonging to different organ systems. Each jacket may be of any type, whether a simple junction jacket with magnetization, such as shown in FIGS. 1 and 2, with magnetization, such as shown in FIGS. 3 and 4, or with magnetization and radiation shielding as shown in FIGS. 5 and 6.

With respect to FIGS. 10 thru 15, each jacket can incorporate one or more electromagnets rather than permanent magnets, where some jackets of the kind depicted in FIGS. 11 and 12 are used to draw magnetically susceptible particle-bound drugs into the diseased local lumen wall, while extraction electromagnet-jackets as shown in FIGS. 13 thru 15 are used to draw magnetically susceptible particle-bound leukocytes out of the passing blood through an elastic slit-valve such as that shown in FIG. 33. For intracorporeal cytapheresis, the same arrangement is used, except as in a conventional dialyzer without magnetic separation capability, the extraction transit window is generally a dialysate diffusion semipermeable membrane or a bundle of semipermeable membrane fibers.

To conserve energy by holding draw-plate 76 in FIGS. 11 and 12 in its last position with the electromagnet not on, a ratcheting mechanism to either side of perforated draw-plate (not shown in this nonprovisional application) is incorporated. An alternative spontaneously adaptive mechanism functions in a similar manner to an ordinary automotive radiator hose clamp, the ratcheting screw thereof turned by a small motor as governed by the values sent by the reflux sensor and other sensors to indicate to the microcontroller the appropriate sphincteric force of constriction. Unlike the marketed product, in this device, expansion and contraction of the surrounding ring is not divided among a plurality of adjacent magnetic cores.

At the same time, and under the control of the same master node, some jackets can meter flow through the digestive tract, for example, to include time-coordinated separate sphincteric and compound multiple contraction-electromagnet jackets such as shown in FIG. 10. When not requiring control coordinated with the automatic treatment of comorbid conditions, peristaltic and/or sphincteric electromagnet-jackets can be controlled at the local level as an independent standalone function by a timing module. A prosthetic lower esophageal sphincter with sensors positioned along the digestive tract to indicate the passage of a bolus, the need expel gas, vomit, gastric acidity, and microcontroller is not limited to the constant, nonadaptive force exerted by a permanent magnet-based prosthesis as currently used, and while even the current technology:

a: Affords an advantage (see, for example, Zhang, H., Dong, D., Liu, Z., He, S., Hu, L., and Lv, Y. 2016. "Revaluation of the Efficacy of Magnetic Sphincter Augmentation for Treating Gastroesophageal Reflux Disease," *Surgical Endoscopy* 30(9):3684-3690; Saino, G., Bonavina, L., Lipham, J. C., Dunn, D., and Ganz, R. A. 2015. "Magnetic Sphincter Augmentation for Gastroesophageal Reflux at 5 Years: Final Results of a Pilot Study Show Long-term Acid Reduction and Symptom Improvement," *Journal of Laparoendoscopic and Advanced Surgical Techniques. Part A.* 25(10): 787-792), b. Carries no power cost, and c. Poses fewer instances of postoperative bloating and an inability to belch and vomit than a traditional laparoscopic Nissen fundoplication, (see, for example, Chen, M. Y., Huang, D. Y., Wu, A., Zhu, Y. B., Zhu, H. P., Lin, L. M., and Cai, X. J. 2017. "Efficacy of Magnetic Sphincter Augmentation versus Nissen Fundoplication for Gastroesophageal Reflux Disease in Short Term: A Meta-Analysis," *Canadian Journal of Gastroenterology and Hepatology* 2017: 9596342; Reynolds, J. L., Zehetner, J., Nieh, A., Bildzukewicz, N., Sandhu, K., Katkhouda, N., and Lipham, J. C. 2016. "Charges, Outcomes, and Complications: A Comparison of Magnetic Sphincter Augmentation versus Laparoscopic Nissen Fundoplication for the Treatment of GERD," *Surgical Endoscopy* 30(8):3225-3230; Reynolds, J. L., Zehetner, J., Wu, P., Shah, S., Bildzukewicz, N., and Lipham, J. C. 2015. "Laparoscopic Magnetic Sphincter Augmentation vs Laparoscopic Nissen Fundoplication: A Matched-pair Analysis of 100 Patients," *Journal of the American College of Surgeons* 21(1):123-128), an adjustable sphincter is easily loosened independently of intrinsic motility before an artificial sphincter comprising magnetic cores of fixed magnetic strength spaced about a circular band would induce dysphagia, produce esophageal erosion, or actually migrate into the esophagus, and the permanent magnets pose more problems for magnetic resolnance imaging than would an electromagnet when off (see, for example, Salvador, R., Costantini, M., Capovilla, G., Polese, L., and Merigliano, S. 2017. "Esophageal Penetration of the Magnetic Sphincter Augmentation Device: History Repeats Itself," *Journal of Laparoendoscopic and Advanced Surgical Techniques. Part A.* 27(8):834-838; Asti, E., Siboni, S., Lazzari, V., Bonitta, G., Sironi, A., and Bonavina, L. 2017. "Removal of the Magnetic Sphincter Augmentation Device: Surgical Technique and Results of a Single-center Cohort Study," Annals of Surgery 265(5):941-945; Al-Mansour, M. R., Perry, K. A., and Hazey, J. W. 2017. "The Current Status of Magnetic Sphincter Augmentation in the Management of Gastroesophageal Reflux Disease," *Annals of Laparoscopic and Endoscopic Surgery September* 2017; 2:146, online at http://ales.amegroups.com/article/view/4136/4989; Bielefeldt, K. 2016. "Adverse Events after Implantation of a Magnetic Sphincter Augmentation Device for Gastroesophageal Reflux," *Clinical Gastroenterology and Hepatology* 14:1507-1512; Bauer, M., Meining, A., Kranzfelder, M., Jell, A., Schirren, R., and 3 others 2015. "Endoluminal Perforation of a Magnetic Antireflux Device," *Surgical Endoscopy* 29(12):3806-3810; Lieberman, T. 2015. "Heartburn Hell on the NBC Today Show: Omitting Things Consumers Might Want to Know about a $14K Device," online at https://www.healthnewsreview.org/2015/03/heartburn-hell-on-the-nbc-today-show-omitting-things-consumers-might-want-to-know-about-a-14k-device/).

As a standalone function, the microcontroller is implanted with the prosthetic sphincteric jacket shown in FIGS. 11 and 12, the prosthetic esophagus in FIGS. 10 thru 12, or the latter where the lowest of the jackets is controlled to serve as a prosthetic lower esophageal sphincter. If originally or later incorporated into a comprehensive system for the diagnosis and treatment of nondigestive comorbidity as well, the microcontroller of the digestive prosthesis is incorporated into the expanded system as a subordinate node of the master node microprocessor. If pertinent to the specific conditions—such as the inappropriate inducement of dysphagia, vomiting, or cramping responsive to chaotic brain function—the master node microprocessor then controls digestive motility in coordination with the comorbid condition in accordance with its prescription-program.

The addition of yet another subsystem or channel of control is best coordinated with digestive function is then governed by the master controller through another node. Where coordination with digestive function is not therapeutically pertinent, the digestive and nondigestive systems function independently. The addition of channels of control to cover one or more additional morbidities that appear after implantation is addressed above in the section entitled Background of the Invention. As indicated, when the esophagus, to include the lower esophageal sphincter, is device assisted or prosthesis replaced, both peristalsis and sphincteric function are controlled as a unit; that is, the most caudal or inferior in the sequence of sphincteric jackets is timed to function as a lower esophageal sphincter, while the jackets craniad or superior to it are controlled to contract at sequentially timed intervals to simulate peristalsis.

If other native sphincters to be coordinated with digestive function are dysfunctional, the sphincteric jackets placed to assist, or if missing, replace these are also controlled centrally by the master controller. Where, for example—as is true of the action of the lower esophageal sphincter in relation to esophageal peristalsis—the function of a sphincter or a jacket used to target drugs, for example, is to be coordinated with the others to optimize the overall physiological action, the individual jackets (depicted toward the top of FIGS. 37 and 38 just beneath the sensors) and drug reservoir outlet pumps are controlled in a unified and coordinated manner by the master node microprocessor in accordance with its prescription-program. Such action is calculated to optimize overall bodily function across the combination of comorbidities for the congenital or postsurgical patient anatomy presented.

Chain-Jackets for Ambulatory Automatic Cytapheresis or Hemodialysis

Chained double-arm magnetic separation jackets suitable for use in an intracorporeal cytaperesis or hemodialysis system are shown in FIGS. 13 thru 15, and flush-line straight through magnetic separation jackets 91, conformed for maximum compactness to allow use in small patients is shown in FIG. 39A. A basic double-arm ductus side-entry jacket is shown in FIG. 7 without an electromagnet interpositioned between the arms. When assembled into a chain, the individual magnets generally do not require a water jacket or followup use thereof as accessory channels, the two inlet arms usually able to support the same functions. Chain magnetic separation, or extraction, jackets are modified ductus side-entry jackets and are placed along the substrate vessel as explained above for basic side-entry jackets such as that shown in FIG. 1 except that the arms can be used in lieu of a water jacket and thereafter drugs added to the dialysate or apheretic fluid. Where targeting to distinct segments along the substrate ductus is sought, accessory channels can, however, be incorporated into the jackets as addressed below.

Thus, not shown in these simplified schematic representations, the chain extraction jackets shown in FIGS. 13 thru 15 and 39A have a razor sharp trepan at the leading edge of the side connector, an aspiration pump connected to a water jacket 7 used to create the opening into the ductus, and the water jacket line 11 used to prevent extravasation during placement thereafter serves as an accessory channel 11. These means minimize if not eliminate any leakage of blood. Double-arm jackets such as that shown in FIG. 7 are inserted thus as well; however, chained double-arm magnetic separation jackets such as shown in FIG. 39A can be placed by applying the aspiration pump to one of the outlet arms 70 and 71.

Exceptionally, depending upon a need to single out a given jacket or segment of the substrate vessel along a chain, magnetic separation jackets are provided with an accessory channel. In FIG. 39A, the plane of section through magnets 74 omits foam lining 3 on the magnet side, foam lining 3 to the near and far sides of the bisecting plane through the magnets 74. Foam lining 3 is essential to avoid compression of the fine nerves and vessels at the surface, or adventitia, of the substrate vessel, here, the inferior vena cava, as such compression would initiate a cascade of atheromatous degredation. In chained double-arm magnetic separation jackets, described above, flush-line 79 does not course through the jacket as in a flush-line straight through magnetic separation jacket, allowing use of a dialysate flush-line 79 larger in caliber, hence, in dialysate capacity.

While manual double-volume whole blood exchange is preferable to conventional automated leukapheresis for leukoreduction in infants and children weighing less than 22 pounds (see, for example, Runco, D. V., Josephson, C. D., Raikar, S. S., Goldsmith, K. C., Lew, G., Pauly, M., and Fasano, R. M. 2018. "Hyperleukocytosis in Infant Acute Leukemia: A role for Manual Exchange Transfusion for Leukoreduction," *Transfusion* 58(5):1149-1156; Creutzig, U., Rossig, C., Dworzak, M., Stary, J., von Stackelberg, A., and 3 others 2016. "Exchange Transfusion and Leukapheresis in Pediatric Patients with AML [acute myeloid leukemia] with High Risk of Early Death by Bleeding and Leukostasis," *Pediatric Blood and Cancer* 63(4):640-645), this is not true of hemodialysis.

Moreover, as addressed above in the section entitled Background of the Invention, extraction of the objectionable analyte or analytes directly from the blood, plasma exchange with a replacement fluid is uninvolved, eliminating the risks, mainly cardiovascular, associated with conventional hemodialysis. Pending the availability of a donor kidney, for example, dialysis—not frequent or continuous whole blood transfusion—is clearly indicated for the treatment of end-stage renal disease regardless of age (see, for example, Levy Erez, D., Krause, I., Dagan, A., Cleper, R., Falush, Y., and Davidovits, M. 2016. "Impact of Pediatric Chronic Dialysis on Long-term Patient Outcome: Single Center Study," *International Journal of Nephrology* 2016:2132387; Feinstein, S., Rinat, C., Becker-Cohen, R., Ben-Shalom, E., Schwartz, S. B., and Frishberg, Y. 2008. "The Outcome of Chronic Dialysis in Infants and Toddlers—Advantages and Drawbacks of Haemodialysis," *Nephrology, Dialysis, Transplantation* 23(4):1336-1345).

Referring now to FIG. 14 showing double-arm chain extraction, or magnetic separation, jackets, the path taken by flush-line 79 is devised to maximize the turbulence and washing force across the face of magnet pole 75. Magnet pole 75 is positioned just behind a one-way elastic slit-valve 81 for cytapheresis and a semipermeable membrane or multiple semipermeable fibers in this schematic representation also designated part number 81 as in a conventional dialyzer for dialysis. The recess between the arms shown in FIG. 7 provides a space to mount a larger and more powerful electromagnet than in flush-line straight through magnetic separation jackets as shown in FIG. 39A, wherein magnets 74 are incorporated into jacket housing 91. FIG. 15 shows a double sided double-arm magnetic separation jacket for more intensive application in an adult.

FIG. 39A shows magnetic separation chain jackets 91 along continuous loop circuit flush-line 79 containing dialysate for intracorporeal hemodialysis, or normal saline, plasma, or water for intracorporeal cytapheresis applied to a substrate vein, shown here as the inferior vena cava, in a patient with surgically intact urinary system. As indicated, for dialysis, part number 81 in the diffusion transit window is a semipermeable membrane or assemblage of semipermeable fibers, while for apheresis, part number 81 is a one-way elastic slit-valve. A basic ductus side-entry jacket with main and sideline connected to a port at the body surface for the delivery of medicinals directly into the inferior vena cava is positioned above the level of the drawing.

Thus, the side-entry jacket positioned above (craniad, superior to) the extraction circuit is available to deliver agents into the substrate ductus, here the interior vena cava, and the accessory channel 11 of each magnetic separation or extraction jacket can deliver an agent, typically a debris solvent or cleaning agent, at the magnetic poles 75. As will all ductus side-entry jackets, jackets in a chain each retain the water jacket accessory channel, or sideline 11 used to connect these to the substrate ductus with minimal if any leakage. In most instances, however, the jacket with main and one or more sidelines craniad to the chain is sufficient for the delivery of drugs and other agents into the vein, and the lead jacket, or that superior to the others, is also available for this purpose. In a chain-jacket, accessory channels 11 are more often used to deliver a solvent where the extract resists being washed away from the magnet pole 75 by flush-line 79.

Peristaltic pump 56 recirculates the dialysate or other fluid past through the flush-line which passes between successive magnet poles 75 and diffusion or valve windows 81, the implanted microprocessor effecting the washing away of any debris adherent to poles 75 at intervals by stopping the pulsing action of magnets 74 and accelerating pump 56 according to a flush timing cycle. Any residual debris observed sonographically at an occasional visit to the clinic to check the operation of the system is dissolved with a solvent introduced through port 16.

FIG. 39B provides a detailed view of the connection between the magnetic separation circuit and the bladder 92, into which the debris is discarded for expulsion in the urine, accomplished by reversing the extraction relation so that debris which had been drawn into flush-line 79 by chain jackets 91 is now drawn into bladder 92 by electromagnet jacket 93 positioned near to the bladder neck 94 on the inferolateral surface of bladder 92. Bladder 92 is shown in a partially filled, semiflaccid or collapsed state. Continued filling of bladder 92 progressively reduces the distance between diffusion membrane or cytapheresis slit-valve 94 in the side of flush-line 79 and a ringed, or framed, about window of complementary shape in bladder 92.

Continued expansion upward of bladder 92 therefore compresses pliant accordion tubing 95 connected to the edges of the two windows as a surround thus darning them about throughout the distance traveled, that is the excursion or throw, from maximum separation with bladder 92 empty to flush apposite relation with bladder 92 full. Depending upon the amount of debris, magnet 93 is used in either of two ways. If the debris is sparse, then patients with a normal urinary system seldom if ever voiding the moment urge sensation is felt, contact between flush-line and bladder transit window ring or frame surrounds persists and sends a signal to the implant microprocessor to energize magnet 93 over a few cycles, or circuits of the flush fluid through flush-line 79. The replacement of the fluid in the flush-line is addressed above in the section entitled Background to the Invention.

Figure 43:
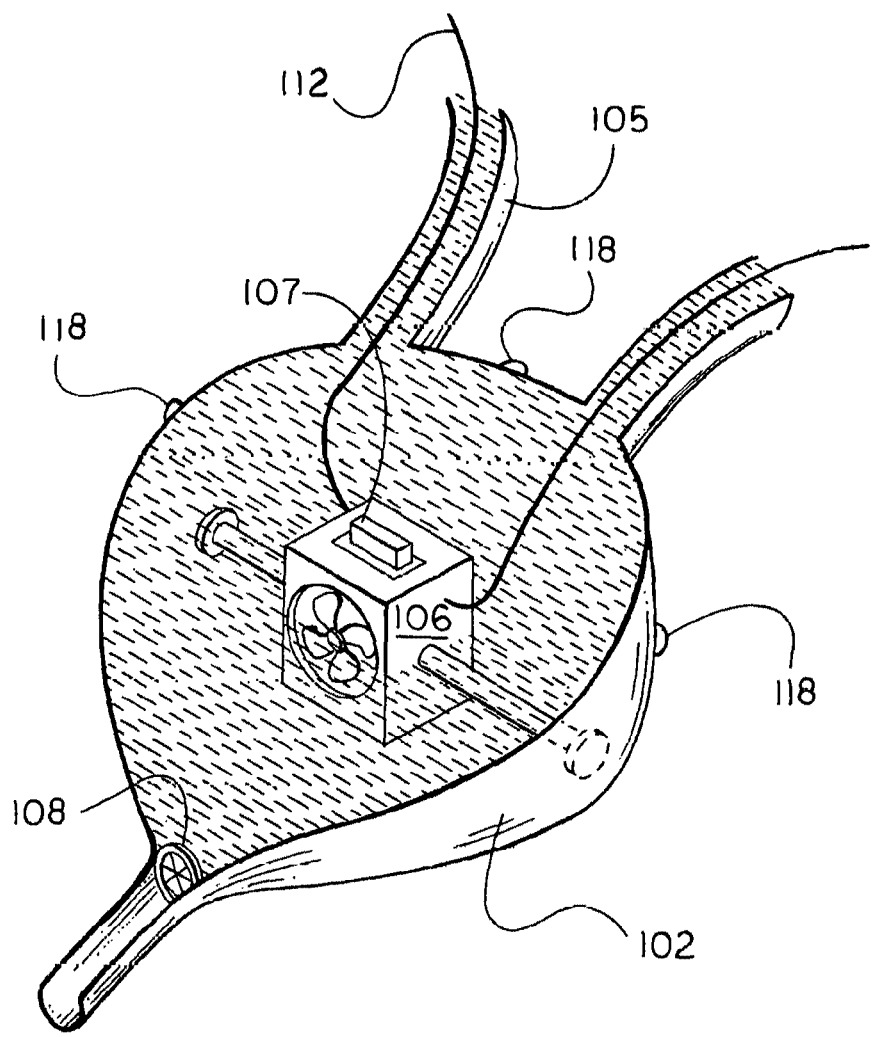
FIG. 43 is a perspective view of the confluence and expulsion chamber shown in FIG. 40 to facilitate evacuation when the patient is recumbent.
Figures 44A, 44B:
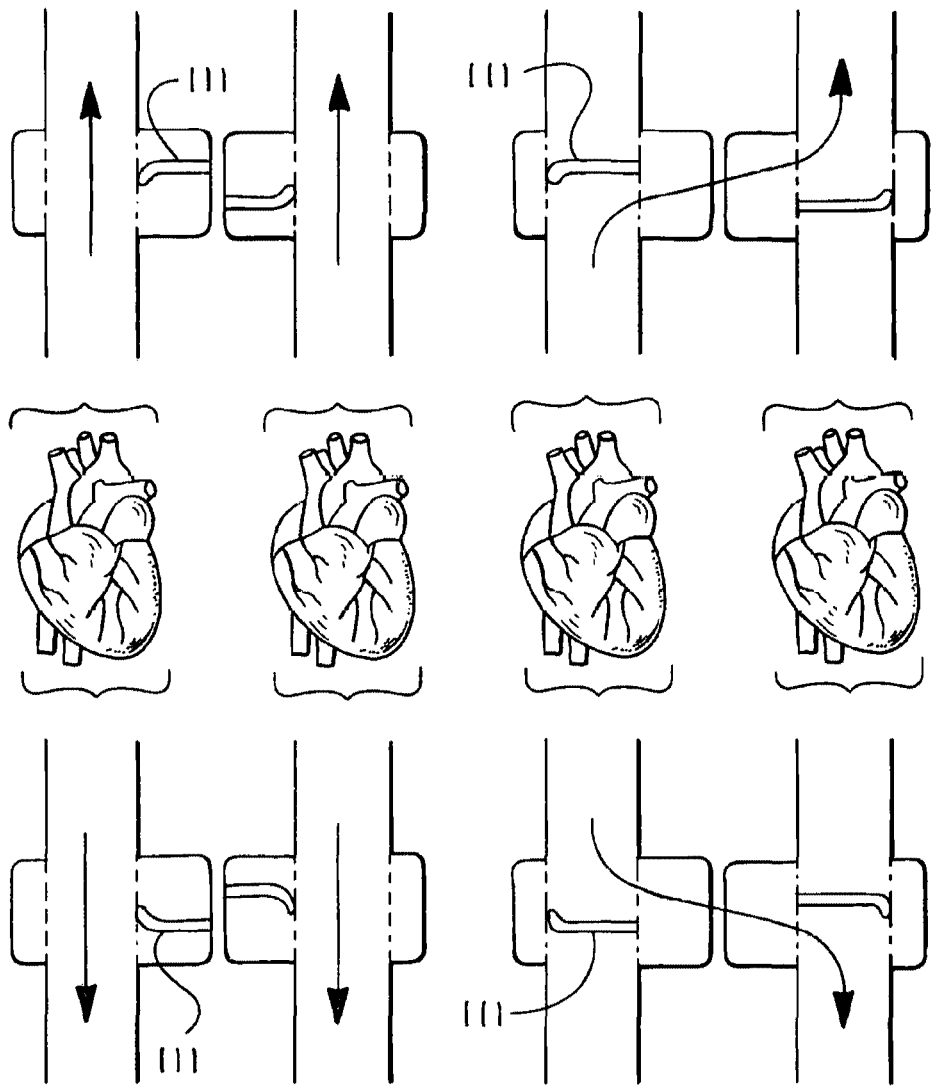
FIG. 44A shows the arrangement in continuous perfusion/zero ischemic time sudden switch solid organ heart transplantation of intravascular diversion valves used to divert the circulation of the recipient to the donor organ before the valves are switched to incorporate the donor heart into the circulatory system of the recipient.
FIG. 44B shows the arrangement in continuous perfusion/zero ischemic time sudden switch solid organ heart transplantation of intravascular diversion valves used to divert the circulation of the recipient to the donor organ after the valves have been switched to incorporate the donor heart into the circulatory system of the recipient at which time the defective native heart is removed.

If the debris is considerable, then the implant microprocessor energizes the solvent reservoir outlet pump to release solvent through the accessory channel 11 of each magnet 74 to assist flush-line 79 in washing away any accumulation of debris, and magnet 93 is periodically energized over a longer interval for higher amplitude field strength pulsing to pull the debris through window 94 and the window in bladder 92 into bladder 92 to include times when bladder 92 is not full. When the patient has been cystectomized, the same arrangement is applied to neoureteral 105 confluence chamber 102 in FIGS. 40 and 43. As shown in FIG. 43, bending of strain gauge 107 in neoureteral 105 confluence chamber 102 causes impeller 106 to empty chamber 102 through one-way elastic slit-valve 108 into collection bag 101 automatically. Patients who have had their entire urinary system removed due to malignancy leaving them fully dependent upon dialysis pending a kidney transplant use a comparable system wherein the debris is drawn into a chamber flushed clean when the fluid is replaced.

Manually Operated Ductus Side-Entry Jacket Intravascular Diversion Valves

Intravascular valves and servovalves comprise numerous embodiments and applications. Manually adjusted valves are of two types—those used in a prosthesis set once by the operative surgeon upon placement to divert urine or blood on a permanent basis, and those which provide a patient with push-pull or Bowden cable knob controls on the body surface port to adjust the valves as desired from fully retracted to allow normal voiding to fully extended to allow diversion into a collection bag. Of these manually adjusted embodiments, only that simplest, that adjusted once for use in a prosthesis, is described here. Such a valve is shown in FIGS. 41 and 42.

Valves equipped with a Bowden cable allow a patient with nocturia (with arousal) or nocturnal enuresis (without arousal), for example, to switch from nondiversion of flow and normal elimination during the day to the direct diversion of urine from the ureters into a collection bag during the night, or a public performer with frequent urination to switch to bag collection when before an audience. Other such valves are used for vascular surgical procedures which necessitate uninterrupted bloodflow, hence, exactly simultaneous advancement into the substrate native lumen of the diversion chute. For this purpose, these valves incorporate a plunger solenoid or a tiny piston which the operator controls from a common switch.

Other valves used for medical management are precisely adjustable microminiature linear motor-based servovalves with built in linear encoder used to control the flow or the diversion of blood among different vessels, mostly to adjust the local blood pressure. Of these various types of ductus side-entry intravascular valves and servovalves, only that manually set once by the operator upon placement as a prosthesis is described here. Use permanently in a prosthesis is made possible by the noncompressive lining in all ductus side-entry jackets and by accessory channels to mollify if not eliminate adverse reactions at the jacket and satisfy a need for agents to maintain the jacket in optimal working condition.

Figure 41:
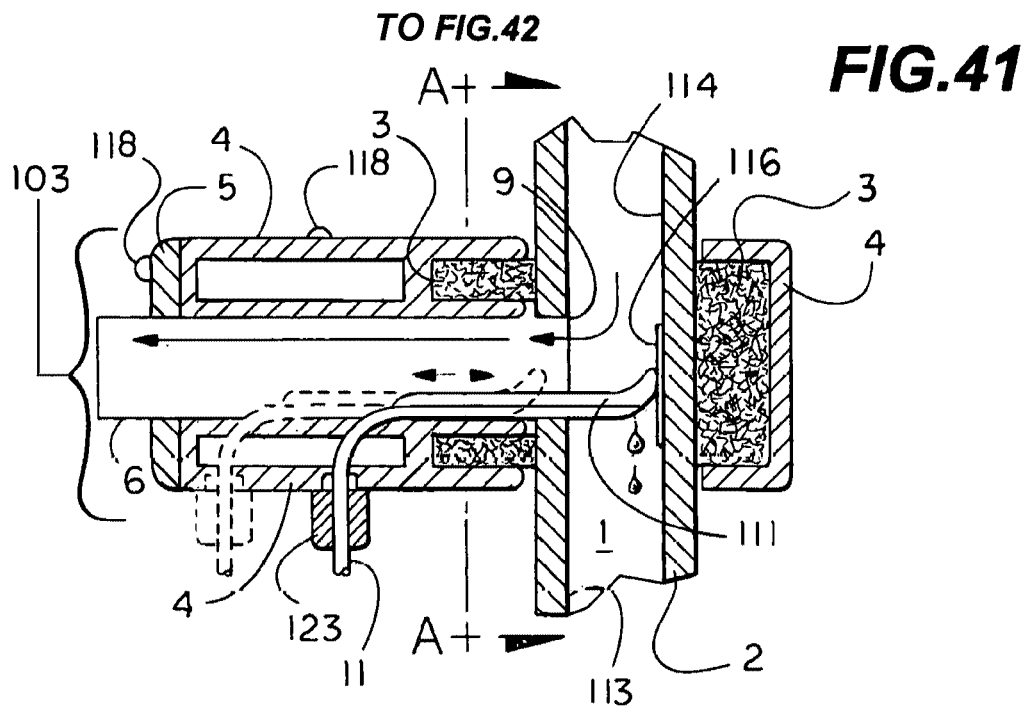
FIG. 41 is a longitudinal section through the nonadjustable intravascular valve shown to the left in FIG. 39.
Figure 42:
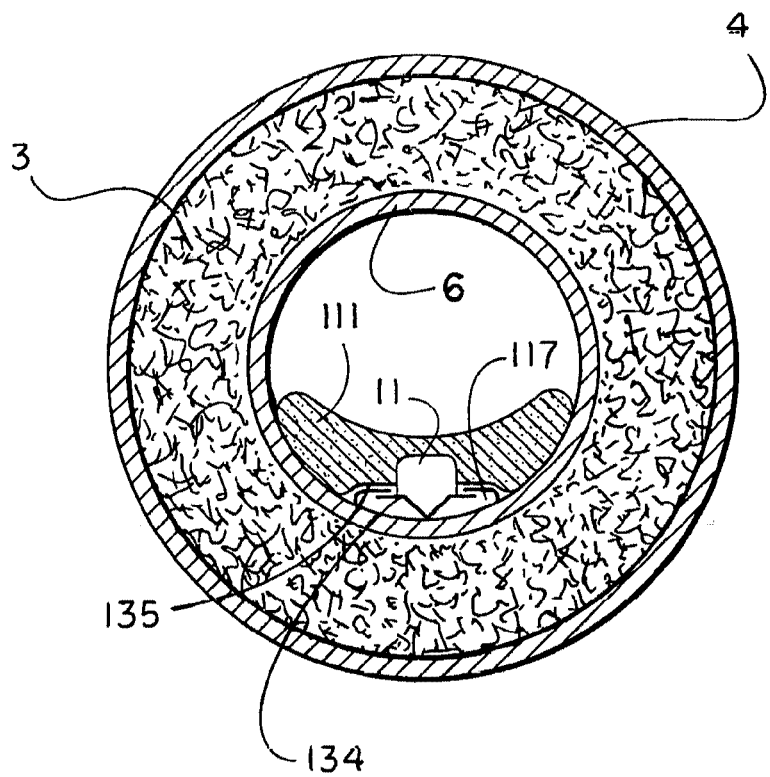
FIG. 42 is a cross section along line A-A' through the nonadjustable intravascular valve shown to the left in FIG. 39.

FIG. 40 provides an overall or plan view of the invention in a nonadjustable embodiment suitable for use as a permanent prosthesis in a patient with an irreversible congenital or traumatic condition of the lower or distal urinary tract, and FIG. 41 is a detailed longitudinal section through the valve shown on the right hand side of FIG. 40. The urine outlet opening in surface port 16 also serves incurrent use to directly target medication, agents to maintain the jacket and line, and to insert cabled devices for therapy and diagnosis.

Intravascular valve diversion jackets 103 divert urine from ureter 104 into neoureter 105 which flows into confluence chamber 102. In FIG. 41, foam 3, unlike in the jackets shown in FIGS. 1 thru 7 10, 13 thru 15, 17 thru 19, 21, 22, 29, 31, 32, and 39A extends out the end of the valve shell 4 rather than lines shell 4 to be completely enclosed. Therefore to prevent protrusion or even contact of shell 4 edges into the substrate encircled ductus—here, a ureter— foam 3 is made to extend past the edges of shell 4, the edges of shell 4 rounded off.

In FIG. 41, part number 113 is the near and 114 the opposing urothelial surface of the substrate right ureter lumen 1. Intravascular valves ductus side-entry jackets modified to incorporate a diversion chute, the part numbers shown in FIG. 41 pertaining to the basic jacket are the same as those shown in FIG. 1 thru 6, the other part numbers defined below Exceptionally, in an intravascular valve, accessory channel 11 for the direct targeting to the jacket site of drugs and other therapeutic substances runs along the bottom center of chute 111.

Not shown for clarity in FIG. 41, ostium obturator 116, co-molded with and therefore integral as unitary with chute 111, is elastic as to comply with the conformation allowed by containment within the jacket sidestem, or side connector 6, and unfolds as soon as trepan leading edge 9 cut the ostium into the substrate ductus, thus serving in lieu of a water jacket to restrain luminal contents, typically, urine or blood, from flowing out through the space overlying chute 111 in the sidestem. Then, when the interventionist or surgical operator advances accessory channel collar 123 to extend chute 111 into lumen 1 along track or slideway 117, obturator 116 is applied flush against urothelium or endothelium 114 on the side of the lumen 1 opposite sidestem 6, creating an unobstructed diversion path for urine or blood to flow over the chute and out the sidestem.

As shown in FIG. 43, confluence chamber 102 contains impeller 106 with strain gauge 107. Filling of confluence chamber 102 causes strain gauge 107 to energize impeller 106 to expel the contents into collection bag 101 regardless whether the patient is asleep or otherwise recumbent. Outlet of confluence chamber 102 is obturated, (blocked, closed off) by one-way elastic slit-valve 108 which yields to the pressure applied by impeller 106 to release the urine into confluence chamber outlet line 109 for outflow through body surface port 16. In FIG. 43, part numbers 112 are the conductors that provide current to impeller 106 and conduct the control signal from strain gauge 107.

Where corrective surgery is contemplated, must be deferred to a later date, or has been accomplished, the embodiment is also suitable for use as a temporary means of diversion away from the affected or operated region, whether unilateral or bilateral. The lower tract dysfunctional or missing, such an embodiment requires an outlet at the body surface to allow drainage into a conventional collection bag 101. In FIG. 40, body surface port 16 is positioned to a side of the mons pubis where it is clearly within view of the patient to remove collection bag 101 for washing, and if applicable, to self-inject medication. The surface of the mons pubis where port 16 is to be placed is electrologically, or electrolytically, treated to permanently remove hair in this area for at least a quarter inch around port 16.

Surface port 16 is shown as cutaneous (above-skin, epidermal) with all openings open to the outside when protective spring-cap covers 110 such as those used to prevent debris from entering machine lubrication points. Use of a cutaneous port allows an outflow opening for emptying of confluence chamber 102, insertion by the clinician of cabled devices such as an angioscope to examine the interior of diversion valves 103, the confluence chamber 102, the lines connecting these, and for the injection of drugs. In this application, outflow line 109 and its opening in port 16 is the mainline and drug injection openings with lines these enter are the sidelines, that is, the accessory, or service, channels. Injection of drugs through port 16 channels these through accessory channels 11 which course craniad (upwards) through line 11 and into diversion jacket 103, where entry into ureteral lumen 1 is by transit of the drug centrally lengthwise along the bottom of diversion chute 111.

Since a cabled device such as an angrioscope inserted through the mainline through the center opening in port 16 allows examination of not only the interior of confluence chamber 102 but of valves 103, surface port can be of the combination cutaneous-subcutaneous type, the drug injection openings positioned subcutaneously with small dots tattooed on the skin to identify the injection points. This allows the clinician to obtain a direct interior view of the apparatus and upper or proximal tract (ureteroscopy, ureteropyeloscopy) by extraurethral entry, as well as to inject drugs or other agents into the apparatus and proximal tract to directly treat an infection, remove crystal, a biofilm, or to obtain a biopsy test sample.

Providing at least one entry portal to one accessory channel (service channel, sideline), the surface port, an integral component of the invention to be described, also allows medication and device maintenance agents, reagents, and reactants to be directly targeted to the side-entry jacket and line, and cabled devices such as scopes and lasers to be passed up through the line to the jacket and beyond. This allows the clinician to obtain a direct interior view of the apparatus and upper or proximal tract (ureteroscopy, ureteropyeloscopy) by extraurethral entry, as well as to inject drugs or other agents into the apparatus and proximal tract to directly treat an infection, dissolve crystal, a biofilm, or to obtain a biopsy test sample.

Unless the ureter distal to the jacket is missing, the surface port additionally incorporates a subdermal or superdermal opening into an accessory or service channel which provides a direct passageway into the distal tract for implant maintenance, diagnosis, and therapy. FIG. 41 provides a detailed view of a fixed or nonadjustable diversionary side-entry jacket suitable for use as a prosthesis. The jacket differs from a simple junction jacket as described in copending application Ser. No. 14/121,365 in incorporating a chute to divert the flow of blood or urine, thus enabling the creation of fluid shunts and bypasses using synthetic tubing, even small in caliber, without the need to harvest or divert a native ductus such as a vein.

Whereas in an intermittent use embodiment as described in the section to follow, the chute is deployable and retractable as desired, in a prosthesis, the chute is fixed in position. This is possible because an accessory channel directly to the jacket and line allows the direct targeting of antimicrobials, when blood is diverted, anticoagulants, and/or crystal encrustation counteractants without which smaller catheters and synthetic tube materials invariably become fouled and/ or occluded. The integral drug delivery accessory channel continues toward the ureteral lumen through a groove running centrally along the underside and extending to the distal tip of the chute, allowing medication to be dripped into the ureter.

FIG. 42 provides a detailed cross sectional view of the diversion chute through mainline end-piece 6 with trepan cutting edge 9 along line A-A.' in FIG. 41. In a nonadjustable embodiment, or prosthesis, urinary diversion chute 111 is never retracted to allow urine to continue through the lower tract. The design of the side-entry diversion jacket shown allows the diversion chute to be advanced into the lumen inside the trepan piece from outside and behind the circular foam and jacket shell, thus eliminating the need for a slot to allow the chute to pass through the foam and shell. The moisture barrier-protected foam enveloping the adventitia (outer surface) of the ureter is thus continuous entirely about the trepan, reducing the importance and cost to achieve the precision essential to provide a leak free slide and slot through which to pass the chute.

While an adjustable embodiment, as addressed in the section to follow, must continue to be controlled remotely after placement, with a nonadjustable embodiment, advancement of the diversion chute is necessary only at the time of placement when the operator has direct access to the treatment site. At the front end of the chute is a side-entry hole obturator essential to prevent incurrent flow, or inflow, into the mainline as the drainage line leading from the trepan to the port connection for the hose to collection bag. To allow the trepan end-piece sufficient cross sectional area to withdraw the tissue plug on placement without presenting any projections into this area on which the plug removed might catch, the side-entry hole obturator must take the form of a restraint/release/deployment-initiation device, that is, the obturator must be folded as to be compact as possible, and self-deploy by unfolding upon having entered and freed to expand within the ureteral lumen.

To self-deploy, or self-unfold, the obturator is preferably molded round and to bias its motional response pattern for quickly yielding to any force applied to it from either side, that is perpendicularly to its flat surfaces. Referring to FIG.

41, when placed, obturator 116, to act as a stopper for preventing backflow past chute 111 when fully retracted, is larger in diameter than the opening made in the ductus. To not injure the opening, diversion chute 111 yields with little if any resistance to accommodative flexion when pushed through the opening whereupon it assumes its unflexed round shape. When advanced to the opposing surface, obturator 111 assumes the complementary convexity to accommodate the concavity or the surface 114 in FIG. 41 without resistance.

Chute 111 and obturator 116 are preferably made unitized, or molded in one piece, of a tough elastic material such as PEBAX® (Arkema, Colombes, Frane), VESTAMID E (Evonik Industries, Essen, Germany) nonbiodegradable polyether block amide thermoplastic elastomer, or if the patient is not allergic to it, hypoallergenic guayule, natural or synthetic rubber latex, or a similar rubbery polymer of medical grade. This material, which must be implantable and unaffected by contact with urine, meets the stringent test of implantability within the eye (see, for example, Sohn, S. W., Noh, M. D., Lee, J. H., Kim, K. N., Kim, C. S., and Ahn, B. H. 2016. "Performance of and Pressure Elevation Formed by Small-diameter Microtubes Used in Constant-flow Sets," *Korean Journal of Ophthalmology* (3):225-233).

Other materials suitable for the chute with integral obturator include elastic nonbiodegradable silicones and polyurethanes (see, for example, Chen, Y., Kim, Y. S., Tillman, B. W., Yeo, W. H., and Chun, Y. 2018. "Advances in Materials for Recent Low-profile Implantable Bioelectronics," *Materials* (Basel, Switzerland) 11(4). pii: E522; Vallejo-Heligon, S. G., Brown, N. L., Reichert, W. M., and Klitzman, B. 2016. "Porous, Dexamethasone-loaded Polyurethane Coatings Extend Performance Window of Implantable Glucose Sensors in Vivo" *Acta Biomaterialia* 30:106-115; Brisbois, E. J., Major, T. C., Goudie, M. J., Bartlett, R. H., Meyerhoff, M. E., and Handa, H. 2016. "Improved Hemocompatibility of Silicone Rubber Extracorporeal Tubing via Solvent Swelling-impregnation of S-nitroso-N-acetylpenicillamine (SNAP) and Evaluation in Rabbit Thrombogenicity Model," *Acta Biomaterialia* 37:111-119; Debelle, A., Hermans, L., Bosquet, M., Dehaeck, S., Lonys, L., and 3 others 2016. "Soft Encapsulation of Flexible Electrical Stimulation Implant: Challenges and Innovations," *European Journal of Translational Myology* 26(4): 6298; Lonys, L., Vanhoestenberghe, A., Julémont, N., Godet, S., Delplancke, M. P., Mathys, P., and Nonclercq, A. 2015. "Silicone Rubber Encapsulation for an Endoscopically Implantable Gastrostimulator," *Medical and Biological Engineering and Computing* 53(4):319-329; Yang, J., Charif, A. C., Puskas, J. E., Phillips, H., Shanahan, K. J., and 7 others 2015. "Biocompatibility Evaluation of a Thermoplastic Rubber for Wireless Telemetric Intracranial Pressure Sensor Coating," *Journal of the Mechanical Behavior of Biomedical Materials* 45:83-89).

Alernatively, chute 111 and obturator 116 can be molded in one piece of a shape-memory polymer (see, for example, Zhao, Q., Zou, W., Luo, Y., and Xie, T. 2016. "Shape Memory Polymer Network with Thermally Distinct Elasticity and Plasticity," *Science Advances* 2(1):e1501297; Hoffman, A. S. 2013. "Stimuli-responsive Polymers: Biomedical Applications and Challenges for Clinical Translation," *Advanced Drug Delivery Reviews* 65(1):10-16; Serrano, M. C. and Ameer, G. A. 2012. "Recent Insights into the Biomedical Applications of Shape-memory Polymers," *Macromolecular Bioscience* 12(9):1156-1171; Lendlein, A., Behl, M., Hiebl, B., and Wischke, C. 2010. "Shape-memory Polymers as a Technology Platform for Biomedical Applications," *Expert Review of Medical Devices* 7(3):357-379; Sokolowski, W., Metcalf, A., Hayashi, S., Yahia, L., and Raymond, J. 2007. "Medical Applications of Shape Memory Polymers." *Biomedical Materials* (Bristol, England) 2(1): S23-527; Yakacki, C. M., Shandas, R., Lanning, C., Rech, B., Eckstein, A., and Gall, K. 2007. "Unconstrained Recovery Characterization of Shape-memory Polymer Networks for Cardiovascular Applications," *Biomaterials* 28(14): 2255-2263; Mohr, R., Kratz, K., Weigel, T., Lucka-Gabor, M., Moneke, M., and Lendlein, A. 2006. "Initiation of Shape-memory Effect by Inductive Heating of Magnetic Nanoparticles in Thermoplastic Polymers," *Proceedings of the National Academy of Sciences of the United States of America* 103(10):3540-3545; Lendlein, A. and Kelch, S. 2002. "Shape-Memory Polymers," Angewandte Chemie International Edition 41(12):2034-2057).

The polymer is soft enough in the elastic state that should it become necessary to remove the diversion device in the absence of a chilling means that would cause it to compact, or fold, the obturator can simply be pulled through the side-entry hole and out into the trepan 9 adluminal edge of sidestem, or side-connector 6 with little if any injury to the margin of the side-entry hole. That the trepan is slightly recessed from the luminal border of the side-entry hole reduces any damage to the obturator if any. Upon placement, the diversion jacket, hence, the obturator is at room temperature, or more likely in terms of the shape state changing temperature differential attained to date, pre-chilled, keeping it in the compact rigid state, and when brought to body temperature, unfolds, or deploys, becoming soft and pliant.

While hypothetically, it always diverts urine away from the lower tract, so that a nonadjustable embodiment requires no side-entry hole obturator, backflow through the space over chute 111 of any matter in the ureter is prevented by it and although unlikely, a potential source of infection prevented. Once placed in an adjustable embodiment as opposed to a prosthesis in which its position is fixed, the obturator moves between two positions, in either of which it complies in curvature to the luminal wall. Rotating the control knob in the surface port retracts the obturator so that it covers over the side-entry hole, sealing off the diversion route limiting the flow of urine to the lower tract, while rotating the knob in the opposite direction advances the obturator against the urothelium opposite the side-entry hole.

While installed with the obturator chilled, should it become necessary to remove the device, recovery to the compact relatively rigid state is unnecessary, because at body temperature, the obturator is sufficiently elastic to be pulled out through the side-entry hole with little if any injury to the ureter. Should preliminary testing reveal that notwithstanding the measures incorporated to prevent such, extended positioning of the obturator in flush relation to the urothelium at either side would provoke an adverse tissue reaction, the accessory channel is used to deliver a counteractant with release from a second jacket positioned above the diversion jacket with the release of medication automated it necessary. The automatic release of drugs from subdermally positioned small flat reservoirs is addressed in copending application Ser. Nos. 14/121,365 and 14/998,495. Closure of the hole following repair and/or healing of the lower tract and permanent removal is addressed above.

In FIGS. 41 and 42, diversion chute 111 comprises a tongue, generally 2.0 millimeters in width and 2.0 millimeters in length when pressed flat, slightly scooped or dished out on the dorsal surface, made of a suitable polymer such as polyether block amide or one sufficiently plasticized to impart a soft rubbery or spongy character where if not phthalate free, any plasticizer residue is removed. Materials for chute 111 are specified above in this section and in the section above entitled Background of the Invention. When advanced into the ureteral lumen, the distal, or adluminal, tip and sides of chute 111 conform to the internal contour thereof, the tip riding up along the walls of the lumen in flush contact as to fully separate, or obturate, the ductus above from that below chute 111.

Running along the bottom center of chute 111 is the continuation of the capillary tube like diametered portion of accessory channel 11 through which drugs and apparatus maintenance agents can be delivered into the urinary tract situated below the chute; agents to be delivered craniad to the chute delivered through a ductus side-entry jacket or refluxed up lumen 1 by delivery through the sidestem, or side-connector, 6. Chute 111 with accessory channel 11 coursing centrally along its bottom travel along raceway or slideway comprised of horizontal extensions or wings that ride within guide restraints that assure smooth and properly aligned movement.

Continuing with FIGS. 41 and 42, over the segment of the proximal groove past the tubular or abluminal portion of accessory channel 11 and extending toward the ureteral lumen 1 or distal to the level half way into the ureteral lumen with the chute deployed, the groove is lined with length of thin inverted V stock stainless steel with a horizontal side wing to either side produced by bending the V stock (beneath accessory channel 11 in FIG. 42) longitudinally along its length with a miniature press brake or draw press.

Referring to FIG. 42, the underside of diversion chute 111 is bonded to a highly slippery ceramic, polymeric gear-grade nylon, or slippery fluoropolymer such as polyfluorotetraethylene underlayer or coating 135 and rides stiffly forward and backward in rectilinear motion upon and along V-stock track 134 along the bottom sides of accessory channel 11. The complementary configurations of the underside of diversion chute 111 and V-stock track 134 comprising an alignment track, that is, a raceway, or slideway.

In addition to smooth and properly aligned advancement of chute 111—in this application into the ureteral lumen rather than into a vessel—the track stiffly maintains chute 111 along a straight line for entry into lumen 1, preventing any deviation such as a downward prolapse into the ureter as would result in a leak. Extension with positive engagement of chute 111 in lumen 1 is maintained and signaled by an audible click when a small detent elevation beneath chute 111 snaps into a complementary depression at the point of full deployment. As indicated by the arrows in FIG. 41, trepan 9 and diversion chute 111 can be moved back and forth together or separately. Shown in FIGS. 1 thru 7, 13 thru 15, 17 thru 20, 22, 23, 29, 32, and 41, to cut the opening or fenestra into the ureter, trepan 9 is moved forward with the chute retracted as shown.

As distal terminus of the mainline 6, trepan 9 is manipulated by loosening lock nut 5, freeing trepan 9 to be reciprocated or rotated while an aspiration pump draws the substrate ductus wall 2 past trepan 9 to cut a tissue plug from the substrate ductus, thus creating an opening or ostium in substrate ductus wall 2 into which mainline 6 is then positioned, creating a leak-free continuum between native lumen 1 and mainline 6 lumen. Once the opening has been cut, trepan 9 is retracted into alignment with the proximal urothelial surface, lock nut 5 used to fix trepan 9 leading edge in position, and chute 111 deployed.

To prevent jamming or sticking of the urine diversion chute 111 when deployed after the jacket has been positioned, the segment at the distal end of sidestem, or side connector 6 with trepan distal edge 9 is made of low friction fluoropolymeric tubing, such as polyfluorotetraethylene. Accessory channel or sideline small gauge catheter 11 is made of a polymer such as polytetrafluoroethylene in a thickness as will bend only so much as to allow the operator to advance the diversion chute into the ureteric lumen. If urging by edge of the entry hole to the side removed from the ureter at the bottom of the jacket is insufficient to guide the accessory channel tube forward, a small curved quarter round guide is bonded to that edge to assure smooth and properly aligned movement of the service channel tube through the entry hole.

Sideways bendability of this material is, however, sufficient as not to interfere with any slight rotation or reciprocation of the trepan the operator may need to create the opening into the ureter. If necessary despite the use of an aspiration, or suction, pump as described above in the section entitled Background to the Invention, the mainline with trepan 9 at its distal terminus can therefore be rotated from side to side to facilitate cutting the opening into the native lumen, then locked in position. Accessory channel 11 is otherwise made of a conventional catheter synthetic. Chute 111 is initially positioned to the rear of mainline 6 and moved forward into the native lumen 1 by pushing sliding accessory channel collar 123 on accessory channel 11 forward.

Because the segment of the accessory channel preceding the diversion chute has been made flexible to assist manipulation of the mainline, advancement of chute 111 into ureteral lumen 1 commences once this segment has been compacted. Visualization is unnecessary, full deployment signaled to the operator by an audible click as well as the resistance of the chute to further extension. Sliding and rotary movement of accessory channel 11 into the jacket is facilitated by accessory channel 11 sliding accessory channel collar 123 made of a hard and slippery gear-grade nylon. Once the opening has been cut, the trepan is retracted and the chute advanced to fully close off the native lumen with a surface inclined and concave as to divert urine into the jacket mainline and out into the collection bag.

Full advancement of chute 111 is signaled to the operator by an audible click when sliding tiny detent (not shown) beneath chute 111 passes over stationary detent (not shown). Extended (deployed, advanced), the chute extends 2.0 or more millimeters into ureteral lumen 1, which should be slightly more than luminal 1 diameter; however, made of a soft rubbery material and placed in apposition or abutment against a native surface itself compliant, the chute seals off the ureteral lumen 1 beneath from that above. As addressed above, the free end of the ureter in a prosthesis is completely sealed, eliminating the entry of urine in the irregular space beneath the chute.

In an adjustable embodiment the simple longitudinal movement provided by a push/pull control cable offsets the greater cost of achieving the degree of precision needed to prevent leaking by replacing the need to reproduce the complex manipulation of the operator. The chute in a prosthesis is fixed in deployed position and therefore omits the push/pull control cables seen in the plan view of an intermittent embodiment. Snug apposition against the surrounding lumen wall is achieved without the need for precise adjustment during placement by making the chute of a highly pliant thin soft rubbery material having a feathered surrounding edge molded with a slight upturn.

The surrounding edge of the chute, feathered to a thin perimeter that fully seals off chute 111 from ureteral stump 115, therefore continues to bend upward in compliance with minimal resistance posed by the surrounding lumen wall, and fanned obturator 116, which serves to close off the mainline side stem diversion path when chute 111 is retracted, is pressed into shape conformity with the surface of the urothelium at the distal end of chute 111. Uroperitoneum, or urinary peritonitis, a medical emergency, it is vital that the thinned or feathered out rubbery outer edge of chute 111 and obturator 116 be flawlessly bonded together, have great durability, and be able to provide leak-free performance indefinitely, the more so since a very slight seepage is likely to continue with the patient eventually experiencing increasing abdominal and suprapubic pain, vomiting, anuria, hematuria, and a lack of alertness, until diagnosed and stopped.

The untreated leakage of urine into the pelvic cavity leads first to systemic inflammatory response syndrome, which left unrepaired, leads to multiple organ dysfunction syndrome, which if not stopped, results in sepsis, renal failure, hyperkalemia, cardiovascular shock, intensified organ dysfunction, and immune suppression with little hope of survival (Kogan, M. I., Naboka, Y. L., Ibishev, K. S., Gudima, I. A., and Naber, K. G. 2015. "Human Urine is Not Sterile—Shift of Paradigm," *Urologia Internationalis* 94(4):445-452; Mischianu, D., Bratu, O., Ilie, C., and Madan, V. 2008. "Notes Concerning the Peritonitis of Urinary Aetiology," *Journal of Medicine and Life* 1(1):66-71) (see also, for example, Palthe, S., Dijkstra, G. A., and Steffens, M. G. 2018. "A Case of Spontaneous Urinary Bladder Rupture Secondary to Urinary Retention Due to an Urethral Stricture," *Urology Case Reports* 17:85-87; Taniguchi, K., Iida, R., Ota, K., Nitta, M., Tsujino, T., and 5 others 2017. "Spontaneous Rupture of the Urinary Bladder (SRUB): Recovery from Cardiopulmonary Arrest," *American Journal of Emergency Medicine* 35(10):1584.e5-1584.e7; Baheti, V. H., Wagaskar, V. G., and Patwardhan, S. K. 2015. "Missed Iatrogenic Bladder Rupture following Normal Vaginal Delivery," *Journal of Clinical and Diagnostic Research* 9(10):PD01-PD02; Kivlin, D., Ross, C., Lester, K., Metro, M., and Ginsberg, P. 2015. "A Case Series of Spontaneous Rupture of the Urinary Bladder," *Current Urology* 8(1):53-56; Dubey, I. B., Mohanty, D., and Jain, B. K. 2012. "Diverse Presentation of Spontaneous Rupture of Urinary Bladder: Review of Two Cases and Literature," *American Journal of Emergency Medicine* 30(5):832.e1-e3).

In this application, where takeoff is at the ureters, bladder microbiota is not relevant (see, for example, Coorevits, L., Heytens, S., Boelens, J., and Claeys, G. 2017. "The Resident Microflora of Voided Midstream Urine of Healthy Controls: Standard Versus Expanded Urine Culture Protocols," *European Journal of Clinical Microbiology and Infectious Diseases* 36(4):635-639; Brubaker, L. and Wolfe, A. 2016. "The Urinary Microbiota: A Paradigm Shift for Bladder Disorders?," *Current Opinion in Obstetrics and Gynecology* 28(5):407-412; Wolfe, A. J. and Brubaker, L. 2015. "Sterile Urine" and the Presence of Bacteria," *European Urology* 68(2):173-174); however, the upper urinary tract can be infected as in pyelonephritis (see, for example, Brubaker, L. and Wolfe, A. J. 2017. "The Female Urinary Microbiota/Microbiome: Clinical and Research Implications," *Rambam Maimonides Medical Journal* 8(2), and urine is a medium for the reproduction of bacteria in the pelvic cavity.

Prolonged exposure to urine is corrosive even if sterile (see, for example, Walke, W. and Przondziono, J. 2012. "Influence of Hardening and Surface Modification of Endourological Wires on Corrosion Resistance," *Acta of Bioengineering and Biomechanics* 14(3):93-99; Berg, R. W., Buckingham, K. W., and Stewart, R. L. 1986. "Etiologic Factors in Diaper Dermatitis: The Role of Urine," *Pediatric Dermatology* 3(2):102-106). The degenerative and carcinogenic effect of urine on the gastrointestinal lining of an ileal conduit used to divert urine to a stoma and the peristomal irritation it causes is addressed above with references in the section entitled Urinary diversion by ureteral takeoff, for example.

FIG. 43 provides a perspective sectional view through neoureter junction, or neoureter convergence or confluence chamber 102, into which each jacket outlet drainage catheter, or neoureter, empties. Depending upon the length and peristaltic sufficiency of the vestigial ureter above the level of the jacket, when the patient is upright, the pressure of the urine on entering the ureteral side-entry jacket and gravity is ordinarily sufficient to expel the urine out through the neoureter 105, the confluence chamber, and through the surface port into the collection bag. In other than a daytime use only embodiment, and then even a daytime use only embodiment when necessary due to impaired ureteric peristalsis, an assist device consisting of an impeller and pressure actuated switch are incorporated into the neoureter confluence chamber.

When the pressure in the chamber exceeds a threshold level nearing that associated with reflux, the assist device automatically expels the chamber contents. The ability to always void while erect or seated will be true only of the intermittent user with an adjustable embodiment for use during the day but not while asleep at night. The neoureter confluence chamber in an adjustable embodiment for nighttime use and a nonadjustable or fixed embodiment for use as a permanent or temporary prosthesis as shown in FIG. 43 therefore includes a pressure actuated switch and impeller connected to a battery housed in the surface port. As shown, the jacket to either side receives a single accessory channel; however, where drugs should not be combined, more than one accessory channel is provided to either jacket.

The wires connecting the switch to the battery are passed from the surface port battery compartment to an accessory channel through leak-proof nylon accessory channel 11 collar 123 and coursed (run, 'snaked'), through either or both accessory channels to the switch. The pressure actuated switch is a microswitch comprised of parallel conductive leaves, one of which is bonded to the side of the impeller. The conductive leaves are separated by a leaf spring which under the threshold pressure, flattens, bringing the leaf above and below the spring into contact. In an intractable stone former already under treatment with only partial success, an accessory channel can be led directly from the surface port to the convergence chamber, thus averting the risk of reflux into the native ureter of a stone solvent (potassium citrate, magnesium potassium citrate, allopurinol, sodium bicarbonate) at a high concentration to prevent encrustation at the chamber outlet.

The pressure actuated switch automatically actuates the neoueter convergence chamber impeller when an increase in resistance to outflow or effluence approaches a level that would induce reflux, as might occur were the user ureterally impaired or sleeping in a position that impeded emptying. The neoureter junction and convergence or confluence chamber therefore incorporates a lightweight subminiature positive displacement impeller without a pressure relief valve. To allow the neoueter convergence chamber impeller to be positioned close to the chamber outlet for maximum evacuation and not obstruct passive flow through when not active, the impeller allows passive flow-through but forcibly ejects urine when actuated by the pressure actuated switch.

Figure 45:
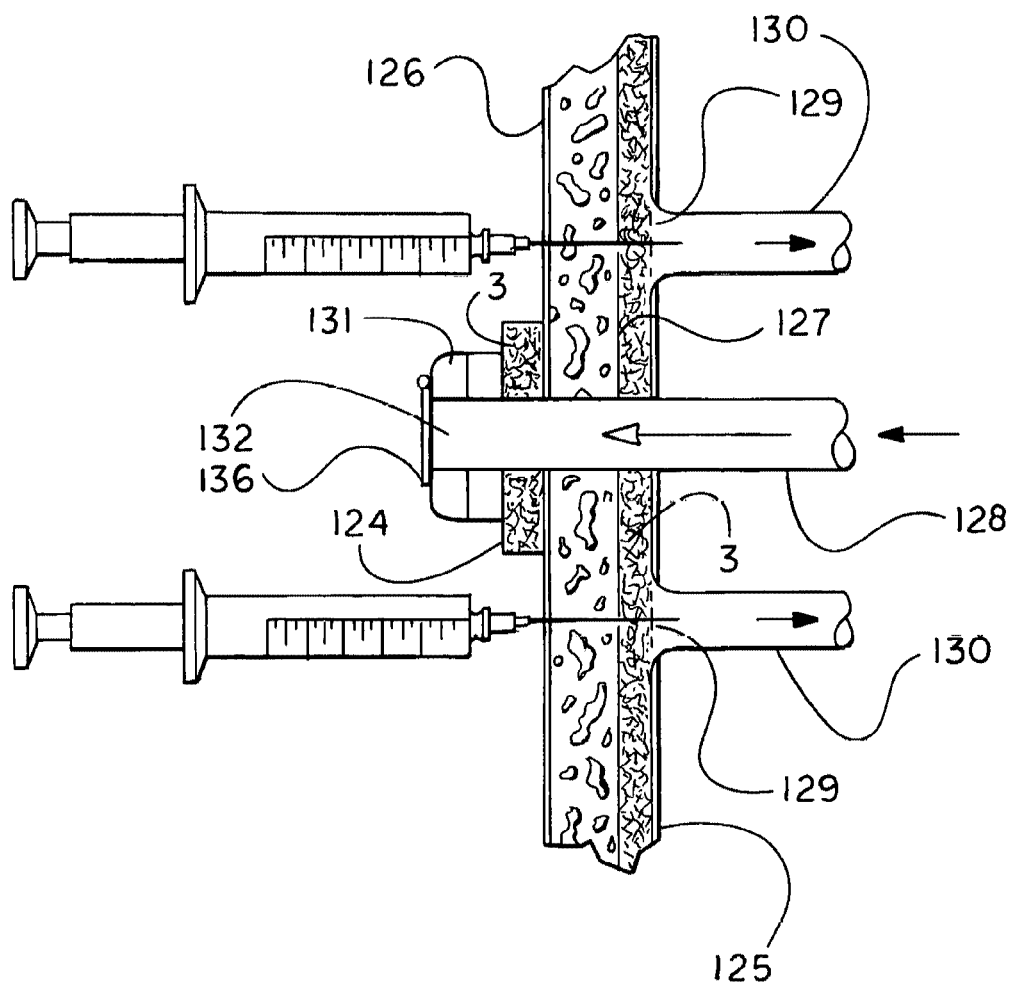
FIG. 45 shows a body surface port for positioning at the surface of the body which includes both cutaneous, or epidermal, and subcutaneous, subdermal, openings.

As shown in FIG. 45, rather than to depend upon transcutaneous or transdermal energy transfer to recharge the battery, which would necessitate implanting additional electronics and a receiving antenna, the small button cell battery or batteries to serve as the power source for neoureter 105 convergence chamber 102 impeller 106 motor is incorporated into port 16 at the body surface to a side of the mons pubis where it is easily viewed by the patient. Figure XX is an overhead planar transverse sectional view through the diversion catheter or neoureter junction and convergence or confluence chamber. Neoureter confluence chamber 102 not only merges the urine from the neoureters led from the ductus side-entry diversion jackets shown in FIG. XX for elimination through the chamber outlet line and out to the collection bag, but provides a housing for a pressure actuated switch and neoureter convergence chamber impeller assist device to expel urine when the wearer is other than erect.

To allow quick replacement, the small battery is housed in the port at the body surface. The sensor and assist device are omitted when the wearer will use the device only during the day while erect, or a functional bladder lacking, an alternative means for increasing the force of expulsion, such as electrostimulation by a neuromodulator implant or diuresis are used to stimulate calyceal peristalsis. FIG. 40 thus provides an overall or plan view of the scheme of a bilateral urinary evacuative prosthesis with ureteral takeoff diversion valves suitable for placement in females having undergone pelvic evisceration for cancer, for example, in which case an Heal conduit and stoma—both associated with problems—is eliminated; a comparable prosthesis to eliminate the need for a colostomy not addressed here.

A single stoma for solid waste and urine combines the complications associated with either of two stomas, the literature not cognizant of prostheses made of synthetic materials in lieu of misappropriated normal tissue to conduct urine, to which it is unadapted and undergoes metaplastic degeneration (see, for example, Gan, J. and Hamid, R. 2017. "Literature Review: Double-barrelled Wet Colostomy (One Stoma) Versus Ileal Conduit with Colostomy (Two Stomas)," *Urologia Internationalis* 98(3):249-254; Salgado-Cruz, L., Espin-Basany, E., Vallribera-Valls, F.2, Sanchez-Garcia, J., Jimenez-Gomez, L. M., Marti-Gallostra, M., and Garza-Maldonado, A. 2014. "Double Barreled Wet Colostomy: Initial Experience and Literature Review," *Scientific World Journal* 2014:961409; Kecmanovic, D. M., Pavlov, M. J., Ceranic, M. S., Masulovic, D. M., Popov, I. P., and Micev, M. T. 2008. "Double-barreled Wet Colostomy: Urinary and Fecal Diversion," *Journal of Urology* 180(1):201-205).

Body Surface Ports

A body surface port is made as small as clear visibility allows and as will not impair its function or functions. Body surface ports may be thought of as specialized nonjacketing side-entry connectors. The injection points in an epidermal, that is, on the skin, cutaneous, port such as that shown in FIGS. 27, 28, and 40 are identified on and protected by spring-hinged covers much like those covering the lubrication pipes in machinery. Subdermal injection points whether individual, or multiple, or for a multi-head jet injector, for example, are identified by one or more small tattooed arrows that point to the injection spot or indicate how the multiple head hypodermic or jet injector is to be oriented or keyed.

Other than more stringent in positioning, subdermal injection is the same as conventional injection through the skin. FIG. 45 provides a diametric transectional view through a body surface port which to pass through an outflow line for urine or dialysate in an intracorporeal hemodialysis system for passage into an external or extracorporeal collection bag or to insert cabled diagnostic and therapeutic devices, for example, must allow egress to the exterior. The port shown in FIG. 45 differs from that shown in FIG. 40, which is completely epidermal, in placing the entry hole into the accessory channels subdermally.

A surface port for the injection of drugs into each accessory channel not requiring an excurrent outlet can be positioned subdermally. That is, when egress to the exterior is unnecessary, the port to serve rather for the injection of drugs or other therapeutic or line maintenance substances to the sites to which the lines connected to the openings lead, however, the port openings into the respective lines or accessory channels can be positioned just inside the skin, that is, subdermally, or subcutaneously. In addition to providing a clearly identifiable point of ingress and egress, a body surface port can also incorporate small components such as rechargeable button cells and a push-pull cable control knob.

FIG. 45 shows a combination port which includes an epidermal outflow line 128 passing to the exterior through the center of port faceplate 124 with moisture barrier-coated open cell viscoelastic polyurethane foam layer 3 bonded onto its integument-facing surface. Faceplate 124 and its foam lining 3 are perforated entirely through to the epidermis, the perforations about the periphery complementary in diameter to the suture used to fasten faceplate 124 to the integument as to prevent exposure to pathogens and allergens. Faceplate 124 has bonded to its outside face a flange disk with screw thread running about its circumference to allow nonperforated protective cap 131 to be screwed onto it, this flange disk perforated through it, its substrate faceplate 124, and subjacent foam 3. When not used to insert a fiberscope or connected to a uring drainage hose, for example, centered opening 132 into urine outlet line 128 is covered by protective spring-hinged cap 136.

Covering over outflow line 128 exit hole 132 in the center of cap 131 is spring-hinged cap 133 similar to those used to cover over oiling points in machinery (not shown), which must be intentionally pulled up to allow a urine drainage tube or dialysate or apheresis fluid exchange tubing to be engaged in outlet opening 132. To prevent exposure to pathogens and allergens, protective cap 131 and spring-hinged cap 133 over its exit opening 132 are not perforated. That is, when protective cap 131 is screwed onto the threaded flange bonded to the face of faceplate 124, the perforations through faceplate 124 and foam 3 down to the surface of the skin, or epidermis 126 are covered over.

Engagement and retention of a urine or magnetic separation fluid in exit opening 132 can be any leak-free secure means, to include barbed or ribbed connector, quick disconnect coupler, or screw threaded. As well as to provide exposure to the air, unscrewing protective cap 131 exposes the perforations through faceplate 124 and through open cell foam 3, allowing antimicrobials and/or anti-inflammatories, for example, to be dripped onto faceplate 124 to wet the surface of the skin 126 allowing irritation of the skin following placement or any time thereafter to be ameliorated.

Backplate 125 provides injection points 129 beyond the outer circumference of faceplate 124, the protrusion of cap 131 over the skin line assisting the self-injecting patient or medical technician to locate these immediately. Backplate 125 is separated from the subdermis 127 by moisture barrier-coated open cell viscoelastic polyurethane foam 3 bonded onto its integument-facing surface. Subdermal injection points 129 can be indicated by tiny tattoo arrows or dots on the skin itself, or faceplate 124 can be extended in diameter to provide needle holes distinct in size from perforations otherwise through it, these holes aligned to the unseen injection points 129 in backplate 125.

Urine outlet line 109 in FIG. 40 is not necessarily interchangeable with outlet line 128 in FIG. 45, which is not limited to use as a urine outlet but equally applicable to an intracorporeal dialysate or apheresis fluid exchange point such as port 16 in FIG. 39B. Unless the operator is already working in an open surgical field, the components of a prosthetic disorder response system or a simpler system such as the urinary diversion application shown in FIG. 40 are placed endoscopically. If having a flared or expanded terminus to assure retention within injection point openings 129 as shown, accessory channels 130 are passed through openings 129 from the outside at the outset of the emplacement procedure, the expanded ends and bonding with a surgical cyanoacrylate cement then preventing the lines from dropping away from the holes after placement.

Otherwise, outlet line 128 is passed through the center hole in perforated backplate 125 and foam layer 3 bonded to it, and accessory channels 130 are inserted into holes in backplate 125 with foam layer 3 bonded to its integument side, these connection bonded with surgical cyanoacrylate cement and outlet line 128 is brought out through the integument with a stab wound (not with a trocar) of just sufficient length to snugly accommodate outlet line 128 without causing tearing forces at the ends of the incision. Backplate 125 is stitched through the perforations about its periphery to the subdermis.

Faceplate 124 with moisture barrier-coated open cell viscoelastic polyurethane foam layer 3 bonded onto its integument-facing surface and urine outlet line 128 is passed over the proximal end of urine outlet line 128 now extending out of the body. Faceplate 124 with foam layer 3 bonded to it is attached to the dermis by passing suture through perforations about its periphery, the suture matched in gauge to the perforations as to completely fill these. Urine outlet 128 now exits the body through the center of perforated faceplate 124 with the outlet hose coupling having been applied, and perforated backplate 125 secures and provides openings into the injection point openings 129 which lead into accessory channels or drug reservoir feed pipes 130. Screw-on port cap 131 is connected to urine outlet 128 which is then trimmed flush to the surface of cap 131.

To keep out pathogens and allergens, screw-on port cap 131 and protective spring hinged center hole cover are not perforated. Periodic instillation of antimicrobials, antiseptic, and anti-inflammatories such as triamcinolone acetonide or dexamethasone into foam 3 is by direct injection at the open sides of the foam 3 on faceplate 124 and through the perforations of backplate 125. In a combination epidermal-subdermal port, to position epidermal and subdermal ports other than as concentric is not preferred: separation thus removes the visual and tactile aid to locating the injection points which the raised center of a faceplate provides, as well as the instilment of coordinated therapeutic conception and treatment, risks possible confusion during self-injection by a cognitively compromised patient, and increases the area for potential adverse tissue reactions.

When more than one opening is subdermal and each is for a different drug or agent, small tattoo arrows or dots on the skin can be used to indicate the subdermal injection points 129, or perforated faceplate 126 can be increased in diameter to cover over the injection points and provide needle insertion guide openings. Competent patients are confirmed to understand which agents are to be injected into each opening. With incompetent patients, the regimen is devised to maximize the intervals between drug administration, and agent injection is by a nurse or other qualified medical staff member.

When the patient is confined to a medical institution, injection point indicators such as faceplate holes and tattooed arrows on the skin can be dispensed with, a handheld ultrasound imager used to guide the needle to the subdermal injection openings 129. With a prosthetic disorder response system, periodic dosing is automated, injection used only to replenish implanted drug reservoir stores. With a reservoir or reservoirs provided, administration of each drug or agent can be controlled by a timing module or microprocessor reservoir outlet pump controller. The frequency of injection for replenishment is minimized increasing the capacity of the implant reservoir or reservoirs.

While it is improbable, a volume of a drug or agent not accommodated thus and otherwise requiring injection at intervals that would injure the integument can be accomplished by providing two or more accessory channels to the same jacket with each entered through a separate opening in the subdermal port. Where no excurrent line is involved, a surface port on the skin serving only to house a button cell battery for quick replacement or recharging, it is preferable to implant the battery with transdermal energy transfer recharging antenna and thus allow the system to be fully implanted, or closed skin. An epidermal port is, however, justified where the need to introduce a cabled device is frequent as would require repeated slitting through the skin to gain entry. When present, urine or magnetic separation fluid outlet line 128 allows the insertion of a cabled device such as a fine fiber scope or laser.

The invention claimed is:

1. A collar adapted for attachment about a tubular anatomical structure, said collar comprising: an outer shell of semicylindrical halves joined together along a common edge where said semicylindrical halves meet by spring-loaded hinges, so that said semicylindrical shell halves when opened and placed to encircle said tubular anatomical structure, the shell halves are configured to grip about said tubular anatomical structure as a stationary collar; a cushioning layer lining the internal surface of each shell half; perforations which pass entirely through said outer shell and said cushioning layer; a first opening in the side of said collar; a side tube with a trepan front edge engaged in said first opening, such that said side tube is rotatable around and reciprocable along its longitudinal axis; wherein the side tube is configured to allow a plug of tissue to be excised from the wall of said tubular anatomical structure so that a lumen of said side tube will be continuous with a lumen of said tubular anatomical structure; said side tube thereafter being configured to be fixable in rotational angle and depth of penetration into the side of said tubular anatomical structure; and a self-locking screw down cap that fits onto an external thread at a base of said side tube and is configured to allow said side tube to be fixed in rotational angle and depth of insertion into said first opening.

2. A collar according to claim 1 wherein said side tube further comprises a second opening and a catheteric side tube engaged in said second opening to allow targeted delivery into said side tube, collar, and tubular anatomical structure.

3. A collar according to claim 1 further comprising a permanent magnet layer along the internal surface of said outer shell, said magnet layer interposed between said outer shell and said cushioning layer and interrupted to accommodate the opening and closing of said collar and the passing through of said perforations, wherein said magnet layer exerts a tractive force centrally toward and perpendicular to the longitudinal axis of said collar.

4. A collar according to claim 1 having an outer layer of radiation shielding, comprising imbricated particles of tungsten bound in a bioabsorbable matrix, said outer layer of radiation shielding situated about the external surface of said outer shell, said outer layer of radiation shielding interrupted to accommodate the opening and closing of said collar, said outer layer of radiation shielding serving to allow the passage through said collar and a line leading to it of low to moderate radiation dose rate radionuclides and radioactive isotopes without causing radiation injury to the surrounding tissue.

5. The collar according to claim 4, wherein the layer of radiation shielding material is in concentric relation to the longitudinal axis of said collar.

6. A collar according to claim 1 further comprising a plurality of small and lightweight electromagnets between said outer shell and said cushioning layer and interrupted to accommodate the opening and closing of said collar and the passing through of said perforations, said plurality of electromagnets selectively energizable to exert tractive force eccentrically and collectively energizable to exert tractive force centrally toward and perpendicular to the longitudinal axis of said collar.

7. A collar according to claim 1, said collar having a long axis, and said collar further comprising an electromagnet having a pole positioned to intersect with the long axis of said collar, a portion of the collar shell removed to admit said pole, and a magnetically susceptible opposing draw-plate such that energizing said electromagnet pulls said draw-plate toward it.

8. A collar according to claim 1 further comprising a port configured to be mounted on the skin from which said port is isolated by a baseplate except for suture spots on the baseplate that are open to allow the administration of an antimicrobial.

9. A collar according to claim 8; wherein said baseplate is separated from the skin by a cushion interposed between the baseplate and the skin.

10. A collar according to claim 1, said collar having a long axis, and wherein a chute is mounted to the collar for rectilinear reciprocal movement normal to the long axis of said tubular anatomical structure wherein the chute closes off and redirects upstream flow through said tubular anatomical structure into another passageway.

11. A train of collars comprising more than one collar according to claim 7, wherein successive energization of each electromagnet is controlled by a timing module so that the collars act sequentially to simulate the intrinsic peristaltic motility of a segment of the alimentary tract that is paralytic or required to be resected.

12. An automatic homeostasis stabilizer and ambulatory prosthetic disorder response system comprising a plurality of collars according to claim 1 further comprising at least one pump supplying fluid medicinals to said collars; wherein said at least one pump is controlled according to a prescription program by a microcontroller; wherein a plurality of physiological parameter sensors are configured to be implanted at different locations in the body and send outputs as subordinate negative feedback loop nodes in a hierarchical control system to said microcontroller; wherein the outputs represent feedback where each signals to the microcontroller an out of range condition that necessitates prescribed medication; wherein the microcontroller is configured to cause said at least one pump to index to and release the fluid medicinals corresponding to the prescribed medication for a given subordinate node in the dose proportional to the out of range feedback signal received; the microcontroller is configured to govern the discharge of the prescription program and dispensing the fluid medicinals through a subsidiary control loop as a subordinate node in a coordinated manner as governed by the prescription program so that dosing among the nodes is interrelated.

13. A train of collars comprising more than one collar according to claim 7, each collar incorporating an electromagnet with pole separated by a flush-line from a window configured to be placed in the side of a blood vessel wherein said flush-line washes away debris from said magnet pole when not energized, said window representing a magnetic separation transit plane spanned by a semipermeable membrane for hemodialysis or an elastic slit-valve for cytapheresis, where said flush-line is configured to communicate with the urinary bladder, a window, and/or electromagnet such that the debris is entered into the urine for expulsion upon voiding.

* * * * *

UNITED STATES PATENT AND TRADEMARK OFFICE
CERTIFICATE OF CORRECTION

PATENT NO. : 11,759,186 B2  
APPLICATION NO. : 15/998002  
DATED : September 19, 2023  
INVENTOR(S) : David S. Goldsmith Page 1 of 1

It is certified that error appears in the above-identified patent and that said Letters Patent is hereby corrected as shown below:

On the Title Page

Column 1, item (54), and in the Specification, Column 1, Lines 1-2 delete "DUCTUS SIDE-ENTRY AND PROSTHETIC DISORDER RESPONSE SYSTEMS" and insert -- DUCTUS SIDE-ENTRY JACKETS AND PROSTHETIC DISORDER RESPONSE SYSTEMS --

Signed and Sealed this  
Fifth Day of March, 2024

Katherine Kelly Vidal  
*Director of the United States Patent and Trademark Office*